United States Patent
Song et al.

(10) Patent No.: US 11,785,847 B2
(45) Date of Patent: Oct. 10, 2023

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Hyun Ju Song, Cheonan-si (KR); Hyo Min Jin, Cheonan-si (KR); Junggeun Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/310,623

(22) Filed: May 2, 2023

(65) Prior Publication Data

US 2023/0276707 A1 Aug. 31, 2023

Related U.S. Application Data

(63) Continuation-in-part of application No. 18/180,625, filed on Mar. 8, 2023, which is a continuation-in-part
(Continued)

(30) Foreign Application Priority Data

Oct. 26, 2020 (KR) .................. 10-2020-0139441

(51) Int. Cl.
*C07D 251/24* (2006.01)
*H01L 51/00* (2006.01)
(Continued)

(52) U.S. Cl.
CPC ....... *H10K 85/6574* (2023.02); *C07D 251/24* (2013.01); *C09K 11/06* (2013.01); *H10K 85/626* (2023.02); *H10K 85/631* (2023.02); *H10K 85/653* (2023.02); *H10K 85/654* (2023.02); *H10K 85/6572* (2023.02); *H10K 85/6576* (2023.02); *C07B 2200/05* (2013.01); *C09K 2211/1018* (2013.01); *H10K 50/11* (2023.02);
(Continued)

(58) Field of Classification Search
CPC .. C07D 251/24; H10K 85/654; H10K 85/631; H10K 85/657
See application file for complete search history.

(56) References Cited

U.S. PATENT DOCUMENTS

| | | |
|---|---|---|
| 2014/0367654 A1 | 12/2014 | Kim et al. |
| 2015/0303379 A1 | 10/2015 | Lee et al. |

(Continued)

FOREIGN PATENT DOCUMENTS

| | | |
|---|---|---|
| KR | 10-2009-0079134 A | 7/2009 |
| KR | 10-2016-0111780 A | 9/2016 |

(Continued)

OTHER PUBLICATIONS

SciFinder Search, 4 pages, Apr. 7, 2021.
STN Search, 351 pages, Apr. 7, 2021.

*Primary Examiner* — Vu A Nguyen
(74) *Attorney, Agent, or Firm* — Vorys, Sater, Seymour and Pease LLP; Mih Suhn Koh

(57) ABSTRACT

Provided are a novel compound capable of improving the light-emitting efficiency, stability, and lifespan of an element; an organic electronic element using same; and an electronic device thereof.

14 Claims, 2 Drawing Sheets

Related U.S. Application Data of application No. 17/212,886, filed on Mar. 25, 2021, now Pat. No. 11,678,577, which is a continuation of application No. 17/096,790, filed on Nov. 12, 2020, now Pat. No. 11,063,226.

(51) Int. Cl.

| | | |
|---|---|---|
| *H01L 51/50* | (2006.01) | |
| *H10K 85/60* | (2023.01) | |
| *C09K 11/06* | (2006.01) | |
| *H10K 50/11* | (2023.01) | |
| *H10K 50/15* | (2023.01) | |
| *H10K 50/16* | (2023.01) | |
| *H10K 50/18* | (2023.01) | |
| *H10K 101/10* | (2023.01) | |
| *H10K 101/00* | (2023.01) | |

(52) U.S. Cl.
CPC ............ *H10K 50/15* (2023.02); *H10K 50/16* (2023.02); *H10K 50/18* (2023.02); *H10K 2101/10* (2023.02); *H10K 2101/90* (2023.02)

(56) References Cited

U.S. PATENT DOCUMENTS

| | | |
|---|---|---|
| 2016/0133674 A1 | 5/2016 | Lee et al. |
| 2018/0072695 A1 | 3/2018 | Byun et al. |
| 2018/0123048 A1 | 5/2018 | So et al. |
| 2018/0151806 A2 | 5/2018 | Park et al. |
| 2018/0261774 A1 | 9/2018 | Park et al. |

FOREIGN PATENT DOCUMENTS

| | | | | |
|---|---|---|---|---|
| WO | 2017/171420 A1 | 10/2017 | | |
| WO | 2019/124902 A1 | 6/2019 | | |
| WO | WO-2020180005 A1 * | 9/2020 | ............ | C07D 213/06 |
| WO | WO-2021049843 A1 * | 3/2021 | ............ | C07D 239/26 |

\* cited by examiner

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATIONS

This application is a Continuation-In-Part of U.S. patent application Ser. No. 18/180,625 filed on Mar. 8, 2023, which was a Continuation-In-Part of U.S. patent application Ser. No. 17/212,886 filed on Mar. 25, 2021, which was a Continuation of U.S. patent application Ser. No. 17/096,790 filed on Nov. 12, 2020, now U.S. Pat. No. 11,063,226 issued on Jul. 13, 2021, which claims the benefit of priority from Korean Patent Application No. 10-2020-0139441 filed on Oct. 26, 2020, the contents of each of which are incorporated herein by reference in its entirety.

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and according to the light emission mechanism, it can be classified into a fluorescent material derived from a singlet excited state of an electron and a phosphorescent material derived from a triplet excited state of an electron. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. At this time, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase.

However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

That is, in order to fully exhibit the excellent characteristics of an organic electronic element, it should be preceded that the material constituting the organic material layer in the device, such as a hole injection material, a hole transport material, a light emitting material, an electron transport material, an electron injection material, etc., is supported by a stable and efficient material. But the development of a stable and efficient organic material layer material for an organic electronic device has not yet been sufficiently made. Therefore, the development of new materials is continuously required, and in particular, the development of a host material for the emitting layer is urgently required.

BRIEF DESCRIPTION OF THE INVENTION

Summary

In order to solve the problems of the above-mentioned background art, the present invention has revealed a compound having a novel structure, and when this compound is applied to an organic electronic element, it has been found that the luminous efficiency, stability and lifespan of the device can be significantly improved.

Accordingly, an object of the present invention is to provide a novel compound, an organic electronic element using the same, and an electronic device thereof.

Technical Solution

In one aspect, the present invention provides an organic electronic element comprising a first electrode; a second electrode; and an organic material layer formed between the first electrode and the second electrode, wherein the organic material layer includes an emitting layer, wherein the emitting layer is a phosphorescent emitting layer, and comprises a first host compound represented by Formula 1 and a second host compound represented by Formula 4 or Formula 5.

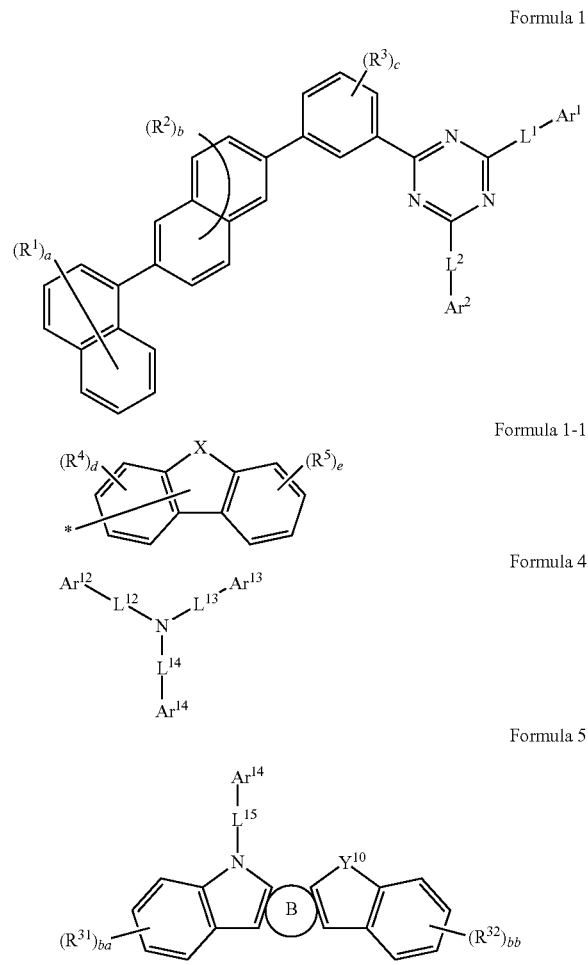

Formula 1

Formula 1-1

Formula 4

Formula 5

In another aspect, the present invention provides an electronic device comprising the organic electronic element.

In another aspect, the present invention provides a compound represented by

Formula 1

Effects of the Invention

By using the compound according to the present invention, high luminous efficiency, low driving voltage and high heat resistance of the element can be achieved, and color purity and lifespan of the element can be greatly improved.

DETAILED DESCRIPTION OF THE INVENTION

Figure 1:
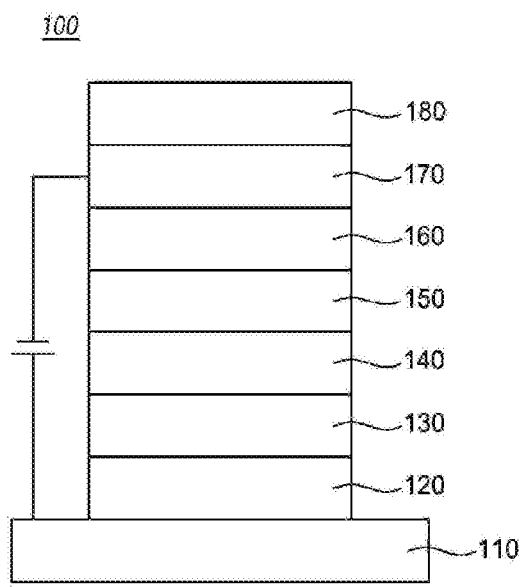
FIG. 1 to FIG. 3 are exemplary views of an organic electroluminescent device according to the present invention.

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an alkyl group bonded to oxygen radical, but is not limited thereto, and has 1 to 60 carbon atoms.

Unless otherwise stated, the term "aryloxyl group" or "aryloxy group", as used herein, means an aryl group bonded to oxygen radical, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

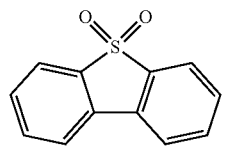 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

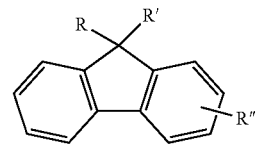

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a C1-C20 alkyl group, a C1-C20 alkoxyl group, a C1-C20 alkylamine group, a C1-C20 alkylthiopen group, a C6-C20 arylthiopen group, a C2-C20 alkenyl group, a C2-C20 alkynyl group, a C3-C20 cycloalkyl group, a C6-C20 aryl group, a C6-C20 aryl group substituted by deuterium, a C8-C20 arylalkenyl group, a silane group, a boron group, a germanium group, and a C2-C20 heterocyclic group, but is not limited to these substituents.

Also, unless there is an explicit explanation, the formula used in the present invention is the same as the definition of the substituent by the exponent definition of the following formula.

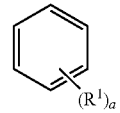

Here, when a is an integer of 0, the substituent R1 is absent, when a is an integer of 1, the sole substituent R1 is linked to any one of the carbon constituting the benzene ring, when a is an integer of 2 or 3, each is combined as follows, where R1 may be the same or different from each other, when a is an integer of 4 to 6, it is bonded to the carbon of the benzene ring in a similar manner, while the indication of the hydrogen bonded to the carbon forming the benzene ring is omitted.

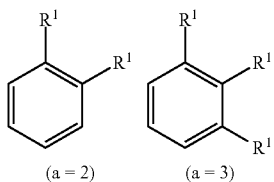

Hereinafter, a layered structure of an organic electronic element including the compound of the present invention will be described with reference to FIGS. 1 to 3.

In adding reference numerals to the components of each figures, it should be noted that the same components have the same numerals as much as possible even if they are displayed on different figures. In addition, in describing the present invention, if it is determined that a detailed description of a related known configuration or function may obscure the gist of the present invention, the detailed description will be omitted.

Figure 2:
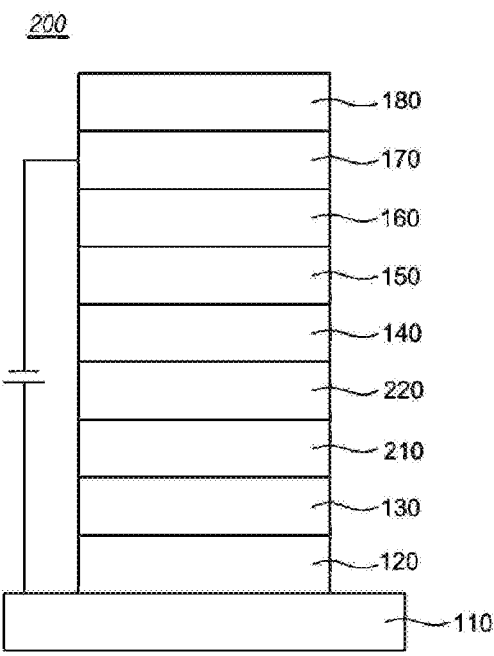
Figure 3:
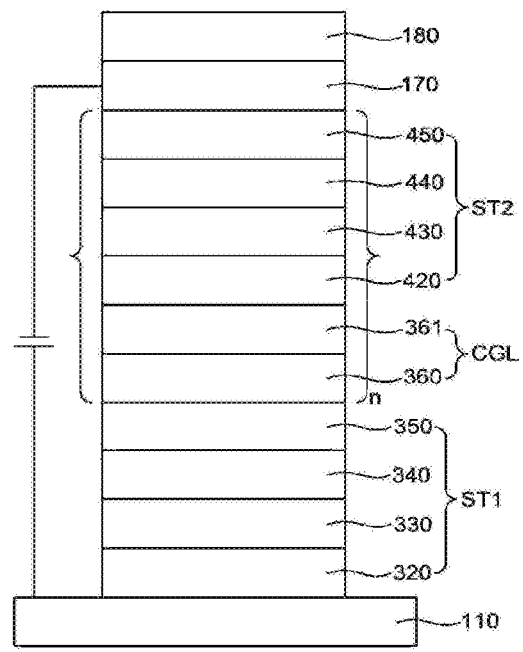
Figure 4:
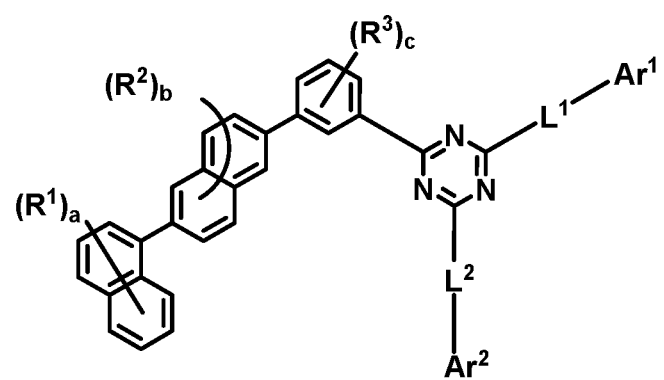
FIG. 4 shows a formula according to one aspect of the present invention. | |
|---|---|
| 100, 200, 300: | organic electronic element |
| 110: | the first electrode |
| 120: | hole injection layer |
| 130: | hole transport layer |
| 140: | emitting layer |
| 150: | electron transport layer |
| 160: | electron injection layer |
| 170: | second electrode |
| 180: | light efficiency enhancing Layer |
| 210: | buffer layer |
| 220: | emitting auxiliary layer |
| 320: | first hole injection layer |
| 330: | first hole transport layer |
| 340: | first emitting layer |
| 350: | first electron transport layer |
| 360: | first charge generation layer |
| 361: | second charge generation layer |
| 420: | second hole injection layer |
| 430: | second hole transport layer |
| 440: | second emitting layer |
| 450: | second electron transport layer |
| CGL: | charge generation layer |
| ST1: | first stack |
| ST2: | second stack |

FIGS. 1 to 3 are exemplary views of an organic electronic element according to an embodiment of the present invention.

Referring to FIG. 1, an organic electronic element (100) according to an embodiment of the present invention includes a first electrode (110), a second electrode (170) formed on a substrate (not shown), and an organic layer formed between a first electrode (110) and the second electrode (170).

The first electrode (110) may be an anode, the second electrode (170) may be a cathode, and in the case of an inverted type, the first electrode may be a cathode and the second electrode may be an anode.

The organic material layer may include a hole injection layer (120), a hole transport layer (130), an emitting layer (140), an electron transport layer (150), and an electron injection layer (160). Specifically, a hole injection layer (120), a hole transport layer (130), an emitting layer (140), an electron transport layer (150), and an electron injection layer (160) may be sequentially formed on the first electrode (110).

Preferably, a light efficiency enhancing layer (180) may be formed on one side not in contact with the organic material layer among both sides of the first electrode (110) or of the second electrode (170), and when the light efficiency enhancing layer (180) is formed, the light efficiency of the organic electronic element may be improved.

For example, the light efficiency enhancing layer (180) may be formed on the second electrode (170), and in the case of a top emission organic light emitting device, the light efficiency enhancing layer (180) is formed, thereby reducing optical energy loss due to surface plasmon polaritons (SPPs) in the second electrode (170), and in the case of a bottom emission organic light emitting device, the light efficiency enhancing layer (180) may function as a buffer for the second electrode (170).

A buffer layer (210) or an emitting auxiliary layer (220) may be further formed between the hole transport layer (130) and the emitting layer (140), which will be described with reference to FIG. 2.

Referring to FIG. 2, an organic electric device (200) according to another embodiment of the present invention includes a hole injection layer (120), a hole transport layer (130), a buffer layer (210), an emitting auxiliary layer (220), an emitting layer (140), an electron transport layer (150), an electron injection layer (160), a second electrode (170), sequentially formed on the first electrode (110), and a light efficiency enhancing layer (180) formed on the second electrode.

Although not shown in FIG. 2, an electron transport auxiliary layer may be further formed between the emitting layer (140) and the electron transport layer (150).

Also, according to another embodiment of the present invention, the organic material layer may have a plurality of stacks including a hole transport layer, an emitting layer, and an electron transport layer. This will be described with reference to FIG. 3.

Referring to FIG. 3, in the organic electronic element (300) according to another embodiment of the present invention, 2 or more sets of stacks (ST1 and ST2) made of a multi-layered organic material layer may be formed between the first electrode (110) and the second electrode (170), and a charge generation layer (CGL) may be formed between the stacks of organic material layers.

Specifically, the organic electronic element according to an embodiment of the present invention includes a first electrode (110), a first stack (ST1), a charge generation layer (CGL), a second stack (ST2), and a second electrode (170) and a light efficiency enhancing layer (180) may be included.

The first stack (ST1) is an organic material layer formed on the first electrode (110) and may include a first hole injection layer (320), a first hole transport layer (330), a first emitting layer (340), and a first electron transport layer (350), and the second stack (ST2) may include a second hole injection layer (420), a second hole transport layer (430), a second emitting layer (440), and a second electron transport layer (450).

As described above, the first stack and the second stack may be organic material layers having the same laminated structure, but may be organic material layers having different laminated structures.

A charge generation layer (CGL) may be formed between the first stack (ST1) and the second stack (ST2). The charge generation layer (CGL) may include a first charge generation layer (360) and a second charge generation layer (361). The charge generation layer (CGL) is formed between the first emitting layer (340) and the second emitting layer (440) to increase the current efficiency generated in each emitting layer and smoothly distribute charge.

When a plurality of emitting layers are formed by the multilayer stack structure method as shown in FIG. 3, an organic electronic element that emits white light by a mixing effect of light emitted from each emitting layer can be manufactured, as well as an organic electronic element that emits light of various colors.

The compounds represented by Formula 1, Formula 4 and 5 of the present invention may be used as a material for a hole injection layer (120, 320, 420), a hole transport layer (130, 330, 430), a buffer layer (210), an emitting auxiliary layer (220), and an electron transport layer (150, 350, 450), the electron injection layer (160), the emitting layer (140, 340, 440), or the light efficiency enhancing layer (180), but preferably, as a host of the emitting layers (140, 340, 440).

Otherwise, even if the same or similar core is used, the band gap, the electrical characteristics, the interface characteristics, and the like may vary depending on which substituent is bonded at which position, therefore It is necessary to study the selection of the core and the combination of sub-substituents bonded thereto, and in particular, when the optimal combination of energy levels and T1 values of each organic material layer and unique properties of materials (mobility, interfacial characteristics, etc.) is achieved, a long lifespan and high efficiency can be achieved at the same time.

The organic electronic element according to an embodiment of the present invention may be manufactured using various deposition methods. It can be manufactured using a vapor deposition method such as PVD or CVD. For example, an anode (110) is formed by depositing a metal or a conductive metal oxide or an alloy thereof on a substrate, and after forming an organic material layer including the hole injection layer (120), the hole transport layer (130), the emitting layer (140), the electron transport layer (150) and the electron injection layer (160) thereon, the organic electroluminescent device according to an embodiment of the present invention can be manufactured by depositing a material that can be used as a cathode (170) thereon.

Also, an emitting auxiliary layer (220) may be further formed between the hole transport layer (130) and the emitting layer (140), and an electron transport auxiliary layer (not shown) may be further formed between the emitting layer (140) and the electron transport layer (150), and as described above, may be formed in a stack structure.

Also, the organic material layer may be manufactured with a smaller number of layers by using various polymer materials and not by a deposition method, but by a solution process, a solvent process, such as a spin coating process, a nozzle printing process, an inkjet printing process, a slot coating process, a dip coating process or a roll-to-roll process, doctor blading process, screen printing process, or a thermal transfer method. Since the organic material layer according to the present invention can be formed by various methods, the scope of the present invention is not limited by the forming method.

In addition, the organic electronic element according to an embodiment of the present invention may be selected from the group consisting of an organic electroluminescent device, an organic solar cell, an organic photoreceptor, an organic transistor, a monochromatic lighting device, and a quantum dot display device.

Another embodiment of the present invention may comprise an electronic device comprising a display device including the organic electronic element; and a control unit for driving the display device. At this time, the electronic device may be a current or future wired/wireless communication terminal, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electronic element according to an aspect of the present invention will be described.

The present invention provides an organic electronic element comprising a first electrode, a second electrode, and an organic material layer formed between the first electrode and the second electrode, wherein the organic material layer comprises an emitting layer, wherein the emitting layer comprises a first host compound represented by Formula 1 and a second host compound represented by Formula 4 or Formula 5 as the phosphorescent emitting layer.

Formula 1

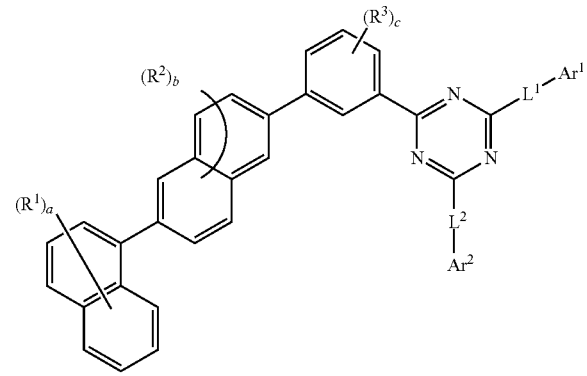

Formula 1-1

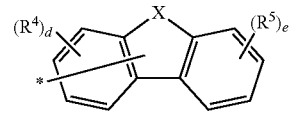

Formula 4

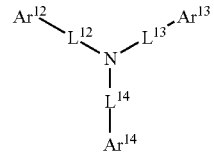

Formula 5

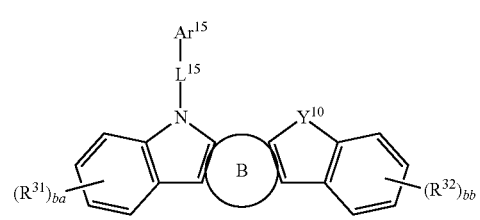

In Formula 1, Formula 1-1, Formula 4 and Formula 5, each symbol may be defined as follows.

R1, R2 and R3 are each the same or different, and each independently selected from the group consisting of hydrogen; deuterium; a C6-C60 aryl group; a fluorenyl group; a C2-C60 heterocyclic group including at least one hetero atom of O, N, S, Si or P; a fused ring group of a C3-C60 aliphatic ring and a C6-C60 aromatic ring; a C3-C60 aliphatic ring; a C1-C50 alkyl group; a C2-C20 alkenyl group; a C2-C20 alkynyl group; a C1-C30 alkoxyl group; and a C6-C30 aryloxy group;

When R1, R2 and R3 are an aryl group, it is preferably a C6-C30 aryl group, more preferably an C6-C25 aryl group, for example, it may be phenyl, biphenyl, terphenyl, naphthalene, phenanthrene and the like.

When R1, $R^2$ and $R^3$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When R1, R2 and R3 are a fused ring group, it is preferably a fused ring group of an C3-C30 aliphatic ring and an C6-C30 aromatic ring, and more preferably a fused ring group of an C3-C24 aliphatic ring and an C6-C24 aromatic ring.

When R1, R2 and R3 are an aliphatic ring group, it is preferably a C3-C30 aliphatic ring group, more preferably a C3-C24 aliphatic ring group.

When R1, R2 and R3 are an alkyl group, it is preferably a C1-C30 alkyl group, and more preferably a C1-C24 alkyl group.

When R1, R2 and R3 are an alkoxyl group, it is preferably a C1-C24 alkoxyl group.

When R1, R2 and R3 are an aryloxy group, it is preferably a C6-C24 aryloxy group.

a is an integer of 0 to 7, b is an integer of 0 to 6, c is an integer of 0 to 4, L1 and L2 are each independently a single bond; or a C6-C60 arylene group;

wherein in case L1 and L2 are an arylene group, it is preferably an C6-C30 arylene group, more preferably an C6-C25 arylene group, for example, it may be phenylene, biphenylene, naphthylene, terphenylene, anthracenylene, and the like.

Ar1 and Ar2 are each independently an C6-C60 aryl group; or a substituent represented by Formula 1-1;

When Ar1 and Ar2 are an aryl group, it is preferably an C6-C30 aryl group, more preferably an C6-C25 aryl group, for example, it may be phenyl, biphenyl, terphenyl, naphthalene, phenanthrene, and the like.

In Formula 1-1,

X is CRaRb, NR' or SiRaRb, provided that when X is bonded to L1 or L2, it is N,

R4 and R5 are each the same or different, and each independently selected from the group consisting of hydrogen; deuterium; a C6-C60 aryl group; a fluorenyl group; a C2-C60 heterocyclic group including at least one hetero atom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{60}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or an adjacent plurality of $R^4$ and plurality of $R^5$ may be bonded to each other to form a ring.

When R4 and R5 are an aryl group, it is preferably an C6-C30 aryl group, more preferably an C6-C25 aryl group, for example, it may be phenyl, biphenyl, terphenyl, naphthalene, phenanthrene and the like.

When R4 and R5 are a heterocyclic group, it is preferably a C2-C30 heterocyclic group, and more preferably a C2-C24 heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When R4 and R5 are a fused ring group, it is preferably a fused ring group of an C3-C30 aliphatic ring and an C6-C30 aromatic ring, and more preferably a fused ring group of an C3-C24 aliphatic ring and an C6-C24 aromatic ring.

When R4 and R5 are an aliphatic ring group, it is preferably a C3-C30 aliphatic ring group, more preferably a C3-C24 aliphatic ring group.

When R4 and R5 are an alkyl group, it is preferably a C1-C30 alkyl group, and more preferably a C1-C24 alkyl group.

When R4 and R5 are an alkoxyl group, it is preferably a C1-C24 alkoxyl group.

When R4 and R5 are an aryloxy group, it is preferably a C6-C24 aryloxy group.

d and e are each independently an integer of 0 to 4;
* denotes a position to be bonded, Ra, Rb and R' are each independently selected from the group consisting of hydrogen; deuterium; a C1-C50 alkyl group; a C6-C60 aryl group; a C2-C60 heterocyclic group including at least one hetero atom of O, N, S, Si or P; alternatively, Ra and Rb may be bonded to each other to form a spiro, When Ra, Rb and R' are an alkyl group, it is preferably a C1-C30 alkyl group, and more preferably a C1-C24 alkyl group.

When Ra, Rb and R' are an aryl group, it is preferably an C6-C30 aryl group, more preferably an C6-C25 aryl group, for example, it may be phenyl, biphenyl, terphenyl, naphthalene, phenanthrene, and the like.

When Ra, Rb and R' are a heterocyclic group, it is preferably a C2-C30 heterocyclic group, and more preferably a C2-C24 heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

In Formula 4,

L12, L13 and L14 are each independently selected from the group consisting of single bond; a C6-C60 arylene group; a fluorenylene group; a fused ring group of a C3-C60 aliphatic ring and a C6-C60 aromatic ring; a C2-C60 heterocyclic group including at least one heteroatom of O, N, S, Si or P;

When L12, L13 and L14 are an arylene group, it is preferably an C6-C30 arylene group, more preferably an C6-C25 arylene group, for example, it may be phenylene, biphenylene, naphthylene, terphenylene, anthracenylene, and the like.

When L12, L13 and L14 are a fused ring group, it is preferably a fused ring group of an C3-C30 aliphatic ring and an C6-C30 aromatic ring, and more preferably a fused ring group of an C3-C24 aliphatic ring and an C6-C24 aromatic ring.

When L12, L13 and L14 are a heterocyclic group, it is preferably a C2-C30 heterocyclic group, and more preferably a C2-C24 heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

Ar12, Ar13 and Ar14 are each independently selected from the group consisting of an C6-C60 aryl group; a fluorenyl group; a C2-C60 heterocyclic group including at least one heteroatom of O, N, S, Si or P; and a fused ring group of a C3-C60 aliphatic ring and a C6-C60 aromatic ring;

When Ar12, Ar13 and Ar14 are an aryl group, it is preferably an C6-C30 aryl group, more preferably an C6-C25 aryl group, for example, it may be phenyl, biphenyl, terphenyl, naphthalene, phenanthrene and the like.

When Ar12, Ar13 and Ar14 are a heterocyclic group, it is preferably a C2-C30 heterocyclic group, and more preferably a C2-C24 heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When Ar12, Ar13 and Ar14 are a fused ring group, it is preferably a fused ring group of an C3-C30 aliphatic ring and an C6-C30 aromatic ring, and more preferably a fused ring group of an C3-C24 aliphatic ring and an C6-C24 aromatic ring.

In Formula 5,

Ring B is an C6-C20 aryl group,

Y10 is O, S, CR51 R52 or NR53,

L15 is selected from the group consisting of single bond; a C6-C60 arylene group; a fluorenylene group; a fused ring group of a C3-C60 aliphatic ring and a C6-C60 aromatic ring; a C2-C60 heterocyclic group including at least one heteroatom of O, N, S, Si or P;

When L15 is an arylene group, it is preferably an C6-C30 arylene group, more preferably an C6-C25 arylene group, for example, it may be phenylene, biphenylene, naphthylene, terphenylene, anthracenylene, and the like.

When L15 is a fused ring group, it is preferably a fused ring group of an C3-C30 aliphatic ring and an C6-C30 aromatic ring, and more preferably a fused ring group of an C3-C24 aliphatic ring and an C6-C24 aromatic ring.

When L15 is a heterocyclic group, it is preferably a C2-C30 heterocyclic group, and more preferably a C2-C24 heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

Ar15 is selected from the group consisting of an C6-C60 aryl group; a fluorenyl group; a C2-C60 heterocyclic group including at least one heteroatom of O, N, S, Si or P; a fused ring group of a C3-C60 aliphatic ring and a C6-C60 aromatic ring; and -L"-NRfRg;

When Ar15 is an aryl group, it is preferably an C6-C30 aryl group, more preferably an C6-C25 aryl group, for example, it may be phenyl, biphenyl, terphenyl, naphthalene, phenanthrene and the like.

When Ar15 is a heterocyclic group, it is preferably a C2-C30 heterocyclic group, and more preferably a C2-C24 heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When Ar15 is a fused ring group, it is preferably a fused ring group of an C3-C30 aliphatic ring and an C6-C30 aromatic ring, and more preferably a fused ring group of an C3-C24 aliphatic ring and an C6-C24 aromatic ring.

R31 and R32 are each the same or different, and each independently selected from the group consisting of hydrogen; deuterium; halogen; cyano group; nitro group; a C6-C60 aryl group; fluorenyl group; a C2-C60 heterocyclic group including at least one heteroatom of O, N, S, Si or P; a fused ring group of a C3-C60 aliphatic ring and a C6-C60 aromatic ring; a C1-C60 alkyl group; a C2-C60 alkenyl group; a C2-C60 alkynyl group; a C1-C60 alkoxy group; and a C6-C60 aryloxy group; or an adjacent plurality of R31 or a plurality of R32 may be bonded to each other to form a ring, When R31 and R32 are an aryl group, it is preferably an C6-C30 aryl group, more preferably an C6-C25 aryl group, for example, it may be phenyl, biphenyl, terphenyl, naphthalene, phenanthrene and the like.

When R31 and R32 are a heterocyclic group, it is preferably a C2-C30 heterocyclic group, and more preferably a C2-C24 heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When R31 and R32 are a fused ring group, it is preferably a fused ring group of an C3-C30 aliphatic ring and an C6-C30 aromatic ring, and more preferably a fused ring group of an C3-C24 aliphatic ring and an C6-C24 aromatic ring.

When R31 and R32 are an alkyl group, it is preferably a C1-C30 alkyl group, and more preferably a C1-C24 alkyl group.

When R31 and R32 are an alkoxyl group, it is preferably a C1-C24 alkoxyl group.

When R31 and R32 are an aryloxy group, it is preferably a C6-C24 aryloxy group.

L" is each independently selected from the group consisting of single bond; a C6-C60 arylene group; a fluorenylene group; a fused ring group of a C3-C60 aliphatic ring and a C6-C60 aromatic ring; a C2-C60 heterocyclic group including at least one heteroatom of O, N, S, Si or P;

When L" is an arylene group, it is preferably an C6-C30 arylene group, more preferably an C6-C25 arylene group, for example, it may be phenylene, biphenylene, naphthylene, terphenylene, anthracenylene, and the like.

When L" is a fused ring group, it is preferably a fused ring group of an C3-C30 aliphatic ring and an C6-C30 aromatic ring, and more preferably a fused ring group of an C3-C24 aliphatic ring and an C6-C24 aromatic ring.

When L" is a heterocyclic group, it is preferably a C2-C30 heterocyclic group, and more preferably a C2-C24 heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

R51, R52 and R53 are each independently selected from the group consisting of a C6-C60 aryl group; fluorenyl group; a C2-C60 heterocyclic group including at least one heteroatom of O, N, S, Si or P; a fused ring group of a C3-C60 aliphatic ring and a C6-C60 aromatic ring; a C1-C60 alkyl group; a C2-C60 alkenyl group; a C2-C60 alkynyl group; a C1-C60 alkoxy group; and a C6-C60 aryloxy group; or R51 and R52 may be bonded to each other to form a ring;

When R51, R52 and R53 are an aryl group, it is preferably an C6-C30 aryl group, more preferably an C6-C25 aryl group, for example, it may be phenyl, biphenyl, terphenyl, naphthalene, phenanthrene and the like.

When R51, R52 and R53 are a heterocyclic group, it is preferably a C2-C30 heterocyclic group, and more preferably a C2-C24 heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When R51, R52 and R53 are a fused ring group, it is preferably a fused ring group of an C3-C30 aliphatic ring and an C6-C30 aromatic ring, and more preferably a fused ring group of an C3-C24 aliphatic ring and an C6-C24 aromatic ring.

When R51, R52 and R53 are an alkyl group, it is preferably a C1-C30 alkyl group, and more preferably a C1-C24 alkyl group.

When R51, R52 and R53 are an alkenyl group, it is preferably a C2-C30 alkenyl group, and more preferably a C2-C24 alkenyl group.

When R51, R52 and R53 are an alkynyl group, it is preferably a C2-C30 alkynyl group, and more preferably a C2-C24 alkynyl group.

When R51, R52 and R53 are an alkoxyl group, it is preferably a C1-C24 alkoxyl group.

When R51, R52 and R53 are an aryloxy group, it is preferably a C6-C24 aryloxy group.

Rf and Rg are each independently selected from the group consisting of a C6-C60 aryl group; fluorenyl group; a C2-C60 heterocyclic group including at least one heteroatom of O, N, S, Si or P; and a C3-C60 aliphatic ring;

When Rf and Rg are an aryl group, it is preferably an C6-C30 aryl group, more preferably an C6-C25 aryl group, for example, it may be phenyl, biphenyl, terphenyl, naphthalene, phenanthrene and the like.

When Rf and Rg are a heterocyclic group, it is preferably a C2-C30 heterocyclic group, and more preferably a C2-C24 heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When Rf and Rg are an aliphatic ring, it is preferably a C3-C30 aliphatic groups, more preferably C3-C24 aliphatic groups.

ba and bb are each independently integers from 0 to 4, wherein the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; silane group; siloxane group; boron group; germanium group; cyano group; nitro group; C1-C20 alkylthio group; C1-C20 alkoxy group; C1-C20 alkyl group; C2-C20 alkenyl group; C2-C20 alkynyl group; C6-C20 aryl group; C6-C20 aryl group substituted with deuterium; a fluorenyl group; C2-C20 heterocyclic group; C3-C20 cycloalkyl group; C7-C20 arylalkyl group; and C8-C20 arylalkenyl group; also the substituents may be bonded to each other to form a saturated or unsaturated ring, wherein the term 'ring' means a C3-C60 aliphatic ring or a C6-C60 aromatic ring or a C2-C60 heterocyclic group or a fused ring formed by the combination thereof.

Also, Ar1 and Ar2 are represented by any one of Formulas (A-1) to (A-11).

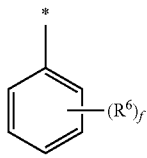

Formula (A-1)

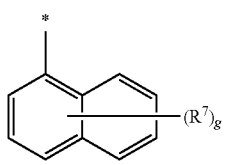

Formula (A-2)

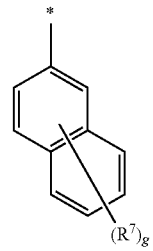

Formula (A-3)

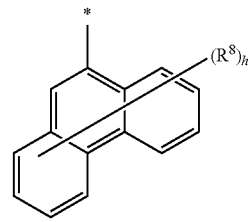

Formula (A-4)

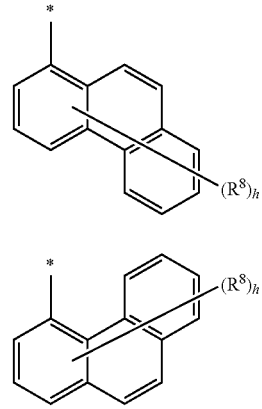

Formula (A-5)

Formula (A-6)

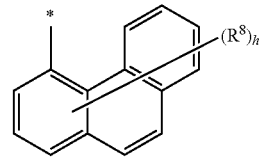

Formula (A-7)

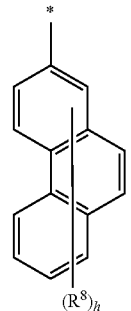

Formula (A-8)

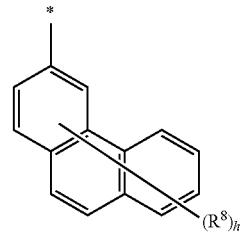

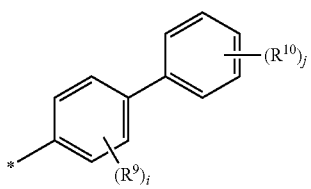
Formula (A-9)

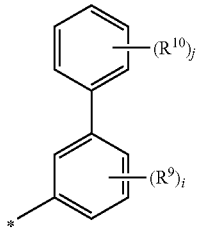
Formula (A-10)

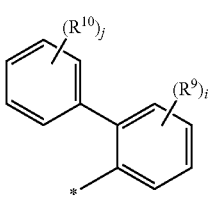
Formula (A-11)

Wherein,
1) R6, R7, R8, R9 and R10 are the same or different from each other, and each independently represent hydrogen; deuterium; C6-C20 aryl group; C6-C20 aryl group substituted with deuterium;
2) f and j are independently an integer of 0 to 5, g is an integer of 0 to 7, h is an integer of 0 to 9, i is an integer of 0 to 4,
3) * means the position to be bonded.

Also, Formula 1-1 is represented by any one of Formula Q-1 to Formula Q-5.

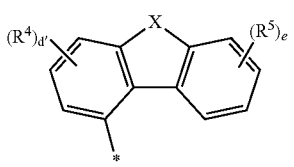
Formula Q-1

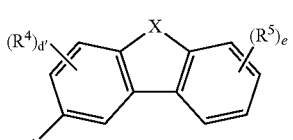
Formula Q-2

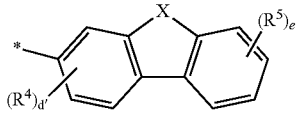
Formula Q-3

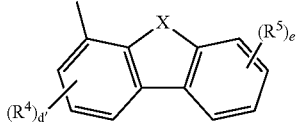
Formula Q-4

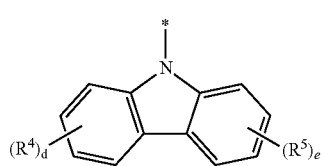
Formula Q-5

Wherein,
X, R4, R5, d, e and * are the same as defined in Formula 1-1,
d' is an integer of 0 to 3.

Preferably, any one of $L^1$ and $L^2$ in Formula 1 is selected from a single bond or any one of Formulas L-1 to L-19.

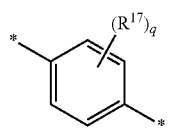
Formula L-1

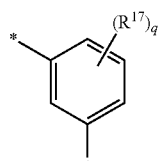
Formula L-2

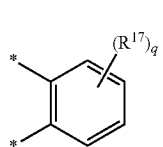
Formula L-3

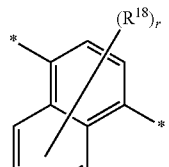
Formula L-4

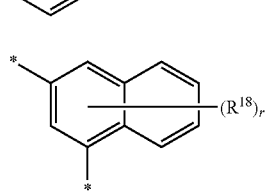
Formula L-5

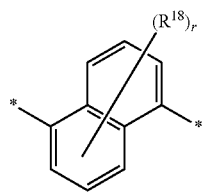
Formula L-6

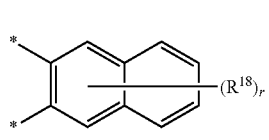
Formula L-7

Formula L-8

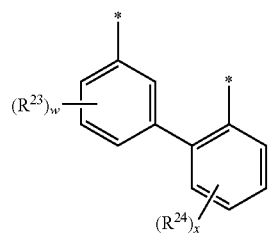

Formula L-17

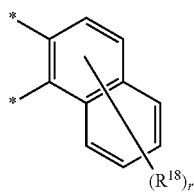

Formula L-9

Formula L-10

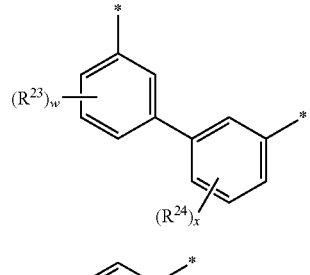

Formula L-18

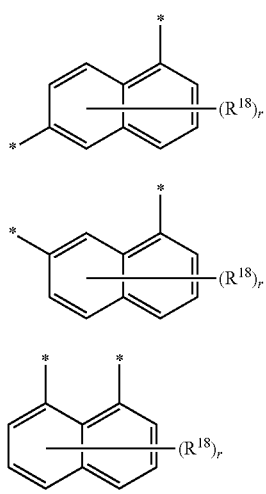

Formula L-11

Formula L-12

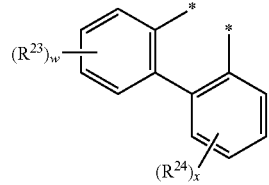

Formula L-19

Formula L-13

Wherein,
1) R17, R18, R19, R20, R21, R22, R23 and R24 are the same as the definition of R1 in Formula 1, or adjacent groups may be bonded to each other to form a ring,
2) p and r are each independently an integer of 0 to 6, q, s u, v, w and x are each independently an integer of 0 to 4, t is an integer of 0 to 2,
3) * means the position to be bonded.

Formula 4 may be represented by any one of Formulas 4-1 to 4-3.

Formula L-14

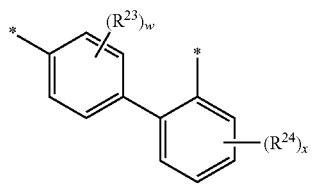

Formula L-15

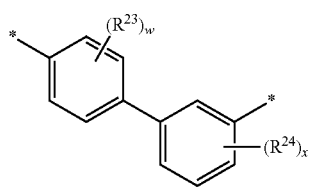

Formula 4-1

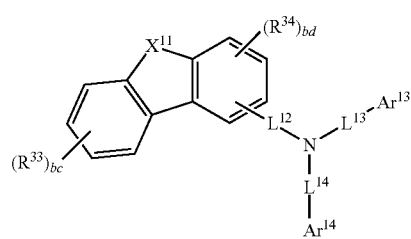

Formula L-16

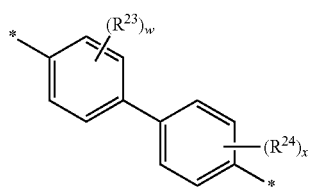

Formula 4-2

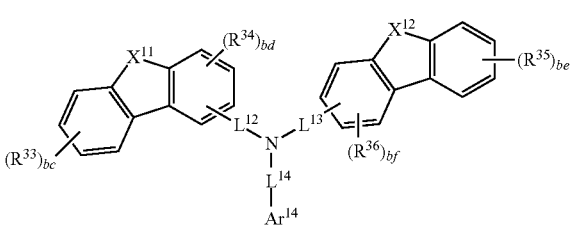

<Formula 4-3>

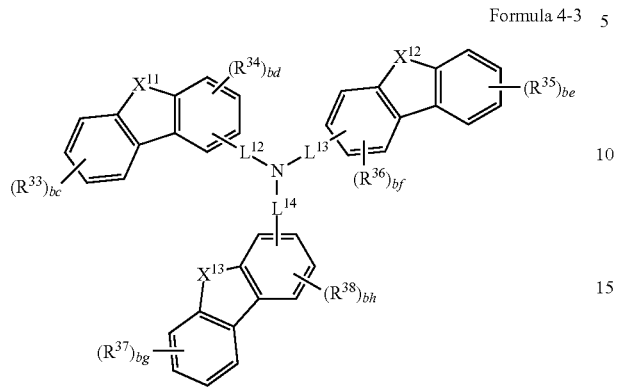

<Formula 5-3>

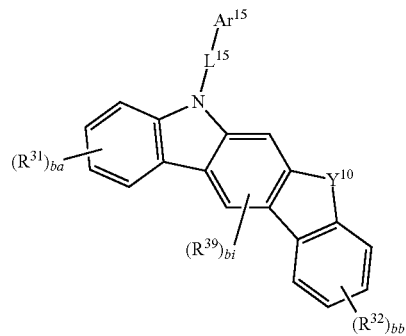

<Formula 5-4>

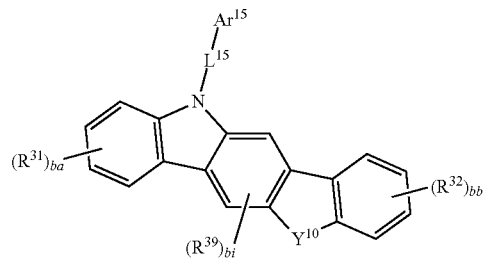

<Formula 5-5>

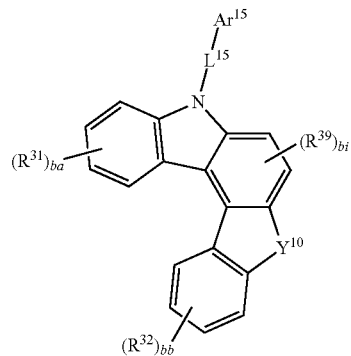

<Formula 5-6>

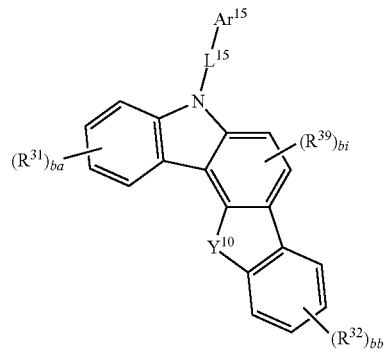

Wherein,

Ar13, Ar14, L12, L13 and L14 are the same as defined in Formula 4,

X11, X12 and X13 are the same as the definition of Y10,

R33, R34, R35, R36, R37 and R38 are the same as the definition of R31, or an adjacent plurality of R33 or a plurality of R34 or a plurality of R35 or a plurality of R36 or a plurality of R37 may be bonded to each other to form a ring, bc, be and bg are each independently an integer of 0 to 4, bd, bf and bh are each independently an integer of 0 to 3.

Formula 5 is represented by any one of Formulas 5-1 to 5-6.

<Formula 5-1>

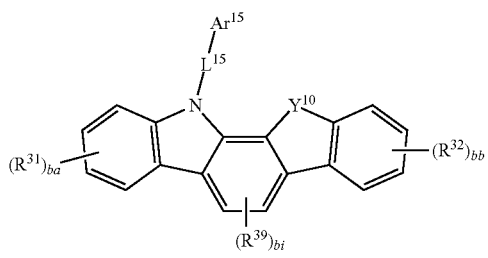

<Formula 5-2>

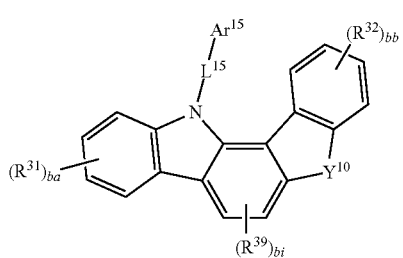

Wherein,

Y10, R31, R32, Ar15, L15, ba and bb are the same as defined in Formula 5,

R39 is the same as the definition of R31, bi is an integer of 0 to 2.

Formula 5 is represented by any one of Formulas 5-7 to 5-9.

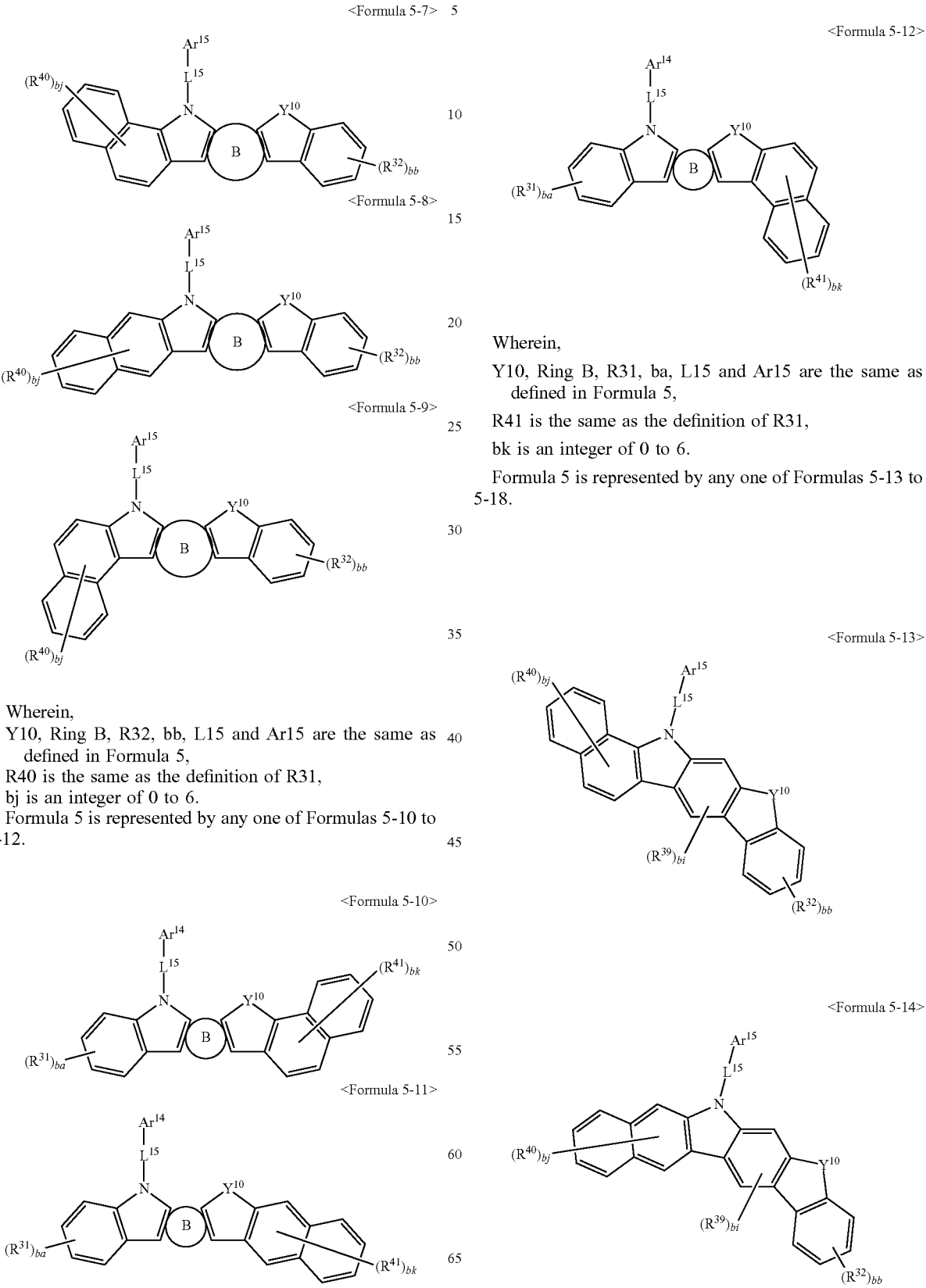

Wherein,
Y10, Ring B, R32, bb, L15 and Ar15 are the same as defined in Formula 5,
R40 is the same as the definition of R31,
bj is an integer of 0 to 6.
Formula 5 is represented by any one of Formulas 5-10 to 5-12.

Wherein,
Y10, Ring B, R31, ba, L15 and Ar15 are the same as defined in Formula 5,
R41 is the same as the definition of R31,
bk is an integer of 0 to 6.
Formula 5 is represented by any one of Formulas 5-13 to 5-18.

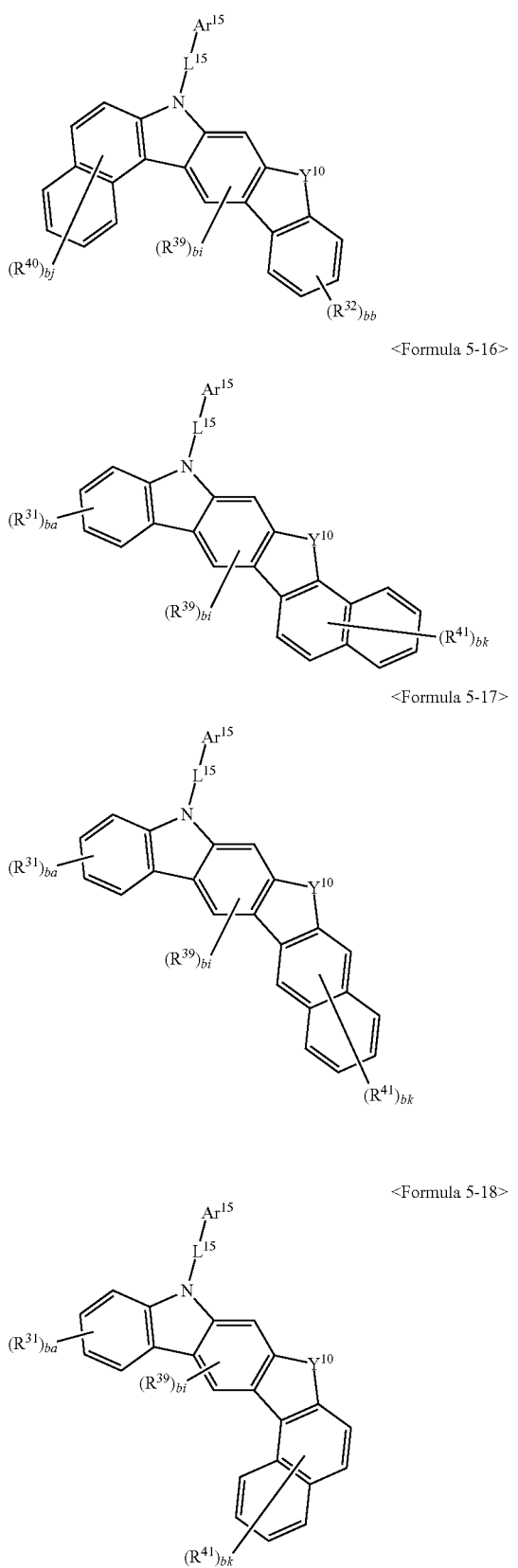

<Formula 5-15>

<Formula 5-16>

<Formula 5-17>

<Formula 5-18>

Wherein,

Y10, R31, R32, ba, bb, L15 and Ar15 are the same as defined in Formula 5,

R39, R40 and R41 are the same as the definition of R31, bi is an integer of 0 to 2, bj and bk are each independently integers from 0 to 6.

Formula 5 is represented by Formula 5-19.

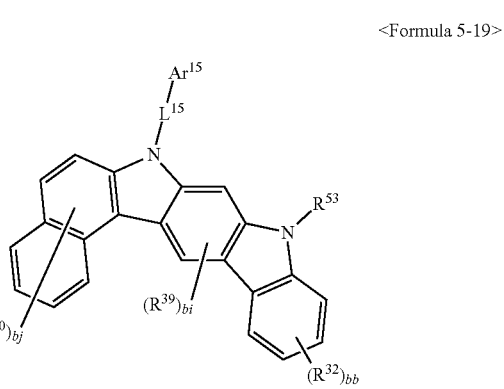

<Formula 5-19>

Wherein,

R32, R53, bb, L15 and Ar15 are the same as defined in Formula 5,

R39 and R40 are the same as the definition of R31, bi is an integer of 0 to 2, bj is each independently integers from 0 to 6.

Also, Formula 1 is represented by any one of the following compounds P-1 to P-104.

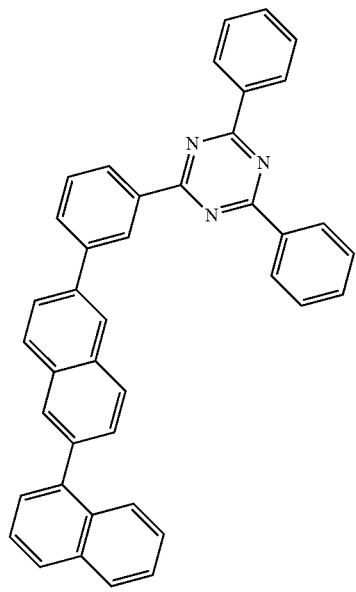

P-1

P-2
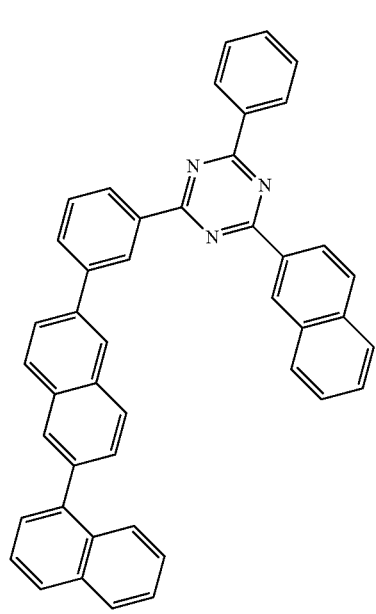
P-4
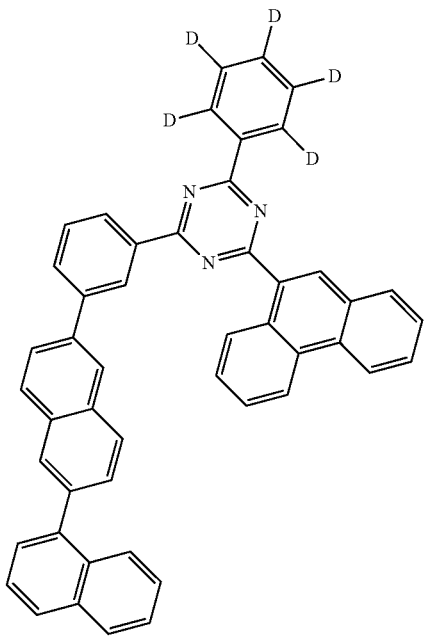
P-3
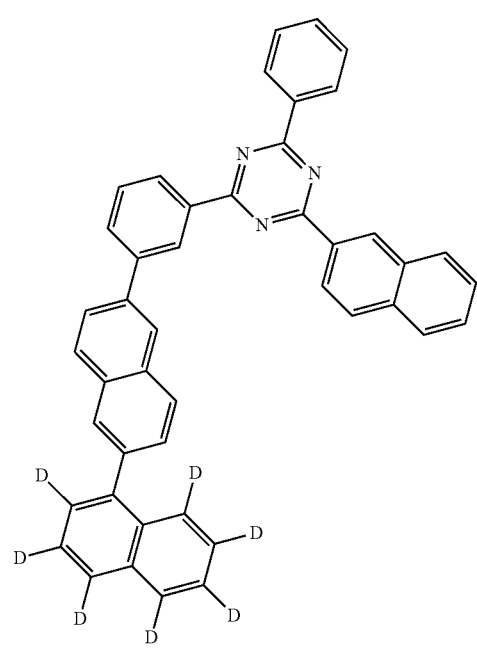
P-5
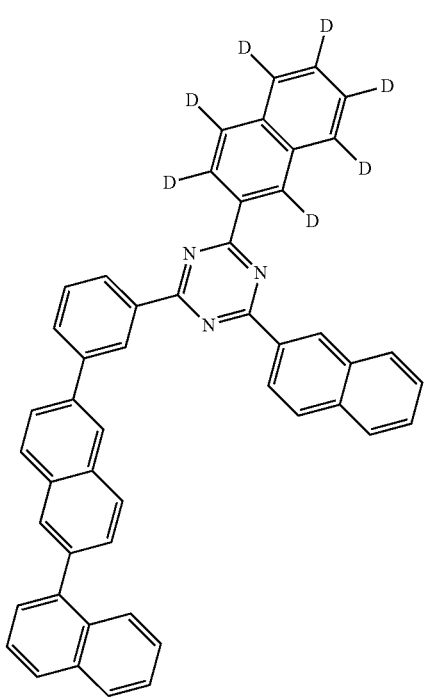

P-6
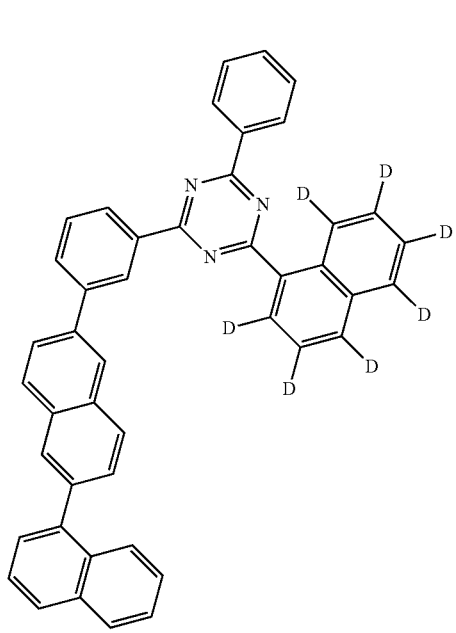
P-8
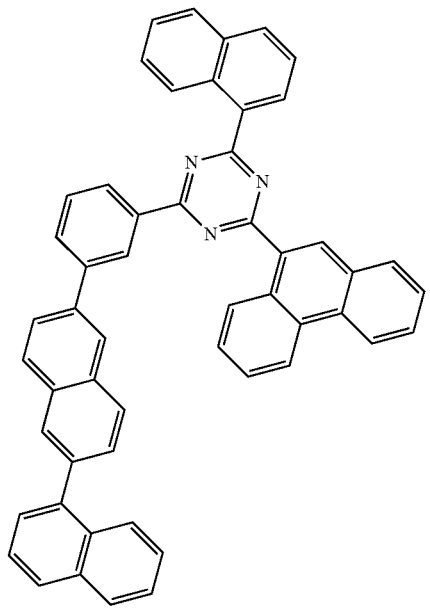
P-7
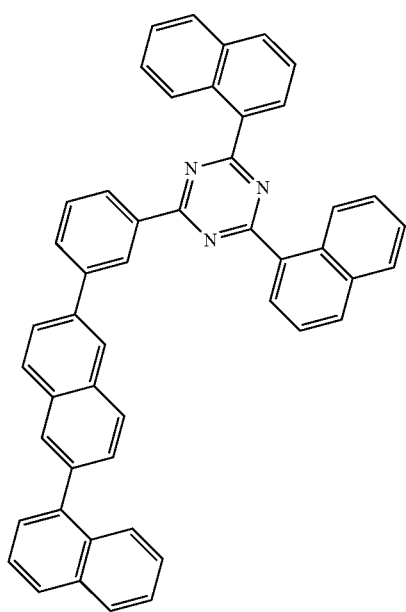
P-9
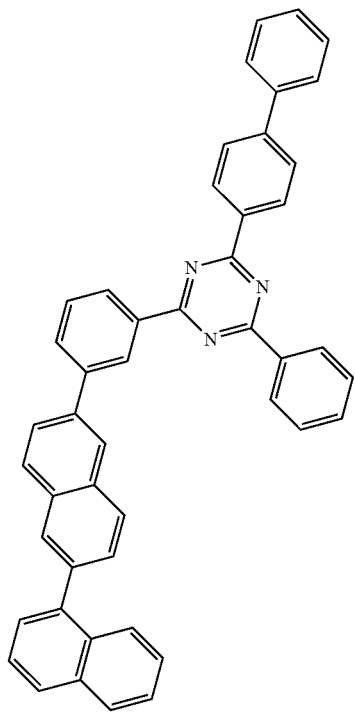

P-10
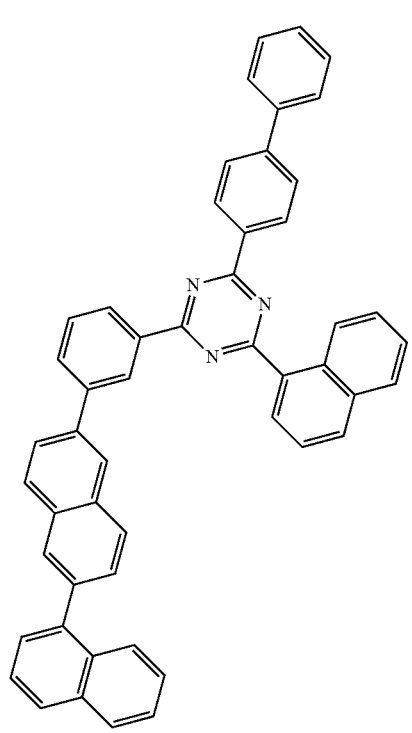
P-11
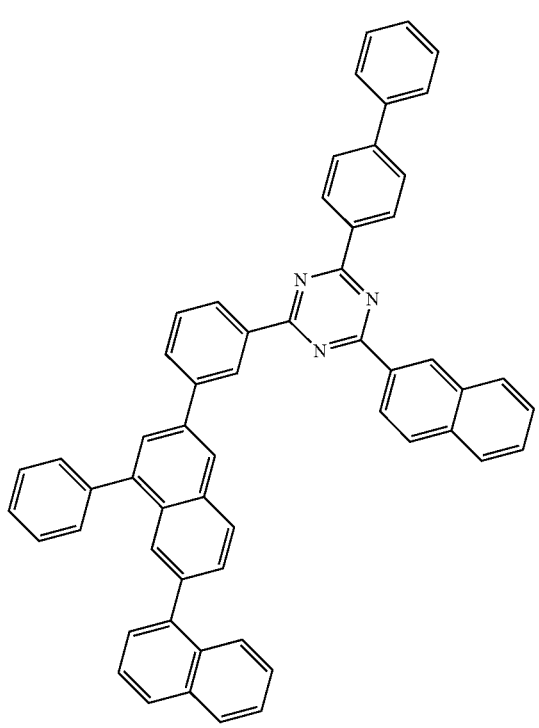
P-12
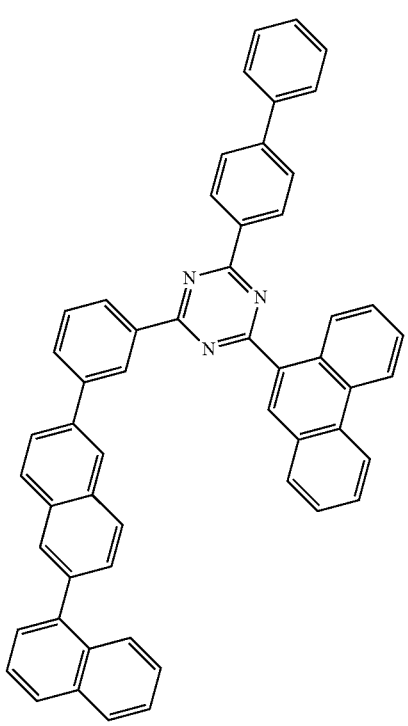
P-13
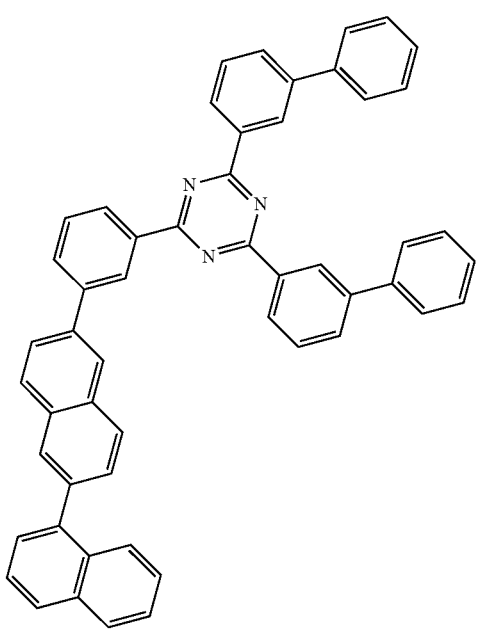

-continued
P-14
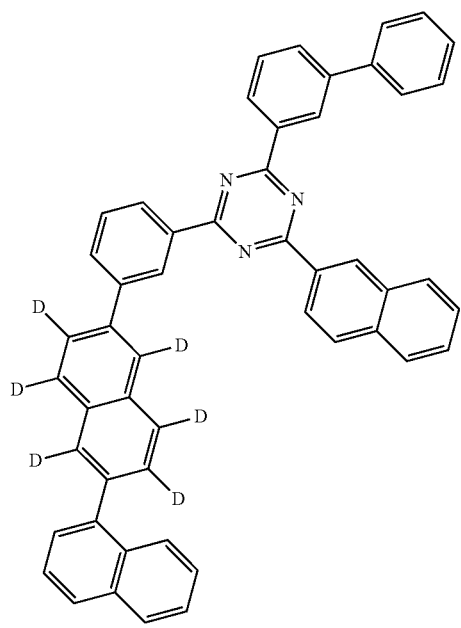
P-15
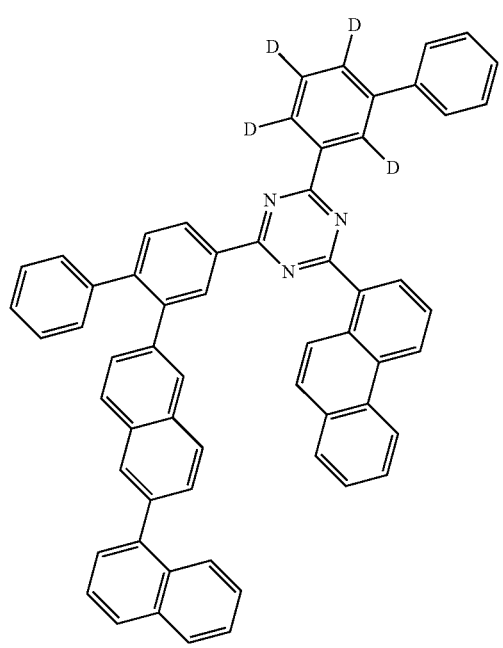
-continued
P-16
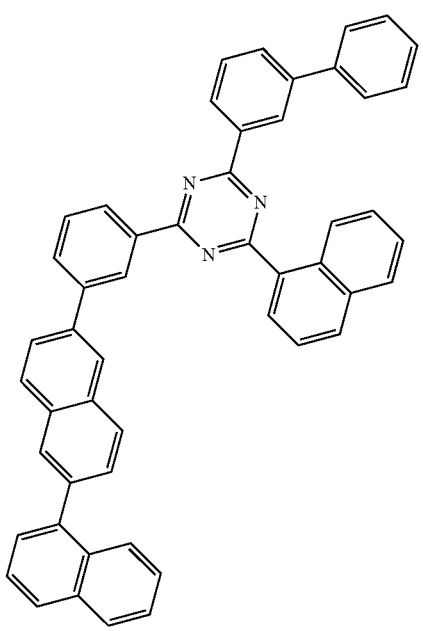
P-17
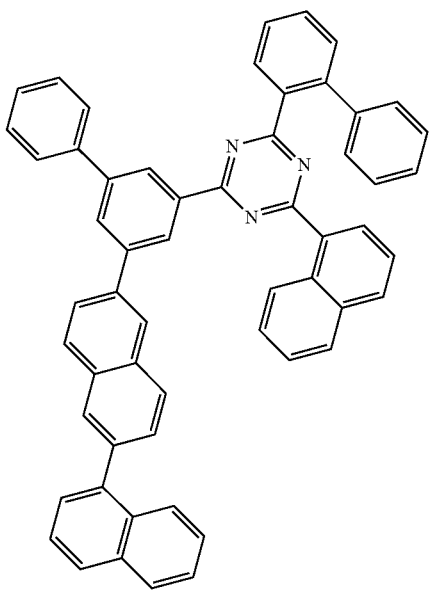

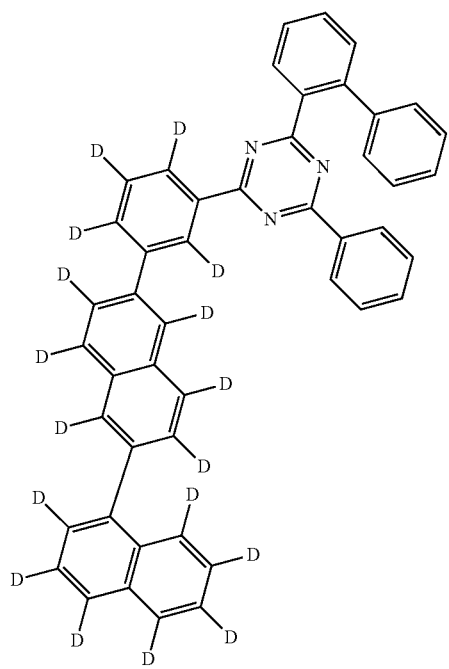

P-22
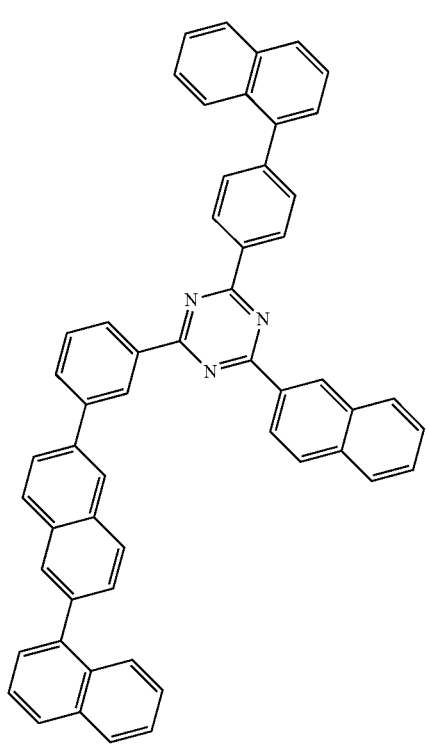
P-23
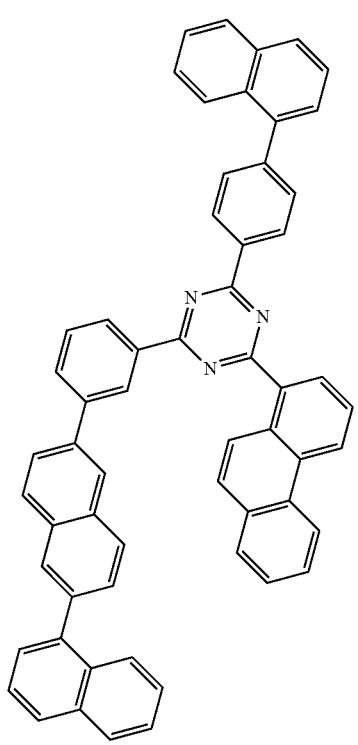
P-24
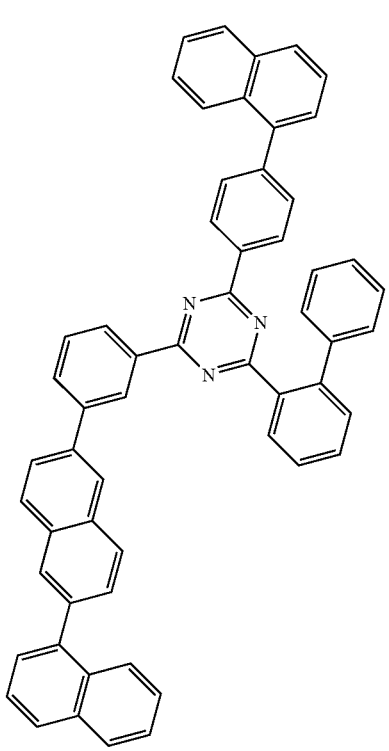
P-25
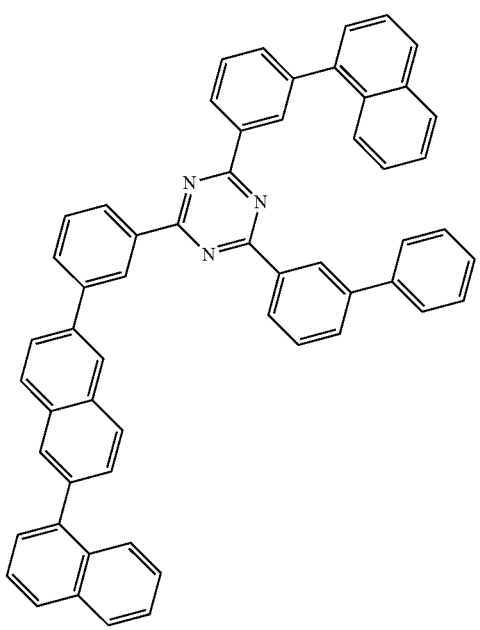

P-26
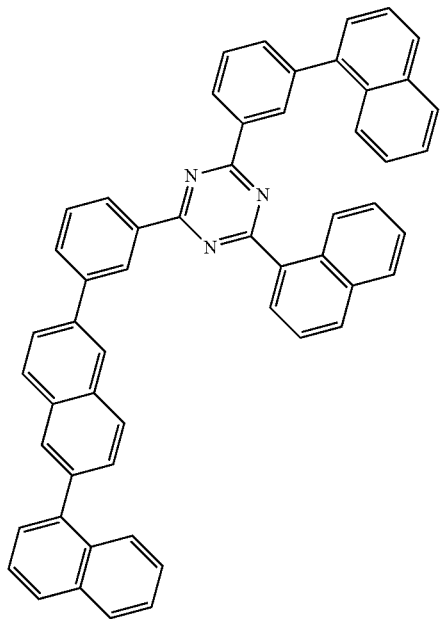
P-27
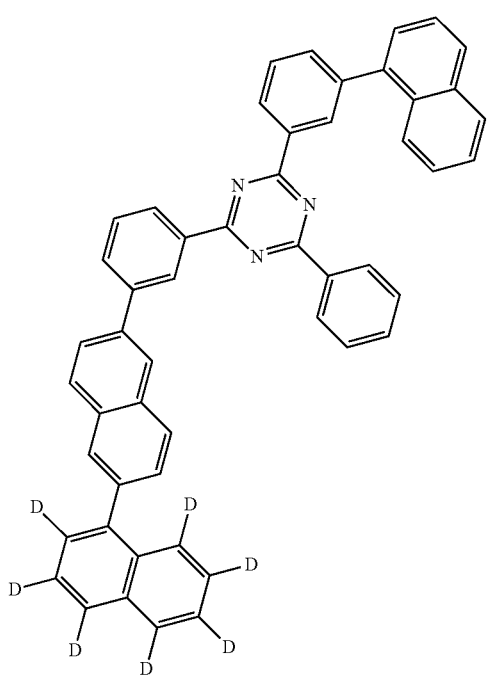
P-28
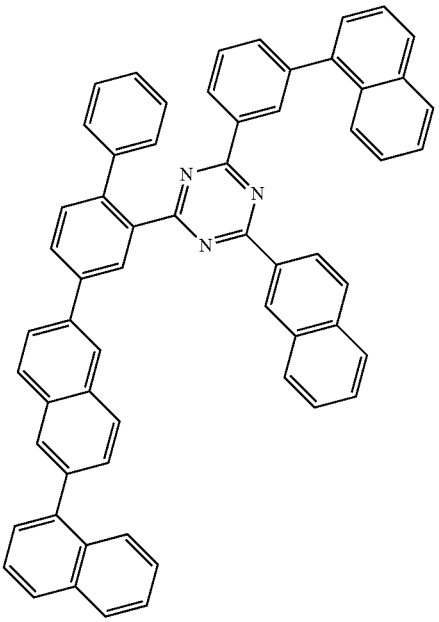
P-29
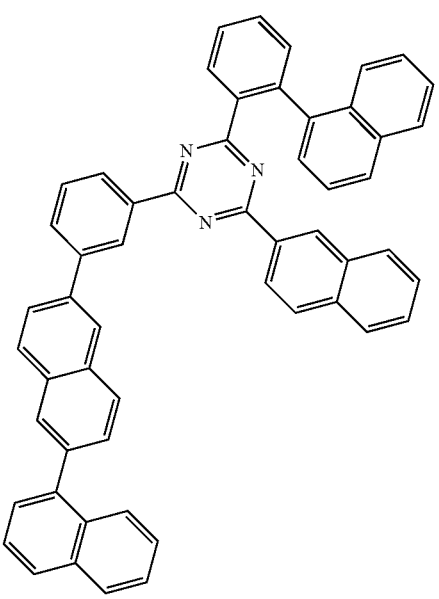

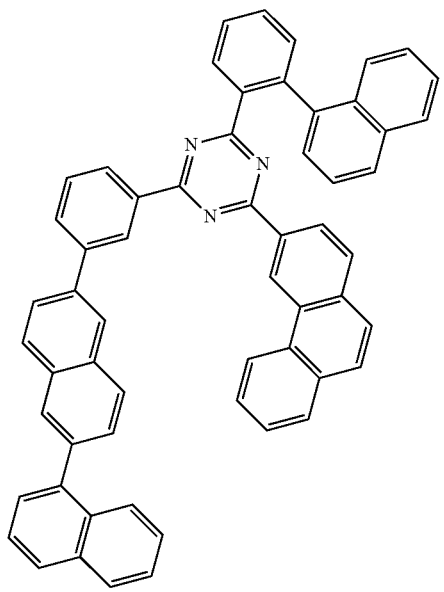
P-30
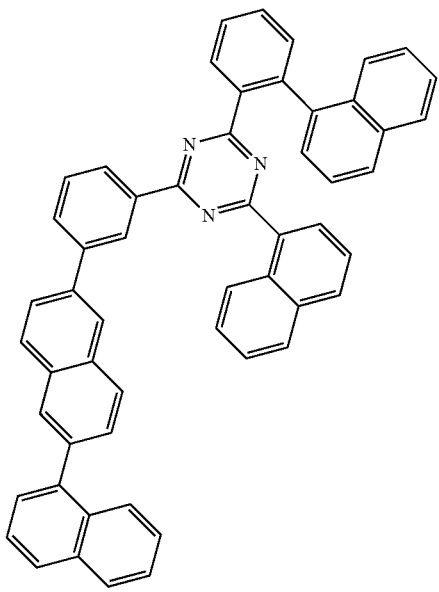
P-32
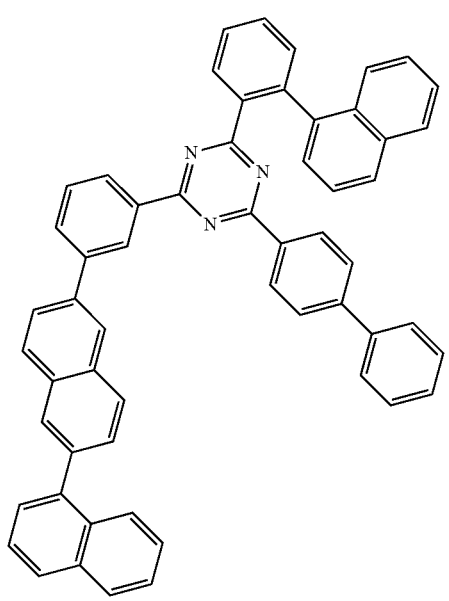
P-31
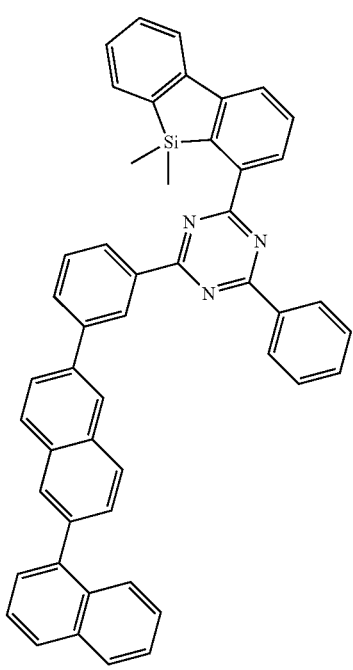
P-33

P-34
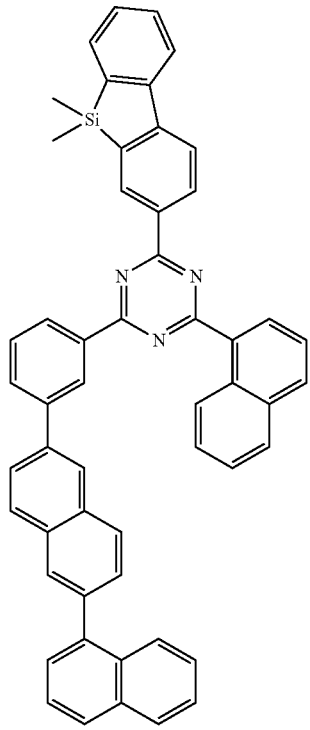
P-36
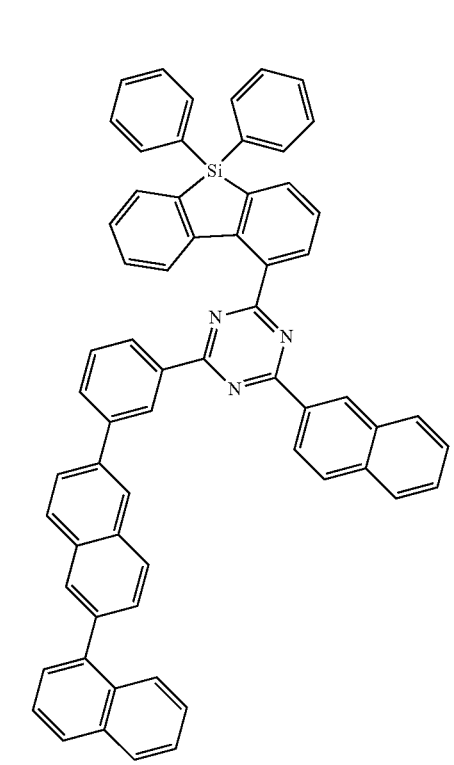
P-35
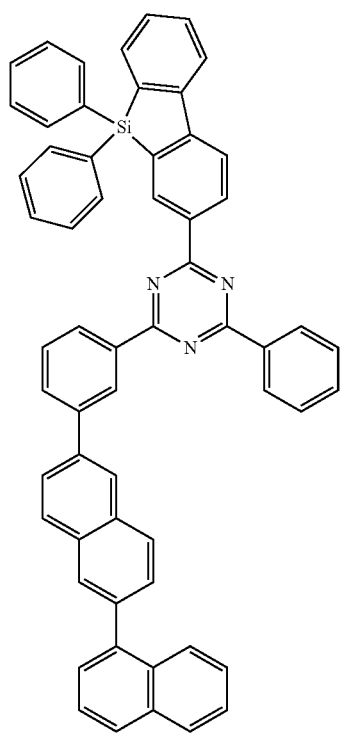
P-37
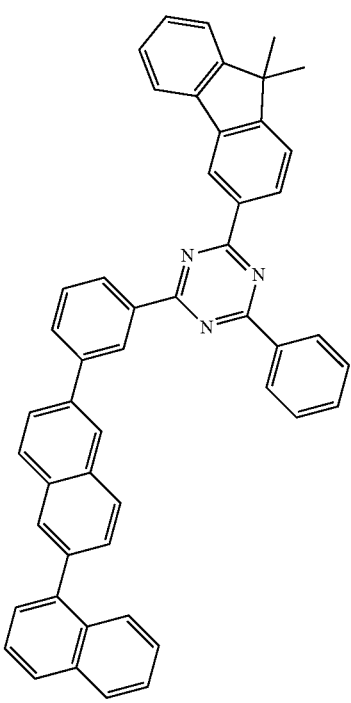

P-38
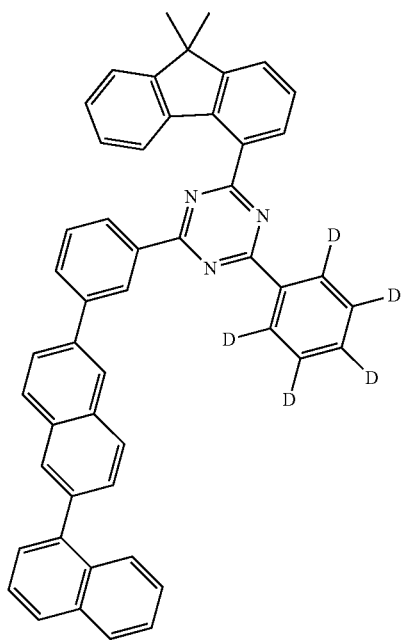
P-39
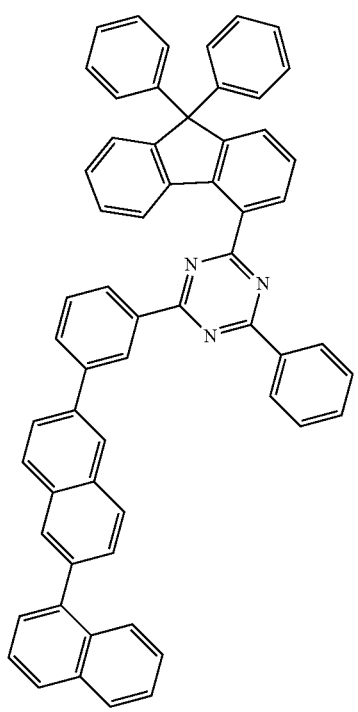
P-40
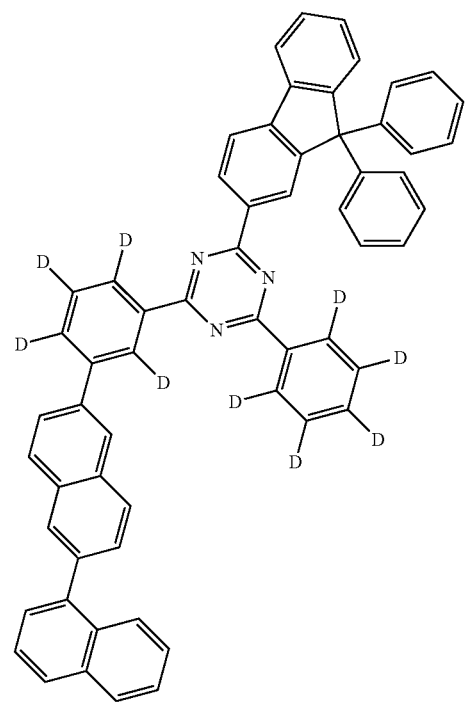
P-41
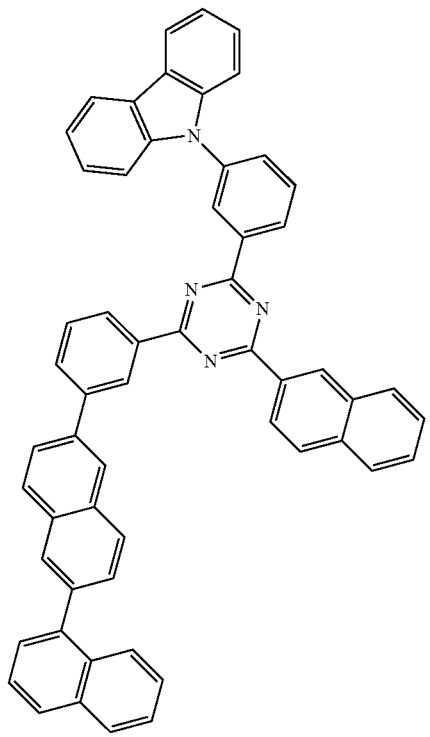

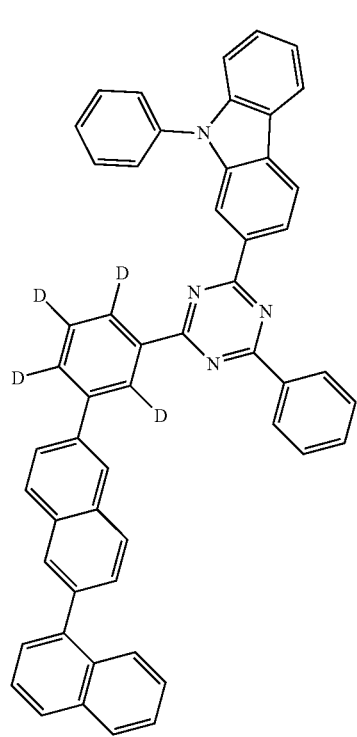
P-42
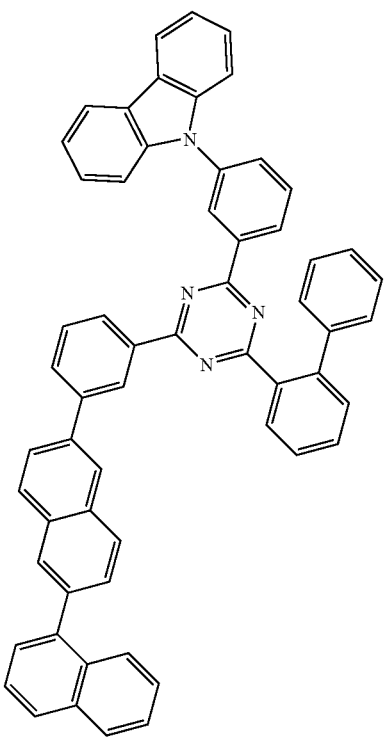
P-44
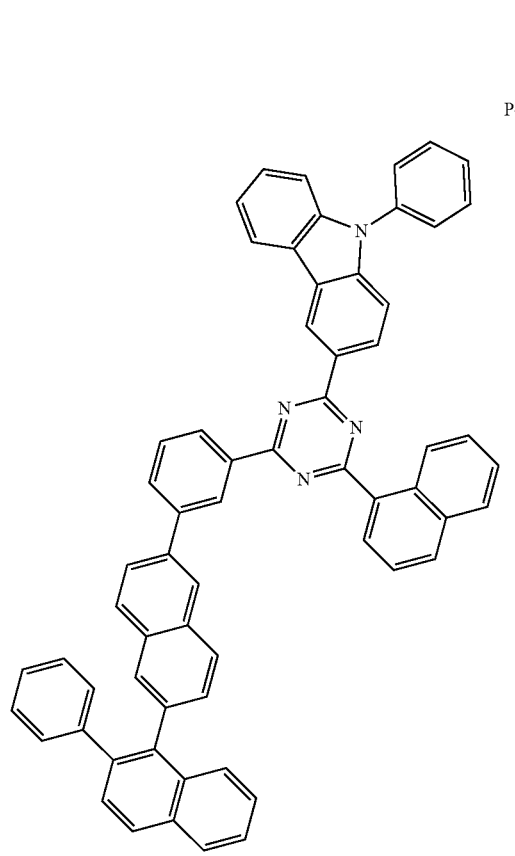
P-43
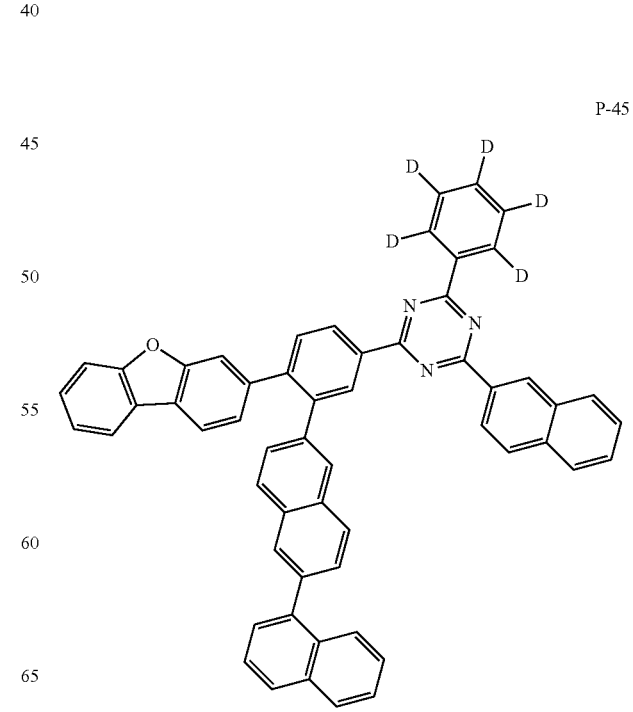
P-45

P-46
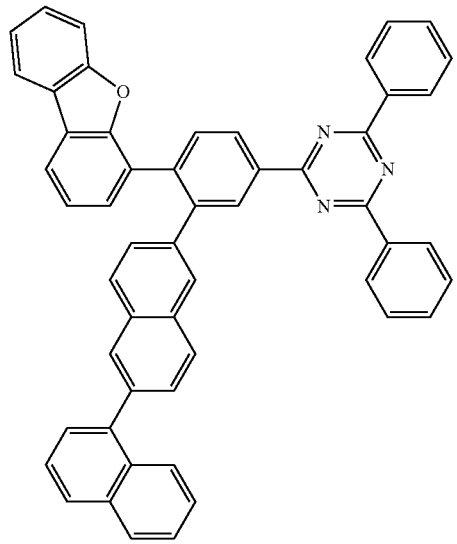
P-47
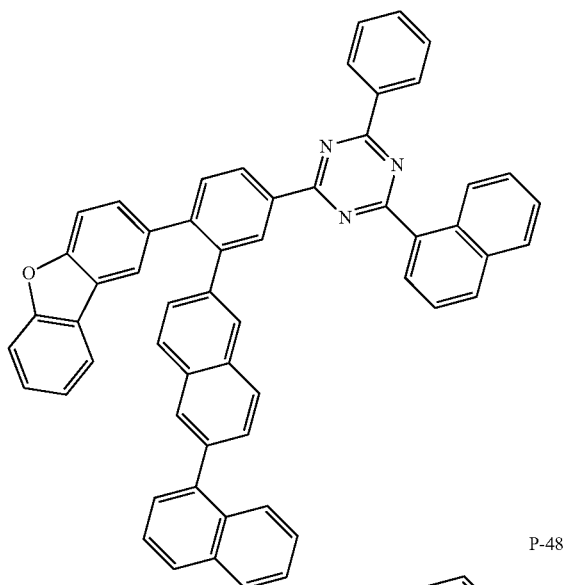
P-48
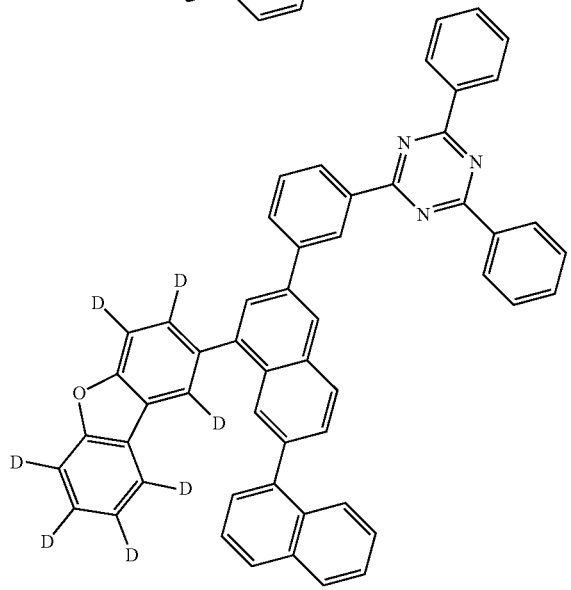
P-49
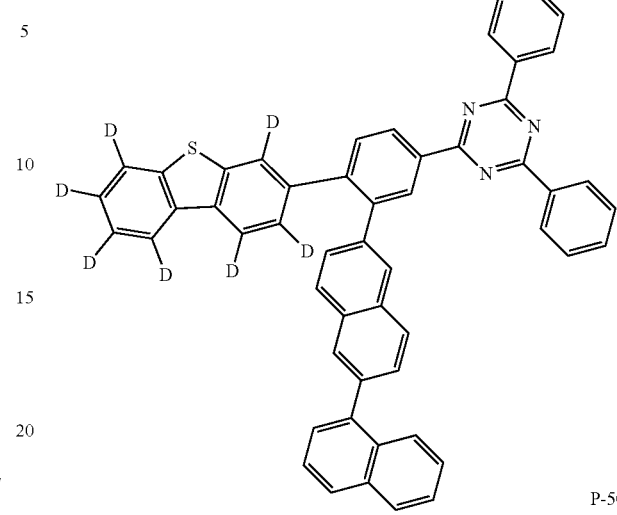
P-50
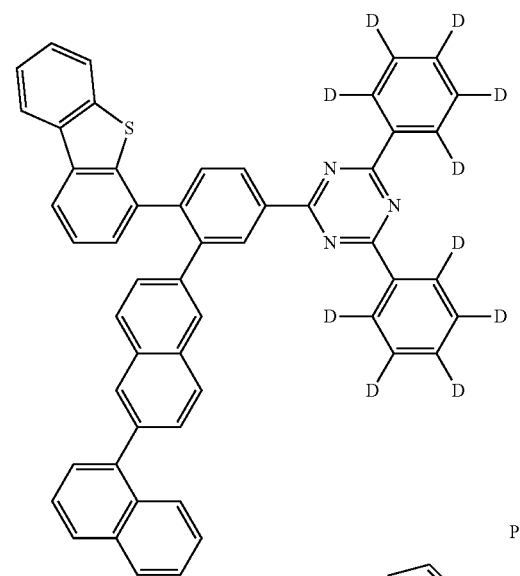
P-51
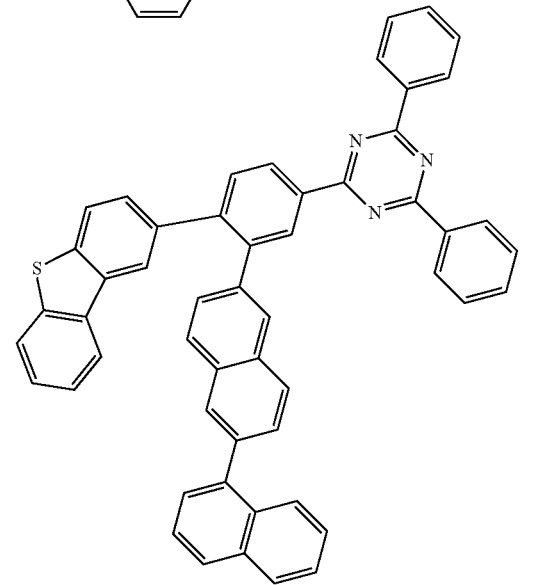

P-52
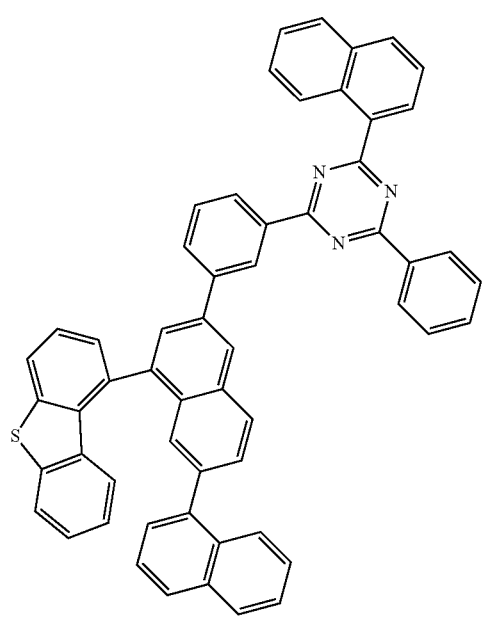
P-54
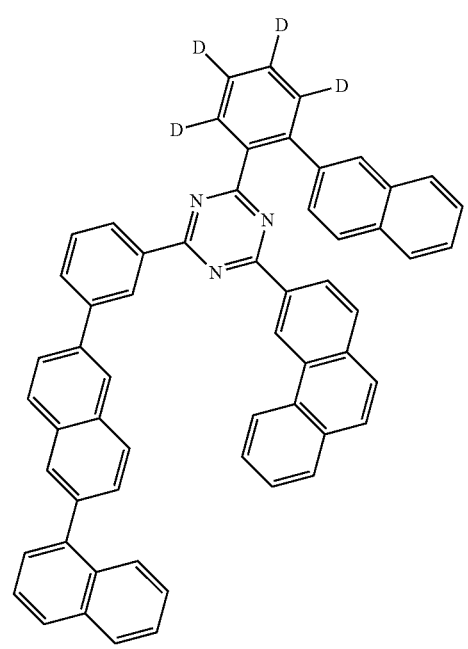
P-53
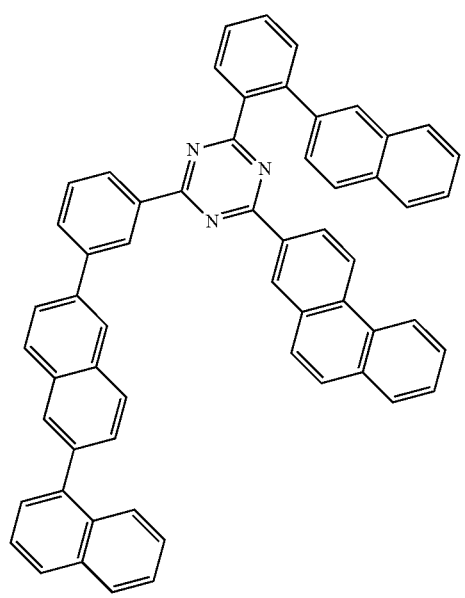
P-55
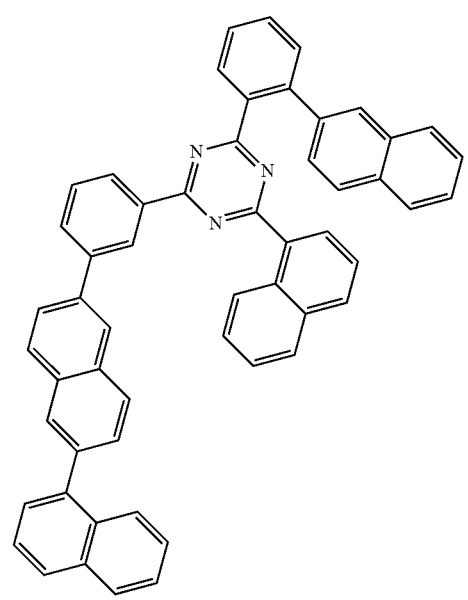

P-56
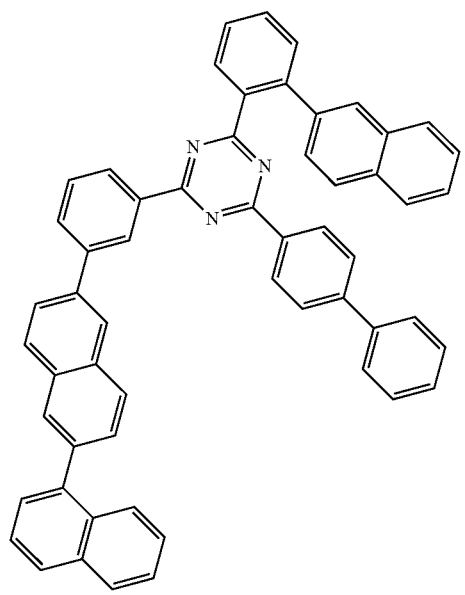
P-58
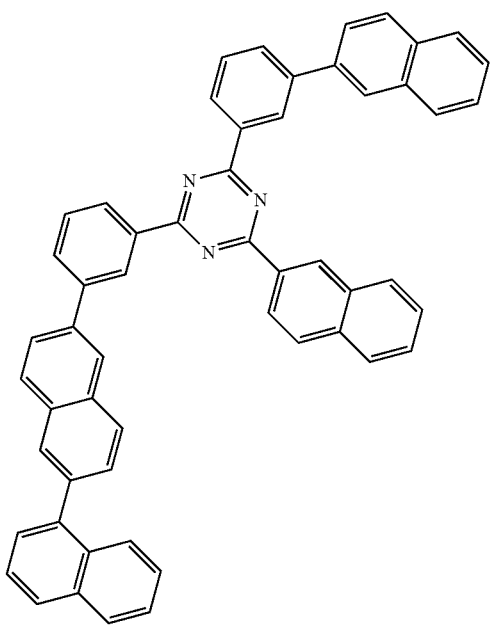
P-57
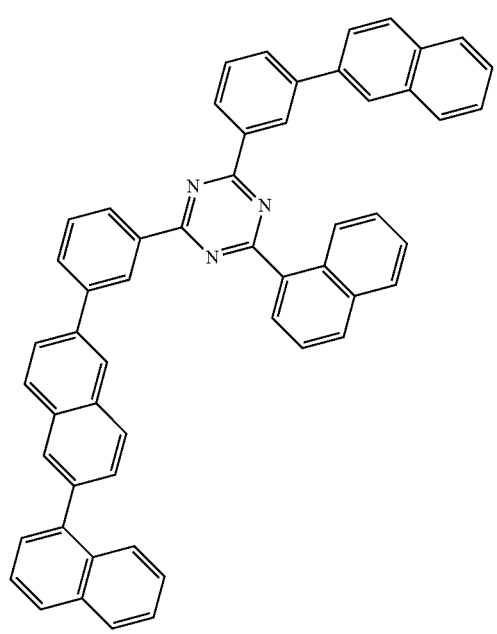
P-59
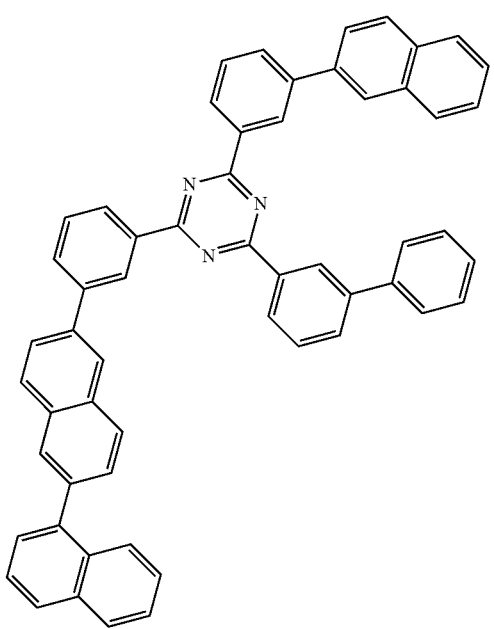

P-60
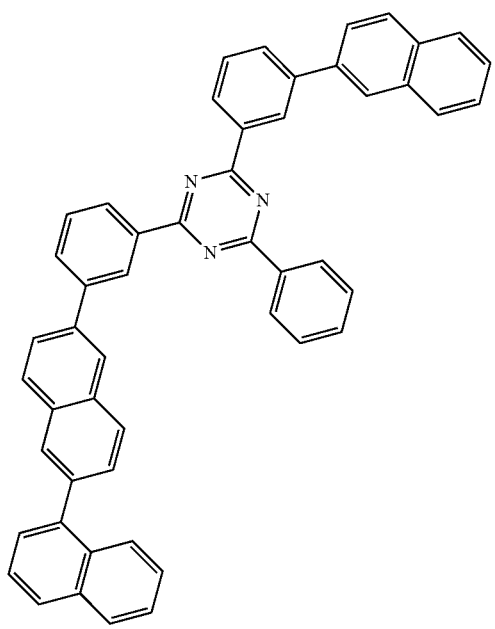
P-61
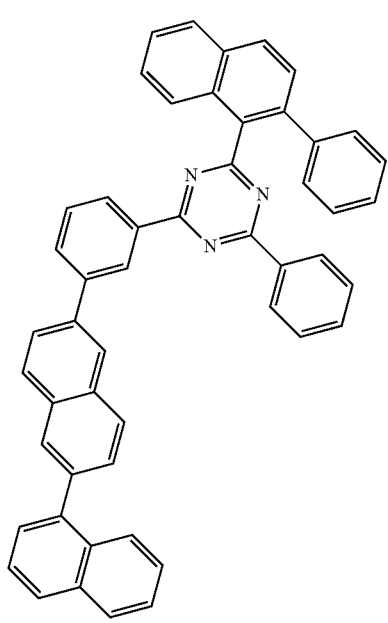
P-62
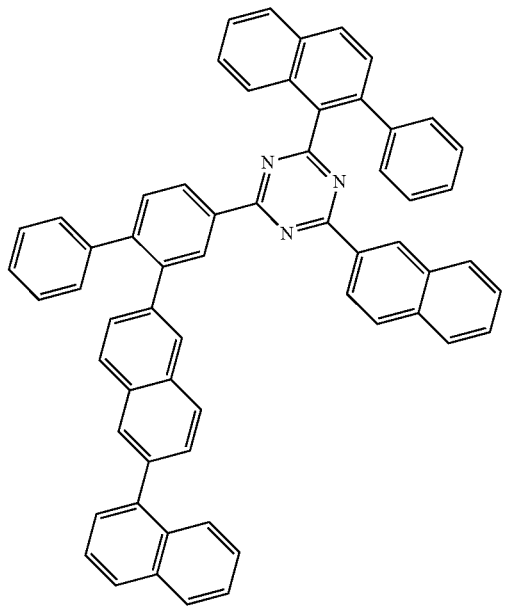
P-63
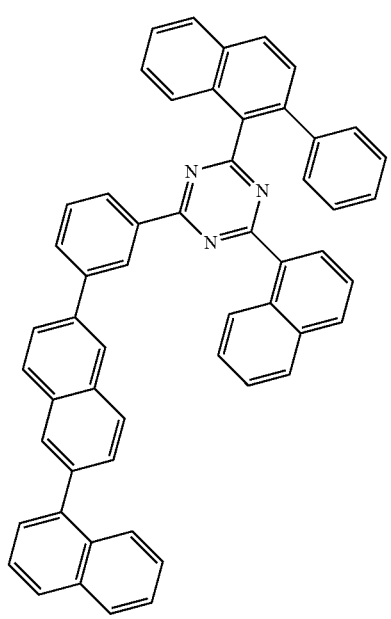

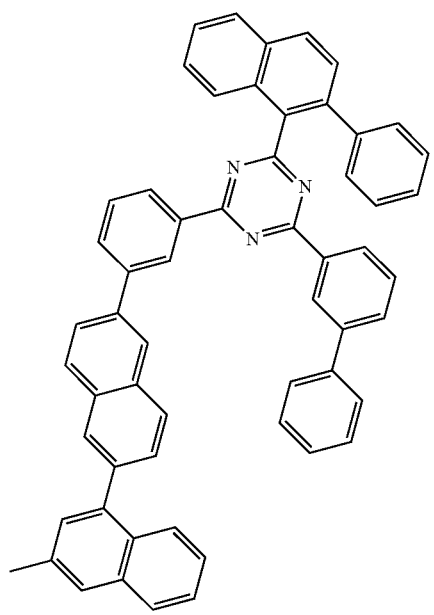
P-64
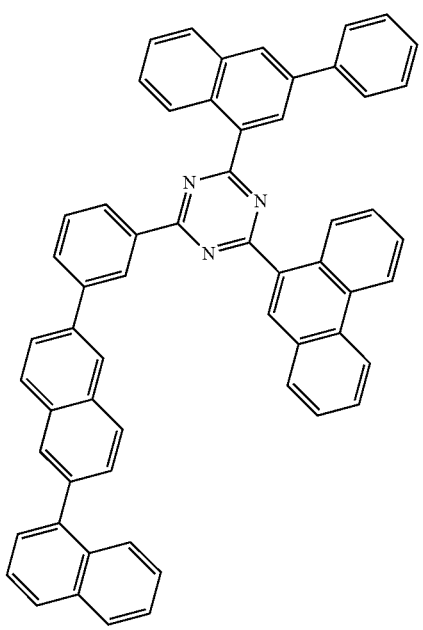
P-66
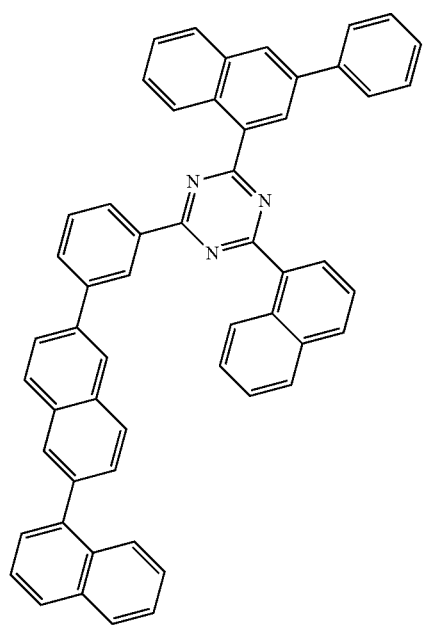
P-65
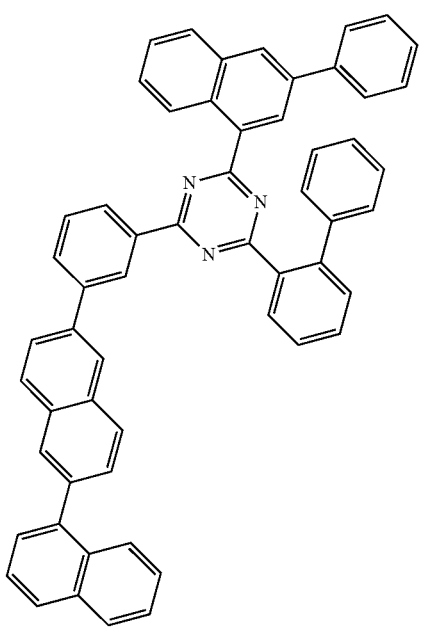
P-67

P-68
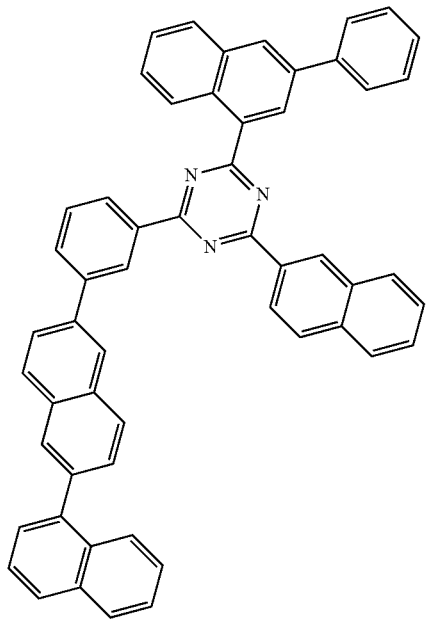
P-69
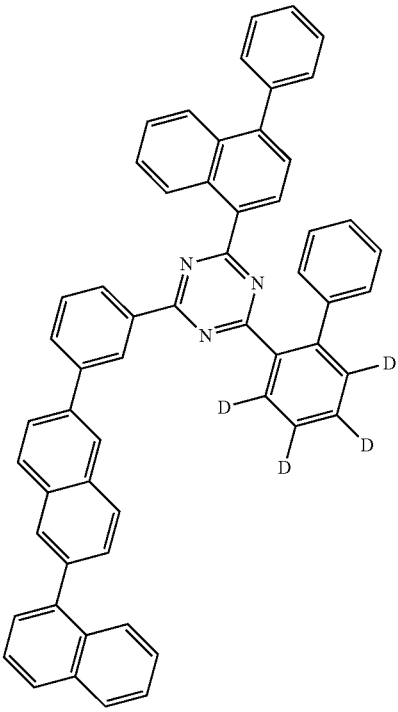
P-70
P-71
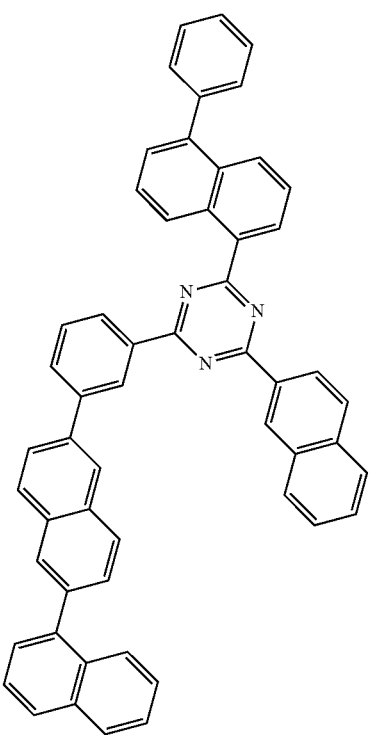

P-72
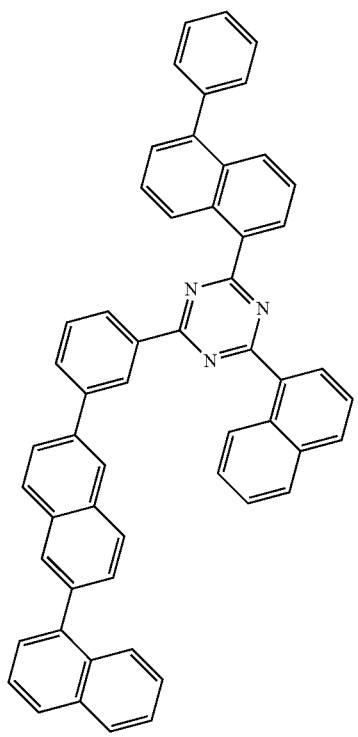
P-73
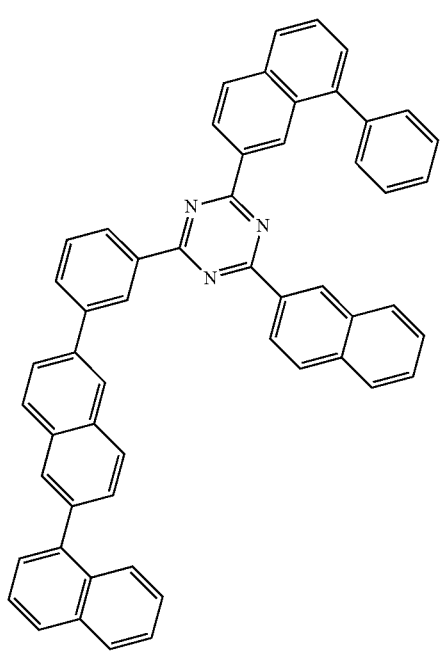
P-74
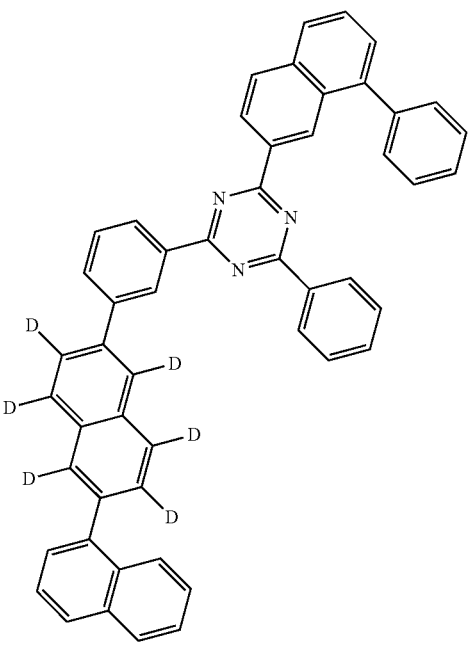
P-75
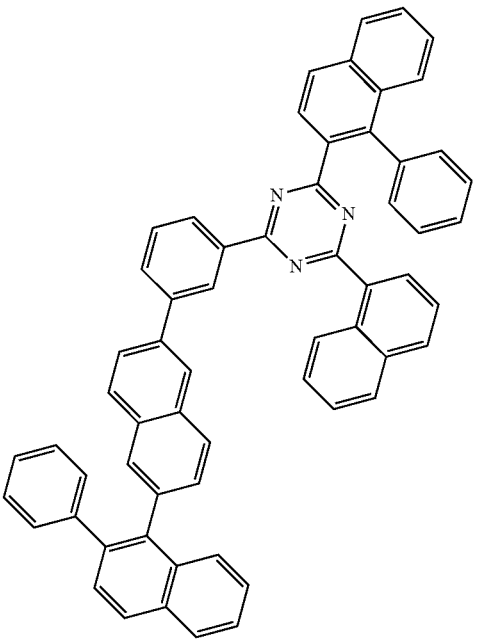

P-76
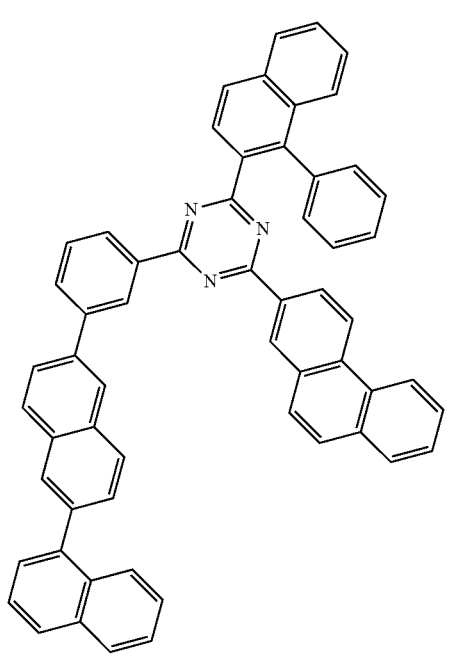
P-78
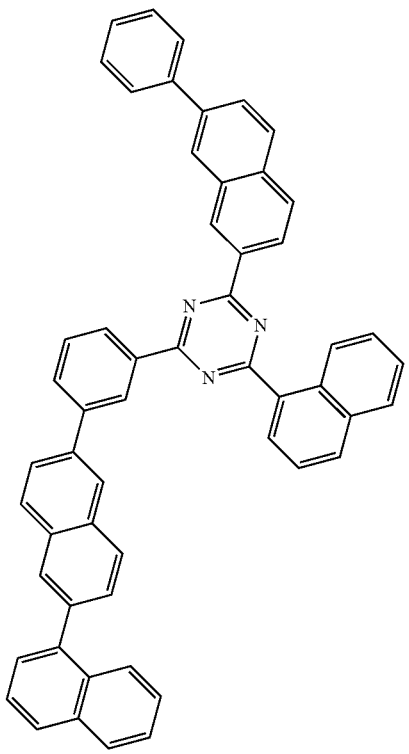
P-77
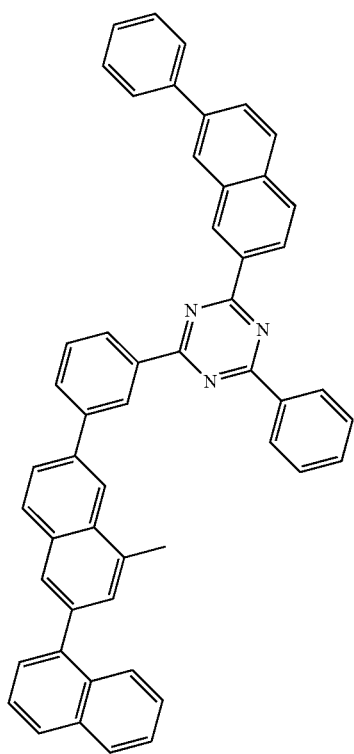
P-79
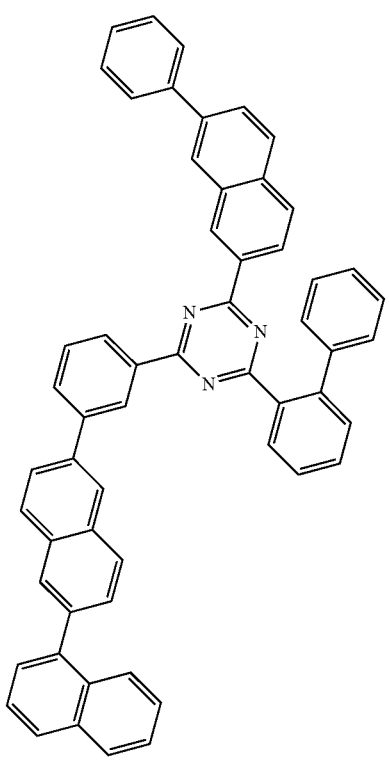

-continued
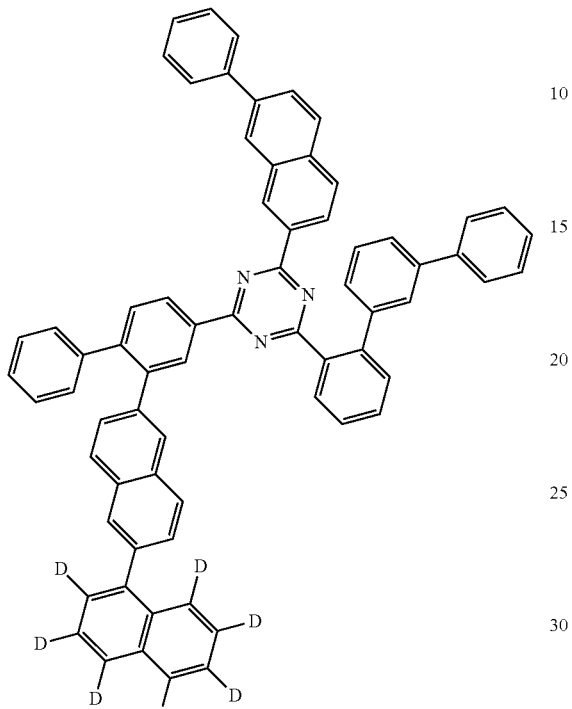
P-80
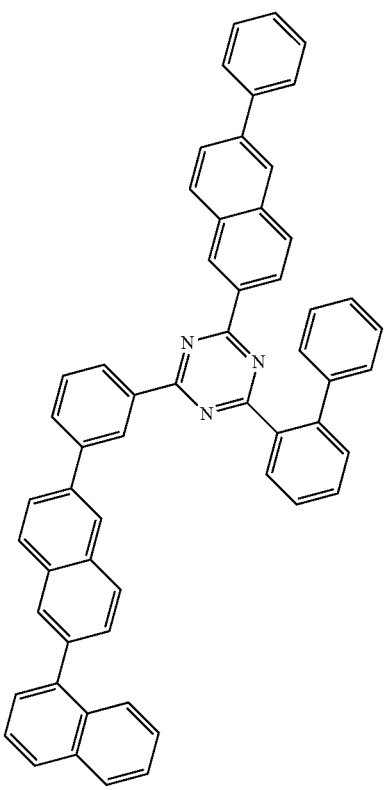
P-82
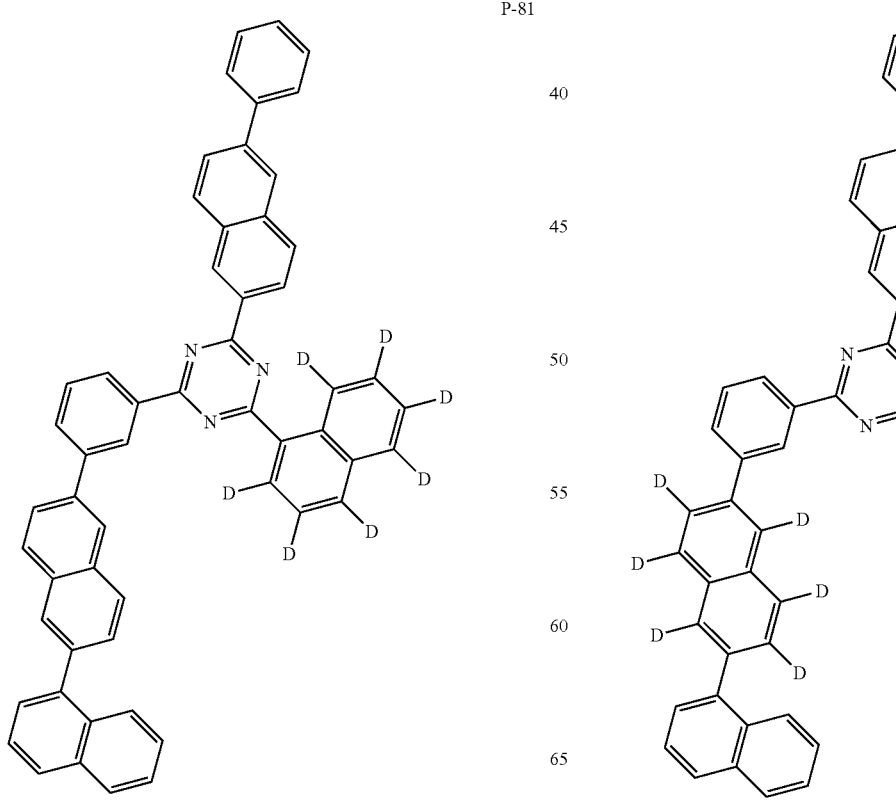
P-81
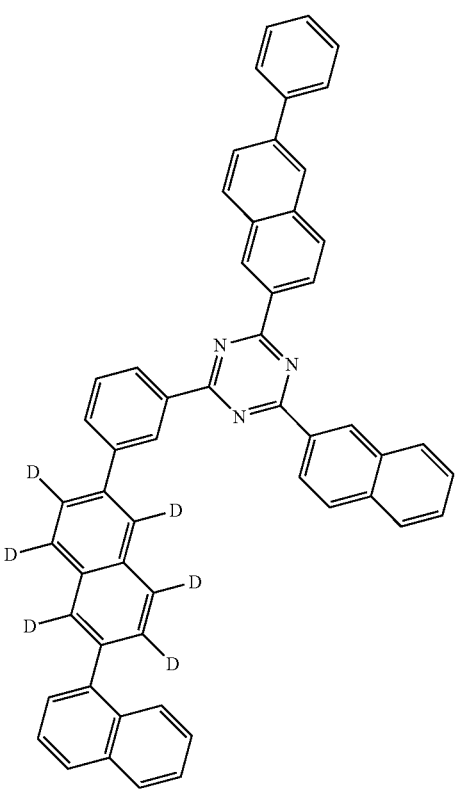
P-83

P-84
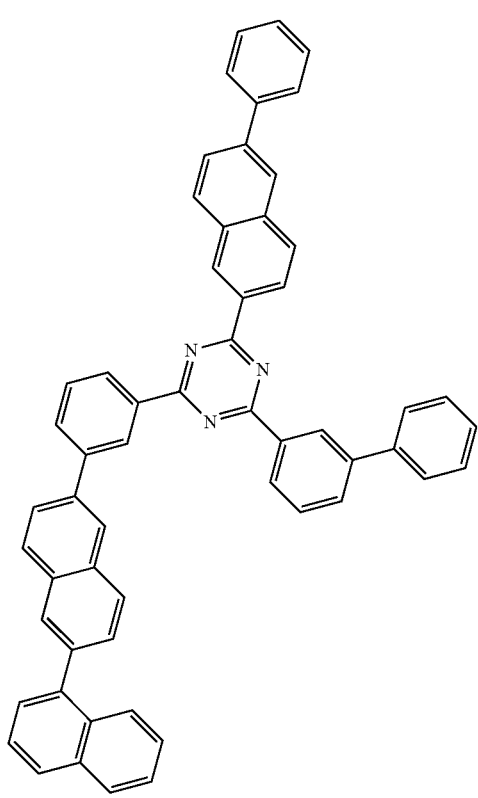
P-85
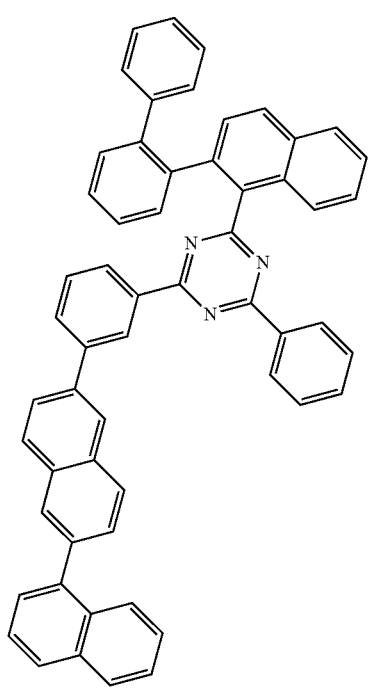
P-86
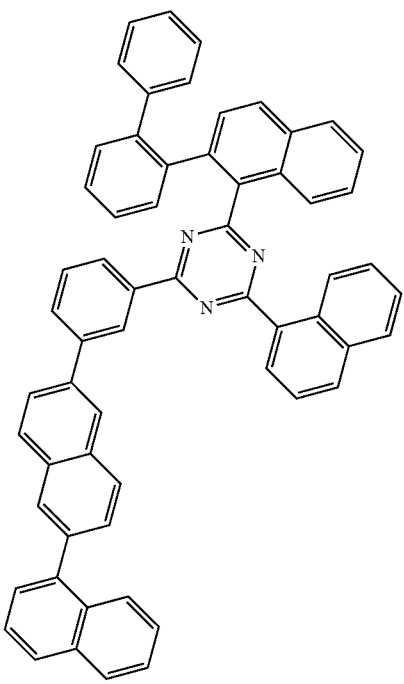
P-87

P-88
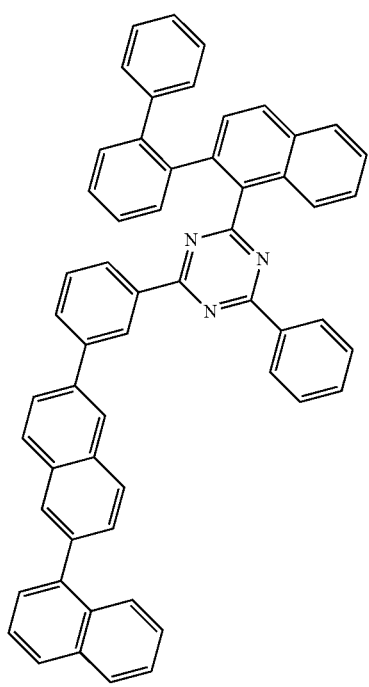
P-89
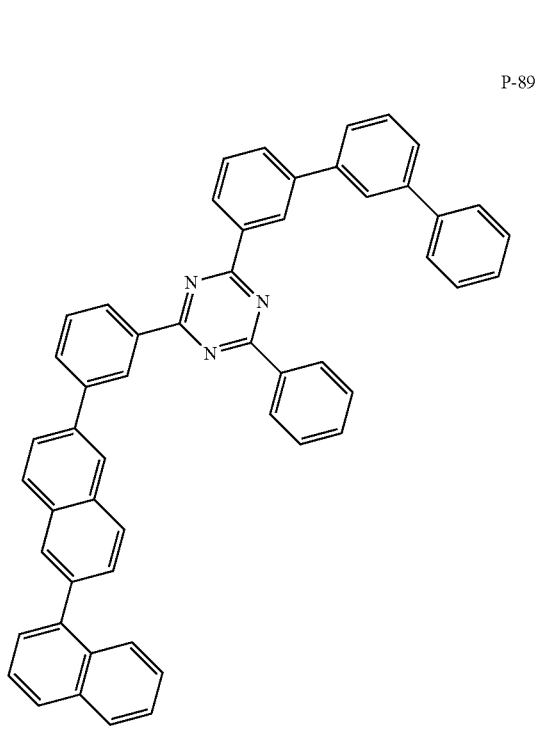
P-90
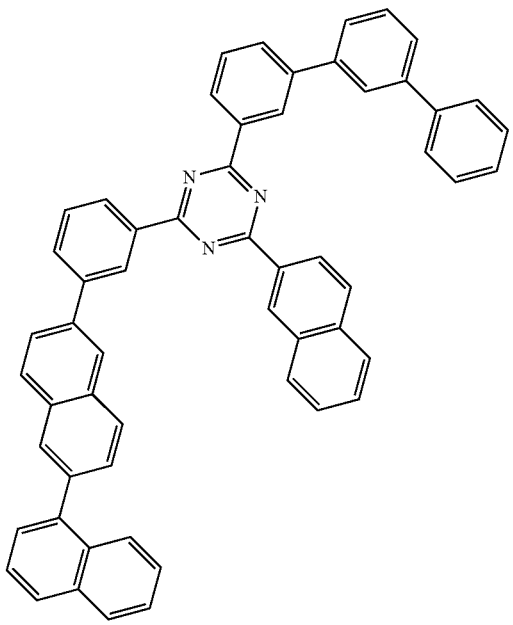
P-91
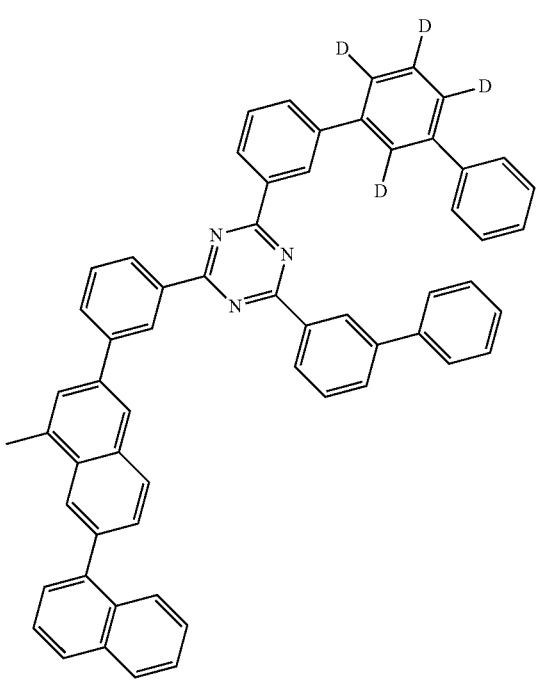

P-92
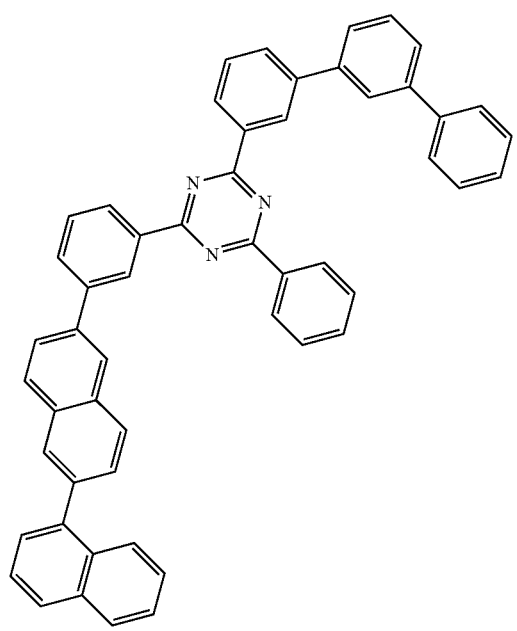
P-94
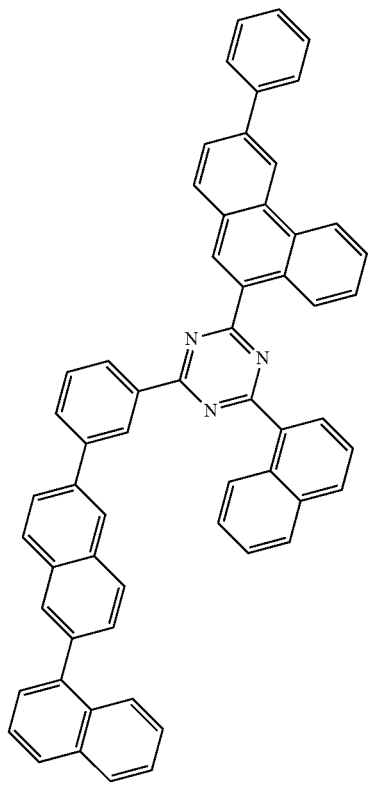
P-93
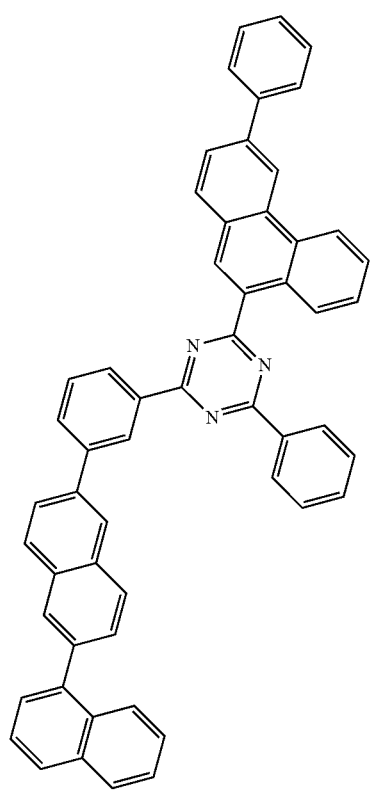
P-95
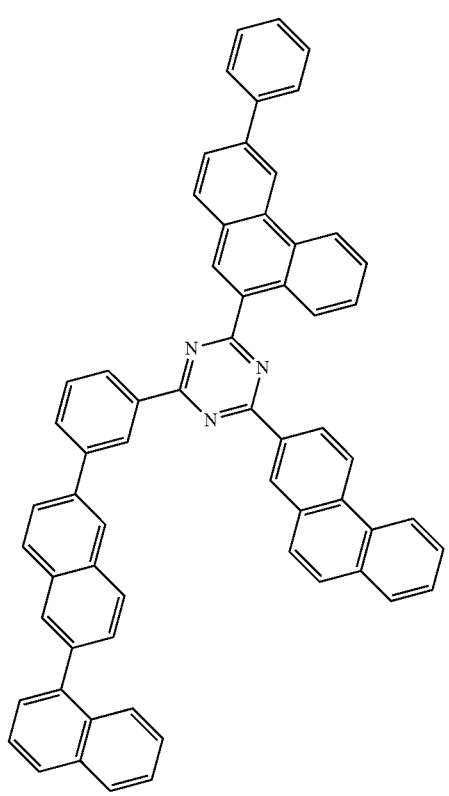

P-96
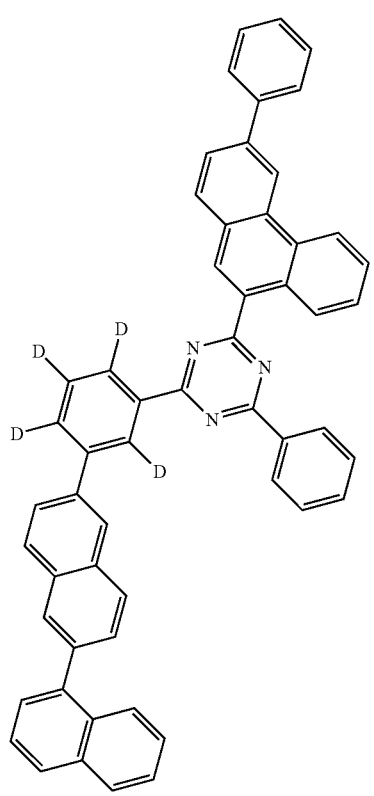
P-97
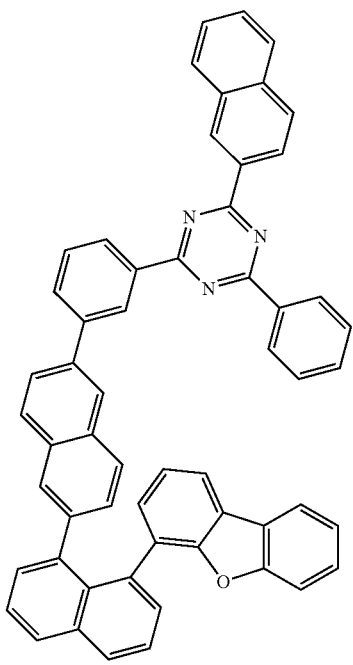
P-98
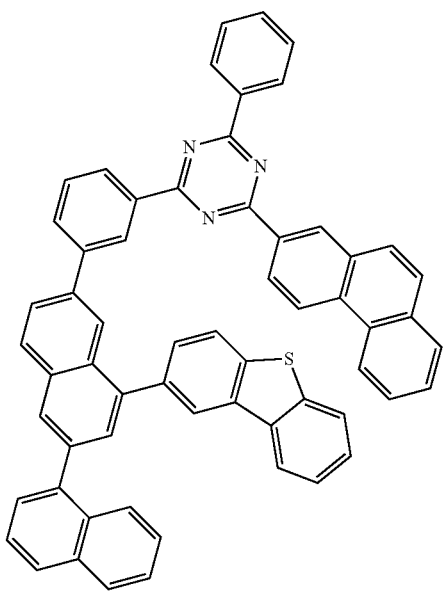
P-99

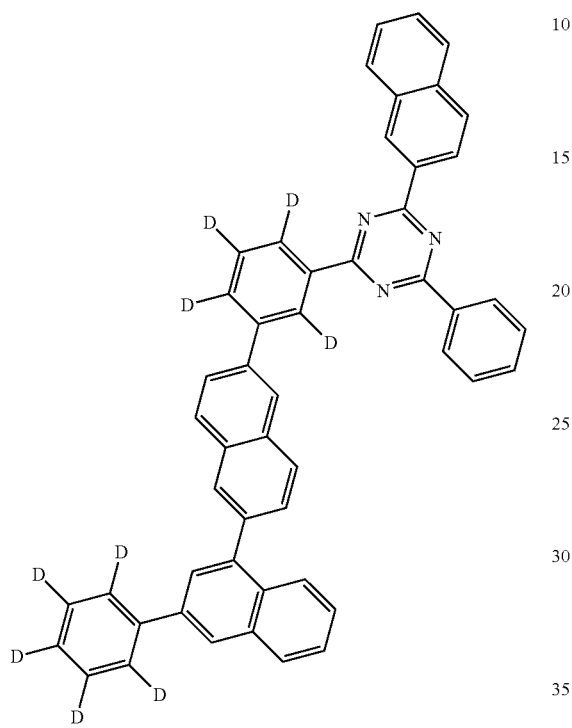
P-100
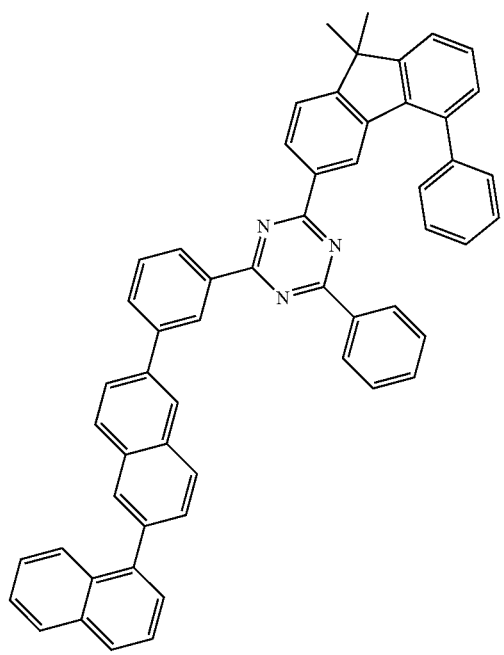
P-102
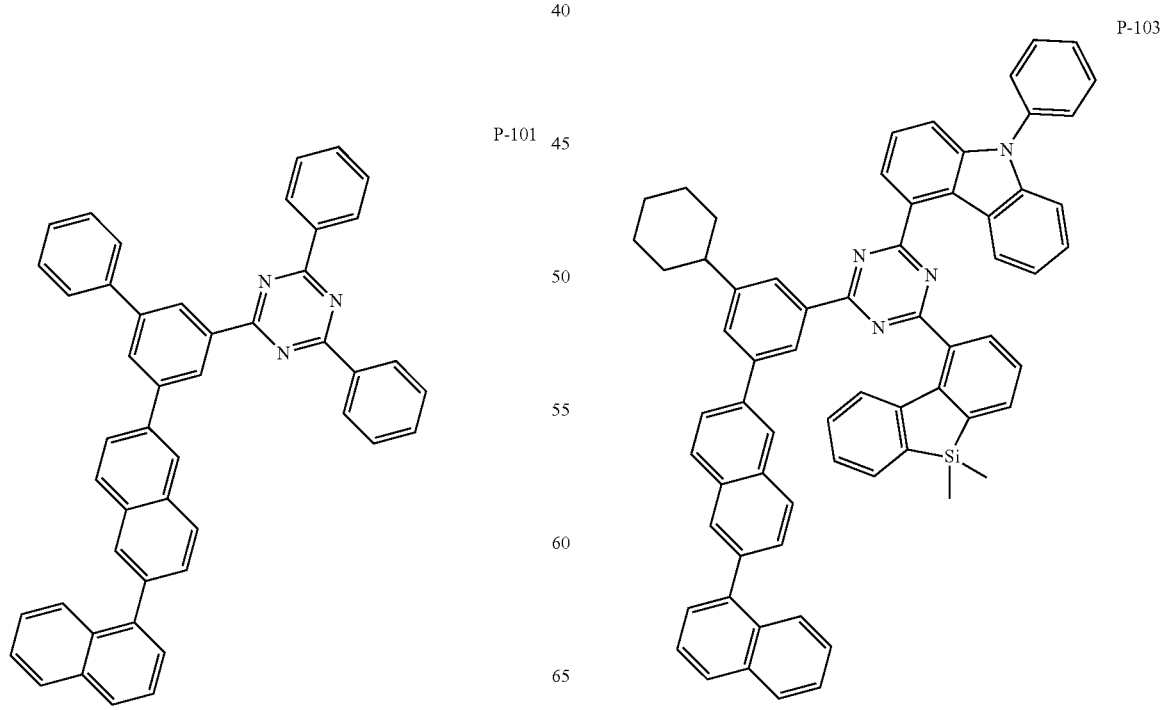
P-101
P-103

P-104
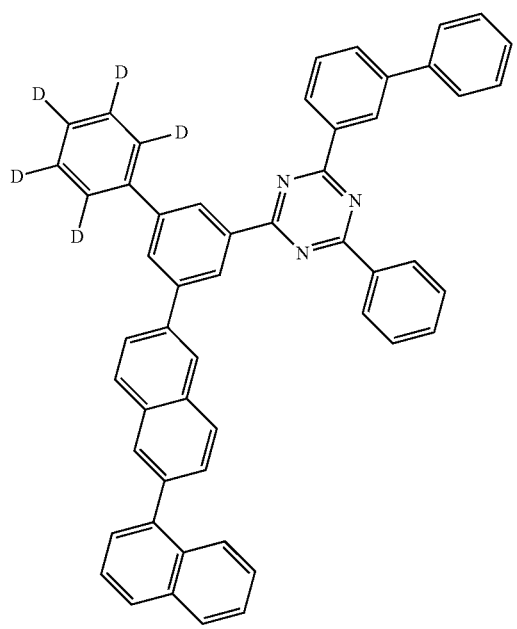
Also, Formula 4 is represented by any one of the following compounds H-1 to H-100.
H-1
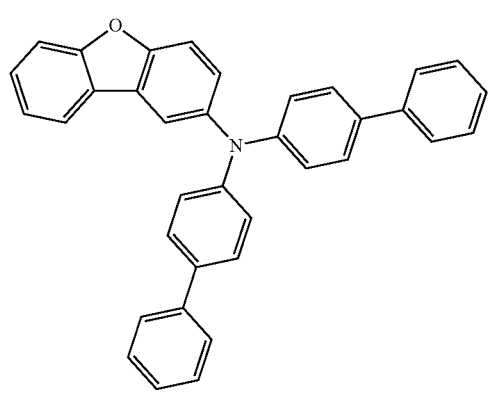
H-2
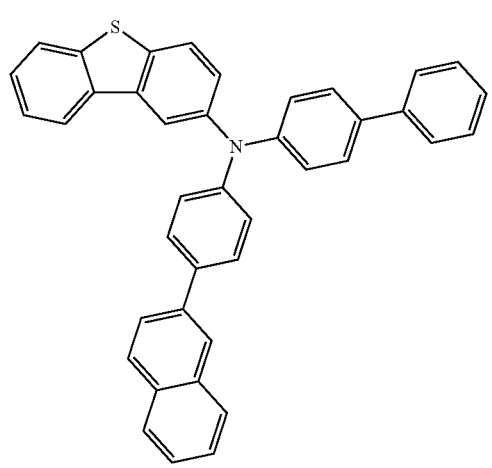
H-3
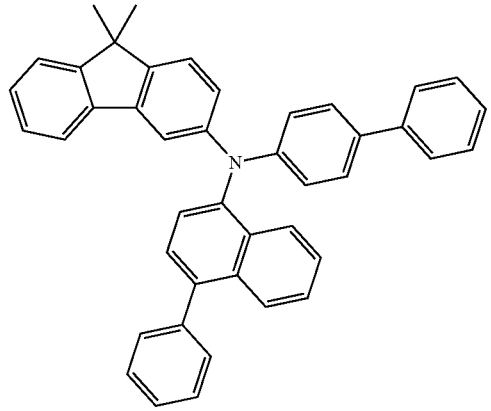
H-4
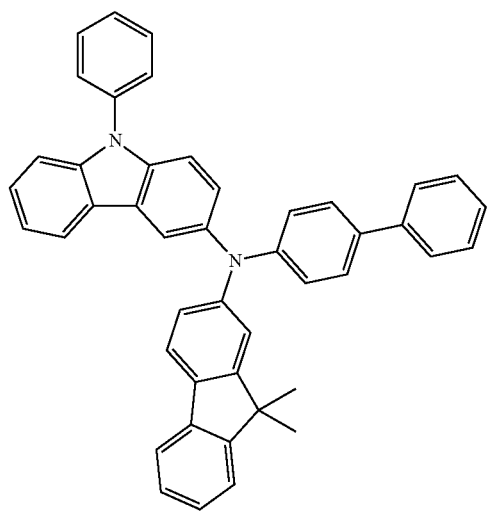
H-5
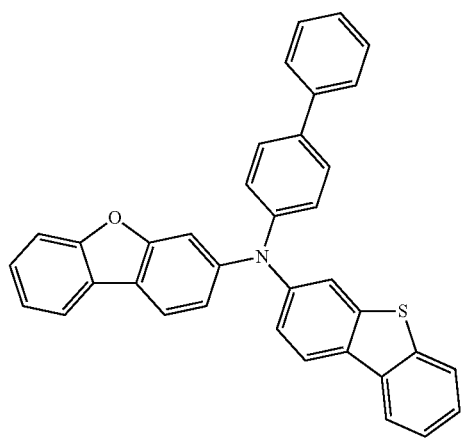

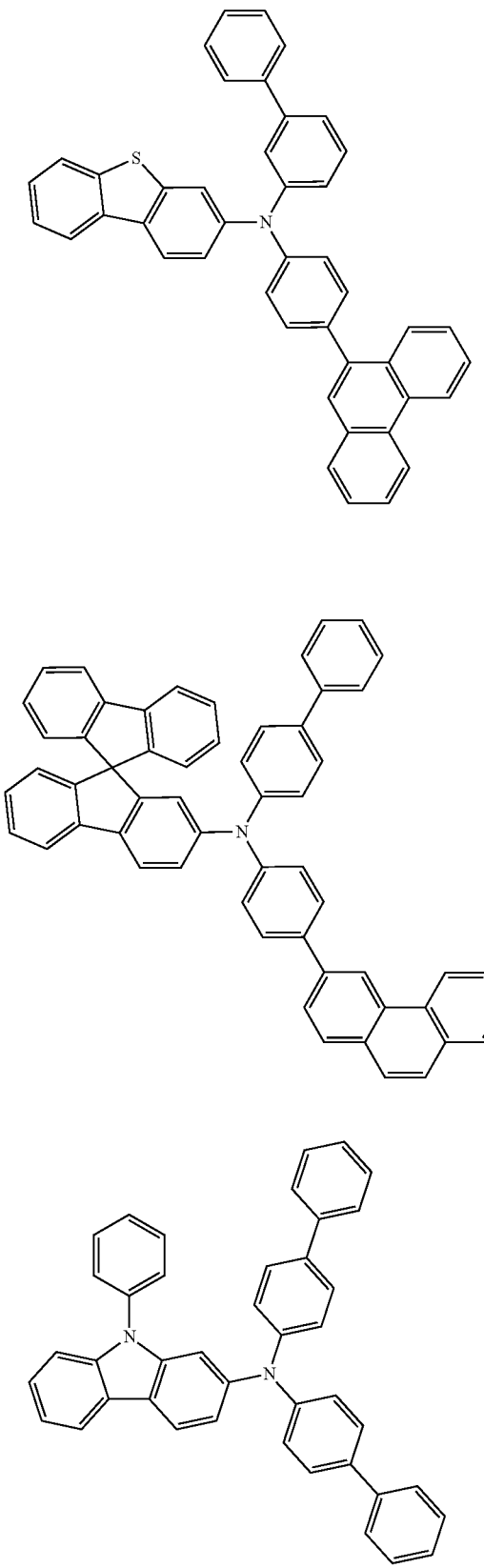
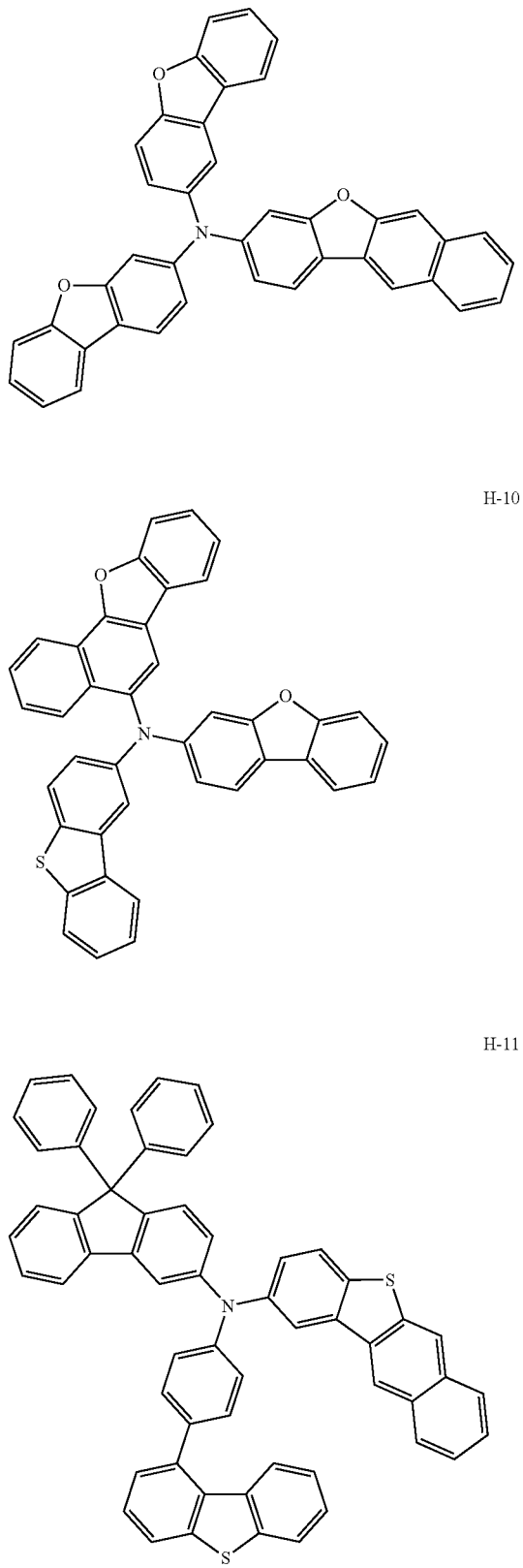

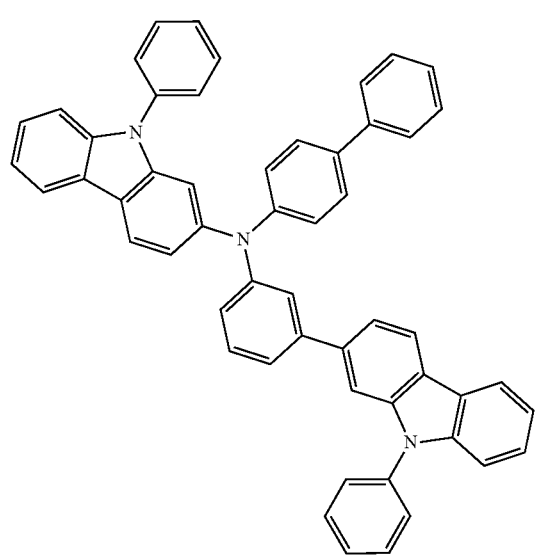
H-12
H-13
H-14
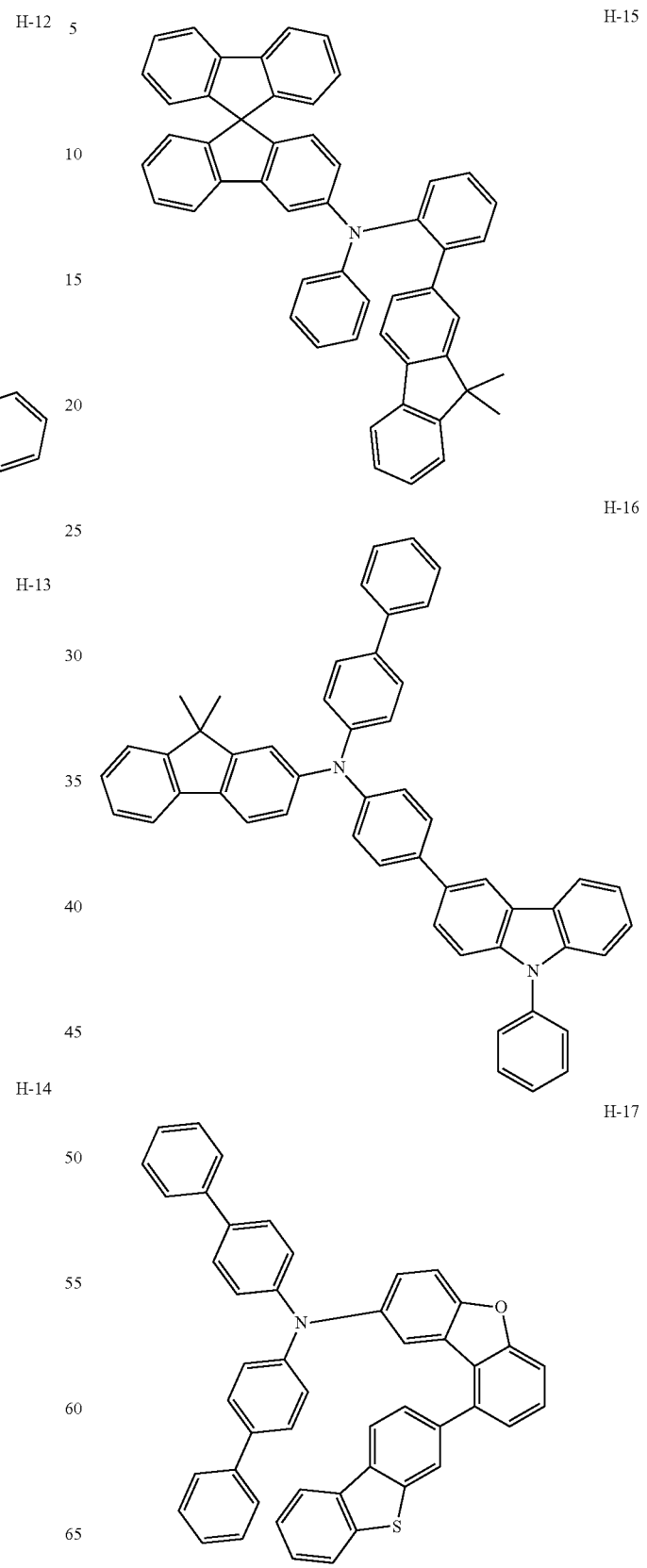
H-15
H-16
H-17

H-18
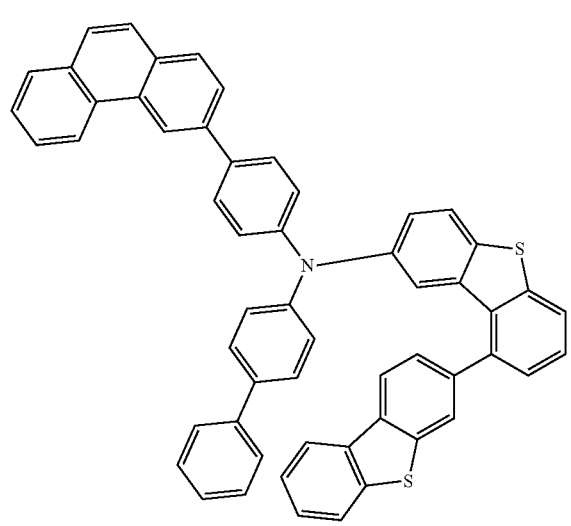
H-19
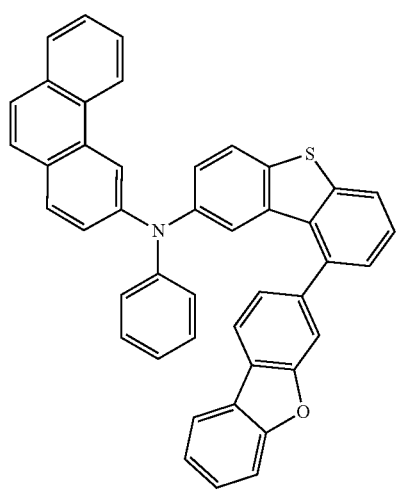
H-20
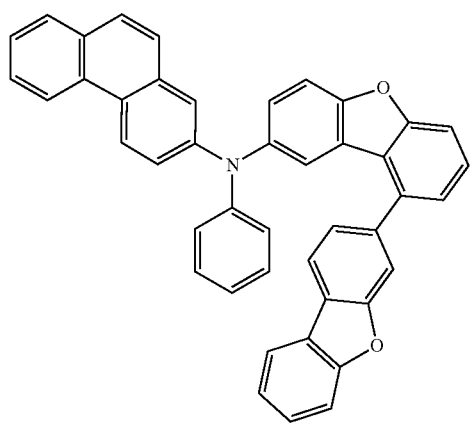
H-21
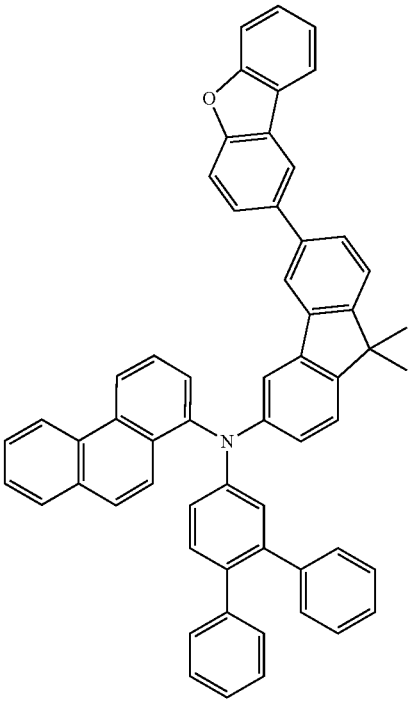
H-22
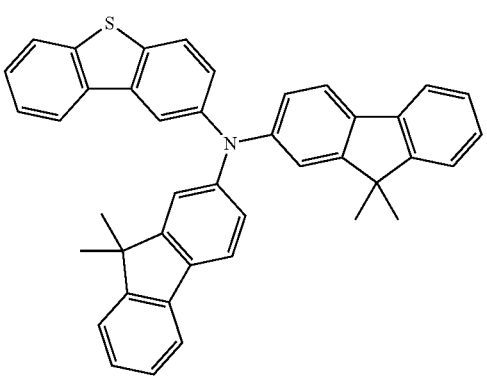
H-23
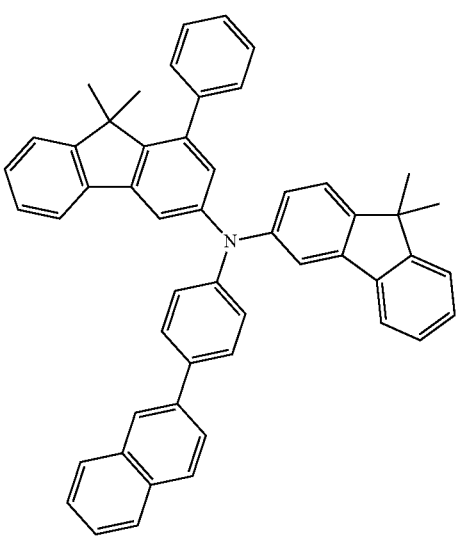

H-24
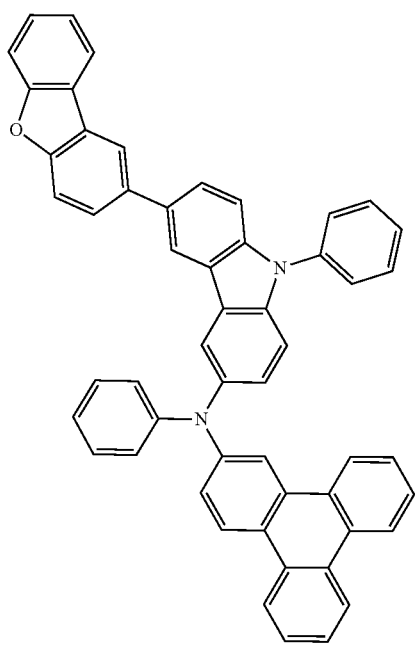
H-27
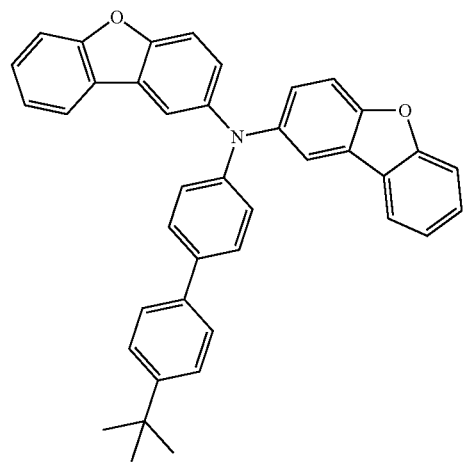
H-25
H-28
H-26
H-29

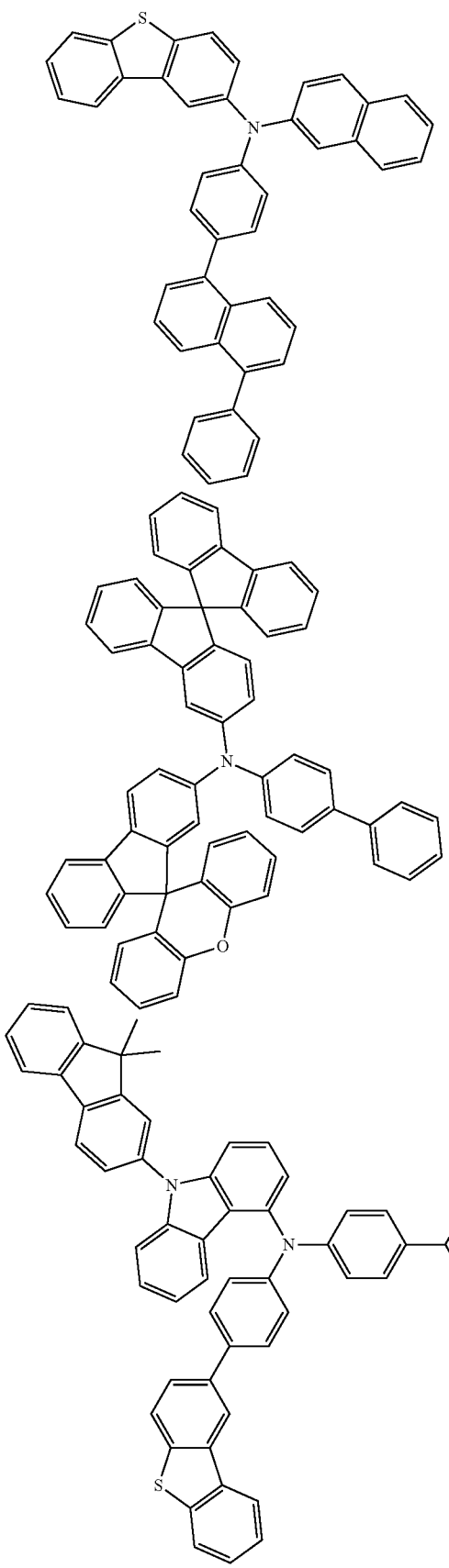
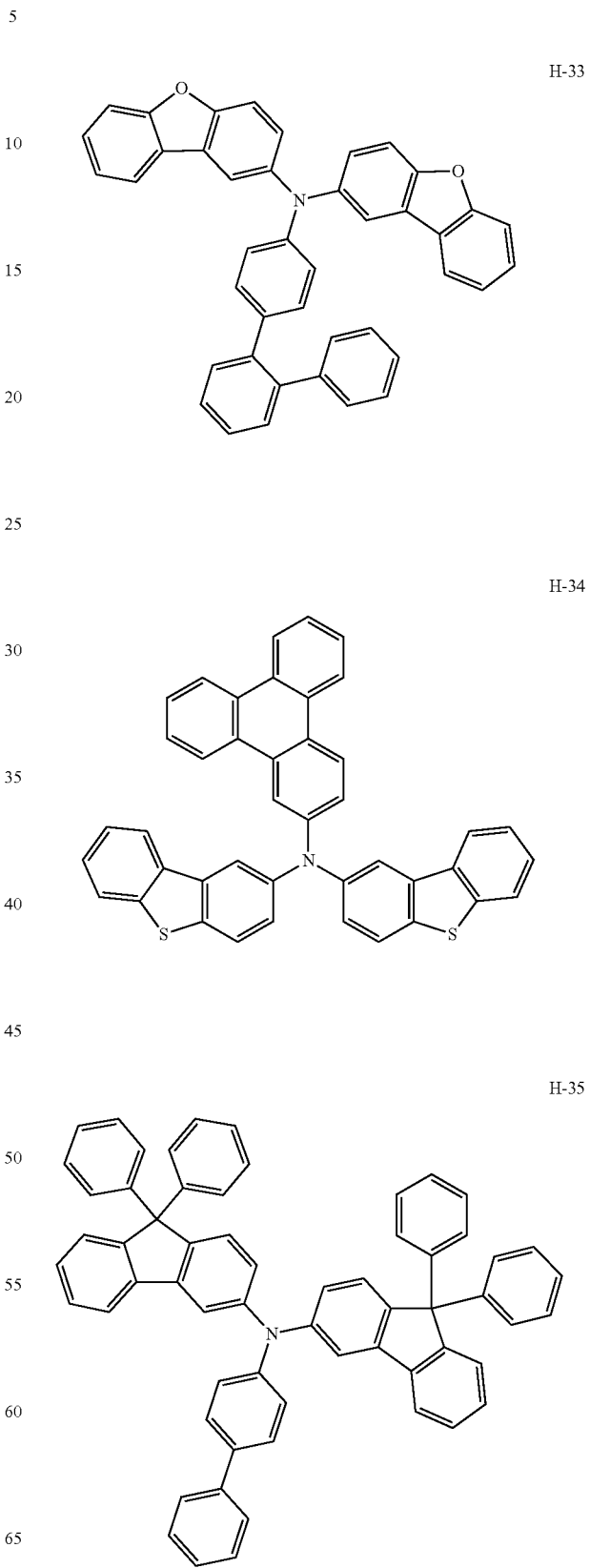

H-36
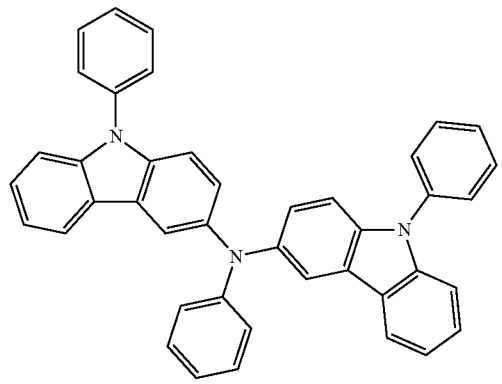
H-37
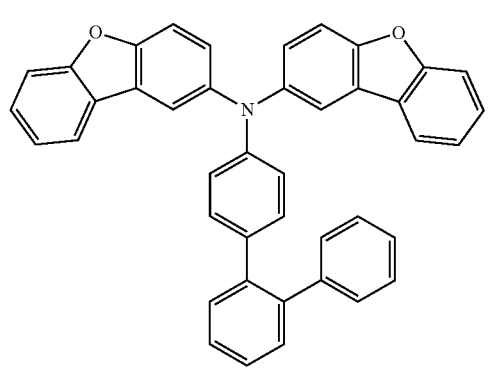
H-38
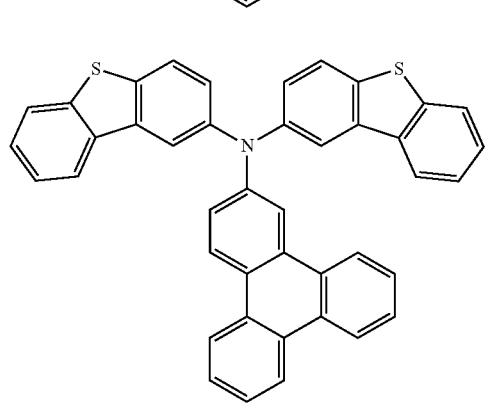
H-39
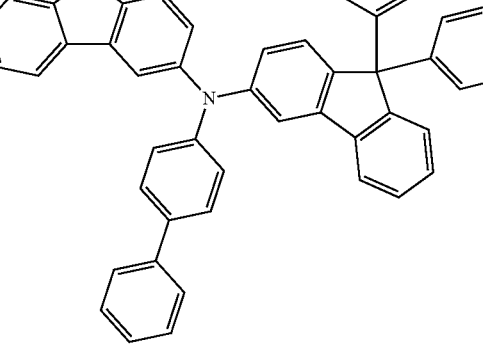
H-40
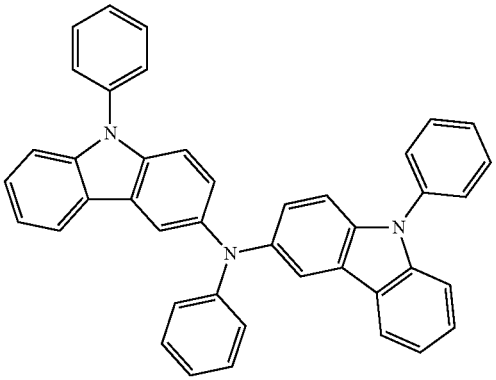
H-41
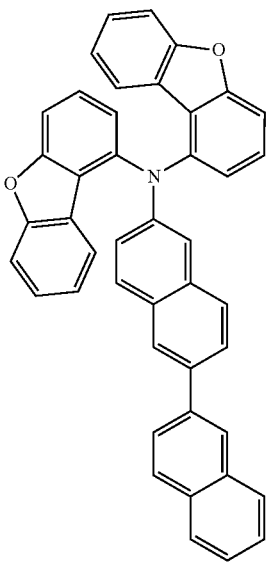
H-42
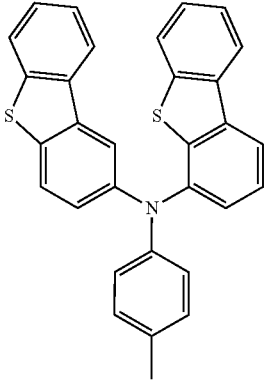

91
-continued
92
-continued
H-43
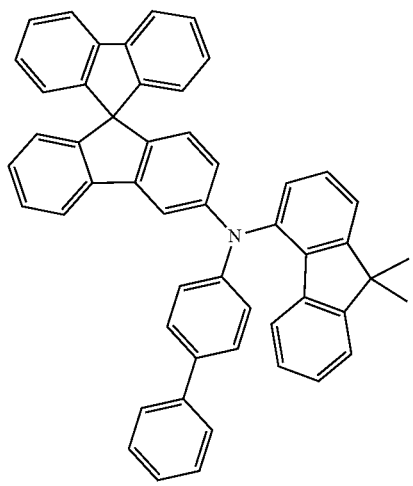
H-44
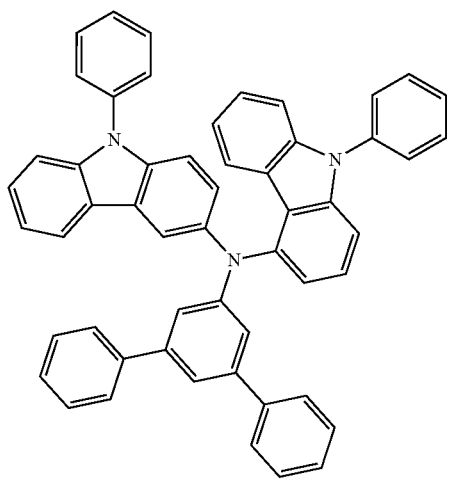
H-45
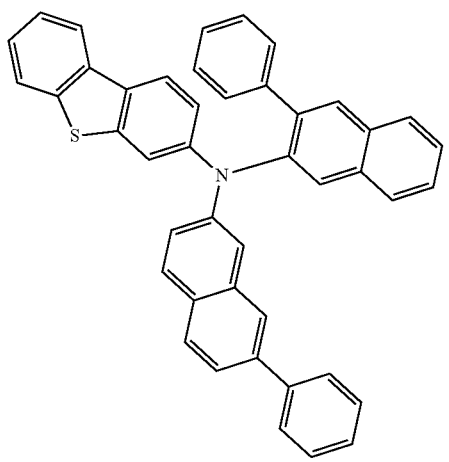
H-46
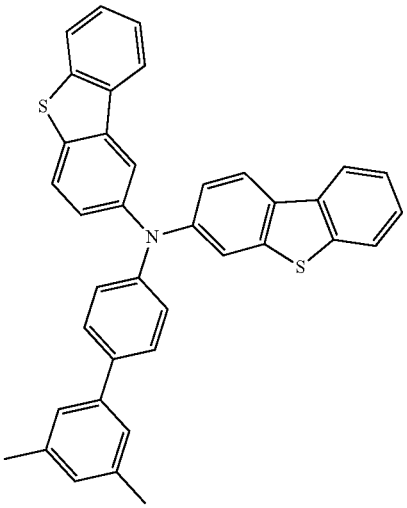
H-47
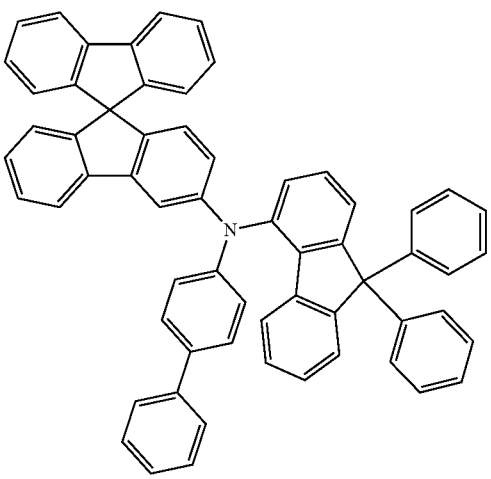
H-48
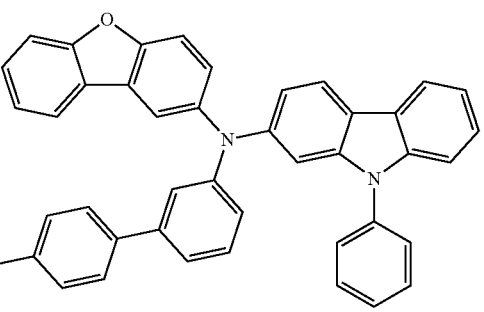

-continued
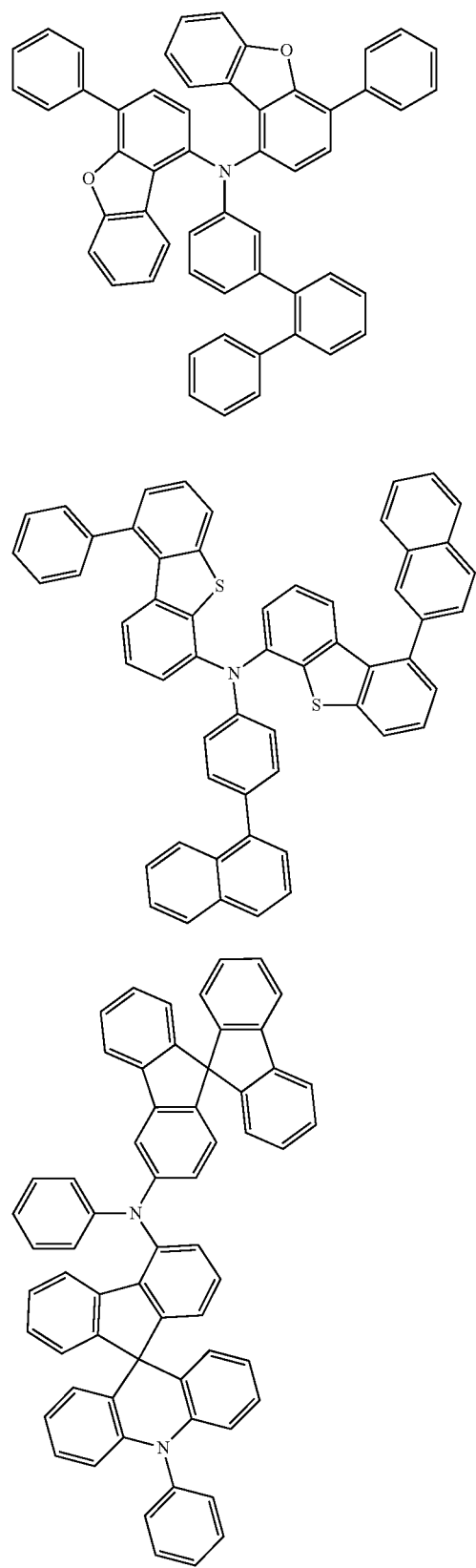
H-49
H-50
H-51
-continued
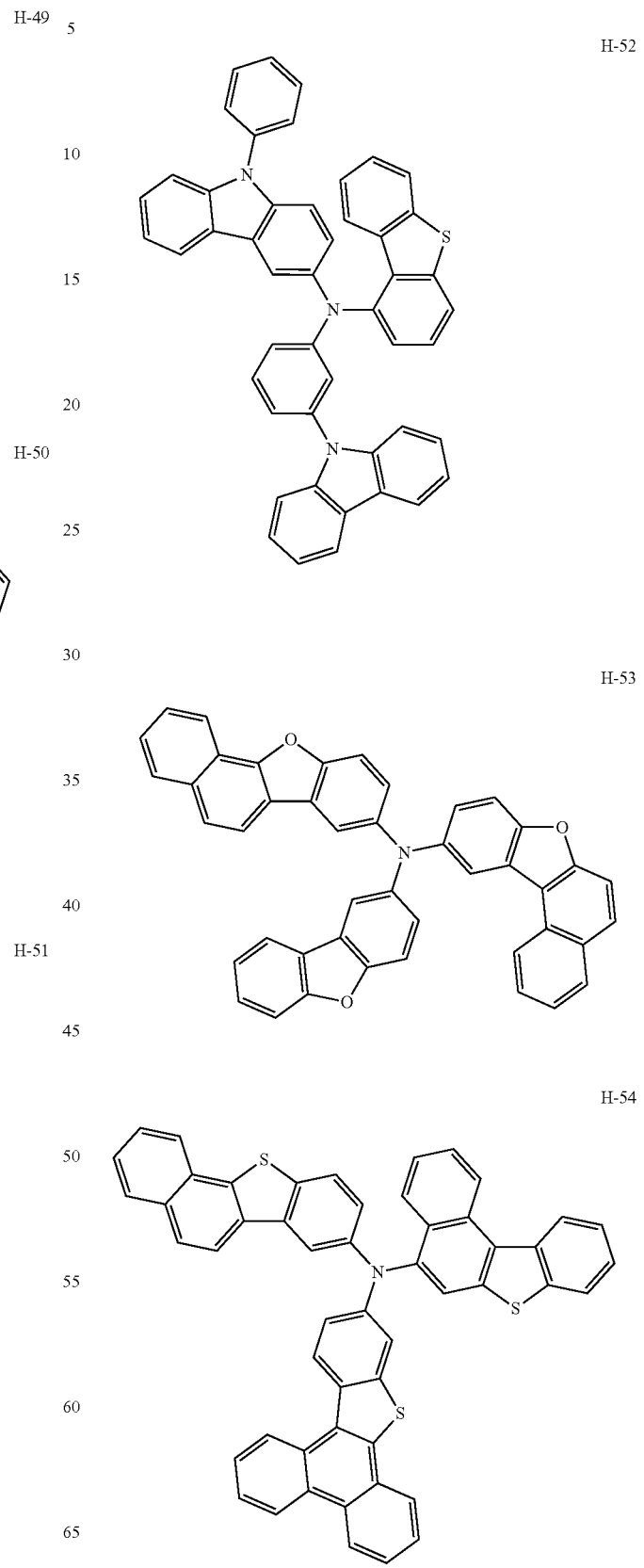
H-52
H-53
H-54

H-55
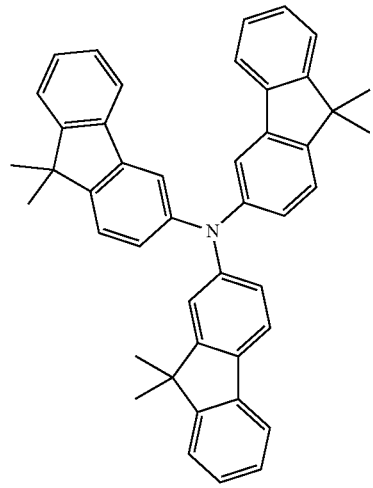
H-58
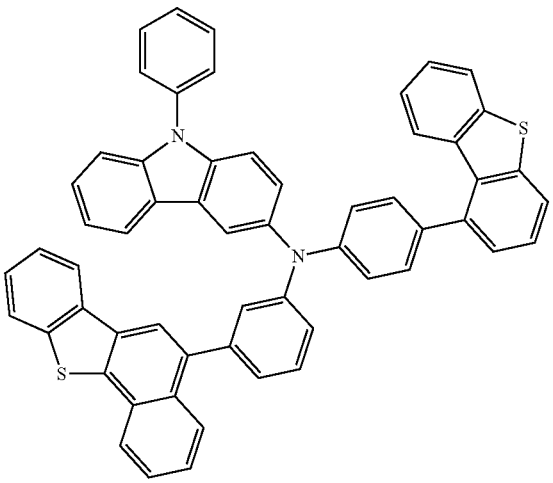
H-56
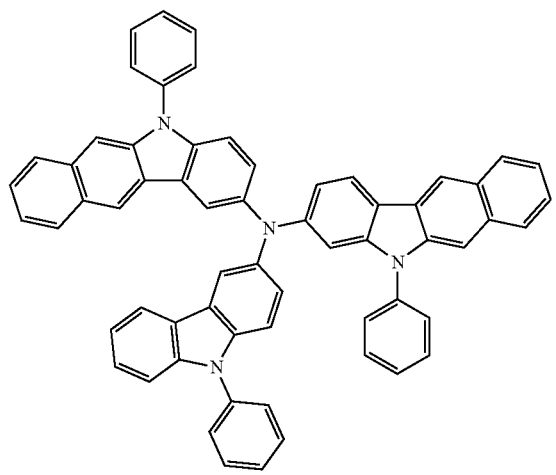
H-59
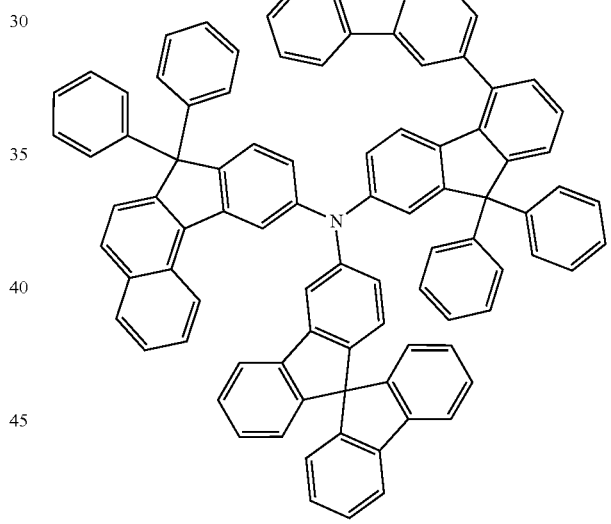
H-57
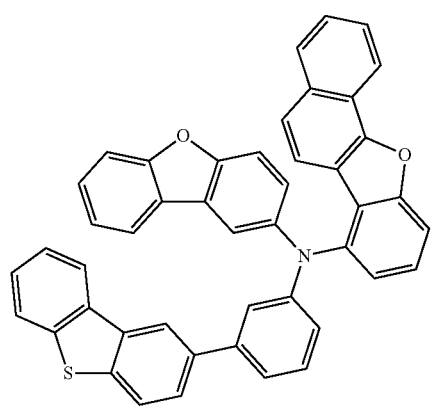
H-60
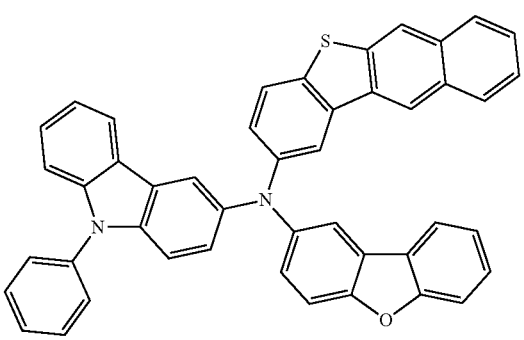

H-61
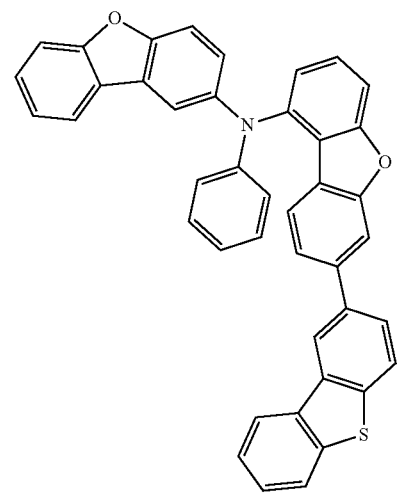
H-62
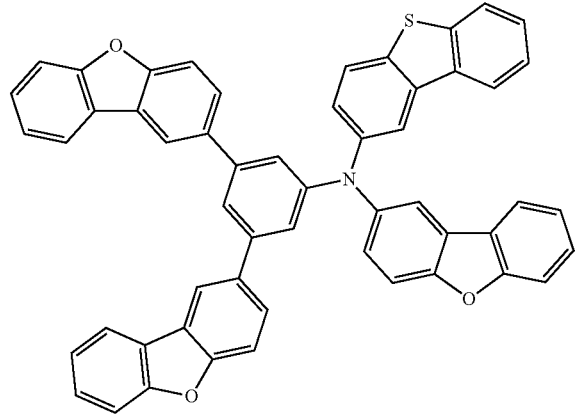
H-63
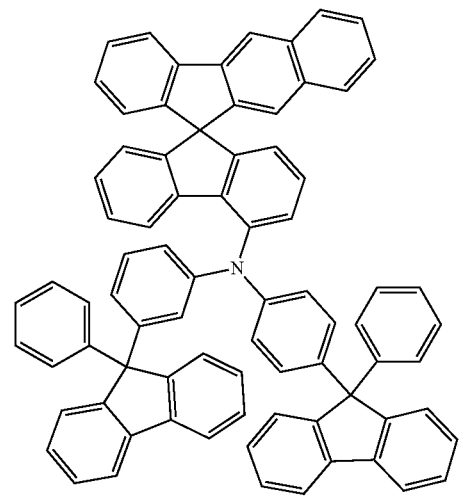
H-64
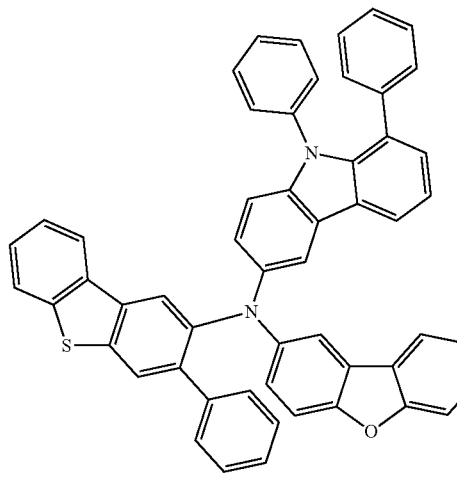
H-65
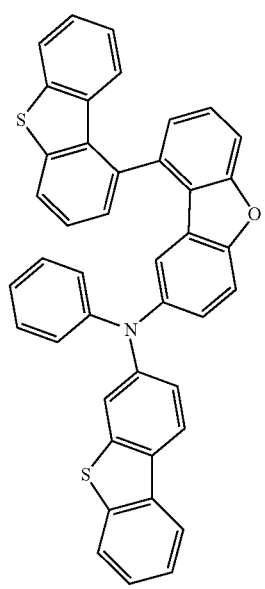
H-66
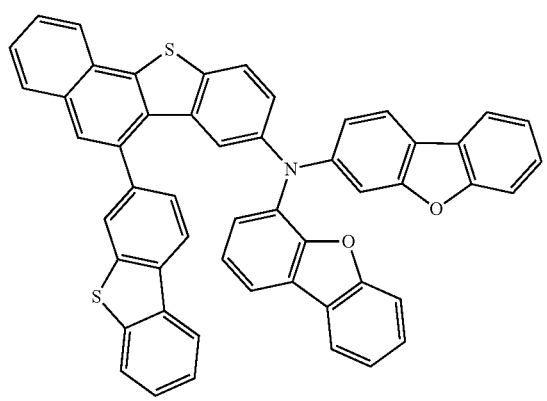

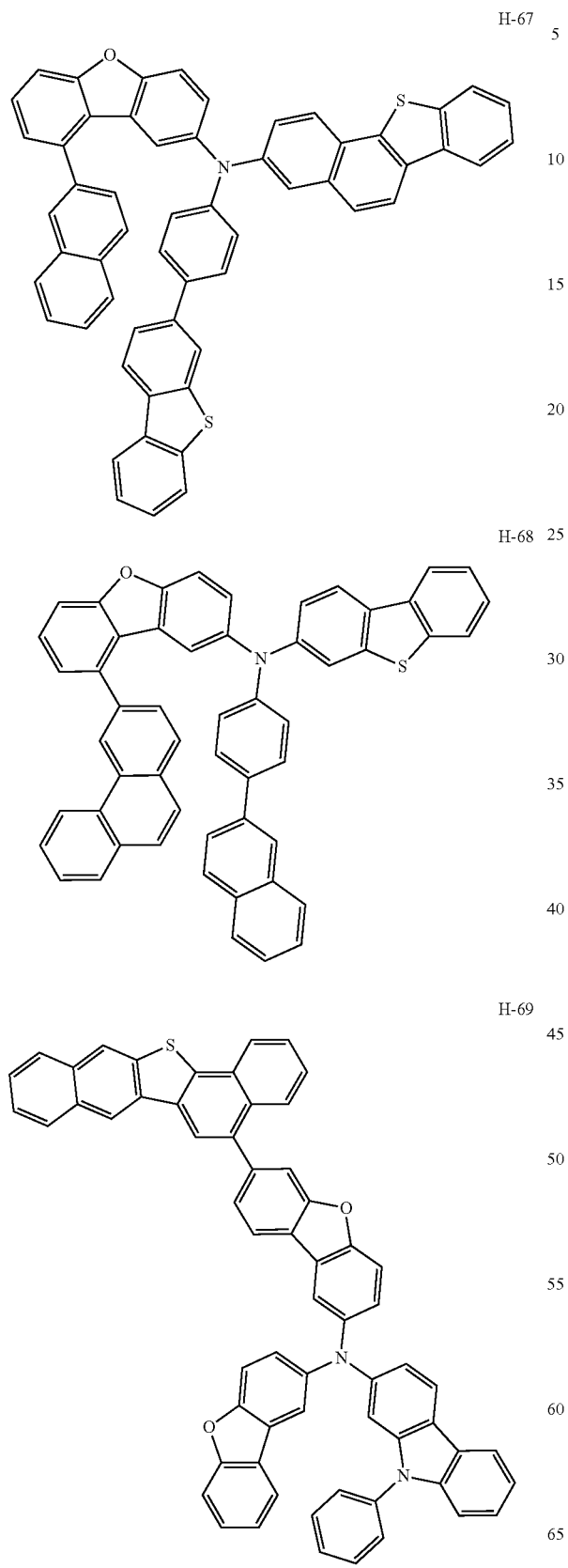
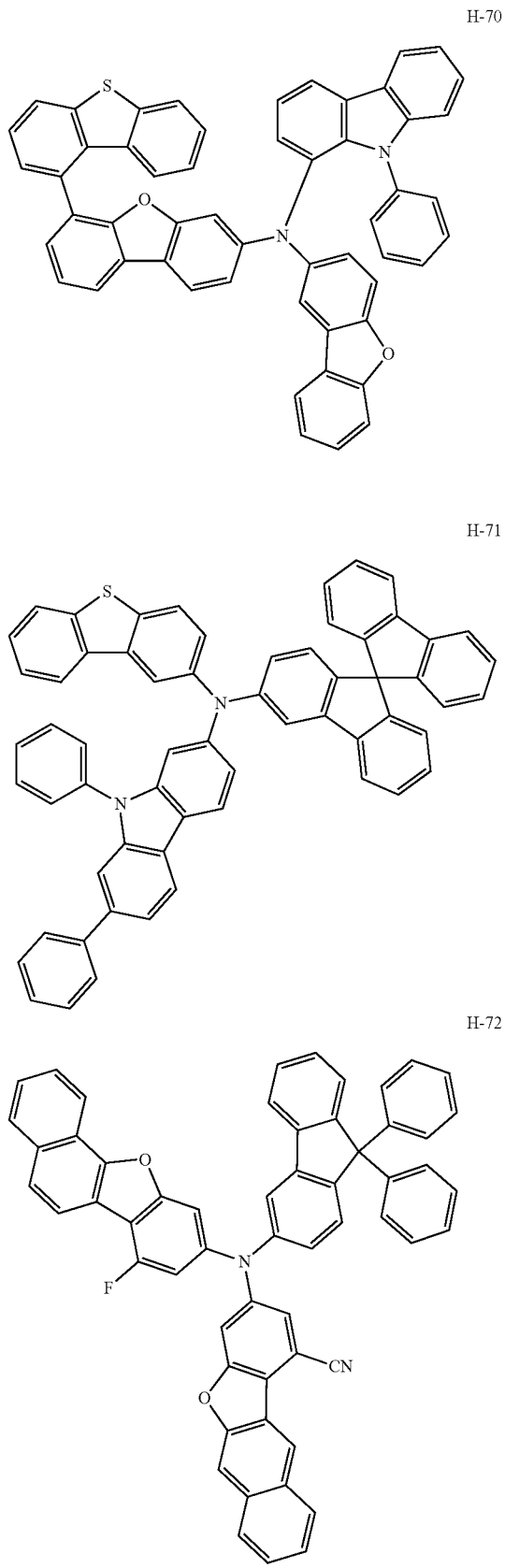

H-73
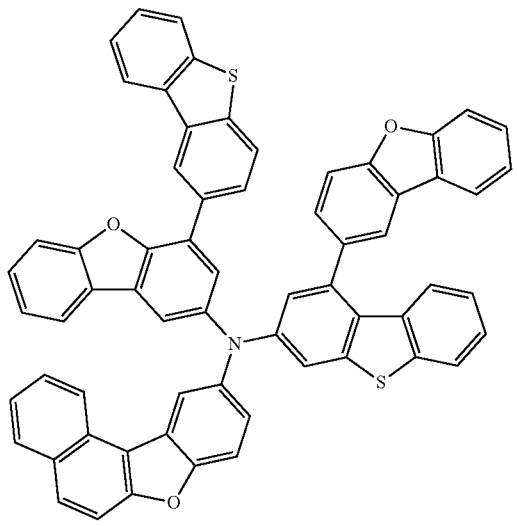
H-74
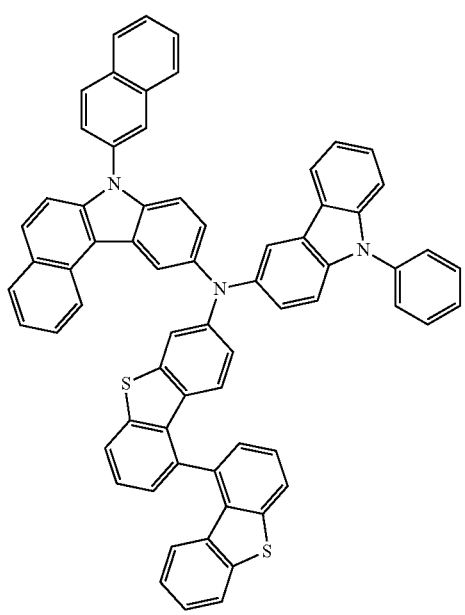
H-75
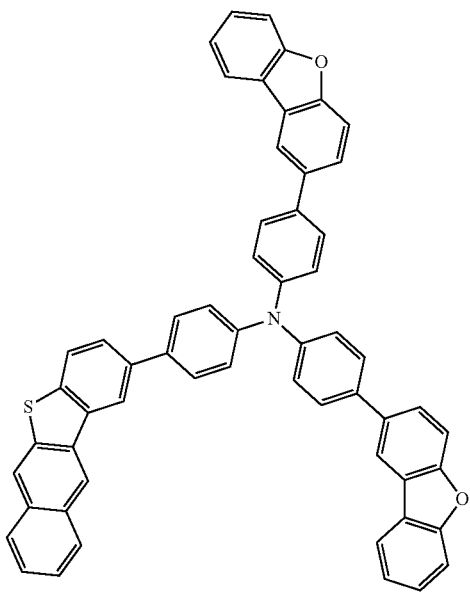
H-76
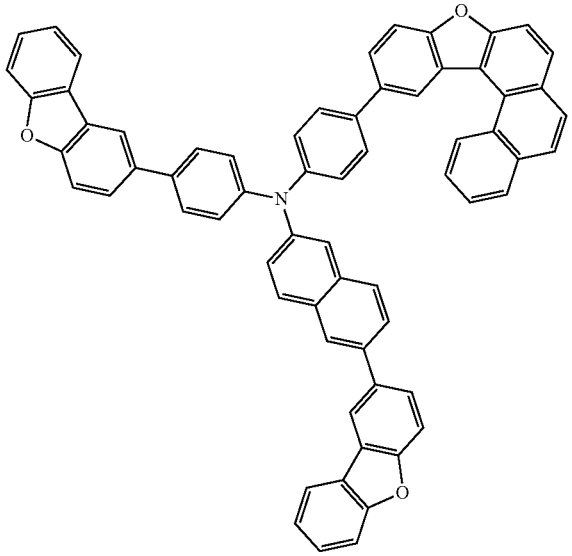

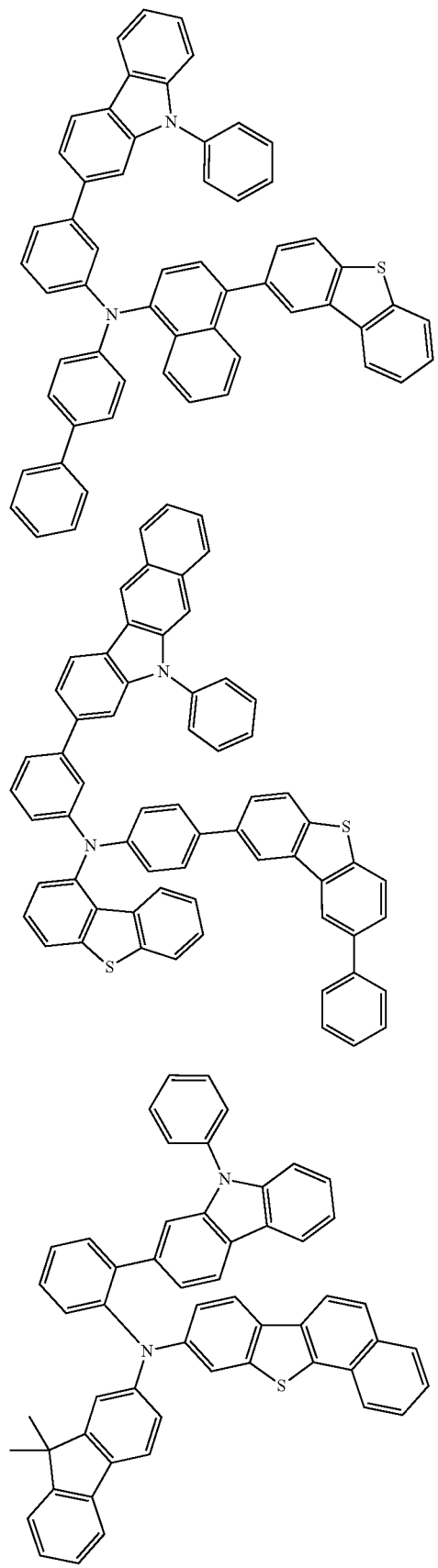
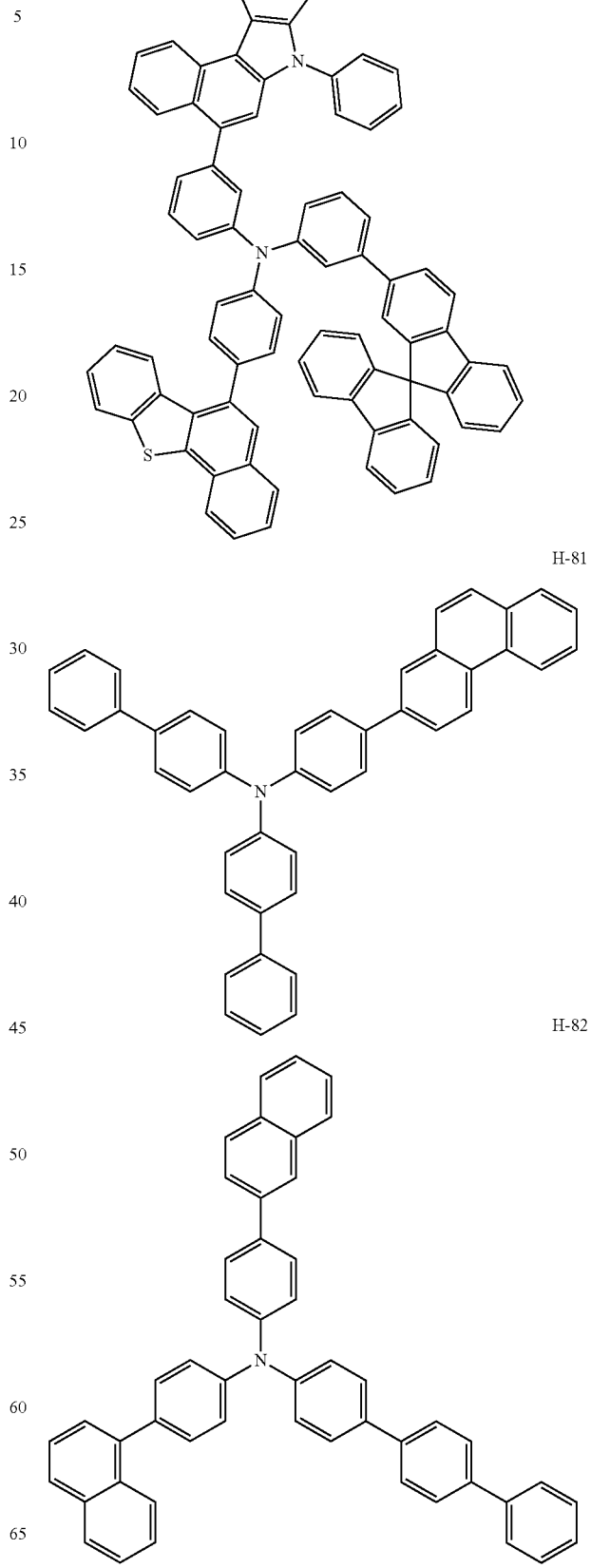

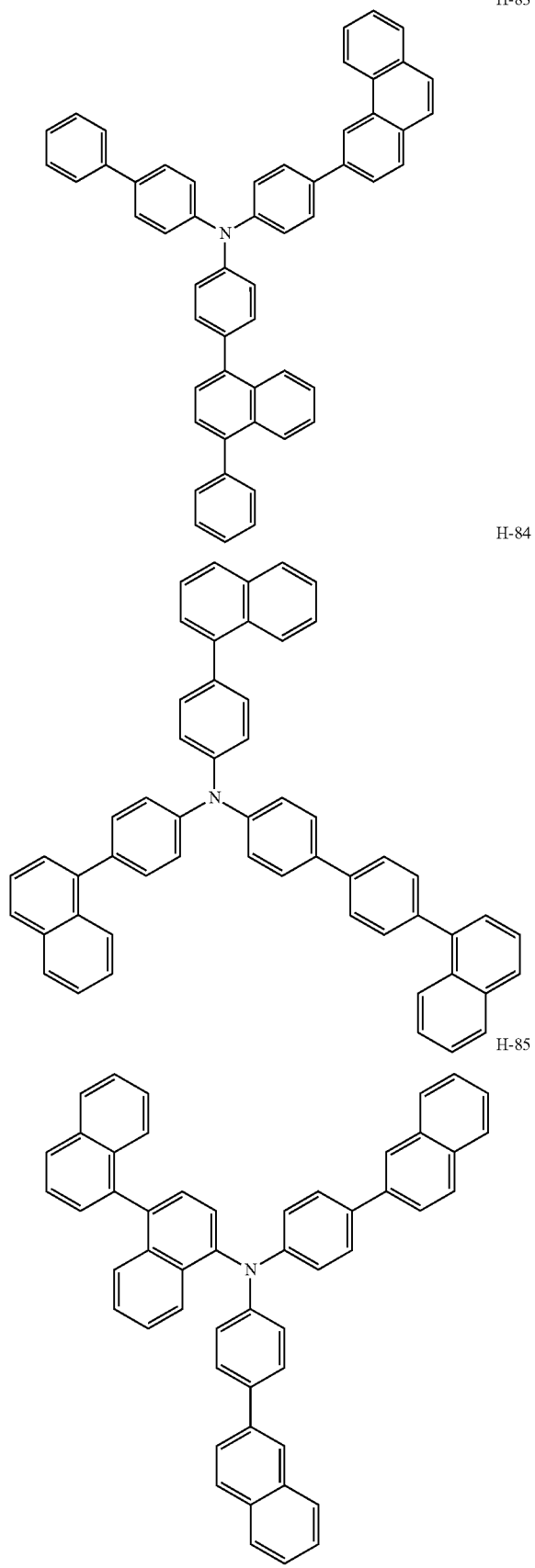
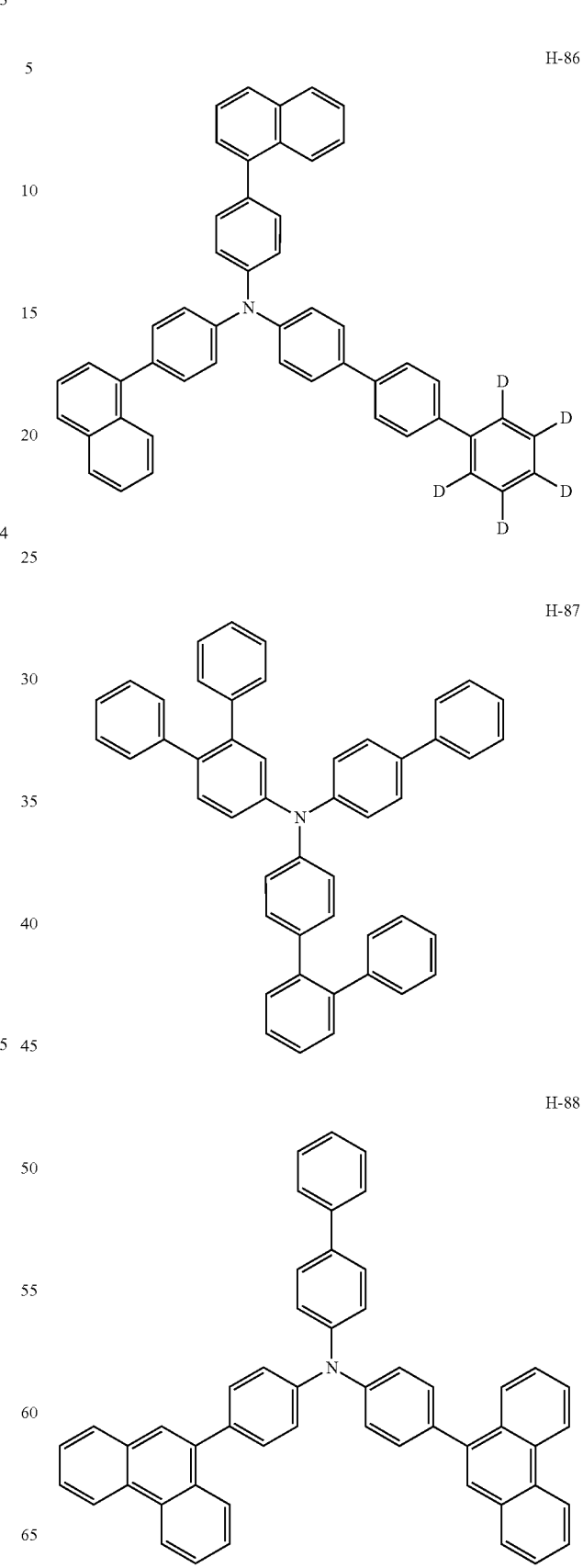

H-89
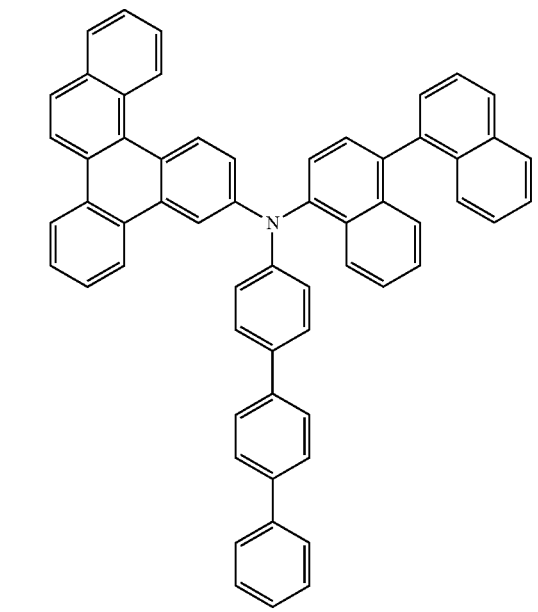
H-90
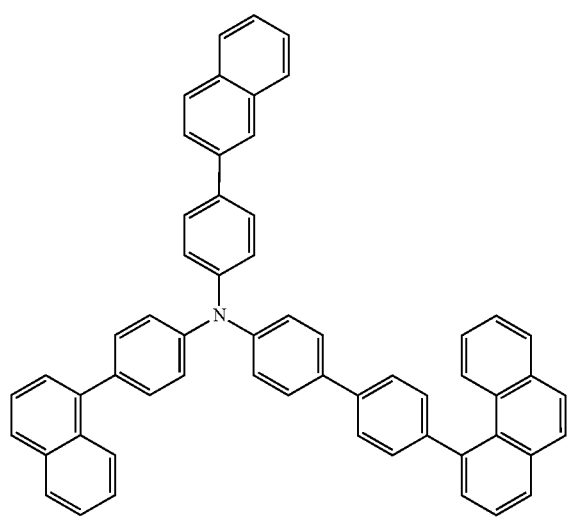
H-91
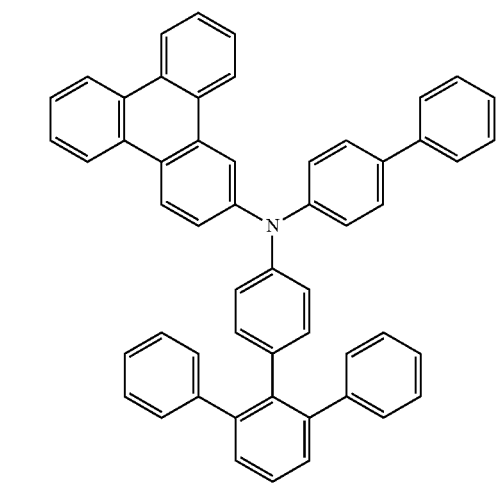
H-92
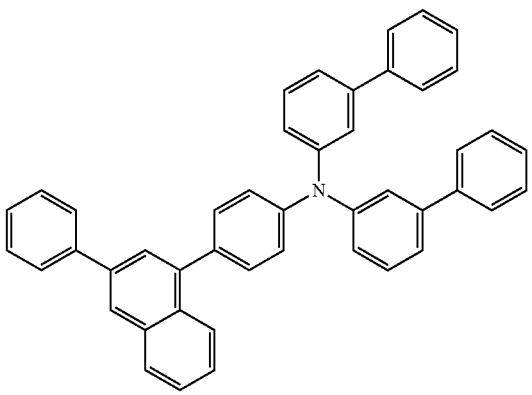
H-93
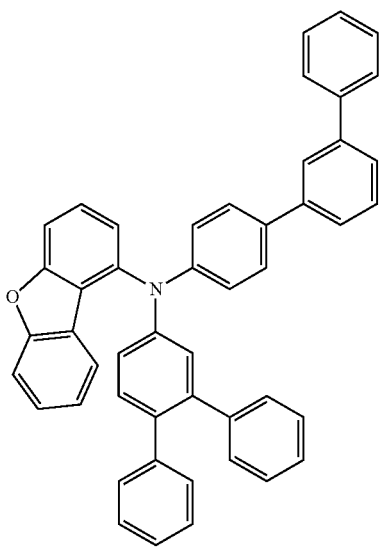
H-94
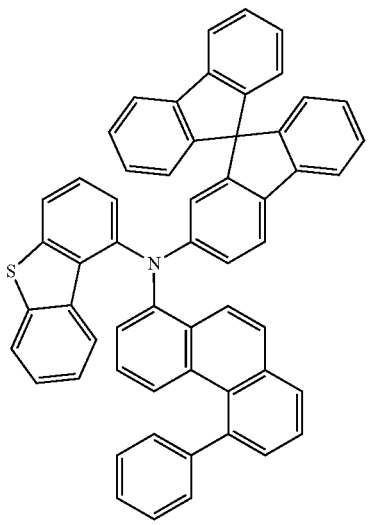

H-95
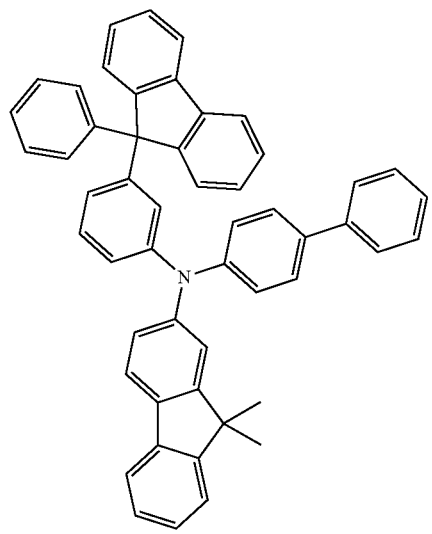
H-96
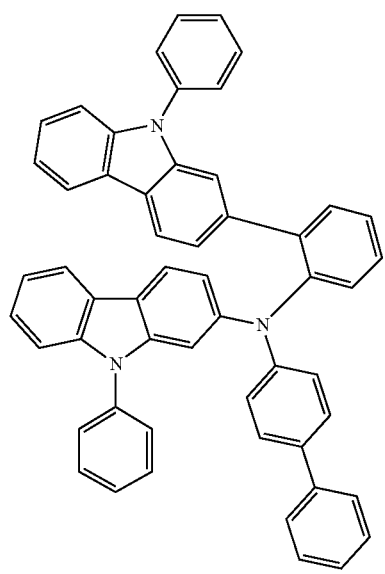
H-97
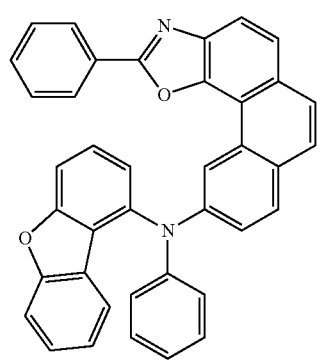
H-98
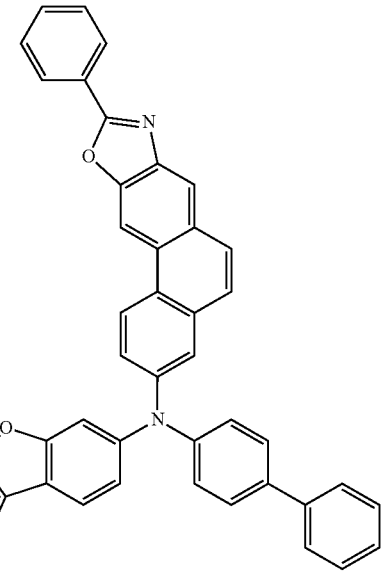
H-99
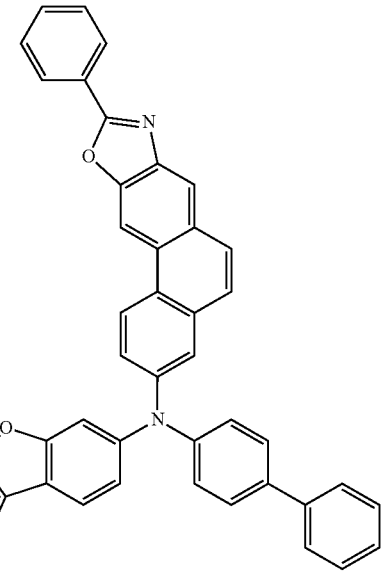
H-100
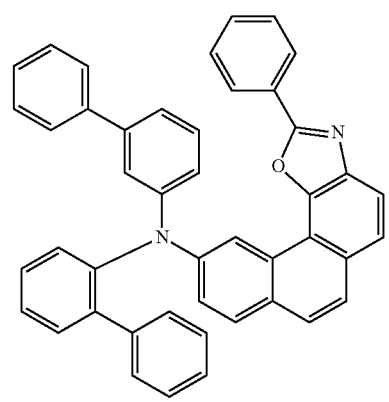

Also, Formula 5 is represented by any one of S-1 to S-108.
S-1
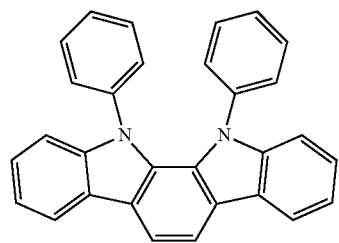
S-2
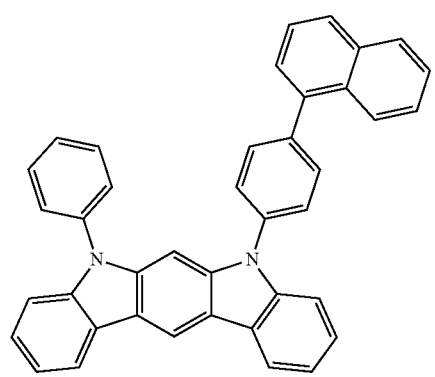
S-3
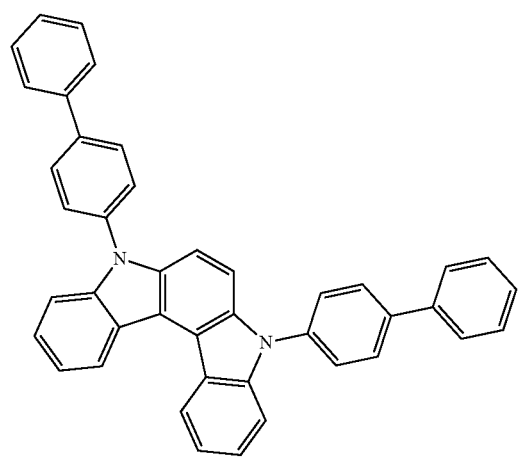
S-4
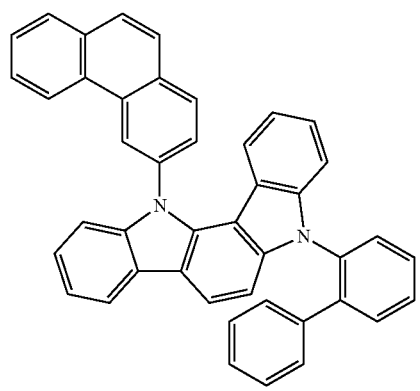
S-5
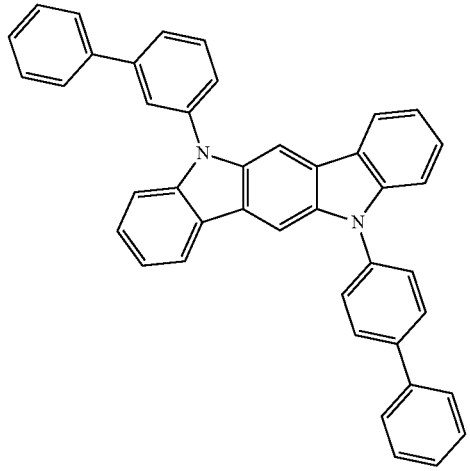
S-6
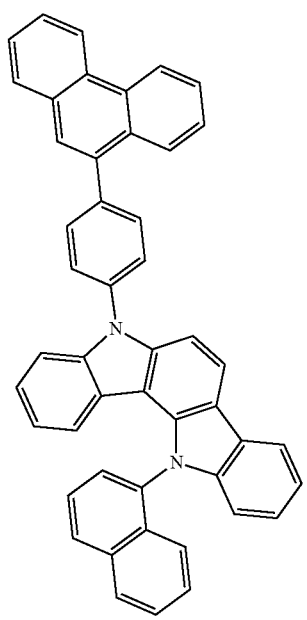
S-7
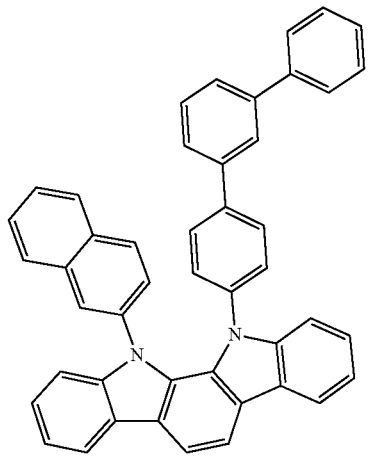

S-8
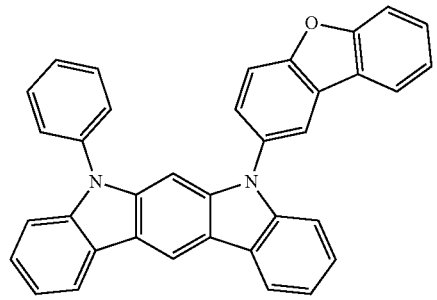
S-9
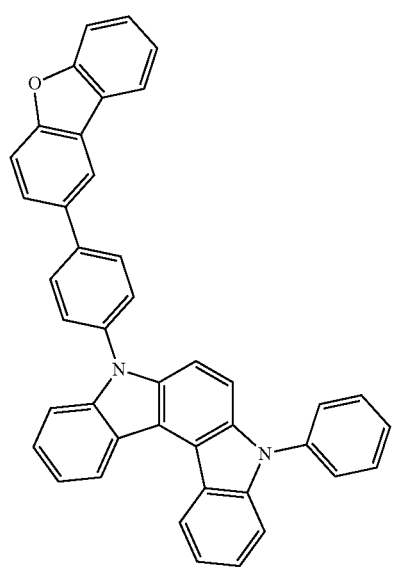
S-10
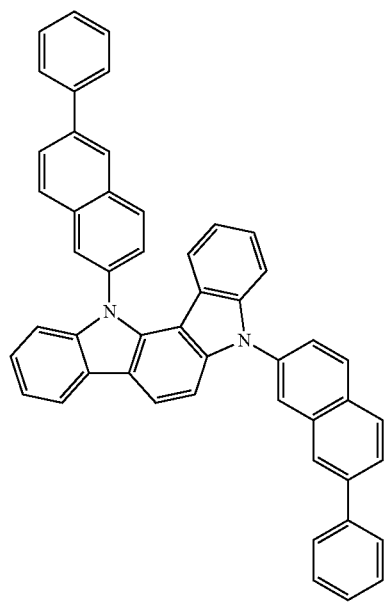
S-11
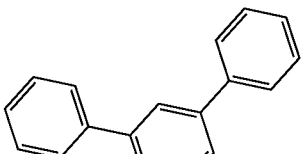
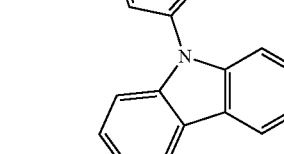
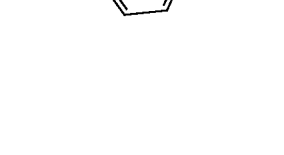
S-12
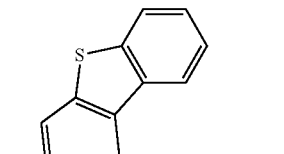
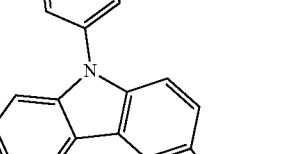
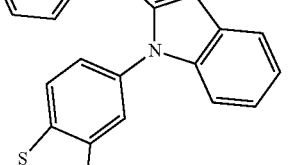
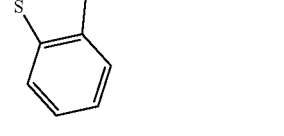
S-13
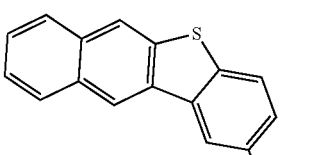
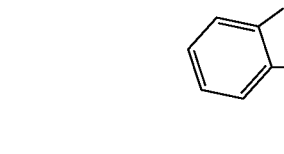

S-14
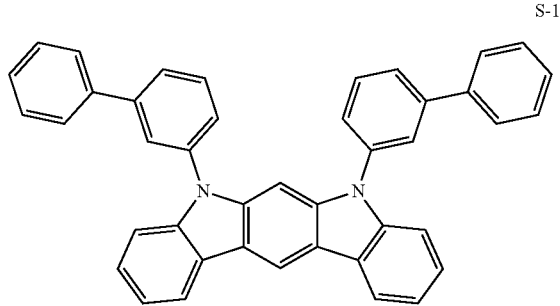
S-15
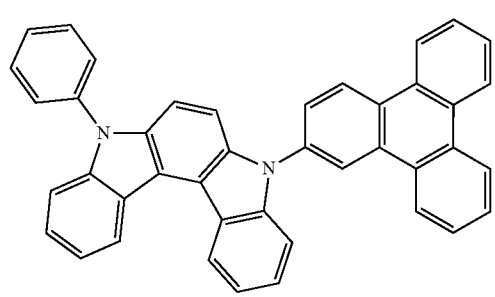
S-16
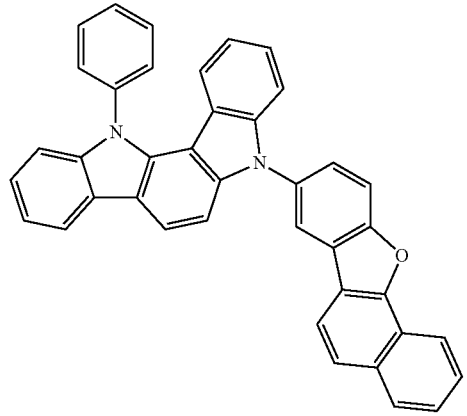
S-17
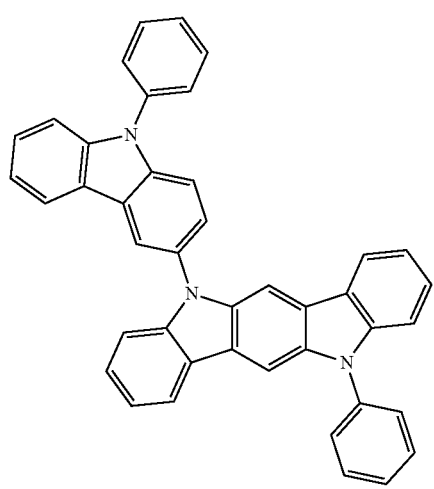
S-18
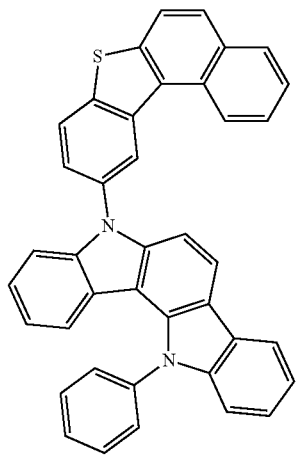
S-19
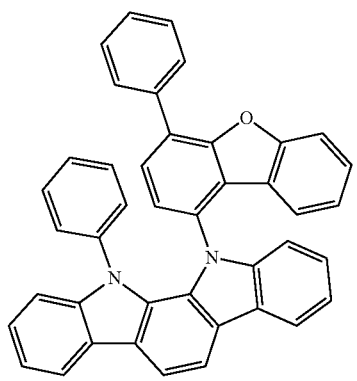
S-20
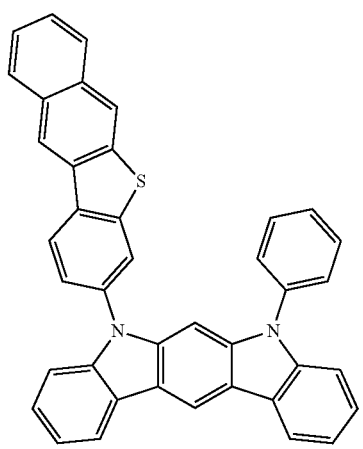

S-21
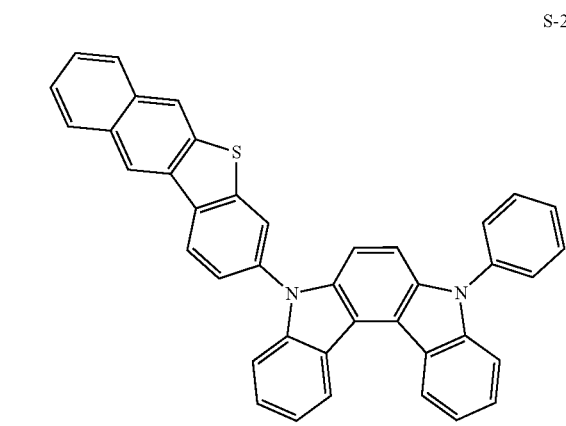
S-22
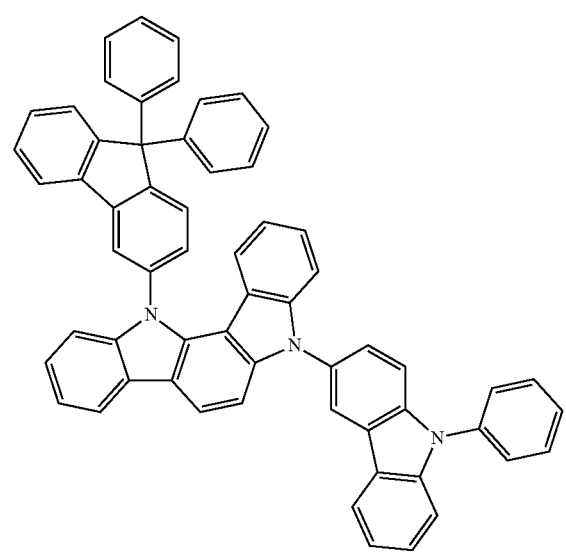
S-23
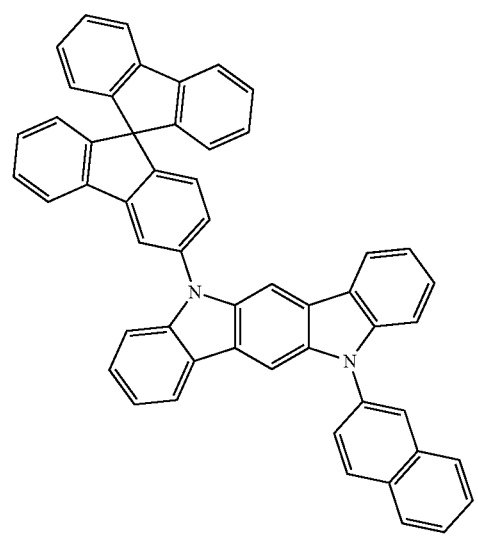
S-24
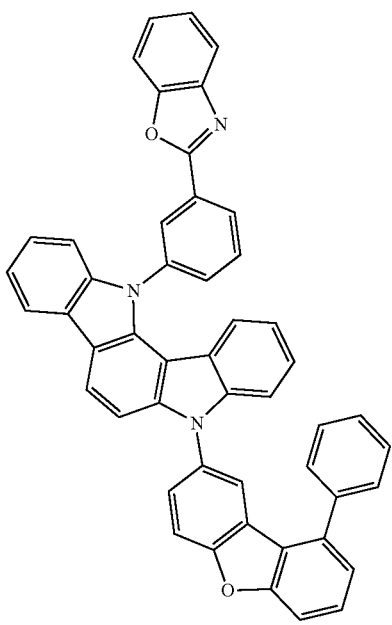
S-25
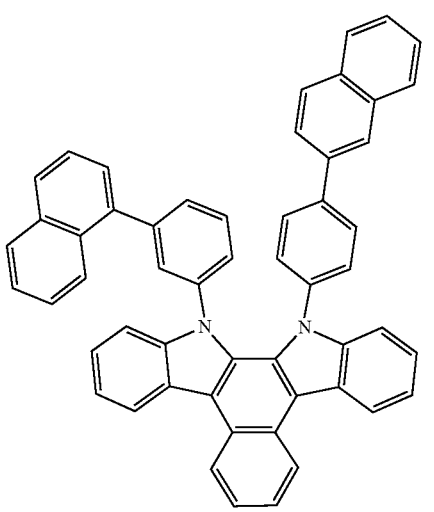
S-26
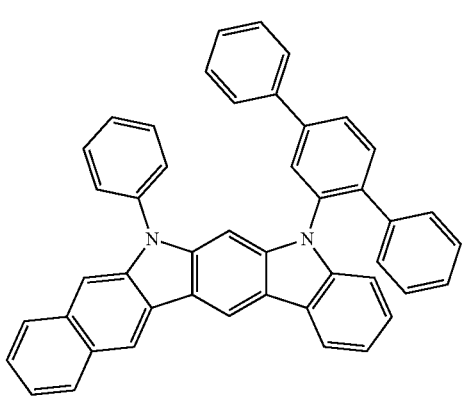

S-27
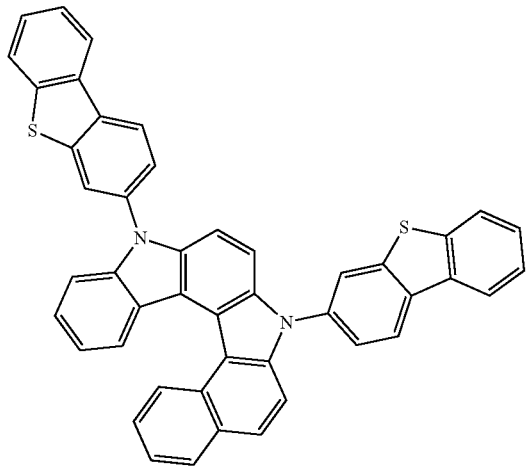
S-28
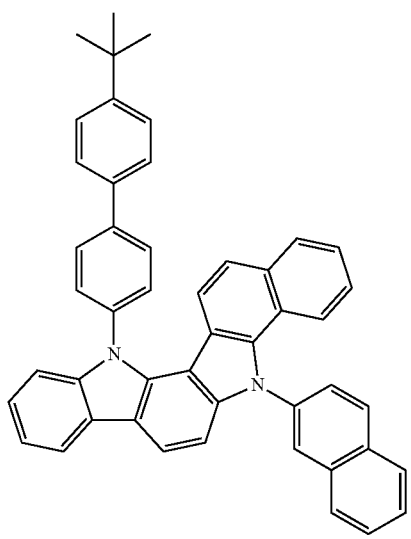
S-29
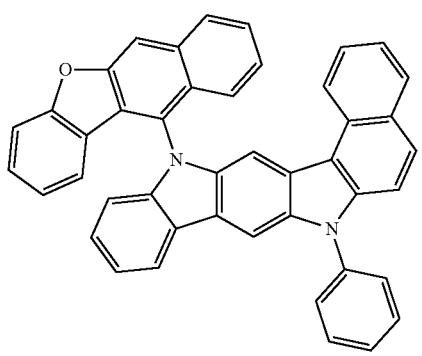
S-30
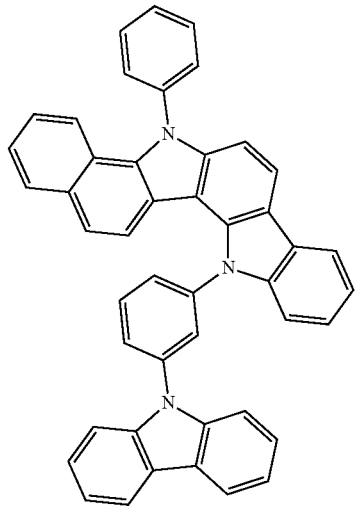
S-31
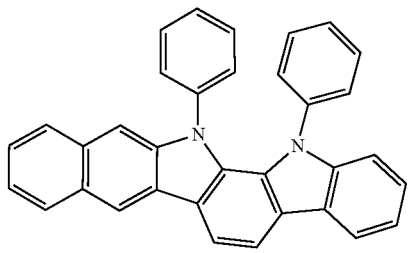
S-32
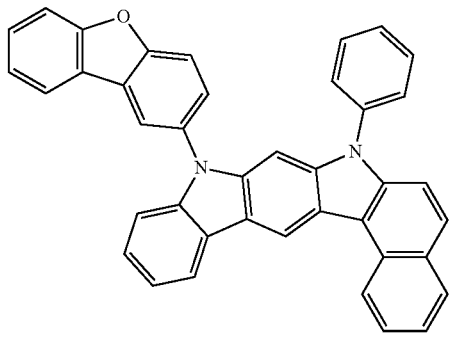
S-33
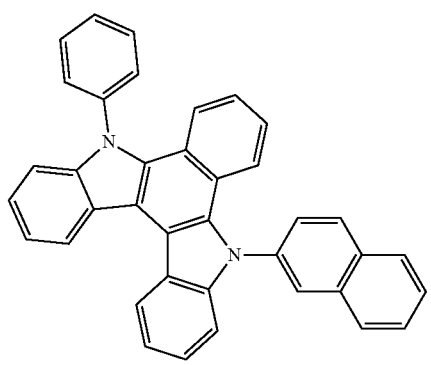

S-34
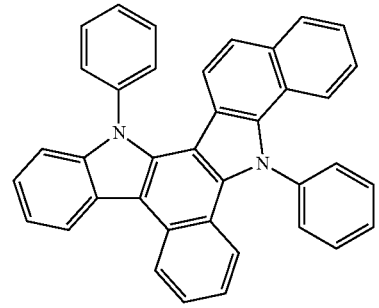
S-35
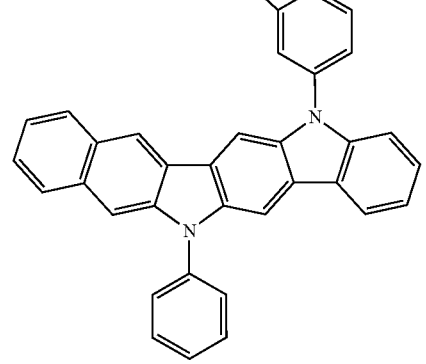
S-36
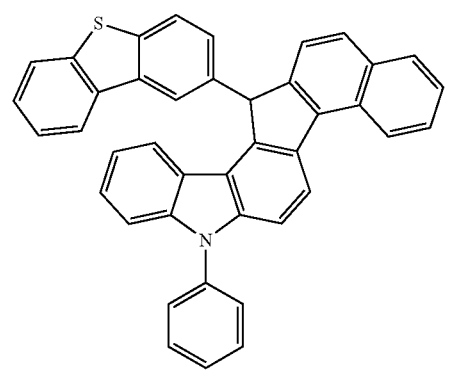
S-37
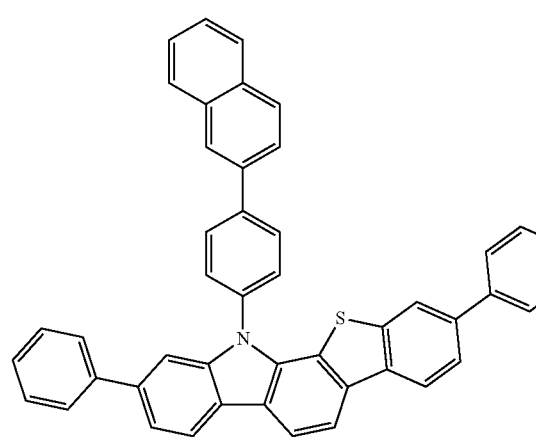
S-38
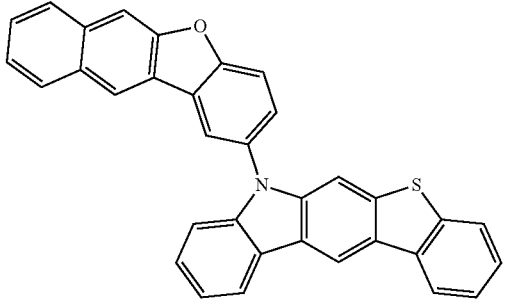
S-39
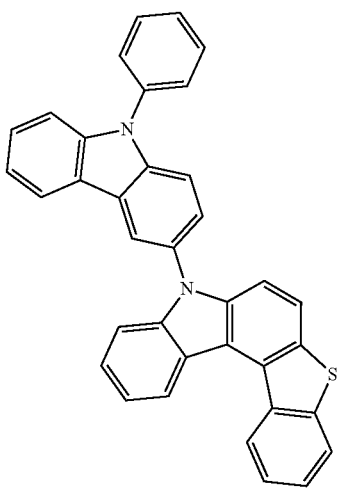
S-40
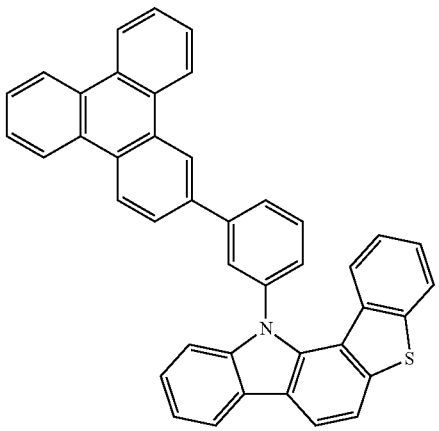

-continued
S-41
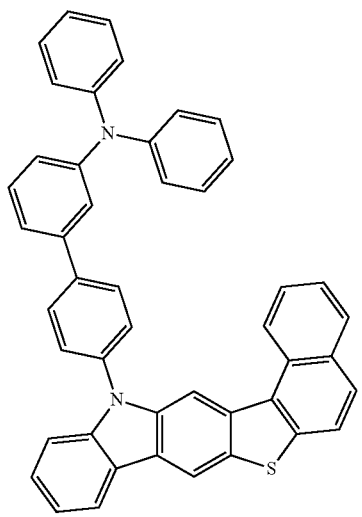
S-42
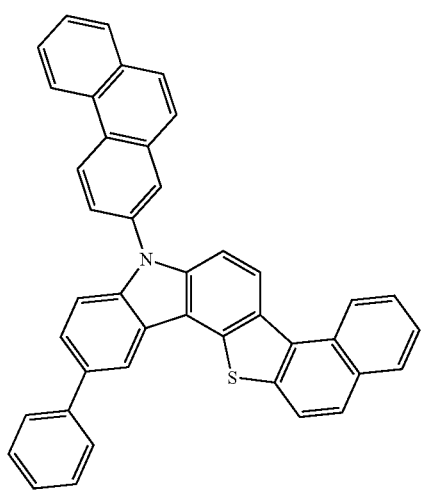
S-43
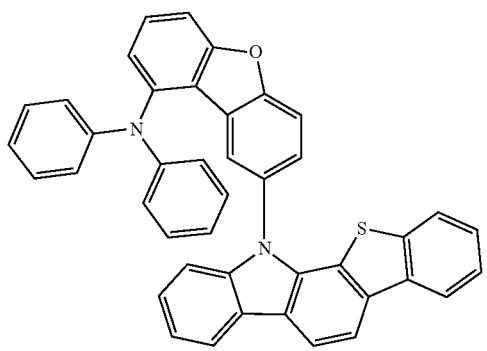
-continued
S-44
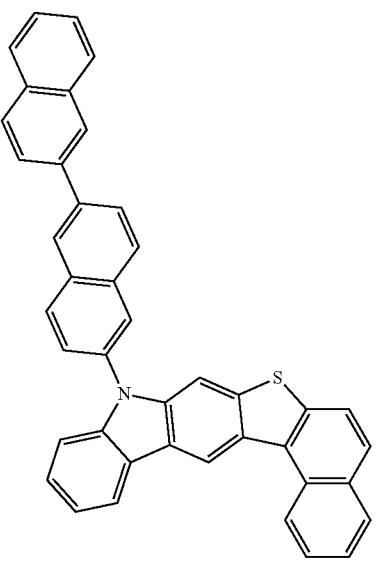
S-45
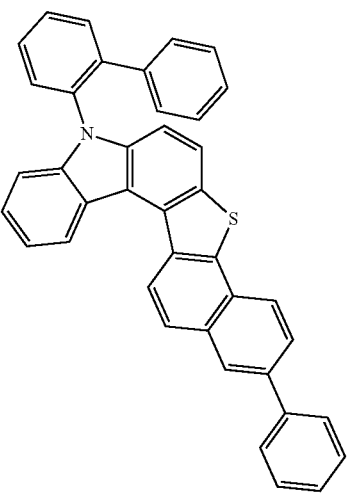
S-46
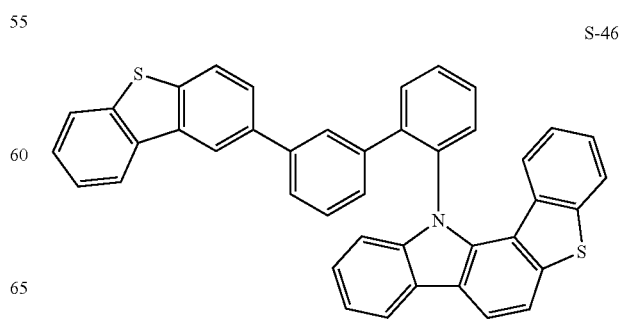

S-47
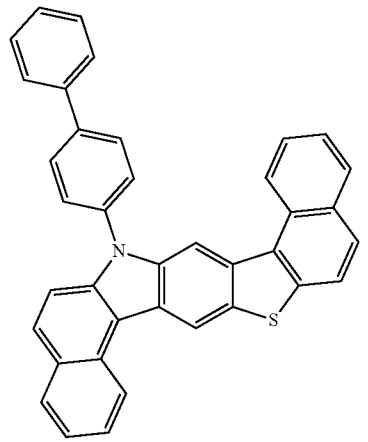
S-48
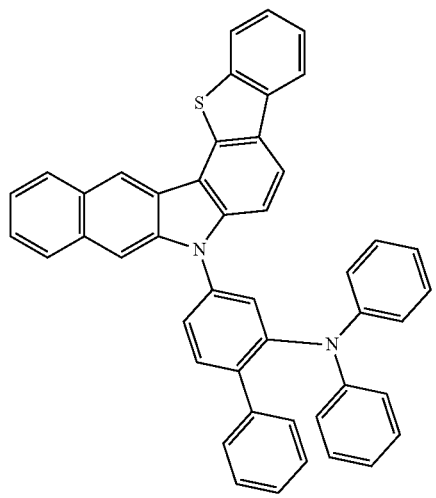
S-49
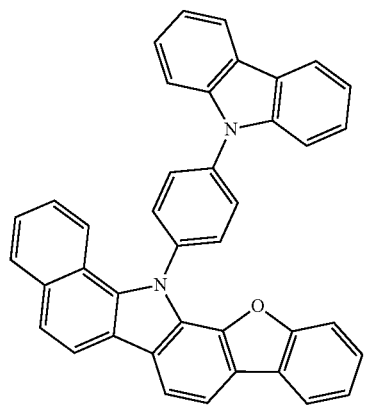
S-50
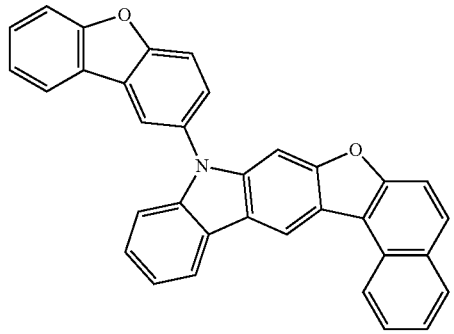
S-51
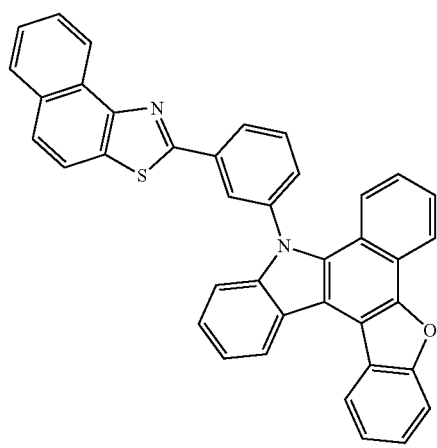
S-52
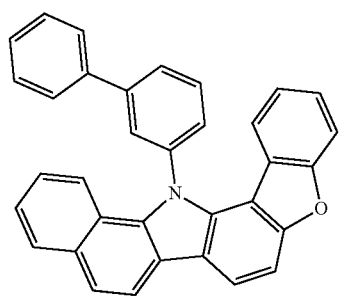
S-53
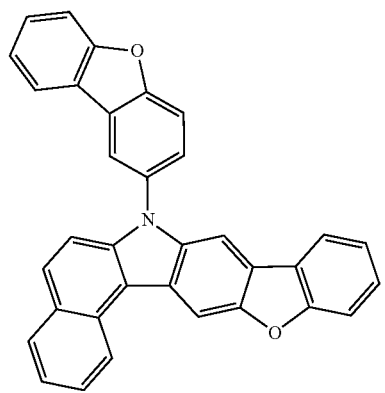

-continued
S-54
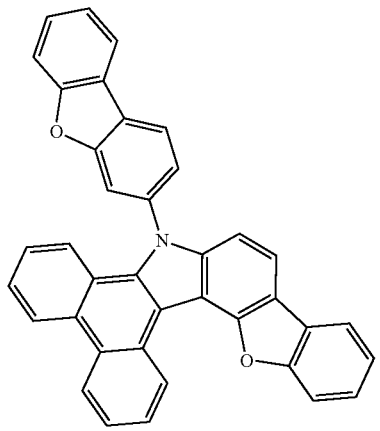
S-55
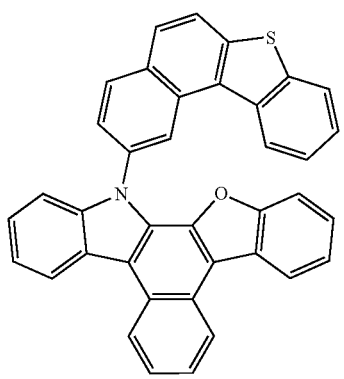
S-56
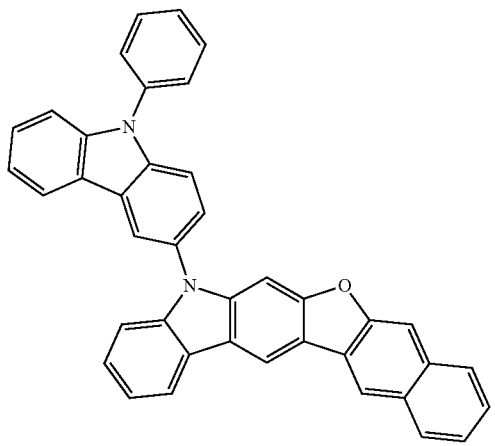
S-57
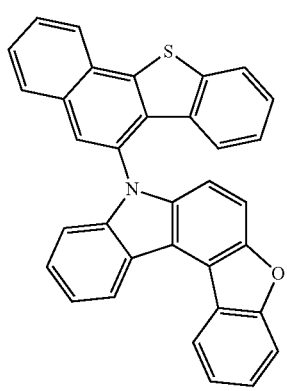
-continued
S-58
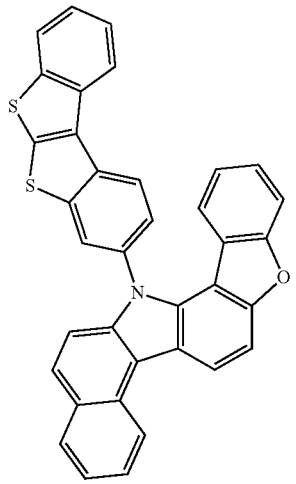
S-59
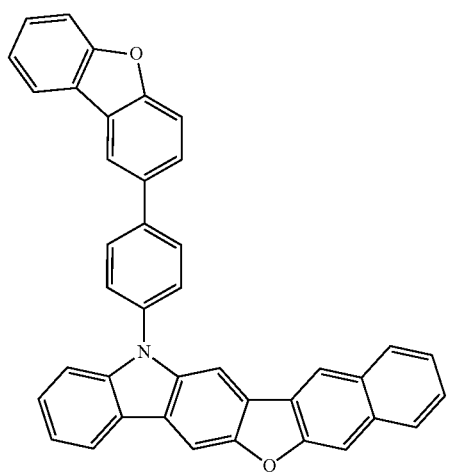
S-60
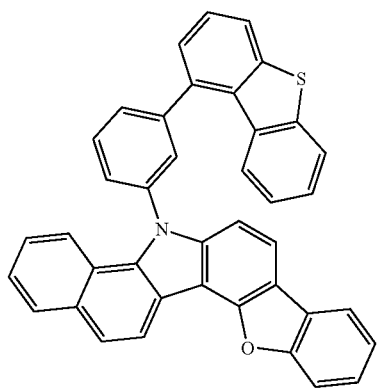

S-61
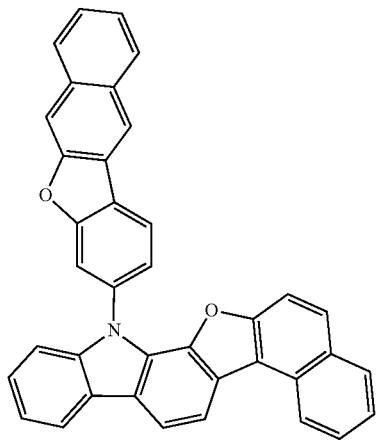
S-62
S-63
S-64
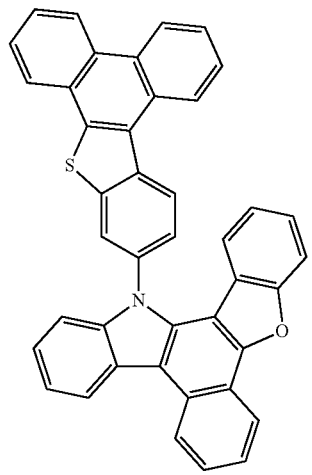
S-65
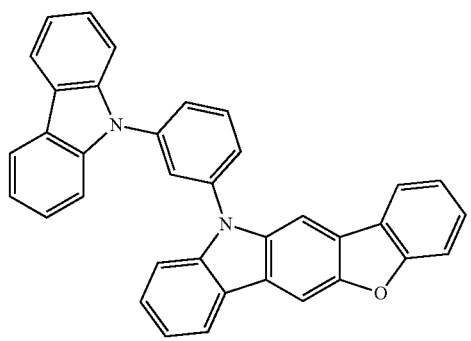
S-66
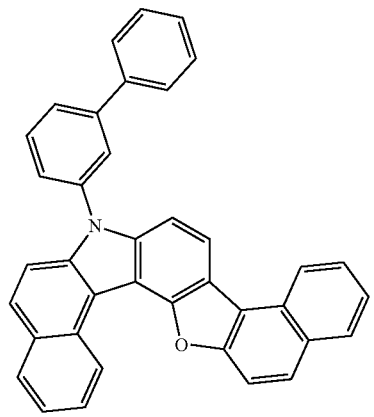
S-67
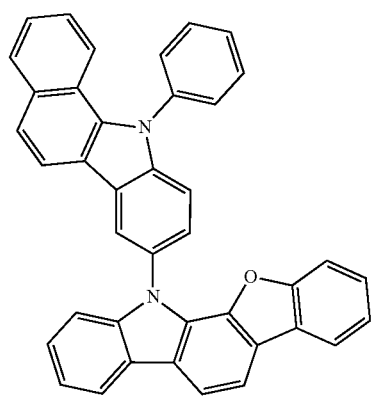

S-68
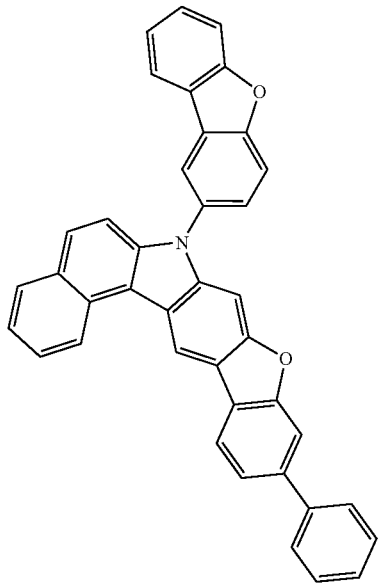
S-69
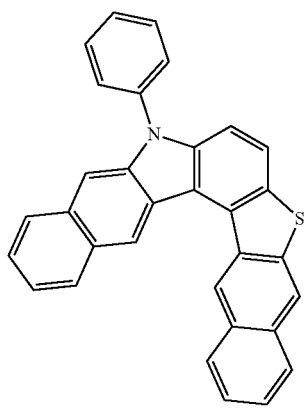
S-70
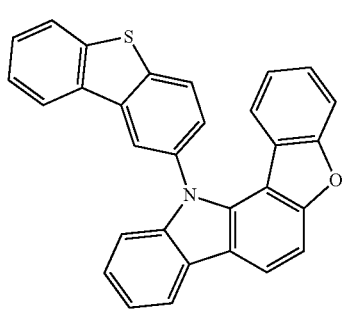
S-71
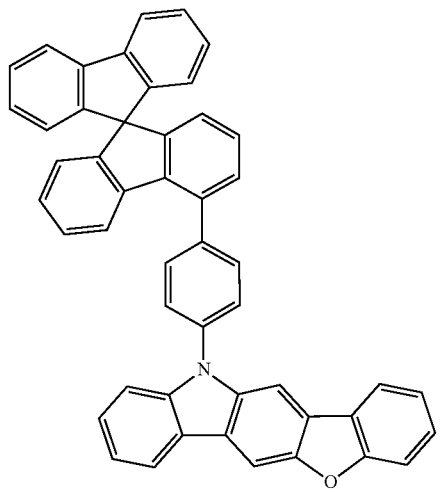
S-72
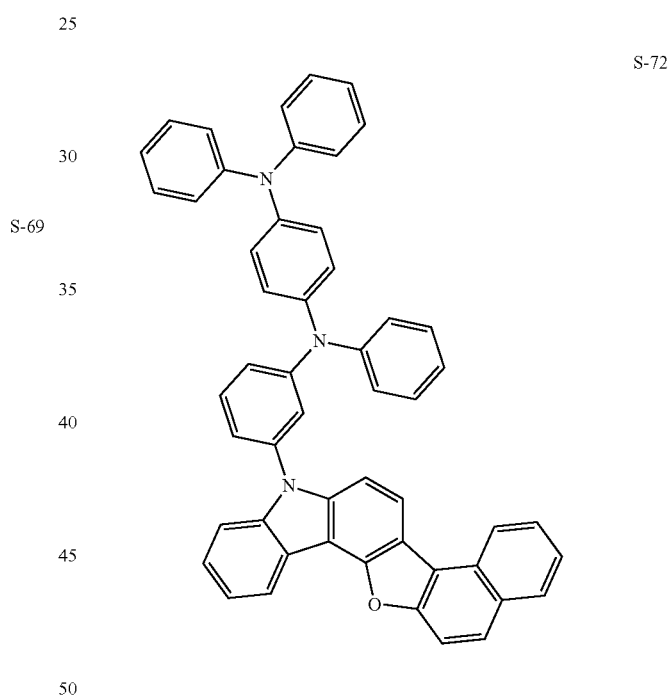
S-73
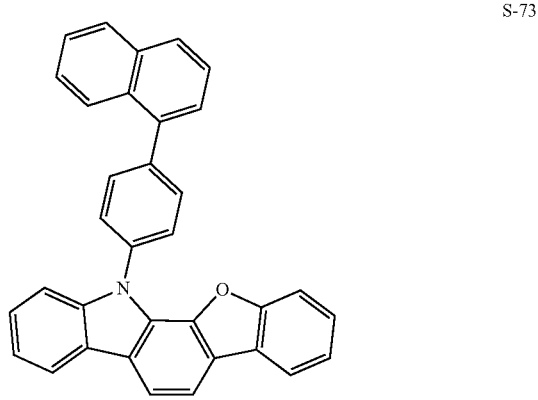

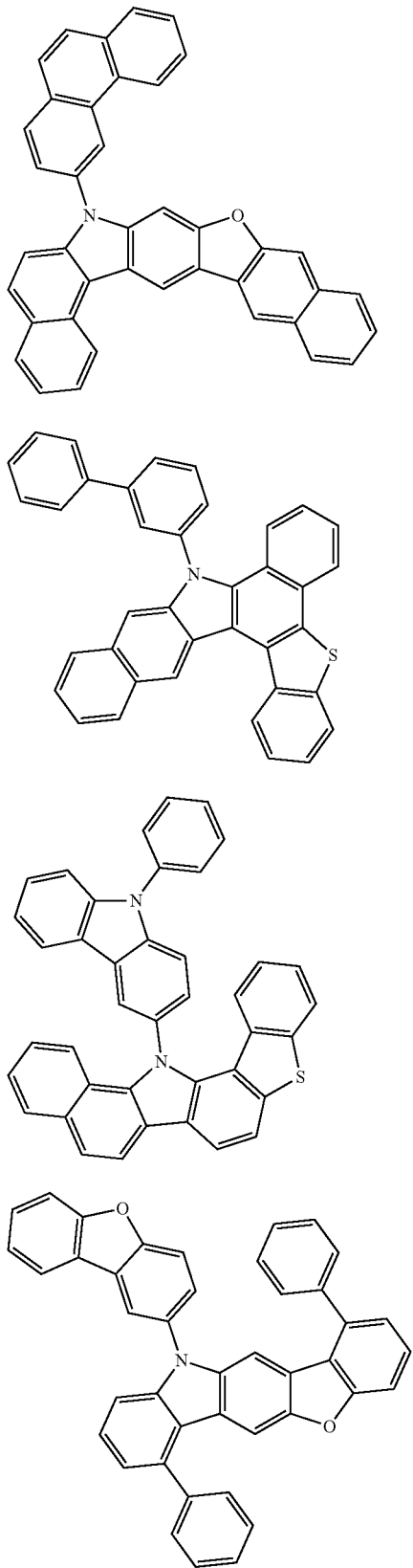
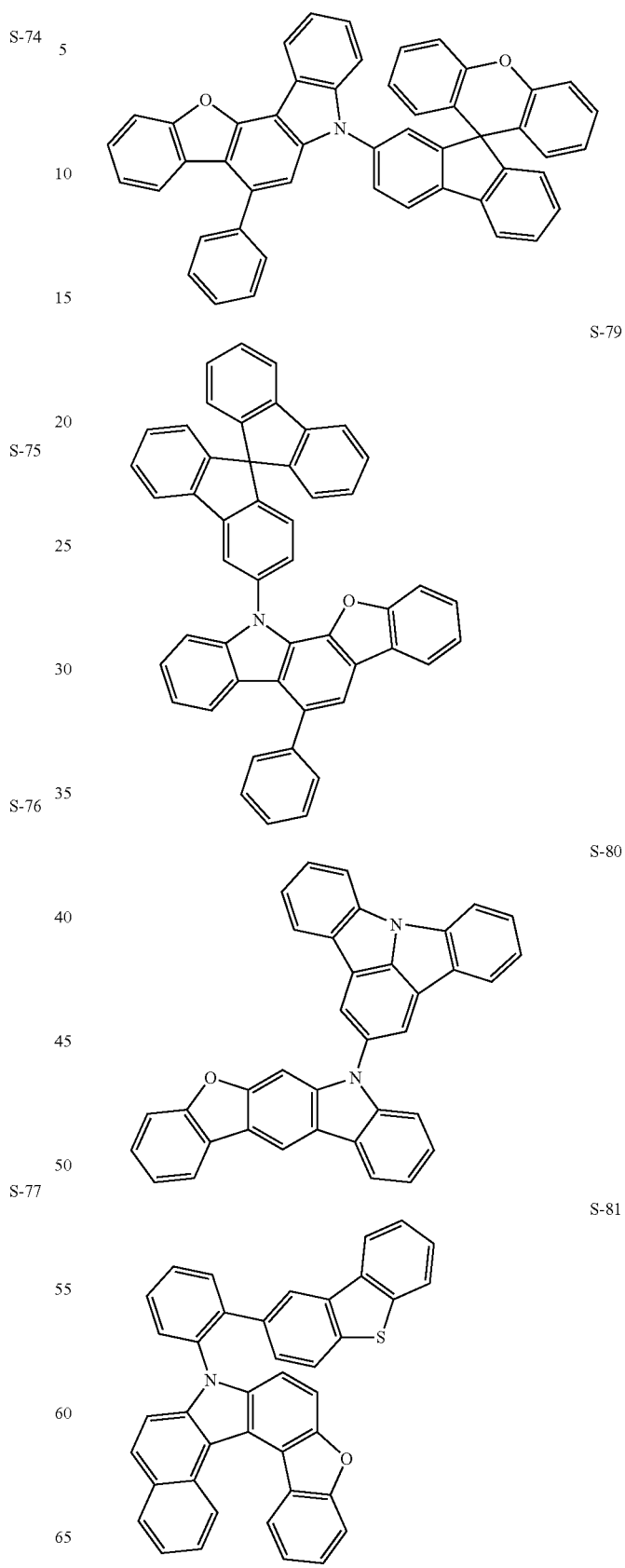

S-82
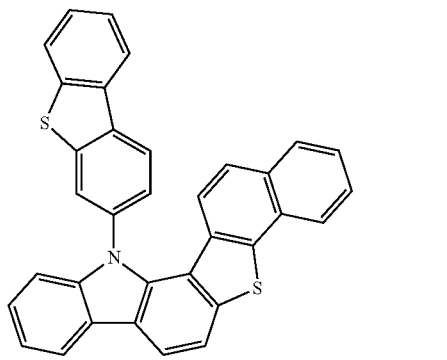
S-83
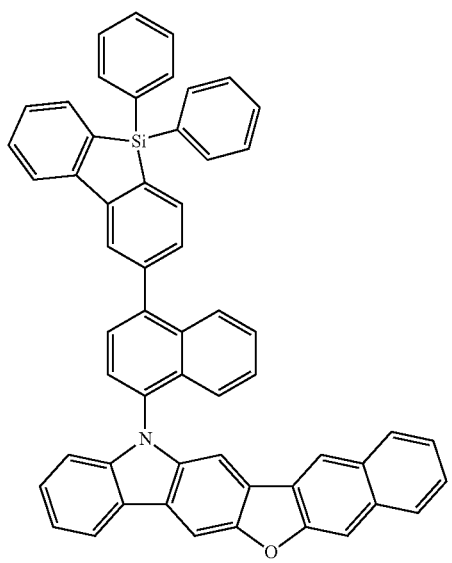
S-84
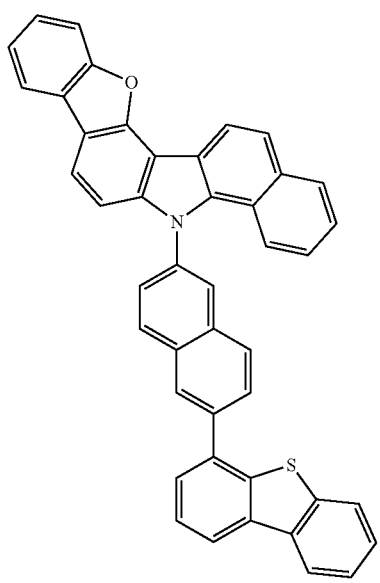
S-85
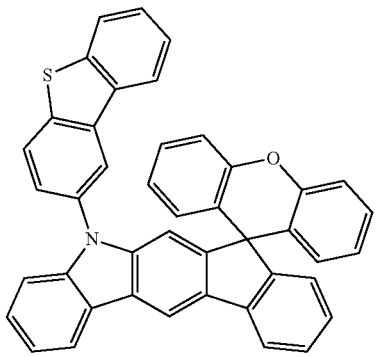
S-86
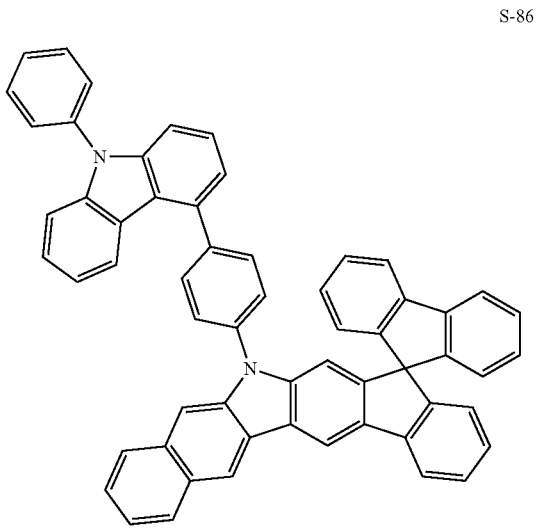
S-87
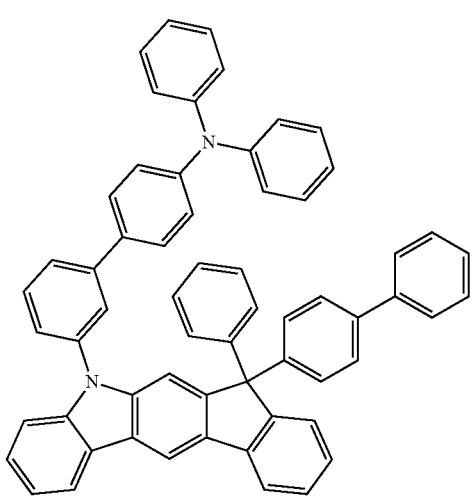

-continued
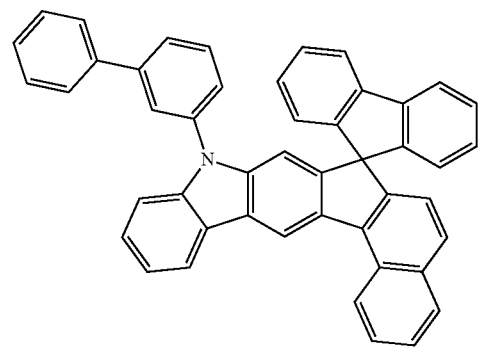
S-88
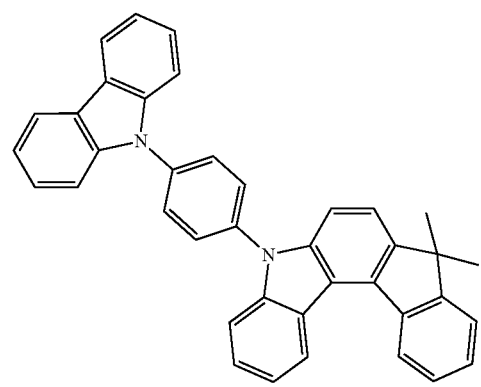
S-89
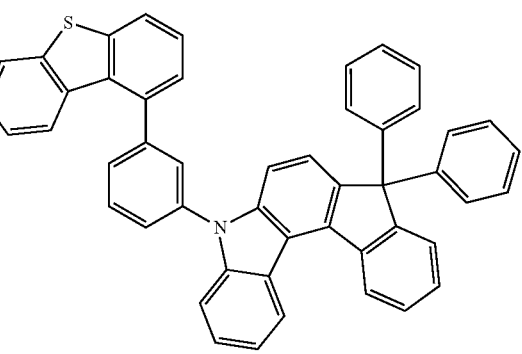
S-90
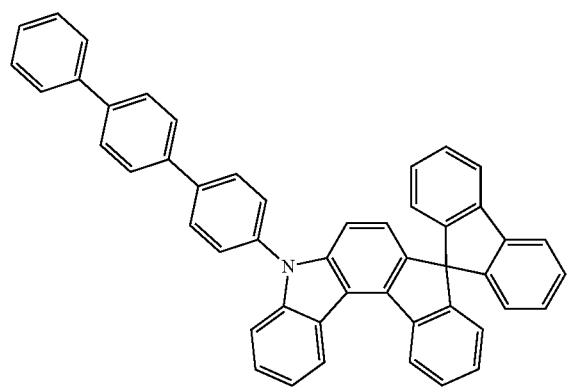
S-91
-continued
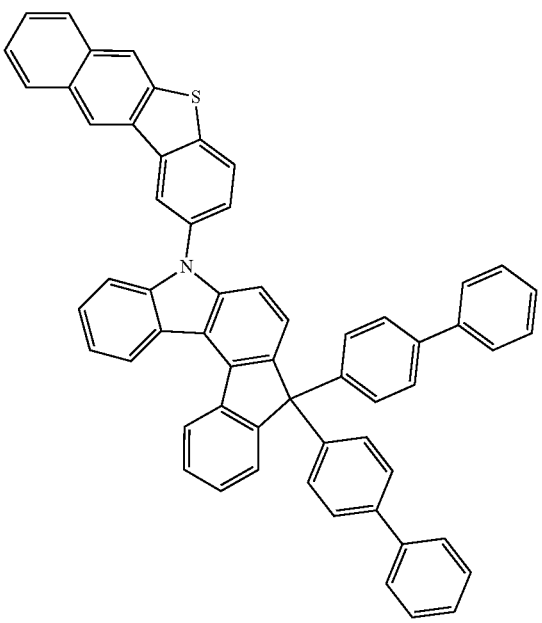
S-92
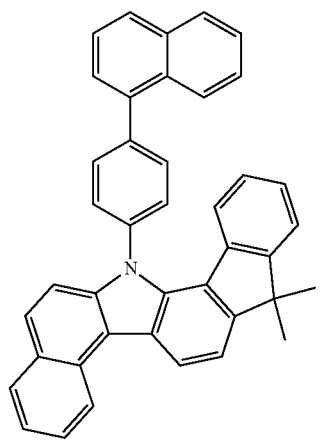
S-93
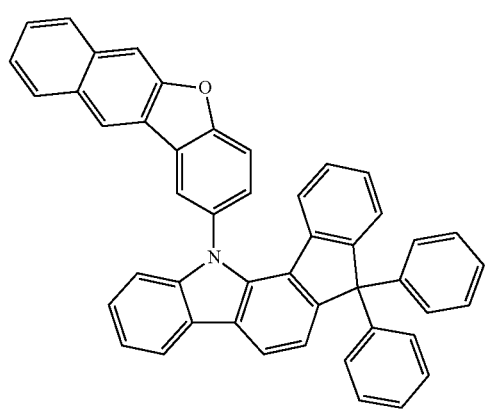
S-94

S-95
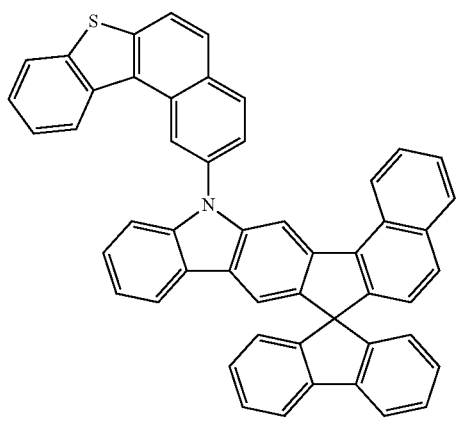
S-96
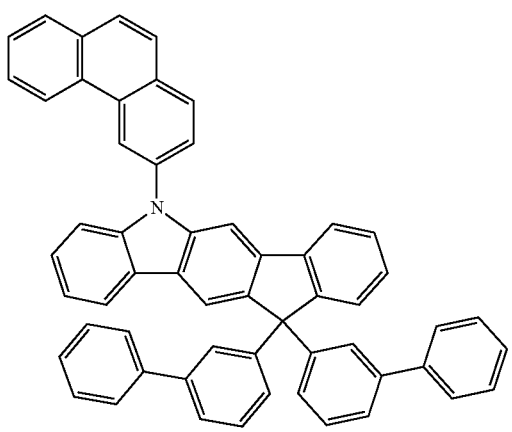
S-97
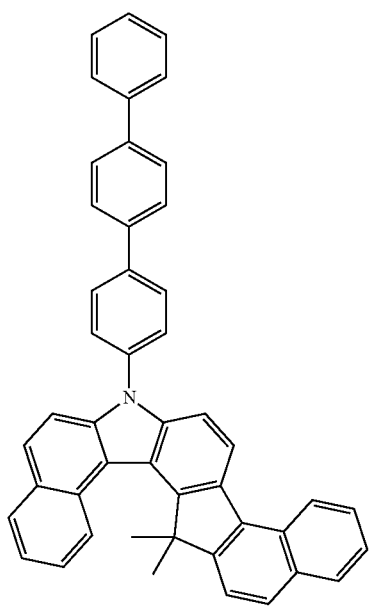
S-98
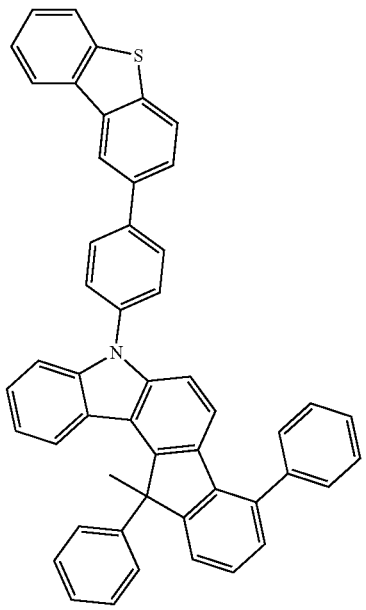
S-99
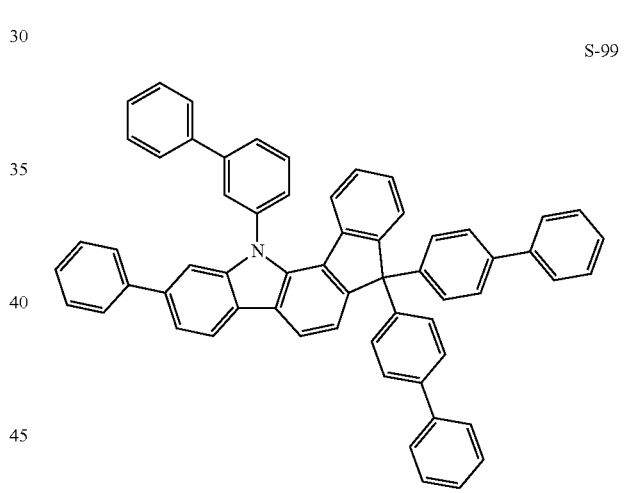
S-100
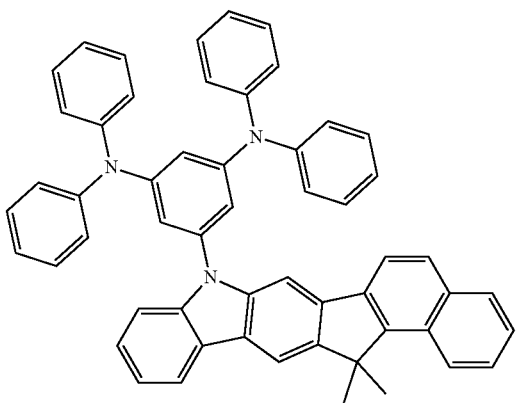

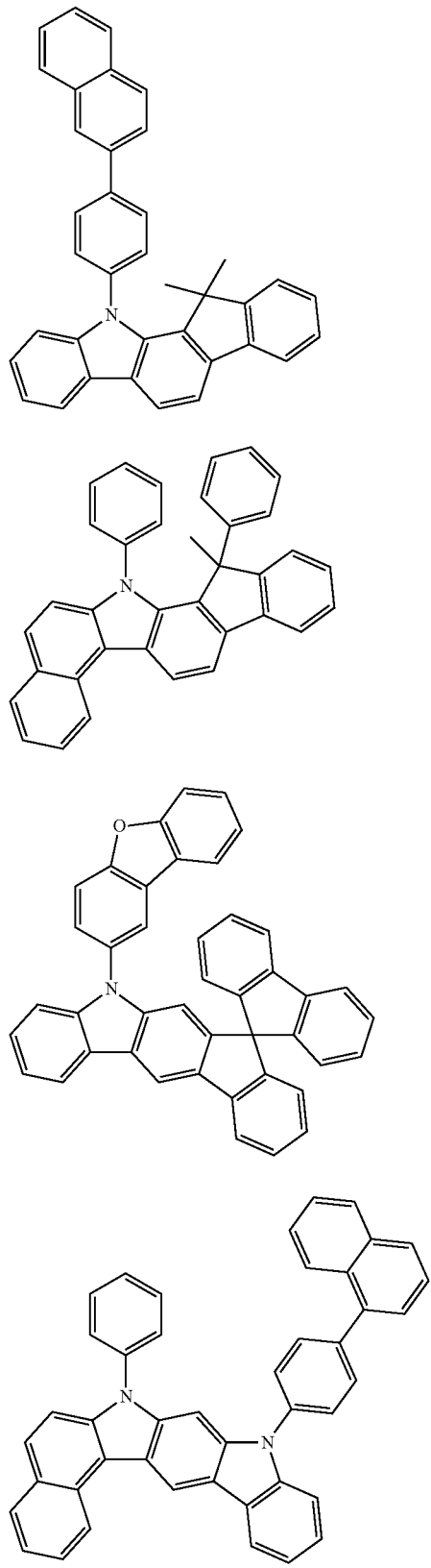
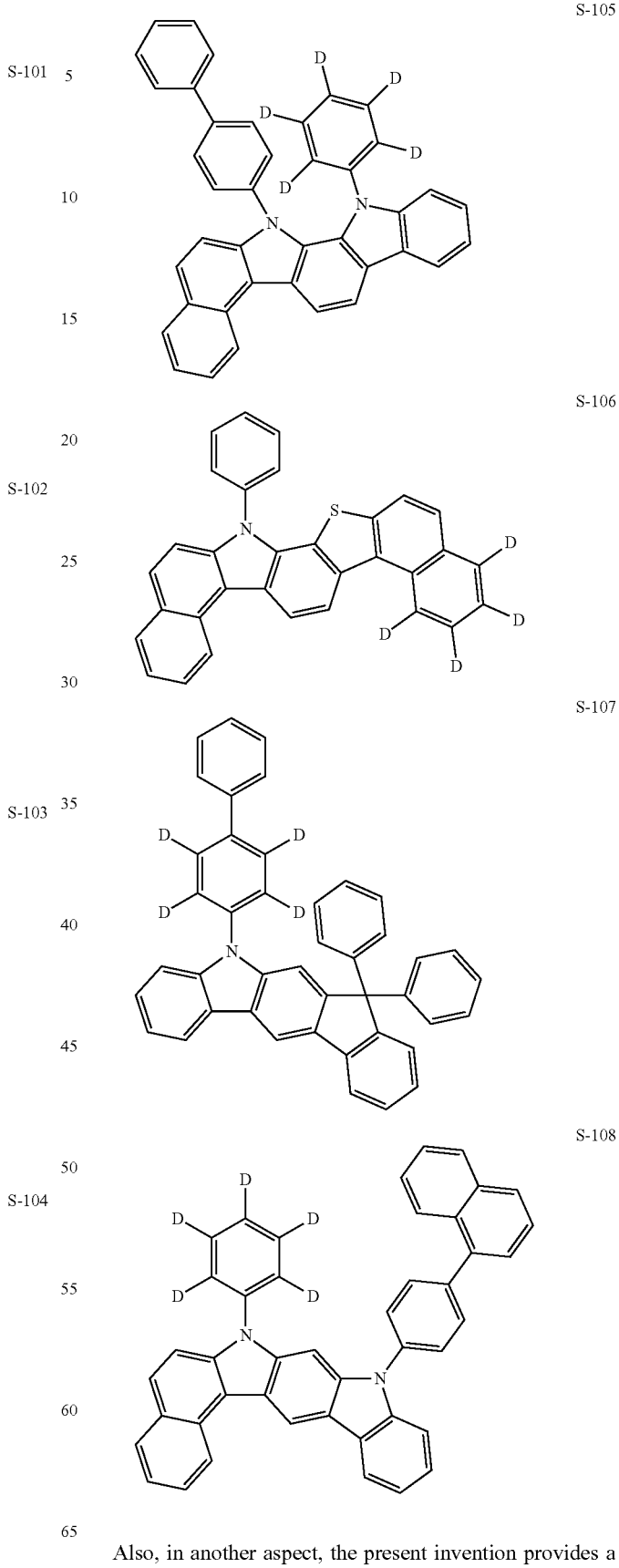
Also, in another aspect, the present invention provides a compound represented by Formula 1.

Formula 1
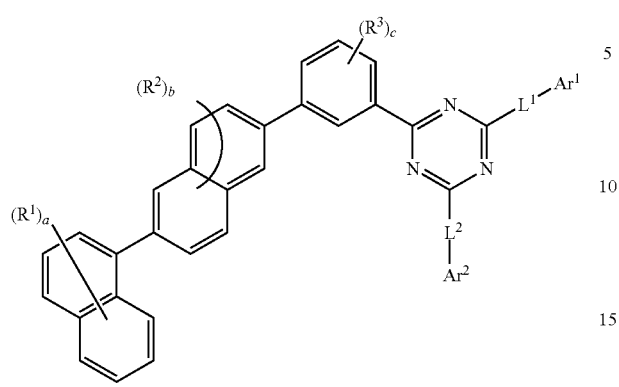
Formula 1-1

Wherein, $L^1$, $L^2$, $Ar^1$, $Ar^2$, $R^1$, $R^2$, $R^3$, $R^4$, R, a, b, c, d, e, X and * are the same as defined above.
Also, $Ar^1$ and $Ar^2$ are represented by any one of Formulas (A-1) to (A-11).
Formula (A-1)
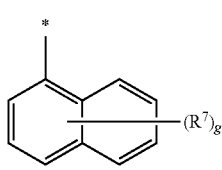
Formula (A-2)
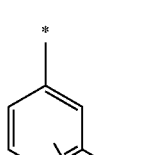
Formula (A-3)
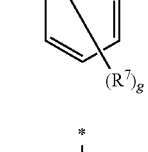
Formula (A-4)
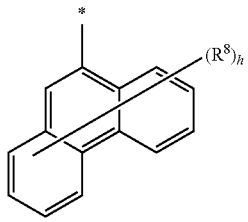
Formula (A-5)
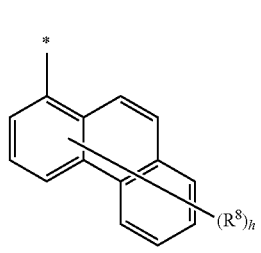
Formula (A-6)
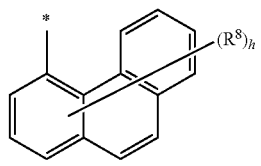
Formula (A-7)
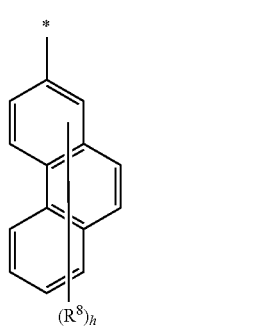
Formula (A-8)
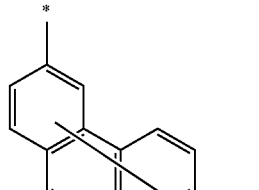
Formula (A-9)
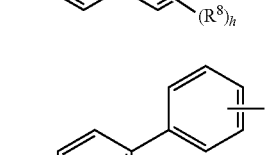
Formula (A-10)
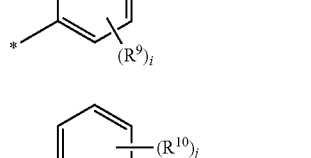
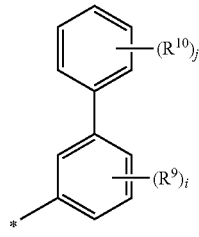

Formula (A-11)

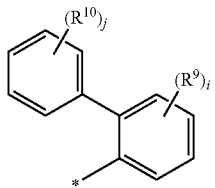

Wherein,
1) R6, R7, R8, R9 and R10 are each the same or different, and each independently represent hydrogen; deuterium; C6-C20 aryl group; C6-C20 aryl group substituted with deuterium;
2) f and j are each independently an integer of 0 to 5, g is an integer of 0 to 7, h is an integer of 0 to 9, i is an integer of 0 to 4,
3) * means the position to be bonded.

Also, Formula 1-1 is represented by any one of Formula Q-1 to Formula Q-5.

Formula Q-1

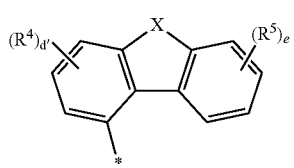

Formula Q-2

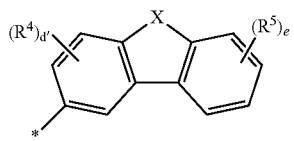

Formula Q-3

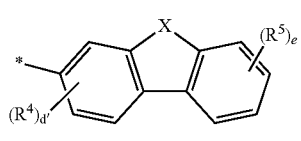

Formula Q-4

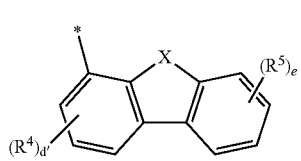

Formula Q-5

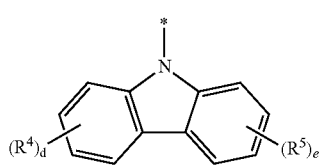

Wherein,
X, R4, R5, d, e and * are the same as defined above,
d' is an integer of 0 to 3.

Also, Formula 1 is represented by any one of the following compounds P-1 to P-104.

P-1

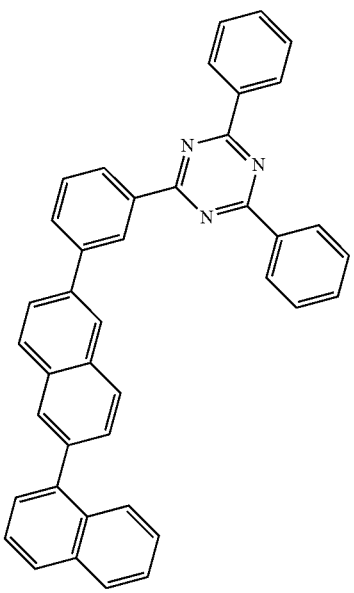

P-2

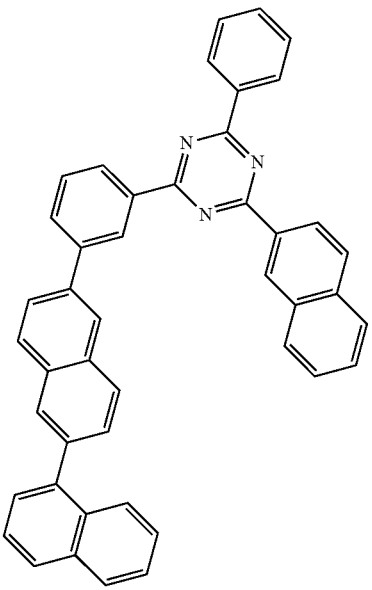

P-3
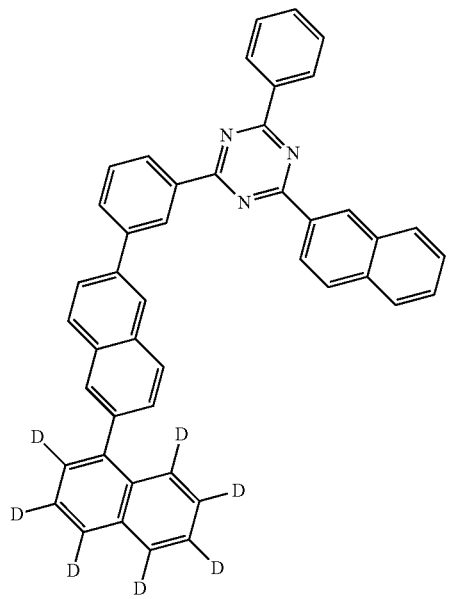
P-4
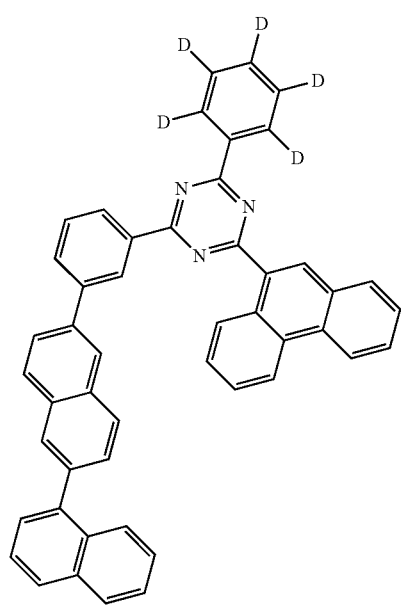
P-5
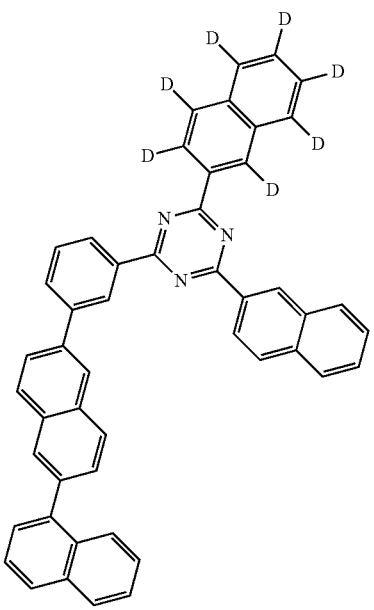
P-6
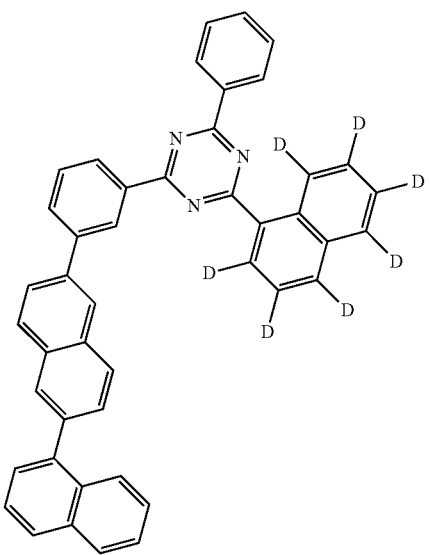

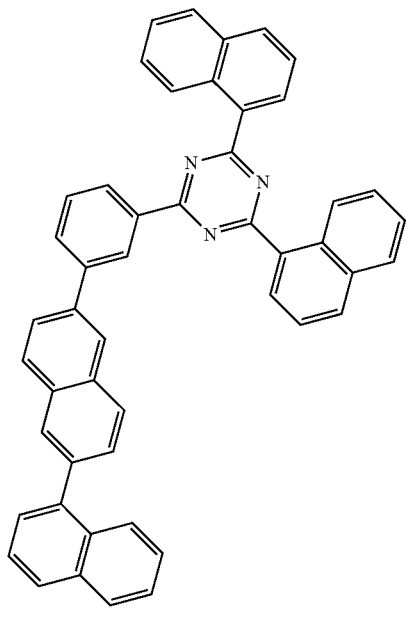
P-7
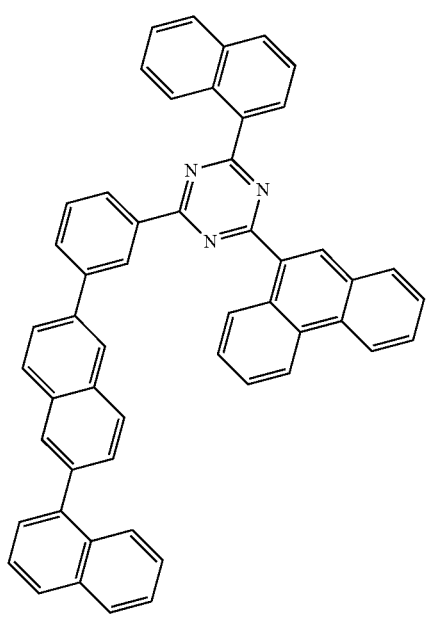
P-8
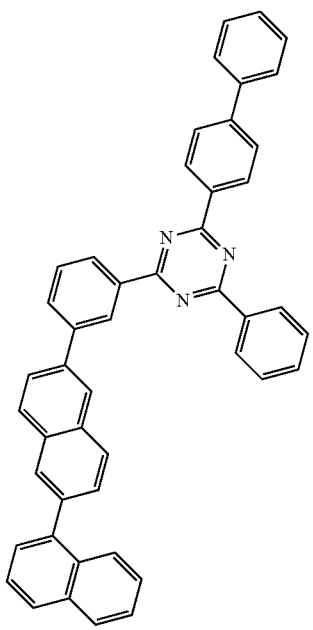
P-9
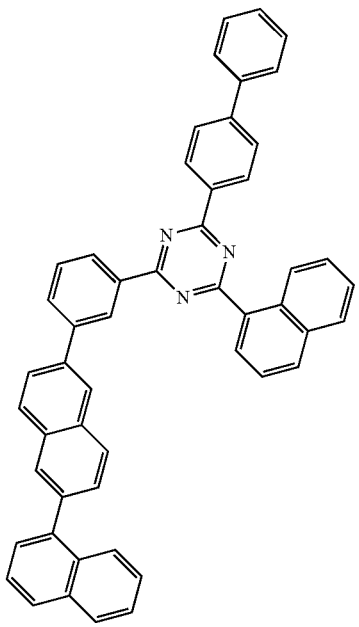
P-10

P-11
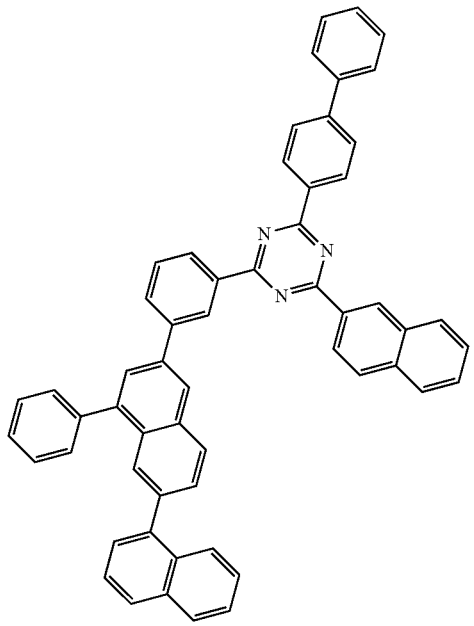
P-12
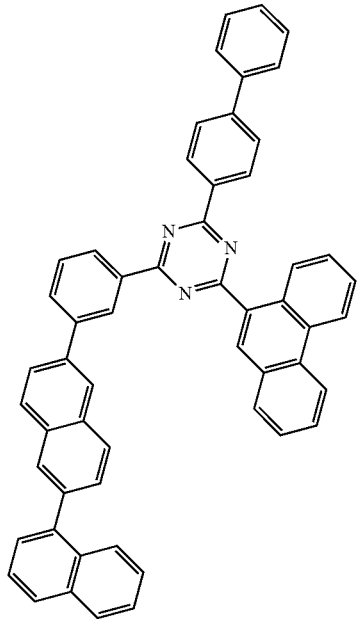
P-13
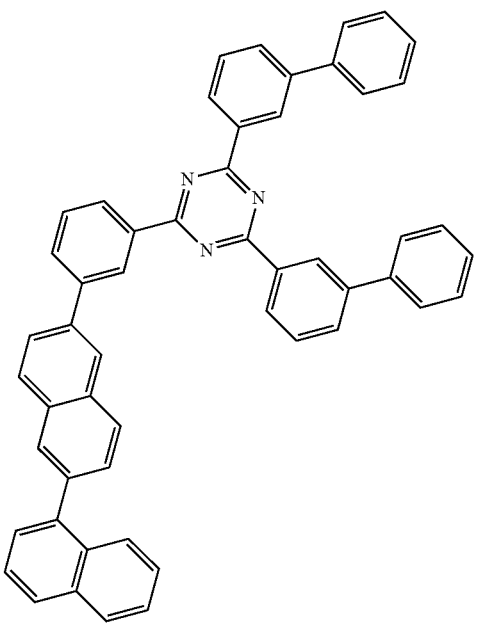
P-14
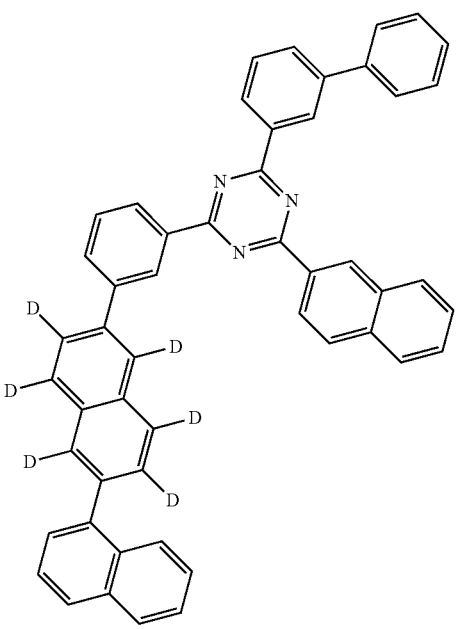

P-15
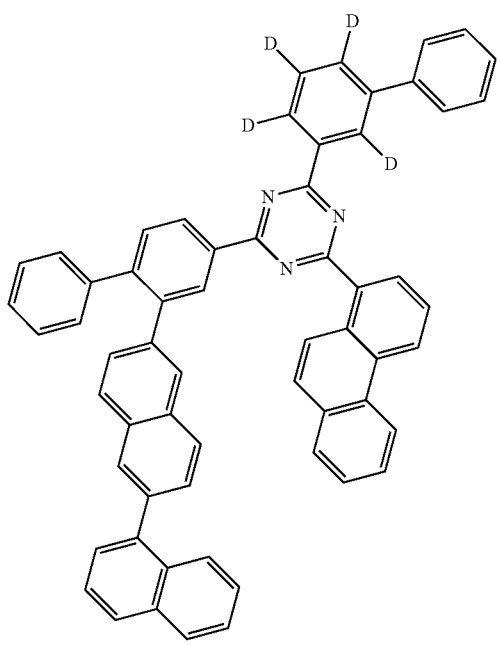
P-16
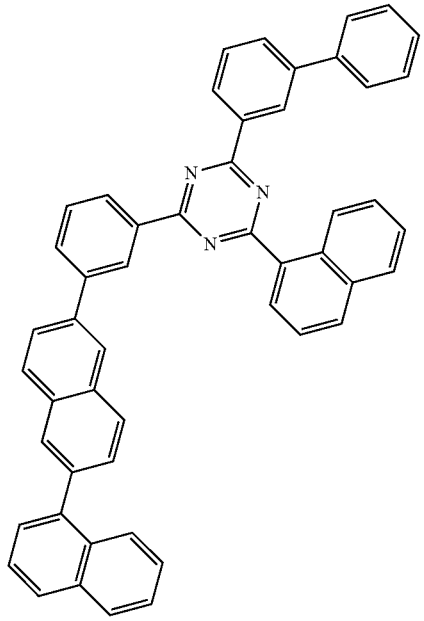
P-17
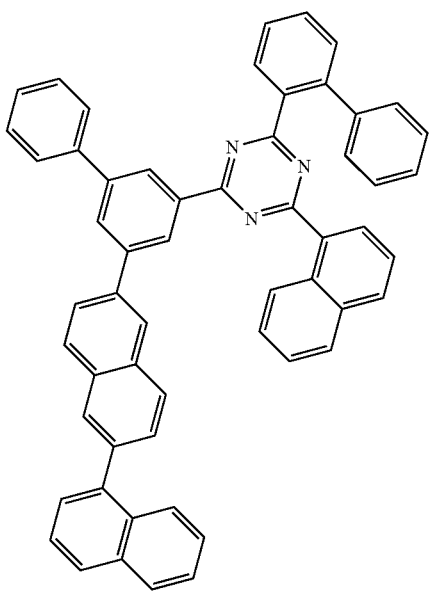
P-18
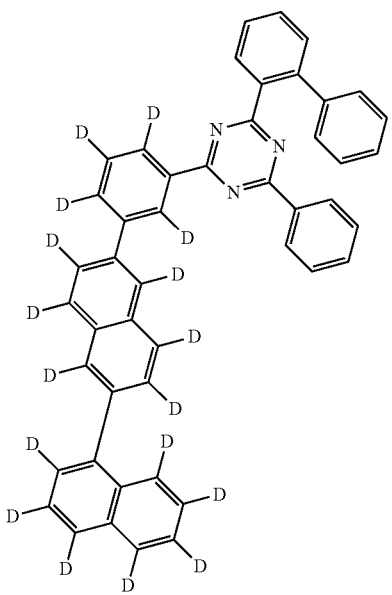

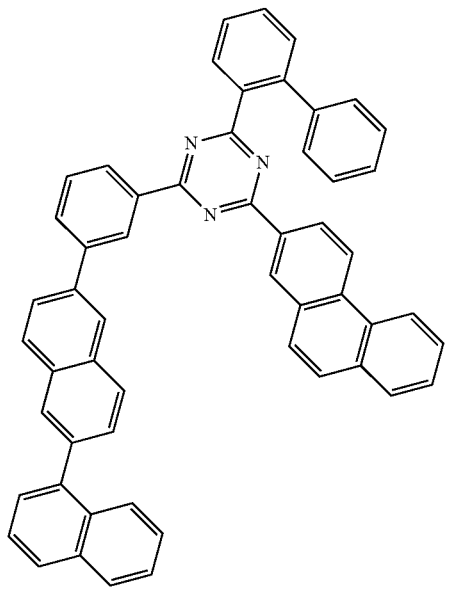
P-19
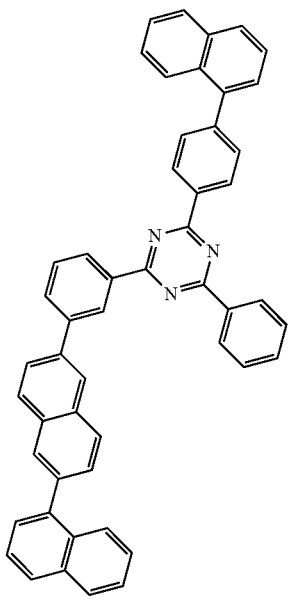
P-20
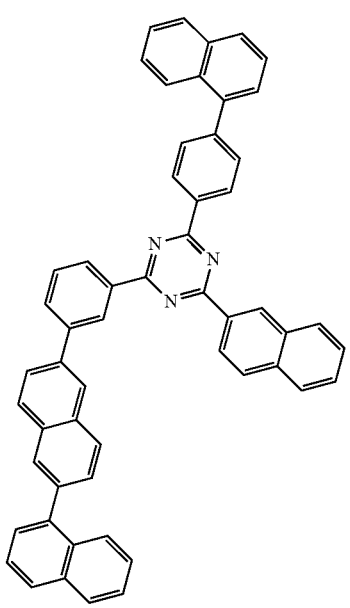
P-21
P-22

P-23
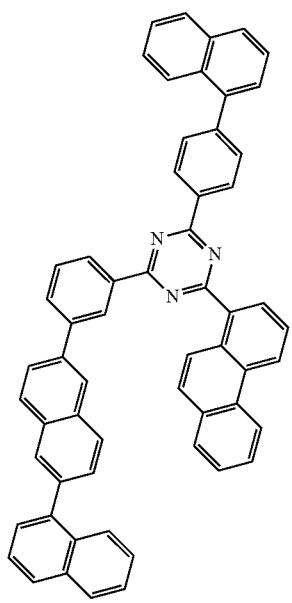
P-24
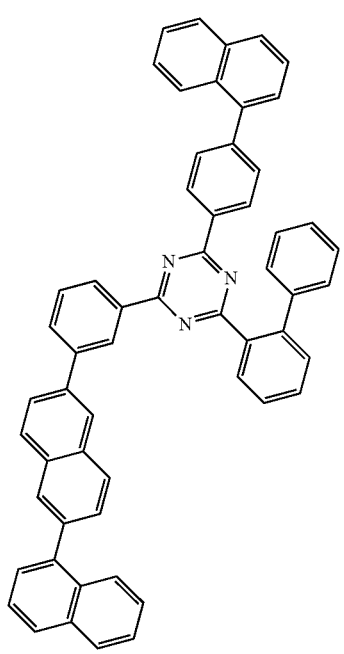
P-25
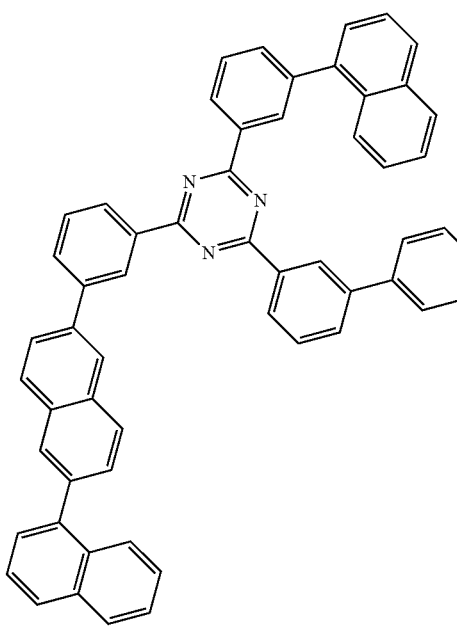
P-26

P-27
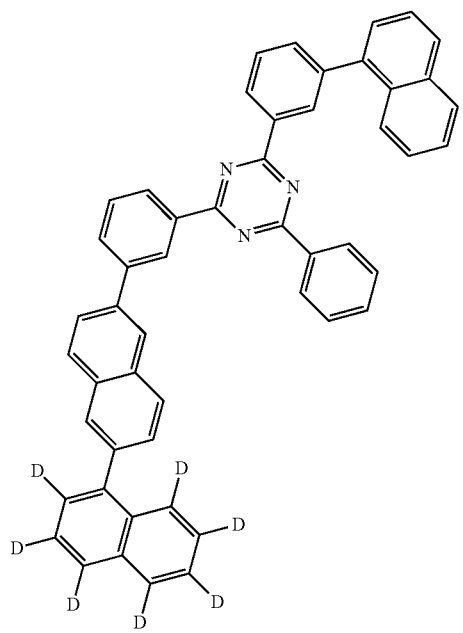
P-29
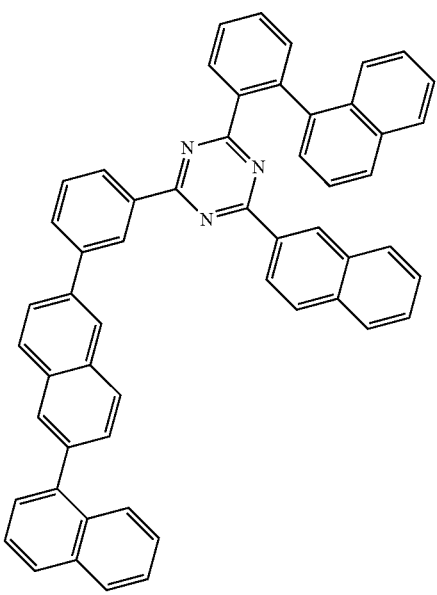
P-28
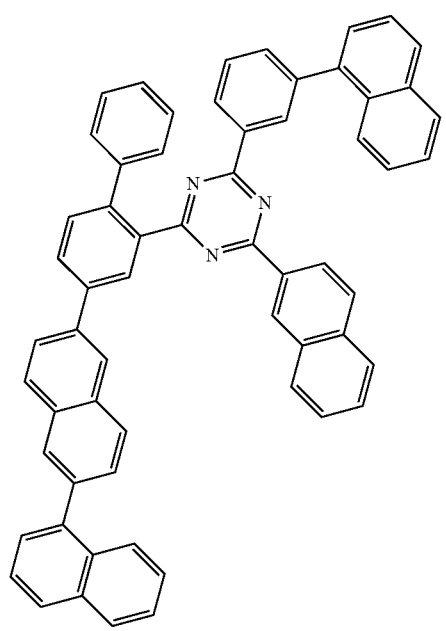
P-30
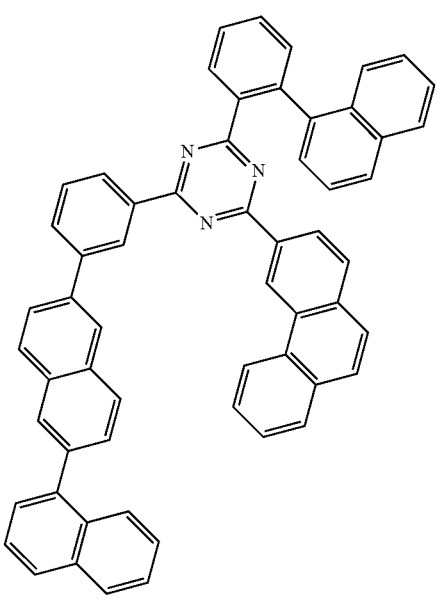

P-31
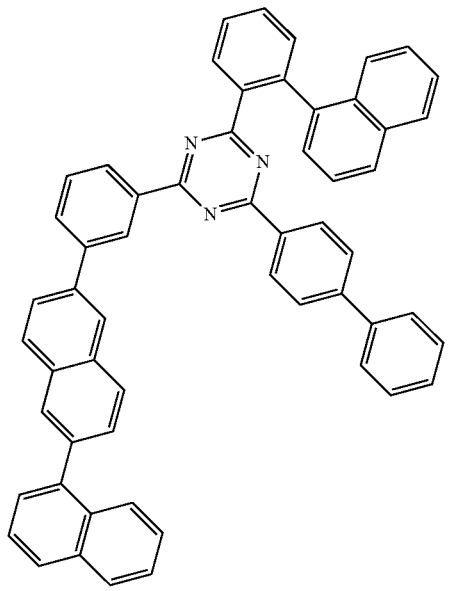
P-32
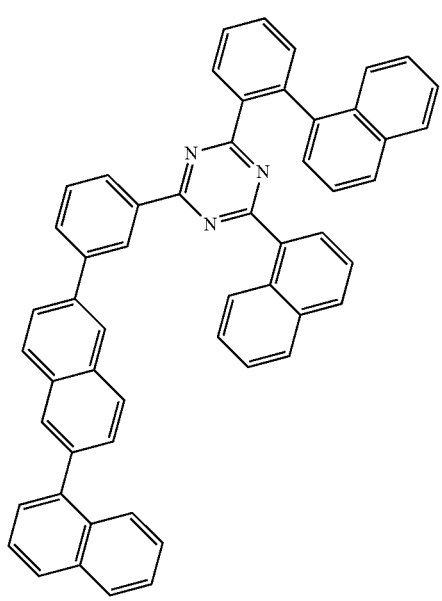
P-33
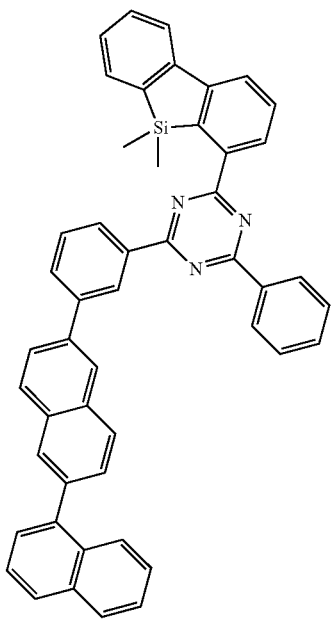
P-34
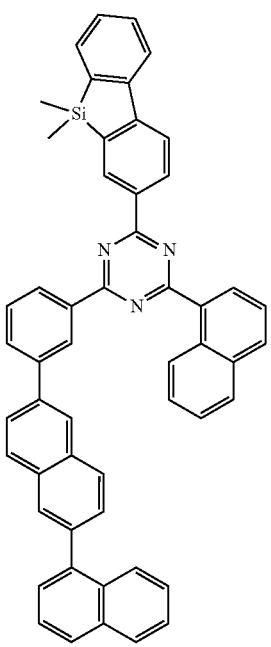

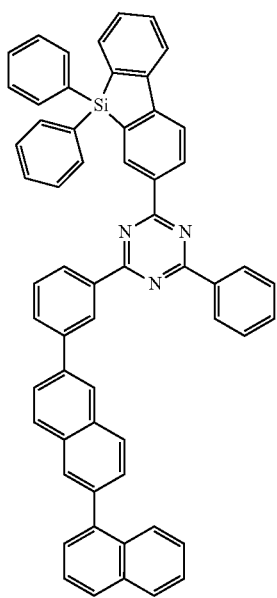
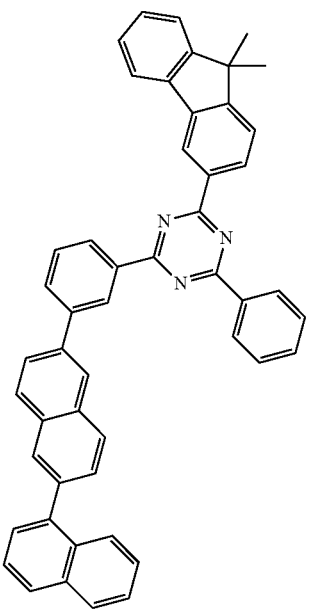
P-35
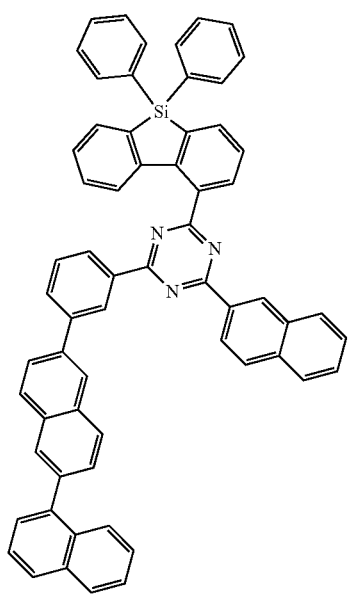
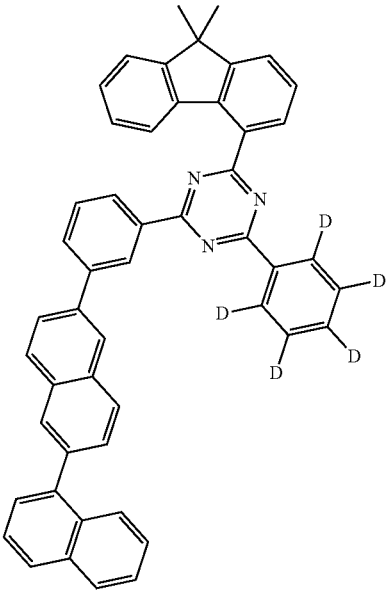
P-36
P-37
P-38

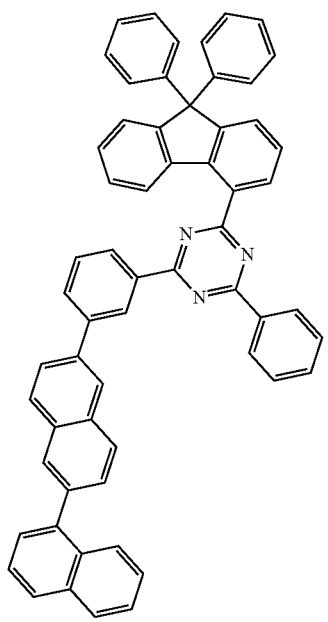
P-39
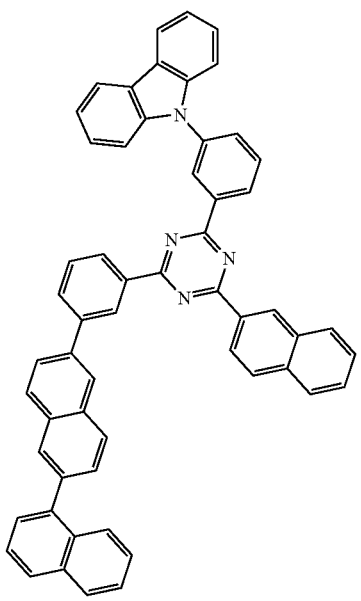
P-41
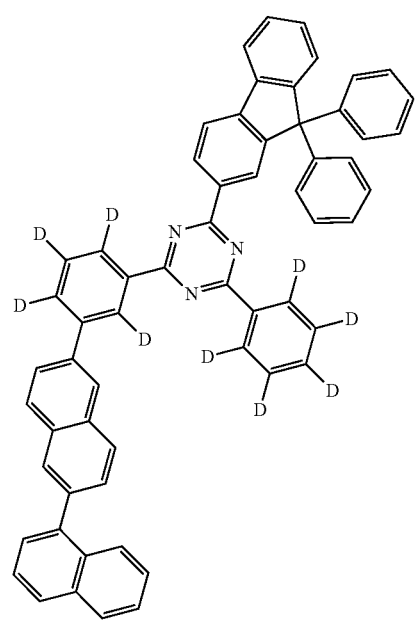
P-40
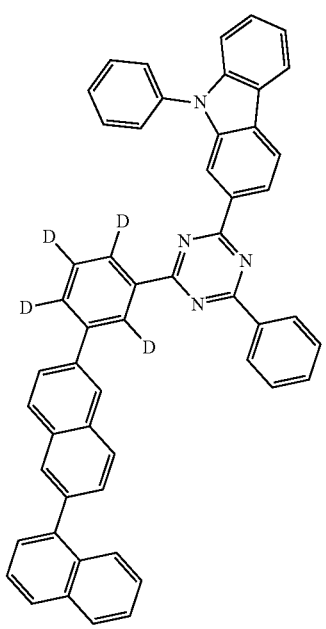
P-42

P-43
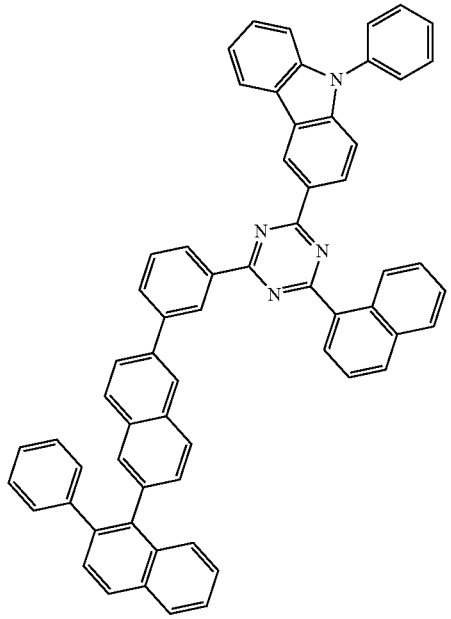
P-44
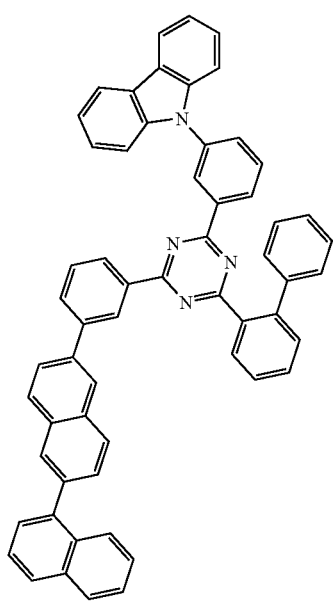
P-45
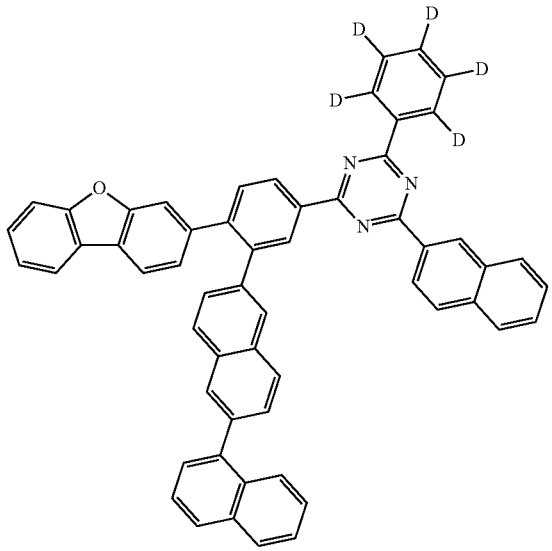
P-46
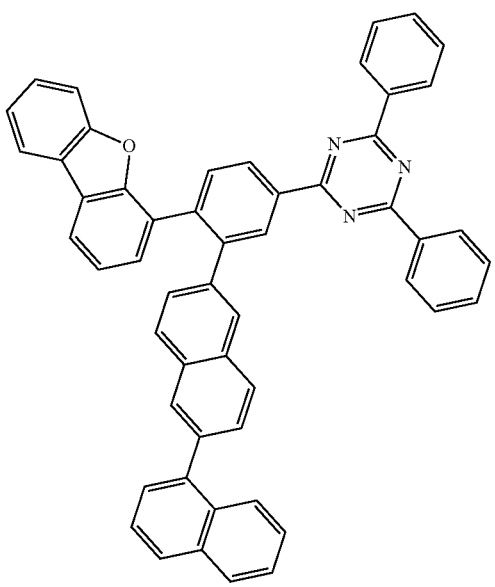

P-47
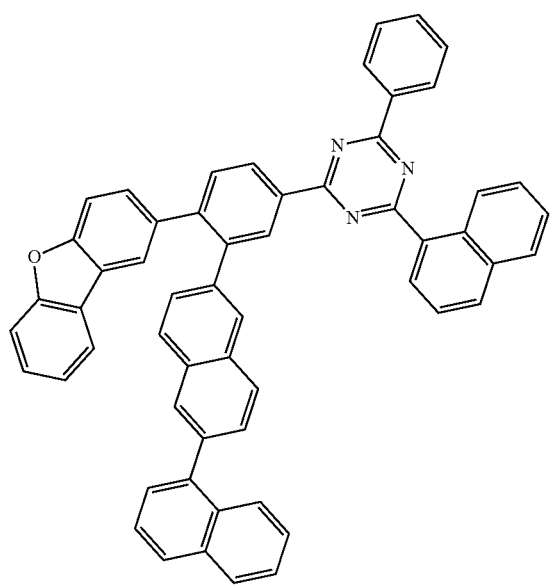
P-48
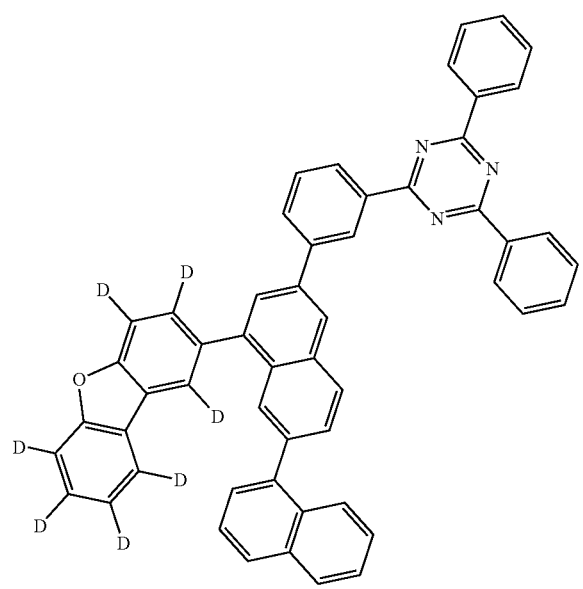
P-49
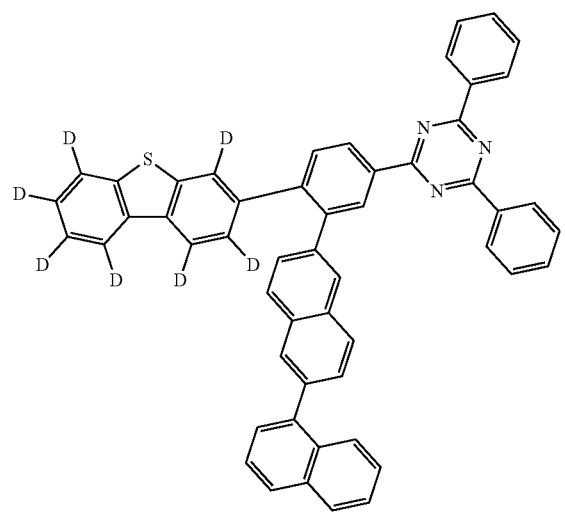
P-50
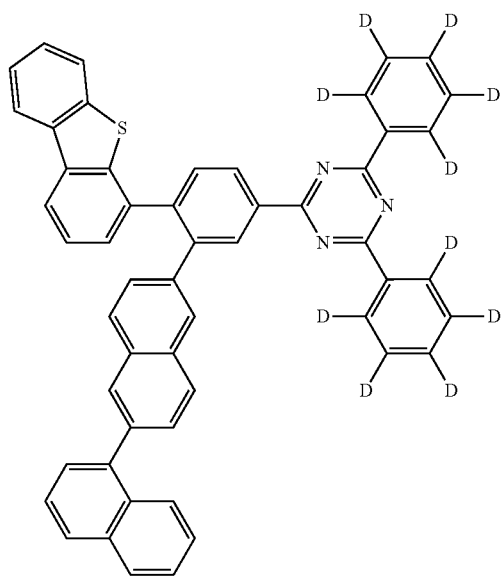

P-51
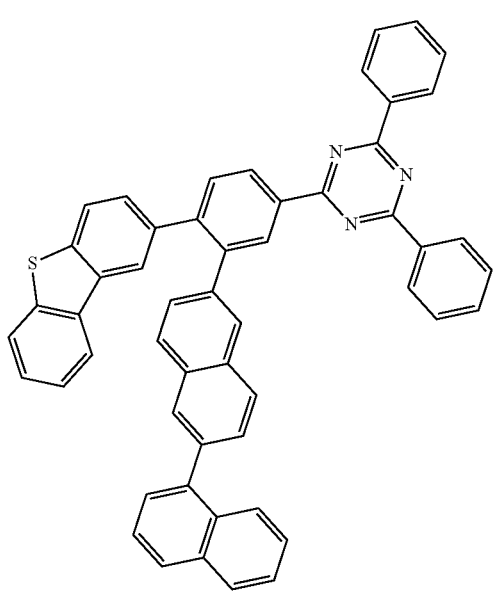
P-52
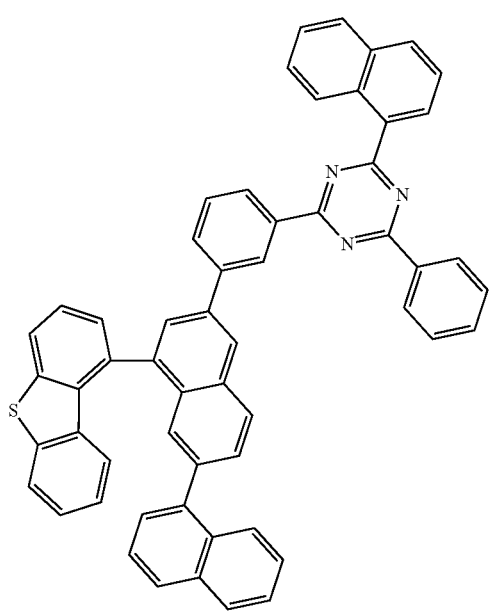
P-53
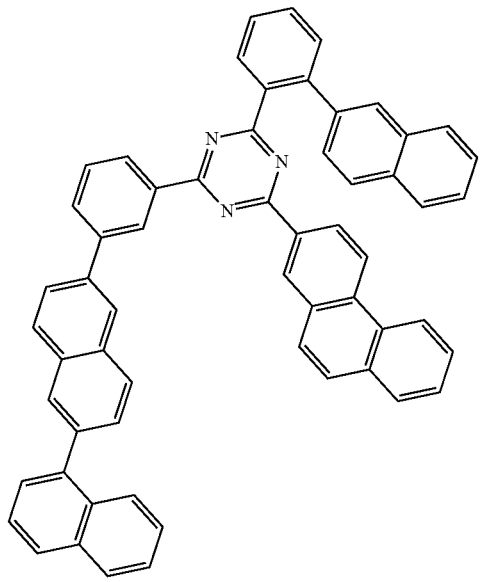
P-54
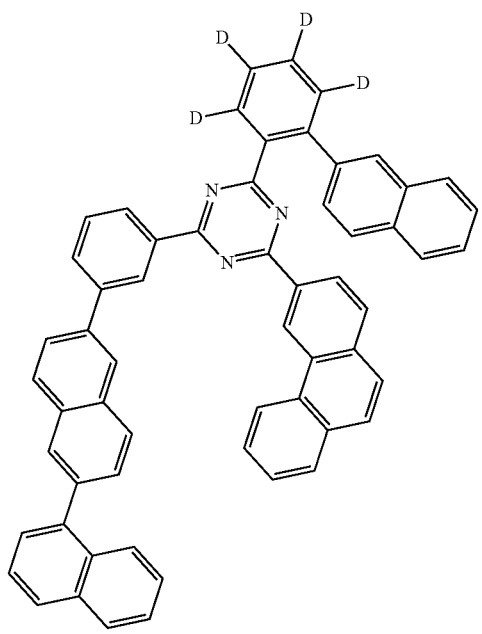

P-55
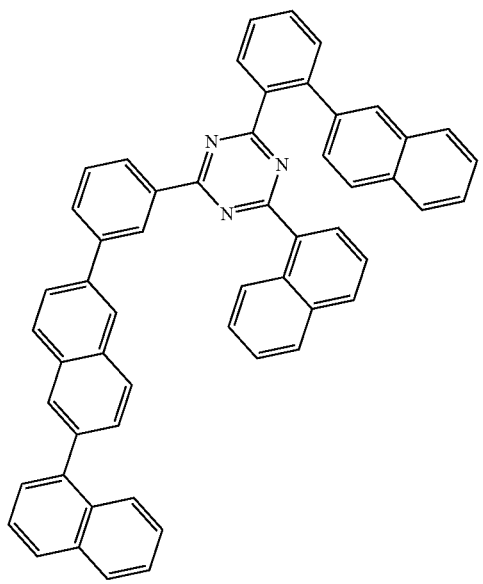
P-56
P-57
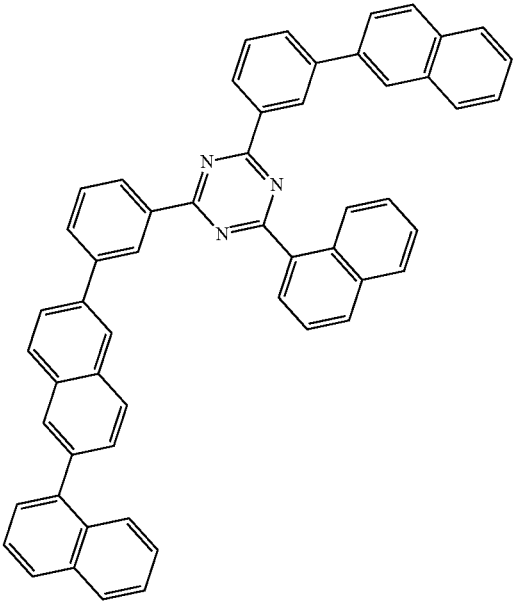
P-58
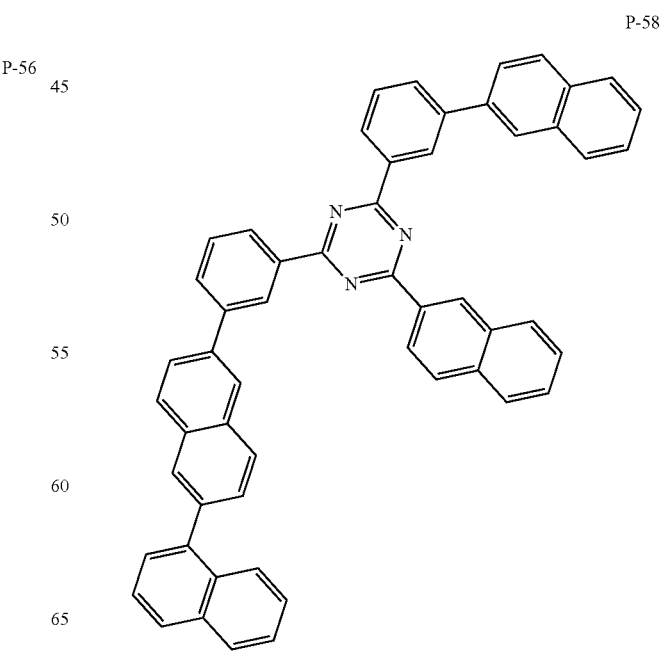

P-59
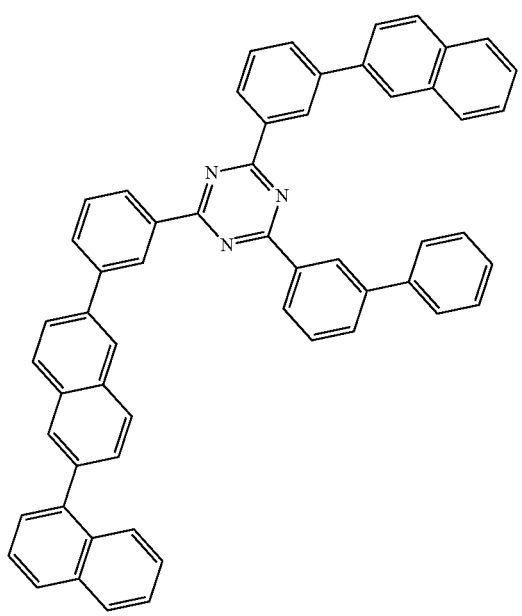
P-60
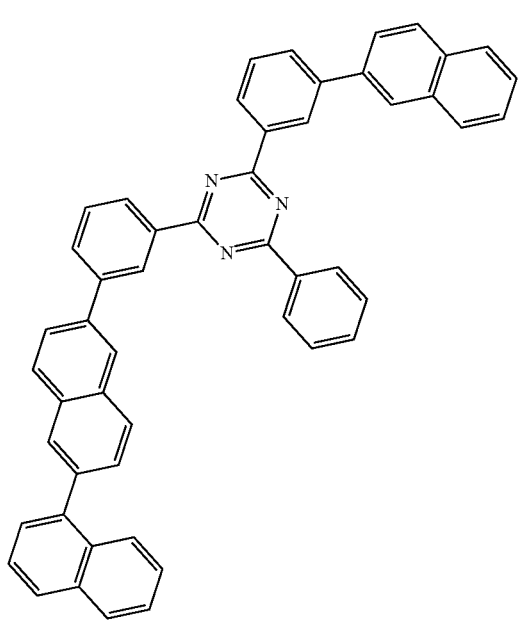
P-61
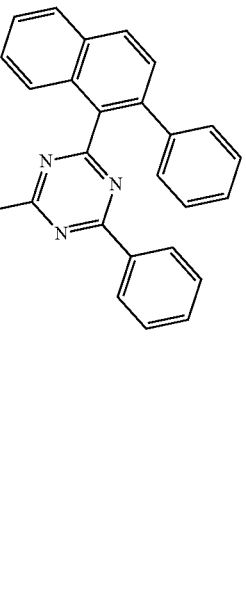
P-62

P-63
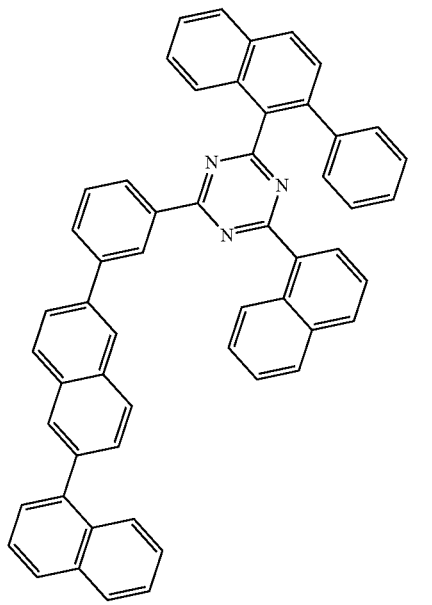
P-65
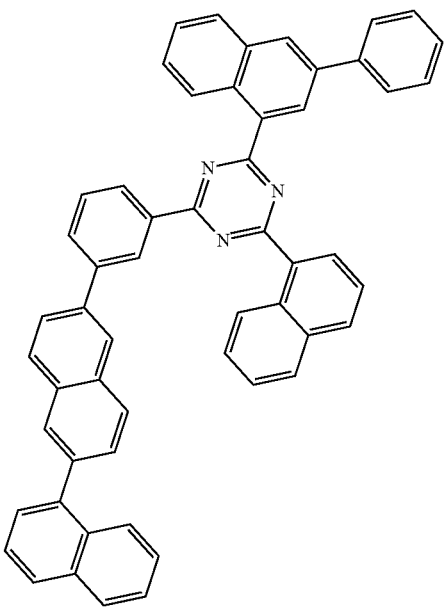
P-64
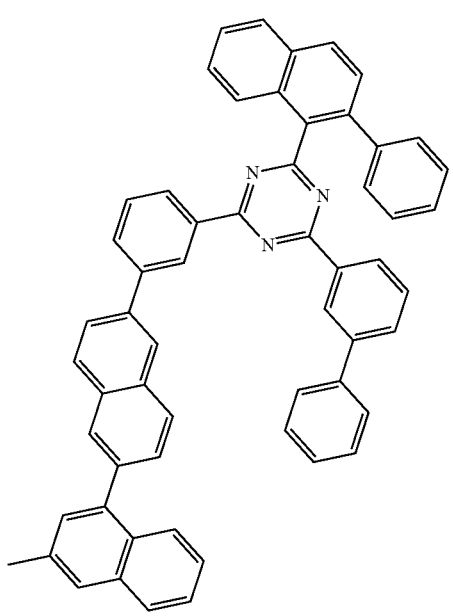
P-66
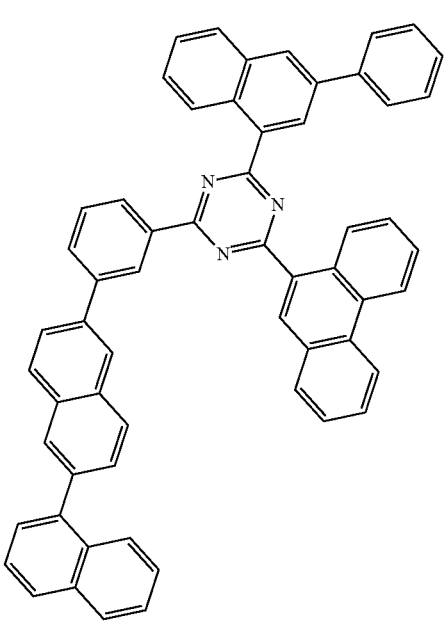

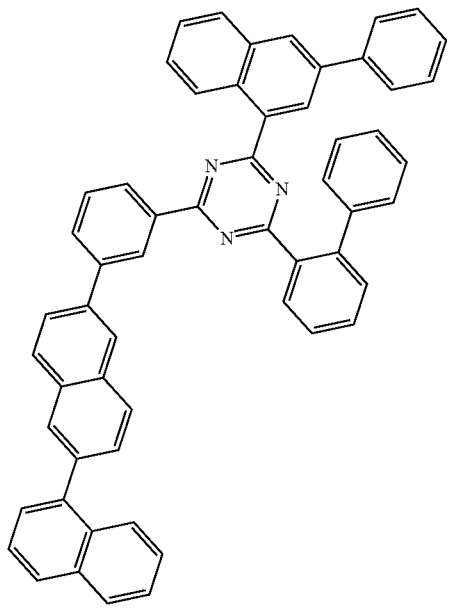
P-67
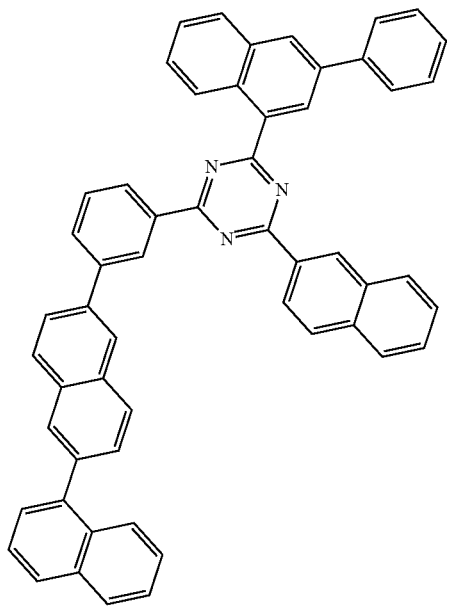
P-68
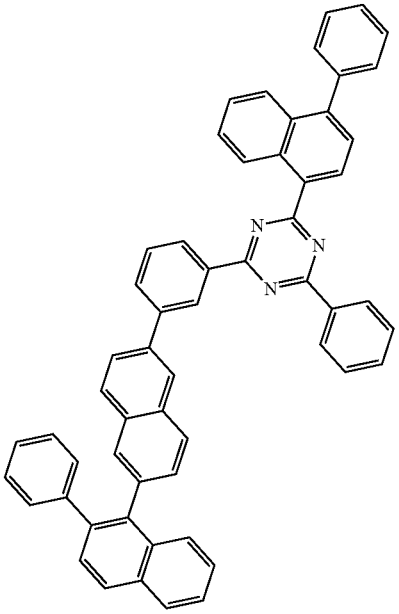
P-69
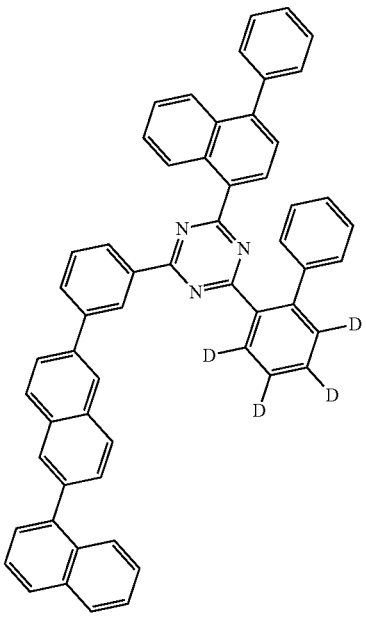
P-70

P-71
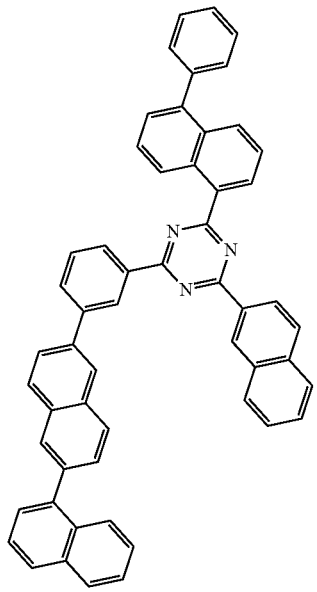
P-73
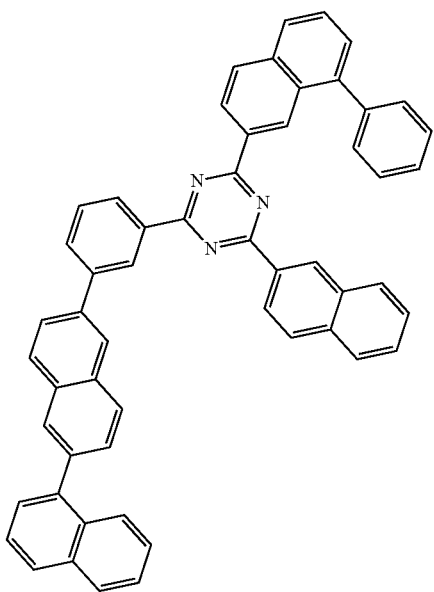
P-72
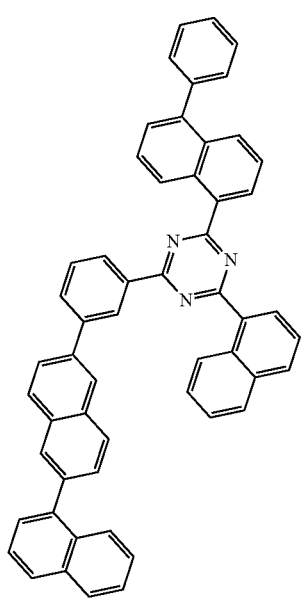
P-74
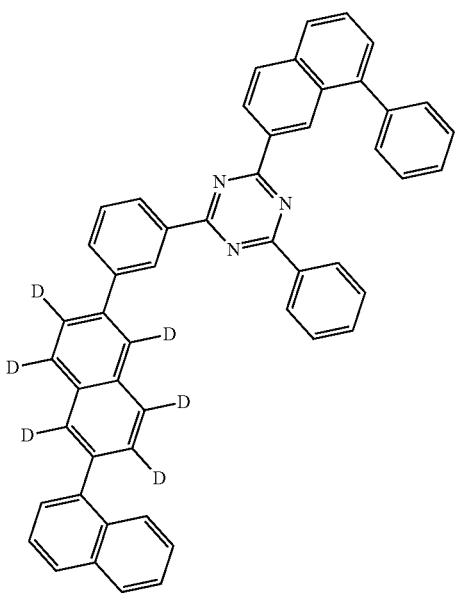

P-75
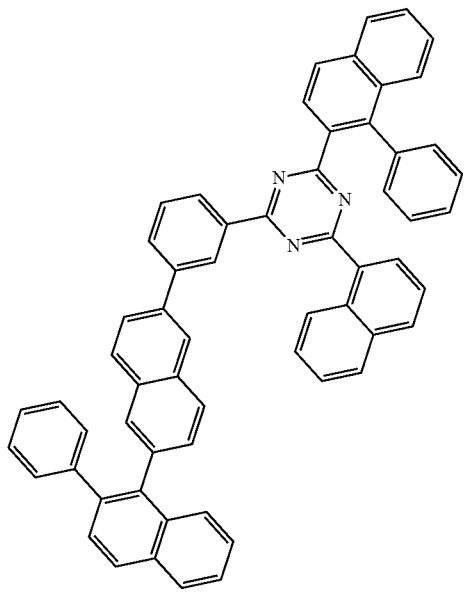
P-77
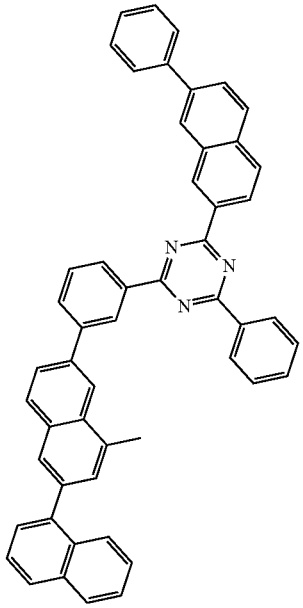
P-76
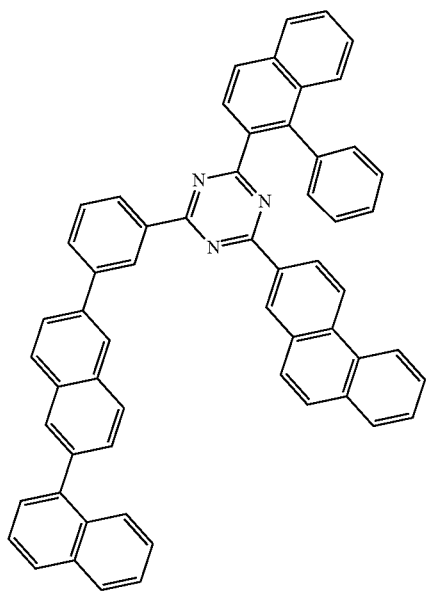
P-78
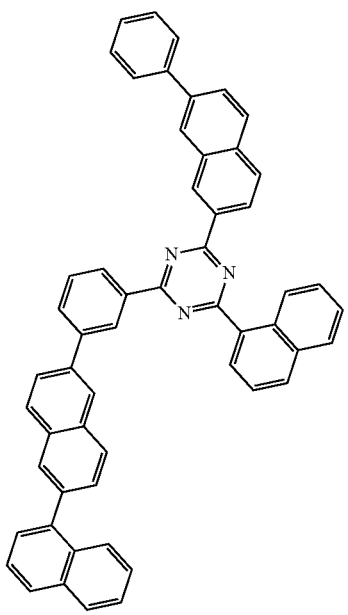

P-79
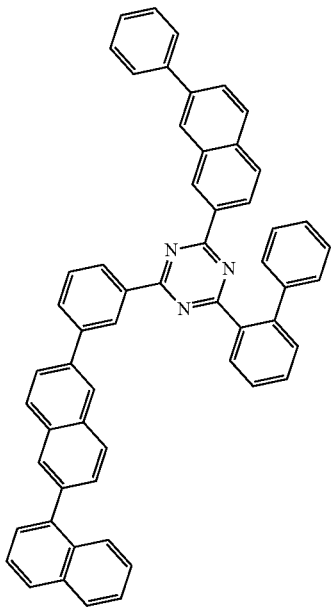
P-81
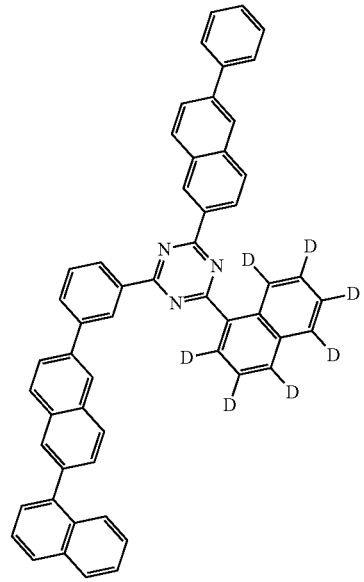
P-80
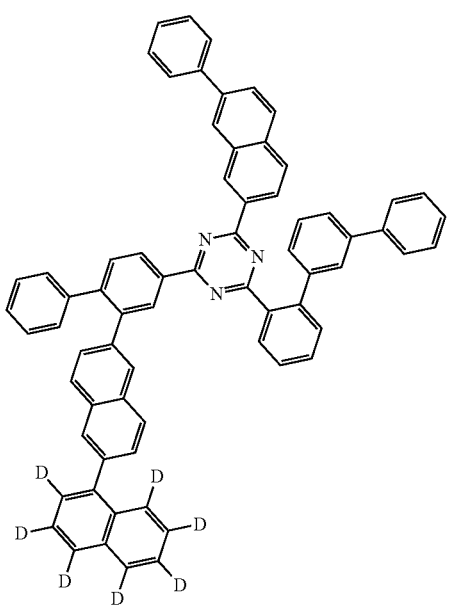
P-82
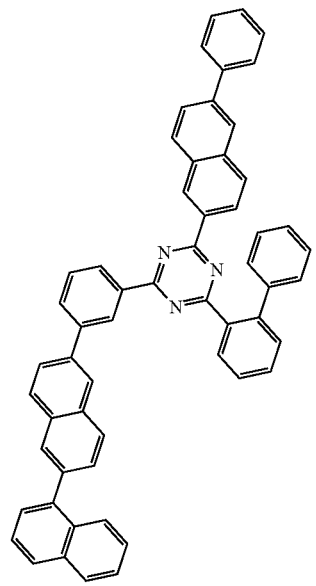

P-83
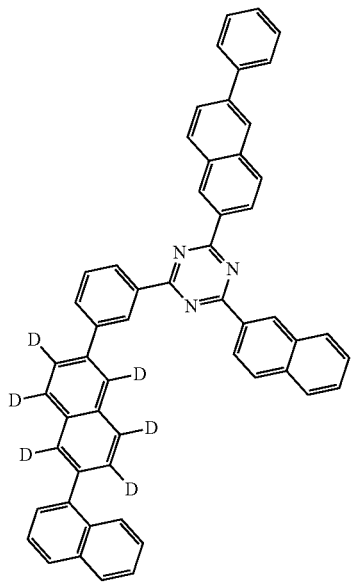
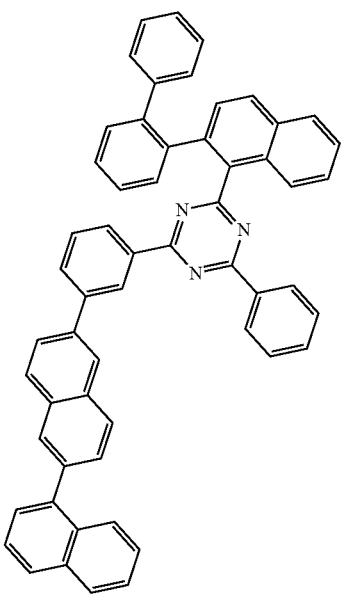
P-85
P-84
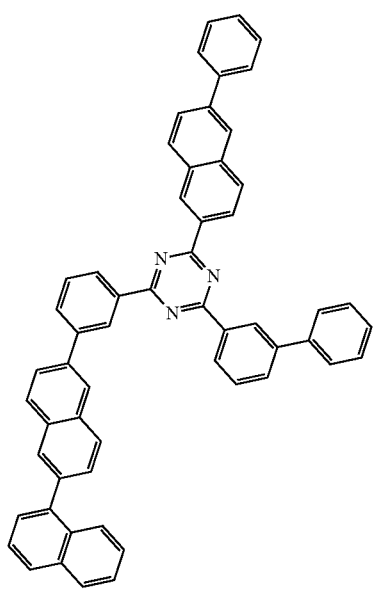
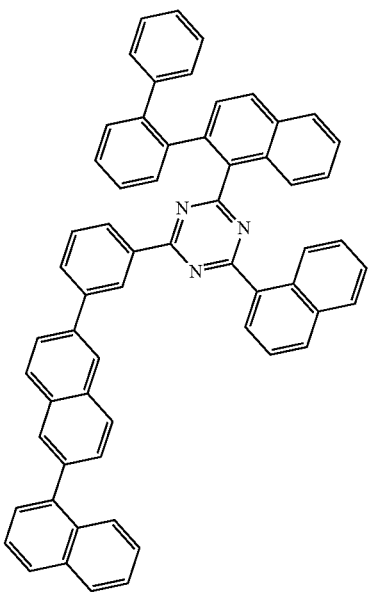
P-86

P-87
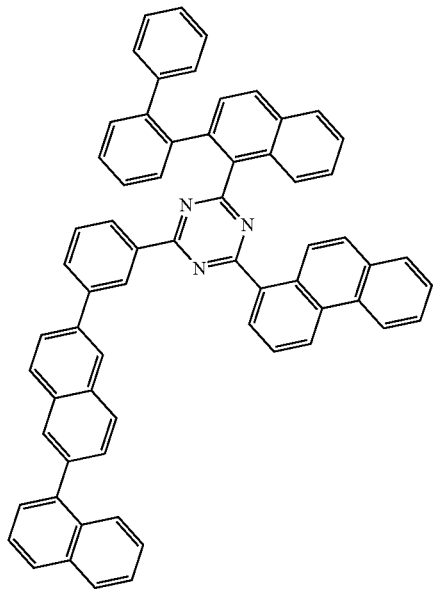
P-89
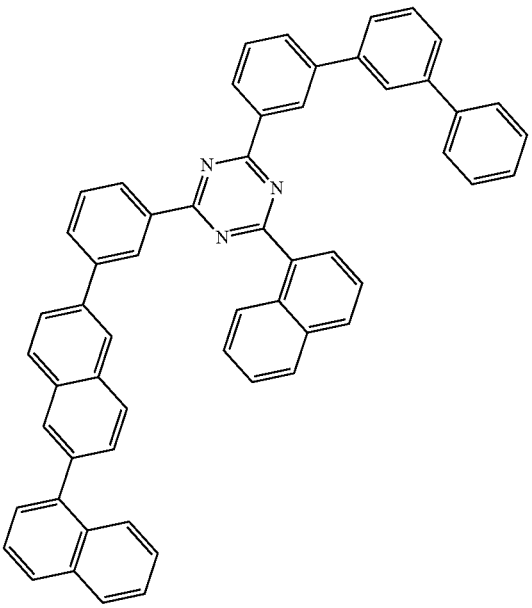
P-88
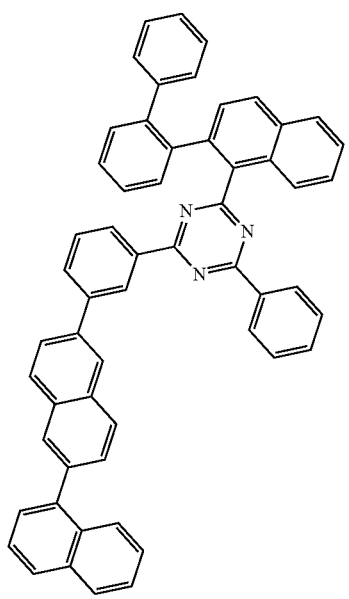
P-90
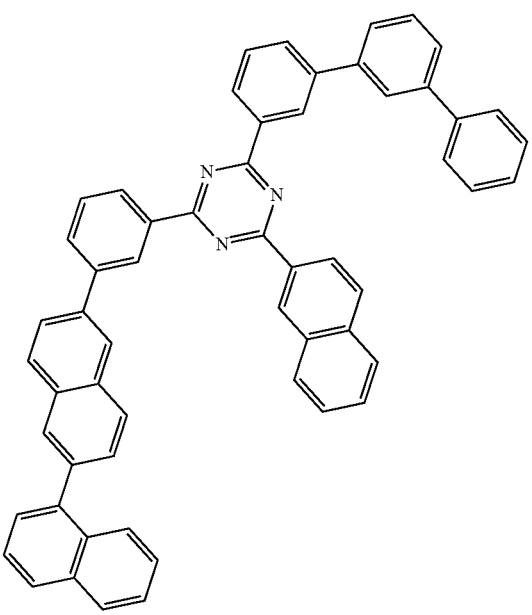

P-91
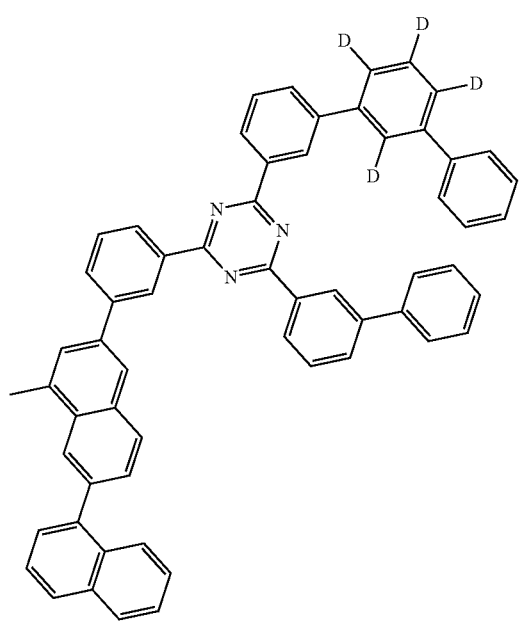
P-93
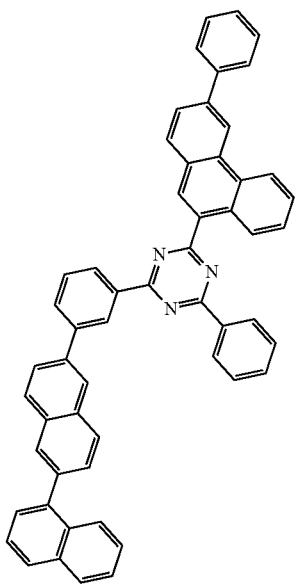
P-92
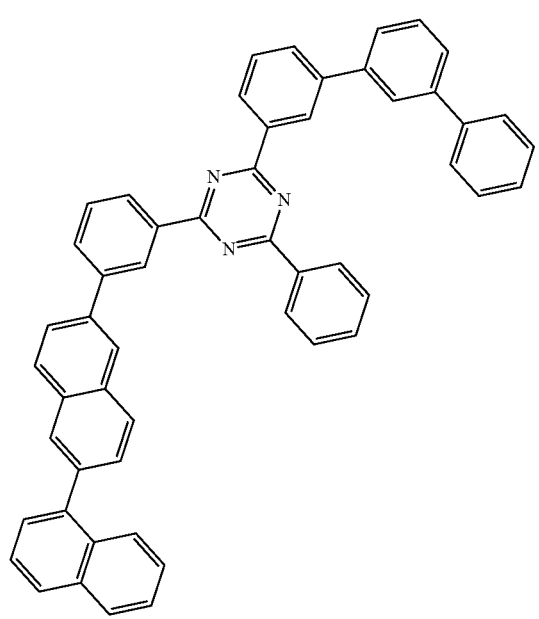
P-94
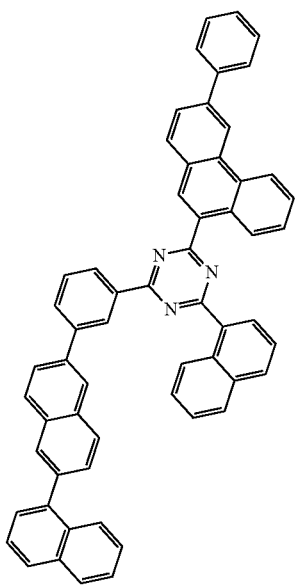

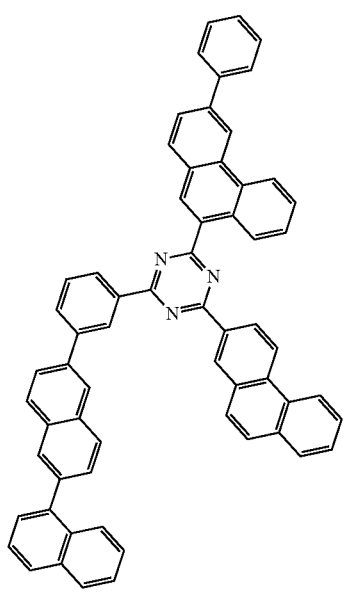
P-95
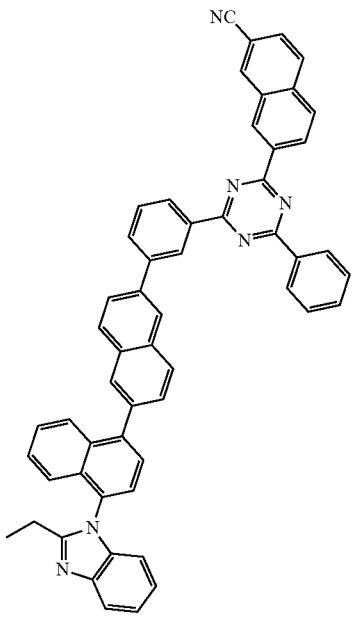
P-97
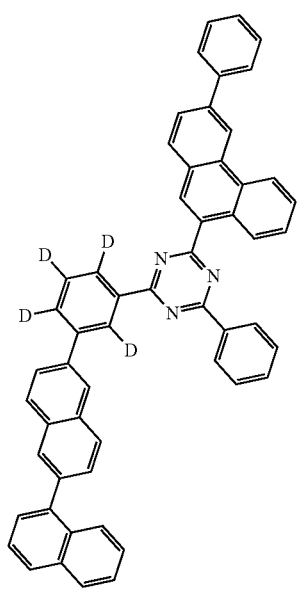
P-96
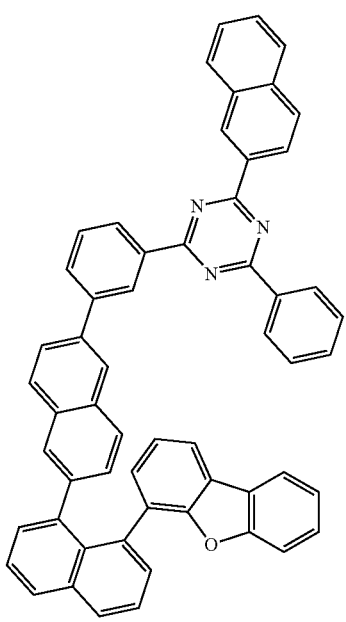
P-98

P-99
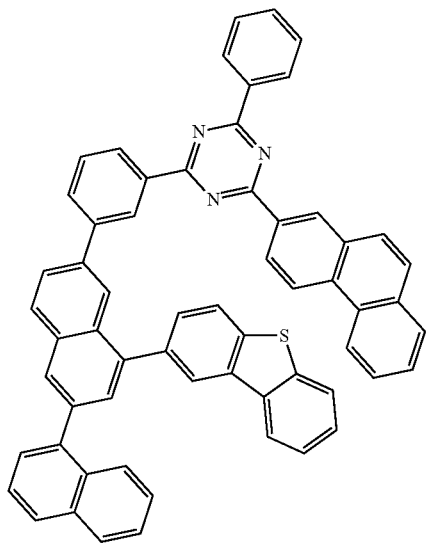
P-100
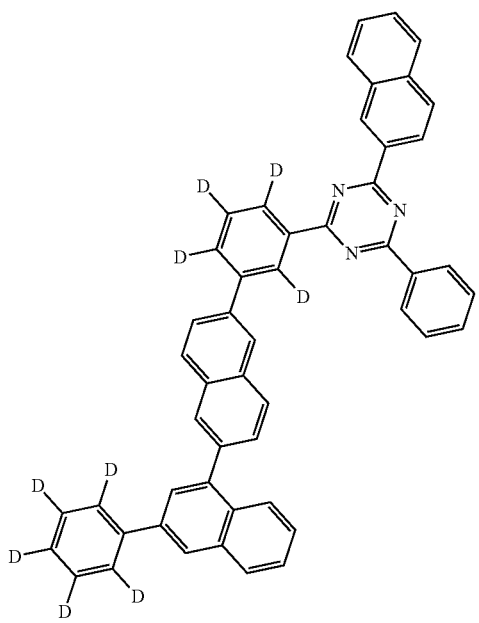
P-101
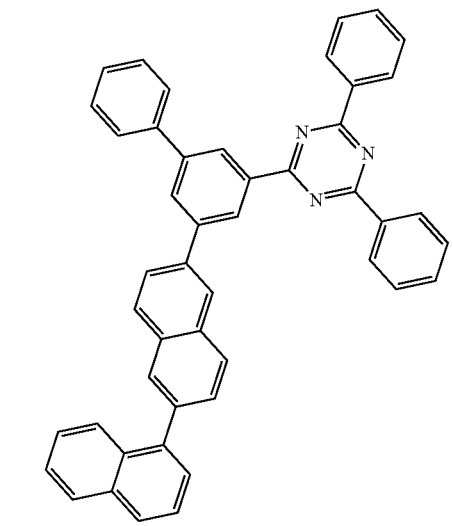
P-102
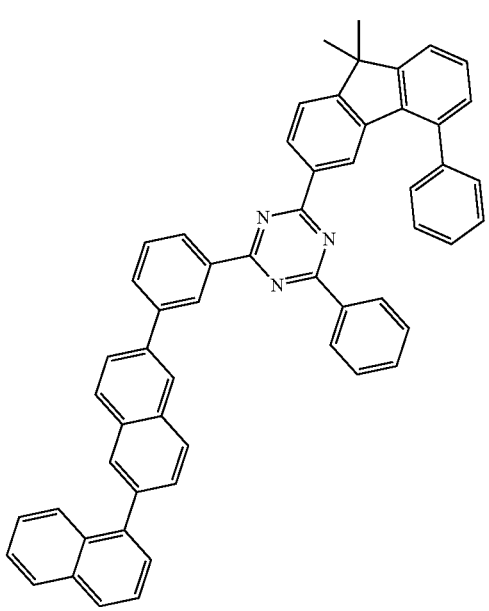

P-103

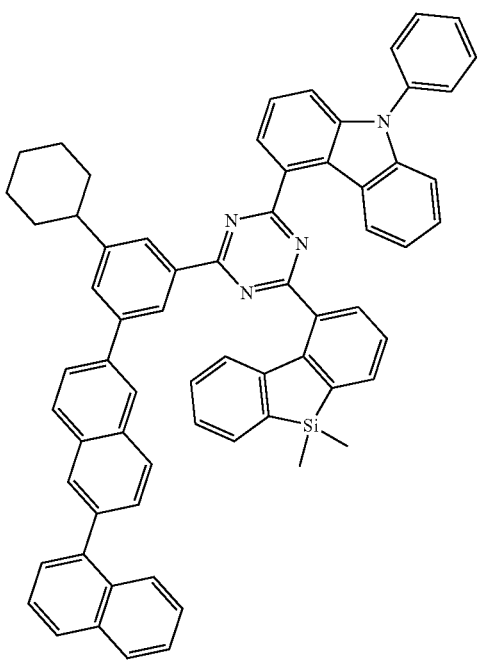

P-104

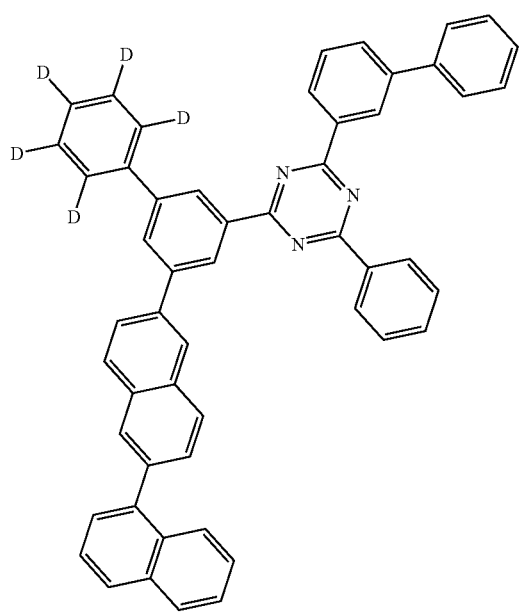

In another aspect, the present invention provides a method for reusing the compound represented by Formula 1, comprising:
 a step of depositing an organic light emitting material including the compound represented by Formula 1;
 a step of removing impurities from the crude organic light emitting material recovered from the deposition apparatus;
 a step of recovering the removed impurities; and
 a step of purifying the recovered impurities to a purity of 99.9% or higher.

The step of removing impurities from the crude organic light emitting material recovered from the deposition apparatus may preferably include performing a preliminary purification process to obtain a purity of 98% or more by recrystallization in a recrystallization solvent.

The recrystallization solvent may be preferably a polar solvent having a polarity index (PI) of 5.5 to 7.2.

The recrystallization solvent may preferably be used by mixing a polar solvent having a polarity index of 5.5 to 7.2 and a non-polar solvent having a polarity index of 2.0 to 4.7.

When a mixture of a polar solvent and a non-polar solvent is used for the recrystallization solvent, the non-polar solvent may be used in an amount of 15% (v/v) or less relative to the polar solvent.

The recrystallization solvent may preferably be used by mixing N-Methylpyrrolidone (NMP) single solvent; or a polar solvent mixed any one selected from the group consisting of 1,3-Dimethyl-2-imidazolidinone, 2-pyrrolidone, N, N-Dimethyl formamide, Dimethylacetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or the polar solvent and the non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

The present invention may further comprise a light efficiency enhancing layer formed on at least one surface of the first electrode and the second electrode, the surface being opposite to the organic material layer.

Also, the organic material layer may include 2 or more stacks comprising a hole transport layer, an emitting layer, and an electron transport layer sequentially formed on the first electrode and may further comprise a charge generation layer formed between the 2 or more stacks.

In another aspect, the present invention also provides an electronic device comprising a display device comprising the organic electronic element; and a control unit for driving the display device. Here, the organic electronic element is at least one of an OLED, an organic solar cell, an organic photo conductor, an organic transistor (organic TFT) and an element for monochromic or white illumination.

Hereinafter, Synthesis examples of compounds represented by Formulas 1, 4 and 5 according to the present invention and examples of manufacturing an organic electronic element will be described in detail with examples, but the present invention is not limited to the following examples.

EXAMPLES

[Synthesis Example 1] Compound Represented by Formula 1

The compound (final products) represented by Formula 1 according to the present invention may be prepared by reacting as in Reaction Scheme 1, but is not limited thereto.

<Reaction Scheme 1>

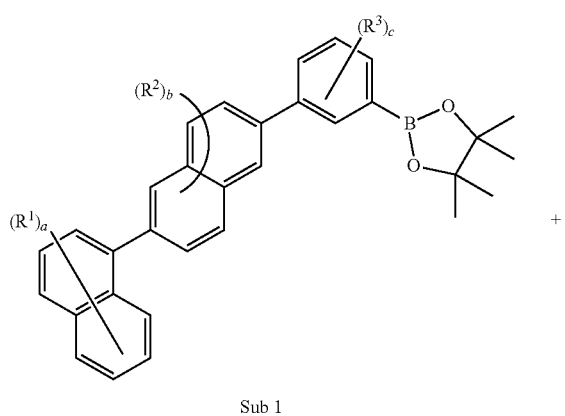

Sub 1

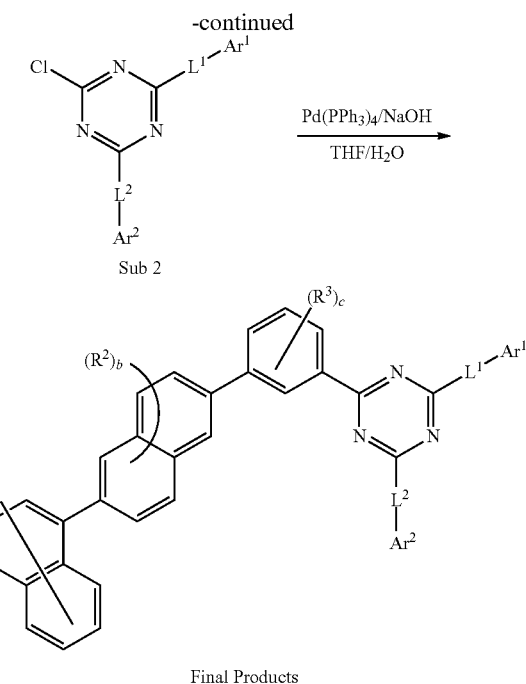

Final Products

Wherein, $R^1$, $R^2$, $R^3$, $Ar^1$, $Ar^2$, $L^1$, $L^2$, a, b and c are the same as defined in Formula 1.

1. Synthesis of Sub-1

Sub 1 of Reaction Scheme 1 may be synthesized by the reaction pathway of Reaction Scheme 2, but is not limited thereto.

<Reaction Scheme 2>

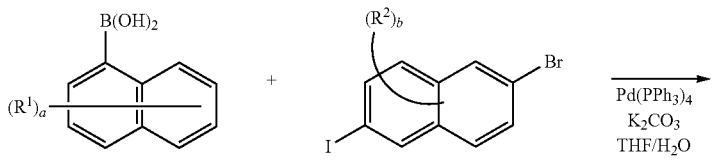

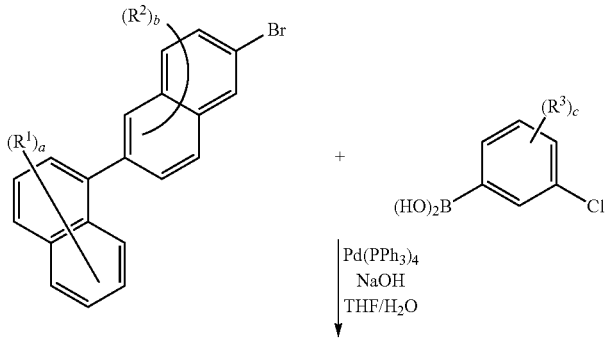

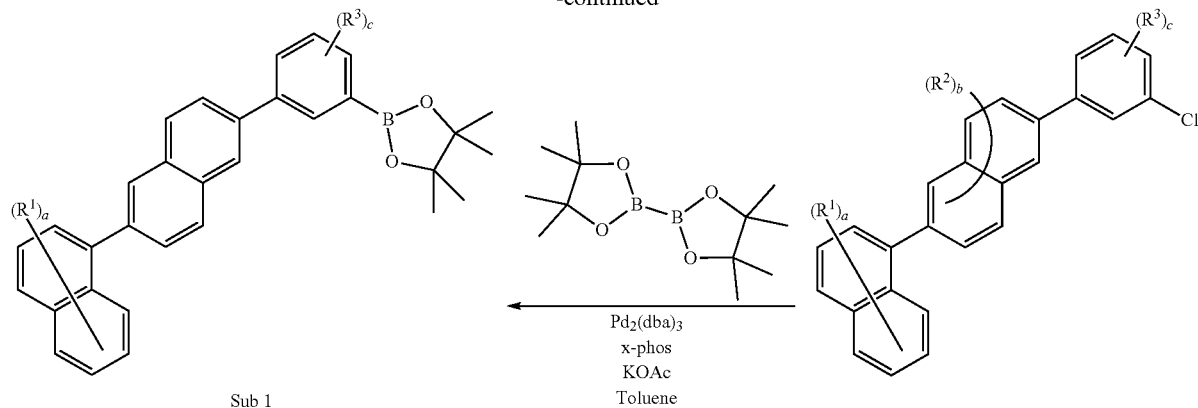

Synthesis examples of specific compounds belonging to Sub 1 are as follows.

1. Synthesis Example of Sub 1-1

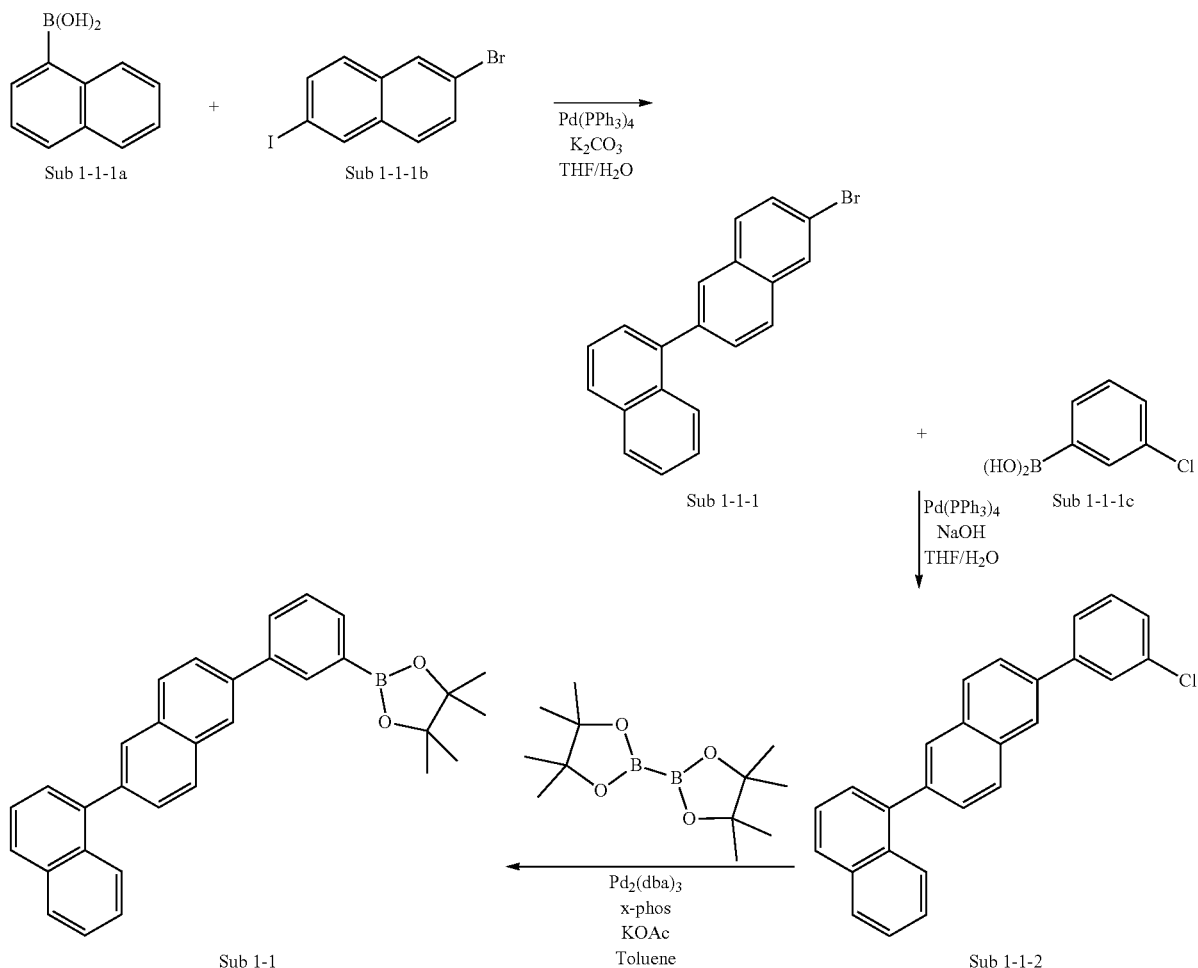

(1) Synthesis of Sub 1-1-1

Sub1-1-1a (20.00 g, 116.29 mmol), Sub1-1-1b (38.72 g, 116.29 mmol), Pd(PPh$_3$)$_4$ (4.03 g, 3.49 mmol), K$_2$CO$_3$ (32.14 g, 232.57 mmol) were placed in a round bottom flask and dissolving in anhydrous THF (387 mL) and water (121 mL), the mixture was refluxed for 12 hours. When the reaction was completed, the reactant was cooled to room temperature, extracted with CH$_2$Cl$_2$ and water, and treated with MgSO$_4$. The product produced by concentrating the organic solvent was recrystallized using a Silicagel Column to obtain 33.71 g (87%) of Sub1-1-1.

(2) Synthesis of Sub 1-1-2

Sub1-1-1 (33.00 g, 99.03 mmol), Sub1-1-1c (15.49 g, 99.03 mmol), Pd(PPh$_3$)$_4$ (3.43 g, 2.97 mmol), NaOH (7.92 g, 198.06 mmol) were placed in a round bottom flask and dissolving in anhydrous THF (380 mL) and water (110 mL), the mixture was refluxed for 12 hours. When the reaction was completed, the reactant was cooled to room temperature, extracted with CH$_2$Cl$_2$ and water, and treated with MgSO$_4$. The product produced by concentrating the organic solvent was recrystallized using a Silicagel Column to obtain 27.10 g (75%) of Sub1-1-2.

(3) Synthesis of Sub 1-1

To Sub1-1-2 (27.00 g, 74.00 mmol), 4,4,4',4',5,5,5',5'-octamethyl-2,2'-bi(1,3,2-dioxaborolane) (24.43 g, 96.20 mmol), Pd$_2$(dba)$_3$ (2.03 g, 2.22 mmol), Xphos (2.12 g, 4.44 mmol), KOAc (14.52 g, 148.00 mmol) were added to DMF (247 mL), and the mixture was stirred at 150° C. for 2 hours. After the reaction was completed, the reaction solvent was removed, and the concentrated organic material was subjected to silica gel column or recrystallization to obtain 26.84 g (78%) of the product Sub1-1.

2. Synthesis Example of Sub 1-2

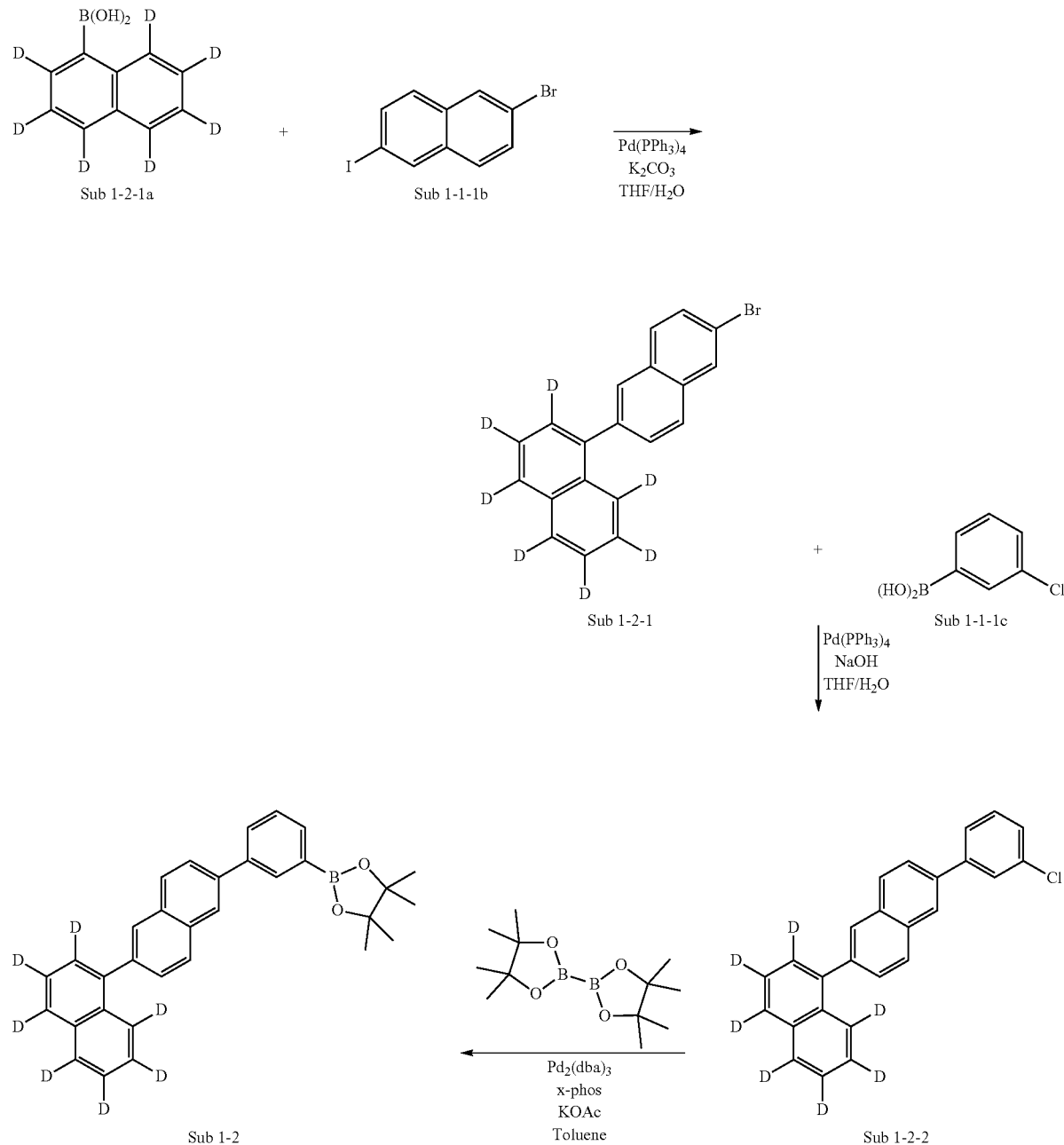

(1) Synthesis of Sub 1-2-1

Sub1-2-1a (25.00 g, 139.64 mmol), Sub1-1-1b (46.50 g, 139.64 mmol), Pd(PPh₃)₄ (4.84 g, 4.19 mmol), K₂CO₃ (38.60 g, 279.28 mmol) were placed in a round bottom flask and dissolving in anhydrous THF (465 mL) and water (155 mL), the mixture was refluxed for 12 hours. When the reaction was completed, the reactant was cooled to room temperature, extracted with CH₂Cl₂ and water, and treated with MgSO₄. The product produced by concentrating the organic solvent was recrystallized using a Silicagel Column to obtain 39.91 g (84%) of Sub1-2-1.

(2) Synthesis of Sub 1-2-2

Sub1-2-1 (39.00 g, 114.61 mmol), Sub1-1-1c (17.92 g, 114.61 mmol), Pd(PPh₃)₄ (3.97 g, 3.44 mmol), NaOH (9.17 g, 229.23 mmol) were placed in a round bottom flask and dissolving in anhydrous THF (382 mL) and water (126 mL), the mixture was refluxed for 12 hours. When the reaction was completed, the reactant was cooled to room temperature, extracted with CH₂Cl₂ and water, and treated with MgSO₄. The product produced by concentrating the organic solvent was recrystallized using a Silicagel Column to obtain 31.11 g (73%) of Sub1-2-2.

(3) Synthesis of Sub 1-2

To Sub1-2-2 (31.00 g, 83.35 mmol), 4,4,4',4',5,5,5',5'-octamethyl-2,2'-bi(1,3,2-dioxaborolane) (27.52 g, 108.36 mmol), Pd₂(dba)₃ (2.29 g, 2.50 mmol), Xphos (2.38 g, 5.00 mmol), KOAc (16.36 g, 166.71 mmol) were added to DMF (278 mL), and the mixture was stirred at 150° C. for 2 hours. After the reaction was completed, the reaction solvent was removed, and the concentrated organic material was subjected to silica gel column or recrystallization to obtain 25.49 g (66%) of the product Sub1-2.

3. Synthesis Example of Sub 1-4

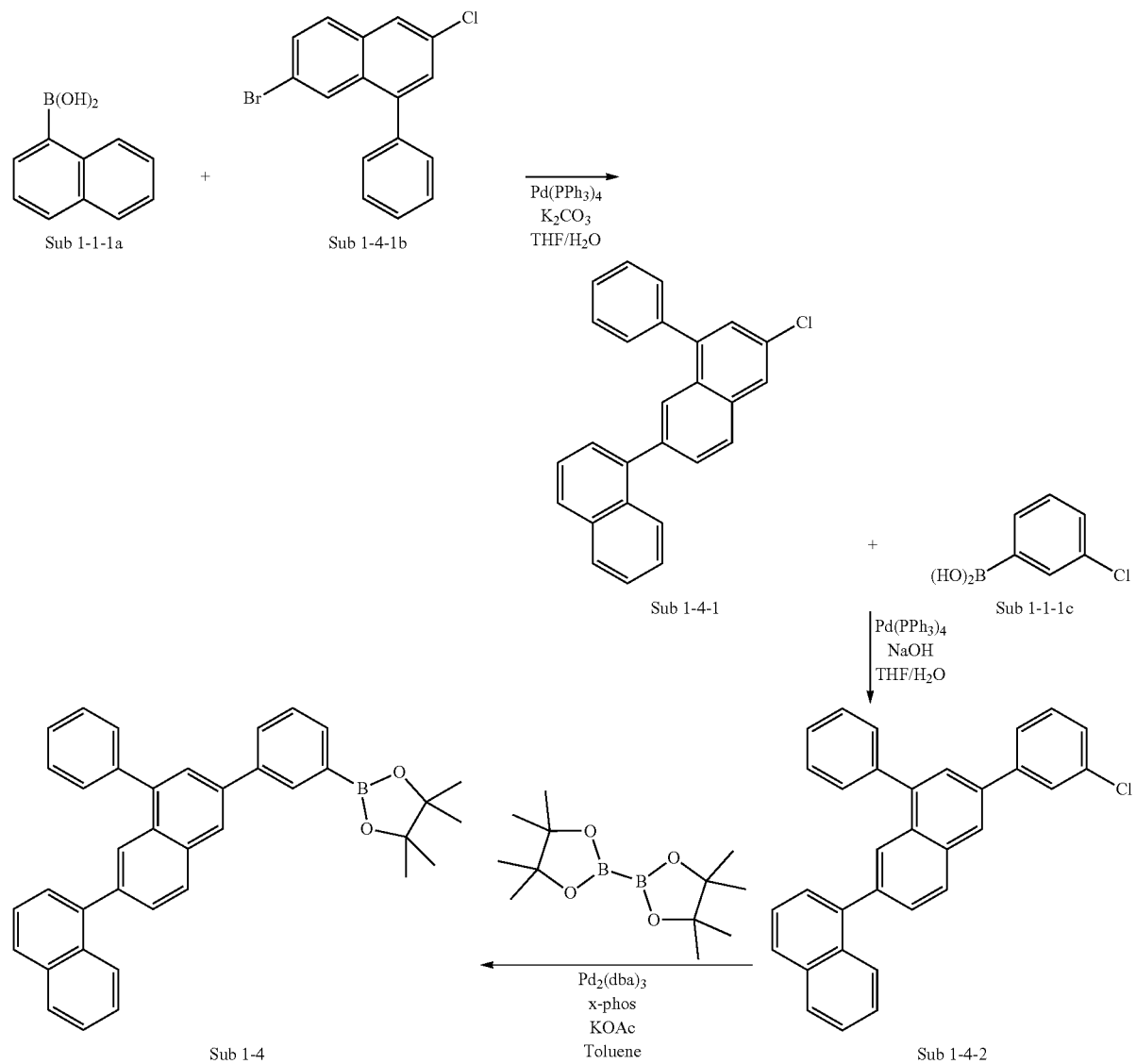

(1) Synthesis of Sub 1-4-1

Sub1-1-1a (30.00 g, 174.43 mmol), Sub1-4-1b (55.40 g, 174.43 mmol), Pd(PPh₃)₄ (6.05 g, 5.23 mmol), K₂CO₃ (48.22 g, 348.86 mmol) were placed in a round bottom flask and dissolving in anhydrous THF (581 mL) and water (160 mL), the mixture was refluxed for 12 hours. When the reaction was completed, the reactant was cooled to room temperature, extracted with CH$_2$Cl$_{12}$ and water, and treated with MgSO$_4$. The product produced by concentrating the organic solvent was recrystallized using a Silicagel Column to obtain 49.64 g (78%) of Sub1-4-1.

(2) Synthesis of Sub 1-4-2

Sub1-4-1 (49.00 g, 134.29 mmol), Sub1-1-1c (21.00 g, 134.29 mmol), Pd(PPh$_3$)$_4$ (4.66 g, 4.03 mmol), NaOH (10.74 g, 268.59 mmol) were placed in a round bottom flask and dissolving in anhydrous THF (447 mL) and water (142 mL), the mixture was refluxed for 12 hours. When the reaction was completed, the reactant was cooled to room temperature, extracted with CH$_2$Cl$_2$ and water, and treated with MgSO$_4$. The product produced by concentrating the organic solvent was recrystallized using a Silicagel Column to obtain 37.90 g (64%) of Sub1-4-2.

(3) Synthesis of Sub 1-4

To Sub1-4-2 (37.00 g, 83.91 mmol), 4,4,4',4',5,5,5',5'-octamethyl-2,2'-bi(1,3,2-dioxaborolane) (27.70 g, 109.08 mmol), Pd$_2$(dba)$_3$ (2.30 g, 2.52 mmol), Xphos (2.40 g, 5.03 mmol), KOAc (16.47 g, 167.81 mmol) were added to DMF (280 mL), and the mixture was stirred at 150° C. for 2 hours. After the reaction was completed, the reaction solvent was removed, and the concentrated organic material was subjected to silica gel column or recrystallization to obtain 31.27 g (70%) of the product Sub1-4.

4. Synthesis Example of Sub 1-10

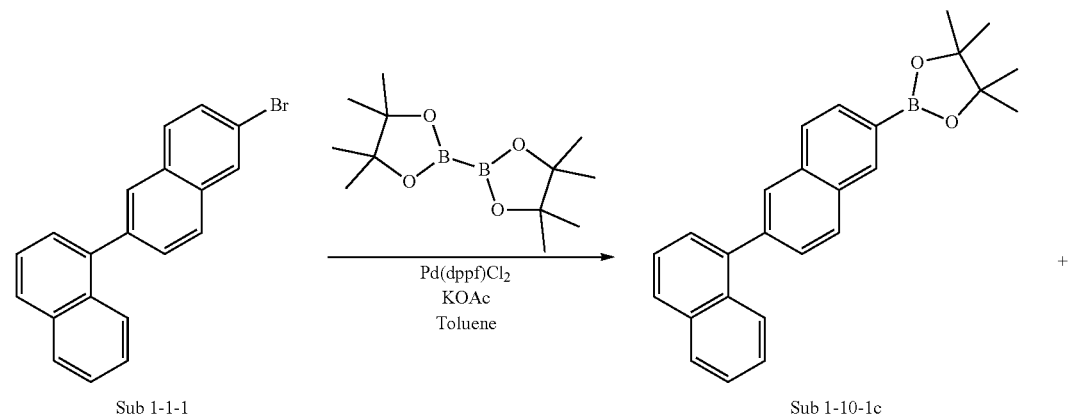

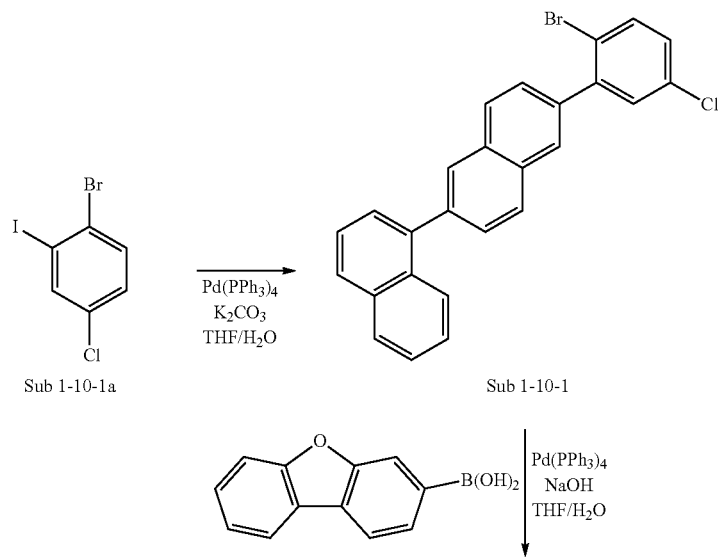

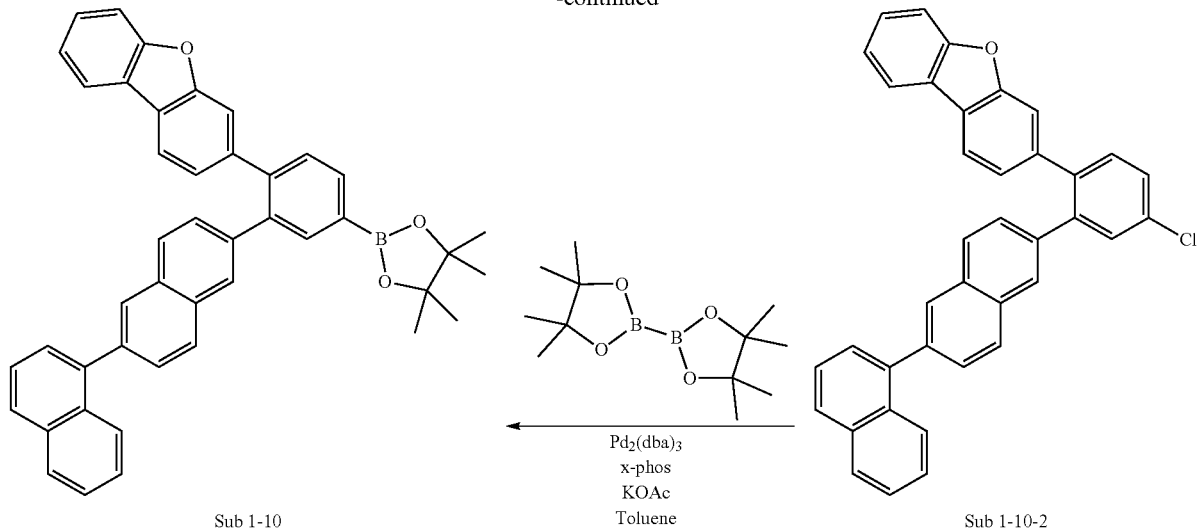

(1) Synthesis of Sub 1-10-1c

Sub1-1-1 (40.00 g, 120.04 mmol), 4,4,4',4',5,5,5',5'-octamethyl-2,2'-bi(1,3,2-dioxaborolane) (39.63 g, 156.05 mmol), Pd(dppf)Cl$_2$ (2.63 g, 3.60 mmol), KOAc (23.56 g, 240.07 mmol) were placed in a round bottom flask and added to DMF (400 mL) and stirred at 150° C. for 2 hours. When the reaction was completed, the reaction solvent was removed, and the concentrated organic material was recrystallized on a silica gel column or recrystallized to obtain 38.80 g (85%) of the product Sub1-10-1c.

(2) Synthesis of Sub 1-10-1

Sub1-10-1c (38.00 g, 99.92 mmol), Sub1-10-1a (31.71 g, 99.92 mmol), Pd(PPh$_3$)$_4$ (3.47 g, 3.00 mmol), K$_2$CO$_3$ (27.62 g, 199.85 mmol) were placed in a round bottom flask and dissolving in anhydrous THE (333 mL) and water (110 mL), and refluxed for 12 hours. When the reaction was completed, the reactant was cooled to room temperature, extracted with CH$_2$Cl$_{12}$ and water, and treated with MgSO$_4$. The product produced by concentrating the organic solvent was recrystallized using a Silicagel Column to obtain 29.71 g (67%) of Sub1-10-1.

(3) Synthesis of Sub 1-10-2

Sub1-10-1 (29.00 g, 65.35 mmol), dibenzofuran-2-ylboronic acid (13.85 g, 65.35 mmol), Pd(PPh$_3$)$_4$ (2.27 g, 1.96 mmol), NaOH (5.23 g, 130.70 mmol) were placed in a round bottom flask and dissolving in anhydrous THE (218 mL) and water (72 mL), and refluxed for 12 hours. When the reaction was completed, the reactant was cooled to room temperature, extracted with CH$_2$Cl$_{12}$ and water, and treated with MgSO$_4$. The product produced by concentrating the organic solvent was recrystallized using a Silicagel Column to obtain 26.72 g (77%) of Sub1-10-2.

(4) Synthesis of Sub 1-10

Sub1-10-2 (26.00 g, 48.96 mmol), 4,4,4',4',5,5,5',5'-octamethyl-2,2'-bi(1,3,2-dioxaborolane) (16.16 g, 63.65 mmol), Pd$_2$(dba)$_3$ (1.34 g, 1.47 mmol), Xphos (1.40 g, 2.94 mmol), KOAc (9.61 g, 97.92 mmol) were added to DMF (163 mL) and stirred at 150° C. for 2 hours. When the reaction was completed, the reaction solvent was removed, and the concentrated organic material was recrystallized on a silica gel column or recrystallized to obtain 23.77 g (78%) of the product Sub1-10.

The compound belonging to Sub 1 may be the following compounds, but is not limited thereto, and Table 1 shows the FD-MS (Field Desorption-Mass Spectrometry) values of the compounds belonging to Sub 1.

TABLE 1

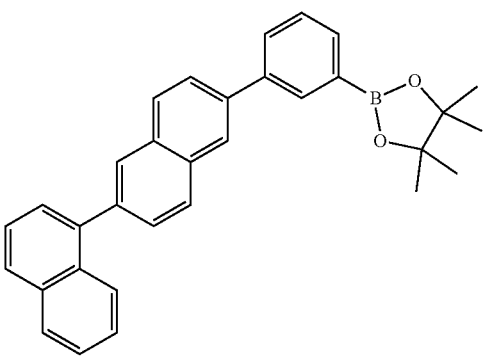

Sub 1-1

TABLE 1-continued
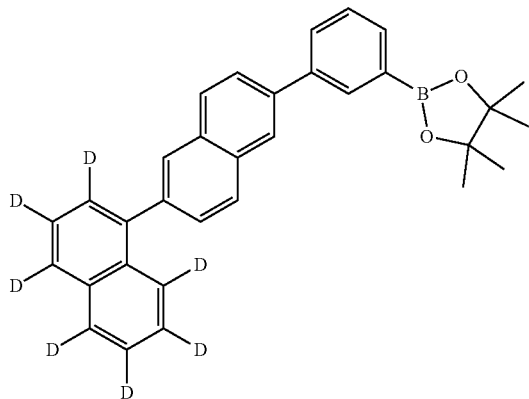
Sub 1-2
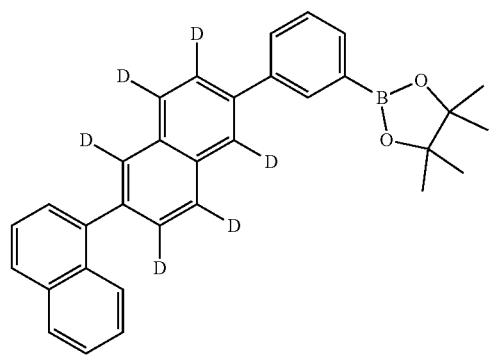
Sub 1-3
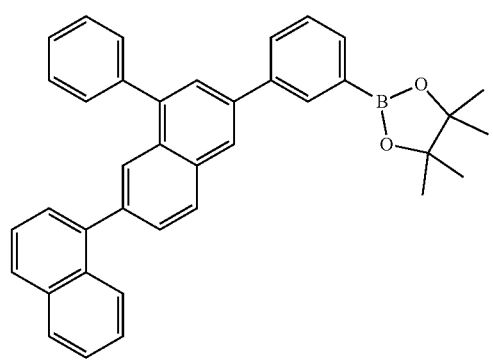
Sub 1-4

TABLE 1-continued
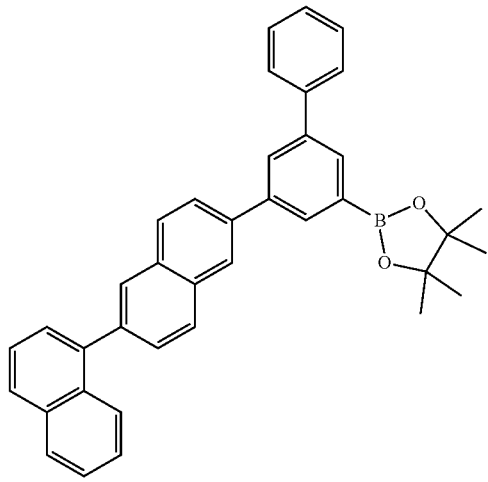
Sub 1-5
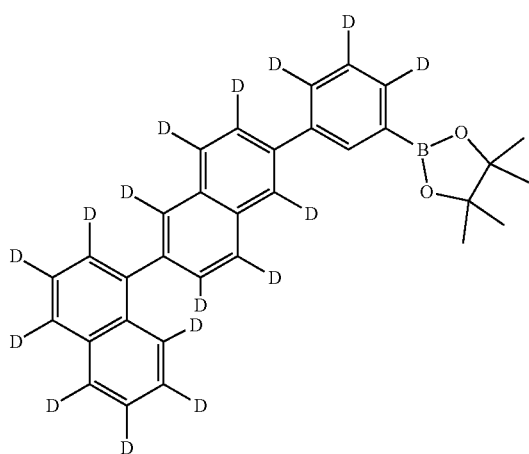
Sub 1-6
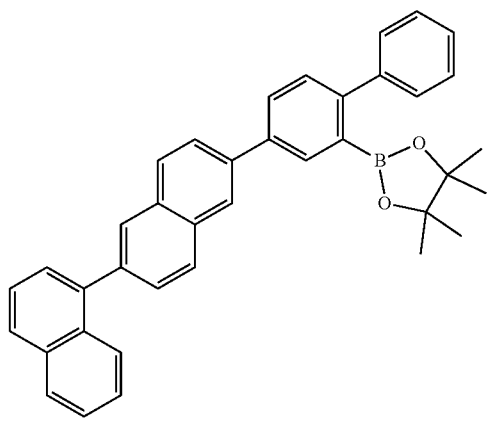
Sub 1-7

TABLE 1-continued
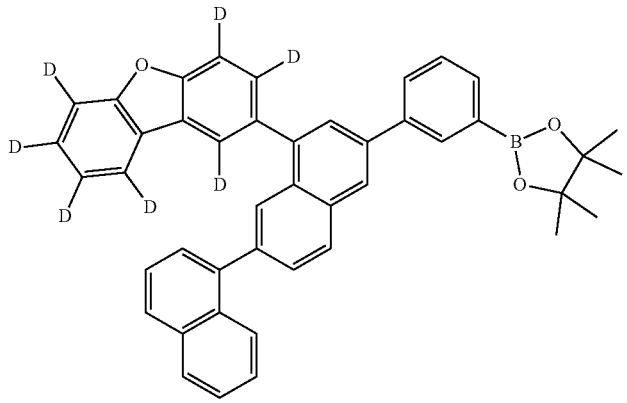
Sub 1-8
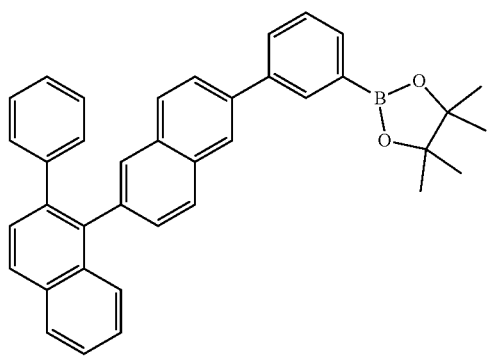
Sub 1-9
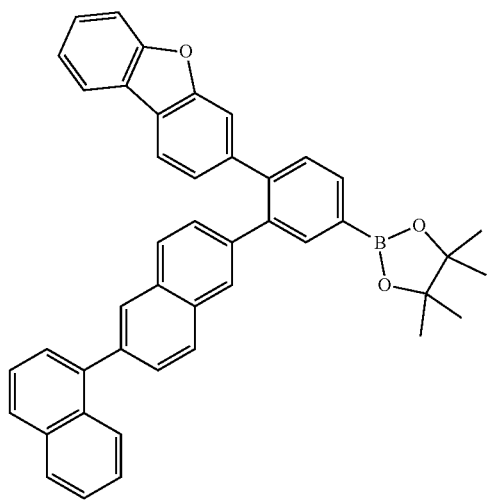
Sub 1-10

TABLE 1-continued
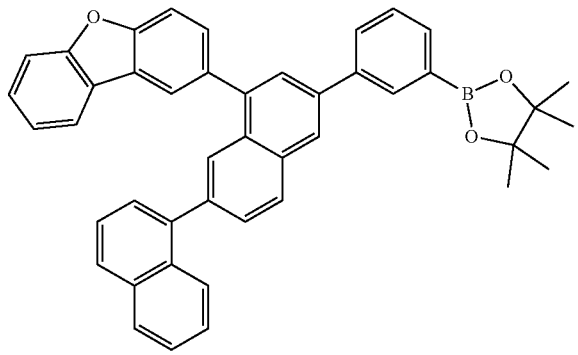
Sub 1-11
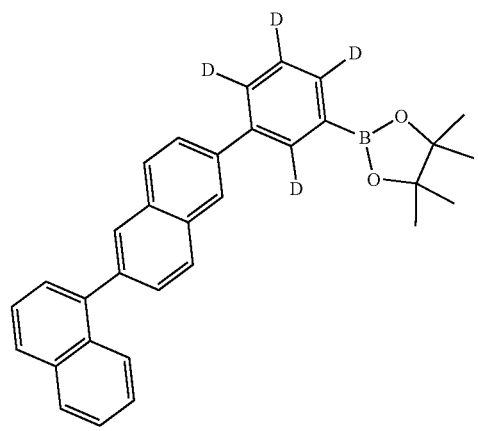
Sub 1-12
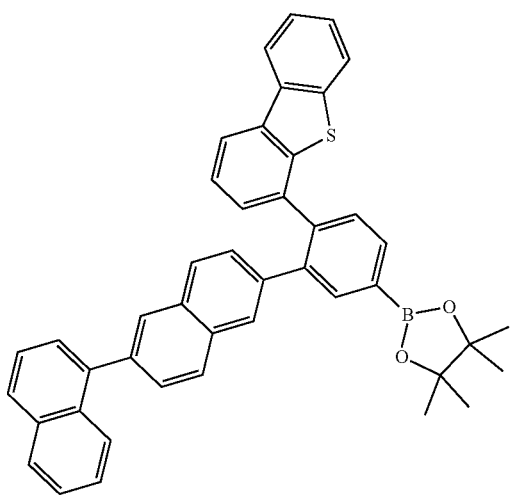
Sub 1-13

TABLE 1-continued
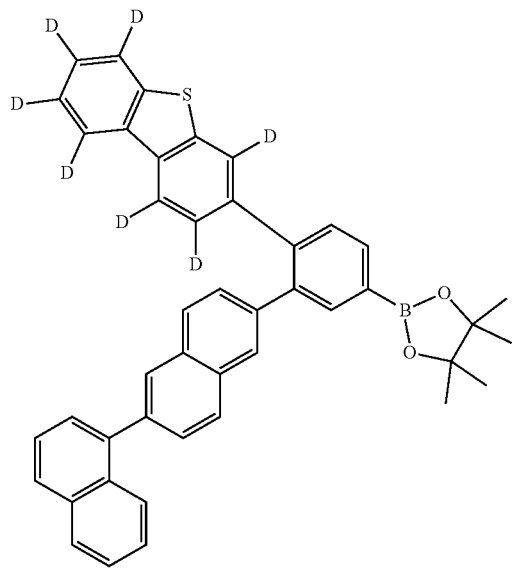
Sub 1-14
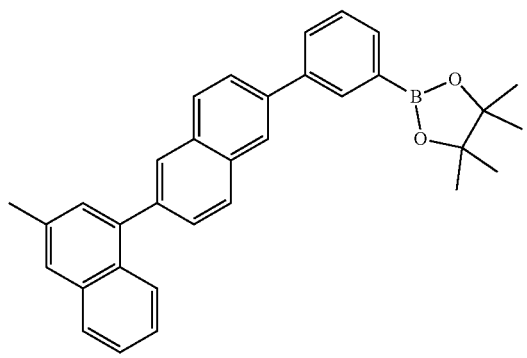
Sub 1-15
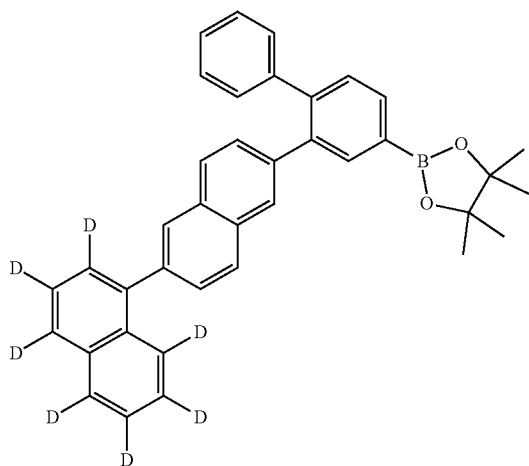
Sub 1-16

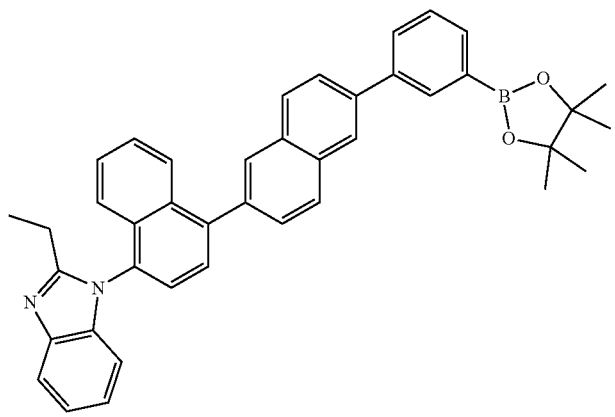
Sub 1-17
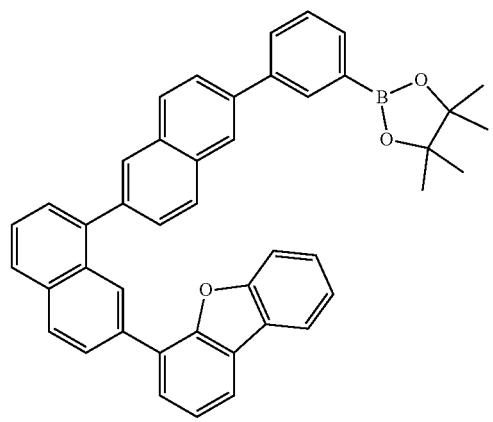
Sub 1-18
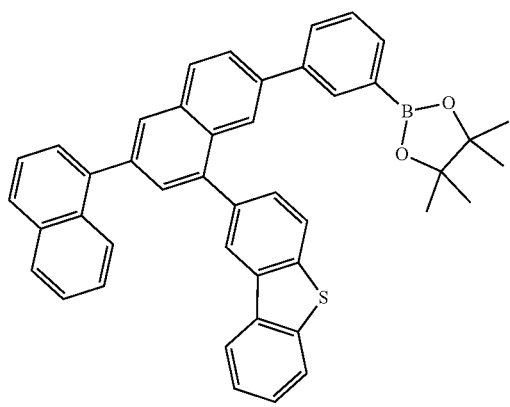
Sub 1-19

TABLE 1-continued
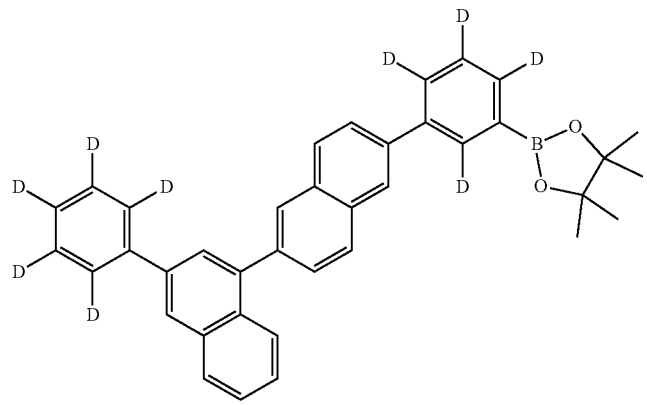
Sub 1-20
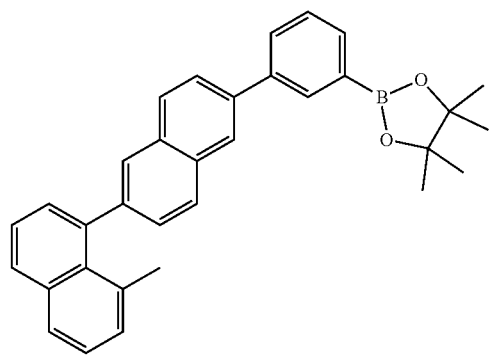
Sub 1-21
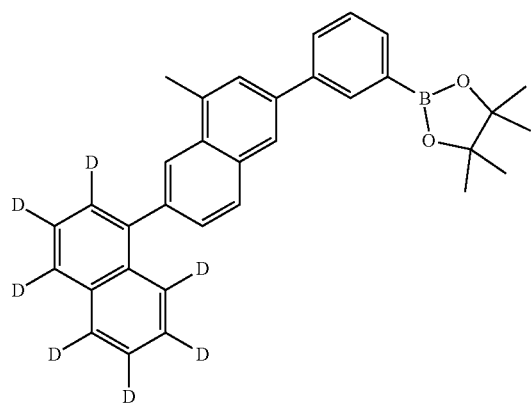
Sub 1-22

TABLE 1-continued
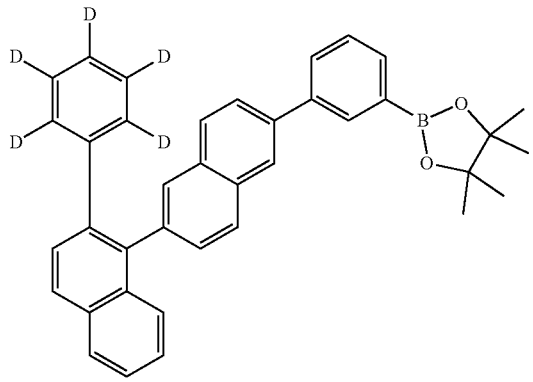
Sub 1-23
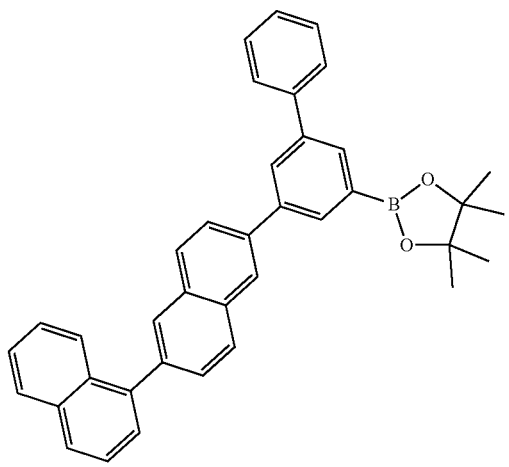
Sub 1-24
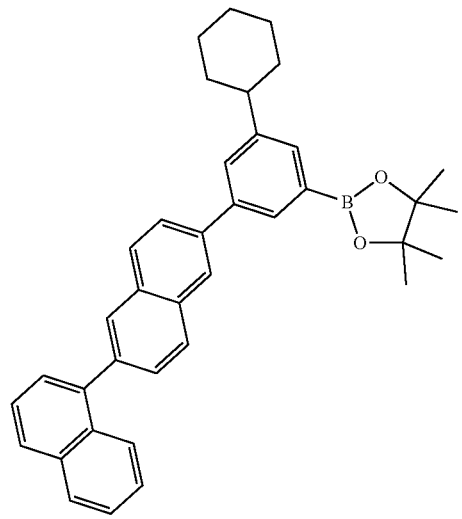
Sub 1-25

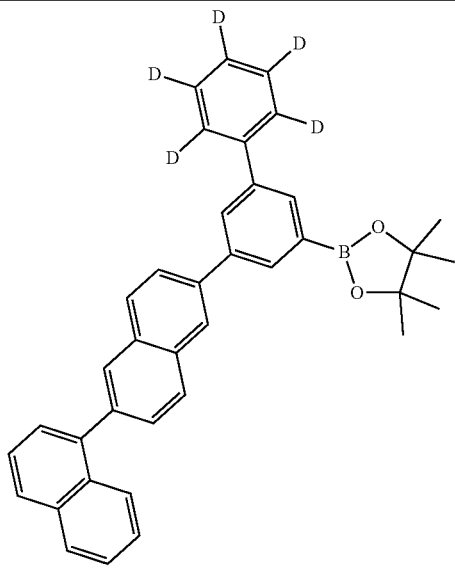

Sub 1-26

| Compound | FD-MS |
|---|---|
| Sub1-1 | m/z = 456.23 ($C_{32}H_{29}BO_2$ = 456.39) |
| Sub1-2 | m/z = 463.27 ($C_{32}H_{22}D_7BO_2$ = 463.43) |
| Sub1-3 | m/z = 462.26 ($C_{32}H_{23}D_6BO_2$ = 462.43) |
| Sub1-4 | m/z = 532.26 ($C_{38}H_{33}BO_2$ = 532.49) |
| Sub1-5 | m/z = 532.26 ($C_{38}H_{33}BO_2$ = 532.49) |
| Sub1-6 | m/z = 473.33 ($C_{32}H_{12}D_{17}BO_2$ = 473.5) |
| Sub1-7 | m/z = 532.26 ($C_{38}H_{33}BO_2$ = 532.49) |
| Sub1-8 | m/z = 629.31 ($C_{44}H_{28}D_7BO_3$ = 629.61) |
| Sub1-9 | m/z = 532.26 ($C_{38}H_{33}BO_2$ = 532.49) |
| Sub1-10 | m/z = 622.27 ($C_{44}H_{35}BO_3$ = 622.57) |
| Sub1-11 | m/z = 622.27 ($C_{44}H_{35}BO_3$ = 622.57) |
| Sub1-12 | m/z = 460.25 ($C_{32}H_{25}D_4BO_2$ = 460.42) |
| Sub1-13 | m/z = 638.25 ($C_{44}H_{35}BO_2S$ = 638.63) |
| Sub1-14 | m/z = 645.29 ($C_{44}H_{28}D_7BO_2S$ = 645.67) |
| Sub1-15 | m/z = 470.24 ($C_{33}H_{31}BO_2$ = 470.42) |
| Sub1-16 | m/z = 539.3 ($C_{38}H_{26}D_7BO_2$ = 539.53) |
| Sub1-17 | m/z = 600.29 ($C_{41}H_{37}BN_2O_2$ = 600.57) |
| Sub1-18 | m/z = 622.27 ($C_{44}H_{35}BO_3$ = 422.57) |
| Sub1-19 | m/z = 638.25 ($C_{44}H_{35}BO_2S$ = 638.63) |
| Sub1-20 | m/z = 541.31 ($C_{38}H_{24}D_9BO_2$ = 541.54) |
| Sub1-21 | m/z = 470.24 ($C_{33}H_{31}BO_2$ = 470.42) |
| Sub1-22 | m/z = 477.29 ($C_{33}H_{24}D_7BO_2$ = 477.46) |
| Sub1-23 | m/z = 537.29 ($C_{38}H_{28}D_5BO_2$ = 537.52) |
| Sub1-24 | m/z = 532.26 ($C_{38}H_{33}BO_2$ = 532.49) |
| Sub1-25 | m/z = 538.30 ($C_{38}H_{39}BO_2$ = 538.54) |
| Sub1-26 | m/z = 537.29 ($C_{38}H_{28}D_5BO_2$ = 537.52) |

II. Synthesis of Sub 2

Sub 2 of Reaction Scheme 1 may be synthesized by the reaction pathway of Reaction Scheme 3, but is not limited thereto.

<Reaction Scheme 3>

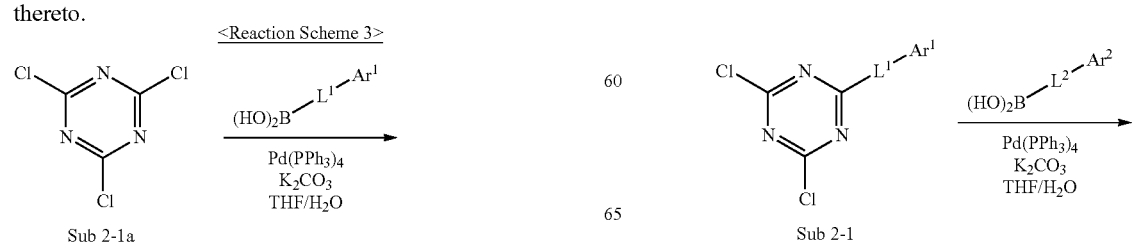

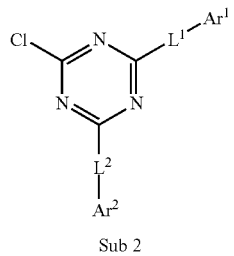

Sub 2

Synthesis examples of specific compounds belonging to Sub 2 are as follows.

1. Synthesis Example of Sub 2-3

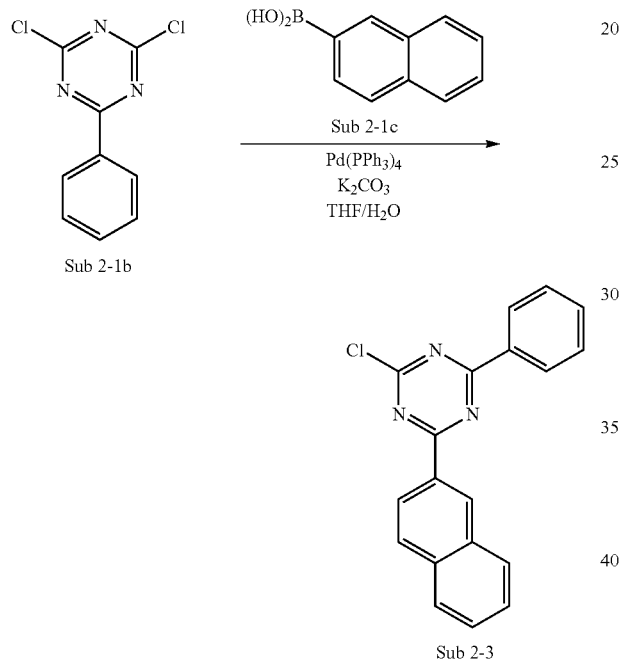

Sub2-1b (86.75 g, 383.74 mmol), Sub2-1c (33.00 g, 191.87 mmol), Pd(PPh$_3$)$_4$ (6.65 g, 5.76 mmol), K$_2$CO$_3$ (53.04 g, 383.74 mmol) were placed in a round bottom flask and dissolving in anhydrous THF (640 mL) and water (220 mL), and refluxed for 12 hours. When the reaction was completed, the reactant was cooled to room temperature, extracted with CH$_2$Cl$_{12}$ and water, and treated with MgSO$_4$. The product produced by concentrating the organic solvent was recrystallized using a Silicagel Column to obtain 37.80 g (62%) of Sub2-3.

2. Synthesis Example of Sub 2-5

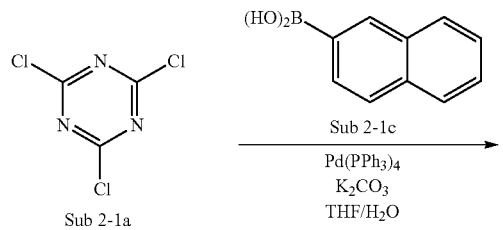

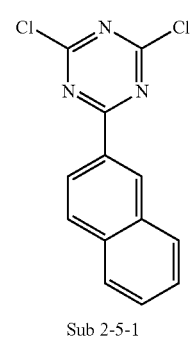

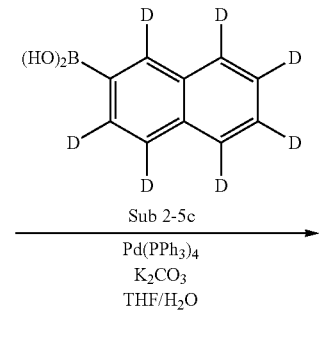

(1) Synthesis of Sub 2-5-1

Sub2-1a (128.66 g, 697.71 mmol), Sub2-1c (60.00 g, 348.86 mmol), Pd(PPh$_3$)$_4$ (12.10 g, 10.47 mmol), K$_2$CO$_3$ (96.43 g, 697.71 mmol) were placed in a round bottom flask and dissolving in anhydrous THE (1163 mL) and water (372 mL), and refluxed for 12 hours. When the reaction was completed, the reactant was cooled to room temperature, extracted with CH$_2$Cl$_{12}$ and water, and treated with MgSO$_4$. The product produced by concentrating the organic solvent was recrystallized using a Silicagel Column to obtain 41.42 g (43%) of Sub2-5-1.

(2) Synthesis of Sub 2-5

Sub2-5-1 (40.10 g, 145.23 mmol), Sub2-5c (13.00 g, 72.61 mmol), Pd(PPh$_3$)$_4$ (2.52 g, 2.18 mmol), K$_2$CO$_3$ (20.07 g, 145.23 mmol) were placed in a round bottom flask and dissolving in anhydrous THE (242 mL) and water (80 mL), and refluxed for 12 hours. When the reaction was completed, the reactant was cooled to room temperature, extracted with CH$_2$Cl$_{12}$ and water, and treated with MgSO$_4$. The product produced by concentrating the organic solvent was recrystallized using a Silicagel Column to obtain 13.88 g (51%) of Sub2-5.

3. Synthesis Example of Sub 2-19

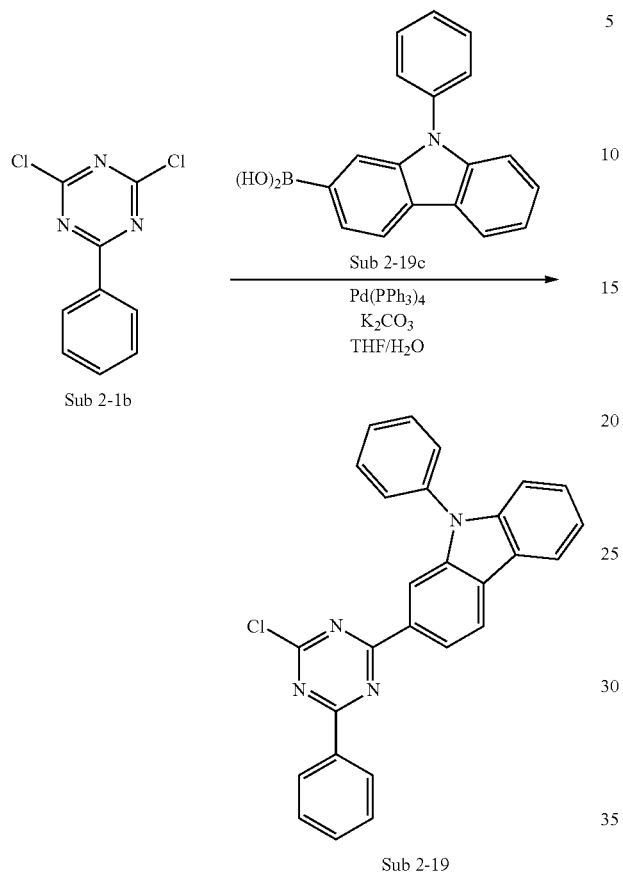

Sub2-1b (31.50 g, 139.36 mmol), Sub2-19c (20.00 g, 69.68 mmol), Pd(PPh$_3$)$_4$ (2.42 g, 2.09 mmol), K$_2$CO$_3$ (19.26 g, 139.36 mmol) were placed in a round bottom flask and dissolving in anhydrous THE (232 mL) and water (80 mL), and refluxed for 12 hours. When the reaction was completed, the reactant was cooled to room temperature, extracted with CH$_2$Cl$_{12}$ and water, and treated with MgSO$_4$. The product produced by concentrating the organic solvent was recrystallized using a Silicagel Column to obtain 20.21 g (67%) of Sub2-19.

4. Synthesis Example of Sub 2-16

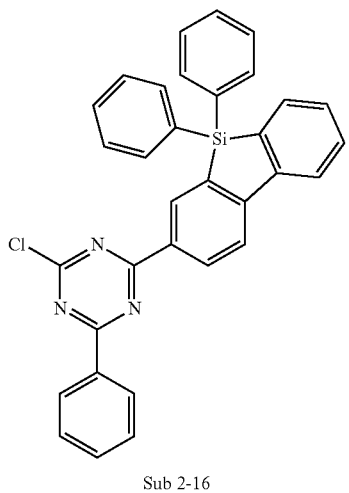

Sub2-1b (41.83 g, 185.03 mmol), Sub2-16c (35.00 g, 92.52 mmol), Pd(PPh$_3$)$_4$ (3.21 g, 2.78 mmol), K$_2$CO$_3$ (25.57 g, 185.03 mmol) were placed in a round bottom flask and dissolving in anhydrous THF (310 mL) and water (103 mL), and refluxed for 12 hours. When the reaction was completed, the reactant was cooled to room temperature, extracted with CH$_2$Cl$_{12}$ and water, and treated with MgSO$_4$. The product produced by concentrating the organic solvent was recrystallized using a Silicagel Column to obtain 22.79 g (47%) of Sub2-16.

5. Synthesis Example of Sub 2-30

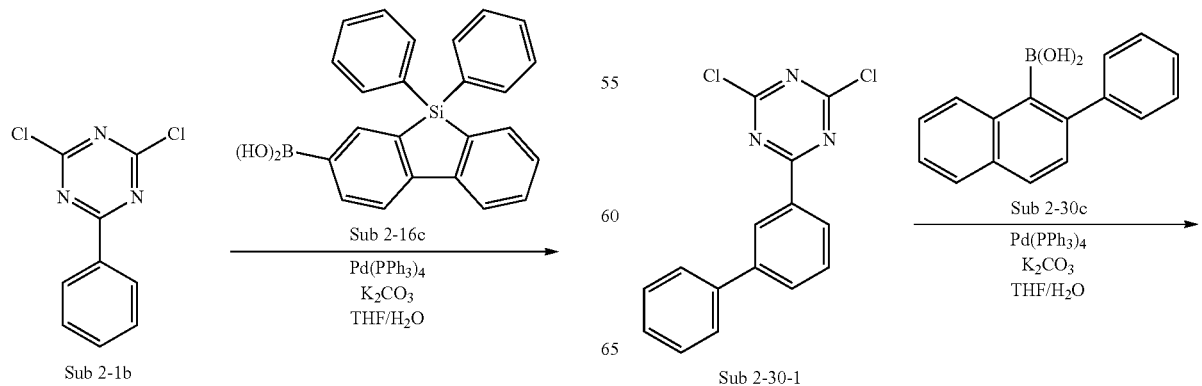

-continued

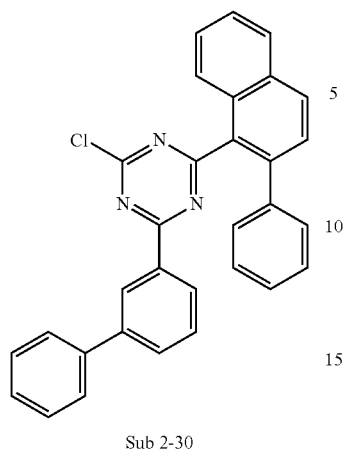

Sub 2-30

(1) Synthesis of Sub 2-30-1

Sub2-1a (93.12 g, 504.97 mmol), Sub2-1d (50.00 g, 252.49 mmol), Pd(PPh$_3$)$_4$ (8.76 g, 7.57 mmol), K$_2$CO$_3$ (69.79 g, 504.97 mmol) were placed in a round bottom flask and dissolving in anhydrous THF (841 mL) and water (280 mL), and refluxed for 12 hours. When the reaction was completed, the reactant was cooled to room temperature, extracted with CH$_2$Cl$_{12}$ and water, and treated with MgSO$_4$. The product produced by concentrating the organic solvent was recrystallized using a Silicagel Column to obtain 40.43 g (53%) of Sub2-30-1.

(2) Synthesis of Sub 2-30

Sub2-30-1 (40.00 g, 132.21 mmol), Sub2-30c (16.40 g, 66.11 mmol), Pd(PPh$_3$)$_4$ (2.29 g, 1.98 mmol), K$_2$CO$_3$ (18.27 g, 132.21 mmol) were placed in a round bottom flask and dissolving in anhydrous THE (221 mL) and water (70 mL), and refluxed for 12 hours. When the reaction was completed, the reactant was cooled to room temperature, extracted with CH$_2$Cl$_{12}$ and water, and treated with MgSO$_4$. The product produced by concentrating the organic solvent was recrystallized using a Silicagel Column to obtain 18.64 g (60%) of Sub2-30.

The compound belonging to Sub 2 may be the following compounds, but is not limited thereto, and Table 2 shows the FD-MS (Field Desorption-Mass Spectrometry) values of the compounds belonging to Sub 2.

TABLE 2

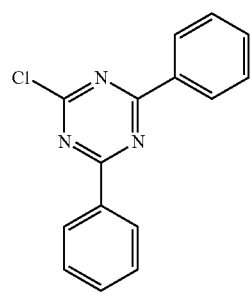

Sub 2-1

TABLE 2-continued

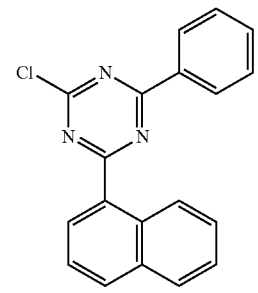

Sub 2-2

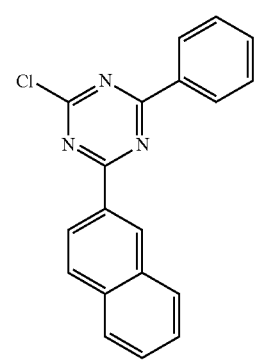

Sub 2-3

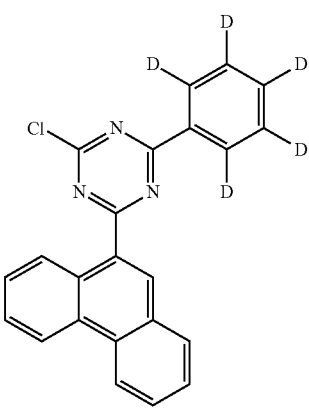

Sub 2-4

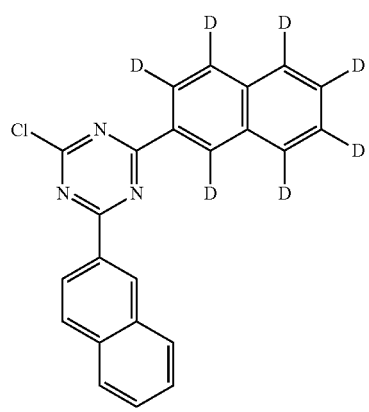

Sub 2-5

TABLE 2-continued
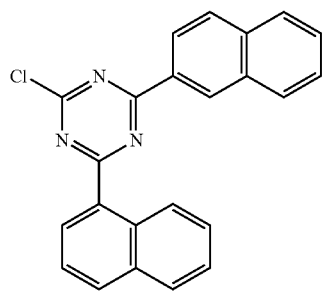
Sub 2-6
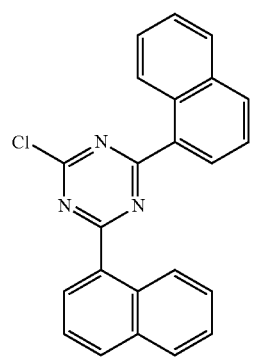
Sub 2-7
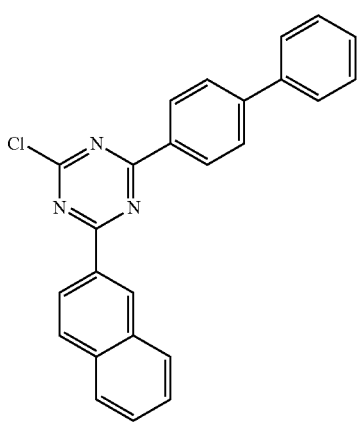
Sub 2-8
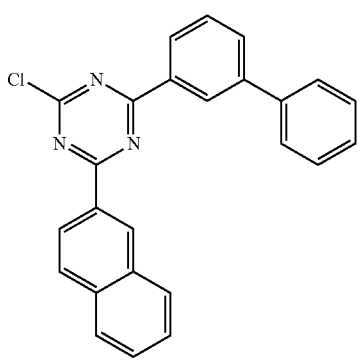
Sub 2-9
TABLE 2-continued
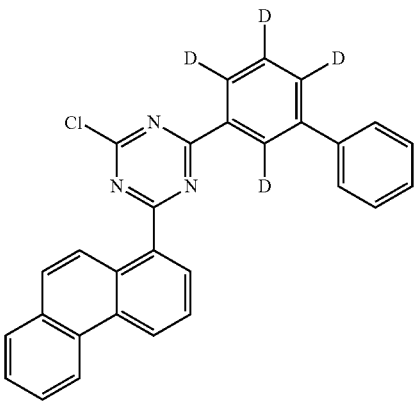
Sub 2-10
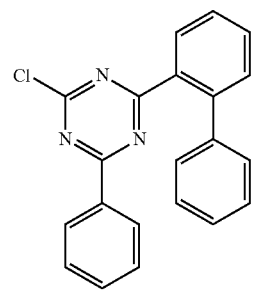
Sub 2-11
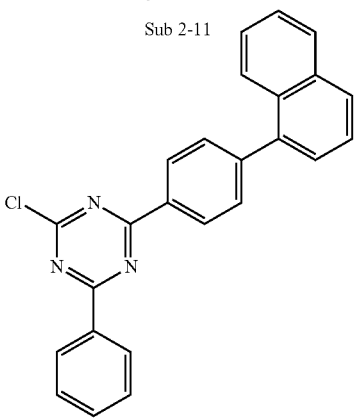
Sub 2-12
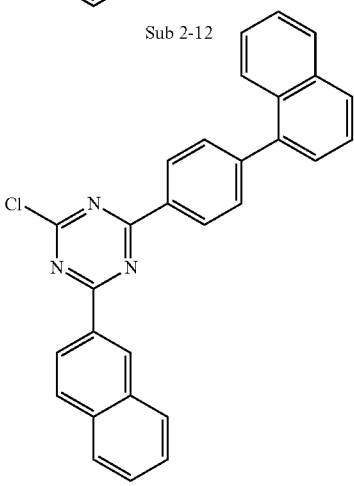
Sub 2-13

TABLE 2-continued
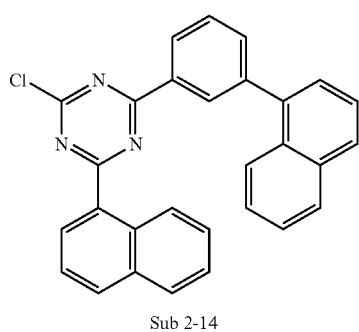 [SMILES: Clc1nc(-c2cccc(-c3cccc4ccccc34)c2)nc(-c2cccc3ccccc23)n1]
Sub 2-14
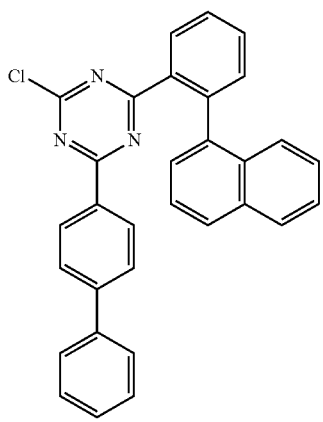
Sub 2-15
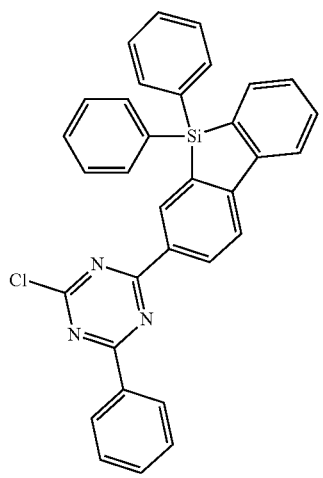
Sub 2-16
TABLE 2-continued
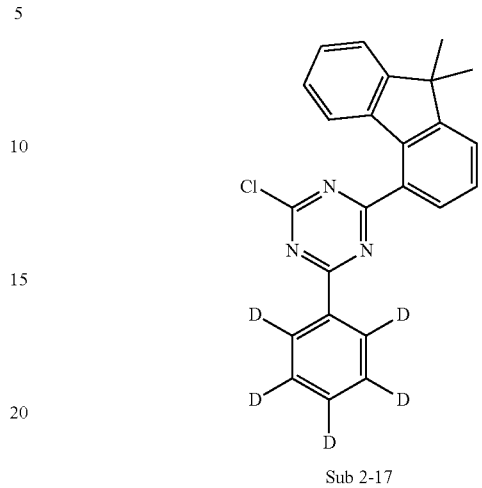
Sub 2-17
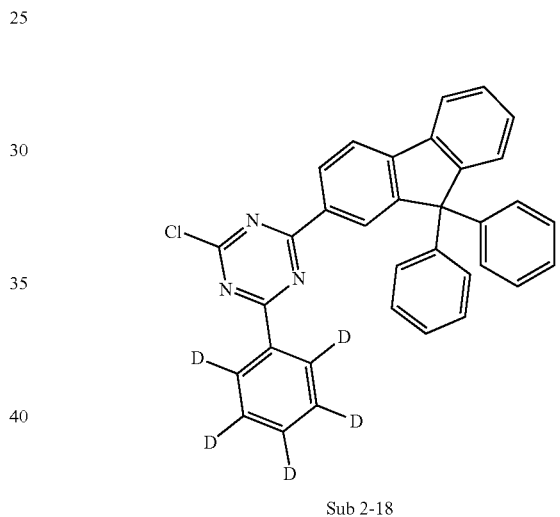
Sub 2-18
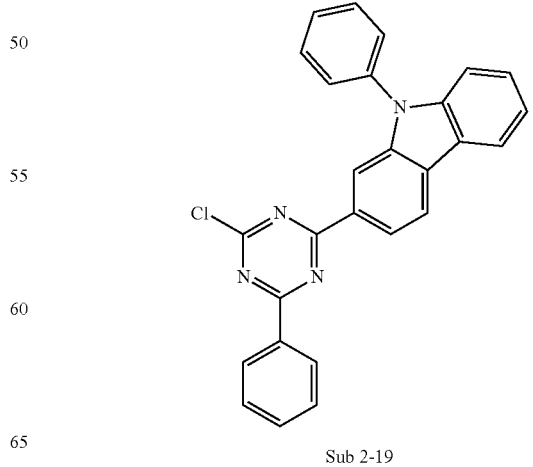
Sub 2-19

TABLE 2-continued
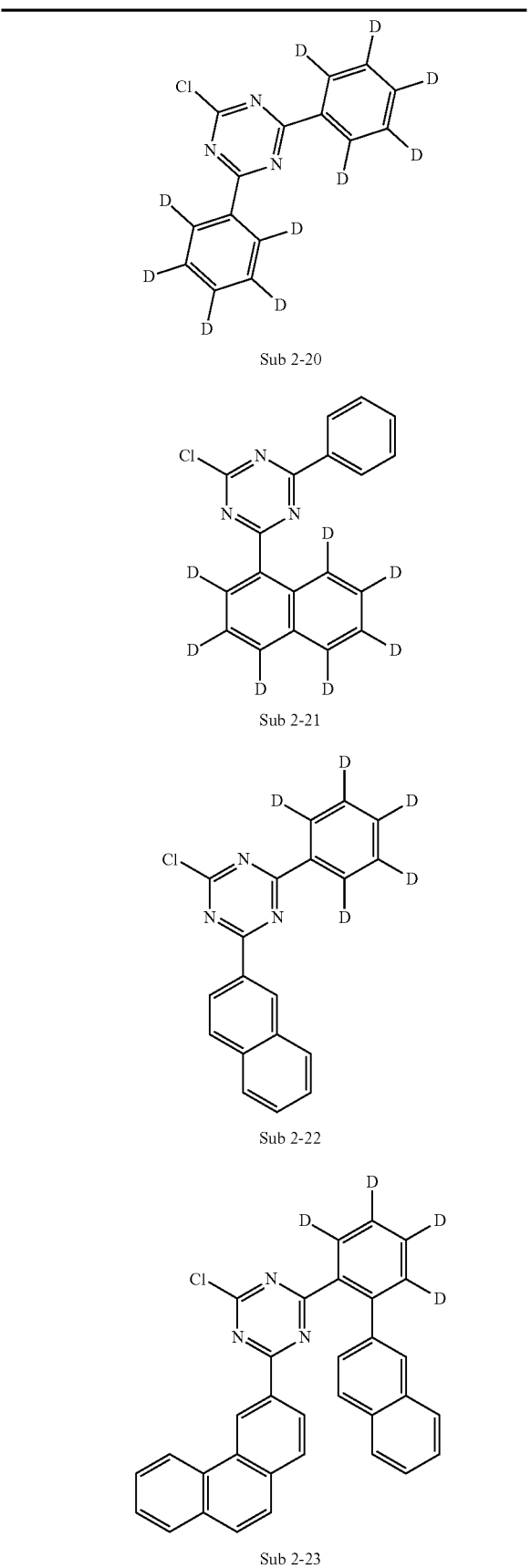
Sub 2-20
Sub 2-21
Sub 2-22
Sub 2-23
TABLE 2-continued
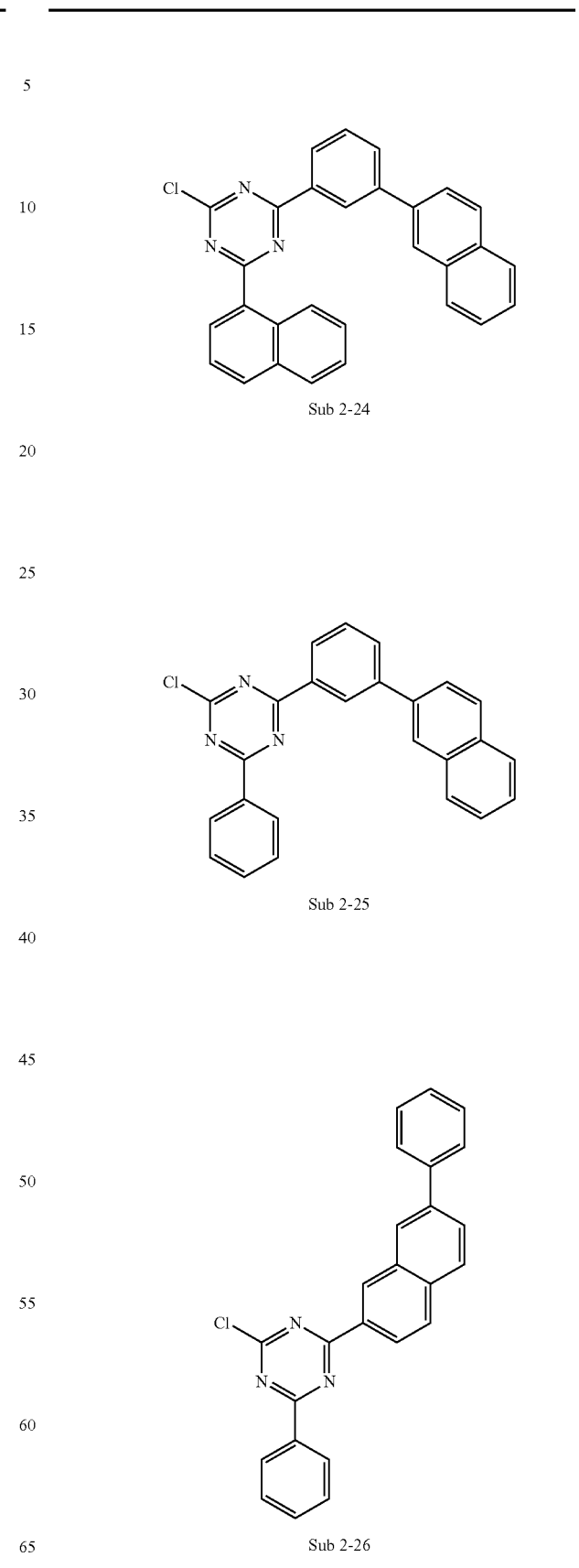
Sub 2-24
Sub 2-25
Sub 2-26

TABLE 2-continued
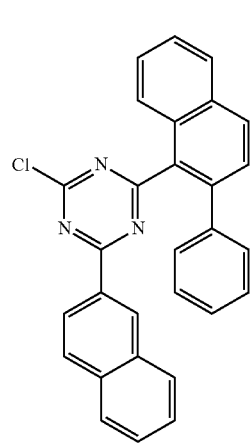
Sub 2-27
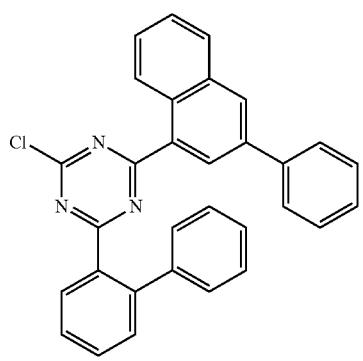
Sub 2-28
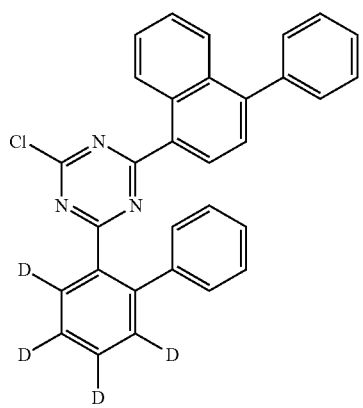
Sub 2-29
TABLE 2-continued
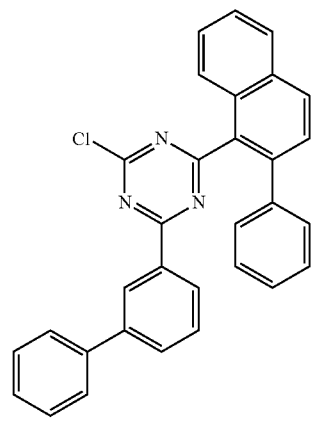
Sub 2-30
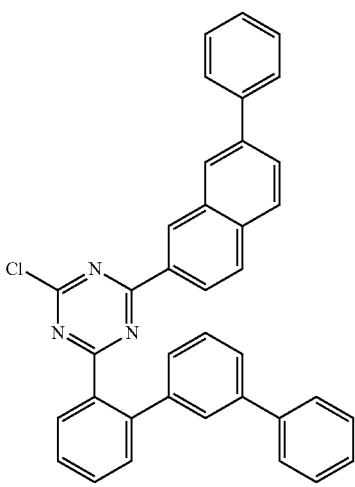
Sub 2-31
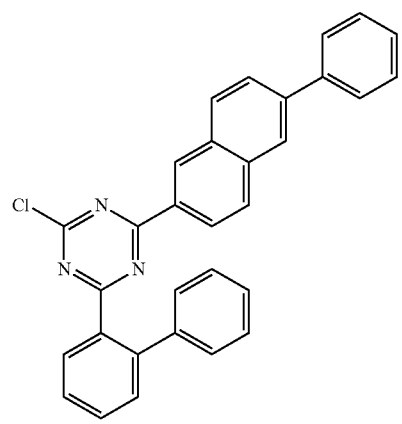
Sub 2-32

TABLE 2-continued
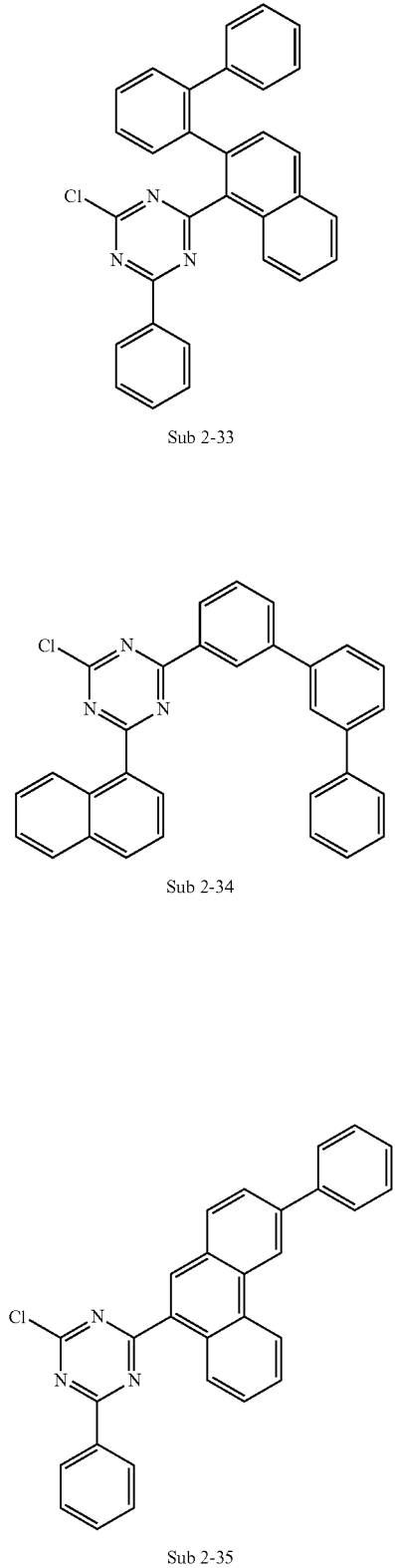
Sub 2-33
Sub 2-34
Sub 2-35
TABLE 2-continued
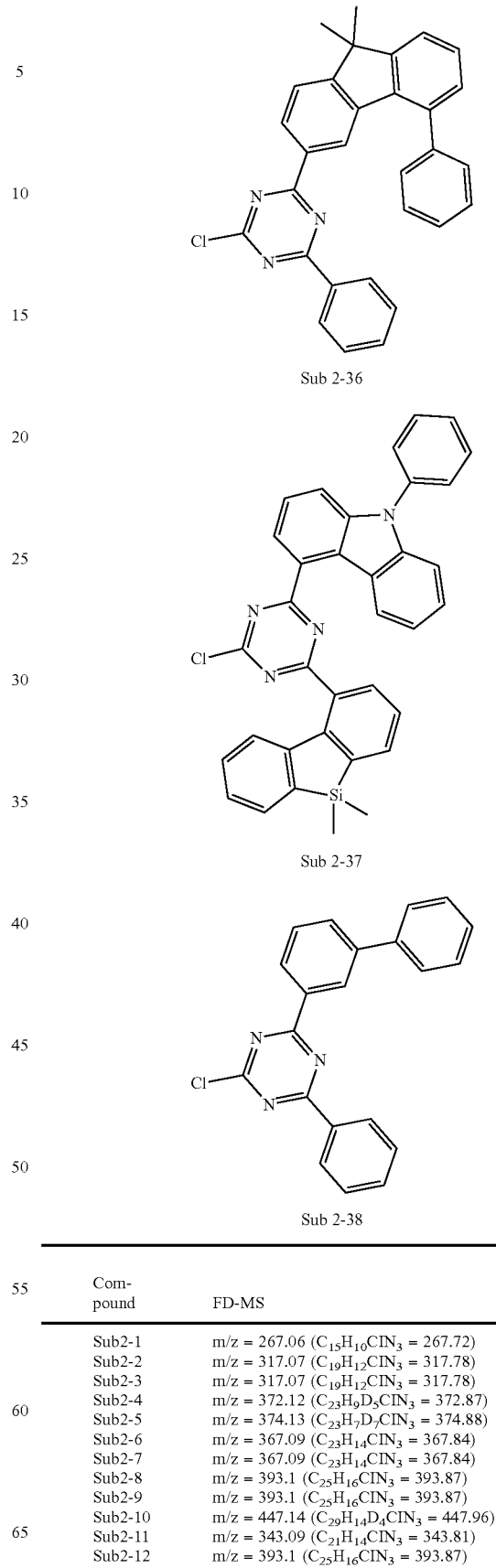
Sub 2-36
Sub 2-37
Sub 2-38
| Compound | FD-MS |
|---|---|
| Sub2-1 | m/z = 267.06 (C$_{15}$H$_{10}$ClN$_3$ = 267.72) |
| Sub2-2 | m/z = 317.07 (C$_{19}$H$_{12}$ClN$_3$ = 317.78) |
| Sub2-3 | m/z = 317.07 (C$_{19}$H$_{12}$ClN$_3$ = 317.78) |
| Sub2-4 | m/z = 372.12 (C$_{23}$H$_9$D$_5$ClN$_3$ = 372.87) |
| Sub2-5 | m/z = 374.13 (C$_{23}$H$_7$D$_7$ClN$_3$ = 374.88) |
| Sub2-6 | m/z = 367.09 (C$_{23}$H$_{14}$ClN$_3$ = 367.84) |
| Sub2-7 | m/z = 367.09 (C$_{23}$H$_{14}$ClN$_3$ = 367.84) |
| Sub2-8 | m/z = 393.1 (C$_{25}$H$_{16}$ClN$_3$ = 393.87) |
| Sub2-9 | m/z = 393.1 (C$_{25}$H$_{16}$ClN$_3$ = 393.87) |
| Sub2-10 | m/z = 447.14 (C$_{29}$H$_{14}$D$_4$ClN$_3$ = 447.96) |
| Sub2-11 | m/z = 343.09 (C$_{21}$H$_{14}$ClN$_3$ = 343.81) |
| Sub2-12 | m/z = 393.1 (C$_{25}$H$_{16}$ClN$_3$ = 393.87) |

TABLE 2-continued

| | |
|---|---|
| Sub2-13 | m/z = 443.12 (C$_{29}$H$_{18}$ClN$_3$ = 443.93) |
| Sub2-14 | m/z = 443.12 (C$_{29}$H$_{18}$ClN$_3$ = 443.93) |
| Sub2-15 | m/z = 469.13 (C$_{31}$H$_{20}$ClN$_3$ = 469.97) |
| Sub2-16 | m/z = 523.13 (C$_{33}$H$_{22}$ClN$_3$Si = 524.1) |
| Sub2-17 | m/z = 388.15 (C$_{24}$H$_{13}$D$_5$ClN$_3$ = 388.91) |
| Sub2-18 | m/z = 512.18 (C$_{34}$H$_{17}$D$_5$ClN$_3$ = 513.05) |
| Sub2-19 | m/z = 432.11 (C$_{27}$H$_{17}$ClN$_4$ = 432.91) |
| Sub2-20 | m/z = 277.12 (C$_{15}$D$_{10}$ClN$_3$ = 277.78) |
| Sub2-21 | m/z = 324.12 (C$_{19}$H$_5$D$_7$ClN$_3$ = 324.82) |
| Sub2-22 | m/z = 322.1 (C$_{19}$H$_7$D$_5$ClN$_3$ = 322.81) |
| Sub2-23 | m/z = 497.16 (C$_{33}$H$_{16}$D$_4$ClN$_3$ = 498.02) |
| Sub2-24 | m/z = 443.12 (C$_{29}$H$_{18}$ClN$_3$ = 443.93) |
| Sub2-25 | m/z = 443.12 (C$_{29}$H$_{18}$ClN$_3$ = 443.93) |
| Sub2-26 | m/z = 393.1 (C$_{25}$H$_{16}$ClN$_3$ = 393.87) |
| Sub2-27 | m/z = 443.12 (C$_{29}$H$_{18}$ClN$_3$ = 443.93) |
| Sub2-28 | m/z = 469.13 (C$_{31}$H$_{20}$ClN$_3$ = 469.97) |
| Sub2-29 | m/z = 473.16 (C$_{31}$H$_{16}$D$_4$ClN$_3$ = 474) |
| Sub2-30 | m/z = 469.13 (C$_{31}$H$_{20}$ClN$_3$ = 469.97) |
| Sub2-31 | m/z = 545.17 (C$_{37}$H$_{24}$ClN$_3$ = 546.07) |
| Sub2-32 | m/z = 469.13 (C$_{31}$H$_{20}$ClN$_3$ = 469.97) |
| Sub2-33 | m/z = 469.13 (C$_{31}$H$_{20}$ClN$_3$ = 469.97) |
| Sub2-34 | m/z = 469.13 (C$_{31}$H$_{20}$ClN$_3$ = 469.97) |
| Sub2-35 | m/z = 443.12 (C$_{29}$H$_{18}$ClN$_3$ = 443.93) |
| Sub2-36 | m/z = 459.15 (C$_{30}$H$_{22}$ClN$_3$ = 459.98) |
| Sub2-37 | m/z = 564.15 (C$_{35}$H$_{25}$ClN$_4$Si = 565.15) |
| Sub2-38 | m/z = 343.09 (C$_{21}$H$_{14}$ClN$_3$ = 343.81) |

III. Synthesis of Final Product

1. Synthesis Example of P-3

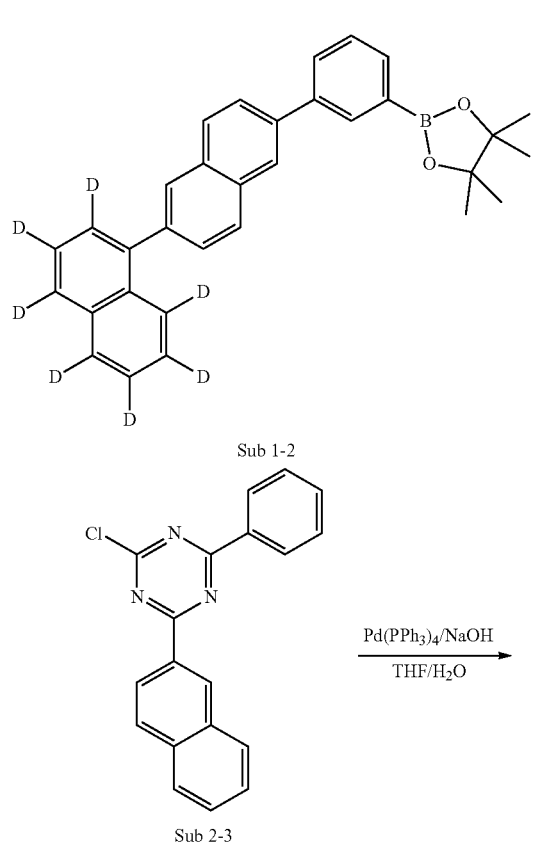

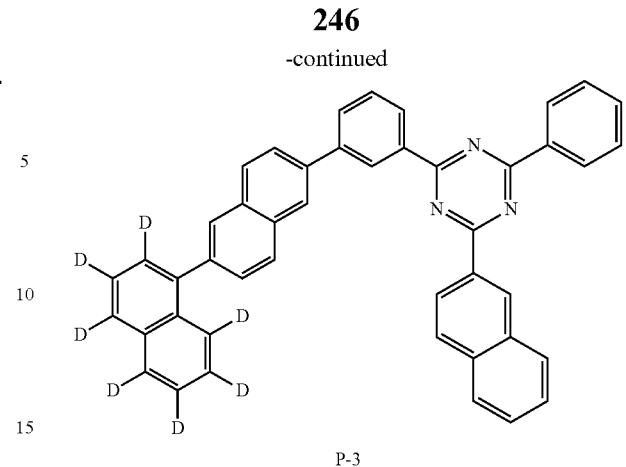

P-3

Sub1-2 (10.00 g, 21.58 mmol), Sub2-3 (6.86 g, 21.58 mmol), Pd(PPh$_3$)$_4$ (0.75 g, 0.65 mmol), NaOH (1.73 g, 43.160 mmol), THF (72 mL) and water (21 mL) were added in a round bottom flask and reacted at 75° C. for 8 hours. When the reaction is completed, the temperature of the reactant is cooled to room temperature, and the reaction solvent is removed. Thereafter, the concentrated reactant was recrystallized using a Silicagel Column to obtain 10.68 g (80%) of product P-3.

2. Synthesis Example of P-5

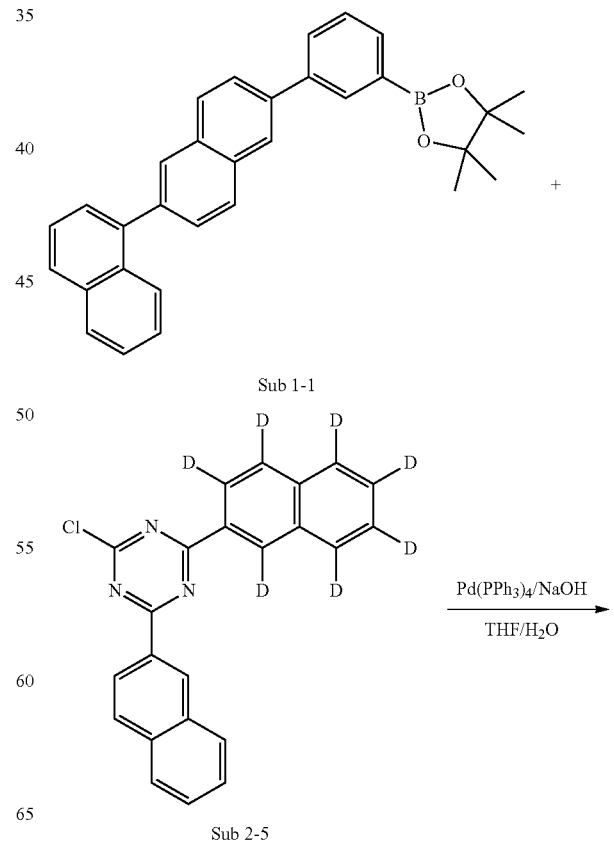

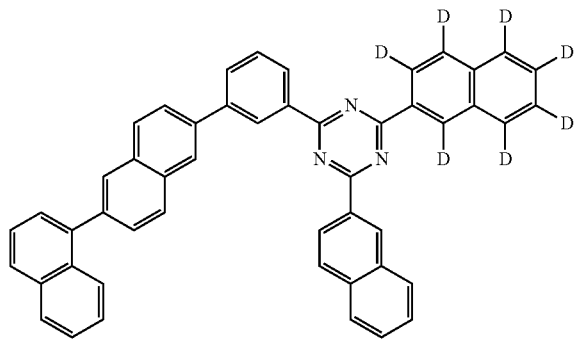

P-5

Sub1-1 (7.00 g, 15.34 mmol), Sub2-5 (5.75 g, 15.34 mmol), Pd(PPh$_3$)$_4$ (0.53 g, 0.46 mmol), NaOH (1.23 g, 30.680 mmol), THF (52 mL) and water (17 mL) were added in a round bottom flask and reacted at 75° C. for 8 hours. When the reaction is completed, the temperature of the reactant is cooled to room temperature, and the reaction solvent is removed. Thereafter, the concentrated reactant was recrystallized using a Silicagel Column to obtain 7.59 g (74%) of product P-5.

3. Synthesis Example of P-11

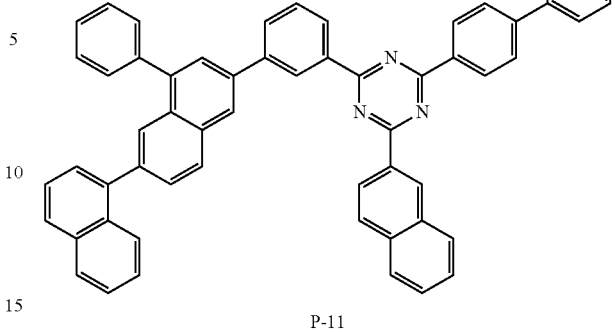

P-11

Sub1-4 (6.80 g, 12.77 mmol), Sub2-8 (5.03 g, 12.77 mmol), Pd(PPh$_3$)$_4$ (0.44 g, 0.38 mmol), NaOH (1.02 g, 25.54 mmol), THF (43 mL) and water (12 mL) were added in a round bottom flask and reacted at 75° C. for 8 hours. When the reaction is completed, the temperature of the reactant is cooled to room temperature, and the reaction solvent is removed. Thereafter, the concentrated reactant was recrystallized using a Silicagel Column to obtain 6.54 g (67%) of product P-11.

4. Synthesis Example of P-42

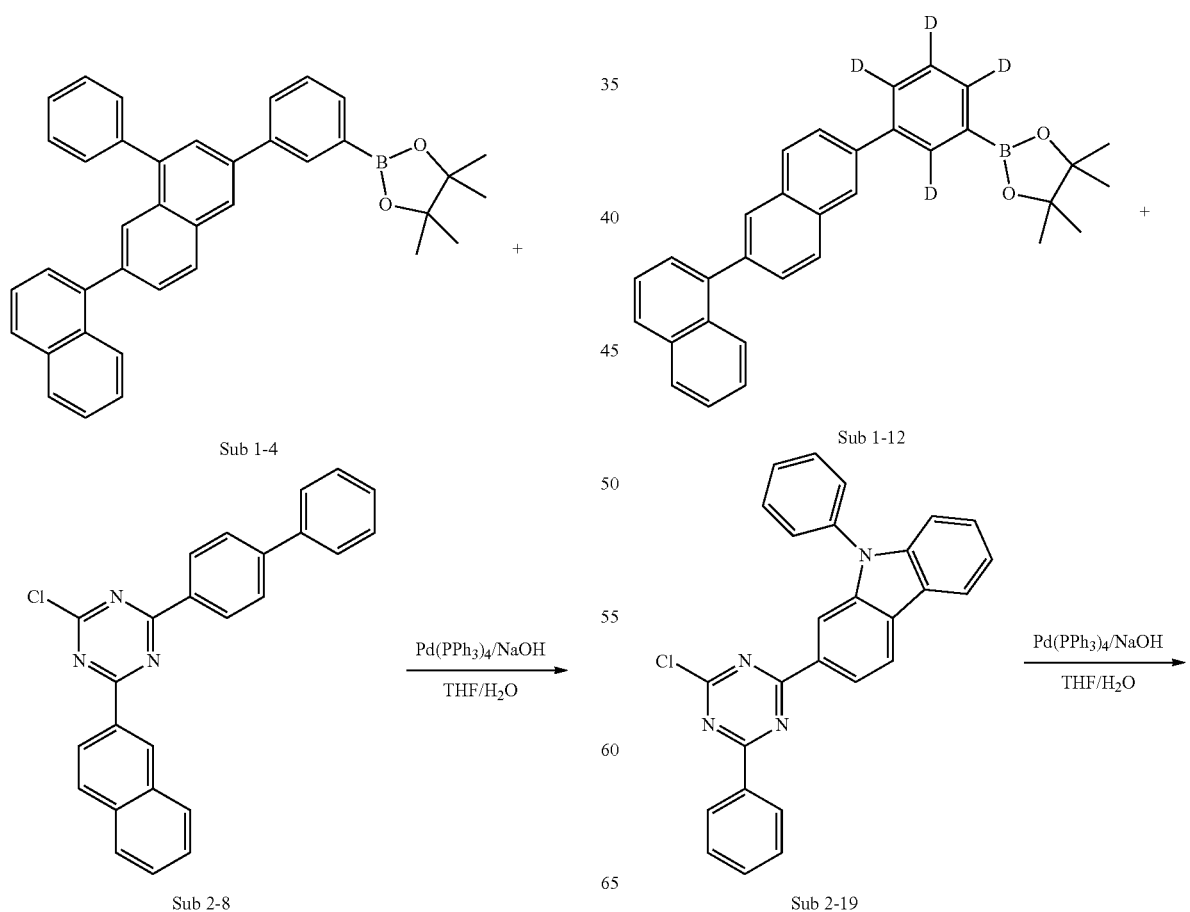

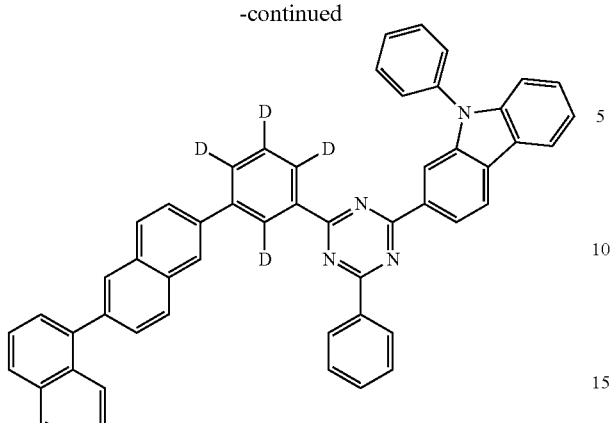

P-42

Sub1-12 (15.00 g, 32.58 mmol), Sub2-19 (14.10 g, 32.58 mmol), Pd(PPh$_3$)$_4$ (1.13 g, 0.98 mmol), NaOH (2.61 g, 65.16 mmol), THF (108 mL) and water (36 mL) were added in a round bottom flask and reacted at 75° C. for 8 hours. When the reaction is completed, the temperature of the reactant is cooled to room temperature, and the reaction solvent is removed. Thereafter, the concentrated reactant was recrystallized using a Silicagel Column to obtain 33.91 g (87%) of product P-42.

5. Synthesis Example of P-45

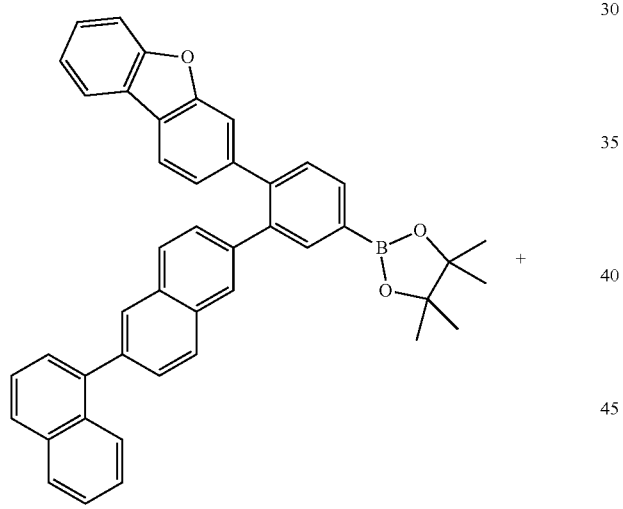

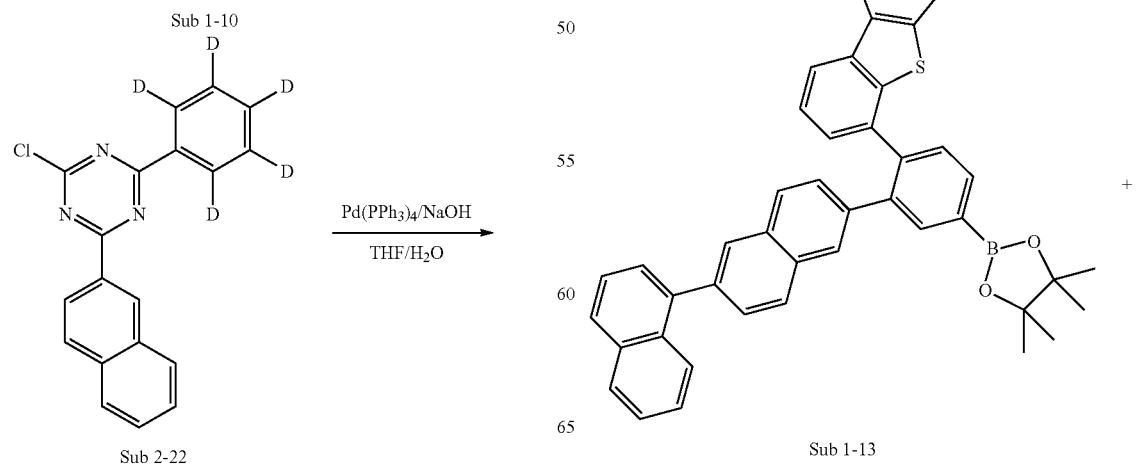

P-45

Sub1-10 (21.00 g, 33.73 mmol), Sub2-22 (10.89 g, 33.73 mmol), Pd(PPh$_3$)$_4$ (1.17 g, 1.01 mmol), NaOH (2.70 g, 67.46 mmol), THF (112 mL) and water (36 mL) were added in a round bottom flask and reacted at 75° C. for 8 hours. When the reaction is completed, the temperature of the reactant is cooled to room temperature, and the reaction solvent is removed. Thereafter, the concentrated reactant was recrystallized using a Silicagel Column to obtain 19.54 g (74%) of product P-45.

6. Synthesis Example of P-50

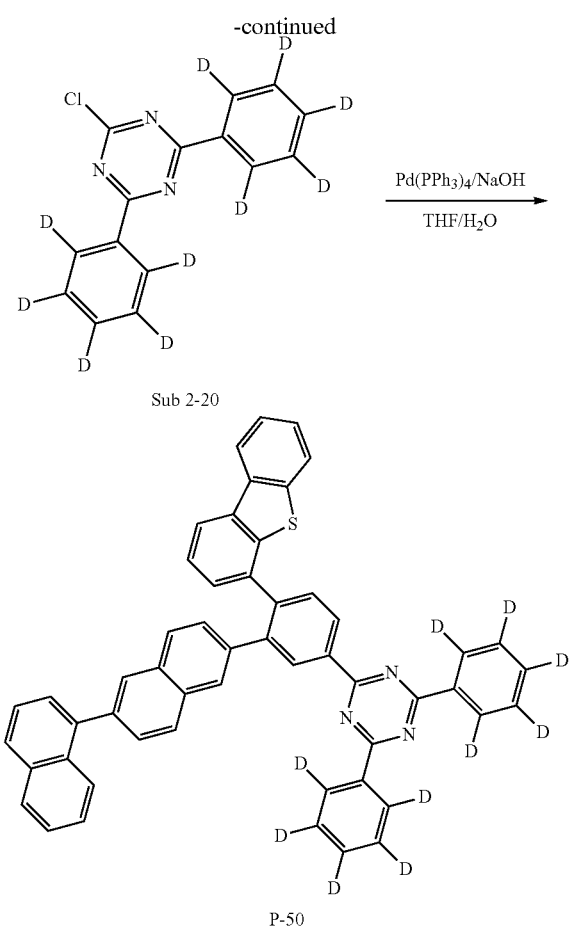

Sub 2-20

P-50

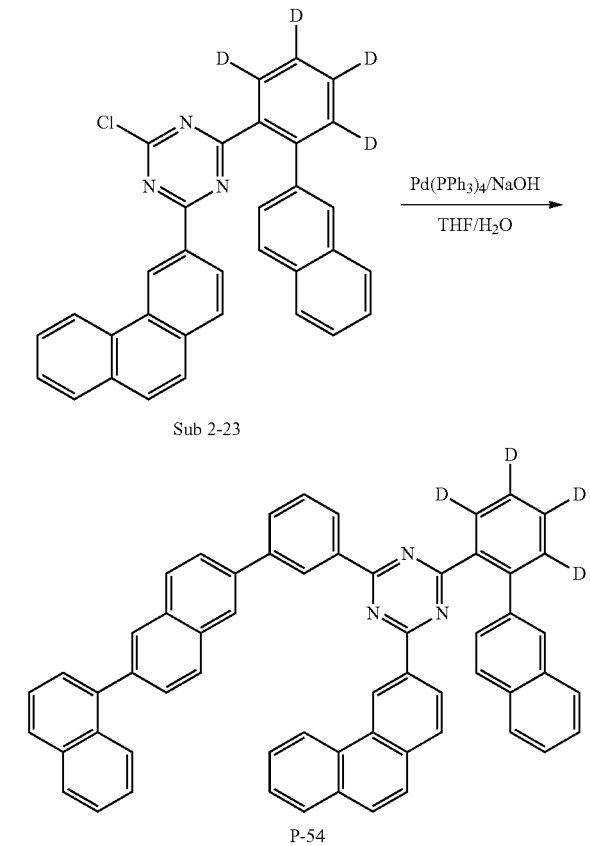

Sub 2-23

P-54

Sub1-13 (12.00 g, 18.79 mmol), Sub2-20 (5.22 g, 18.79 mmol), Pd(PPh₃)₄ (0.65 g, 0.56 mmol), NaOH (1.50 g, 37.58 mmol), THF (63 mL) and water (21 mL) were added in a round bottom flask and reacted at 75° C. for 8 hours. When the reaction is completed, the temperature of the reactant is cooled to room temperature, and the reaction solvent is removed. Thereafter, the concentrated reactant was recrystallized using a Silicagel Column to obtain 11.33 g (77%) of product P-50.

Sub1-1 (16.00 g, 35.06 mmol), Sub2-23 (17.46 g, 35.06 mmol), Pd(PPh₃)₄ (1.22 g, 1.05 mmol), NaOH (2.80 g, 70.12 mmol), THF (118 mL) and water (39 mL) were added in a round bottom flask and reacted at 75° C. for 8 hours. When the reaction is completed, the temperature of the reactant is cooled to room temperature, and the reaction solvent is removed. Thereafter, the concentrated reactant was recrystallized using a Silicagel Column to obtain 20.00 g (72%) of product P-54.

7. Synthesis Example of P-54

8. Synthesis Example of P-64

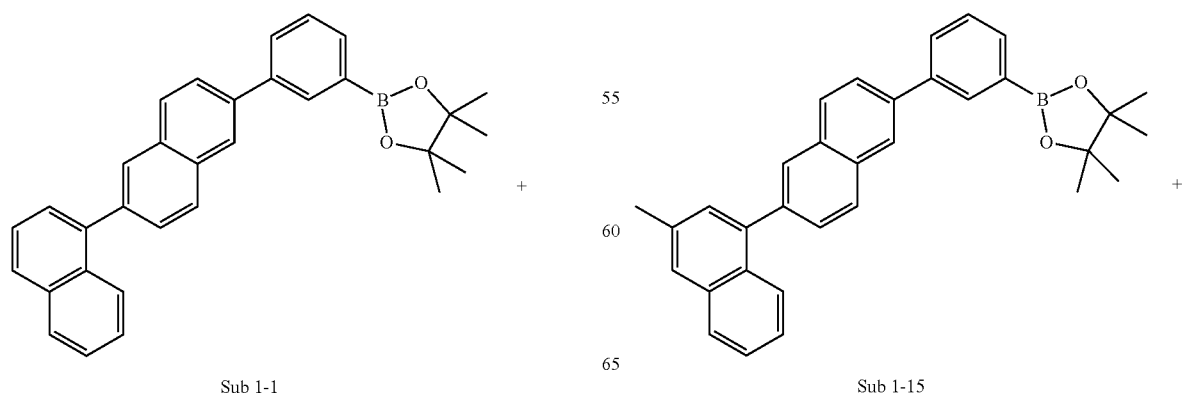

Sub 1-1

Sub 1-15

253

-continued

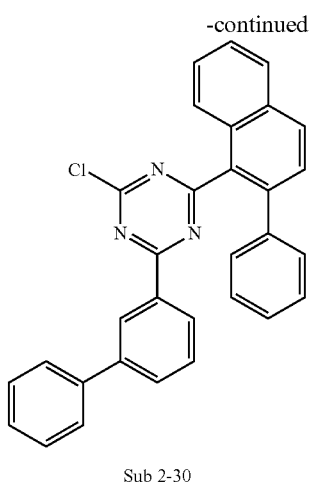

Sub 2-30

254

-continued

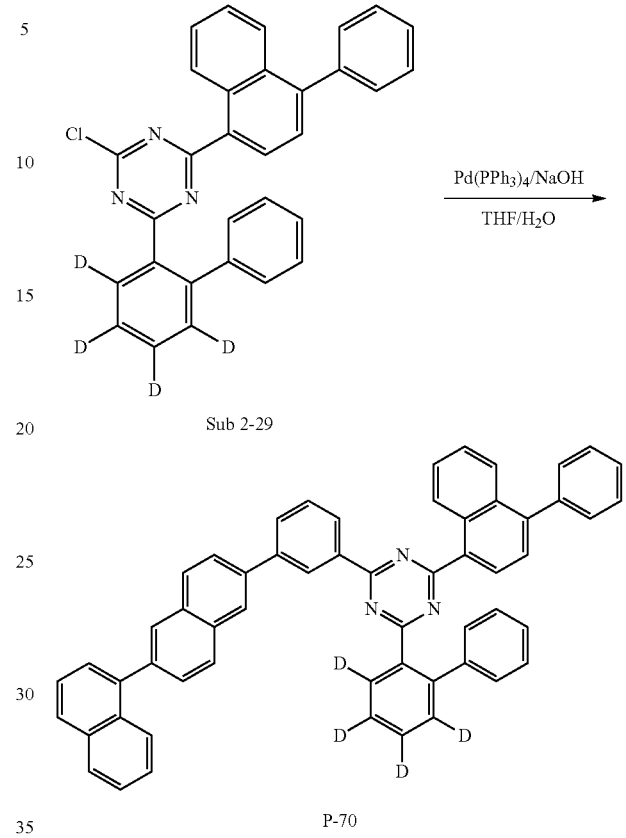

Sub1-15 (13.00 g, 27.63 mmol), Sub2-30 (12.99 g, 27.63 mmol), Pd(PPh₃)₄ (0.96 g, 0.83 mmol), NaOH (2.21 g, 55.27 mmol), THF (93 mL) and water (31 mL) were added in a round bottom flask and reacted at 75° C. for 8 hours. When the reaction is completed, the temperature of the reactant is cooled to room temperature, and the reaction solvent is removed. Thereafter, the concentrated reactant was recrystallized using a Silicagel Column to obtain 16.34 g (76%) of product P-64.

Sub1-1 (14.00 g, 30.68 mmol), Sub2-29 (14.54 g, 30.68 mmol), Pd(PPh₃)₄ (1.06 g, 0.92 mmol), NaOH (2.45 g, 61.35 mmol), THF (102 mL) and water (30 mL) were added in a round bottom flask and reacted at 75° C. for 8 hours. When the reaction is completed, the temperature of the reactant is cooled to room temperature, and the reaction solvent is removed. Thereafter, the concentrated reactant was recrystallized using a Silicagel Column to obtain 18.37 g (78%) of product P-70.

9. Synthesis Example of P-70

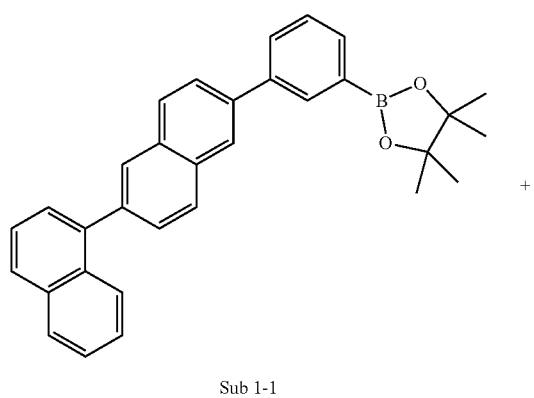

Sub 1-1

+

10. Synthesis Example of P-100

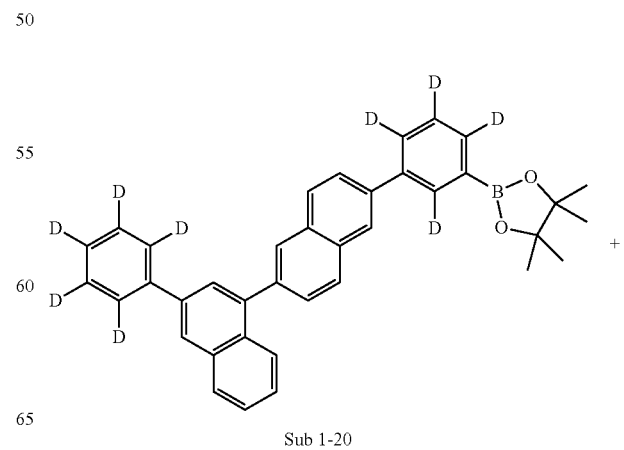

Sub 1-20

+

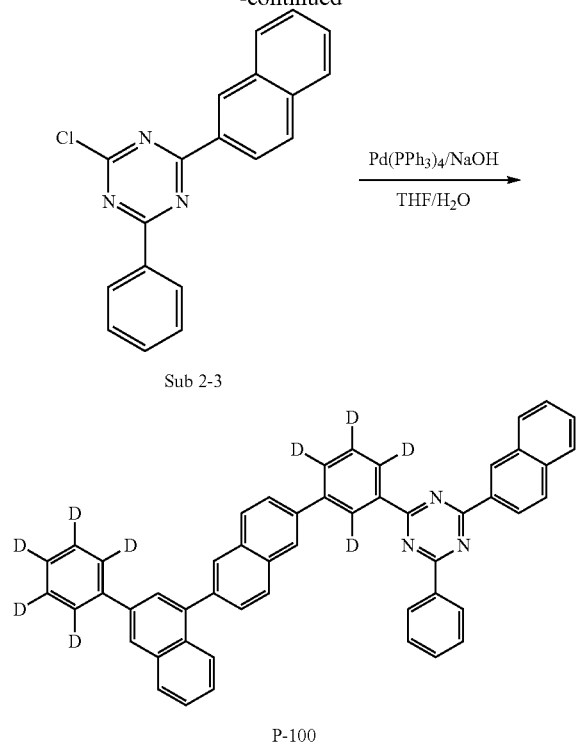

Sub1-20 (12.00 g, 22.16 mmol), Sub2-3 (7.04 g, 22.16 mmol), Pd(PPh₃)₄ (0.77 g, 0.66 mmol), NaOH (1.77 g, 44.32 mmol), THF (73.86 mL) and water (24 mL) were added in a round bottom flask and reacted at 75° C. for 8 hours. When the reaction is completed, the temperature of the reactant is cooled to room temperature, and the reaction solvent is removed. Thereafter, the concentrated reactant was recrystallized using a Silicagel Column to obtain 10.35 g (67%) of product P-100.

Otherwise, the FD-MS values of the compounds P-1 to P-104 of the present invention prepared according to the Synthesis Example as described are shown in Table 3.

TABLE 3

| Compound | FD-MS |
| --- | --- |
| P-1 | m/z = 561.22($C_{41}H_{27}N_3$ = 561.69) |
| P-2 | m/z = 611.24($C_{45}H_{29}N_3$ = 611.75) |
| P-3 | m/z = 618.28($C_{45}H_{22}D_7N_3$ = 618.79) |
| P-4 | m/z = 666.28($C_{49}H_{26}D_5N_3$ = 666.84) |
| P-5 | m/z = 668.3($C_{49}H_{24}D_7N_3$ = 668.85) |
| P-6 | m/z = 618.28($C_{45}H_{22}D_7N_3$ = 618.79) |
| P-7 | m/z = 661.25($C_{49}H_{31}N_3$ = 661.81) |
| P-8 | m/z = 711.27($C_{53}H_{33}N_3$ = 711.87) |
| P-9 | m/z = 637.25($C_{47}H_{31}N_3$ = 637.79) |
| P-10 | m/z = 687.27($C_{51}H_{33}N_3$ = 687.85) |
| P-11 | m/z = 763.3($C_{57}H_{37}N_3$ = 763.94) |
| P-12 | m/z = 737.28($C_{55}H_{35}N_3$ = 737.91) |
| P-13 | m/z = 713.28($C_{53}H_{35}N_3$ = 713.88) |
| P-14 | m/z = 693.31($C_{51}H_{27}D_6N_3$ = 693.88) |
| P-15 | m/z = 817.34($C_{61}H_{35}D_4N_3$ = 818.03) |
| P-16 | m/z = 687.27($C_{51}H_{33}N_3$ = 687.85) |
| P-17 | m/z = 763.3($C_{57}H_{37}N_3$ = 763.94) |
| P-18 | m/z = 654.36($C_{47}H_{14}D_{17}N_3$ = 654.89) |
| P-19 | m/z = 737.28($C_{55}H_{35}N_3$ = 737.91) |
| P-20 | m/z = 737.28($C_{55}H_{35}N_3$ = 737.91) |
| P-21 | m/z = 687.27($C_{51}H_{33}N_3$ = 687.85) |
| P-22 | m/z = 737.28($C_{55}H_{35}N_3$ = 737.91) |
| P-23 | m/z = 787.3($C_{59}H_{37}N_3$ = 787.97) |
| P-24 | m/z = 763.3($C_{57}H_{37}N_3$ = 763.94) |
| P-25 | m/z = 763.3($C_{57}H_{37}N_3$ = 763.94) |
| P-26 | m/z = 737.28($C_{55}H_{35}N_3$ = 737.91) |
| P-27 | m/z = 694.31($C_{51}H_{26}D_7N_3$ = 694.89) |
| P-28 | m/z = 813.31($C_{61}H_{39}N_3$ = 814) |
| P-29 | m/z = 737.28($C_{55}H_{35}N_3$ = 737.91) |
| P-30 | m/z = 787.3($C_{59}H_{37}N_3$ = 787.97) |
| P-31 | m/z = 763.3($C_{57}H_{37}N_3$ = 763.94) |
| P-32 | m/z = 737.28($C_{55}H_{35}N_3$ = 737.91) |
| P-33 | m/z = 693.26($C_{49}H_{35}N_3Si$ = 693.92) |
| P-34 | m/z = 743.28($C_{53}H_{37}N_3Si$ = 743.99) |
| P-35 | m/z = 817.29($C_{59}H_{39}N_3Si$ = 818.07) |
| P-36 | m/z = 867.31($C_{63}H_{41}N_3Si$ = 868.13) |
| P-37 | m/z = 677.28($C_{50}H_{35}N_3$ = 677.85) |
| P-38 | m/z = 682.31($C_{50}H_{30}D_5N_3$ = 682.88) |
| P-39 | m/z = 801.31($C_{60}H_{39}N_3$ = 801.99) |
| P-40 | m/z = 810.37($C_{60}H_{30}D_9N_3$ = 811.05) |
| P-41 | m/z = 776.29($C_{57}H_{36}N_4$ = 776.94) |
| P-42 | m/z = 730.30($C_{53}H_{30}D$ = 730.91) |
| P-43 | m/z = 852.33($C_{63}H_{40}N_4$ = 853.04) |
| P-44 | m/z = 802.31($C_{59}H_{38}N_4$ = 802.98) |
| P-45 | m/z = 782.31($C_{57}H_{30}D_5N_3O$ = 782.96) |
| P-46 | m/z = 727.26($C_{53}H_{33}N_3O$ = 727.87) |
| P-47 | m/z = 777.28($C_{57}H_{35}N_3O$ = 777.93) |
| P-48 | m/z = 734.31($C_{53}H_{26}D_7N_3O$ = 734.91) |
| P-49 | m/z = 750.28($C_{53}H_{26}D_7N_3S$ = 750.97) |
| P-50 | m/z = 753.3($C_{53}H_{23}D_{10}N_3S$ = 753.99) |
| P-51 | m/z = 743.24($C_{53}H_{33}N_3S$ = 743.93) |
| P-52 | m/z = 793.26($C_{57}H_{35}N_3S$ = 793.99) |
| P-53 | m/z = 787.3($C_{59}H_{37}N_3$ = 787.97) |
| P-54 | m/z = 791.32($C_{59}H_{33}D_4N_3$ = 791.99) |
| P-55 | m/z = 737.28($C_{55}H_{35}N_3$ = 737.91) |
| P-56 | m/z = 763.3($C_{57}H_{37}N_3$ = 763.94) |
| P-57 | m/z = 737.28($C_{55}H_{35}N_3$ = 737.91) |
| P-58 | m/z = 737.28($C_{55}H_{35}N_3$ = 737.91) |
| P-59 | m/z = 763.3($C_{57}H_{37}N_3$ = 763.94) |
| P-60 | m/z = 687.27($C_{51}H_{33}N_3$ = 687.85) |
| P-61 | m/z = 687.27($C_{51}H_{33}N_3$ = 687.85) |
| P-62 | m/z = 737.28($C_{55}H_{35}N_3$ = 737.91) |
| P-63 | m/z = 737.28($C_{55}H_{35}N_3$ = 737.91) |
| P-64 | m/z = 737.28($C_{55}H_{35}N_3$ = 737.91) |
| P-65 | m/z = 737.28($C_{55}H_{35}N_3$ = 737.91) |
| P-66 | m/z = 763.3($C_{57}H_{37}N_3$ = 763.94) |
| P-67 | m/z = 763.3($C_{57}H_{37}N_3$ = 763.94) |
| P-68 | m/z = 763.3($C_{57}H_{37}N_3$ = 763.94) |
| P-69 | m/z = 763.3($C_{57}H_{37}N_3$ = 763.94) |
| P-70 | m/z = 737.28($C_{55}H_{35}N_3$ = 737.91) |
| P-71 | m/z = 737.28($C_{55}H_{35}N_3$ = 737.91) |
| P-72 | m/z = 737.28($C_{55}H_{35}N_3$ = 737.91) |
| P-73 | m/z = 737.28($C_{55}H_{35}N_3$ = 737.91) |
| P-74 | m/z = 813.31($C_{61}H_{39}N_3$ = 814.00) |
| P-75 | m/z = 813.31($C_{61}H_{39}N_3$ = 814.00) |
| P-76 | m/z = 701.28($C_{52}H_{35}N_3$ = 701.87) |
| P-77 | m/z = 701.28($C_{52}H_{35}N_3$ = 701.87) |
| P-78 | m/z = 763.3($C_{57}H_{37}N_3$ = 763.94) |
| P-79 | m/z = 763.3($C_{57}H_{37}N_3$ = 763.94) |
| P-80 | m/z = 744.33($C_{55}H_{28}D_7N_3$ = 744.95) |
| P-81 | m/z = 744.33($C_{55}H_{28}D_7N_3$ = 744.95) |
| P-82 | m/z = 743.32($C_{55}H_{29}D_6N_3$ = 743.94) |
| P-83 | m/z = 743.32($C_{55}H_{29}D_6N_3$ = 743.94) |
| P-84 | m/z = 763.3($C_{57}H_{37}N_3$ = 763.94) |
| P-85 | m/z = 763.3($C_{57}H_{37}N_3$ = 763.94) |
| P-86 | m/z = 863.33($C_{65}H_{41}N_3$ = 864.06) |
| P-87 | m/z = 863.33($C_{65}H_{41}N_3$ = 864.06) |
| P-88 | m/z = 763.3($C_{57}H_{37}N_3$ = 763.94) |
| P-89 | m/z = 763.3($C_{57}H_{37}N_3$ = 763.94) |
| P-90 | m/z = 713.28($C_{53}H_{35}N_3$ = 713.88) |
| P-91 | m/z = 807.36($C_{60}H_{37}D_4N_3$ = 808.03) |
| P-92 | m/z = 787.3($C_{59}H_{37}N_3$ = 787.97) |
| P-93 | m/z = 737.28($C_{55}H_{35}N_3$ = 737.91) |
| P-94 | m/z = 741.31($C_{55}H_{31}D_4N_3$ = 741.93) |
| P-95 | m/z = 837.31($C_{63}H_{39}N_3$ = 838.03) |
| P-96 | m/z = 837.31($C_{63}H_{39}N_3$ = 838.03) |
| P-97 | m/z = 780.30($C_{55}H_{36}N_6$ = 780.93) |
| P-98 | m/z = 777.28($C_{57}H_{35}N_3O$ = 777.93) |

TABLE 3-continued

| Compound | FD-MS |
|---|---|
| P-99 | m/z = 843.27($C_{61}H_{37}N_3S$ = 844.05) |
| P-100 | m/z = 696.32($C_{51}H_{24}D_9N_3$ = 696.90) |
| P-101 | m/z = 637.25($C_{47}H_{31}N_3$ = 637.79) |
| P-102 | m/z = 753.31($C_{56}H_{39}N_3$ = 753.95) |
| P-103 | m/z = 940.40($C_{67}H_{52}N_4Si$ = 941.27) |
| P-104 | m/z = 718.31($C_{53}H_{30}D_5N_3$ = 718.91) |

Synthesis Example 2

1. Synthesis Example of H-12

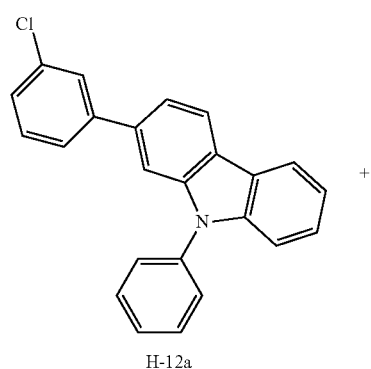

H-12a

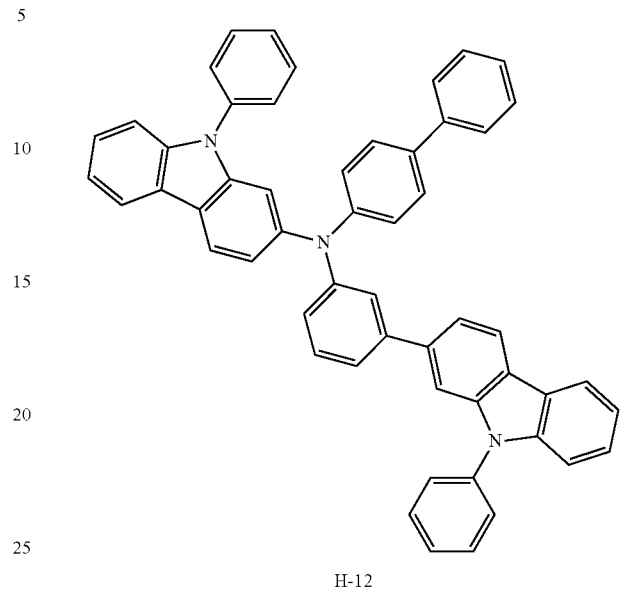

H-12

After dissolving H-12a (30 g, 0.08 mol) in Toluene (170 mL) in a round bottom flask, H-12b (34.8 g, 0.08 mol), $Pd_2(dba)_3$ (2.3 g, 0.003 mol), NaOt-Bu (24.5 g, 0.25 mol), $P(t-Bu)_3$ (2.1 g, 0.005 mol) were added, and stirred at 135° C. for 6 hours. After the reaction was completed, extraction was performed with $CH_2Cl_2$ and water, and the organic layer was dried with $MgSO_4$, concentrated, and the resulting compound was recrystallized using a silicagel column to obtain 53 g of the product. (Yield: 85.8%)

2. Synthesis Example of H-19

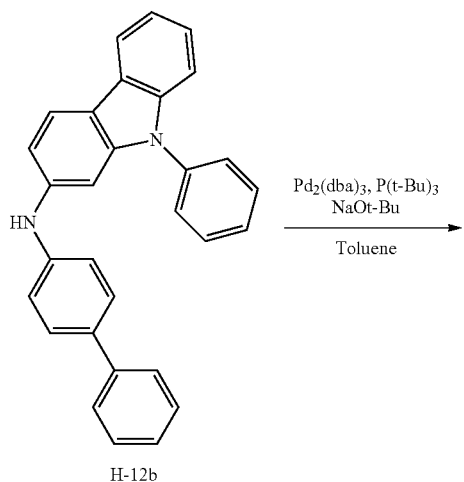

H-12b

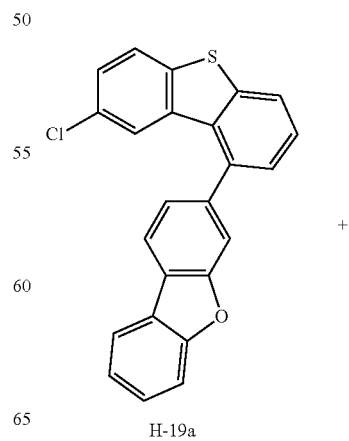

H-19a

-continued
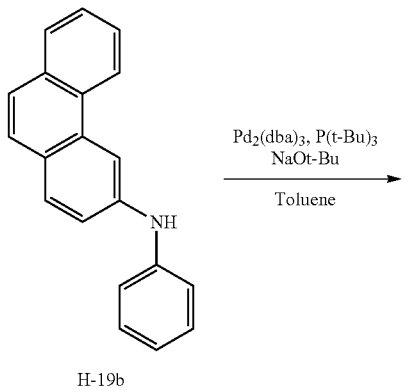
H-19b
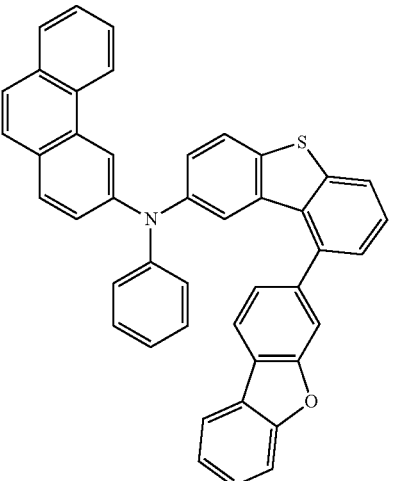
H-19
H-19a (50 g, 0.13 mol), H-19b (35 g, 0.13 mol), Pd₂(dba)₃ (3.6 g, 0.004 mol), NaOt-Bu (37.6 g, 0.40 mol), P(t-Bu)₃ (3.2 g, 0.008 mol), Toluene (260 mL) in a round bottom flask were tested in the same manner as in H-12 to obtain 67 g of product. (Yield: 83.4%)
3. Synthesis Example of S-32
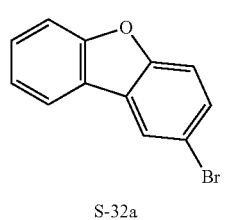
S-32a
-continued
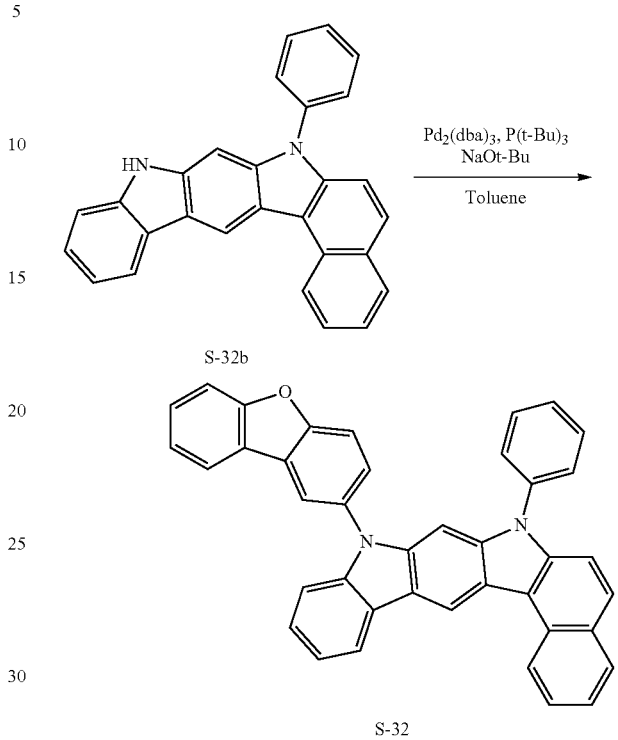
S-32b
S-32
S-32a (10 g, 0.04 mol), S-32b (15.6 g, 0.04 mol), Pd₂(dba)₃ (1.1 g, 0.001 mol), NaOt-Bu (11.7 g, 0.12 mol), P(t-Bu)₃ (1.0 g, 0.002 mol), Toluene (80 mL) were tested in the same manner as in H-12 to obtain 18 g of product. (Yield: 80.8%)
4. Synthesis Example of S-74
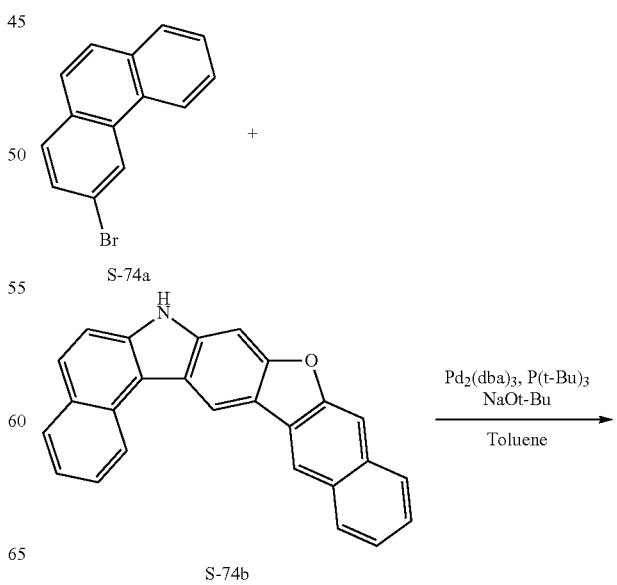
S-74a
S-74b

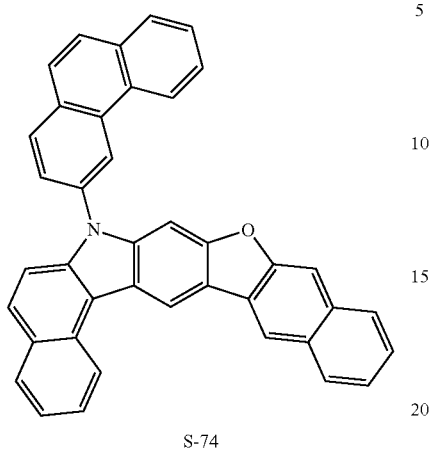

S-74

S-74a (15 g, 0.06 mol), S-74b (20.9 g, 0.06 mol), Pd$_2$(dba)$_3$ (1.6 g, 0.002 mol), NaOt-Bu (16.9 g, 0.18 mol), P(t-Bu)$_3$ (1.4 g, 0.004 mol), Toluene (120 mL) were tested in the same manner as in H-12 to obtain 27 g of product. (Yield: 86.4%)

5. Synthesis Example of S-104

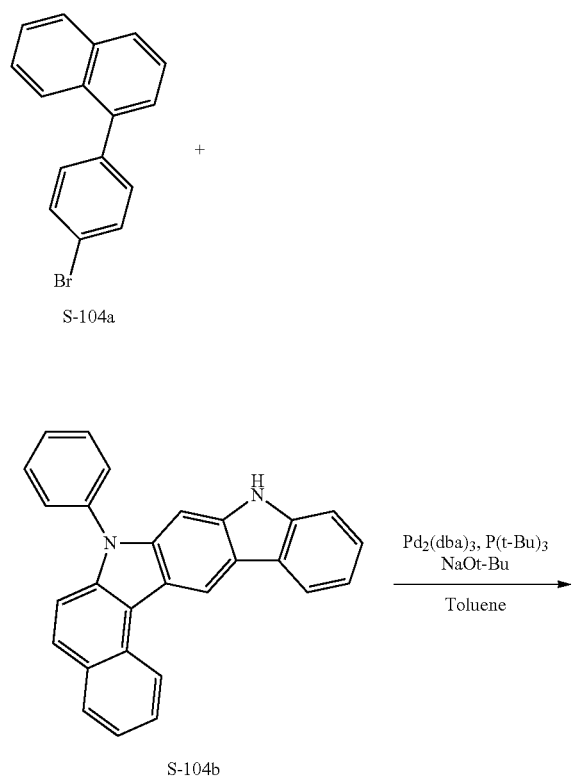

S-104a

S-104b

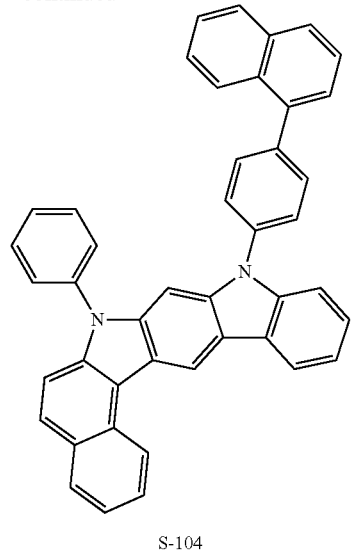

S-104

S-104a (30 g, 0.13 mol), S-104b (48.2.9 g, 0.13 mol), Pd$_2$(dba)$_3$ (3.5 g, 0.004 mol), NaOt-Bu (36.4 g, 0.38 mol), P(t-Bu)$_3$ (3.1 g, 0.008 mol), Toluene (250 mL) were tested in the same manner as in H-12 to obtain 60 g of product. (Yield: 81.5%)

The FD-MS values of the compounds H-1 to H-100 and S-1 to S-108 of the present invention prepared according to the synthesis examples as described are shown in Tables 4 and 5.

TABLE 4

| Compound | FD-MS |
|---|---|
| H-1 | m/z = 487.19($C_{36}H_{25}NO$ = 487.6) |
| H-2 | m/z = 553.19($C_{40}H_{27}NS$ = 553.72) |
| H-3 | m/z = 563.26($C_{43}H_{33}N$ = 563.74) |
| H-4 | m/z = 602.27($C_{45}H_{34}N_2$ = 602.78) |
| H-5 | m/z = 517.15($C_{36}H_{23}NOS$ = 517.65) |
| H-6 | m/z = 603.2($C_{44}H_{29}NS$ = 603.78) |
| H-7 | m/z = 735.29($C_{57}H_{37}N$ = 735.93) |
| H-8 | m/z = 562.24($C_{42}H_{30}N_2$ = 562.72) |
| H-9 | m/z = 565.17($C_{40}H_{23}NO_3$ = 565.63) |
| H-10 | m/z = 581.14($C_{40}H_{23}NO_2S$ = 581.69) |
| H-11 | m/z = 823.24($C_{59}H_{37}NS_2$ = 824.07) |
| H-12 | m/z = 727.3($C_{54}H_{37}N_3$ = 727.91) |
| H-13 | m/z = 627.22($C_{46}H_{29}NO_2$ = 627.74) |
| H-14 | m/z = 633.16($C_{44}H_{27}NS_2$ = 633.83) |
| H-15 | m/z = 675.29($C_{52}H_{37}N$ = 675.88) |
| H-16 | m/z = 678.3($C_{51}H_{38}N_2$ = 678.88) |
| H-17 | m/z = 669.21($C_{48}H_{31}NOS$ = 669.84) |
| H-18 | m/z = 785.22($C_{56}H_{35}NS_2$ = 786.02) |
| H-19 | m/z = 617.18($C_4H_{27}NOS$ = 617.77) |
| H-20 | m/z = 601.2($C_{44}H_{27}NO_2$ = 601.71) |
| H-21 | m/z = 779.32($C_{59}H_{41}NO$ = 779.98) |
| H-22 | m/z = 583.23($C_{42}H_{33}NS$ = 583.79) |
| H-23 | m/z = 679.32($C_{52}H_{41}N$ = 679.91) |
| H-24 | m/z = 726.27($C_{54}H_{34}N_2O$ = 726.88) |
| H-25 | m/z = 593.18($C_{42}H_{27}NOS$ = 593.74) |
| H-26 | m/z = 774.22($C_{54}H_{34}N_2S_2$ = 775) |
| H-27 | m/z = 557.24($C_{40}H_{31}NO_2$ = 557.69) |
| H-28 | m/z = 652.25($C_{48}H_{32}N_2O$ = 652.8) |
| H-29 | m/z = 619.29($C_{46}H_{37}NO$ = 619.81) |
| H-30 | m/z = 603.2($C_{44}H_{29}NS$ = 603.78) |
| H-31 | m/z = 813.3($C_{62}H_{39}NO$ = 814) |
| H-32 | m/z = 784.29($C_{57}H_{40}N_2S$ = 785.02) |
| H-33 | m/z = 577.2($C_{42}H_{27}NO_2$ = 577.68) |
| H-34 | m/z = 607.14($C_{42}H_{25}NS_2$ = 607.79) |
| H-35 | m/z = 801.34($C_{62}H_{43}N$ = 802.03) |
| H-36 | m/z = 575.24($C_{42}H_{29}N_3$ = 575.72) |

TABLE 4-continued

| Compound | FD-MS |
| --- | --- |
| H-37 | m/z = 577.2($C_{42}H_{27}NO_2$ = 577.68) |
| H-38 | m/z = 607.14($C_{42}H_{25}NS_2$ = 607.79) |
| H-39 | m/z = 801.34($C_{62}H_{43}N$ = 802.03) |
| H-40 | m/z = 575.24($C_{42}H_{29}N_3$ = 575.72) |
| H-41 | m/z = 601.2($C_{44}H_{27}NO_2$ = 601.71) |
| H-42 | m/z = 471.11($C_{31}H_{21}NS_2$ = 471.64) |
| H-43 | m/z = 675.29($C_{52}H_{37}N$ = 675.88) |
| H-44 | m/z = 727.3($C_{54}H_{37}N_3$ = 727.91) |
| H-45 | m/z = 603.2($C_{44}H_{29}NS$ = 603.78) |
| H-46 | m/z = 561.16($C_{38}H_{27}NS_2$ = 561.76) |
| H-47 | m/z = 799.32($C_{62}H_{41}N$ = 800.02) |
| H-48 | m/z = 702.27($C_{52}H_{34}N_2O$ = 702.86) |
| H-49 | m/z = 729.27($C_{54}H_{35}NO_2$ = 729.88) |
| H-50 | m/z = 785.22($C_{56}H_{35}NS_2$ = 786.02) |
| H-51 | m/z = 812.32($C_{62}H_{40}N_2$ = 813.02) |
| H-52 | m/z = 681.22($C_{48}H_{31}N_3S$ = 681.86) |
| H-53 | m/z = 615.18($C_{44}H_{25}NO_3$ = 615.69) |
| H-54 | m/z = 763.15($C_{52}H_{29}NS_3$ = 763.99) |
| H-55 | m/z = 593.31($C_{45}H_{39}N$ = 593.81) |
| H-56 | m/z = 840.33($C_{62}H_{40}N_4$ = 841.03) |
| H-57 | m/z = 657.18($C_{46}H_{27}NO_2S$ = 657.79) |
| H-58 | m/z = 824.23($C_{58}H_{36}N_2S$ = 825.06) |
| H-59 | m/z = 1195.42($C_{91}H_{57}NS$ = 1196.52) |
| H-60 | m/z = 656.19($C_{46}H_{28}N_2OS$ = 656.8) |
| H-61 | m/z = 607.16($C_{42}H_{25}NO_2S$ = 607.73) |
| H-62 | m/z = 773.2($C_{54}H_{31}NO_3S$ = 773.91) |
| H-63 | m/z = 1013.4($C_{79}H_{51}N$ = 1014.28) |
| H-64 | m/z = 758.24($C_{54}H_{34}N_2OS$ = 758.94) |
| H-65 | m/z = 623.14($C_{42}H_{25}NOS_2$ = 623.79) |
| H-66 | m/z = 763.16($C_{52}H_{29}NO_2S_2$ = 763.93) |
| H-67 | m/z = 799.2($C_{56}H_{33}NOS_2$ = 800.01) |
| H-68 | m/z = 743.23($C_{54}H_{33}NOS$ = 743.92) |
| H-69 | m/z = 872.25($C_{62}H_{36}N_2OS$ = 873.04) |
| H-70 | m/z = 772.22($C_{54}H_{32}N_2O_2S$ = 772.92) |
| H-71 | m/z = 830.28($C_{61}H_{38}N_2S$ = 831.05) |
| H-72 | m/z = 808.25($C_{58}H_{33}FN_2O_2$ = 808.91) |
| H-73 | m/z = 929.21($C_{64}H_{35}NO_3S_2$ = 930.11) |
| H-74 | m/z = 963.27($C_{68}H_{41}N_3S_2$ = 964.22) |
| H-75 | m/z = 809.24($C_{58}H_{35}NO_2S$ = 809.98) |
| H-76 | m/z = 893.29($C_{66}H_{39}NO_3$ = 894.04) |
| H-77 | m/z = 794.28($C_{58}H_{38}N_2S$ = 795.02) |
| H-78 | m/z = 900.26($C_{64}H_{40}N_2S_2$ = 901.16) |
| H-79 | m/z = 758.28($C_{55}H_{38}N_2S$ = 758.98) |
| H-80 | m/z = 1082.37($C_{81}H_{50}N_2S$ = 1083.37) |
| H-81 | m/z = 573.25($C_4H_{31}N$ = 573.74) |
| H-82 | m/z = 649.28($C_{50}H_{35}N$ = 649.84) |
| H-83 | m/z = 699.29($C_{54}H_{37}N$ = 699.9) |
| H-84 | m/z = 699.29($C_{54}H_{37}N$ = 699.9) |
| H-85 | m/z = 673.28($C_{52}H_{35}N$ = 673.86) |
| H-86 | m/z = 649.28($C_{50}H_{35}N$ = 649.84) |
| H-87 | m/z = 625.28($C_{48}H_{35}N$ = 625.82) |
| H-88 | m/z = 673.28($C_{52}H_{35}N$ = 673.86) |
| H-89 | m/z = 773.31($C_{60}H_{39}N$ = 773.98) |
| H-90 | m/z = 749.31($C_{58}H_{39}N$ = 749.96) |
| H-91 | m/z = 699.29($C_{54}H_{37}N$ = 699.9) |
| H-92 | m/z = 599.26($C_{46}H_{33}N$ = 599.78) |
| H-93 | m/z = 639.26($C_{48}H_{33}NO$ = 639.8) |
| H-94 | m/z = 765.25($C_{57}H_{35}NS$ = 765.97) |
| H-95 | m/z = 677.31($C_{52}H_{39}N$ = 677.89) |
| H-96 | m/z = 727.3($C_{54}H_{37}N_3$ = 727.91) |
| H-97 | m/z = 552.18($C_{39}H_{24}N_2O_2$ = 552.63) |
| H-98 | m/z = 628.22($C_{45}H_{28}N_2O_2$ = 628.73) |
| H-99 | m/z = 614.24($C_{45}H_{30}N_2O$ = 614.75) |
| H-100 | m/z = 614.24($C_{45}H_{30}N_2O$ = 614.75) |

TABLE 5

| Compound | FD-MS |
| --- | --- |
| S-1 | m/z = 408.16($C_{30}H_{20}N_2$ = 408.5) |
| S-2 | m/z = 534.21($C_{40}H_{26}N_2$ = 534.66) |
| S-3 | m/z = 560.23($C_{42}H_{28}N_2$ = 560.7) |
| S-4 | m/z = 584.23($C_{44}H_{28}N_2$ = 584.72) |
| S-5 | m/z = 560.23($C_{42}H_{28}N_2$ = 560.7) |
| S-6 | m/z = 634.24($C_{48}H_{30}N_2$ = 634.78) |
| S-7 | m/z = 610.24($C_{46}H_{30}N_2$ = 610.76) |
| S-8 | m/z = 498.17($C_{36}H_{22}N_2O$ = 498.59) |
| S-9 | m/z = 574.2($C_{42}H_{26}N_2O$ = 574.68) |
| S-10 | m/z = 660.26($C_{50}H_{32}N_2$ = 660.82) |
| S-11 | m/z = 686.27($C_{52}H_{34}N_2$ = 686.86) |
| S-12 | m/z = 620.14($C_{42}H_{24}N_2S_2$ = 620.79) |
| S-13 | m/z = 640.2($C_{46}H_{28}N_2S$ = 640.8) |
| S-14 | m/z = 560.23($C_{42}H_{28}N_2$ = 560.7) |
| S-15 | m/z = 558.21($C_{42}H_{26}N_2$ = 558.68) |
| S-16 | m/z = 548.19($C_{40}H_{24}N_2O$ = 548.65) |
| S-17 | m/z = 573.22($C_{42}H_{27}N_3$ = 573.7) |
| S-18 | m/z = 564.17($C_{40}H_{24}N_2S$ = 564.71) |
| S-19 | m/z = 574.2($C_{42}H_{26}N_2O$ = 574.68) |
| S-20 | m/z = 564.17($C_{40}H_{24}N_2S$ = 564.71) |
| S-21 | m/z = 564.17($C_{40}H_{24}N_2S$ = 564.71) |
| S-22 | m/z = 813.31($C_{61}H_{39}N_3$ = 814) |
| S-23 | m/z = 696.26($C_{53}H_{32}N_2$ = 696.85) |
| S-24 | m/z = 691.23($C_{49}H_{29}N_3O_2$ = 691.79) |
| S-25 | m/z = 710.27($C_{54}H_{34}N_2$ = 710.88) |
| S-26 | m/z = 610.24($C_{46}H_{30}N_2$ = 610.76) |
| S-27 | m/z = 670.15($C_{46}H_{26}N_2S_2$ = 670.85) |
| S-28 | m/z = 640.29($C_{48}H_{36}N_2$ = 640.83) |
| S-29 | m/z = 598.2($C_{44}H_{26}N_2O$ = 598.71) |
| S-30 | m/z = 623.24($C_{46}H_{29}N_3$ = 623.76) |
| S-31 | m/z = 458.18($C_{34}H_{22}N_2$ = 458.56) |
| S-32 | m/z = 548.19($C_{40}H_{24}N_2O$ = 548.65) |
| S-33 | m/z = 508.19($C_{38}H_{24}N_2$ = 508.62) |
| S-34 | m/z = 508.19($C_{38}H_{24}N_2$ = 508.62) |
| S-35 | m/z = 623.24($C_{46}H_{29}N_3$ = 623.76) |
| S-36 | m/z = 564.17($C_{40}H_{24}N_2S$ = 564.71) |
| S-37 | m/z = 627.2($C_{46}H_{29}NS$ = 627.81) |
| S-38 | m/z = 505.1($C_{34}H_{19}NS_2$ = 505.65) |
| S-39 | m/z = 514.15($C_{36}H_{22}N_2S$ = 514.65) |
| S-40 | m/z = 575.17($C_{42}H_{25}NS$ = 575.73) |
| S-41 | m/z = 642.21($C_{46}H_{30}N_2S$ = 642.82) |
| S-42 | m/z = 575.17($C_{42}H_{25}NS$ = 575.73) |
| S-43 | m/z = 606.18($C_{42}H_{26}N_2O_2$ = 606.74) |
| S-44 | m/z = 575.17($C_{42}H_{25}NS$ = 575.73) |
| S-45 | m/z = 551.17($C_{40}H_{25}NS$ = 551.71) |
| S-46 | m/z = 607.14($C_{42}H_{25}NS_2$ = 607.79) |
| S-47 | m/z = 525.16($C_{38}H_{23}NS$ = 525.67) |
| S-48 | m/z = 642.21($C_{46}H_{30}N_2S$ = 642.82) |
| S-49 | m/z = 548.19($C_{40}H_{24}N_2O$ = 548.65) |
| S-50 | m/z = 473.14($C_{34}H_{19}NO_2$ = 473.53) |
| S-51 | m/z = 566.15($C_{39}H_{22}N_2OS$ = 566.68) |
| S-52 | m/z = 459.16($C_{34}H_{21}NO$ = 459.55) |
| S-53 | m/z = 473.14($C_{34}H_{19}NO_2$ = 473.53) |
| S-54 | m/z = 523.16($C_{38}H_{21}NO_2$ = 523.59) |
| S-55 | m/z = 539.13($C_{38}H_{21}NOS$ = 539.65) |
| S-56 | m/z = 548.19($C_{40}H_{24}N_2O$ = 548.65) |
| S-57 | m/z = 489.12($C_{34}H_{19}NOS$ = 489.59) |
| S-58 | m/z = 545.09($C_{36}H_{19}NOS_2$ = 545.67) |
| S-59 | m/z = 549.17($C_{40}H_{23}NO_2$ = 549.63) |
| S-60 | m/z = 565.15($C_{40}H_{23}NOS$ = 565.69) |
| S-61 | m/z = 523.16($C_{38}H_{21}NO_2$ = 523.59) |
| S-62 | m/z = 598.2($C_{44}H_{26}N_2O$ = 598.71) |
| S-63 | m/z = 539.13($C_{38}H_{21}NOS$ = 539.65) |
| S-64 | m/z = 589.15($C_{42}H_{23}NOS$ = 589.71) |
| S-65 | m/z = 498.17($C_{36}H_{22}N_2O$ = 498.59) |
| S-66 | m/z = 509.18($C_{38}H_{23}NO$ = 509.61) |
| S-67 | m/z = 548.19($C_{40}H_{24}N_2O$ = 548.65) |
| S-68 | m/z = 549.17($C_{40}H_{23}NO_2$ = 549.63) |
| S-69 | m/z = 449.12($C_{32}H_{19}NS$ = 449.57) |
| S-70 | m/z = 439.1($C_{30}H_{17}NOS$ = 439.53) |
| S-71 | m/z = 647.22($C_{49}H_{29}NO$ = 647.78) |
| S-72 | m/z = 717.28($C_{52}H_{35}N_3O$ = 717.87) |
| S-73 | m/z = 459.16($C_{34}H_{21}NO$ = 459.55) |
| S-74 | m/z = 533.18($C_{40}H_{23}NO$ = 533.63) |
| S-75 | m/z = 525.16($C_{38}H_{23}NS$ = 525.67) |
| S-76 | m/z = 564.17($C_{40}H_{24}N_2S$ = 564.71) |
| S-77 | m/z = 575.19($C_{42}H_{25}NO_2$ = 575.67) |
| S-78 | m/z = 663.22($C_{49}H_{29}NO_2$ = 663.78) |
| S-79 | m/z = 647.22($C_{49}H_{29}NO$ = 647.78) |
| S-80 | m/z = 496.16($C_{36}H_{20}N_2O$ = 496.57) |
| S-81 | m/z = 565.15($C_{40}H_{23}NOS$ = 565.69) |
| S-82 | m/z = 505.1($C_{34}H_{19}NS_2$ = 505.65) |
| S-83 | m/z = 765.25($C_{56}H_{35}NOSi$ = 765.99) |
| S-84 | m/z = 615.17($C_{44}H_{25}NOS$ = 615.75) |

TABLE 5-continued

| Compound | FD-MS |
|---|---|
| S-85 | m/z = 603.17($C_{43}H_{25}NOS$ = 603.74) |
| S-86 | m/z = 772.29($C_{59}H_{36}N_2$ = 772.95) |
| S-87 | m/z = 802.33($C_{61}H_{42}N_2$ = 803.02) |
| S-88 | m/z = 607.23($C_{47}H_{29}N$ = 607.76) |
| S-89 | m/z = 524.23($C_{39}H_{28}N_2$ = 524.67) |
| S-90 | m/z = 665.22($C_{49}H_{31}NS$ = 665.85) |
| S-91 | m/z = 633.25($C_{49}H_{31}N$ = 633.79) |
| S-92 | m/z = 775.29($C_{59}H_{37}NO$ = 775.95) |
| S-93 | m/z = 535.23($C_{41}H_{29}N$ = 535.69) |
| S-94 | m/z = 623.22($C_{47}H_{29}NO$ = 623.76) |
| S-95 | m/z = 687.2($C_{51}H_{29}NS$ = 687.86) |
| S-96 | m/z = 735.29($C_{57}H_{37}N$ = 735.93) |
| S-97 | m/z = 611.26($C_{47}H_{33}N$ = 611.79) |
| S-98 | m/z = 679.23($C_{50}H_{33}NS$ = 679.88) |
| S-99 | m/z = 787.32($C_{61}H_{41}N$ = 788.01) |
| S-100 | m/z = 743.33($C_{55}H_{41}N_3$ = 743.95) |
| S-101 | m/z = 485.21($C_{37}H_{27}N$ = 485.63) |
| S-102 | m/z = 471.2($C_{36}H_{25}N$ = 471.6) |
| S-103 | m/z = 571.19($C_{43}H_{25}NO$ = 571.68) |
| S-104 | m/z = 584.23($C_{44}H_{28}N_2$ = 584.72) |
| S-105 | m/z = 539.24($C_{40}H_{21}D_5N_2$ = 539.69) |
| S-106 | m/z = 453.15($C_{32}H_{15}NS$ = 471.6) |
| S-107 | m/z = 563.26($C_{43}H_{26}D_4NO$ = 563.74) |
| S-108 | m/z = 589.26($C_{44}H_{23}D_5N_2$ = 584.72) |

Otherwise, the synthesis examples of the present invention represented by the Formula 1, Formula 4 and Formula 5 have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095), Pd(II)-catalyzed oxidative cyclization reaction (*Org. Lett.* 2011, 13, 5504), and $PPh_3$-mediated reductive cyclization reaction (*J. Org. Chem.* 2005, 70, 5014), and those skilled in the art will easily understand that the reaction proceeds even when other substituents defined in Formula 1, Formula 4 and Formula 5 are bonded in addition to the substituents specified in the specific synthesis examples.

Manufacturing Evaluation of Organic Electronic Elements

[Example 1] Red Organic Light Emitting Device (Phosphorescent Host)

After vacuum depositing $N^1$-(naphthalen-2-yl)-$N^4$,$N^4$-bis(4-(naphthalen-2-yl(phenyl)amino)phenyl)-$N^1$-phenylbenzene-1,4-diamine (hereinafter abbreviated as 2-TNATA) on the ITO layer (anode) formed on the glass substrate to form a hole injection layer with a thickness of 60 nm, a hole transport layer was formed by vacuum depositing N,N'-bis(1-naphthalenyl)-N,N'-bis-phenyl-(1,1'-biphenyl)-4,4'-diamine (hereinafter abbreviated as NPB) to a thickness of 60 nm on the hole injection layer.

Subsequently, tris(4-(9H-carbazol-9-yl)phenyl)amine (hereinafter abbreviated as TCTA) was vacuum-deposited to a thickness of 10 nm on the hole transport layer to form an emitting-auxiliary layer. Then, the host of the emitting layer uses P-2, the compound of the present invention as a first host, H-17, the compound of the present invention as a second host, but a mixture obtained by mixing the first host and the second host in a weight ratio of 5:5 is used, and bis-(1-phenylisoquinolyl)iridium(III) acetylacetonate (hereinafter abbreviated as '$(piq)_2Ir(acac)$') was used as a dopant, but the dopant was doped so that the weight ratio of the host and the dopant was 95:5 to form an emitting layer having a thickness of 30 nm.

Next, (1,1'-biphenyl-4-olato)bis(2-methyl-8-quinolinolato)aluminum (hereinafter abbreviated as BAlq) was vacuum deposited on the emitting layer to form a hole blocking layer having a thickness of 10 nm, bis(10-hydroxybenzo[h]quinolinato)beryllium (hereinafter abbreviated as $BeBq_2$) was vacuum deposited on the hole blocking layer to a thickness of 40 nm to form an electron transport layer. Thereafter, 8-quinolinolato lithium (hereinafter abbreviated as Liq) was deposited on the electron transport layer to form an electron injection layer having a thickness of 0.2 nm, and then Al was deposited to form a cathode having a thickness of 150 nm.

[Example 2] to [Example 40]

An organic light emitting device was manufactured in the same manner as in Example 1, except that the compound of the present invention described in Table 6 was used as the host material of the emitting layer.

[Comparative Example 1] and [Comparative Example 2]

An organic light emitting device was manufactured in the same manner as in Example 1, except that Comparative Compound A or Comparative Compound B was used as the first host as the host material of the emitting layer.

[Comparative Compound A]

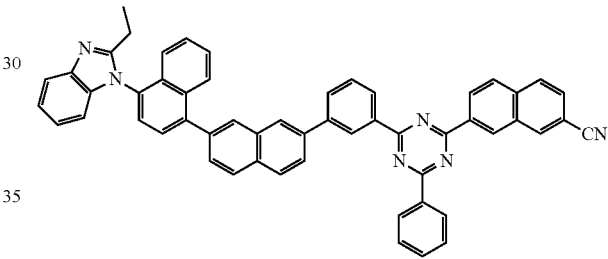

[Comparative Compound B]

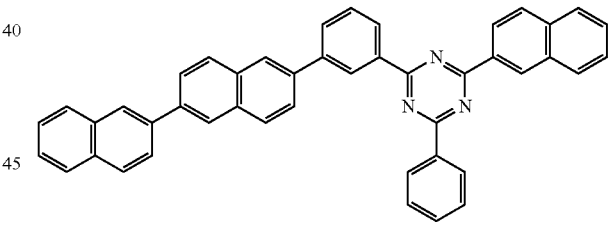

To the organic electroluminescent device manufactured by Examples 1 to 40, Comparative Examples 1 and 2 of the present invention, Electroluminescence (EL) characteristics were measured with a PR-650 of Photoresearch Co., by applying a forward bias DC voltage. As a result of the measurement, T95 life was measured at a standard luminance of 2,500 $cd/m^2$ through life measuring apparatus manufactured by McScience. Table 6 shows the results of device fabrication and evaluation.

This measuring apparatus is unaffected by possible daily fluctuations in deposition rate, vacuum quality or other parameters, and can evaluate the performance of a new material compared to a comparative compound under the same conditions.

In the evaluation, since one batch contains four identically prepared OLEDs containing the comparative compound, and the performance of a total of 12 OLEDs is evaluated in three batches, the values of the experimental results thus obtained show statistical significance.

TABLE 6

| | First host | Second host | Voltage | Current Density (mA/cm²) | Brightness (cd/m²) | Efficiency (cd/A) | T(95) |
|---|---|---|---|---|---|---|---|
| comparative example1 | comparative compound A | H-17 | 5.5 | 10.2 | 2500.0 | 24.5 | 101.9 |
| comparative example2 | comparative compound B | H-17 | 5.7 | 11.2 | 2500.0 | 22.4 | 99.7 |
| example1 | P-2 | H-17 | 4.8 | 7.7 | 2500.0 | 32.3 | 121.3 |
| example2 | P-6 | H-17 | 4.8 | 7.7 | 2500.0 | 32.4 | 122.3 |
| example3 | P-8 | H-17 | 4.9 | 7.9 | 2500.0 | 31.6 | 120.6 |
| example4 | P-13 | H-17 | 4.8 | 7.5 | 2500.0 | 33.4 | 130.7 |
| example5 | P-15 | H-17 | 4.9 | 8.0 | 2500.0 | 31.2 | 120.5 |
| example6 | P-21 | H-17 | 4.8 | 7.7 | 2500.0 | 32.5 | 122.9 |
| example7 | P-23 | H-17 | 4.9 | 7.8 | 2500.0 | 32.1 | 122.7 |
| example8 | P-33 | H-17 | 4.9 | 7.6 | 2500.0 | 33.0 | 131.1 |
| example9 | P-37 | H-17 | 5.0 | 8.2 | 2500.0 | 30.6 | 121.0 |
| example10 | P-49 | H-17 | 5.0 | 7.9 | 2500.0 | 31.6 | 129.9 |
| example11 | P-53 | H-17 | 4.9 | 8.0 | 2500.0 | 31.4 | 122.4 |
| example12 | P-64 | H-17 | 5.0 | 8.1 | 2500.0 | 30.9 | 122.2 |
| example13 | P-74 | H-17 | 5.0 | 7.8 | 2500.0 | 31.9 | 121.8 |
| example14 | P-87 | H-17 | 5.1 | 8.1 | 2500.0 | 30.8 | 126.9 |
| example15 | P-107 | H-17 | 5.0 | 7.8 | 2500.0 | 32.1 | 130.9 |
| example16 | P-2 | H-84 | 4.9 | 7.9 | 2500.0 | 31.7 | 120.7 |
| example17 | P-13 | H-84 | 4.9 | 7.6 | 2500.0 | 32.9 | 129.5 |
| example18 | P-37 | H-84 | 5.1 | 7.7 | 2500.0 | 32.5 | 120.9 |
| example19 | P-49 | H-84 | 5.1 | 8.1 | 2500.0 | 30.9 | 129.0 |
| example20 | P-53 | H-84 | 5.0 | 8.1 | 2500.0 | 31.0 | 121.9 |
| example21 | P-107 | H-84 | 5.1 | 7.9 | 2500.0 | 31.8 | 130.0 |
| example22 | P-2 | H-98 | 4.8 | 7.8 | 2500.0 | 32.0 | 122.1 |
| example23 | P-13 | H-98 | 4.8 | 7.6 | 2500.0 | 33.1 | 130.8 |
| example24 | P-37 | H-98 | 5.0 | 7.6 | 2500.0 | 32.9 | 121.3 |
| example25 | P-49 | H-98 | 5.1 | 8.0 | 2500.0 | 31.4 | 130.4 |
| example26 | P-53 | H-98 | 5.1 | 7.9 | 2500.0 | 31.5 | 122.6 |
| example27 | P-107 | H-98 | 4.9 | 7.8 | 2500.0 | 32.1 | 131.2 |
| example28 | P-2 | S-16 | 5.0 | 7.8 | 2500.0 | 31.9 | 123.3 |
| example29 | P-13 | S-16 | 5.0 | 7.7 | 2500.0 | 32.3 | 136.9 |
| example30 | P-37 | S-16 | 5.2 | 7.8 | 2500.0 | 32.0 | 123.5 |
| example31 | P-49 | S-16 | 5.1 | 7.7 | 2500.0 | 32.3 | 135.4 |
| example32 | P-53 | S-16 | 5.2 | 8.1 | 2500.0 | 30.9 | 124.0 |
| example33 | P-107 | S-16 | 5.0 | 7.9 | 2500.0 | 31.6 | 137.1 |
| example34 | P-2 | S-108 | 5.0 | 7.9 | 2500.0 | 31.5 | 124.9 |
| example35 | P-13 | S-108 | 5.0 | 7.8 | 2500.0 | 32.0 | 137.7 |
| example36 | P-33 | S-108 | 5.0 | 7.8 | 2500.0 | 31.9 | 137.2 |
| example37 | P-37 | S-108 | 5.1 | 8.3 | 2500.0 | 30.1 | 124.1 |
| example38 | P-53 | S-108 | 5.2 | 8.2 | 2500.0 | 30.4 | 124.9 |
| example39 | P-64 | S-108 | 5.3 | 8.1 | 2500.0 | 30.9 | 124.5 |
| example40 | P-107 | S-108 | 5.1 | 8.0 | 2500.0 | 31.3 | 137.5 |

As can be seen from the results of Table 6, when a red organic light emitting device was manufactured by using the material for an organic light emitting device of the present invention as a host material of the emitting layer, the driving voltage, luminous efficiency and lifespan of the organic light emitting device can be improved compared to Comparative Example using Comparative Compound A or Comparative Compound B having a similar basic skeleton to the compound of the present invention.

Comparative Compound A and Comparative Compound B are similar to the compounds of the present invention in that a triazine is substituted with a group represented by 'phenyl-naphthyl-naphthyl', but the location of substitution of 'phenyl-naphthyl-naphthyl' is different from the present invention.

In order to check the energy level of the compound according to the substitution position although the type of substituent is similar, the data measured using the DFT method (B3LYP/6-31g(D)) of the Gaussian program for the compound P-2 of the present invention, which has a high similarity to Comparative Compound A and Comparative Compound B, are shown in Table 7.

TABLE 7

| | P-2 | Comparative compound A | Comparative compound B |
|---|---|---|---|
| HOMO(eV) | −5.5621 | −5.8420 | −5.5242 |
| LUMO(eV) | −1.9342 | −2.3247 | −1.9287 |
| Eg(eV) | 3.6279 | 3.5173 | 3.5955 |
| T1(eV) | 2.4971 | 2.4754 | 2.4354 |
| S1(eV) | 3.0505 | 3.2751 | 3.284 |
| ΔST(eV) | 0.5534 | 0.7997 | 0.8486 |

As can be seen from the results of Table 7, although the elements constituting the substituents are similar, it can be confirmed that the physical properties of the molecule change remarkably depending on the position in which the constituents are substituted.

In more detail, since Compound P-2 of the present invention has HOMO, LUMO, S1, and T1 energy levels that facilitate charge transfer from the electron transport region and hole transport region than Comparative Compound A or Comparative Compound B, and moreover has a smaller Δ ST (eV) value than Comparative Compound A and Comparative Compound B, and the energy transfer from the host to the dopant is facilitated, so that the luminous efficiency of the device increases, furthermore, it was confirmed that the lifespan was remarkably increased by well transferring the unstable excited state energy. Through this, it can be seen that the compound of the present invention exhibits a remarkable effect in organic electronic elements compared to other compounds having similar structures not described herein.

That is, as can be seen from the results of Tables 6 and 7, even if the compound has a similar composition, it can be confirmed that the compound of the present invention, which satisfies all of the complex factors such as the type of specific substituent and the specific substitution position of the substituent, exhibits a remarkable effect in the organic electronic element, through this, it can be seen that the compound of the present invention exhibits a remarkable effect in organic electronic elements compared to other compounds having similar structures not described herein.

In other words, these results suggests that even for compounds with similar molecular components, the properties of compounds such as hole properties, light efficiency properties, energy level, hole injection and mobility properties of molecules, charge balance between holes and electrons, volume density and distance between molecules, etc. can vary significantly to the extent that it is difficult to predict, depending on the type and position of the substituent to be substituted, and also the performance of the device may vary due to complex factors, rather than one configuration affecting the overall result of the device.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed:

1. An organic electronic element comprising:

a first electrode; a second electrode;

an organic material layer formed between the first electrode and the second electrode, wherein the organic material layer comprises an emitting layer, wherein the emitting layer is a phosphorescent emitting layer comprising a first host compound represented by Formula 1 and a second host compound represented by Formula 4 or Formula 5:

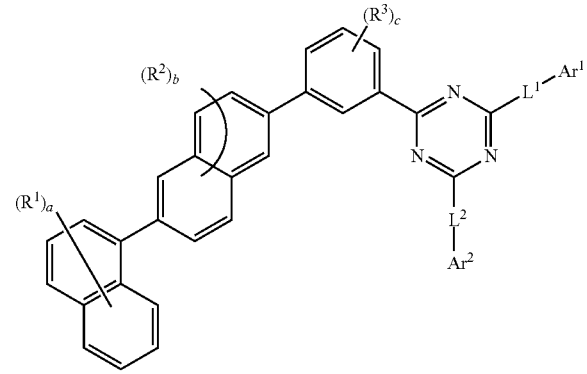

Formula 1

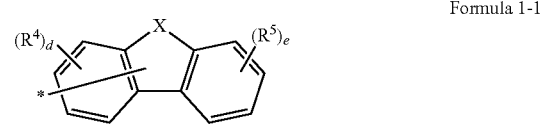

Formula 1-1

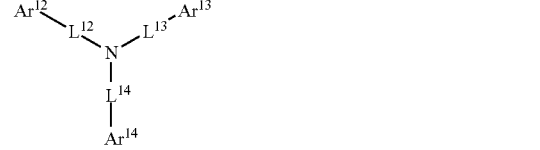

Formula 4

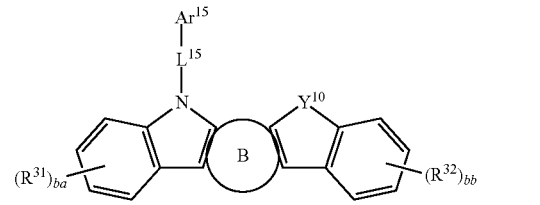

Formula 5 wherein:
$R^1$, $R^2$ and $R^3$ are each the same or different, and each independently selected from the group consisting of hydrogen; deuterium; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{60}$alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;
a is an integer of 0 to 7, b is an integer of 0 to 6, c is an integer of 0 to 4,
$L^1$ and $L^2$ are each independently a single bond; or a $C_6$-$C_{60}$ arylene group;
$Ar^1$ and $Ar^2$ are each an $C_6$-$C_{60}$ aryl group; or a substituent represented by Formula 1-1;
X is $CR^aR^b$, NR' or $SiR^aR^b$, provided that when X is bonded to $L^1$ or $L^2$, it is N,
$R^4$ and $R^5$ are each the same or different, and each independently selected from the group consisting of hydrogen; deuterium; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{60}$alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or adjacent plurality of $R^4$ and plurality of $R^5$ may be bonded to each other to form a ring, d and e are independently of each other an integer of 0 to 4;
* denotes a position to be bonded, $R^a$, $R^b$ and R' are each independently selected from the group consisting of hydrogen; deuterium; a $C_1$-$C_{60}$alkyl group; a $C_6$-$C_{60}$ aryl group; a $C_2$-$C_{60}$ heterocyclic group including at least one hetero atom of O, N, S, Si or P; alternatively, $R^a$ and $R^b$ may be bonded to each other to form a spiro, In Formula 4, $L^{12}$, $L^{13}$ and $L^{14}$ are each independently selected from the group consisting of single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P;

$Ar^{12}$, $Ar^{13}$ and $Ar^{14}$ are each independently selected from the group consisting of an $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

In Formula 5,

Ring B is an $C_6$-$C_{20}$ aryl group, $Y^{10}$ is O, S, $CR^{51}R^{52}$ or $NR^{53}$, $L^{15}$ is selected from the group consisting of single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P;

$Ar^{15}$ is selected from the group consisting of an $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L"-$NR^fR^g$;

$R^{31}$ and $R^{32}$ are each the same or different, and each independently selected from the group consisting of hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_6$ alkyl group; a $C_2$-$C_{60}$alkenyl group; a $C_2$-$C_{60}$alkynyl group; a $C_1$-$C_{60}$alkoxy group; and a $C_6$-$C_{60}$ aryloxy group; or an adjacent plurality of $R^{31}$ or a plurality of $R^{32}$ may be bonded to each other to form a ring, L" is each independently selected from the group consisting of single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P;

$R^{51}$, $R^{52}$ and $R^{53}$ are each independently selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_6$ alkyl group; a $C_2$-$C_{60}$alkenyl group; a $C_2$-$C_{60}$alkynyl group; a $C_1$-$C_{60}$alkoxy group; and a $C_6$-$C_{60}$ aryloxy group; or $R^{51}$ and $R^{52}$ may be bonded to each other to form a ring;

$R^f$ and $R^g$ are each independently selected from the group consisting of a $C_6$-$C_{60}$ aryl group; fluorenyl group; a $C_2$-$C_{60}$ heterocyclic group including at least one heteroatom of O, N, S, Si or P; and a $C_3$-$C_{60}$ aliphatic ring;

ba and bb are independently integers from 0 to 4, wherein the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The compound of claim 1, wherein $Ar^1$ and $Ar^2$ are represented by any one of Formulas (A-1) to (A-11):

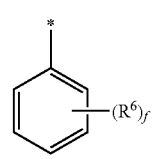

Formula (A-1)

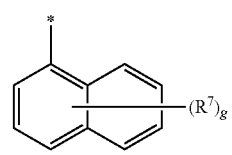

Formula (A-2)

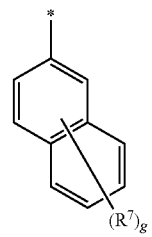

Formula (A-3)

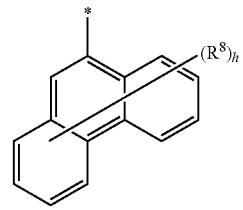

Formula (A-4)

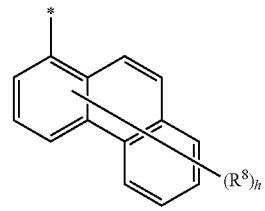

Formula (A-5)

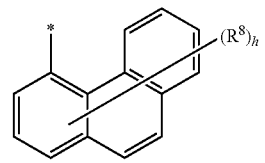

Formula (A-6)

Formula (A-7)

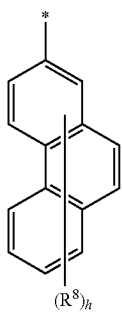

Formula (A-8)

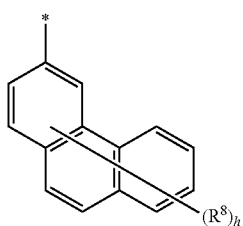

Formula (A-9)

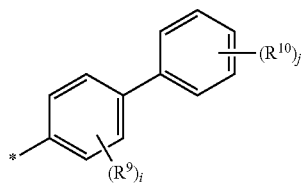

Formula (A-10)

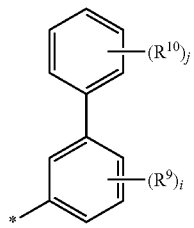

Formula (A-11)

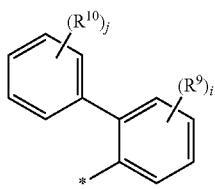

wherein:
1) $R^6$, $R^7$, $R^8$, $R^9$ and $R^{10}$ are the same or different from each other, and each independently represents hydrogen; deuterium; $C_6$-$C_{20}$ aryl group; or $C_6$-$C_{20}$ aryl group substituted with deuterium;
2) f and j are independently an integer of 0 to 5, g is an integer of 0 to 7, h is an integer of 0 to 9, i is an integer of 0 to 4,
3) * is the position to be bonded.

3. The organic electronic element of claim 1, wherein Formula 1 is represented by any of Compounds P-1 to P-104:

P-1

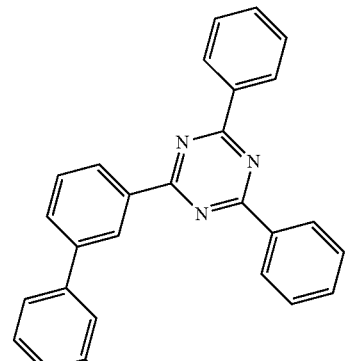

P-2

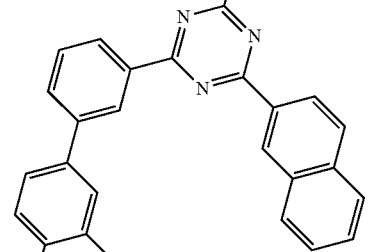

P-3

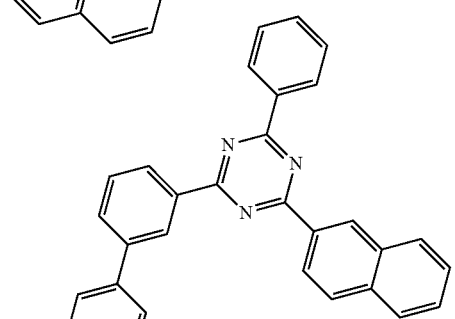

-continued
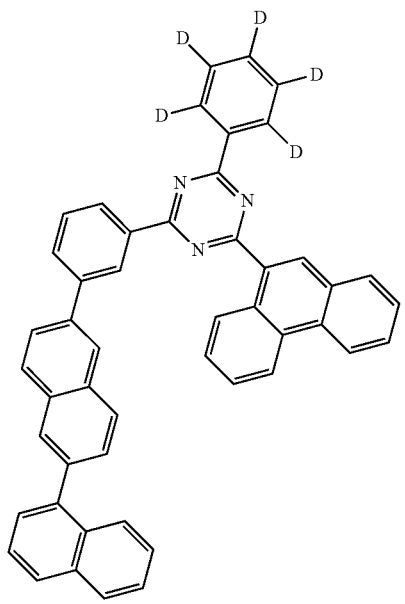
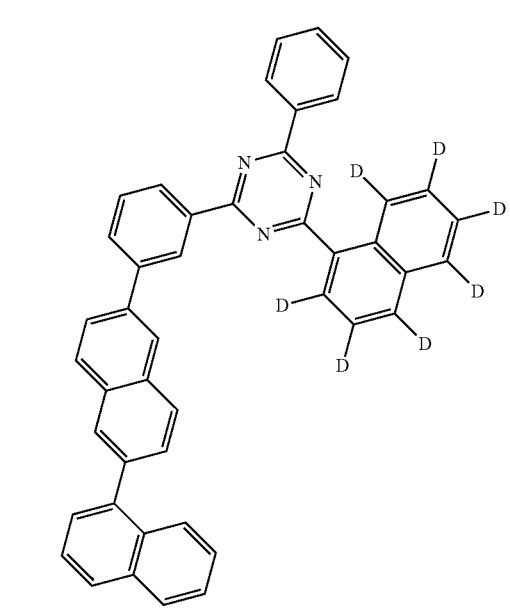
P-4
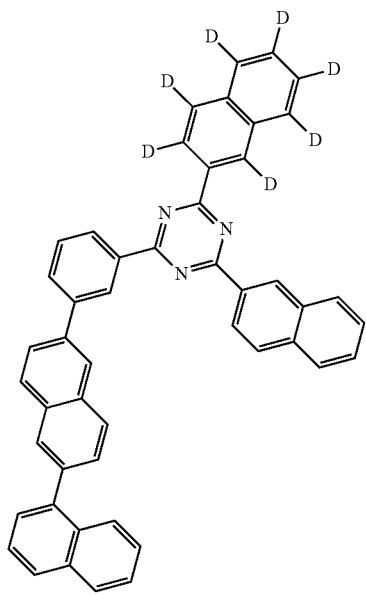
P-5
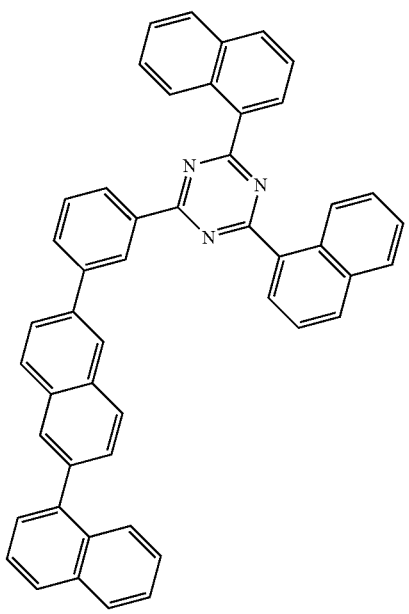
P-6
P-7

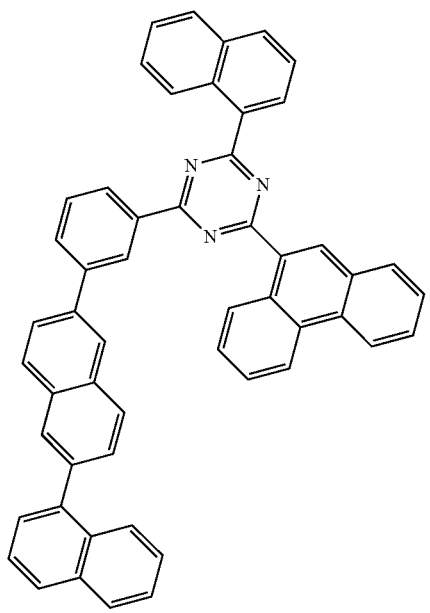
P-8
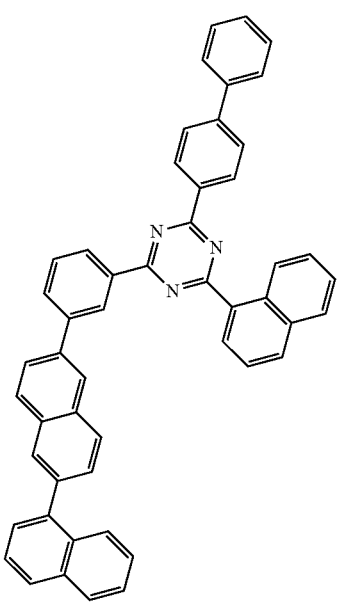
P-10
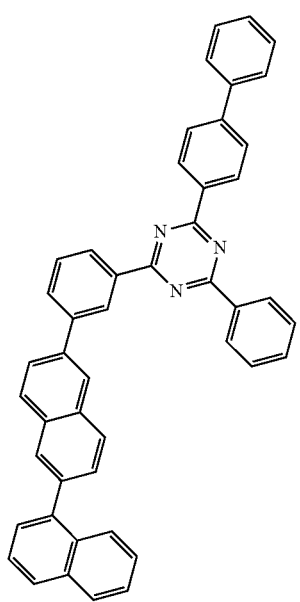
P-9
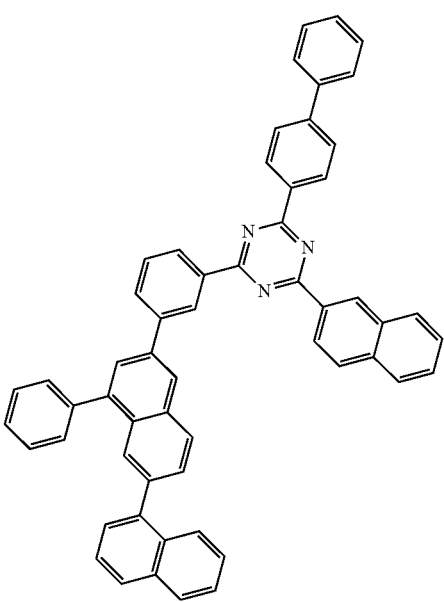
P-11

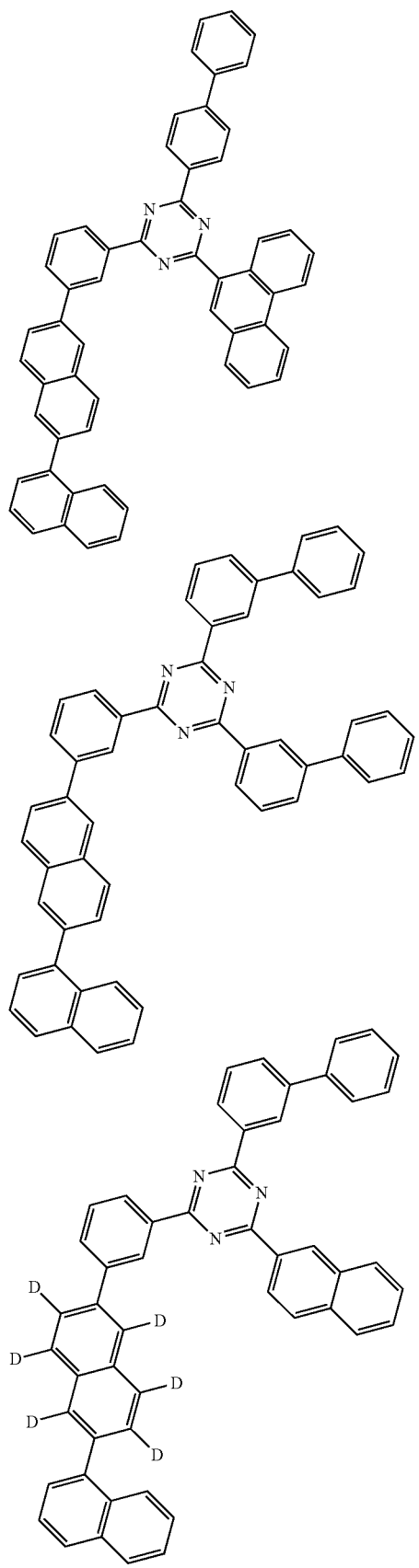
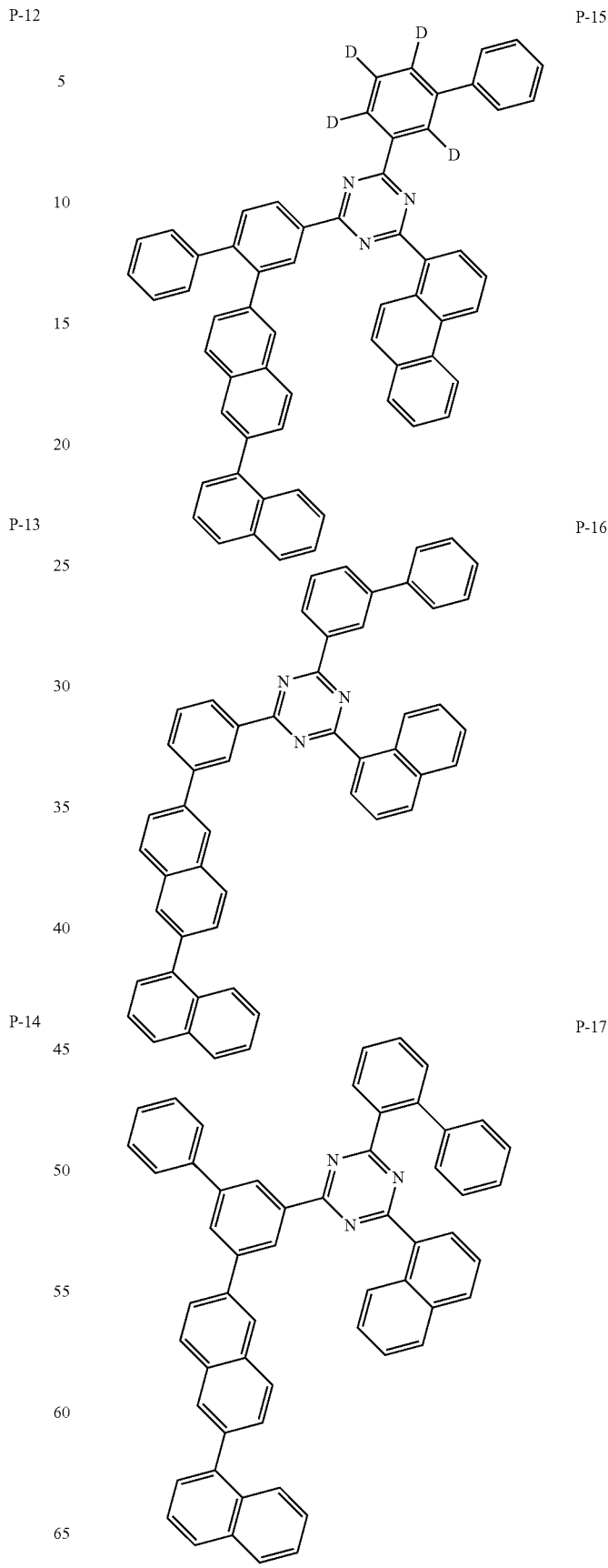

P-18
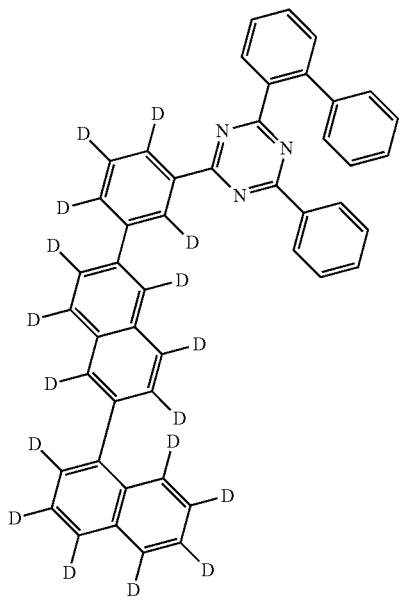
P-20
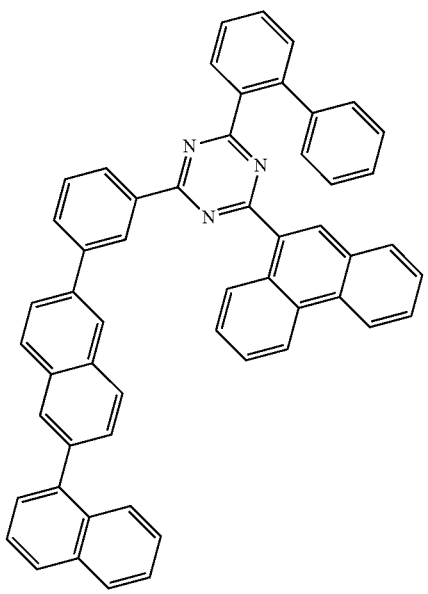
P-19
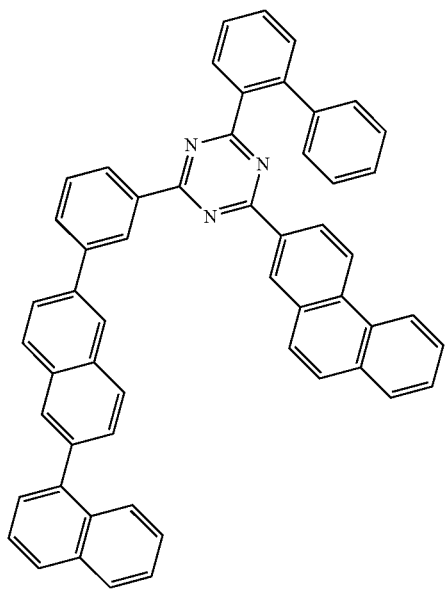
P-21
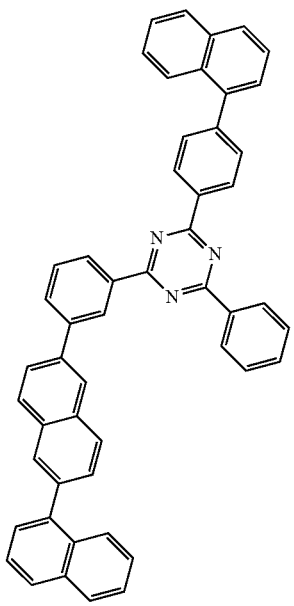

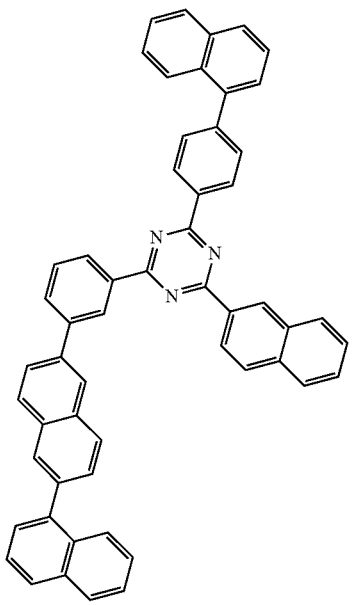
P-22
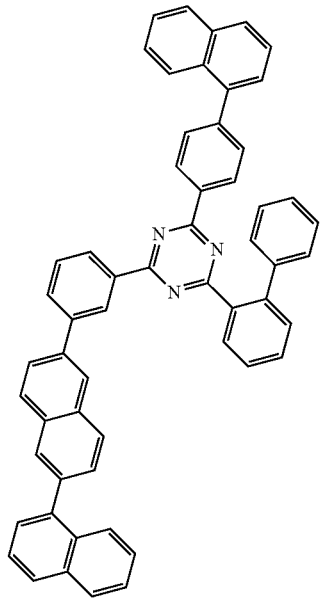
P-24
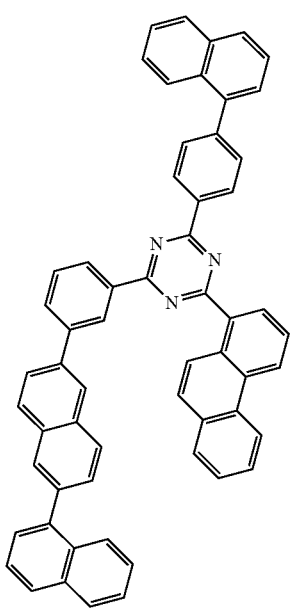
P-23
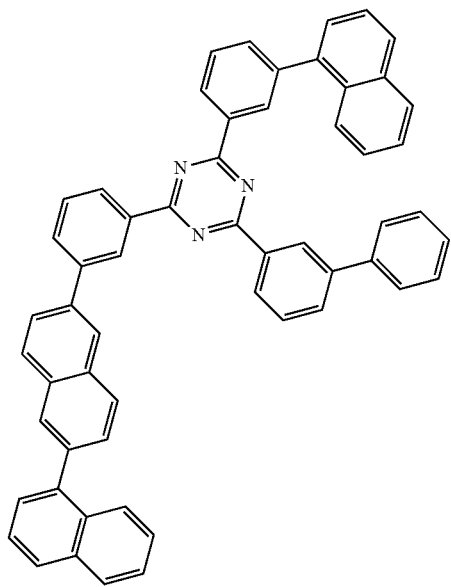
P-25

P-26
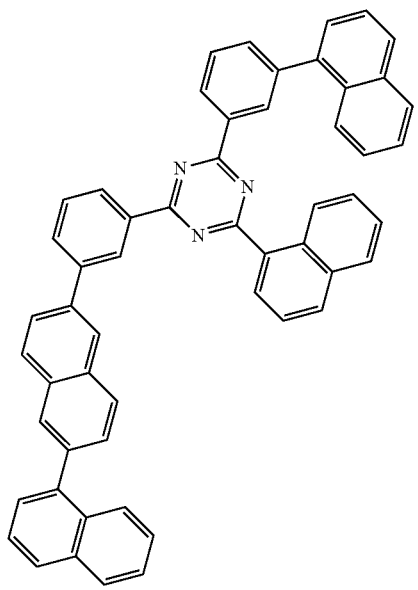
P-27
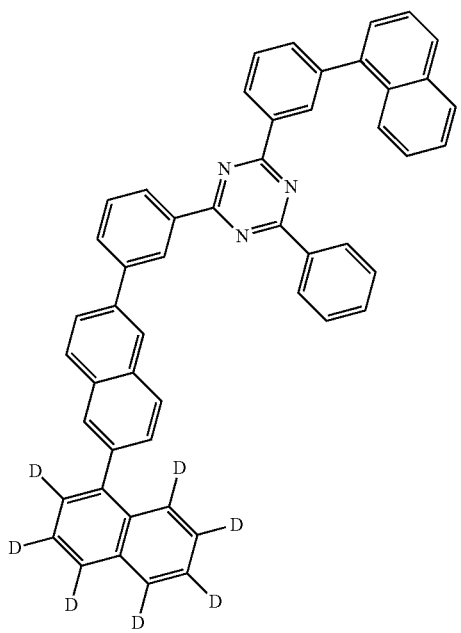
P-28
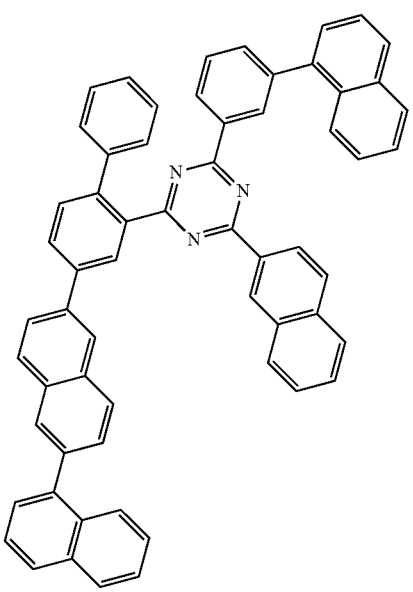
P-29
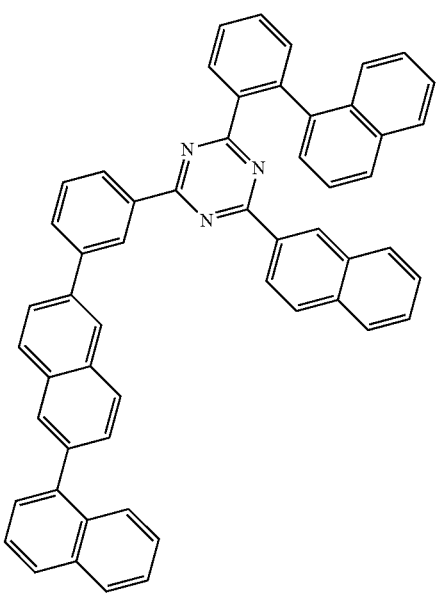

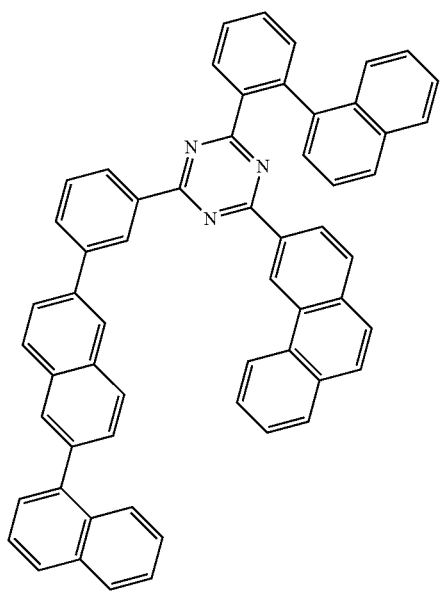
P-30
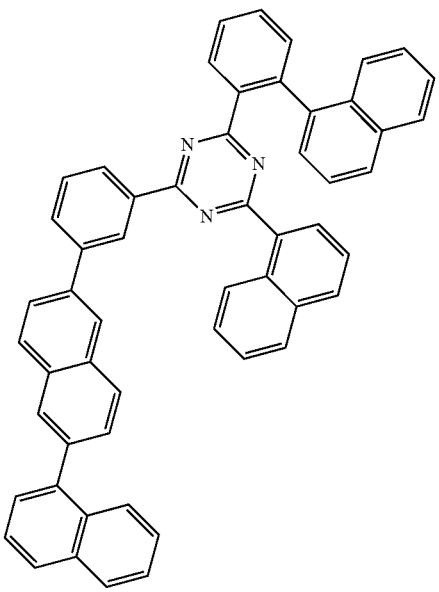
P-32
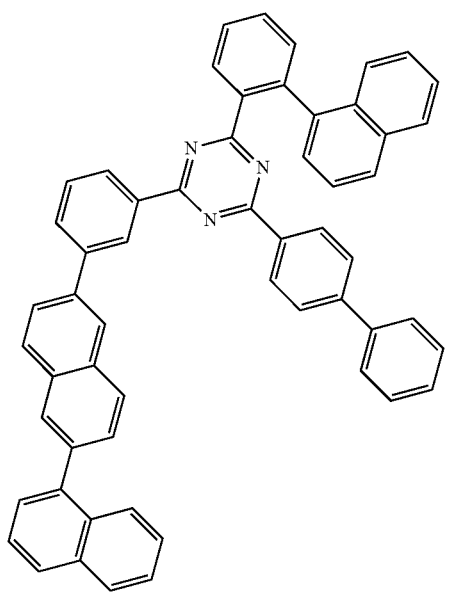
P-31
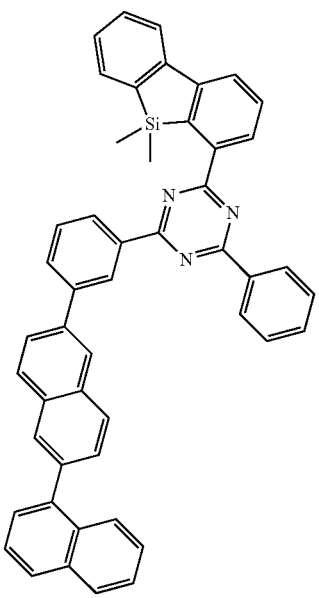
P-33

P-34
P-36
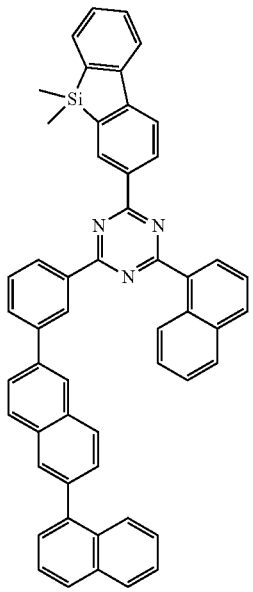
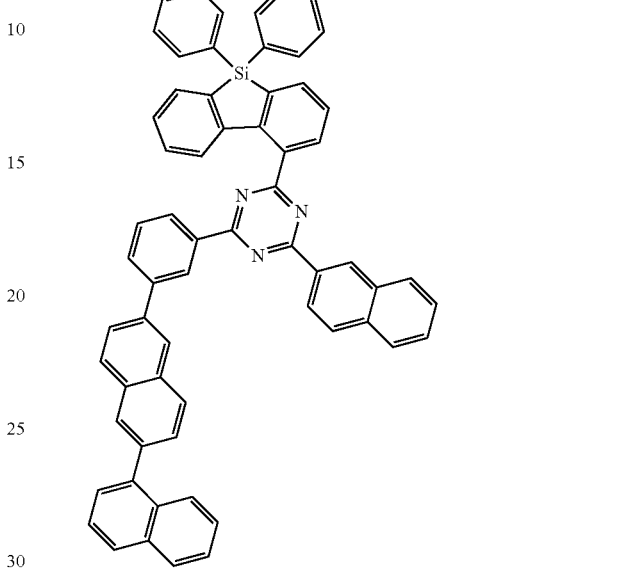
P-35
P-37
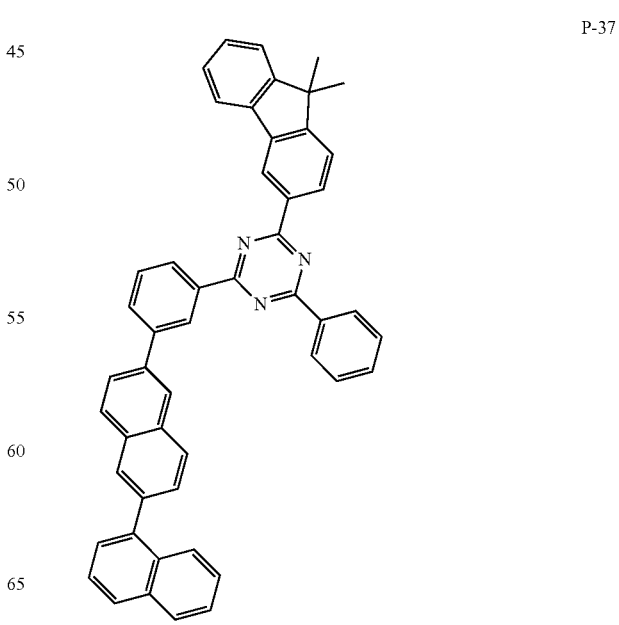

291
-continued
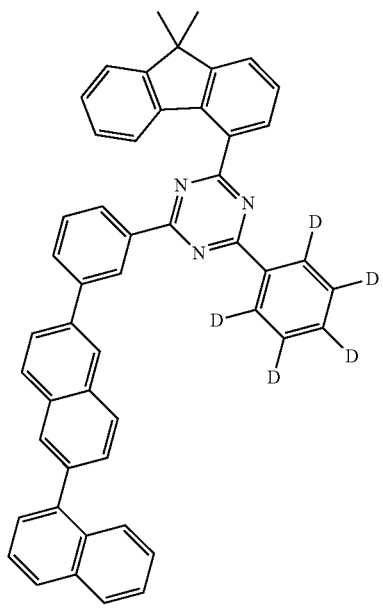
292
-continued
P-38
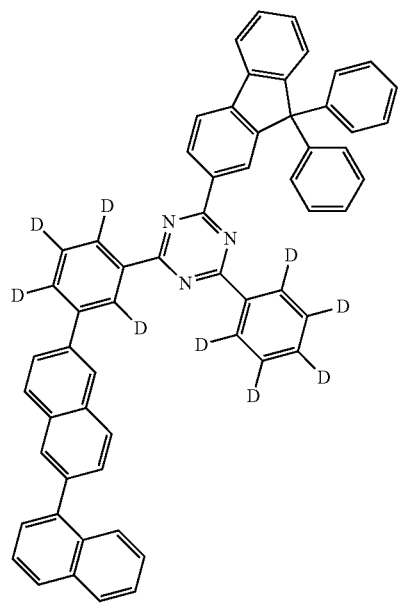
P-40
P-39
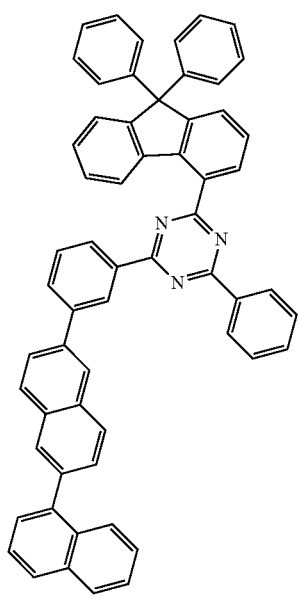
P-41
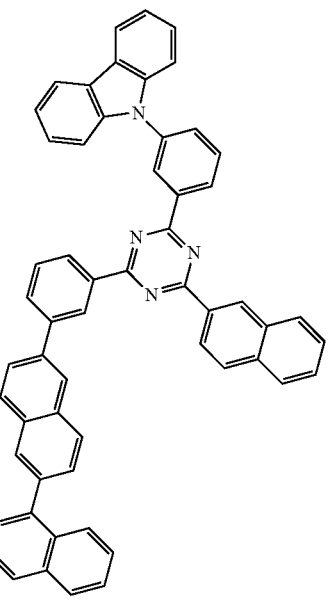

P-42
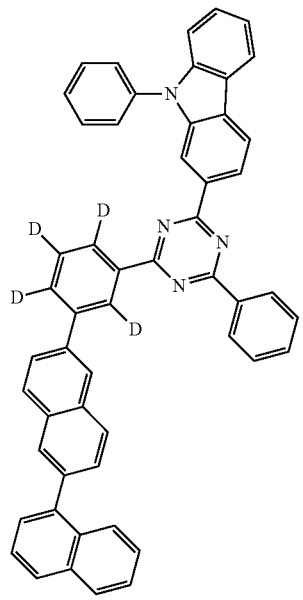
P-43
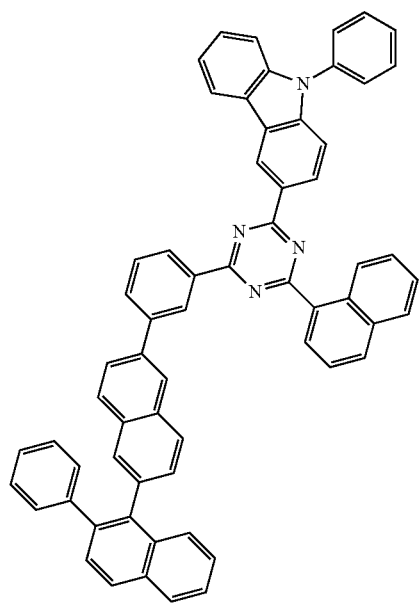
P-44
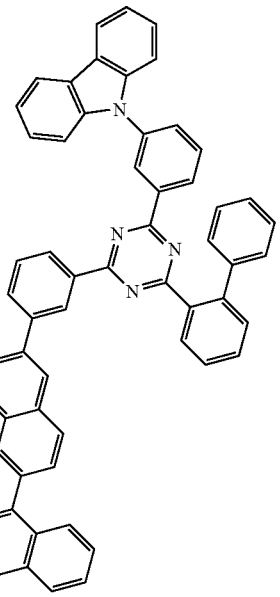
P-45
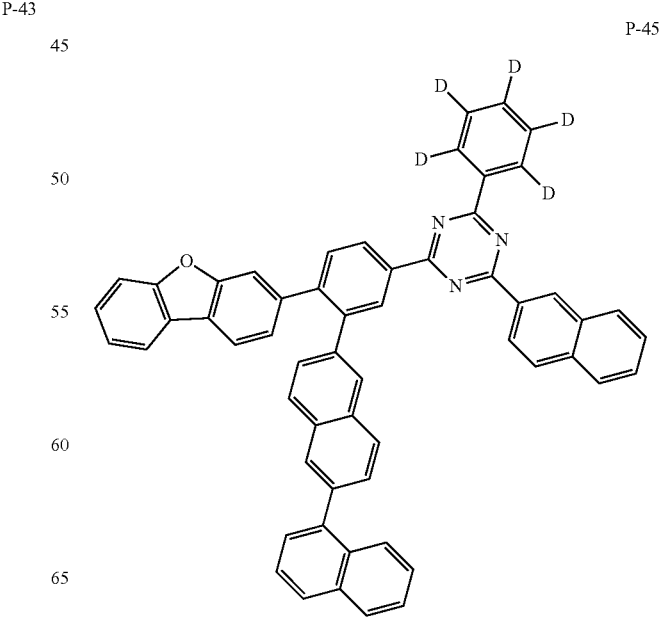

P-46
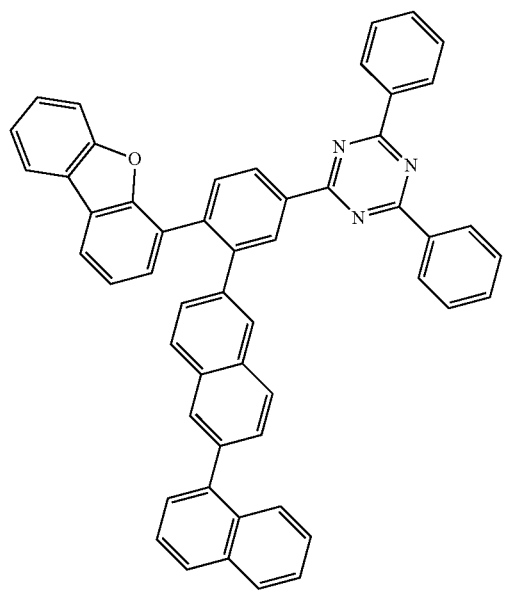
P-47
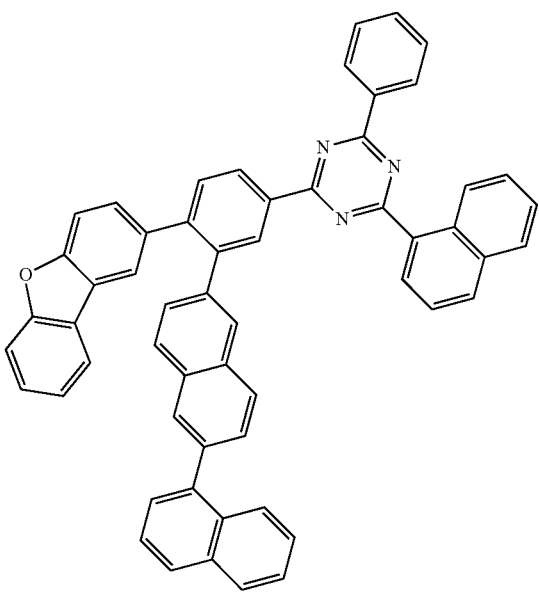
P-48
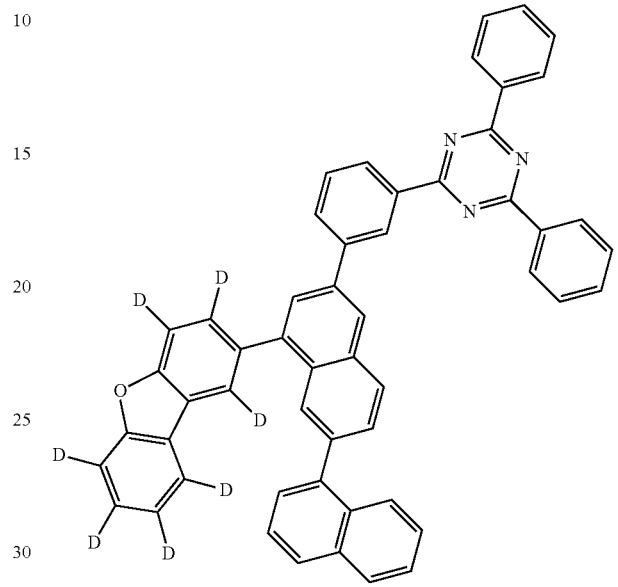
P-49
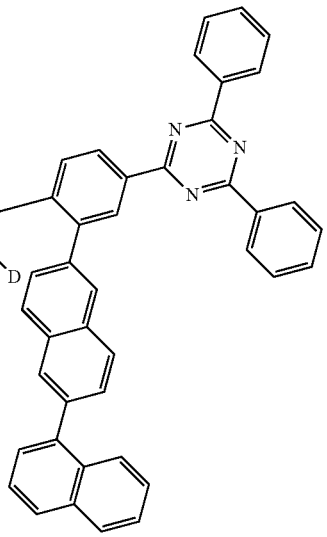

P-50
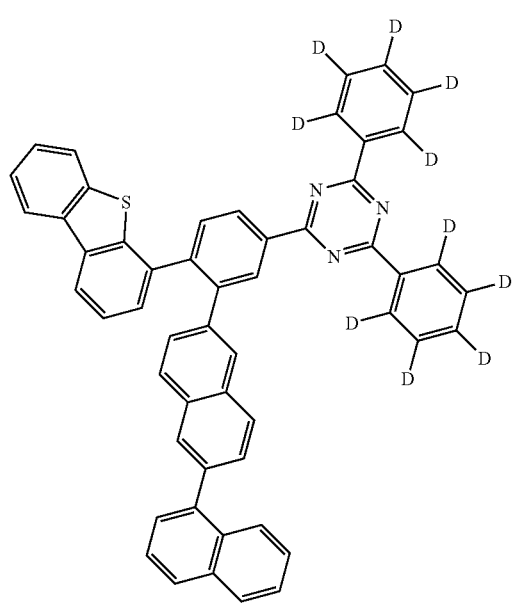
P-52
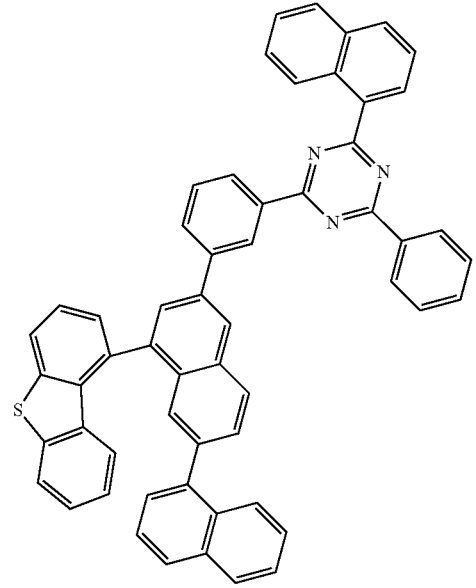
P-51
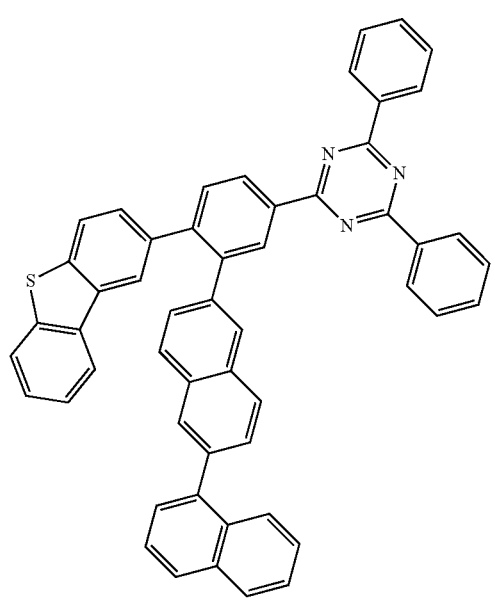
P-53
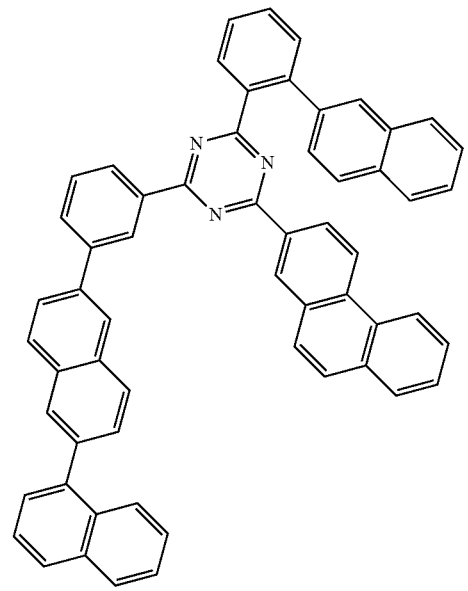

P-54
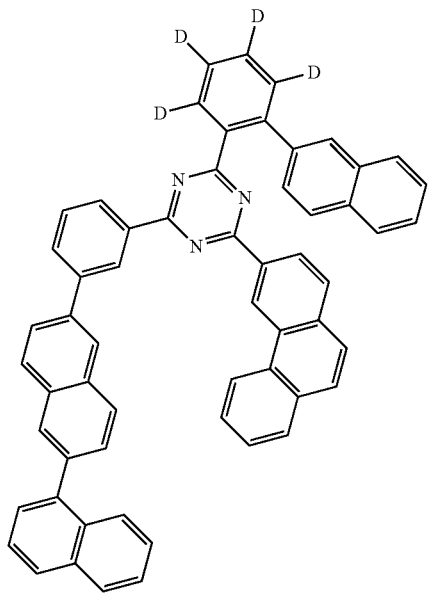
P-55
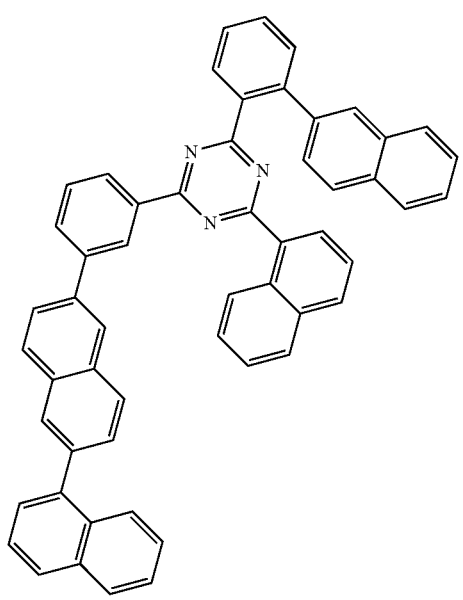
P-56
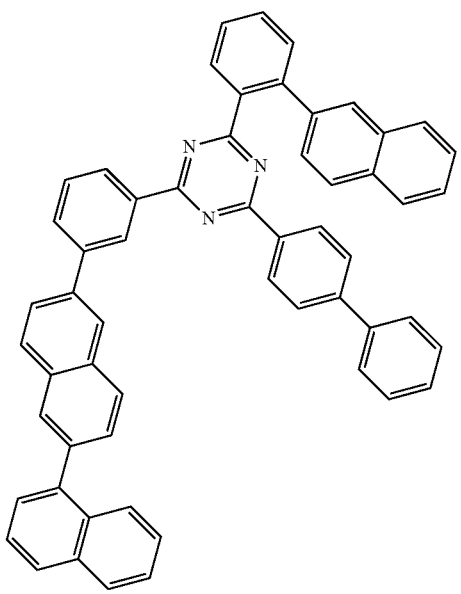
P-57
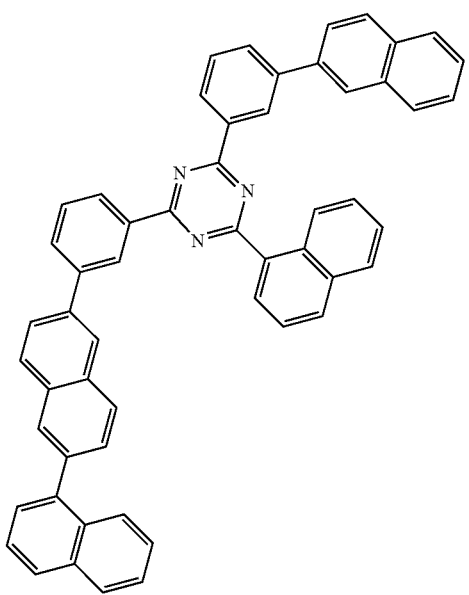

301
-continued
P-58
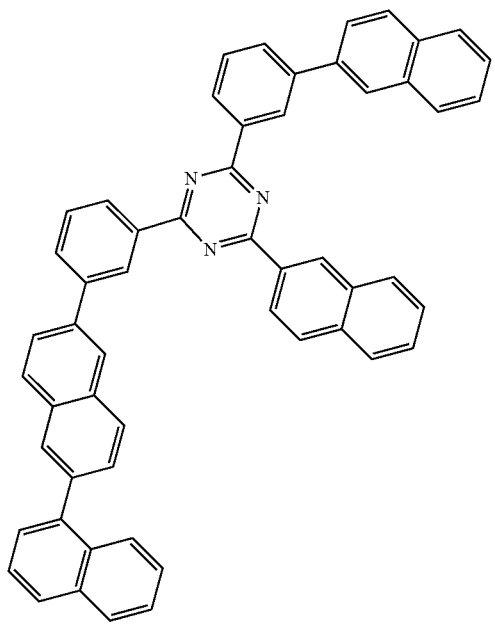
P-59
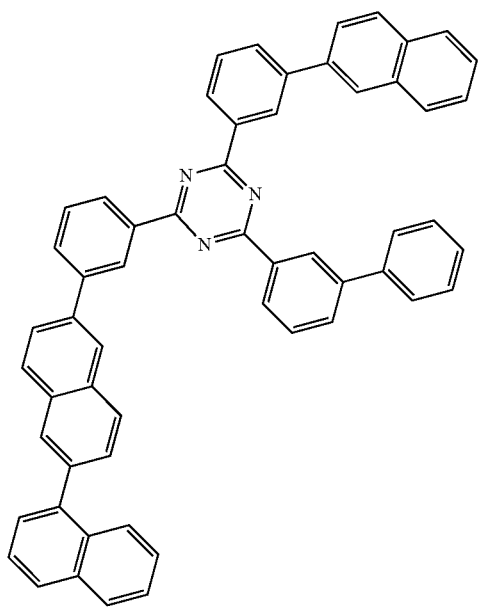
302
-continued
P-60
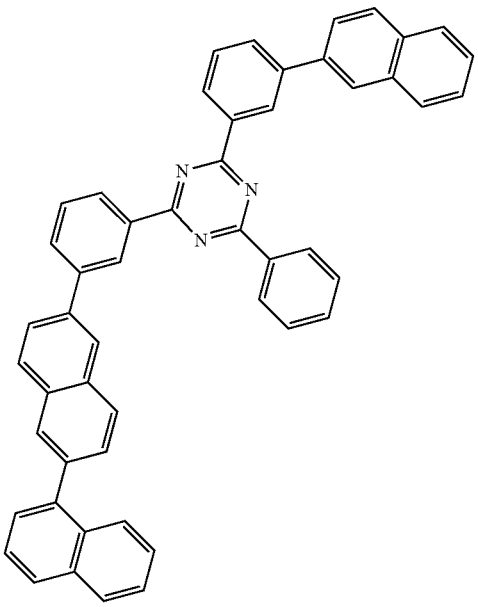
P-61
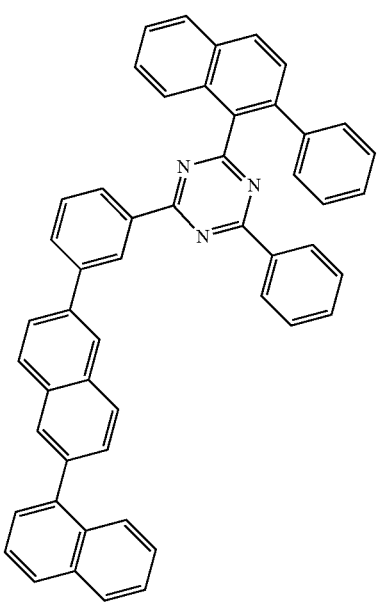

P-62
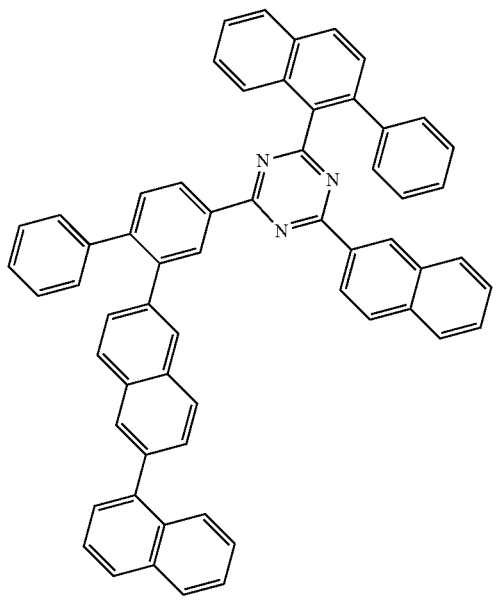
P-63
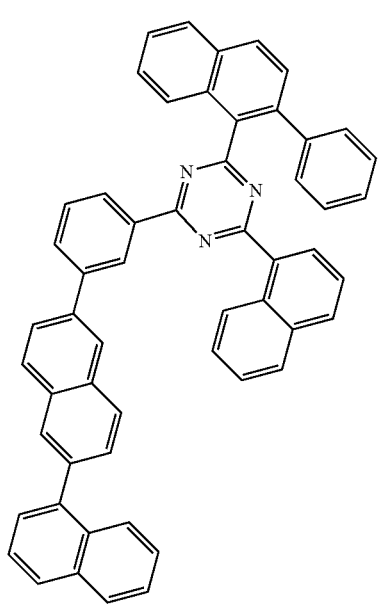
P-64
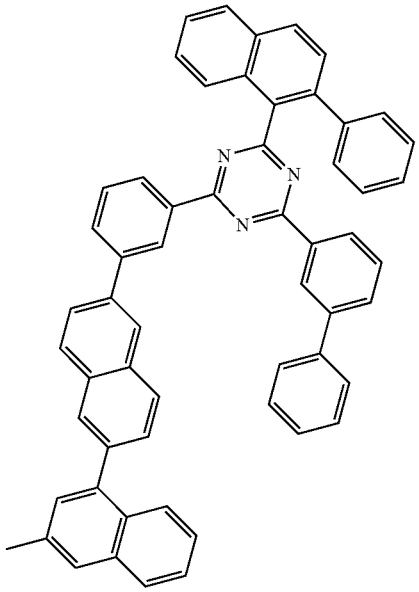
P-65
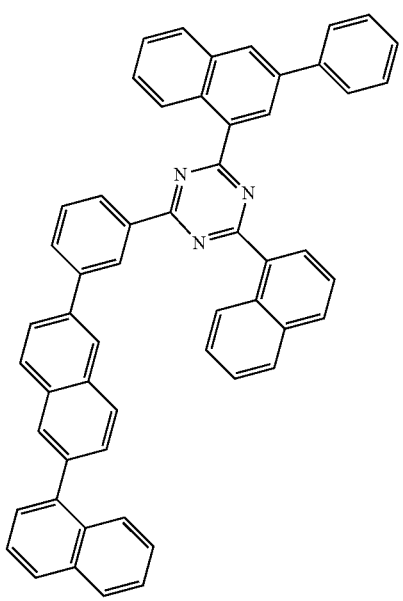

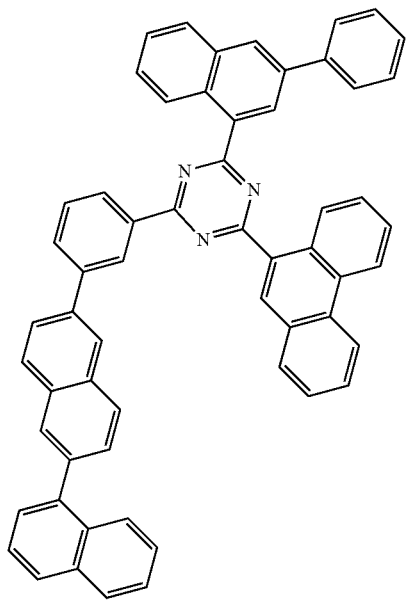
P-66
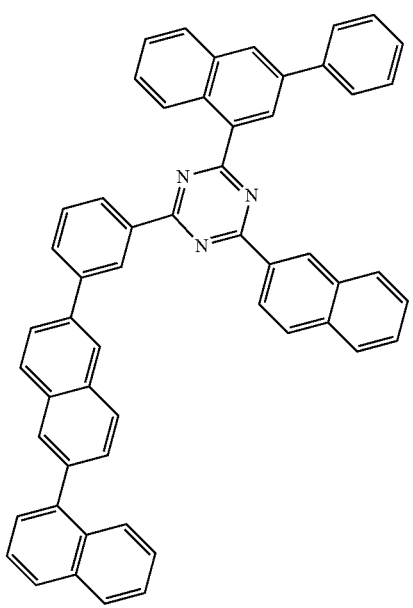
P-68
P-67
P-69
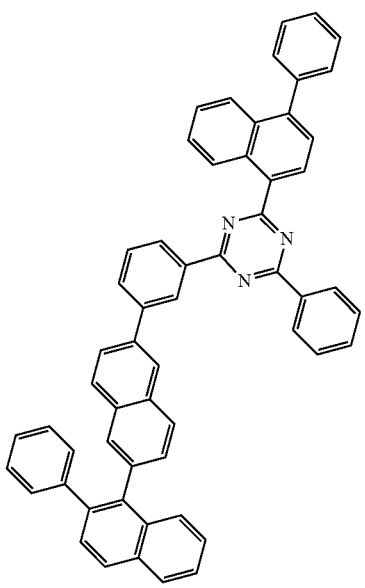

P-70 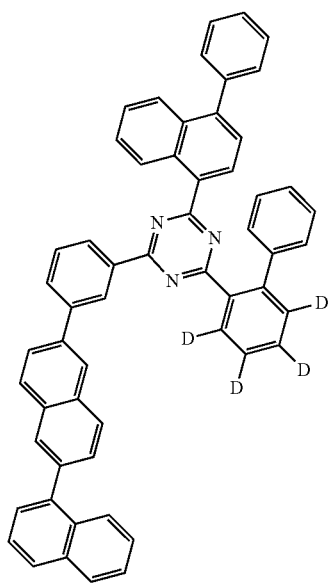
P-71
P-72 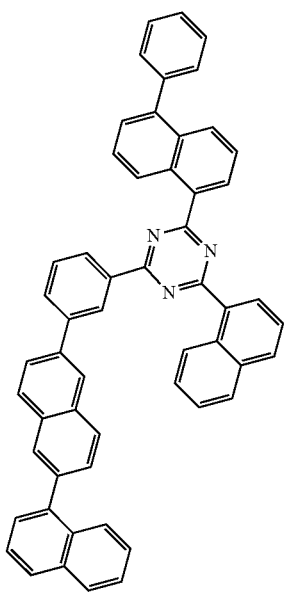
P-73 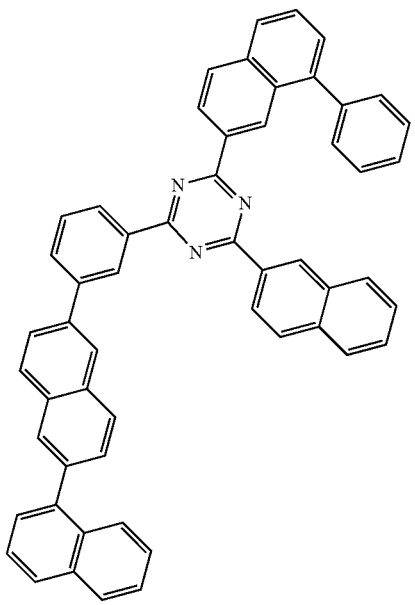

P-74
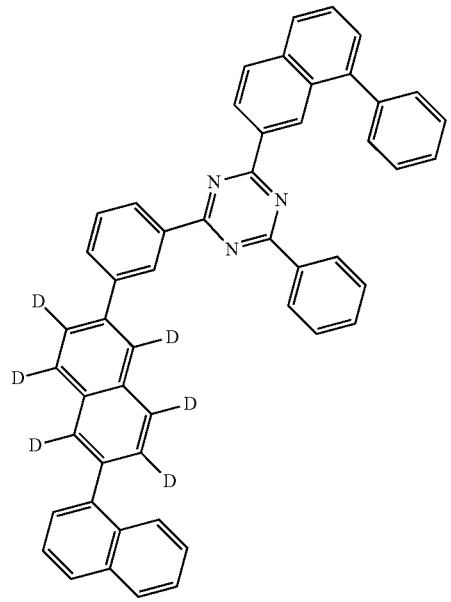
P-75
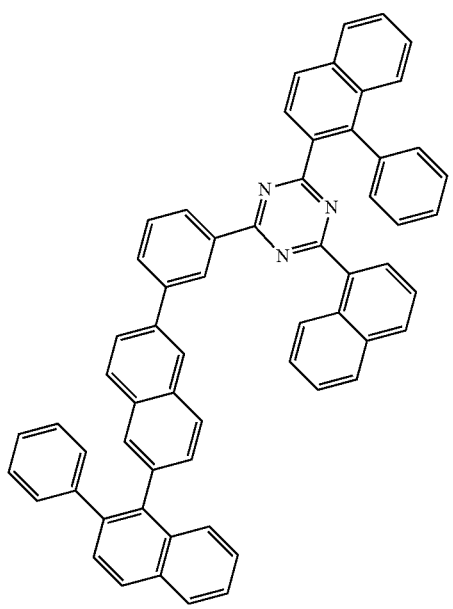
P-76
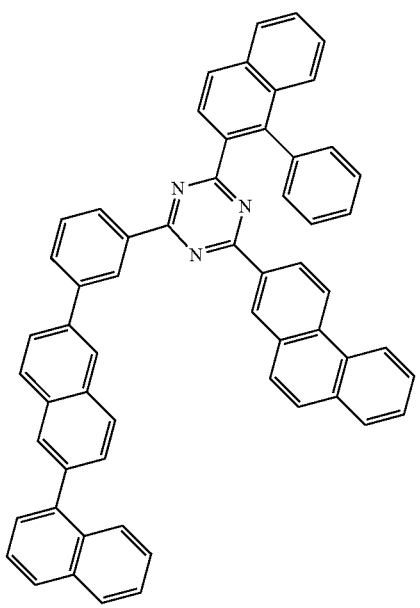
P-77
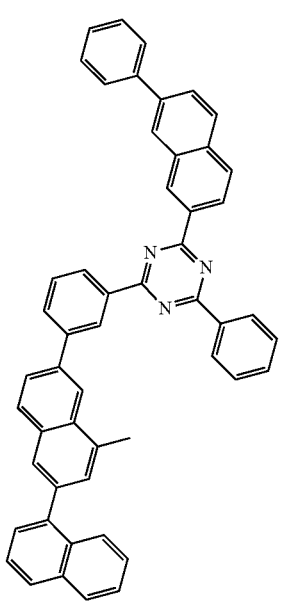

311
-continued
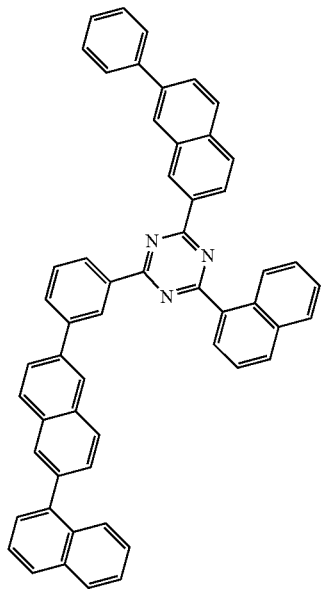
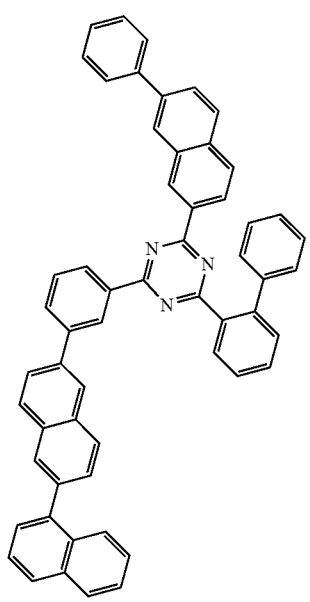
312
-continued
P-78
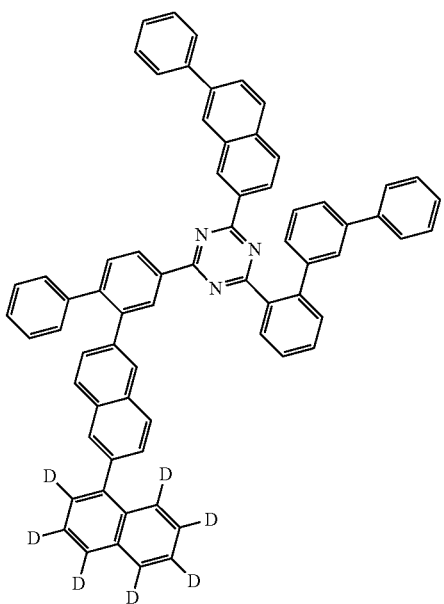
P-80
P-79
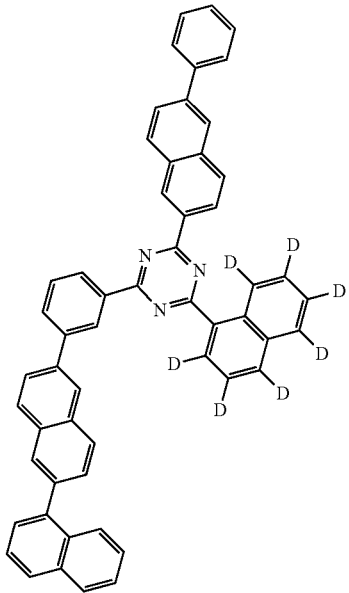
P-81

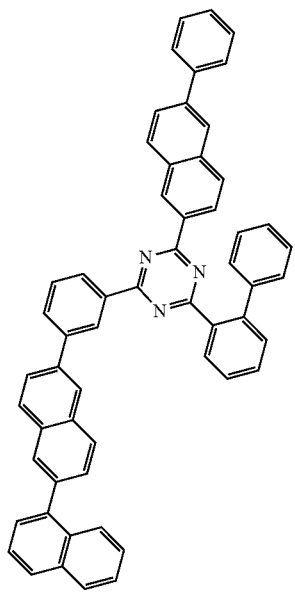
P-82
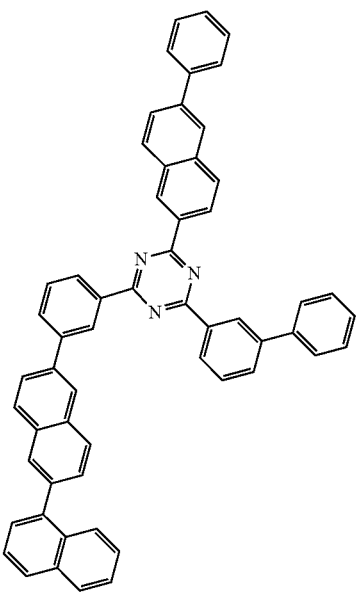
P-84
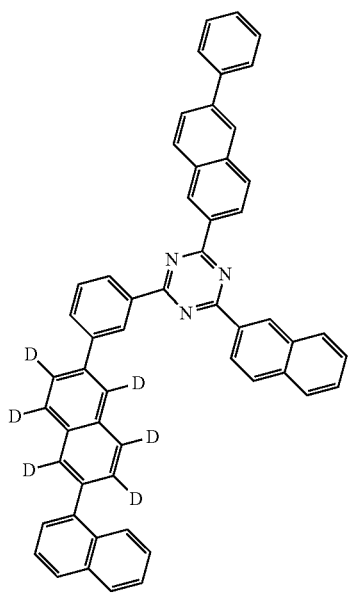
P-83
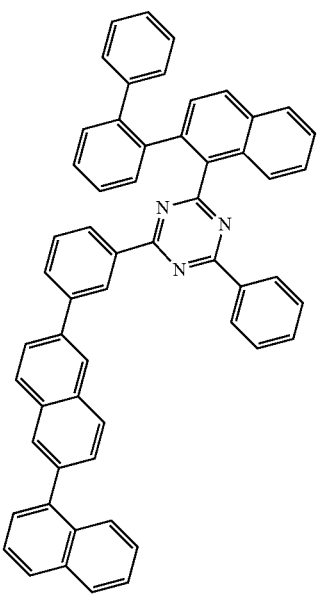
P-85

-continued
P-86
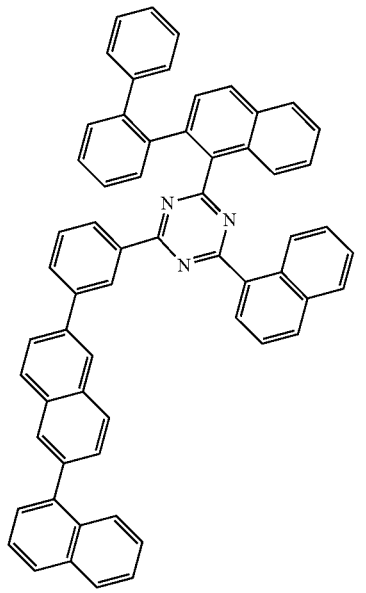
P-87
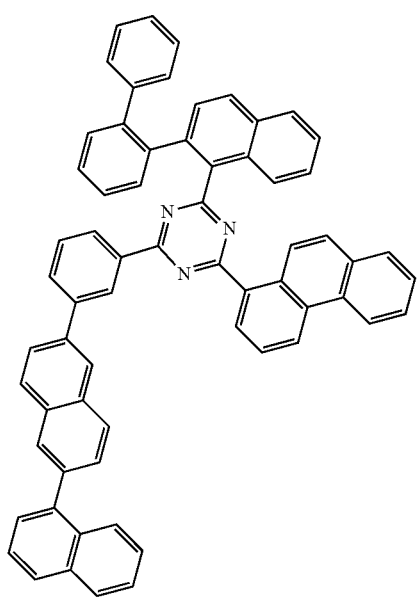
P-88
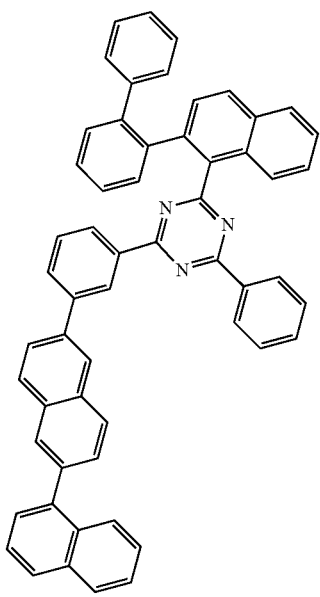
P-89
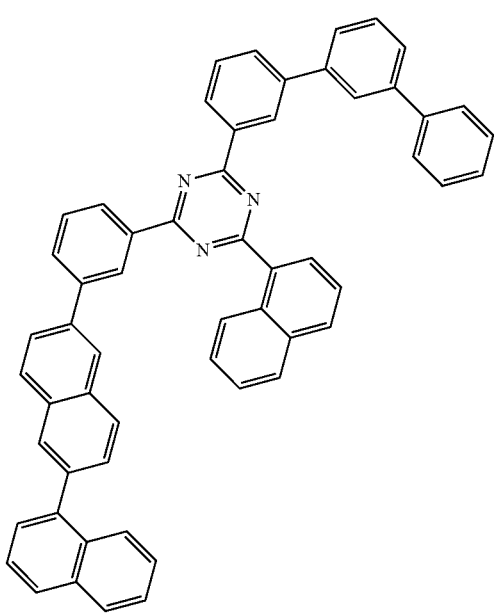

P-90
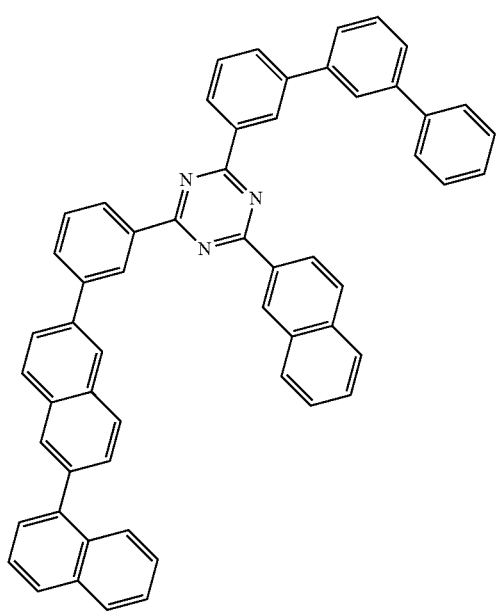
P-92
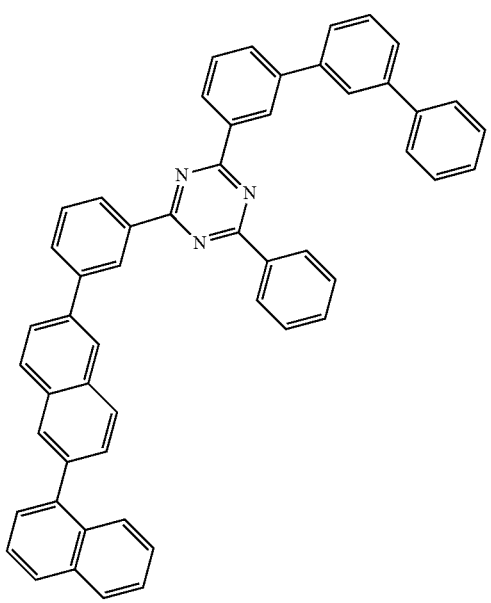
P-91
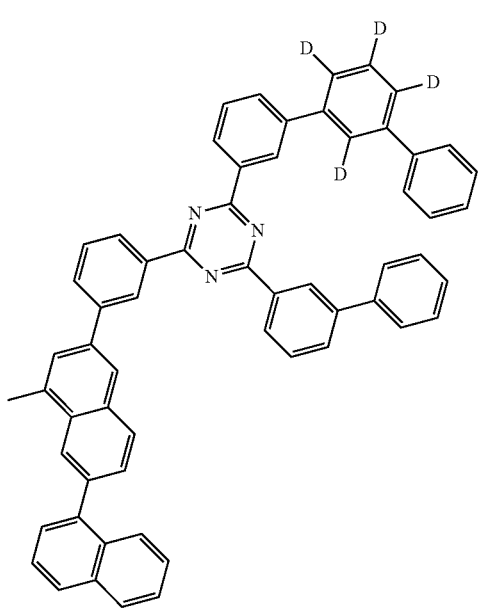
P-93
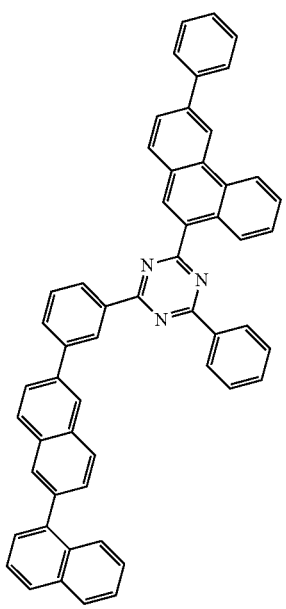

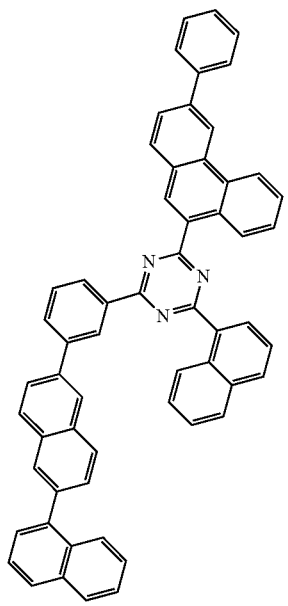
P-94
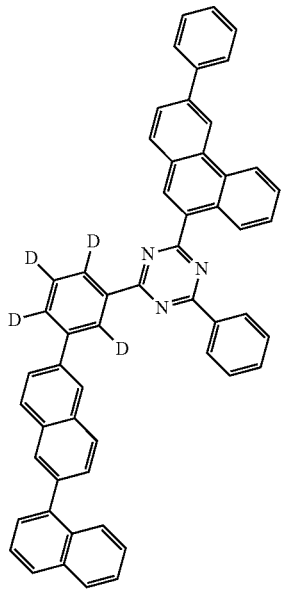
P-96
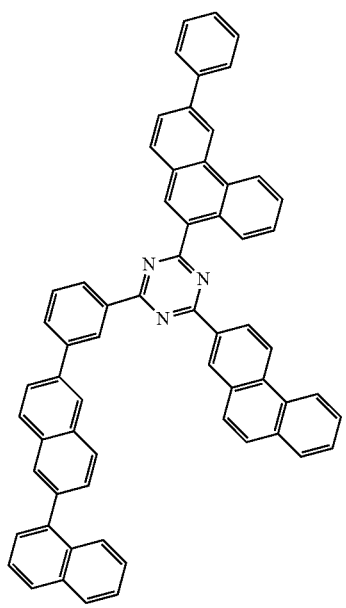
P-95
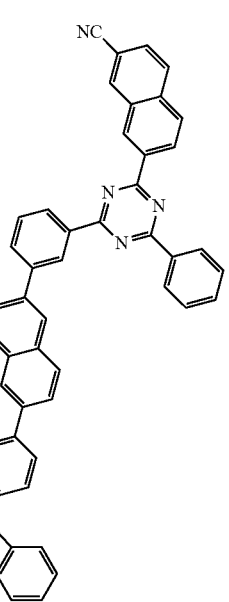
P-97

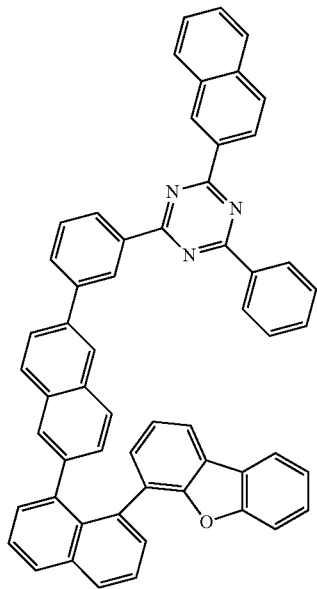
P-98
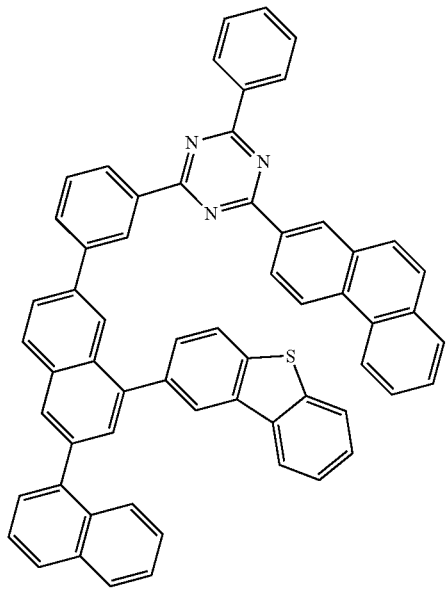
P-99
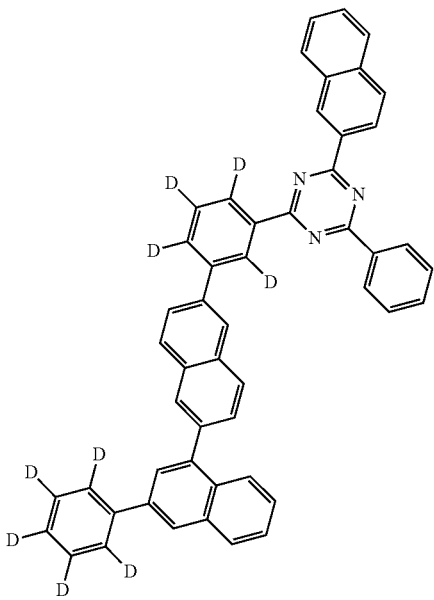
P-100
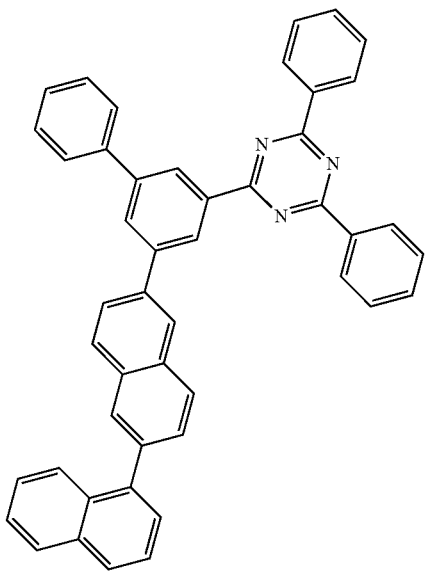
P-101

P-102
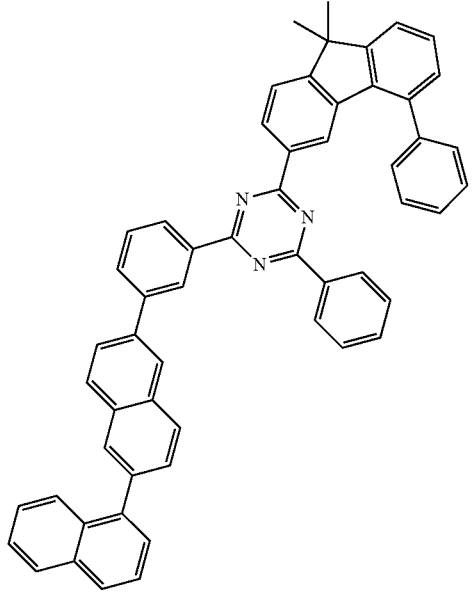
P-104
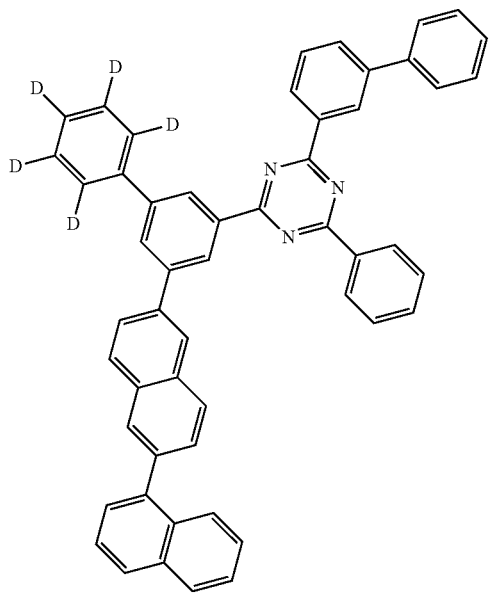
4. The organic electronic element of claim 1, wherein Formula 4 is represented by any one of the following compounds H-1 to H-100:
H-1
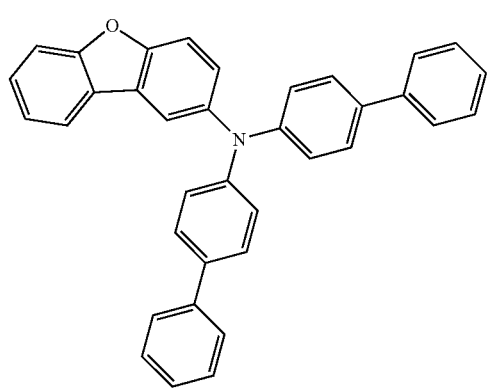
P-103
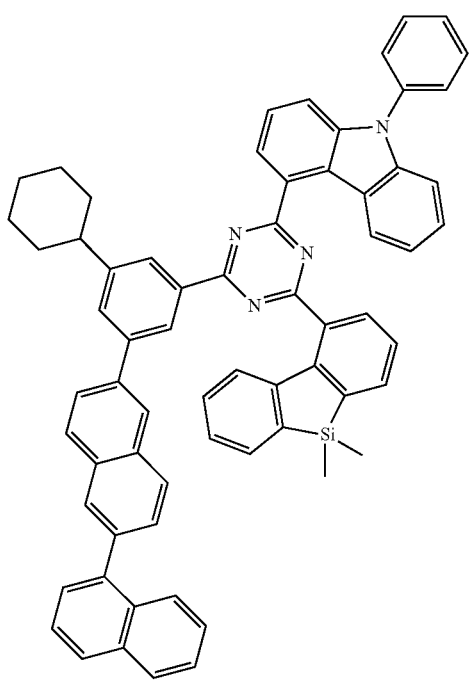
H-2
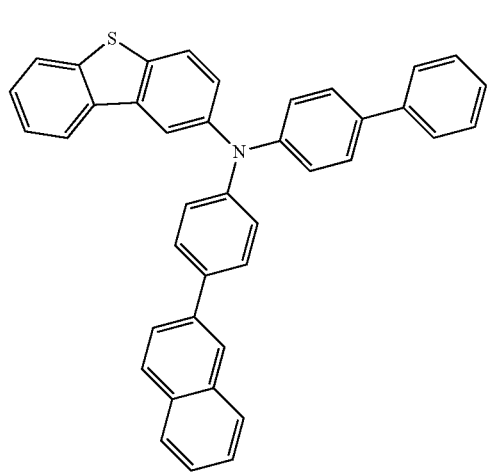

325
-continued
326
-continued
H-3
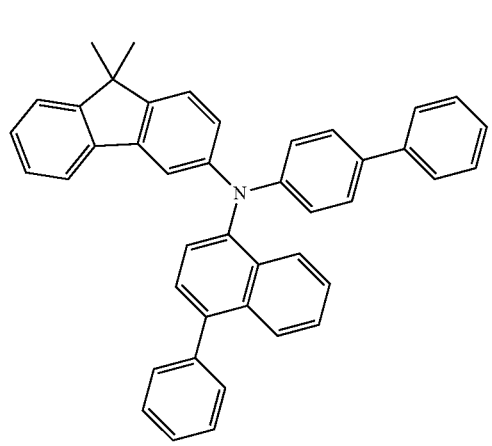
H-4
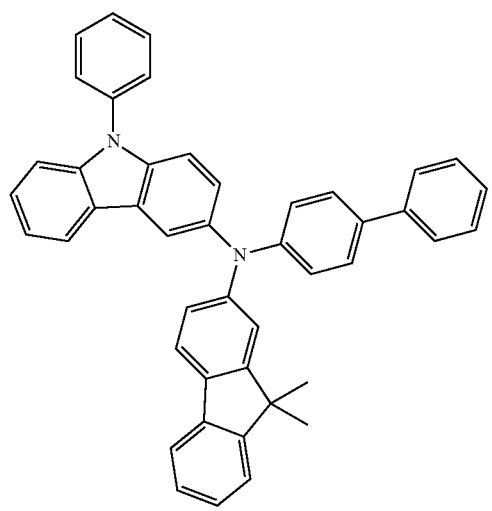
H-5
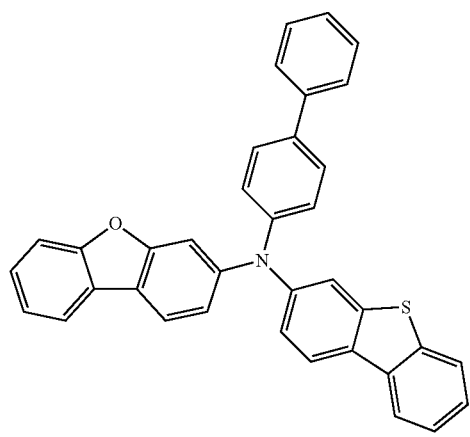
H-6
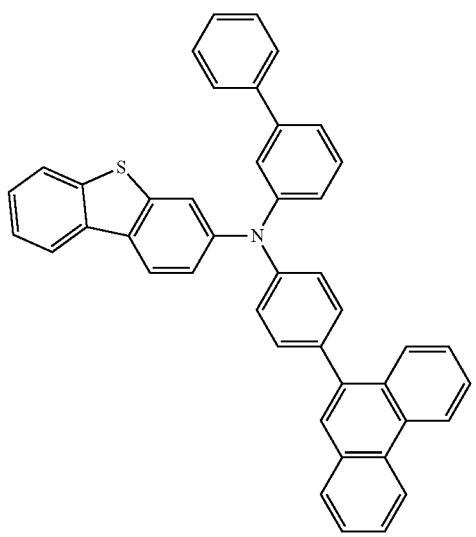
H-7
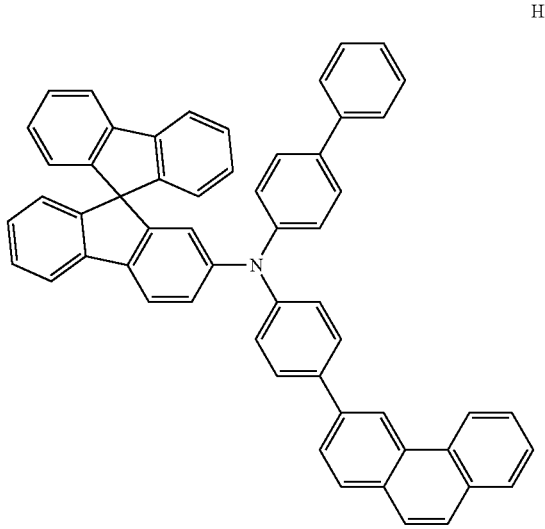
H-8
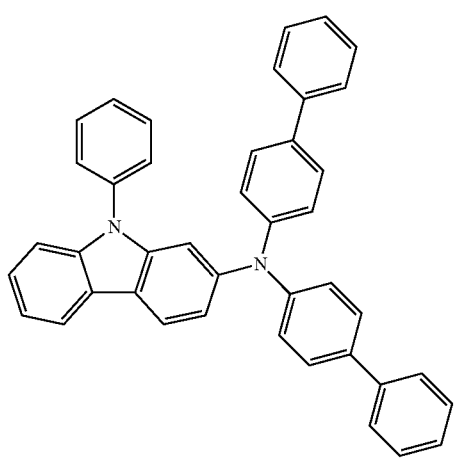

H-9
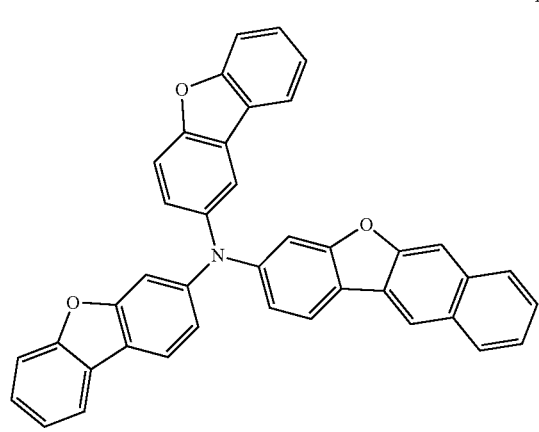
H-10
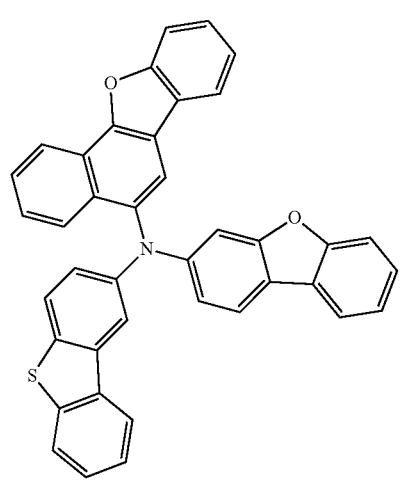
H-11
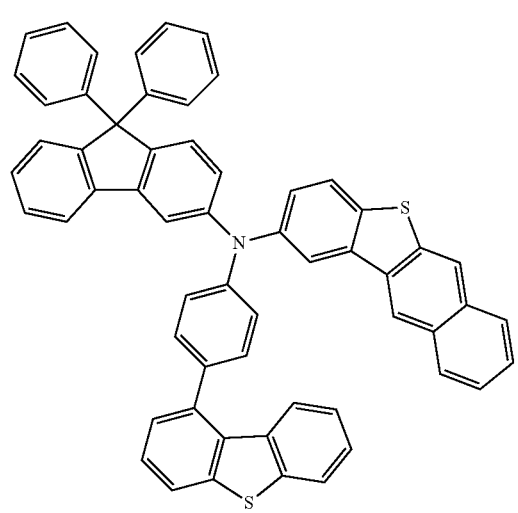
H-12
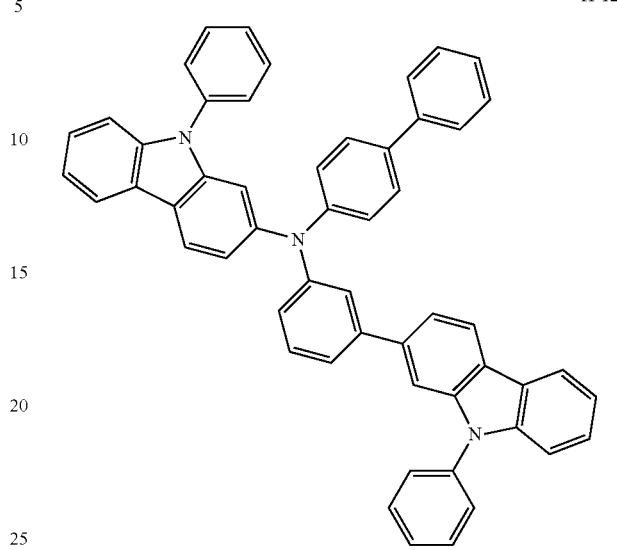
H-13
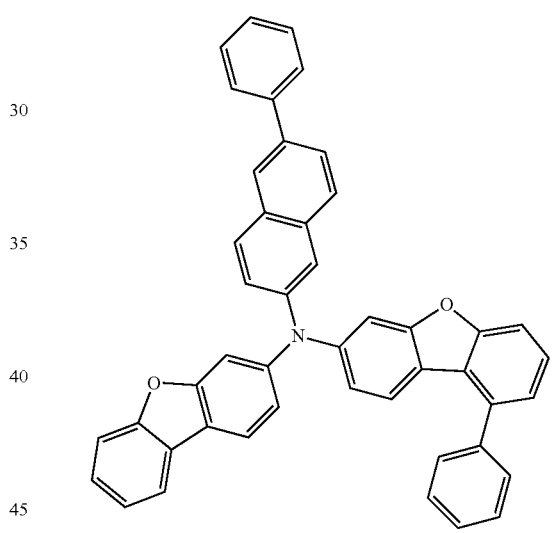
H-14
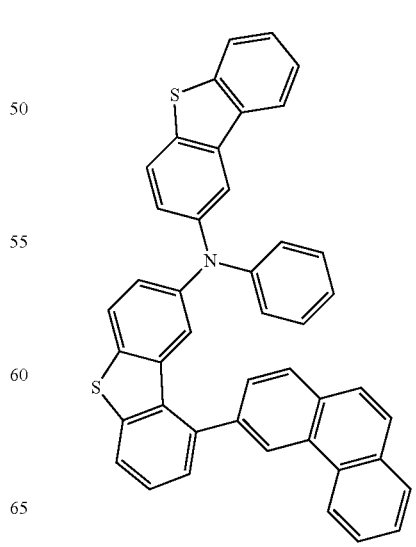

H-15
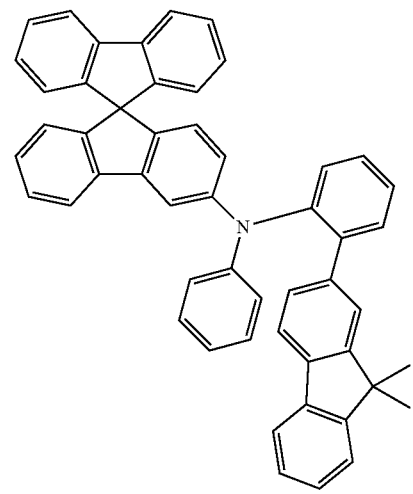
H-16
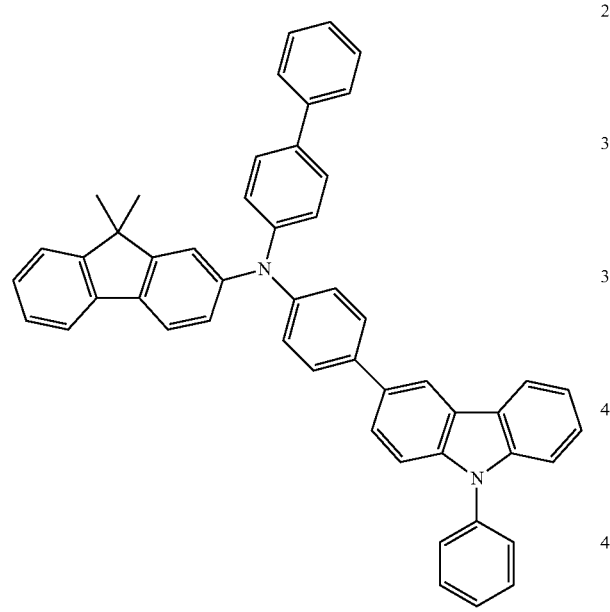
H-17
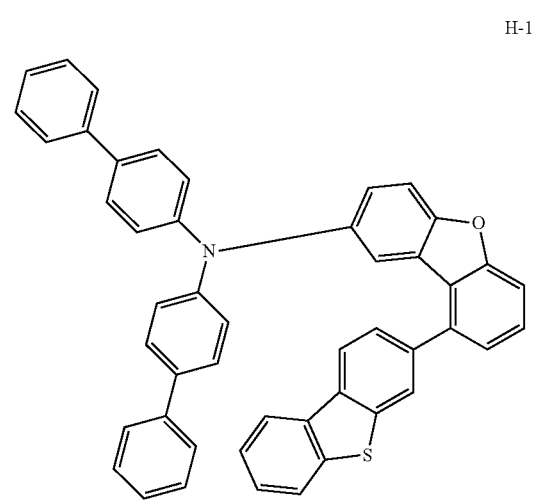
H-18
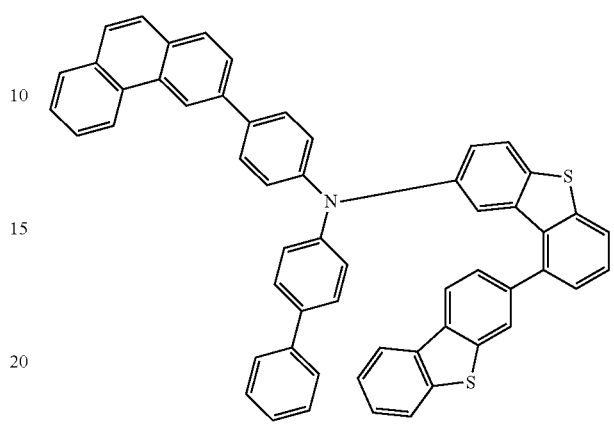
H-19
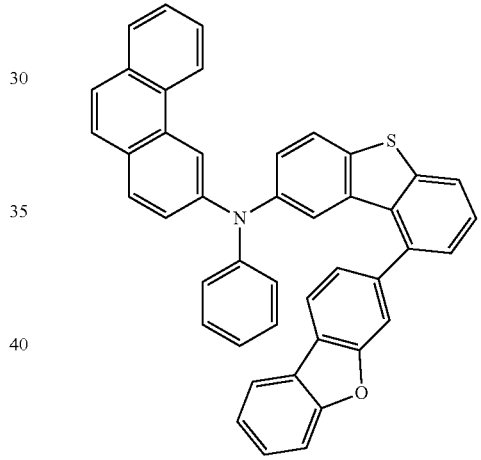
H-20
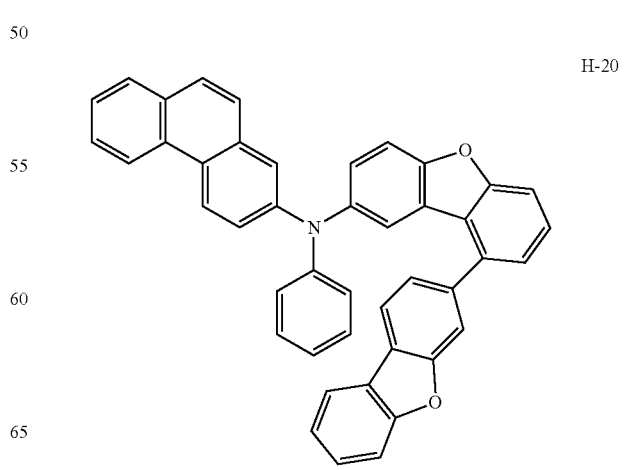

-continued
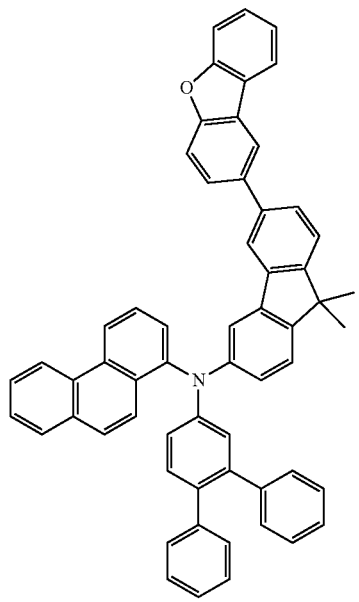
H-21
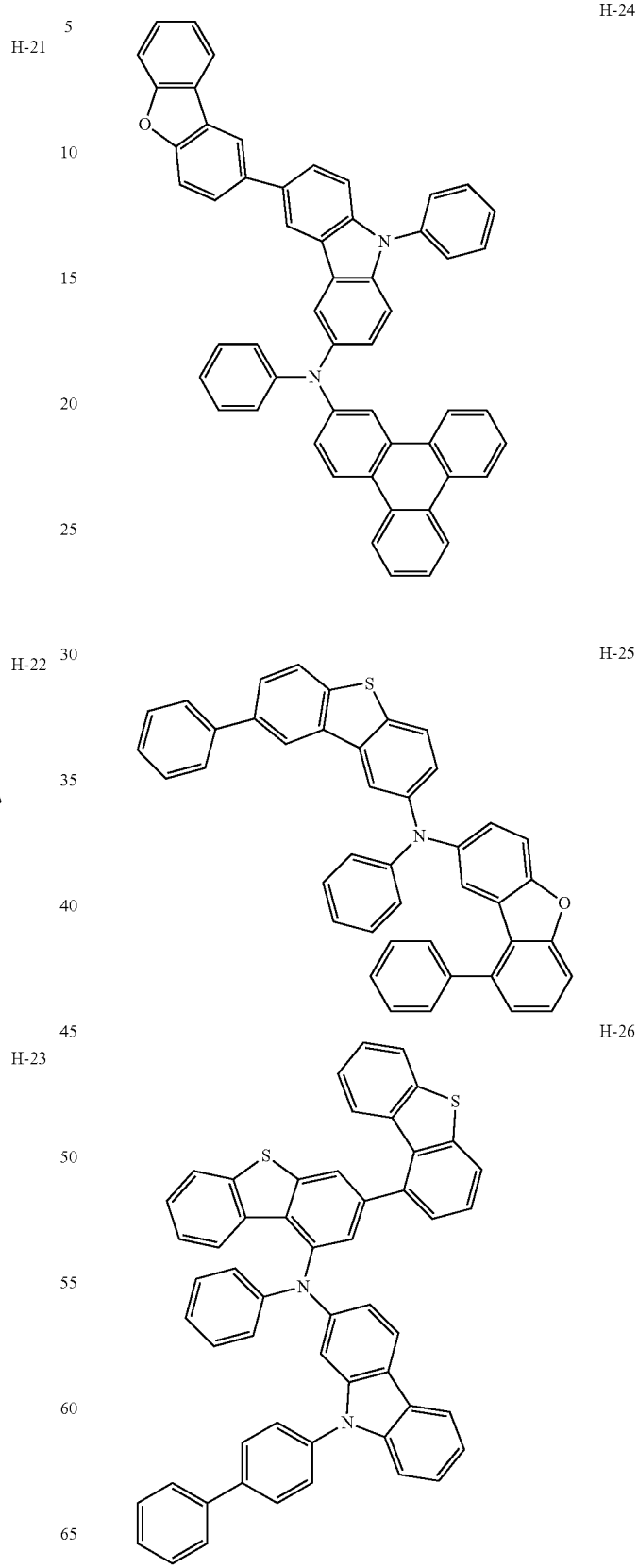

H-27
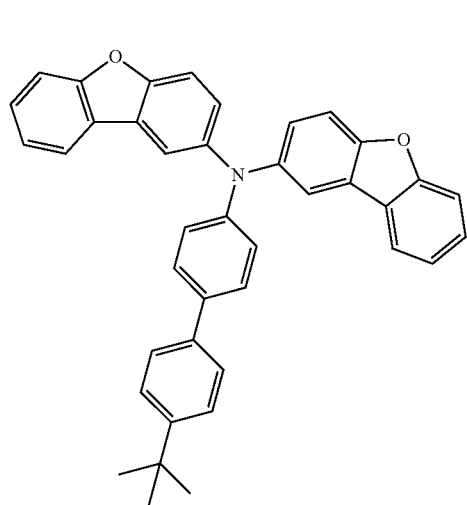
H-28
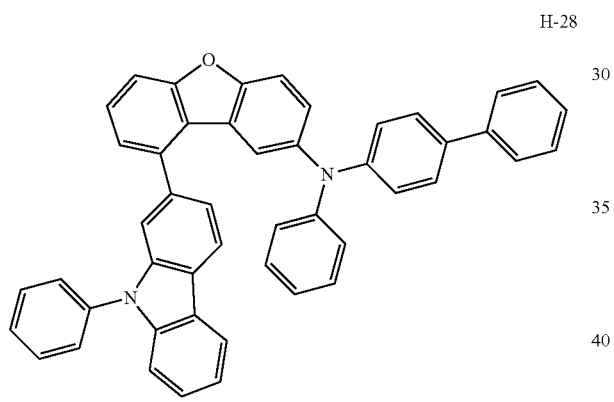
H-30
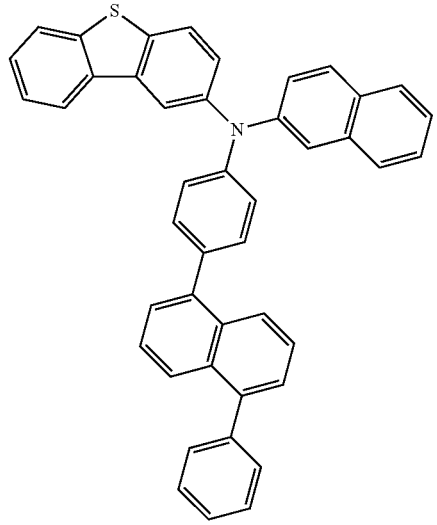
H-31
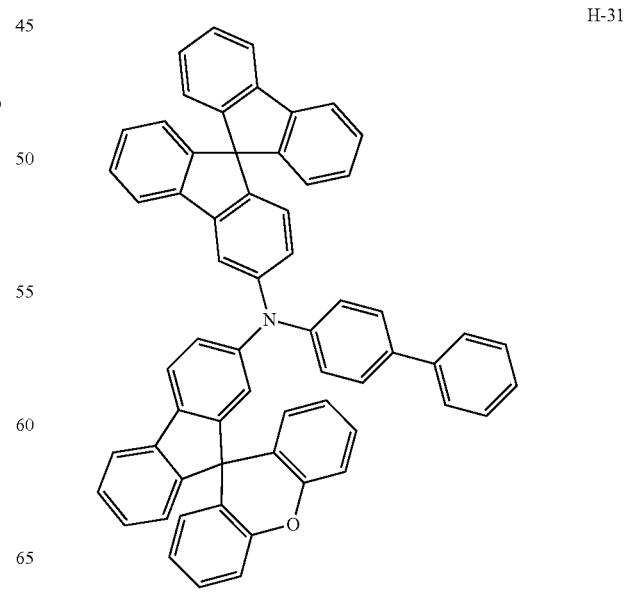
H-29

H-32
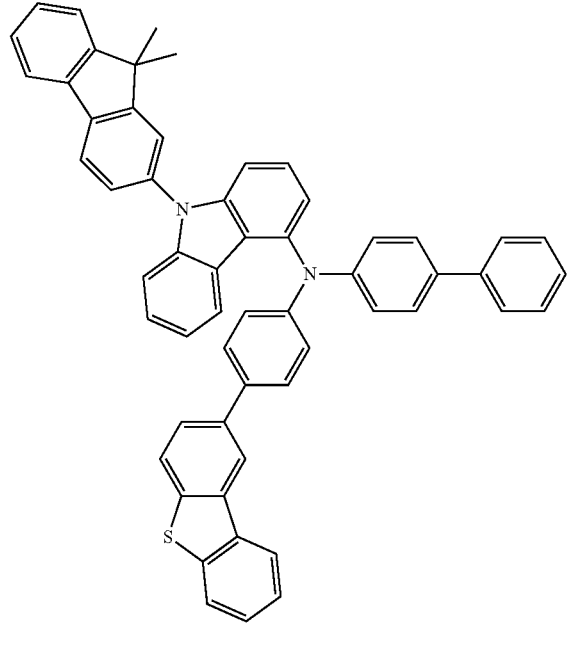
H-33
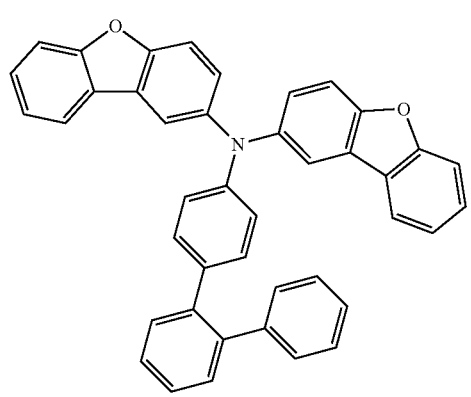
H-34
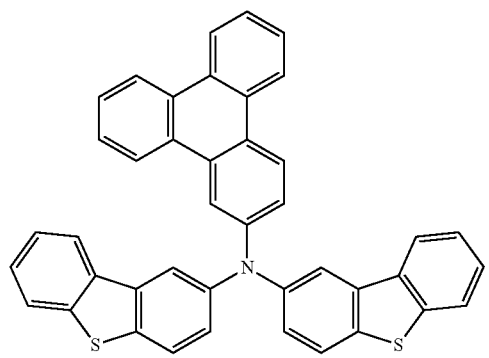
H-35
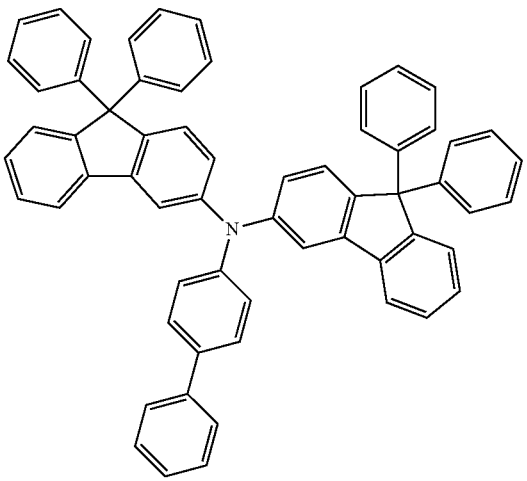
H-36
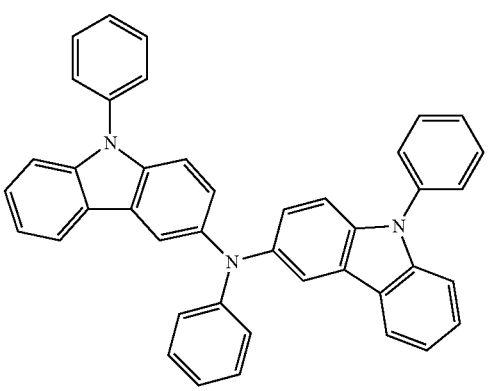
H-37
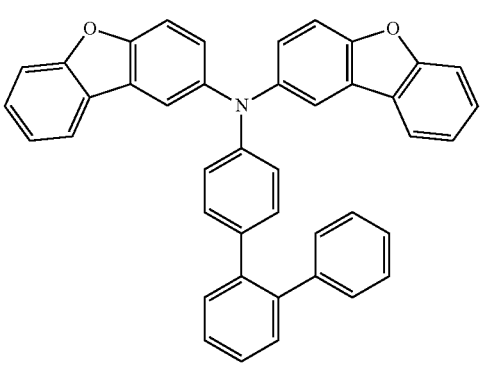
H-38
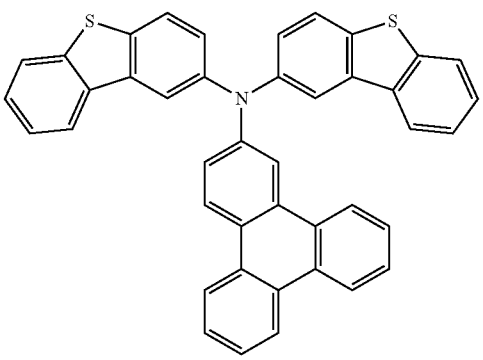

-continued
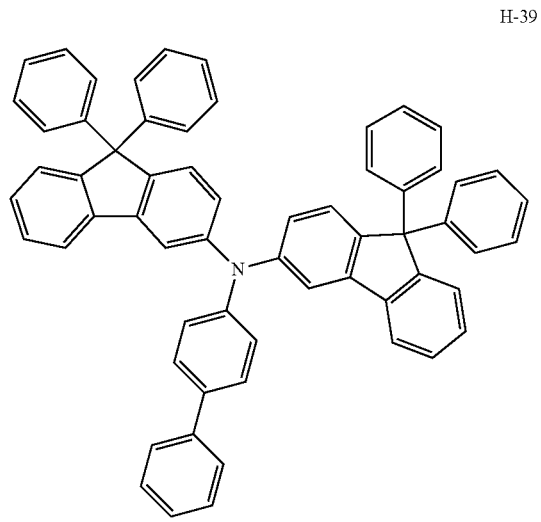
H-39
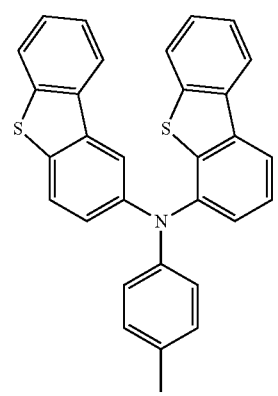
H-42
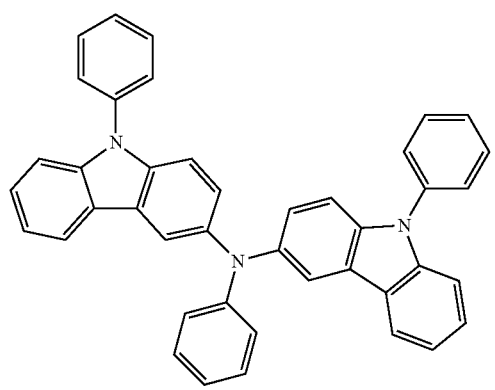
H-40
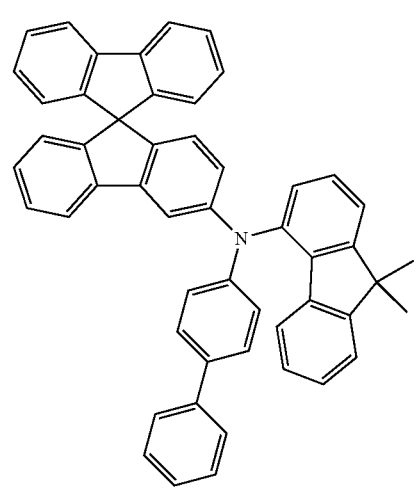
H-43
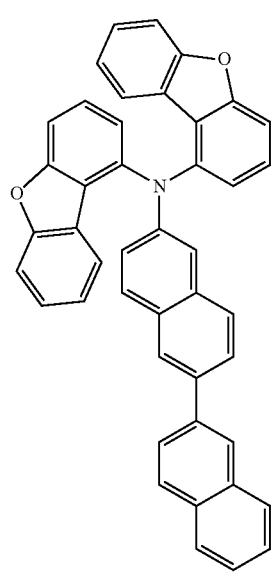
H-41
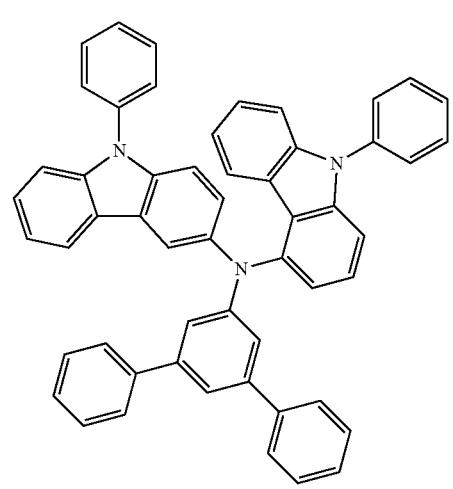
H-44

H-45
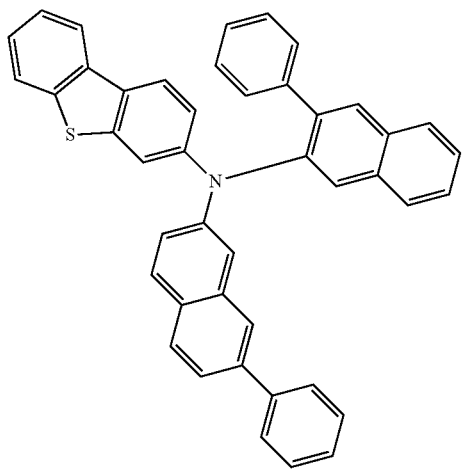
H-48
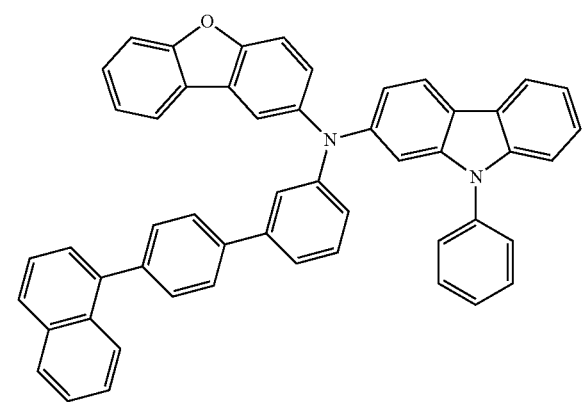
H-46
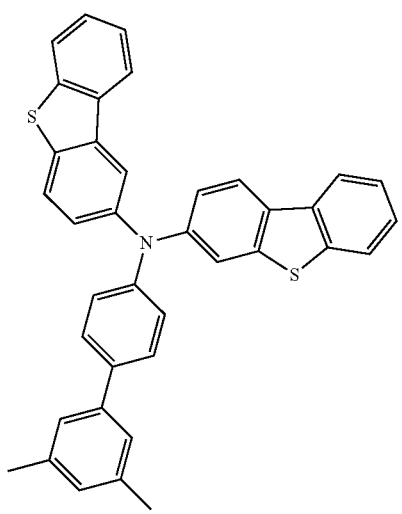
H-49
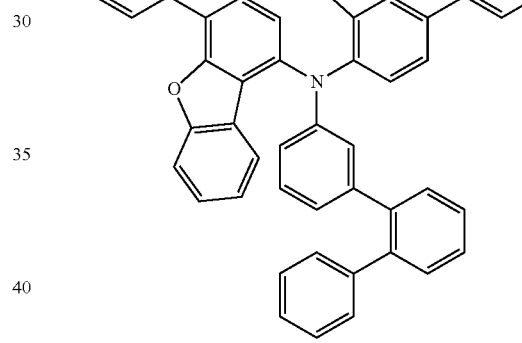
H-47
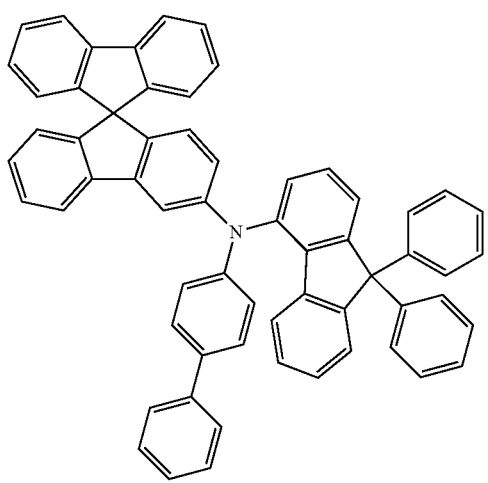
H-50
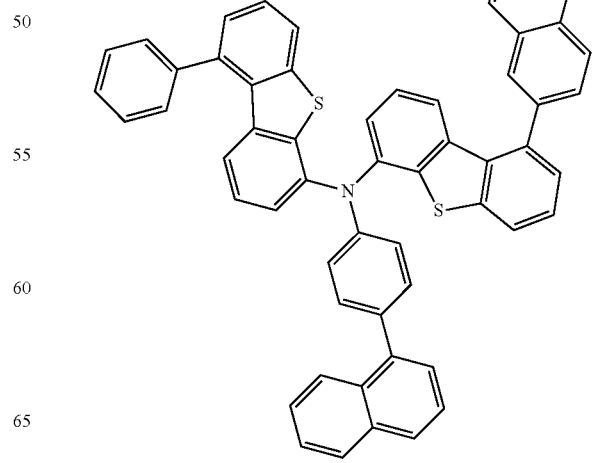

341
-continued
H-51
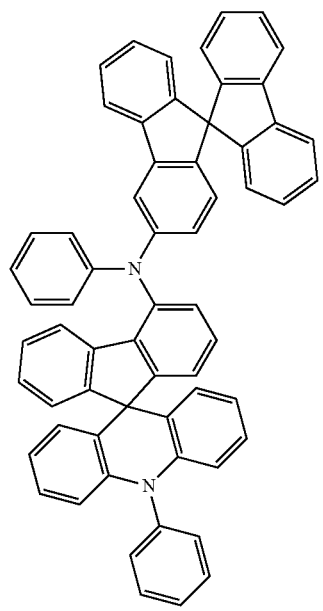
H-52
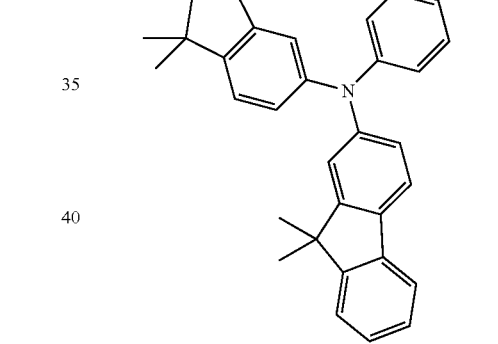
H-53
342
-continued
H-54
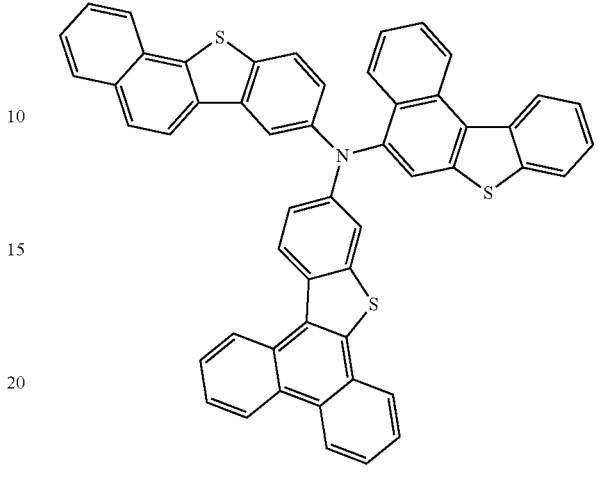
H-55
H-56
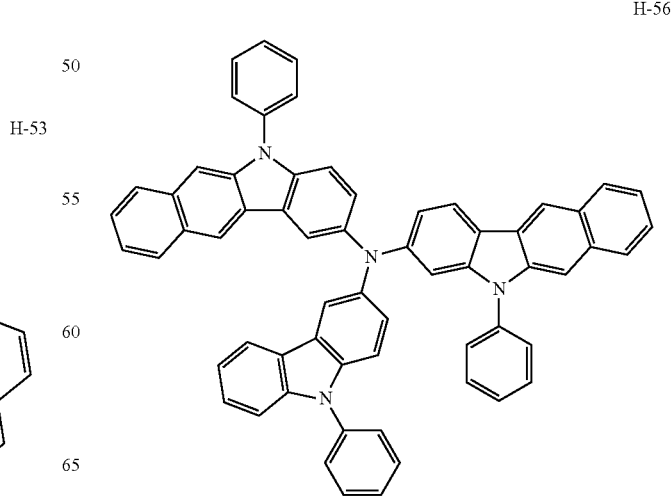

H-57
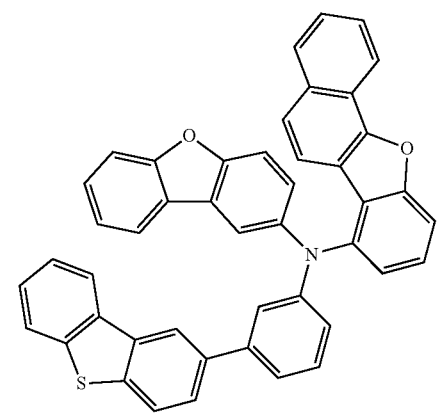
H-58
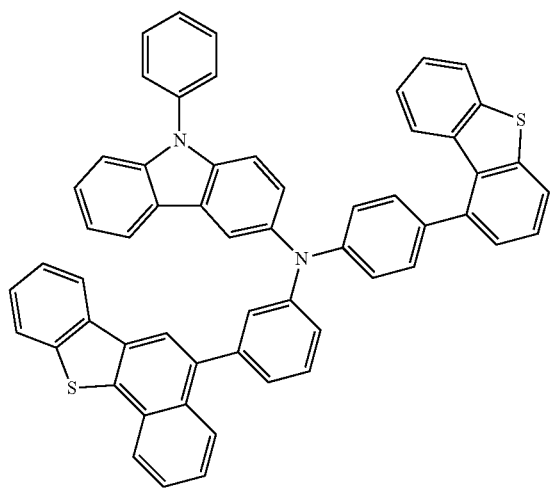
H-59
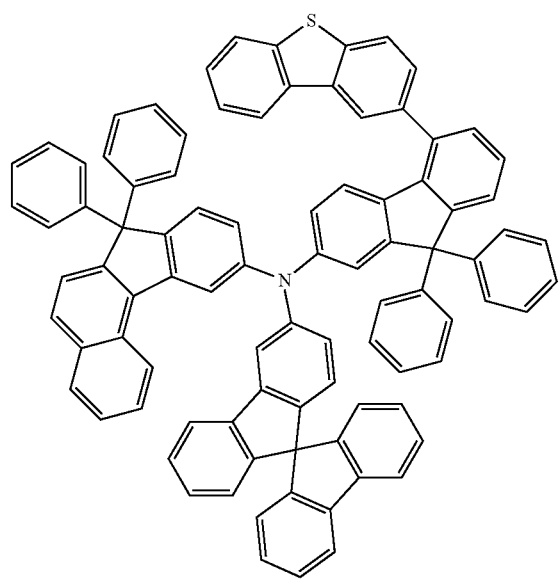
H-60
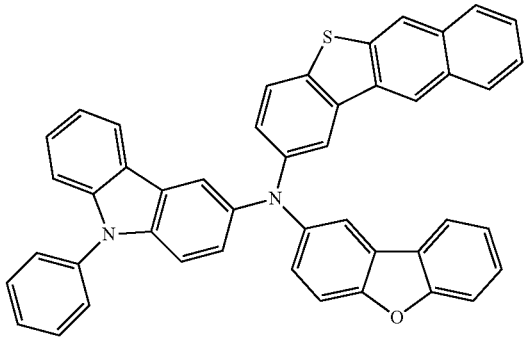
H-61
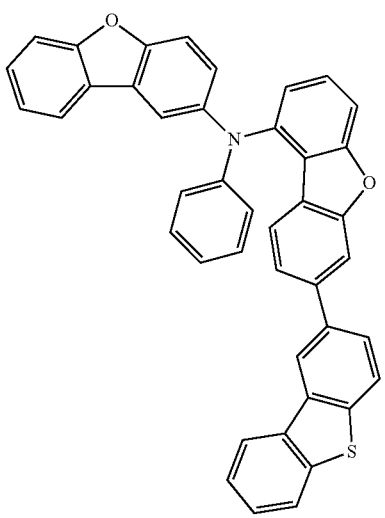
H-62
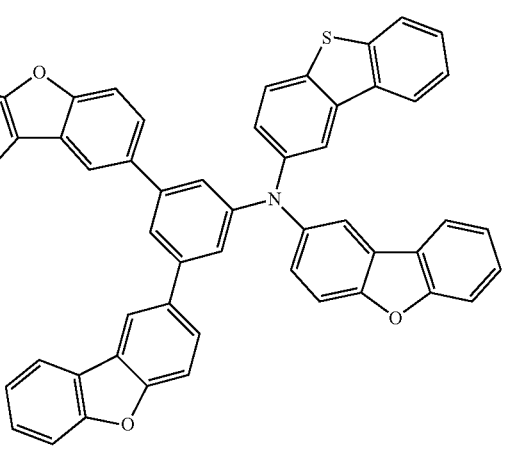

H-63
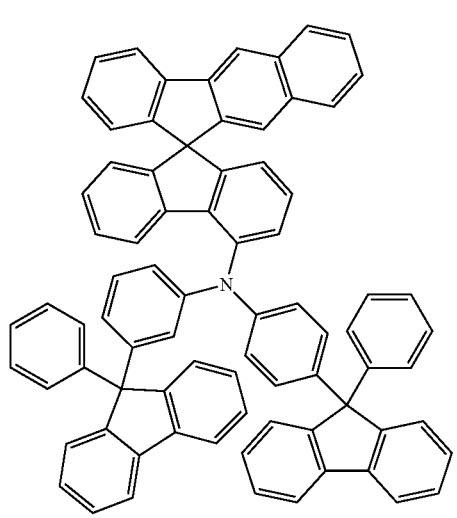
H-66
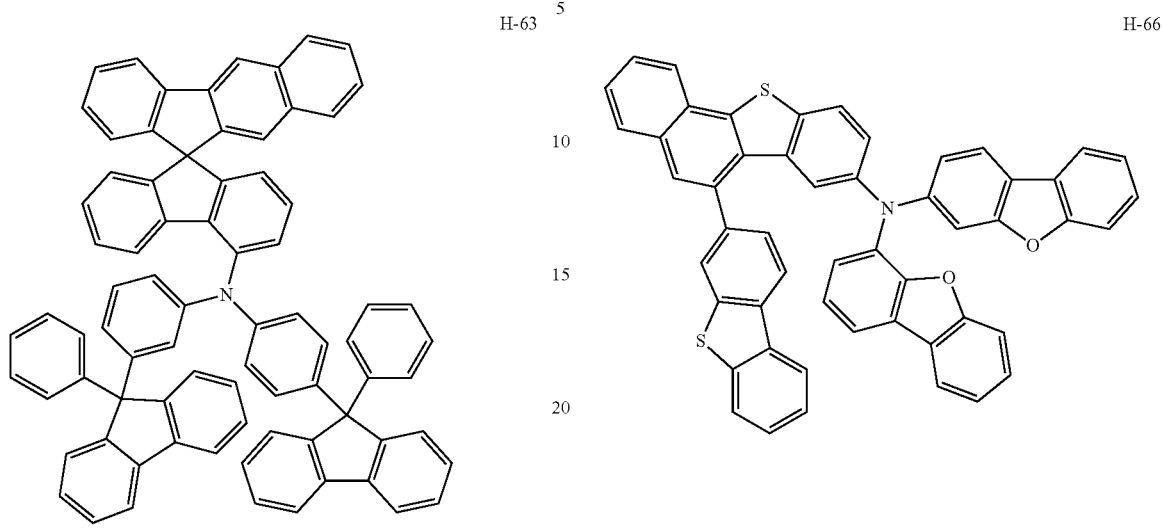
H-64
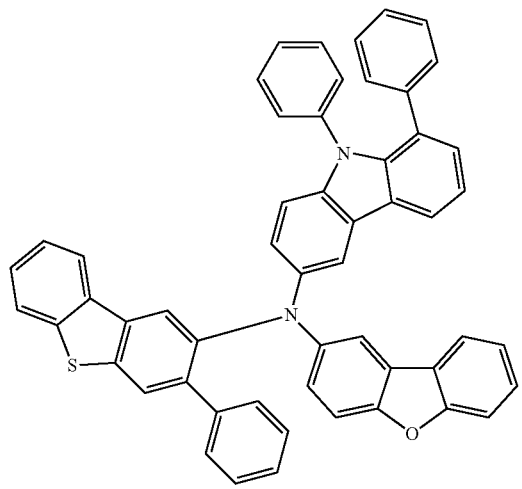
H-67
H-65
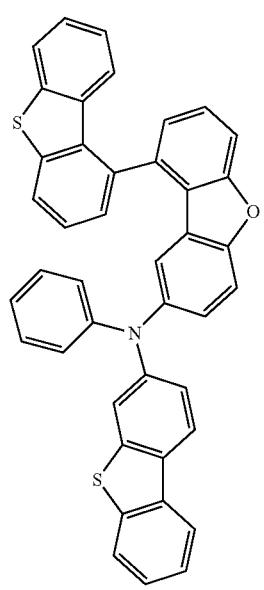
H-68
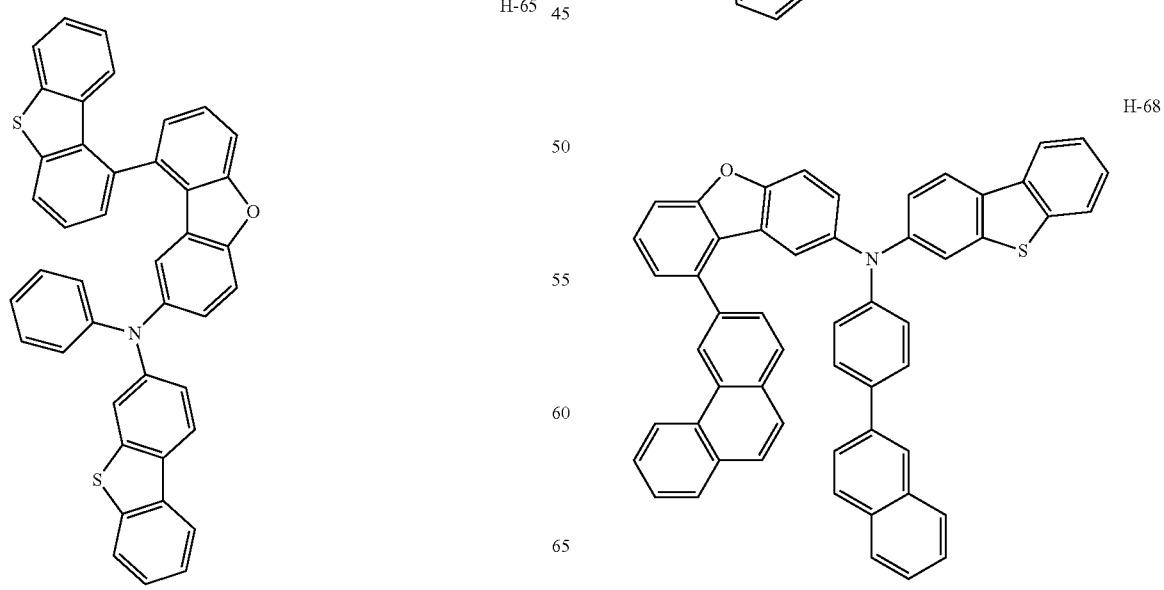

-continued
H-69
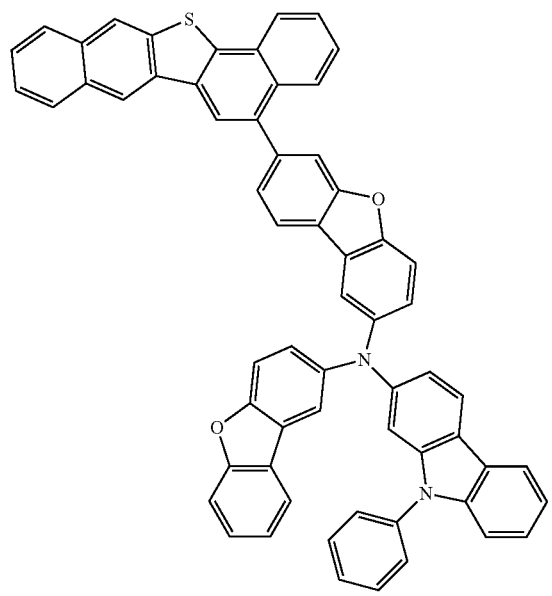
H-70
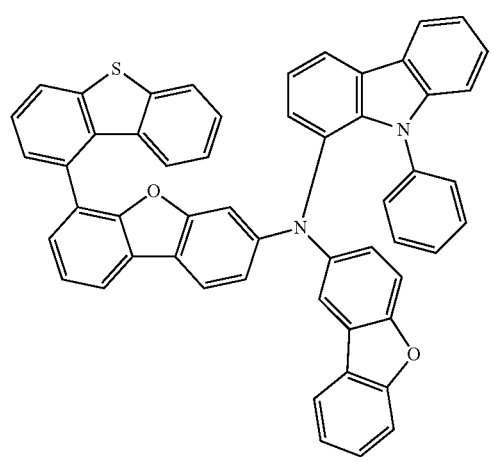
H-71
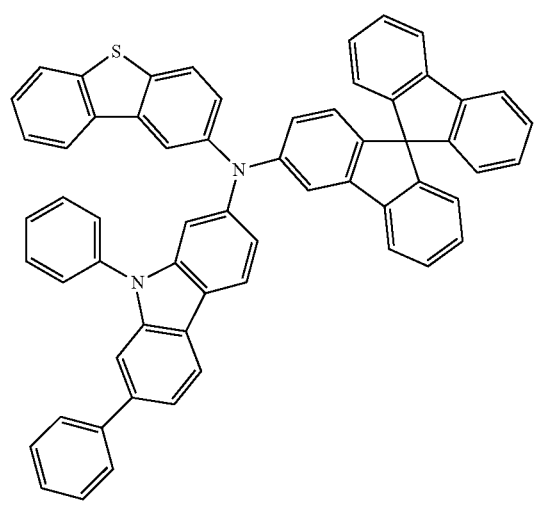
-continued
H-72
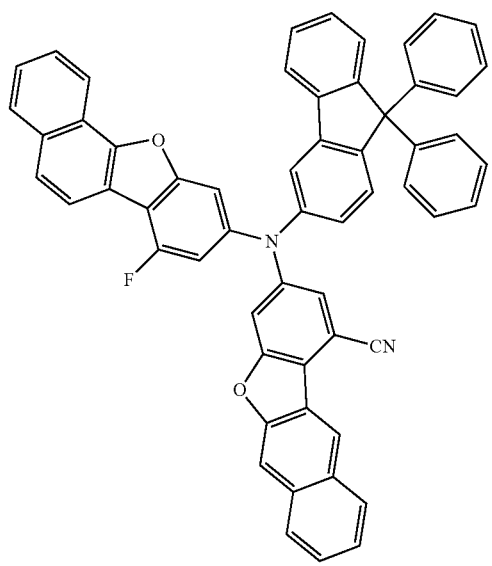
H-73
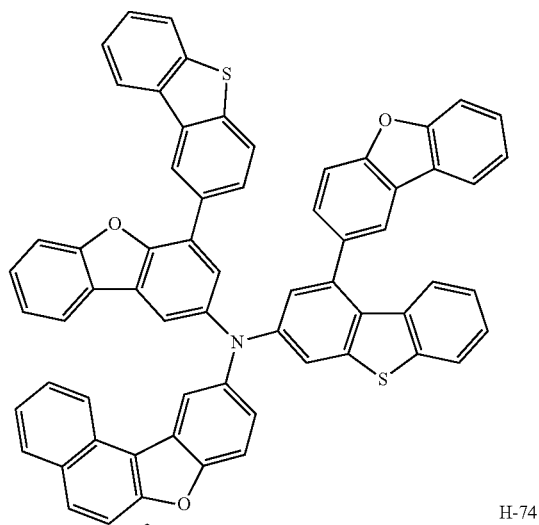
H-74
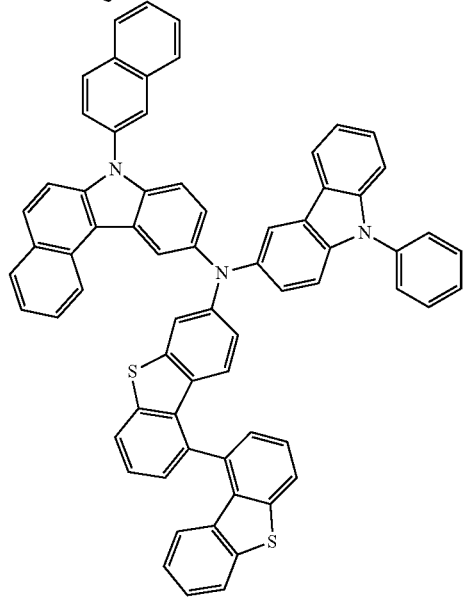

-continued
H-75
H-76
H-77
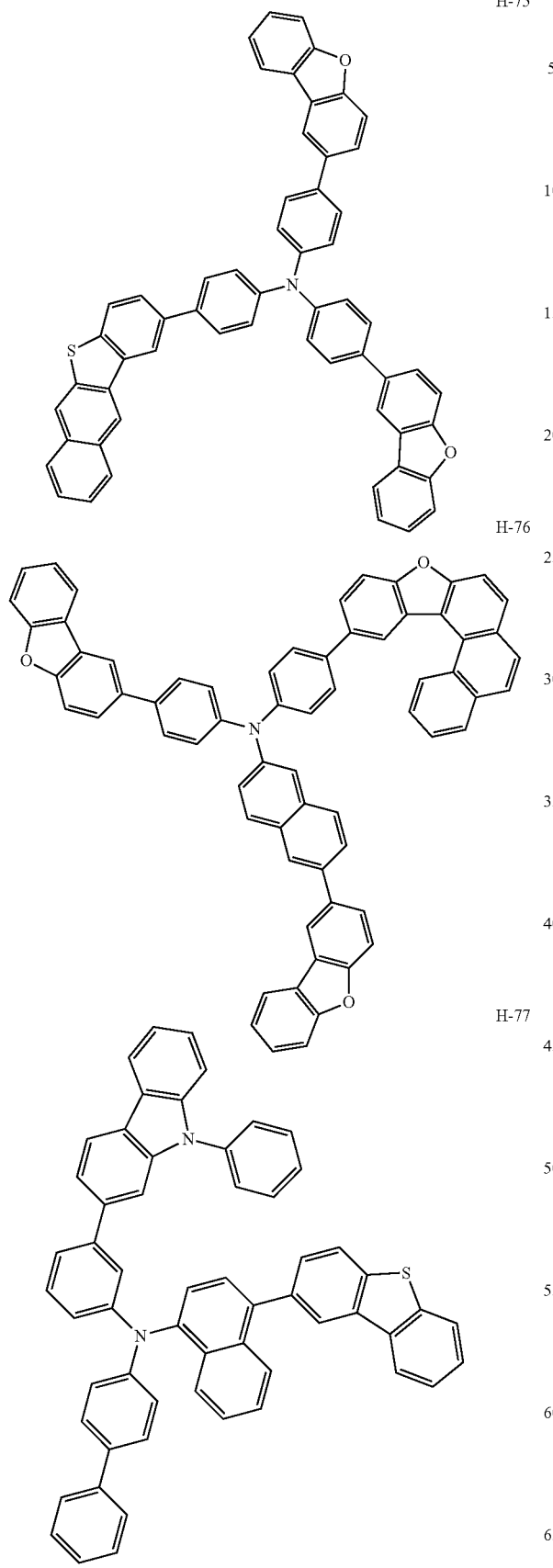
-continued
H-78
H-79
H-80
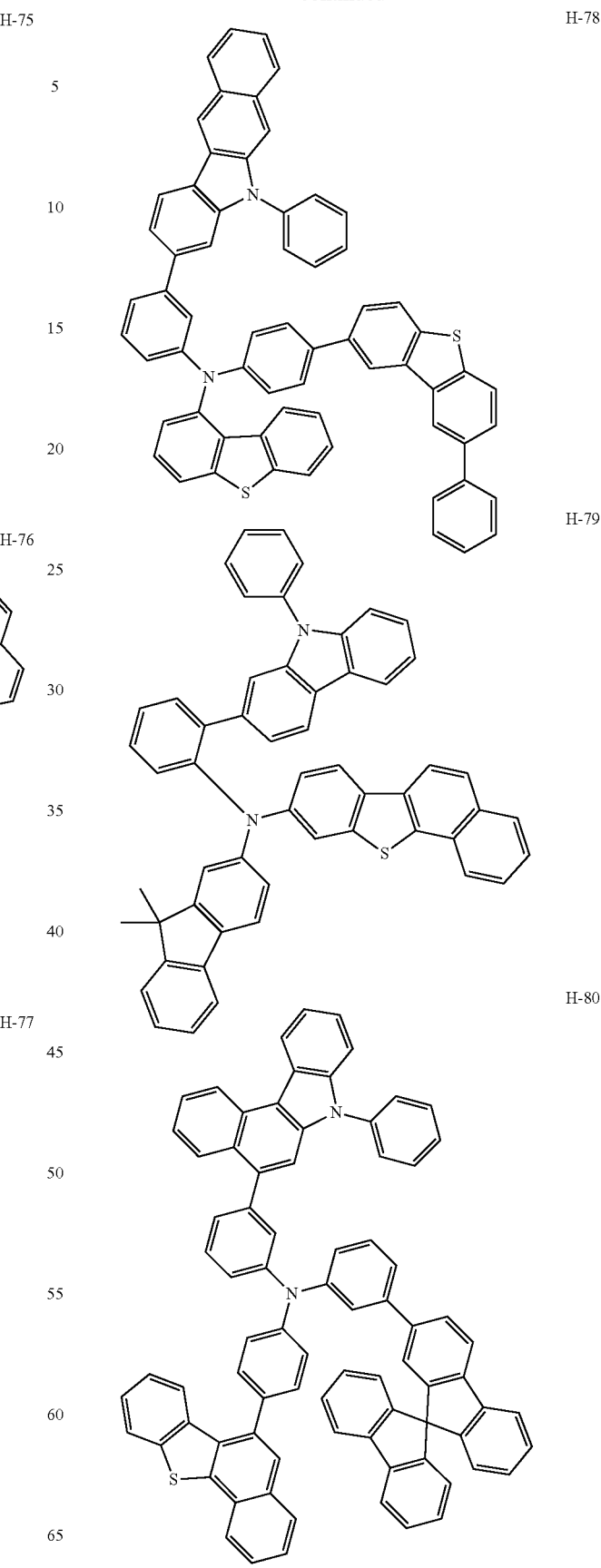

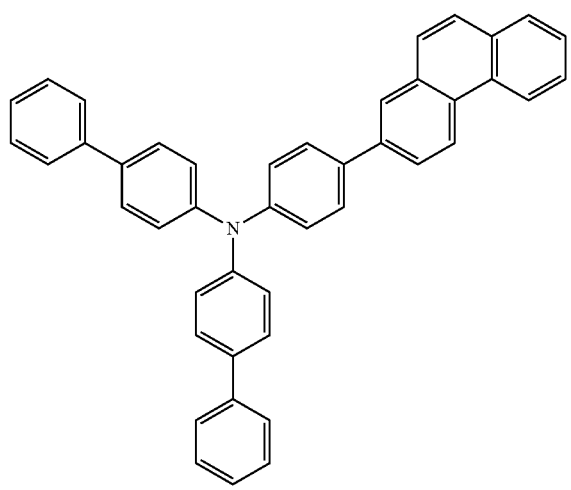
H-81
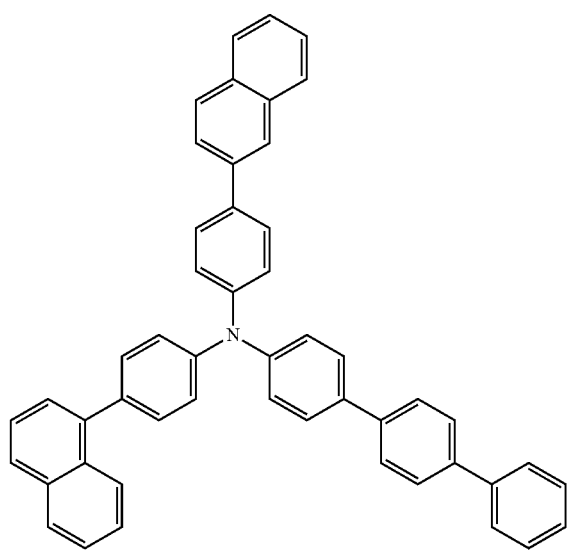
H-82
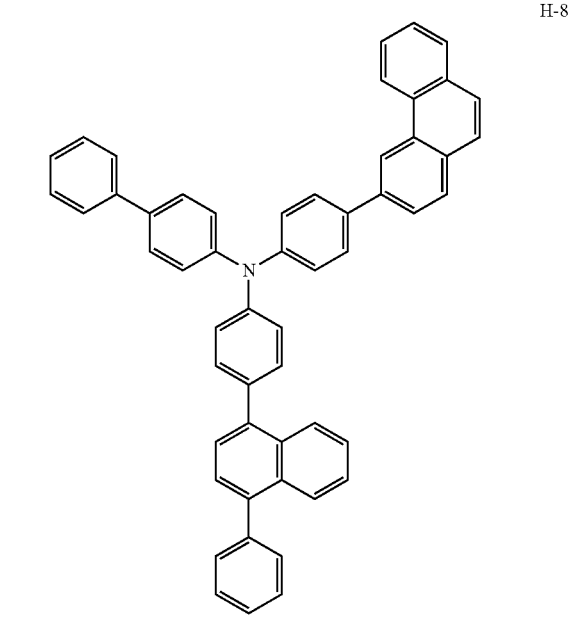
H-83
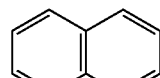
H-84
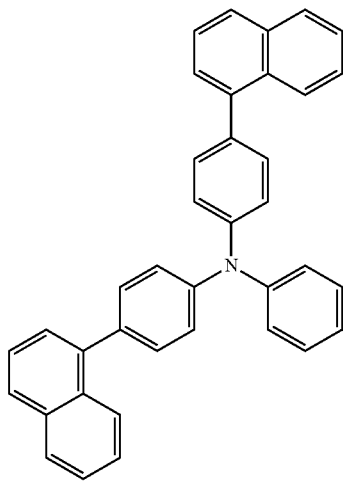
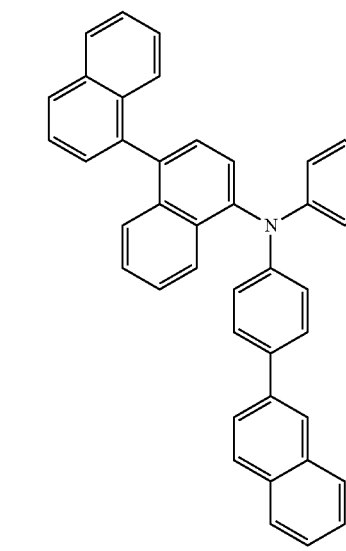
H-85
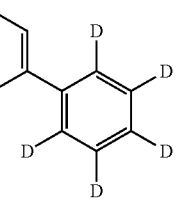
H-86

H-87
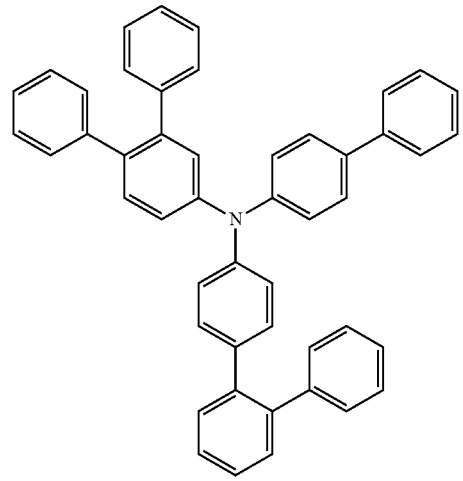
H-88
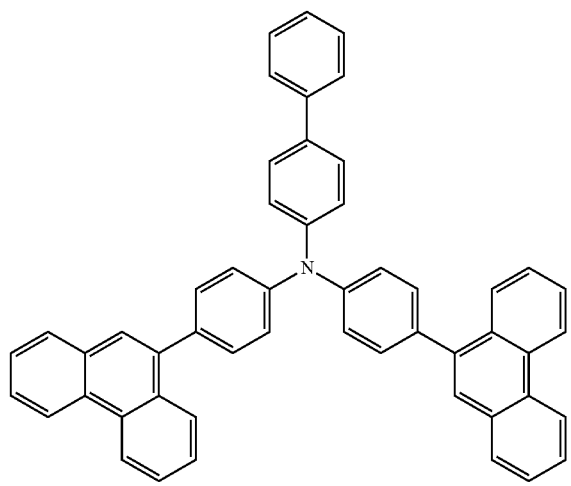
H-89
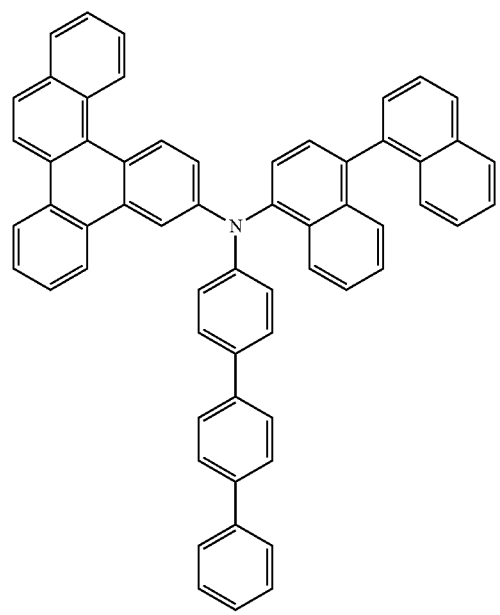
H-90
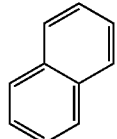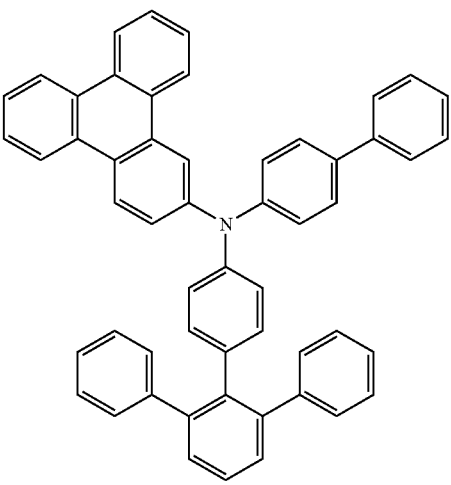
H-91
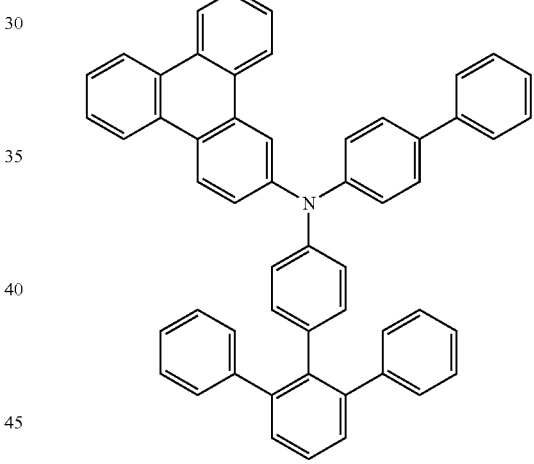
H-92
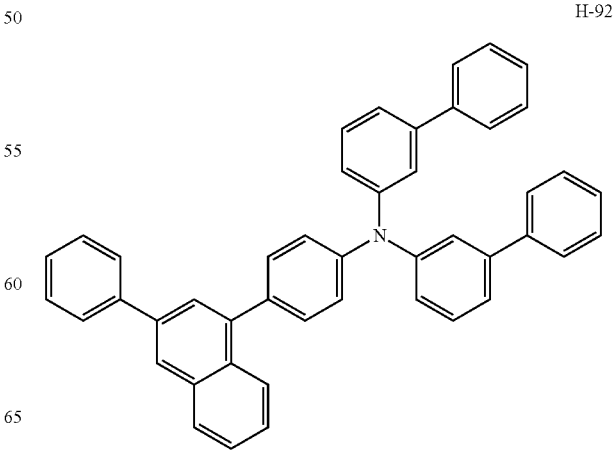

355
-continued
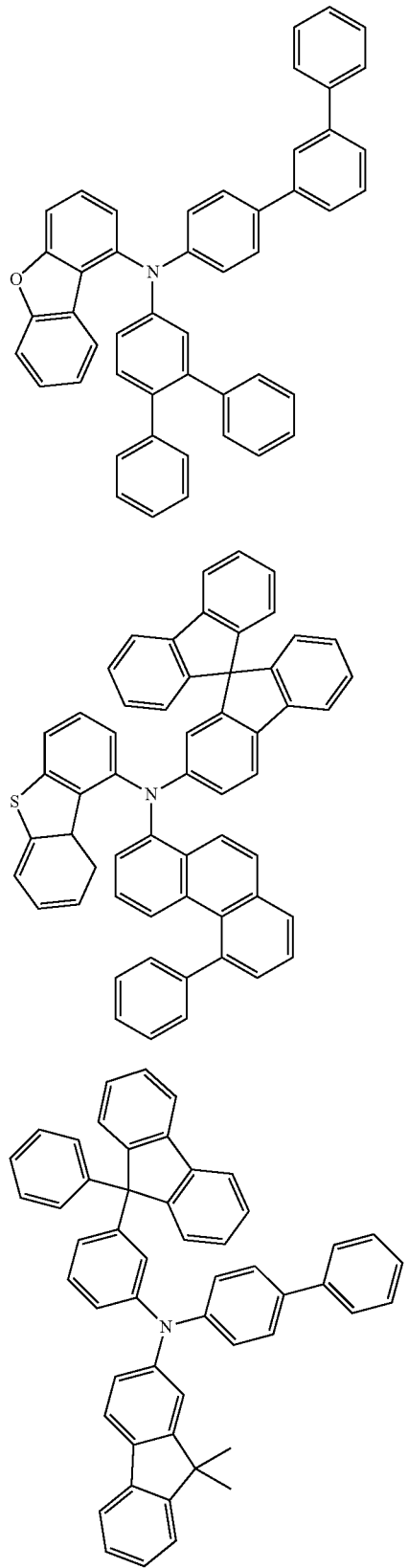
H-93
H-94
H-95
356
-continued
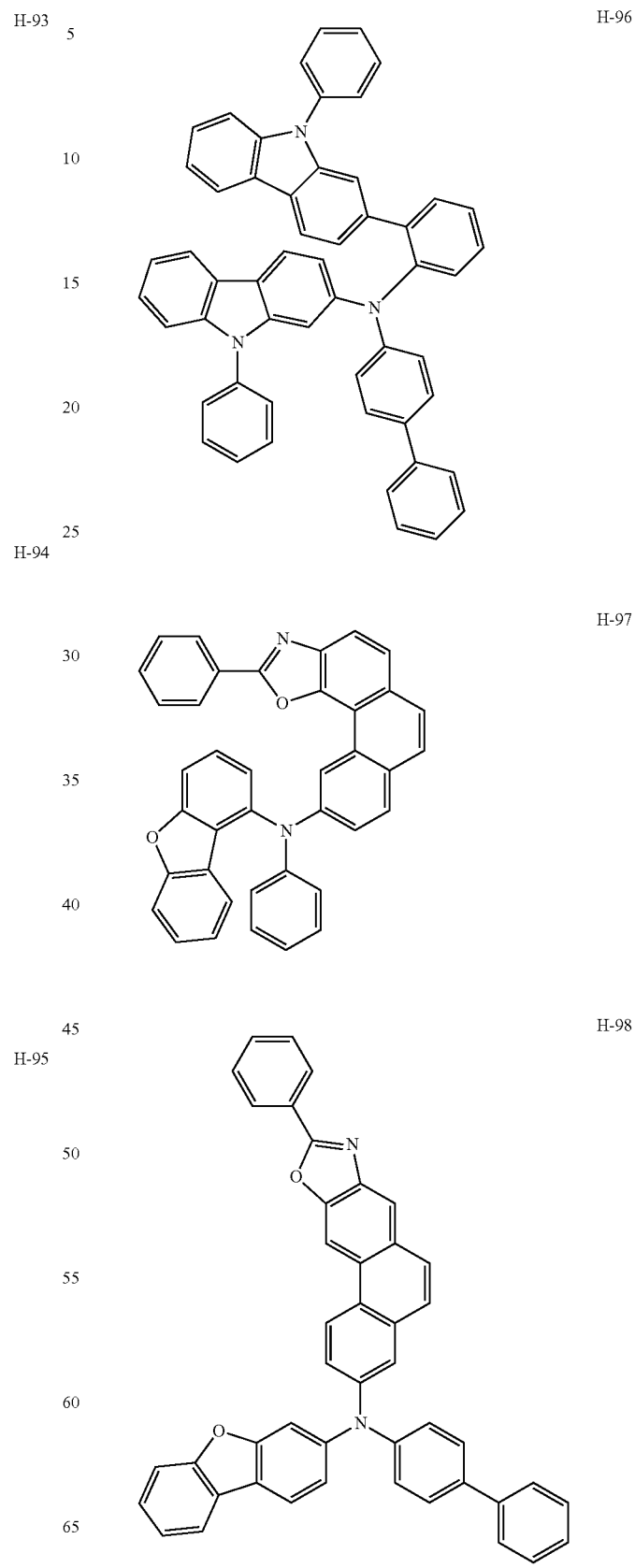
H-96
H-97
H-98

H-99
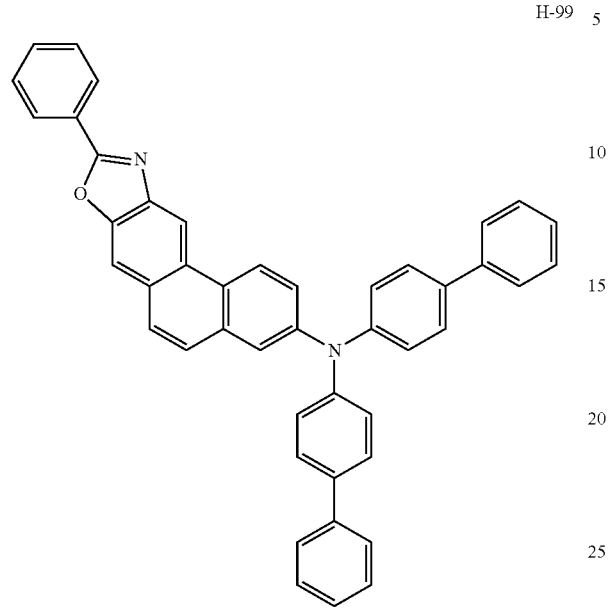
S-2
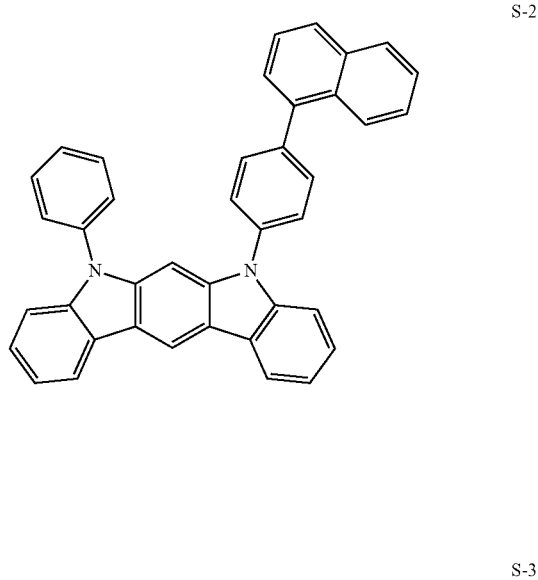
H-100
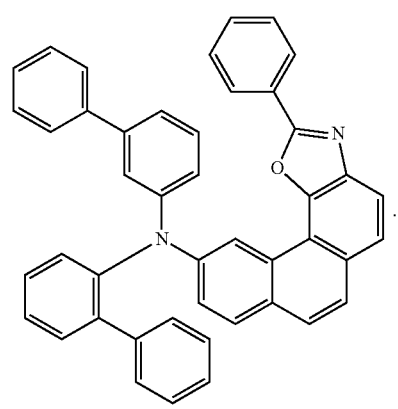
S-3
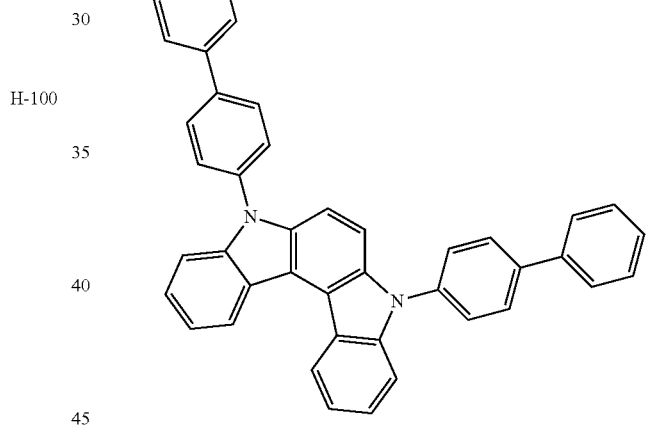
5. The organic electronic element of claim 1, wherein Formula 5 is represented by any one of S-1 to S-108:
S-4
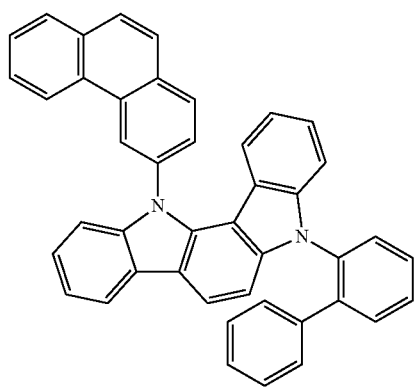
S-1
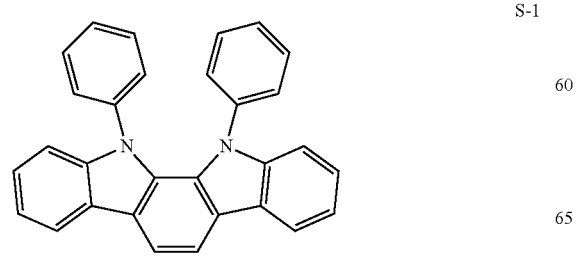

-continued
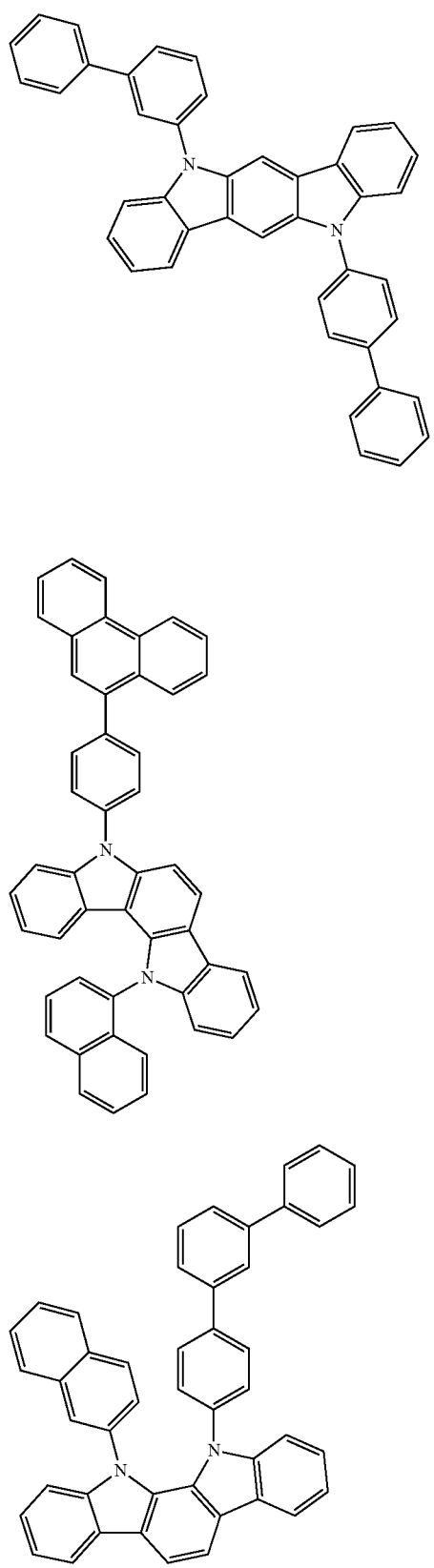
S-5
S-6
S-7
-continued
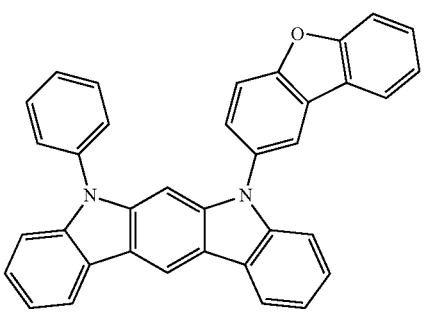
S-8
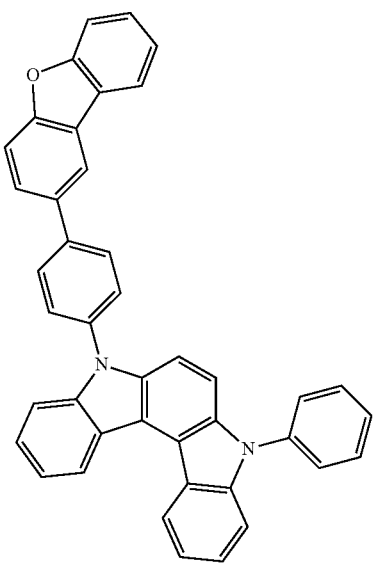
S-9
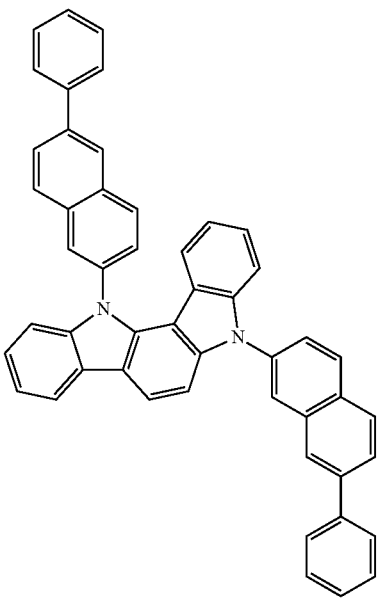
S-10

-continued
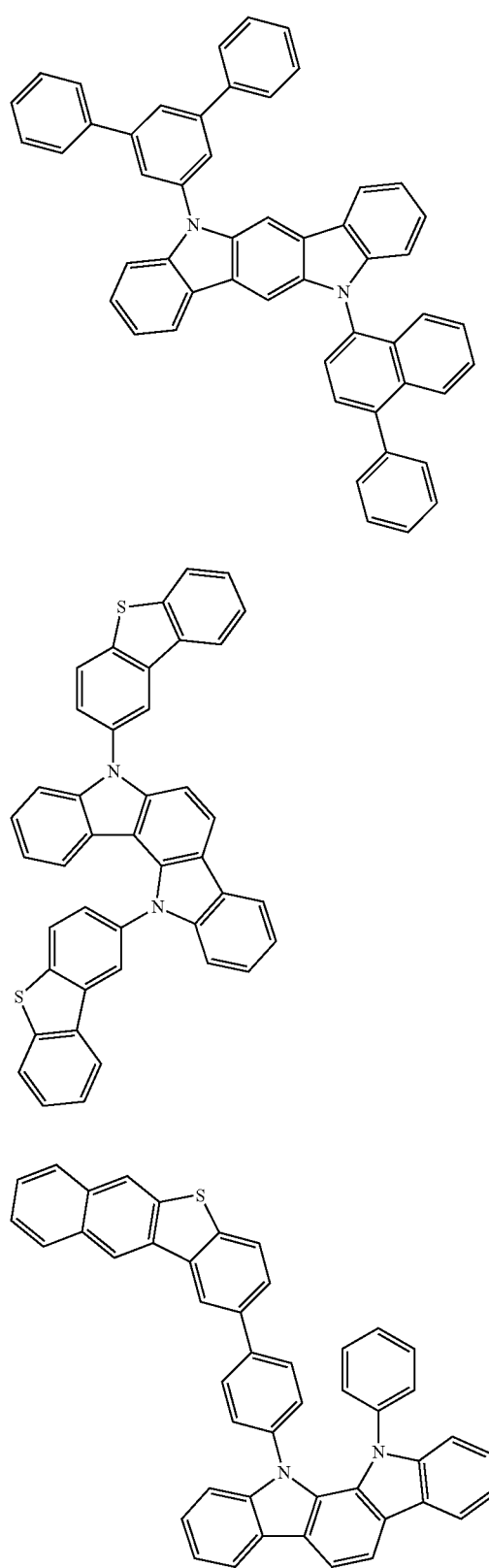
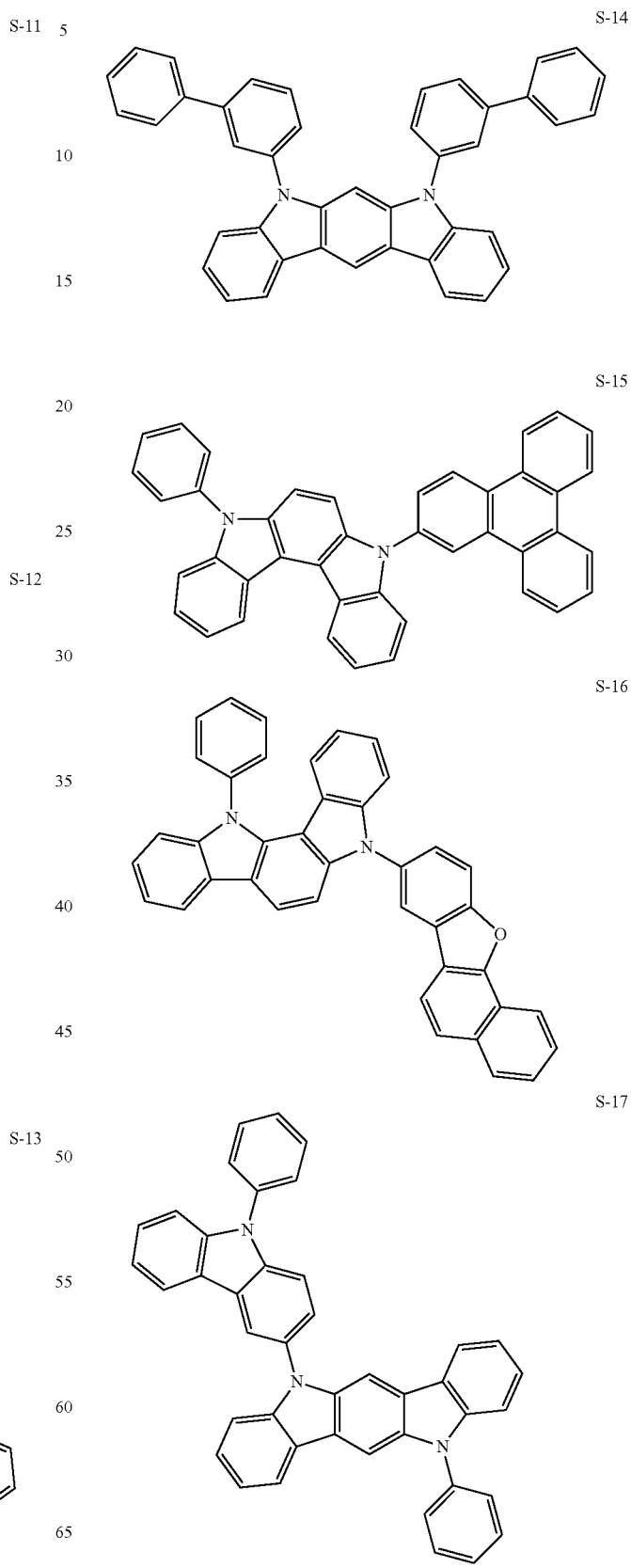

-continued
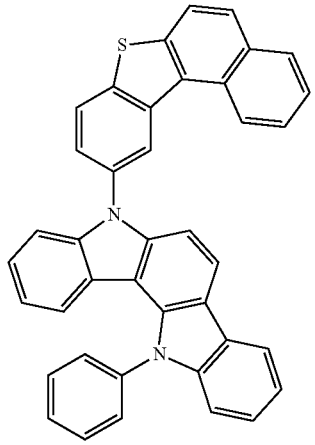
S-18
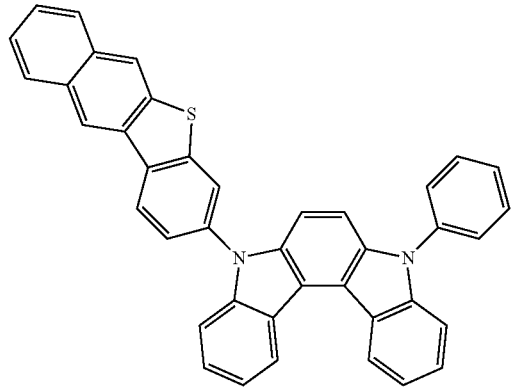
S-21
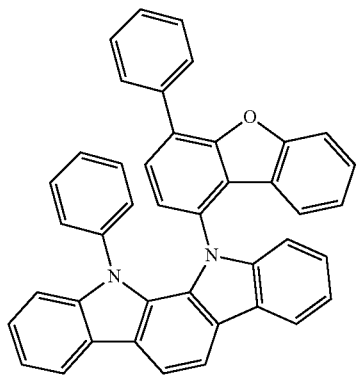
S-19
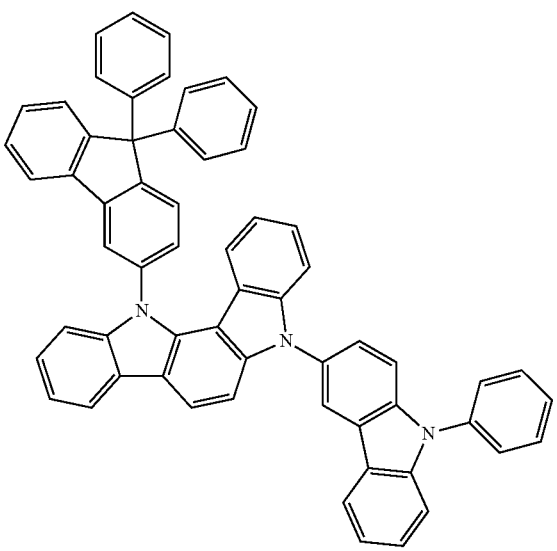
S-22
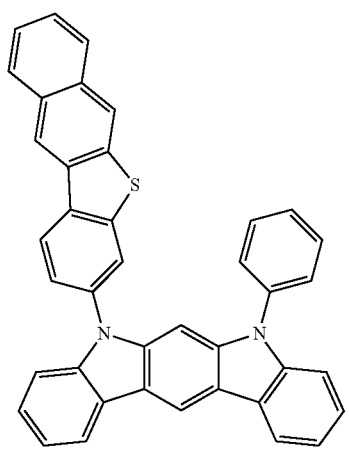
S-20
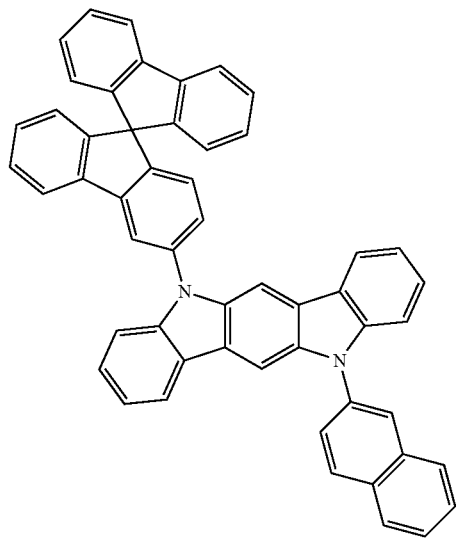
S-23

-continued
S-24
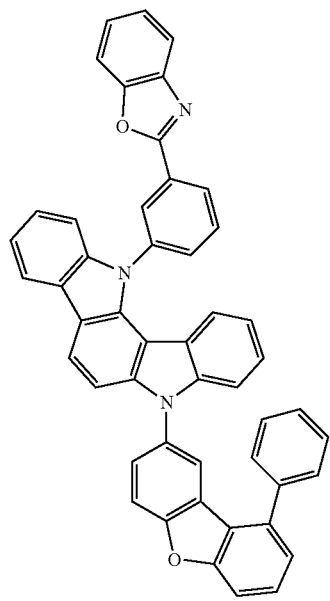
S-25
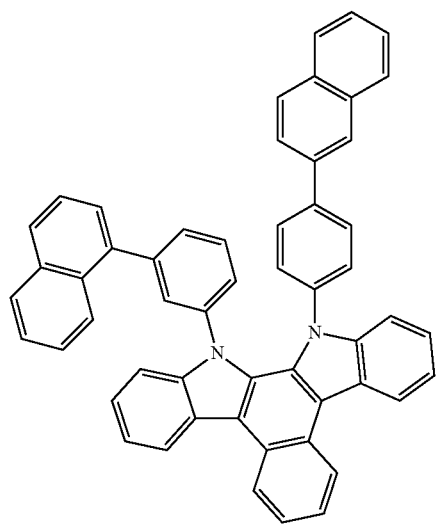
S-26
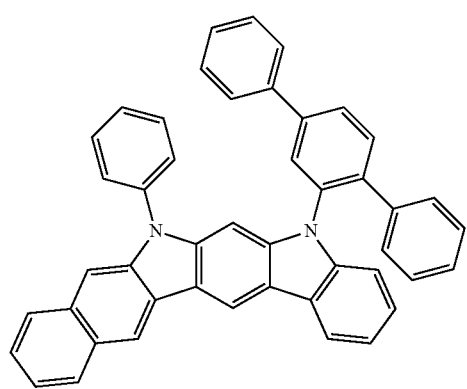
-continued
S-27
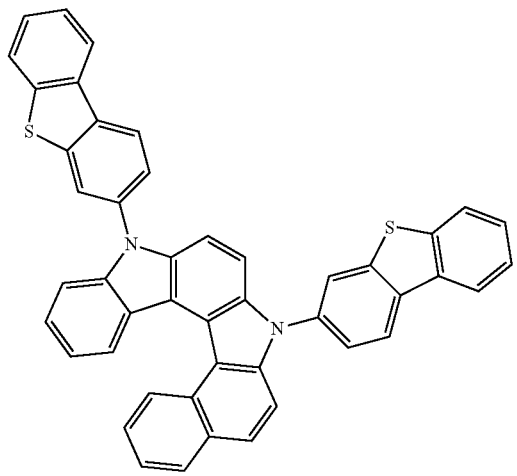
S-28
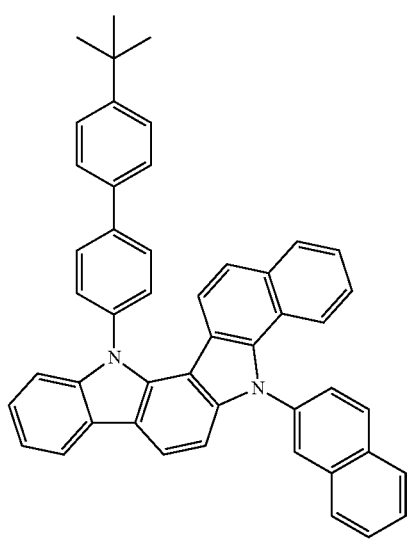
S-29
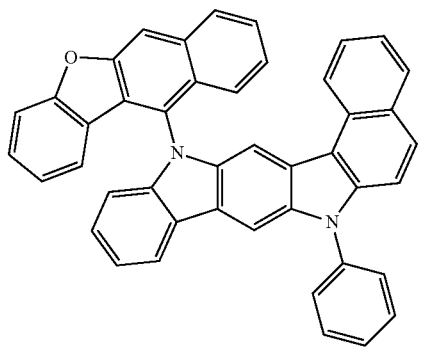

-continued
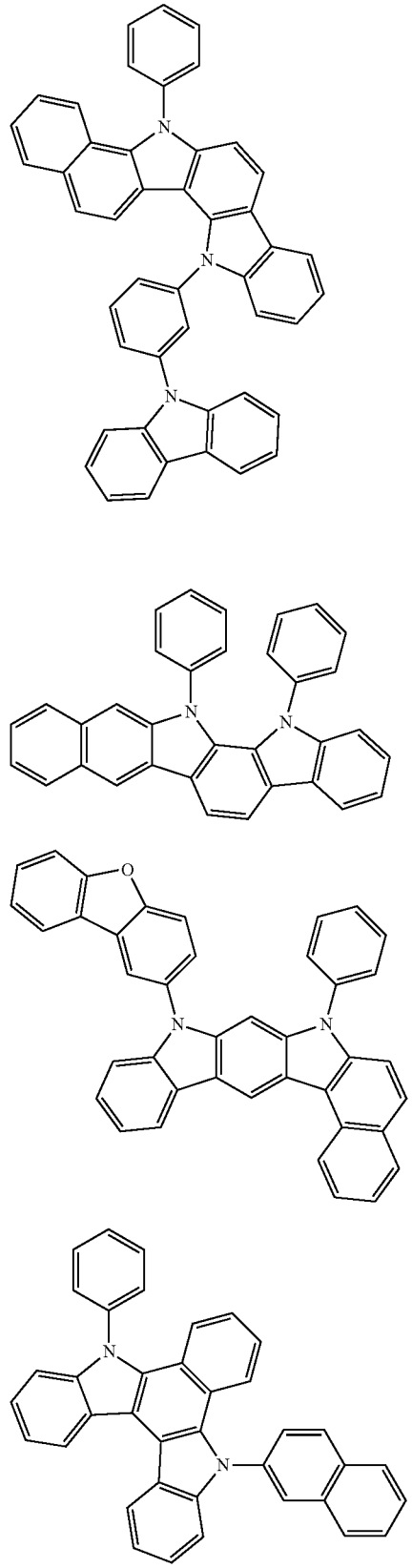
S-30
S-31
S-32
S-33
-continued
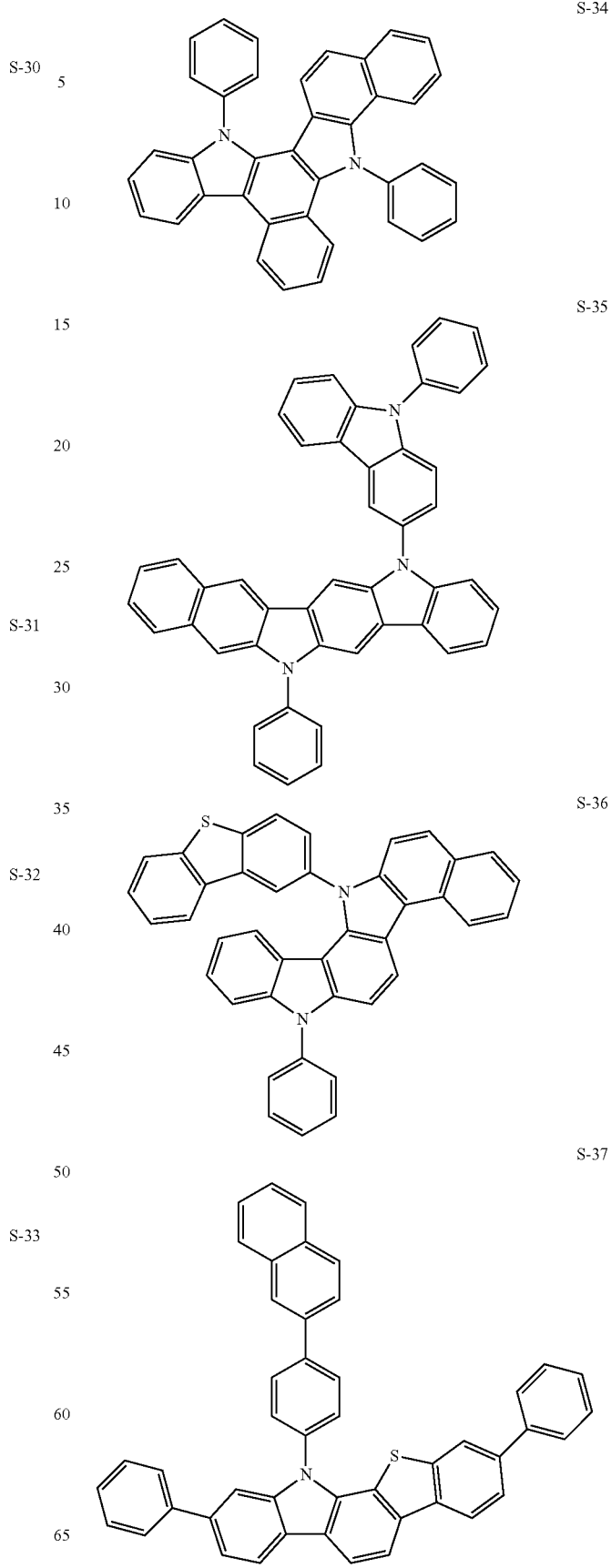
S-34
S-35
S-36
S-37

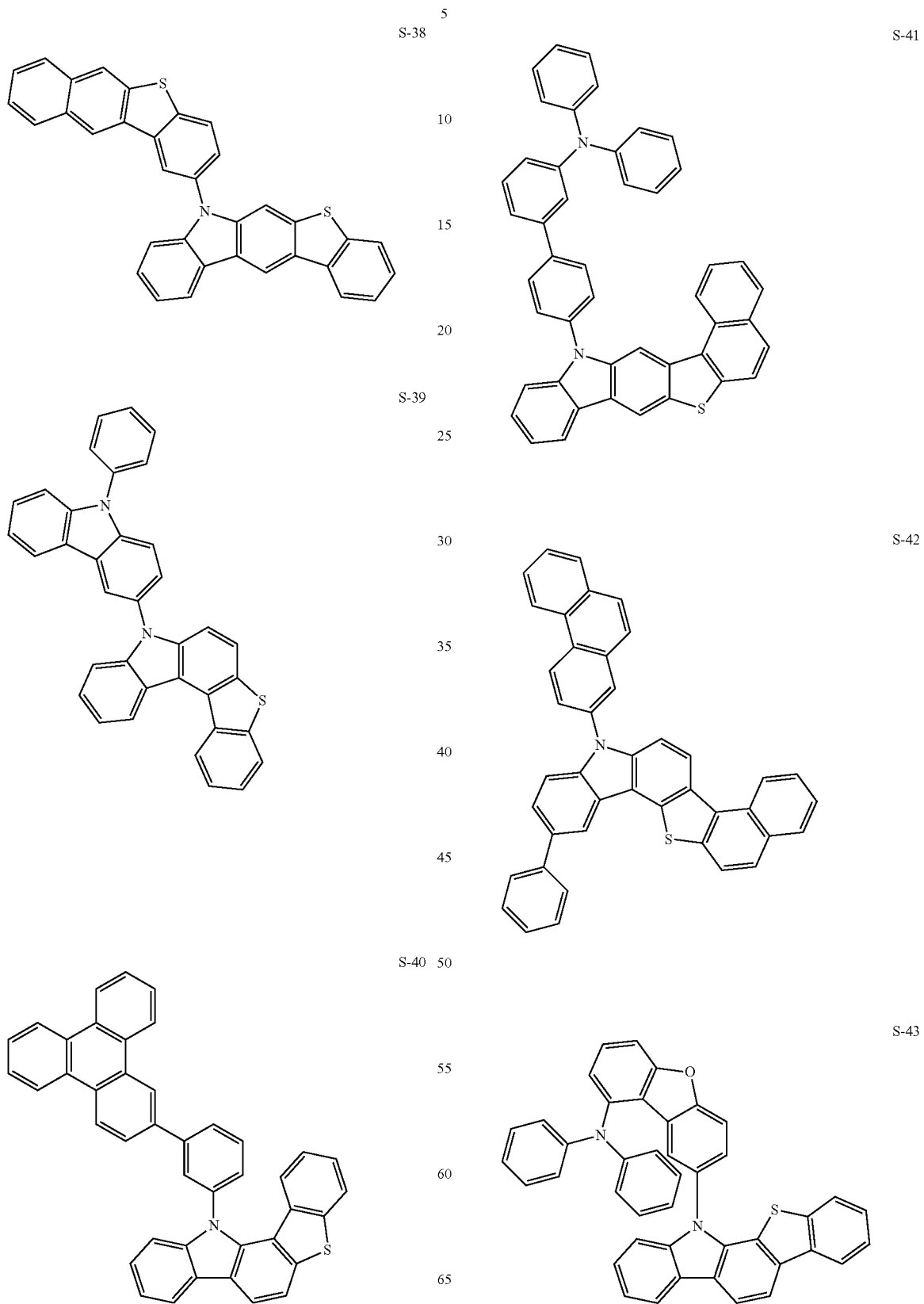

-continued
S-44
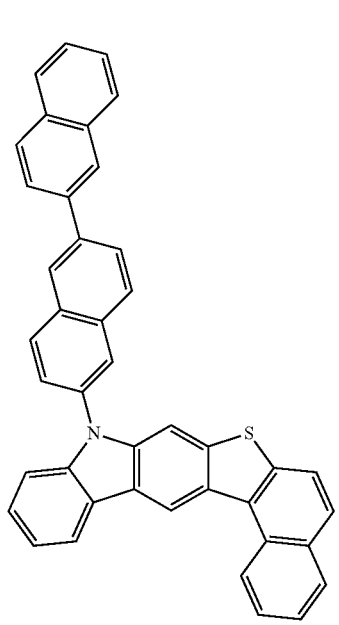
S-45
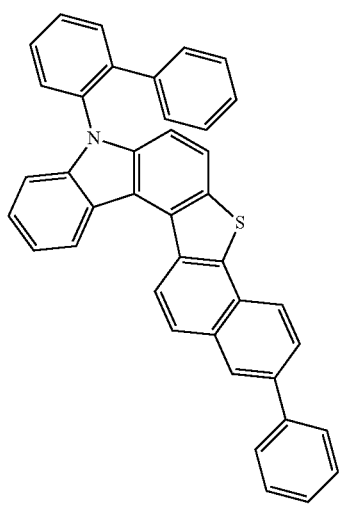
S-46
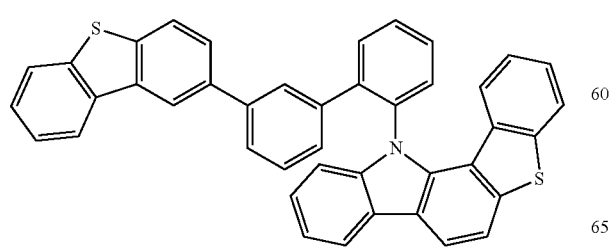
-continued
S-47
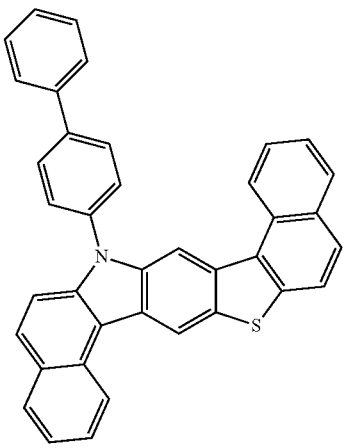
S-48
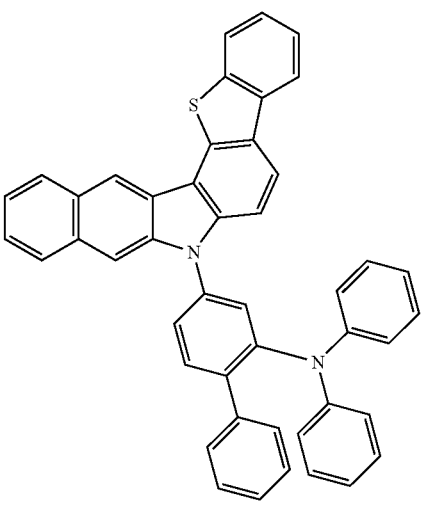
S-49
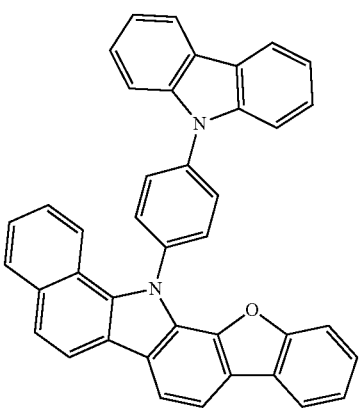

-continued
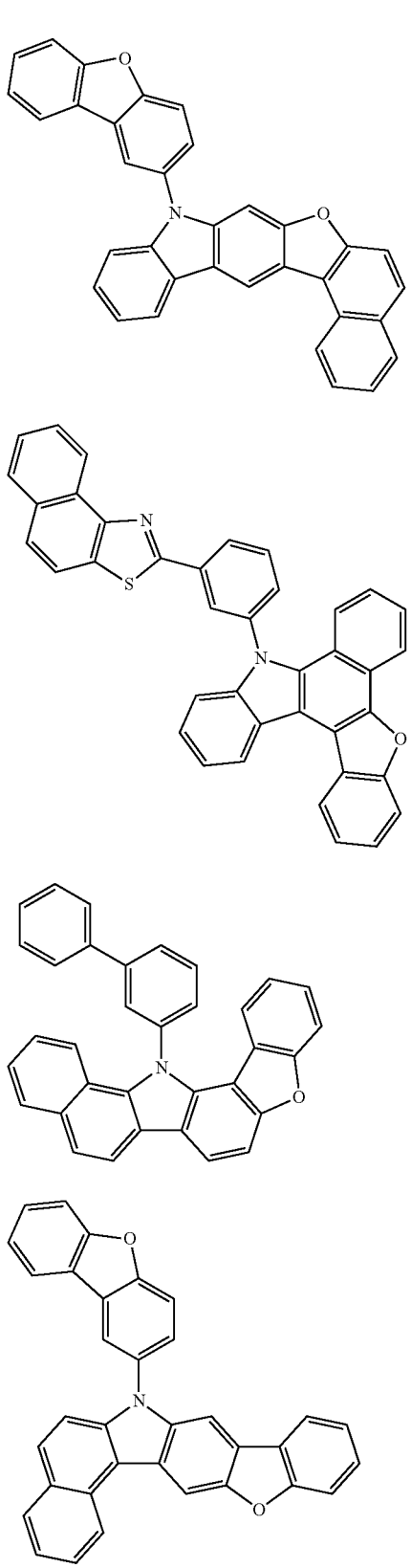
S-50
S-51
S-52
S-53
-continued
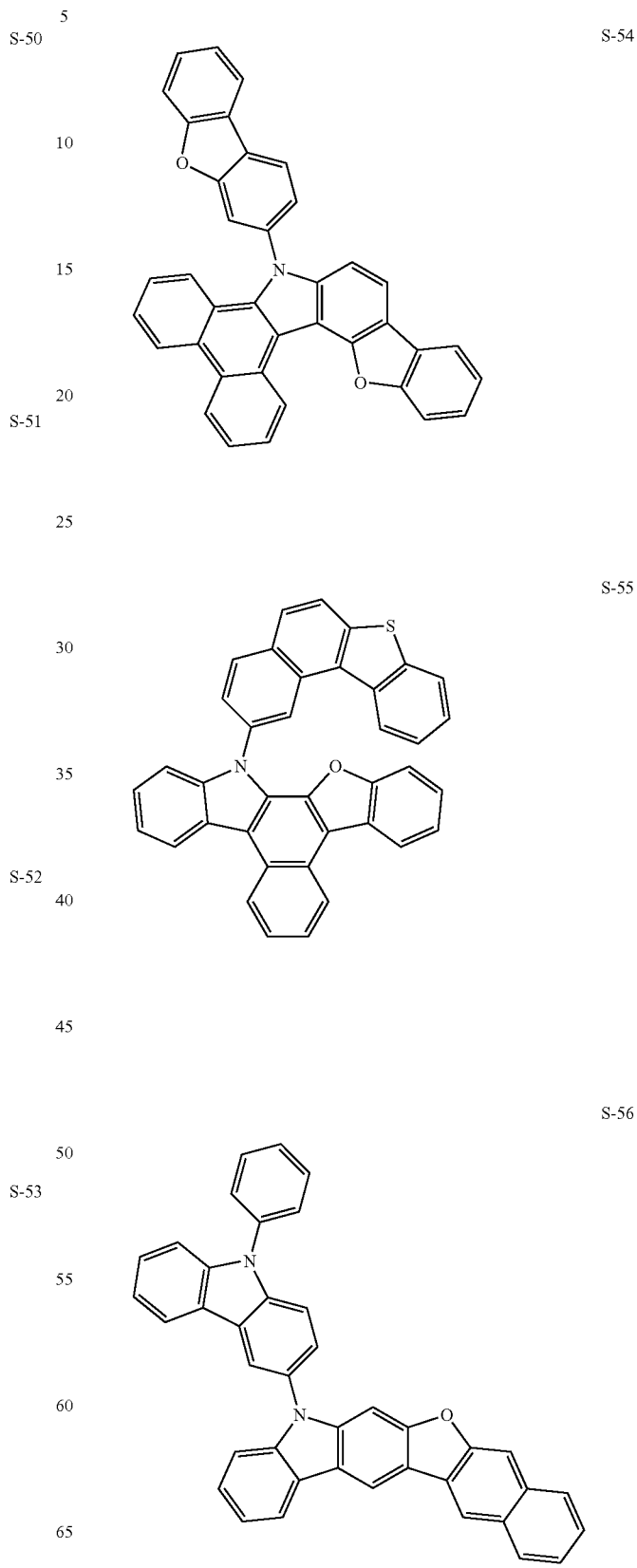
S-54
S-55
S-56

S-57
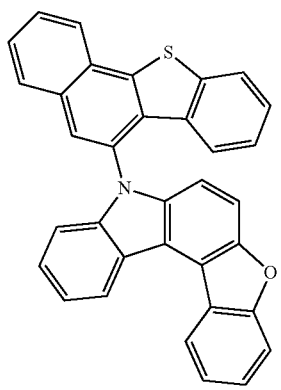
S-58
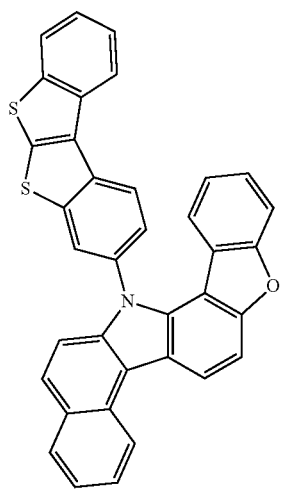
S-59
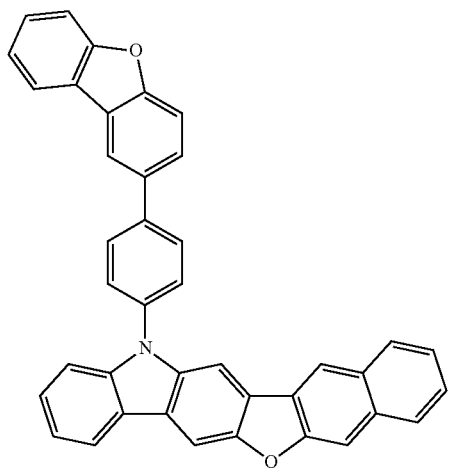
S-60
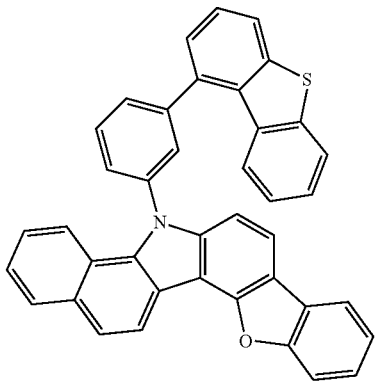
S-61
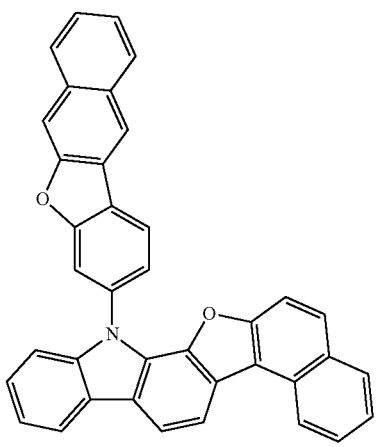
S-62
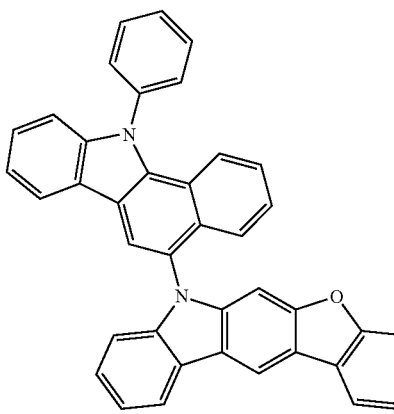

S-63
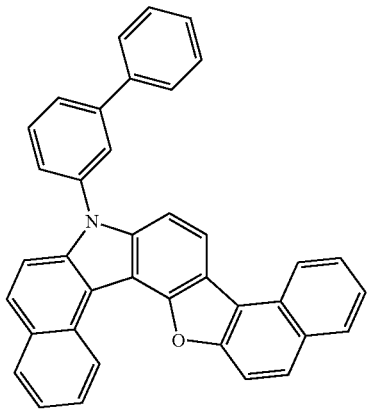
S-64
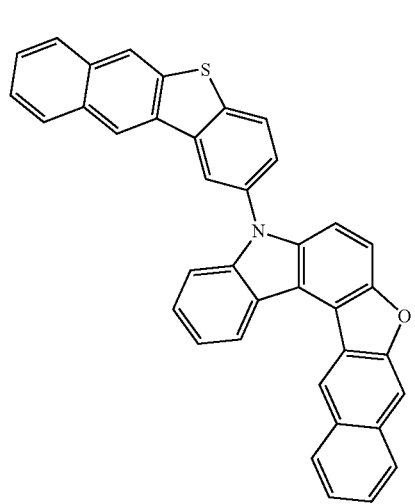
S-66
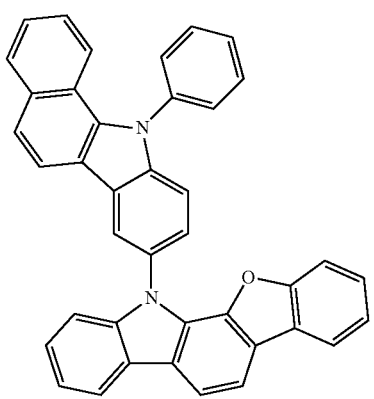
S-67
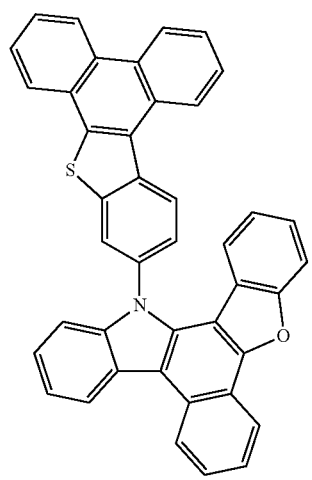
S-65
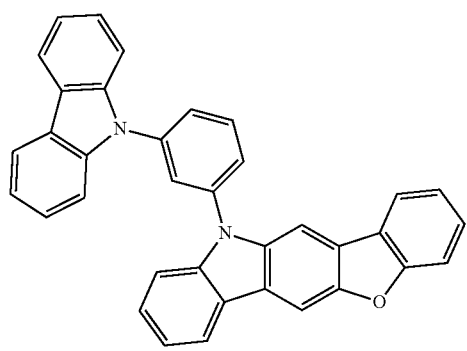
S-68
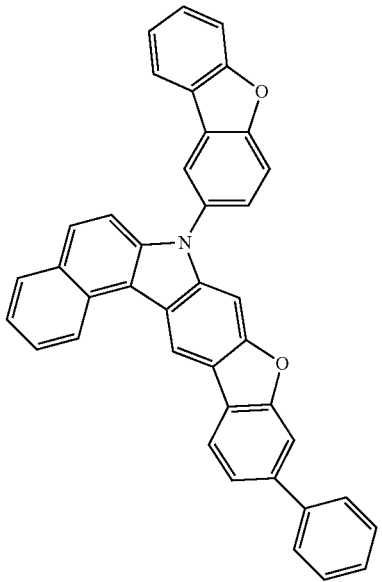

S-69
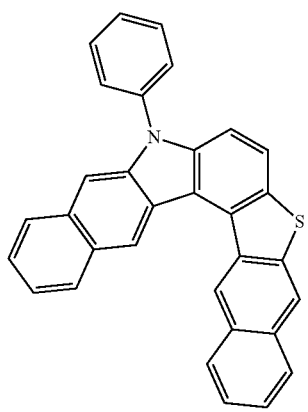
S-70
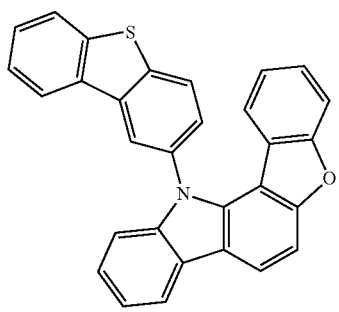
S-71
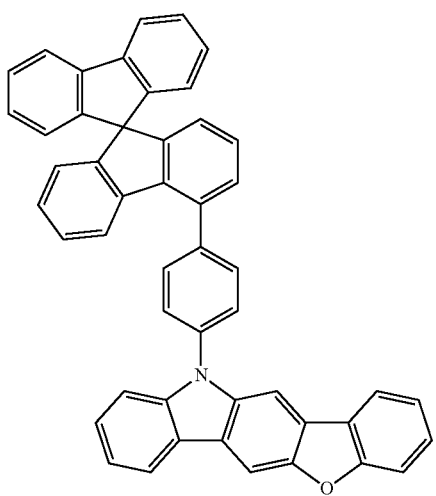
S-72
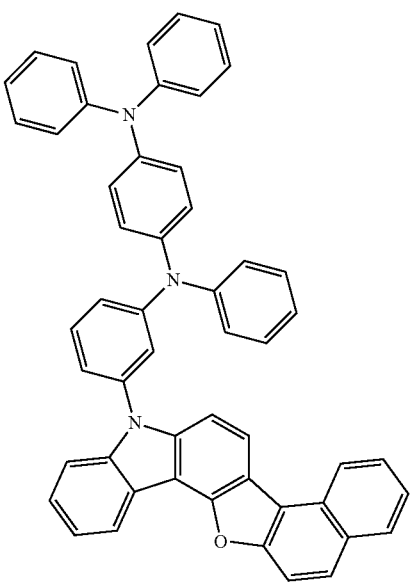
S-73
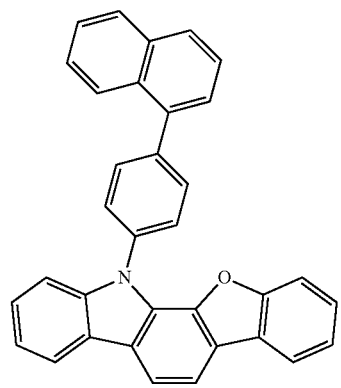
S-74
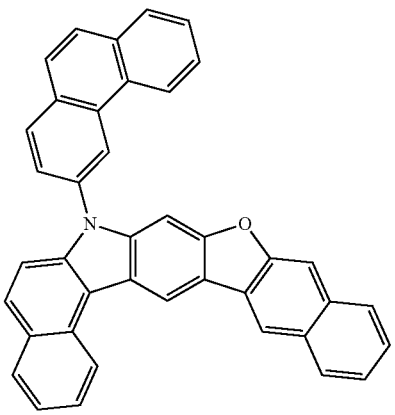

-continued
S-75
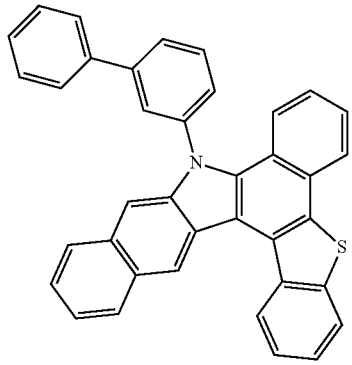
S-76
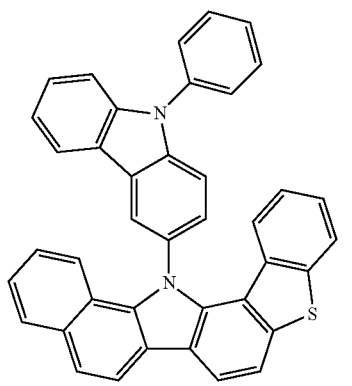
S-77
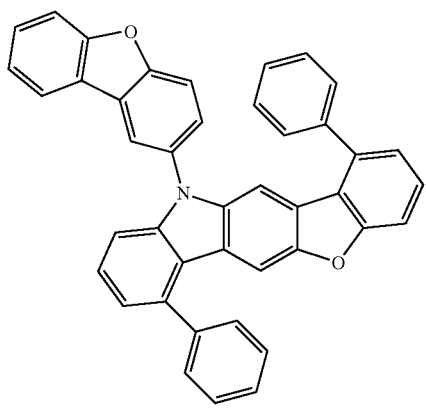
S-78
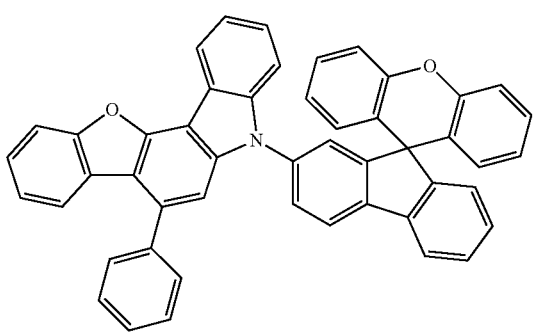
S-79
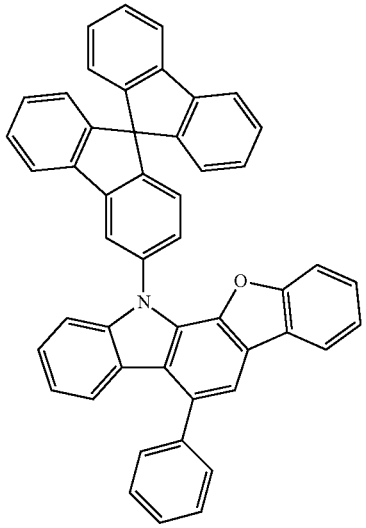
S-80
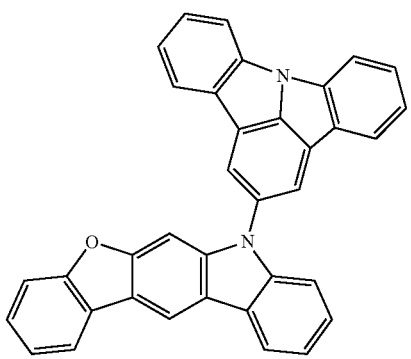
S-81
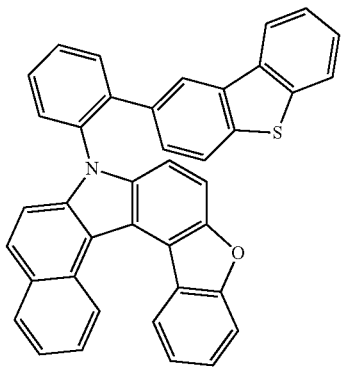
S-82
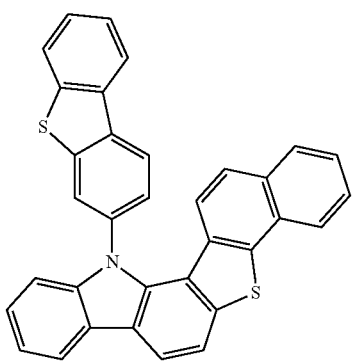

383
-continued
384
-continued
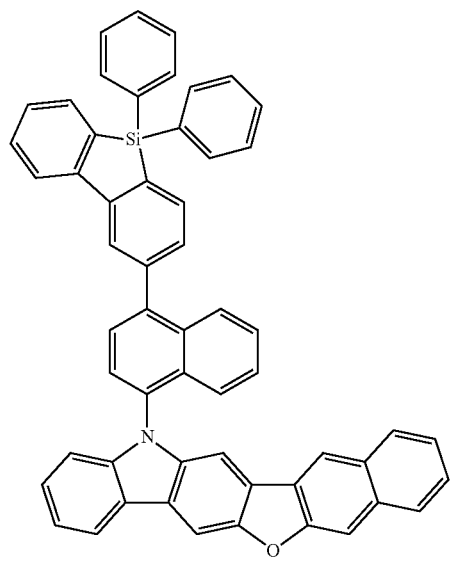
S-83
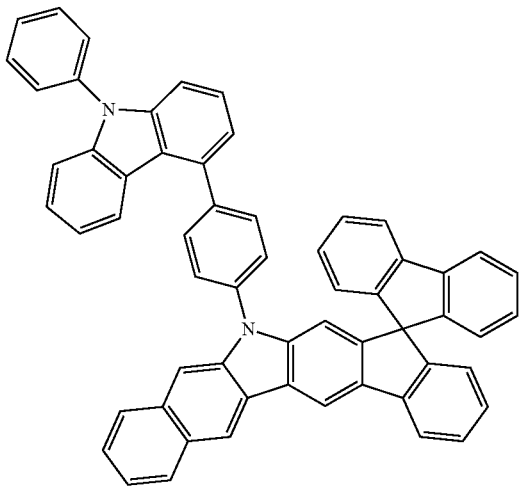
S-86
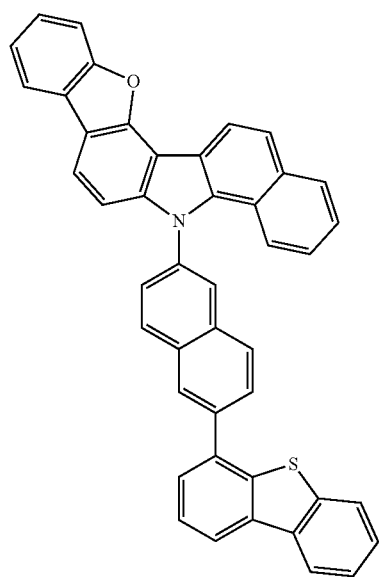
S-84
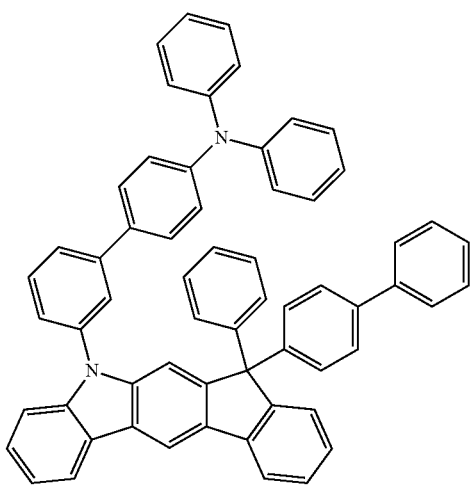
S-87
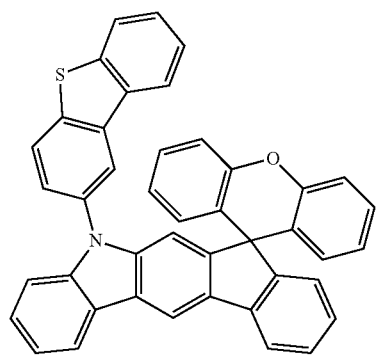
S-85
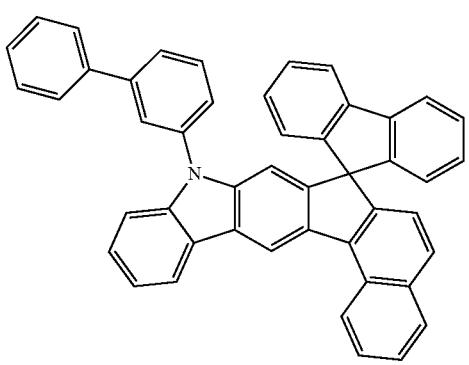
S-88

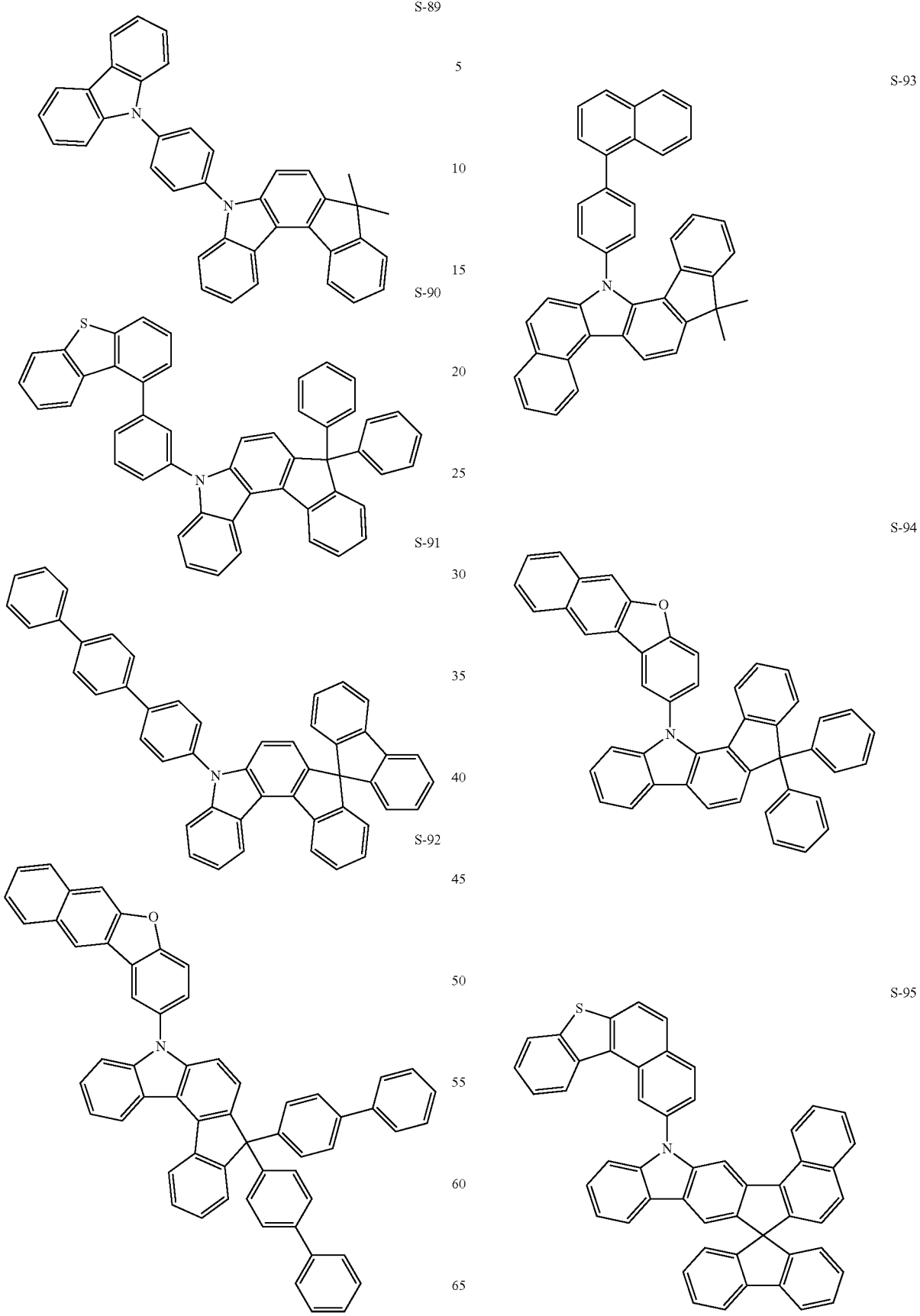

S-96
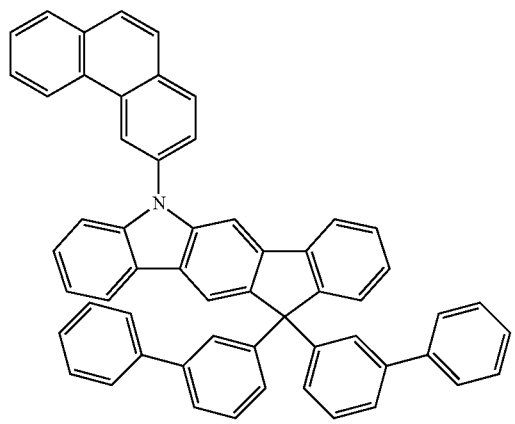
S-97
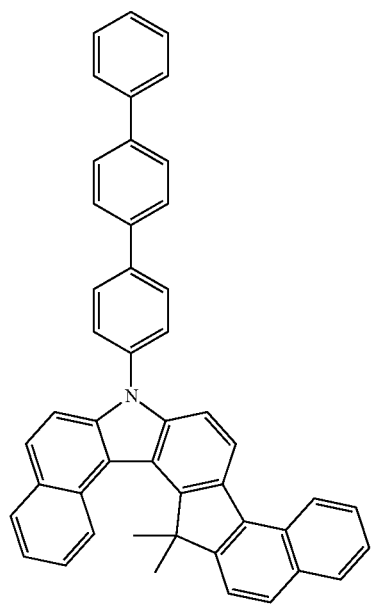
S-98
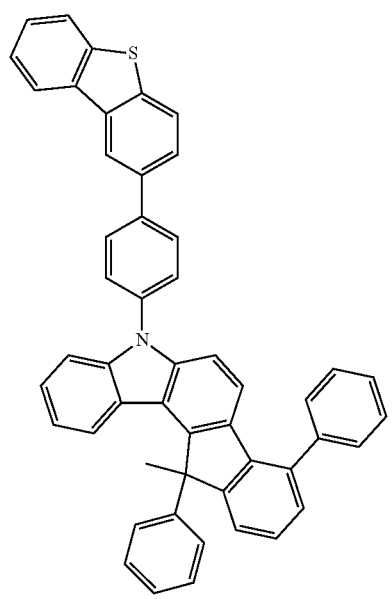
S-99
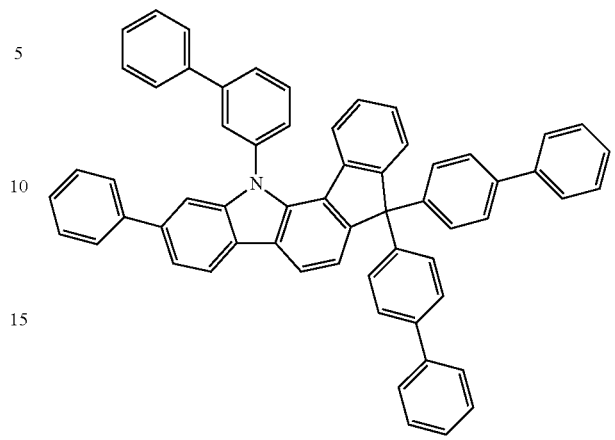
S-100
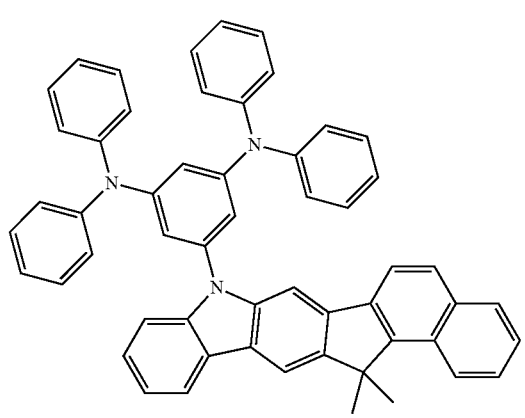
S-101
S-102
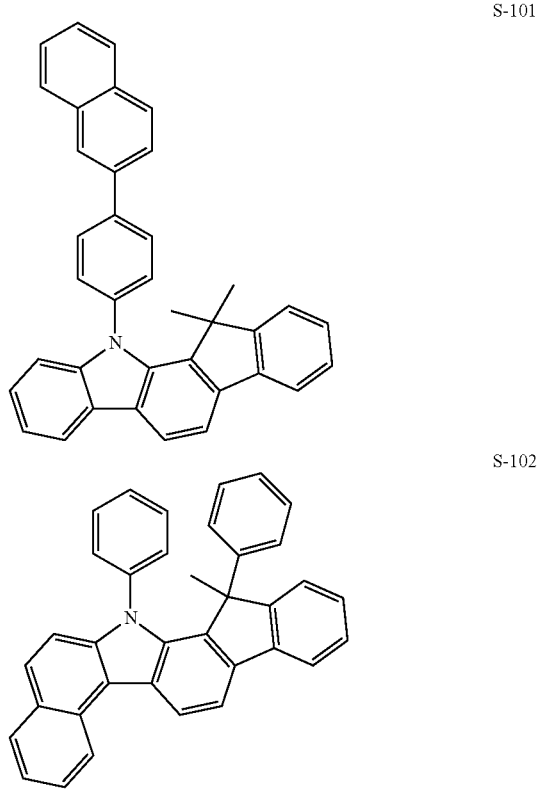

S-103 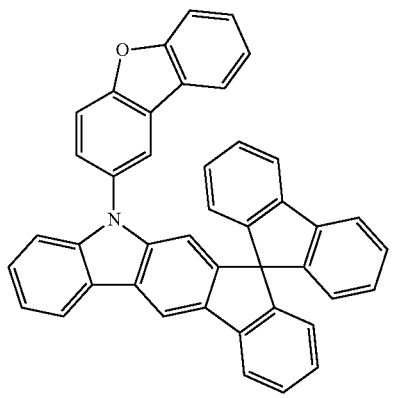
S-104 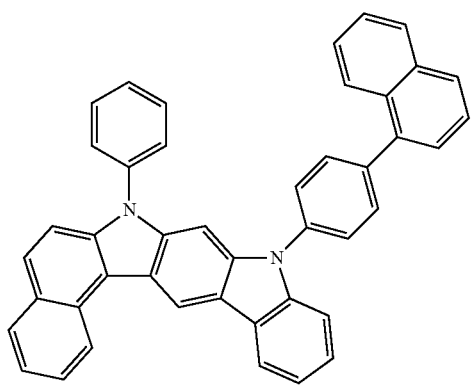
S-105 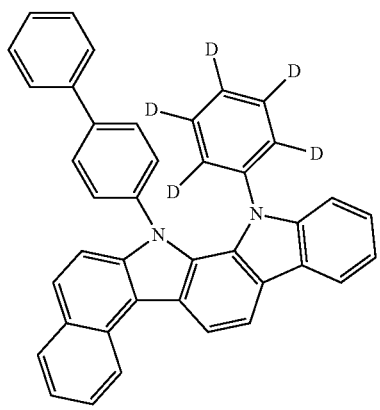
S-106 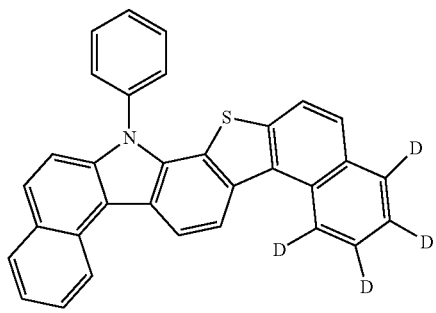
S-107 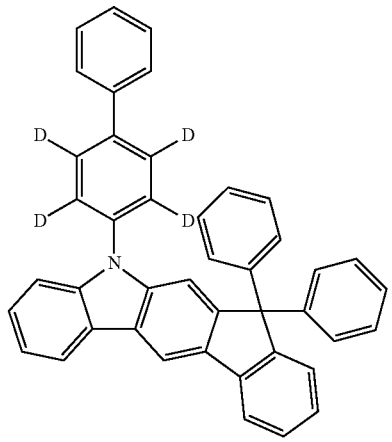
S-108 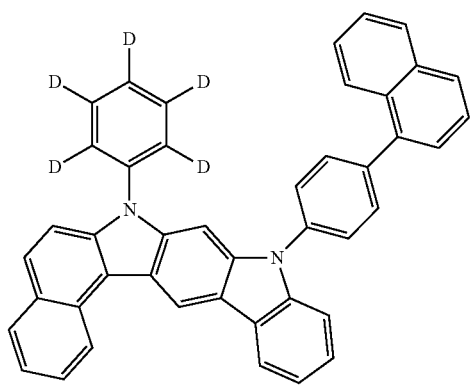
6. A compound represented by Formula 1:
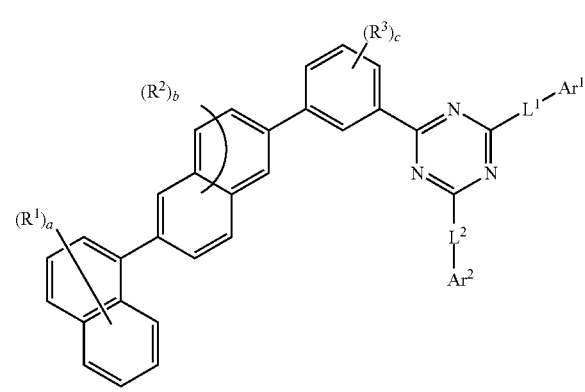
Formula 1
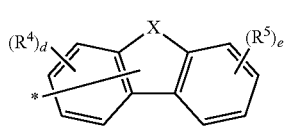
Formula 1-1
wherein,
$L^1$ and $L^2$ are each independently a single bond; or a $C_6$-$C_{60}$ arylene group;
$Ar^1$ and $Ar^2$ are each independently an $C_6$-$C_{60}$ aryl group; or a substituent represented by Formula 1-1;

$R^1$, $R^2$, $R^3$, $R^4$ and $R^5$ are each the same or different, and each independently selected from the group consisting of hydrogen; deuterium; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{60}$alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or an adjacent plurality of $R^4$ and plurality of $R^5$ may be bonded to each other to form a ring, a is an integer of 0 to 7, b is an integer of 0 to 6, c, d and e are each independently an integer of 0 to 4, X is $CR^aR^b$, $NR'$ or $SiR^aR^b$, provided that when X is bonded to $L^1$ or $L^2$, it is N, $R^a$, $R^b$ and R' are each independently selected from the group consisting of hydrogen; deuterium; a $C_1$-$C_{60}$alkyl group; a $C_6$-$C_{60}$ aryl group; and a $C_2$-$C_{60}$ heterocyclic group including at least one hetero atom of O, N, S, Si or P; alternatively, $R^a$ and $R^b$ may be bonded to each other to form a spiro,

* denotes a position to be bonded, wherein the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

7. The compound of claim 6, wherein $Ar^1$ and $Ar^2$ are represented by any one of Formulas (A-1) to (A-11):

Formula (A-1)

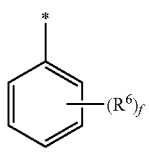
$(R^6)_f$

Formula (A-2)

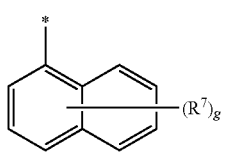
$(R^7)_g$

Formula (A-3)

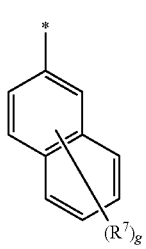
$(R^7)_g$

Formula (A-4)

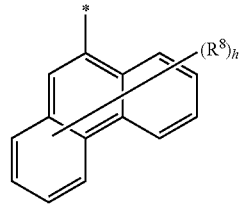
$(R^8)_h$

Formula (A-5)

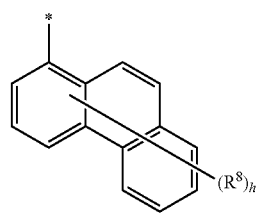
$(R^8)_h$

Formula (A-6)

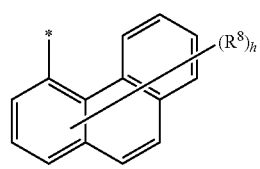
$(R^8)_h$

Formula (A-7)

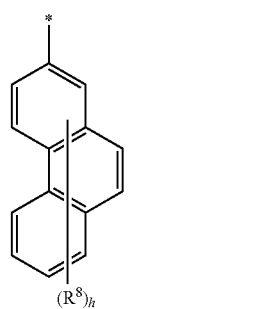
$(R^8)_h$

Formula (A-8)

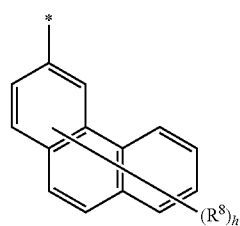
$(R^8)_h$

Formula (A-9)

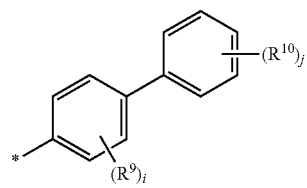
$(R^{10})_j$
$(R^9)_i$

Formula (A-10)

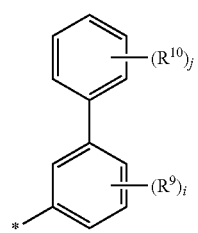
$(R^{10})_j$
$(R^9)_i$

Formula (A-11)

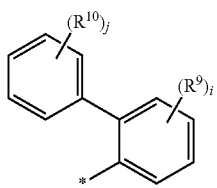

wherein:
1) $R^6$, $R^7$, $R^8$, $R^9$ and $R^{10}$ are the same or different from each other, and each independently represents hydrogen; deuterium; $C_6$-$C_{20}$ aryl group; or $C_6$-$C_{20}$ aryl group substituted with deuterium;
2) f and j are each independently an integer of 0 to 5, g is an integer of 0 to 7, h is an integer of 0 to 9, i is an integer of 0 to 4,
3) * means the position to be bonded.

8. The compound of claim 6, wherein Formula 1 is represented by any of Compounds P-1 to P-104:

P-1

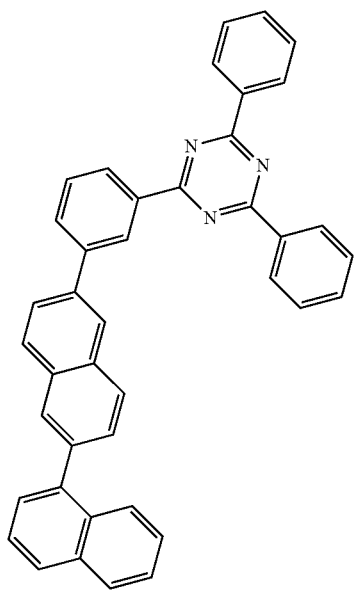

P-2

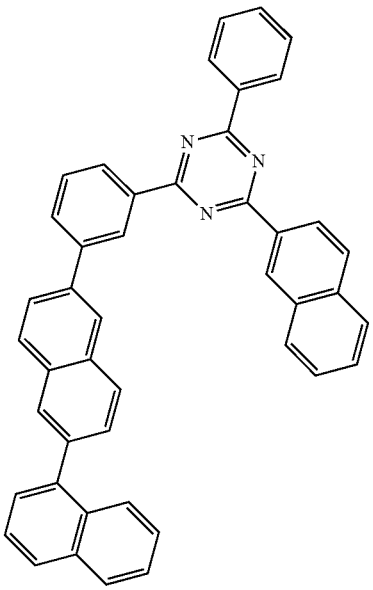

P-3

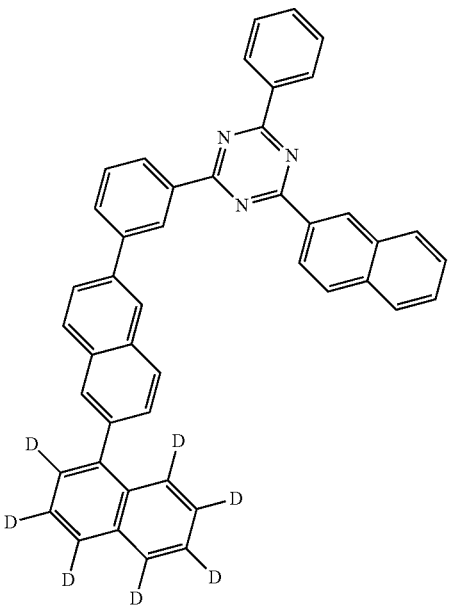

395
-continued
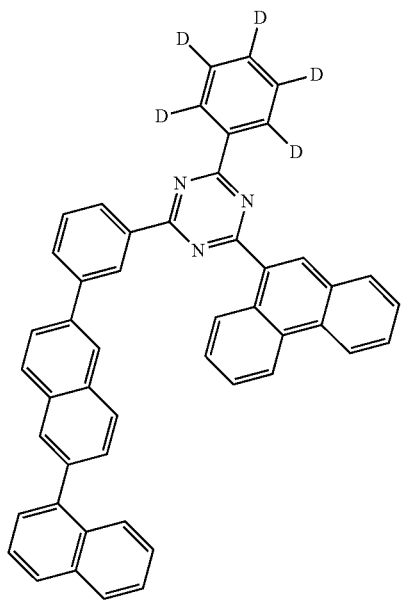
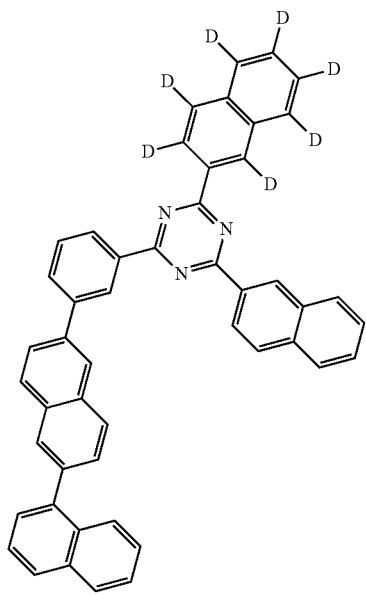
396
-continued
P-4
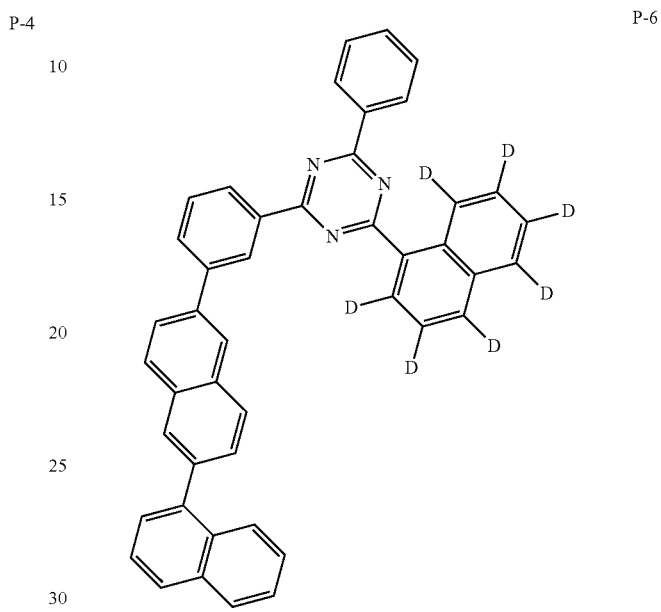
P-5
P-6
P-7
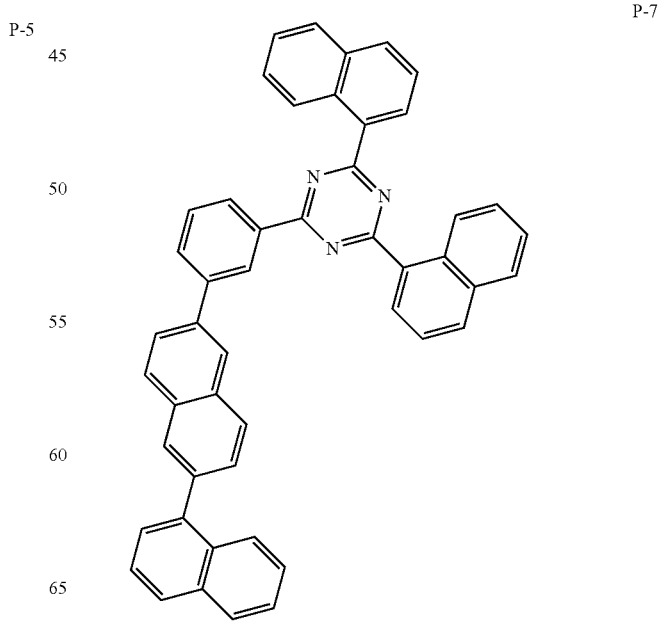

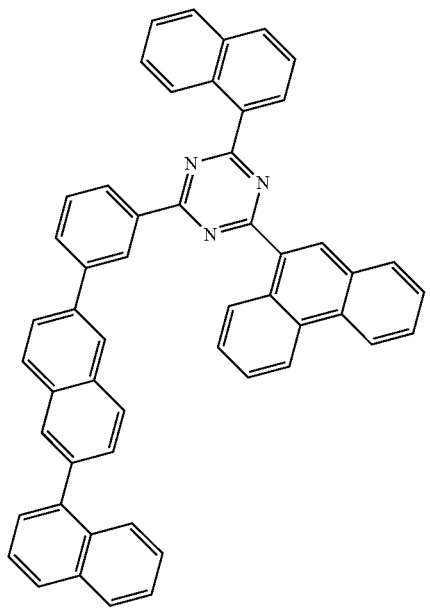
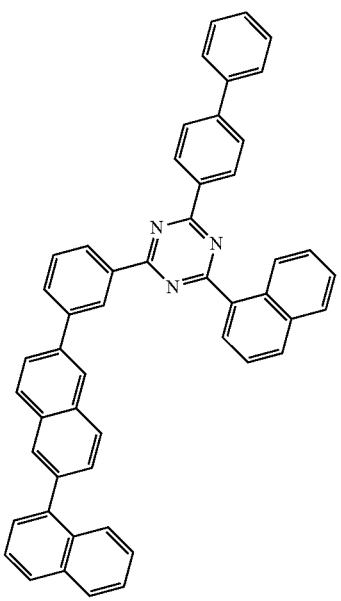
P-8
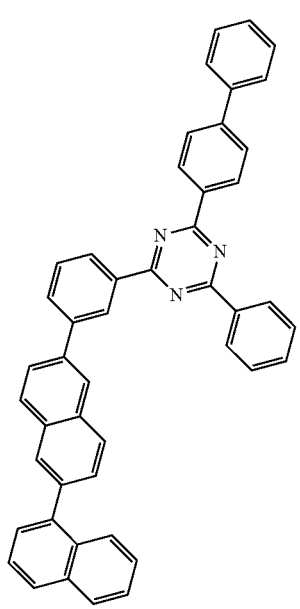
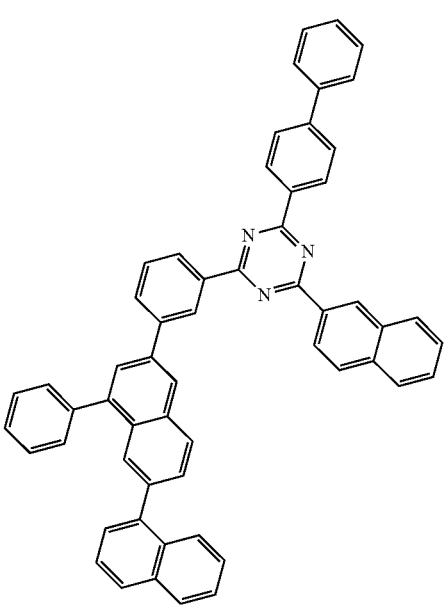
P-10
P-9
P-11

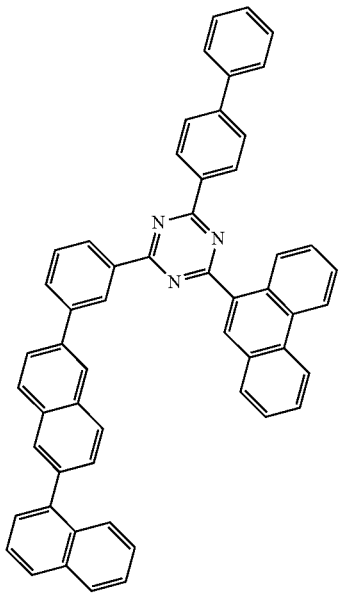
P-12
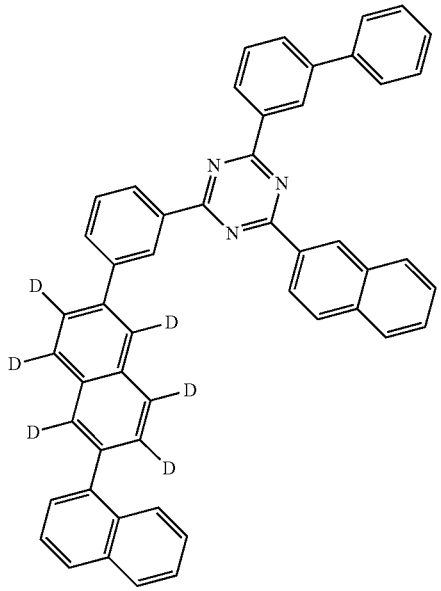
P-14
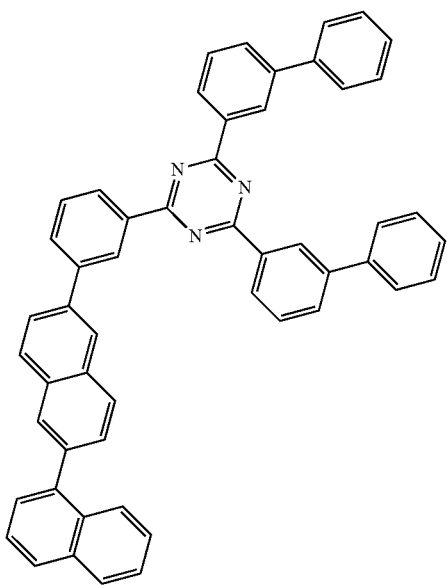
P-13
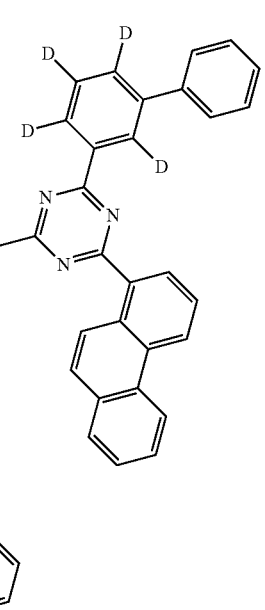
P-15

401
-continued
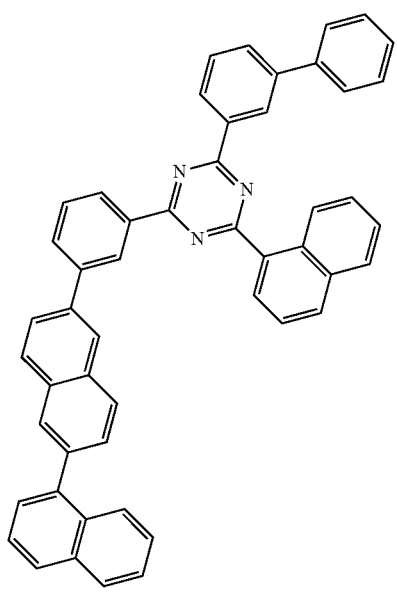
P-16
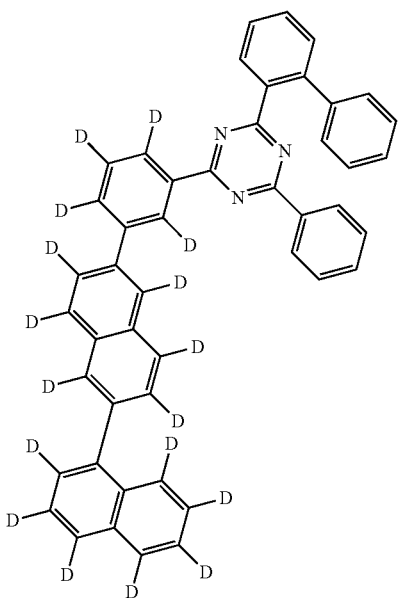
P-17
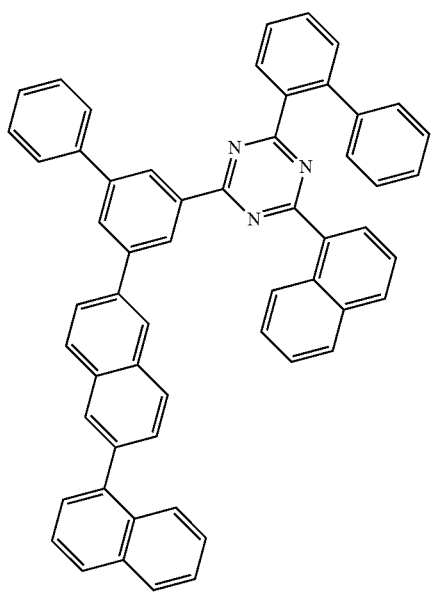
402
-continued
P-18
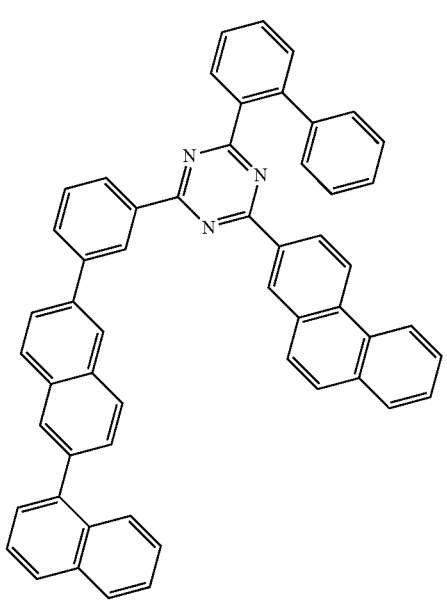
P-19

403
-continued
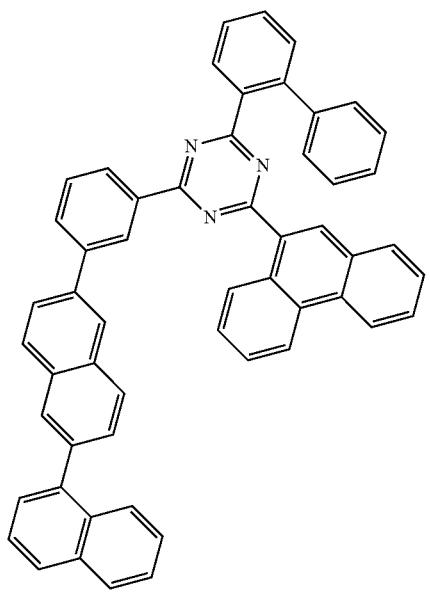
P-20
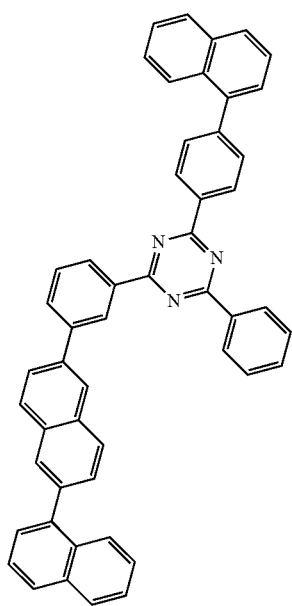
P-21
404
-continued
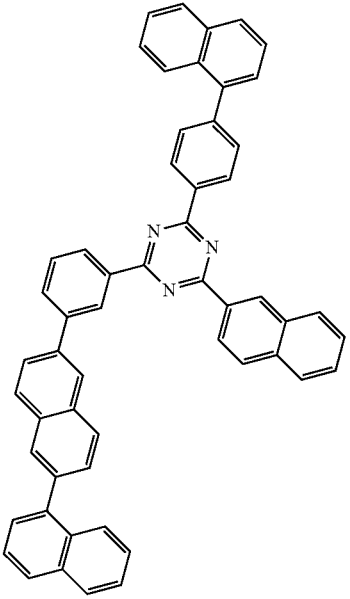
P-22
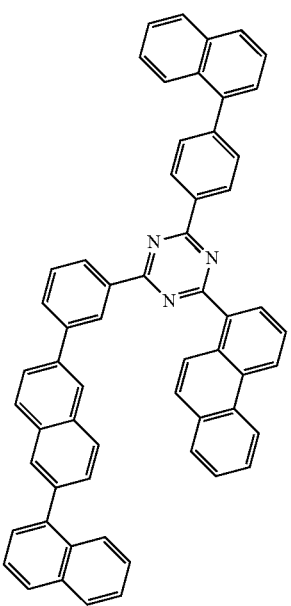
P-23

P-24
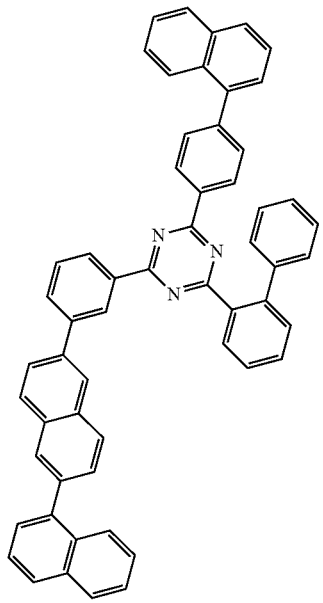
P-26
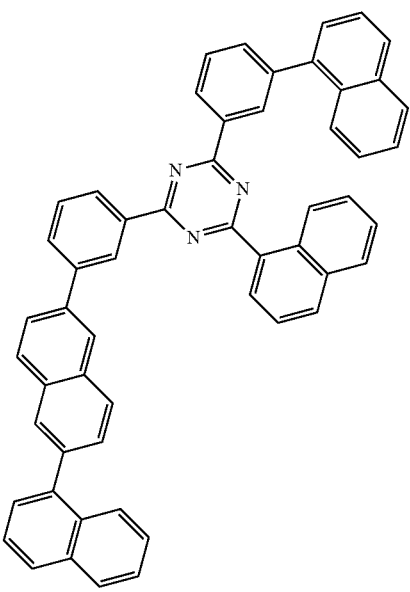
P-25
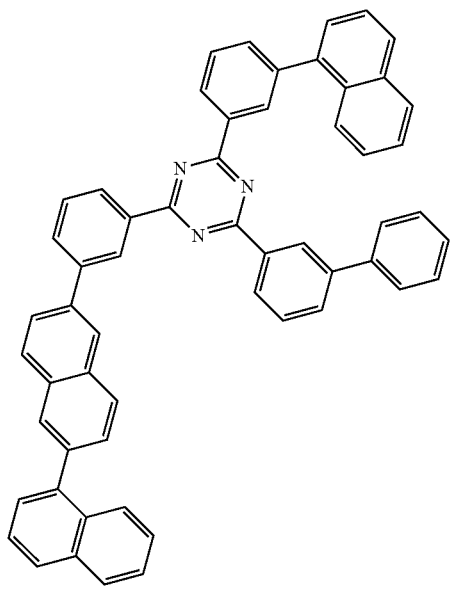
P-27
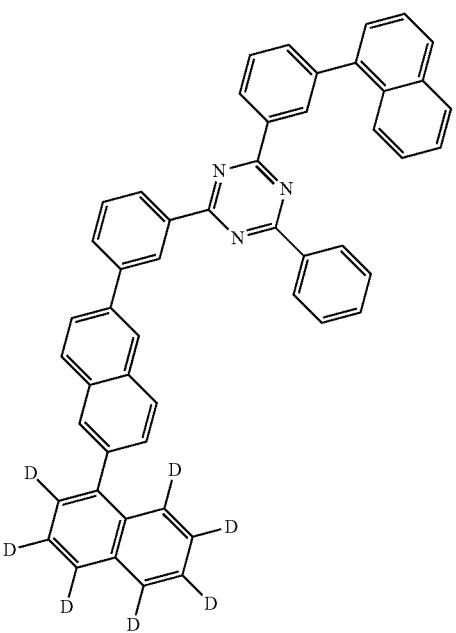

P-28
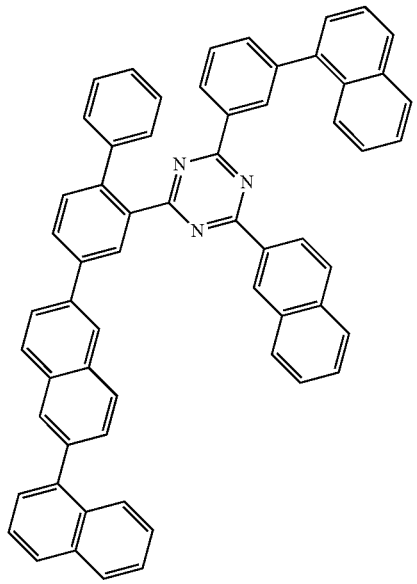
P-29
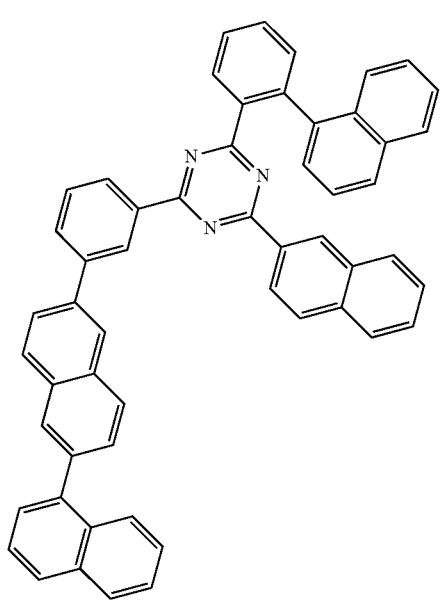
P-30
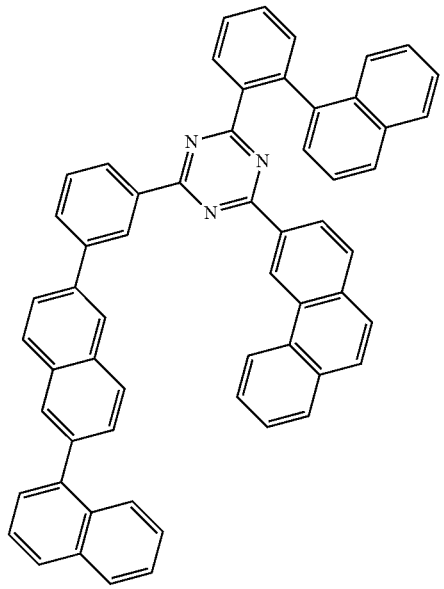
P-31
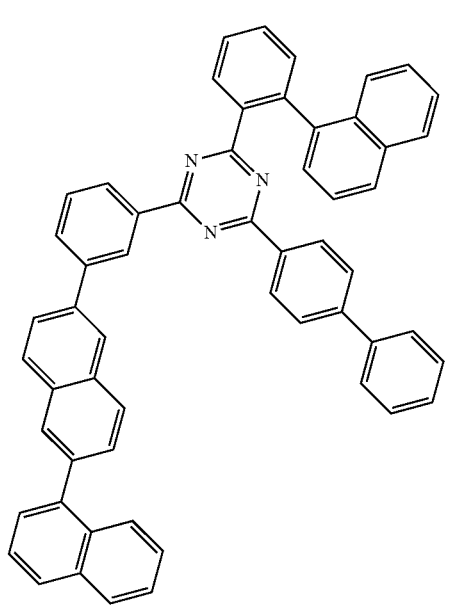

-continued
P-32
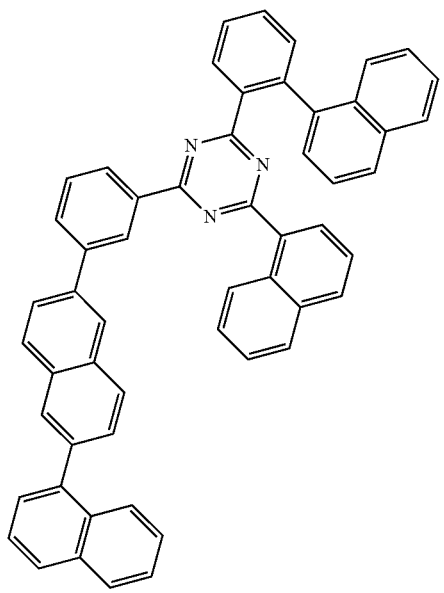
P-33
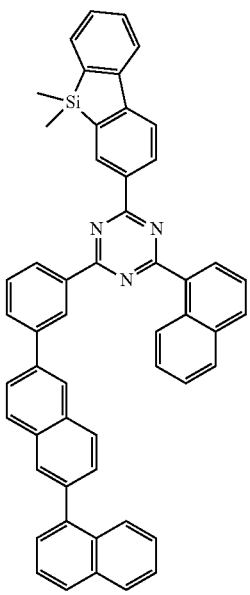
P-34
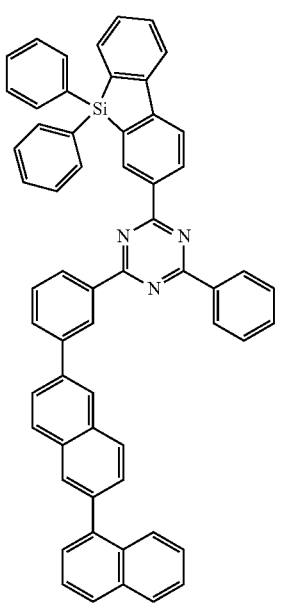
P-35

411
-continued
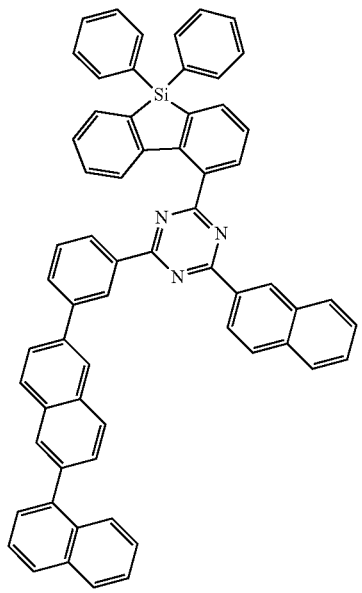
P-36
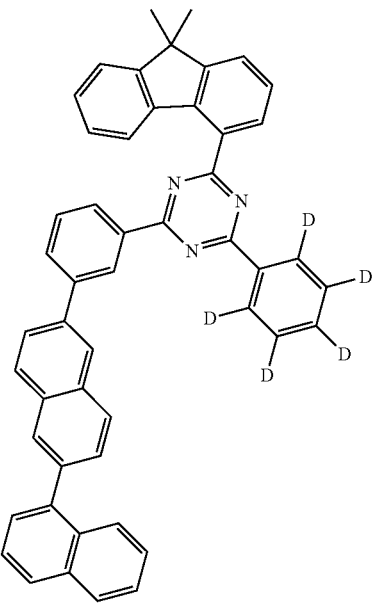
P-38
P-37
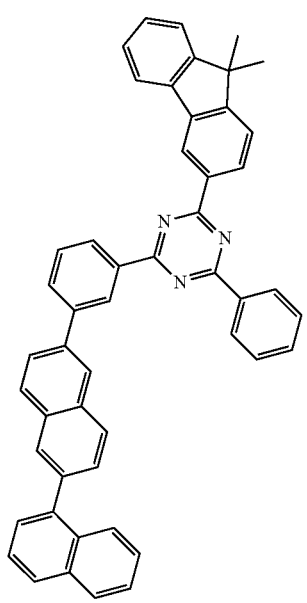
412
-continued
P-39
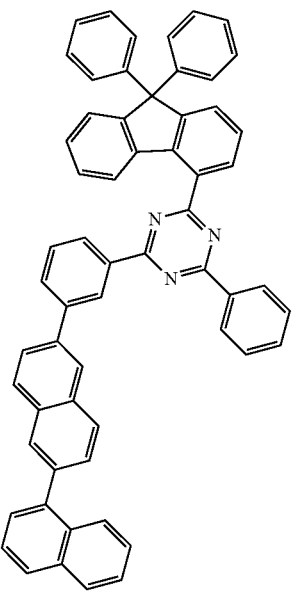

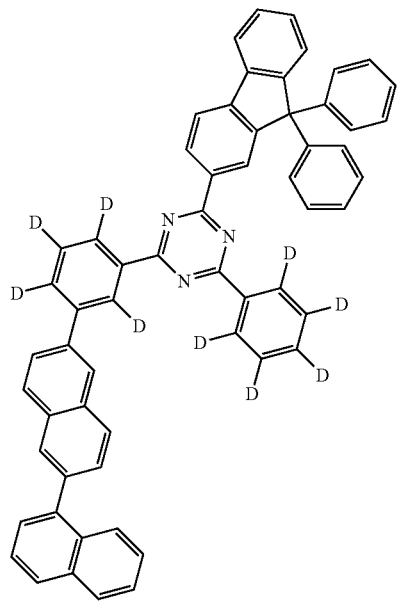
P-40
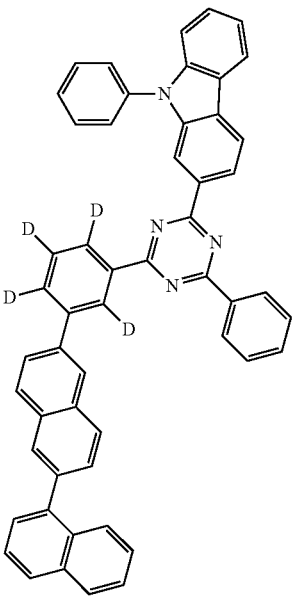
P-42
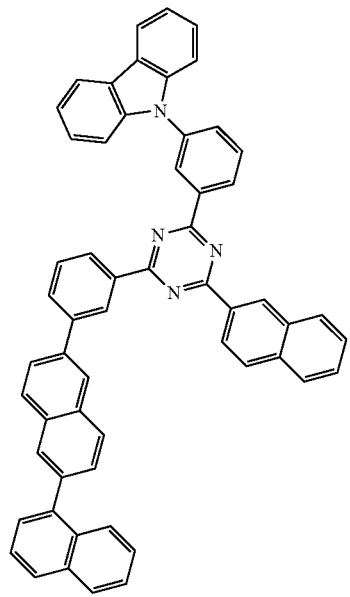
P-41
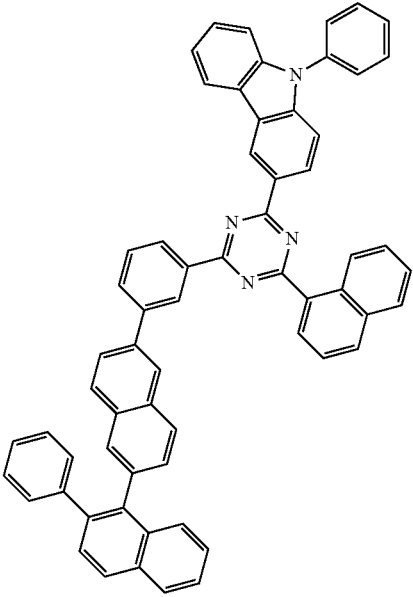
P-43

415
-continued
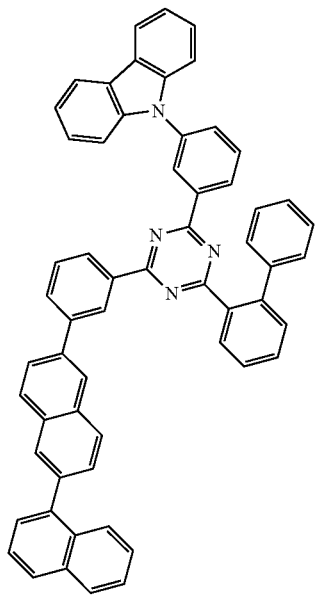
P-44
416
-continued
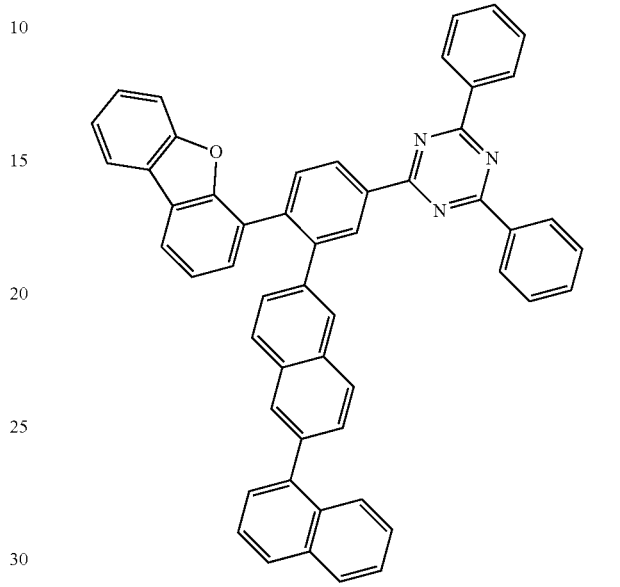
P-45
P-46
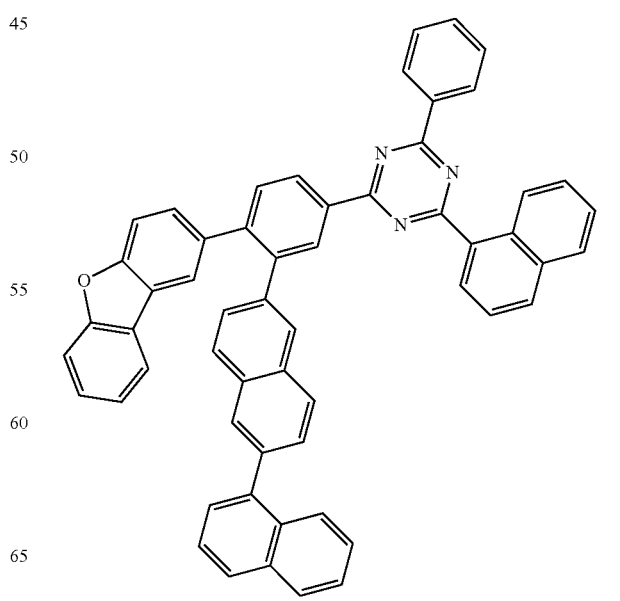
P-47

P-48
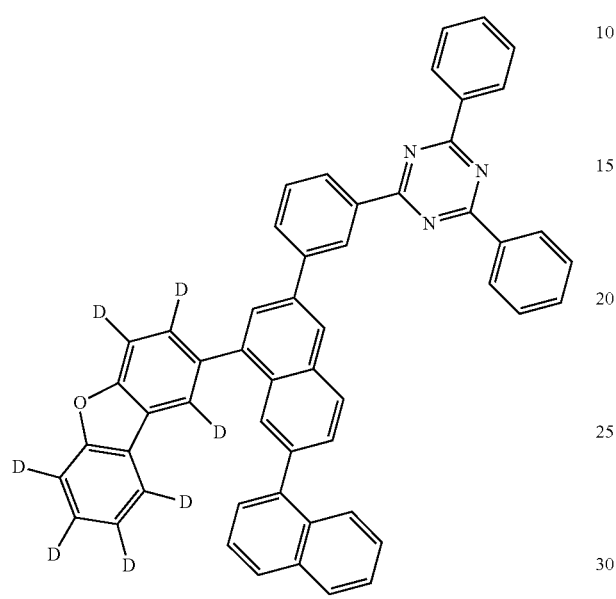
P-49
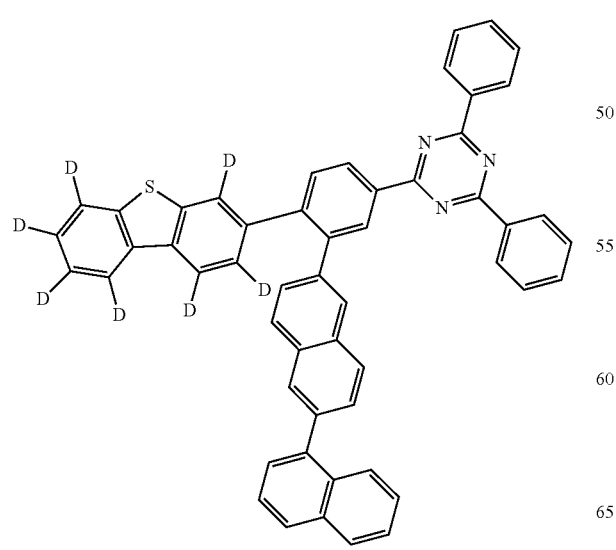
P-50
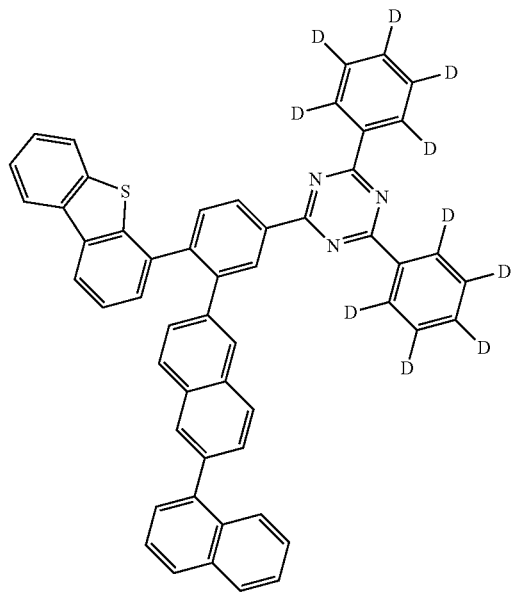
P-51
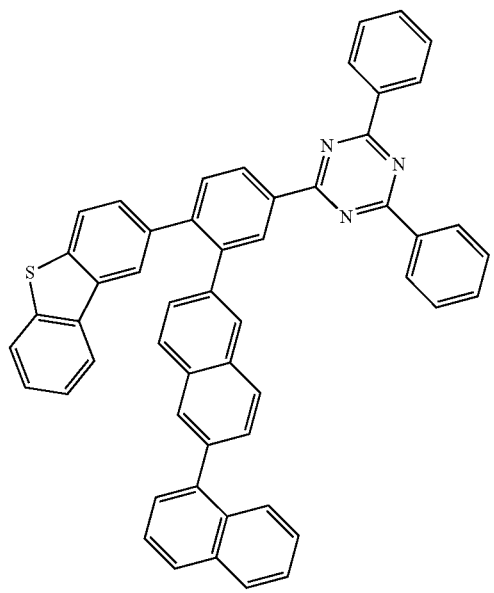

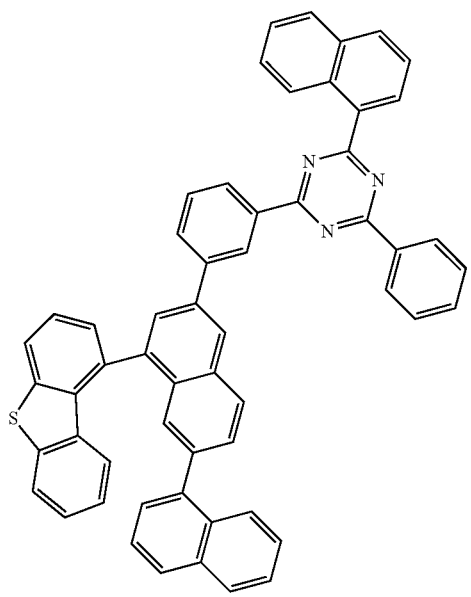
P-52
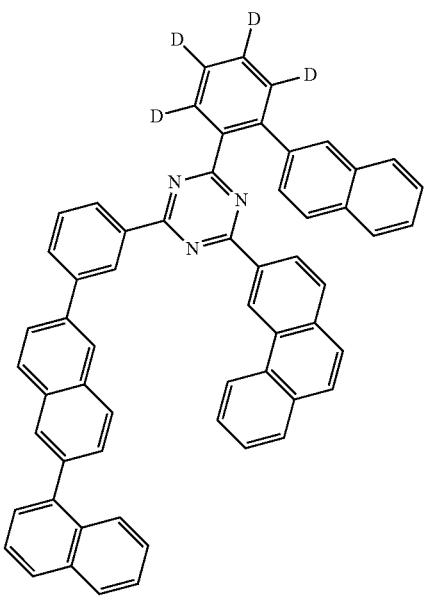
P-54
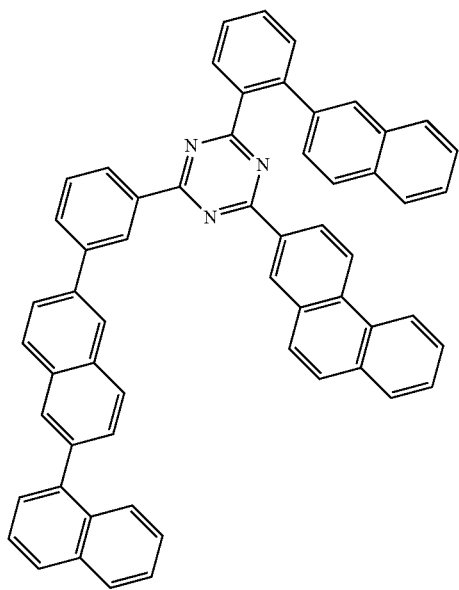
P-53
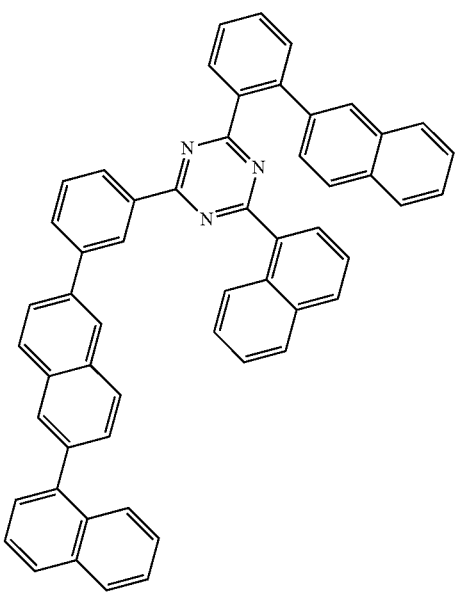
P-55

P-56
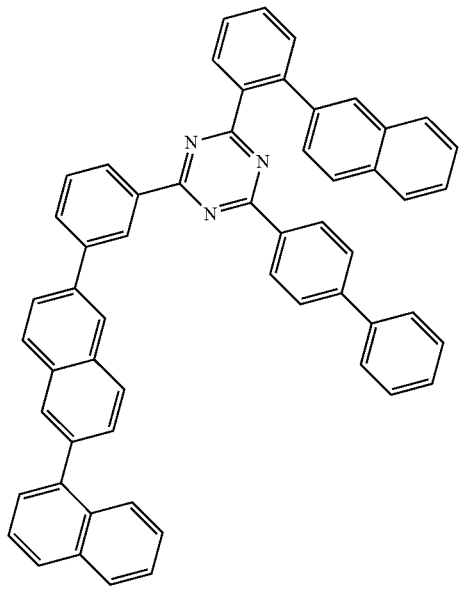
P-57
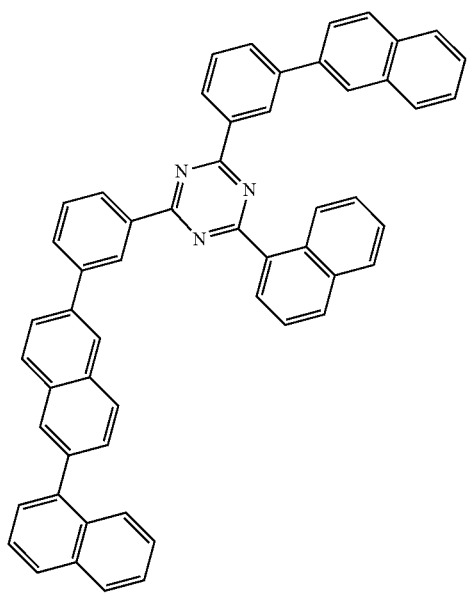
P-58
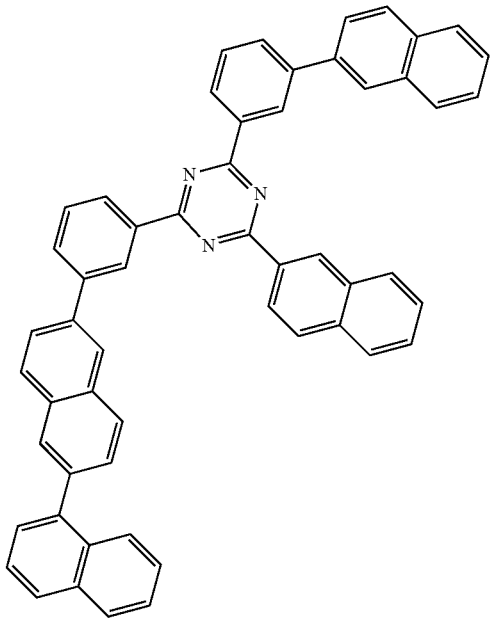
P-59
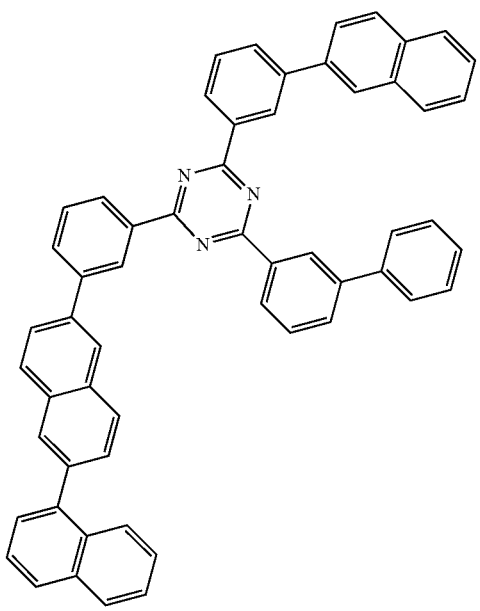

P-60
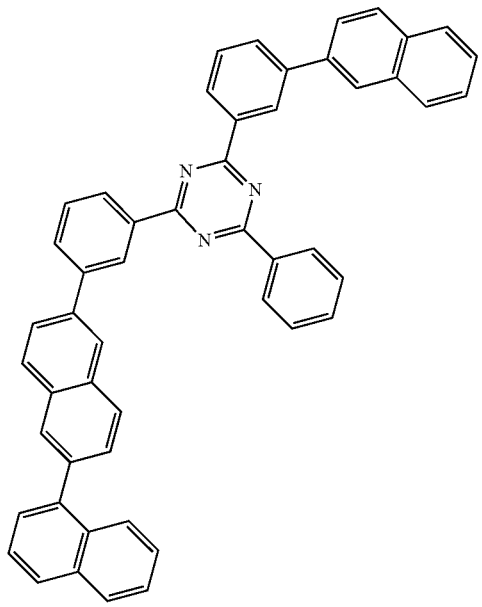
P-61
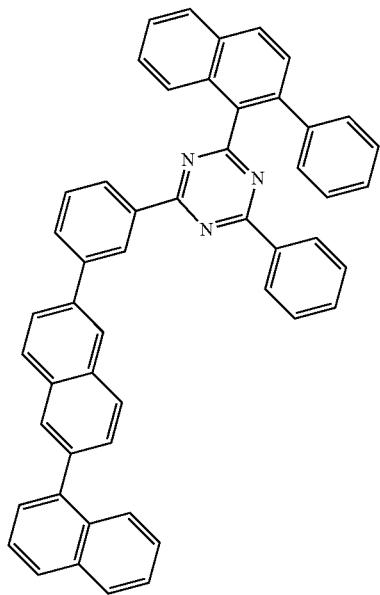
P-62
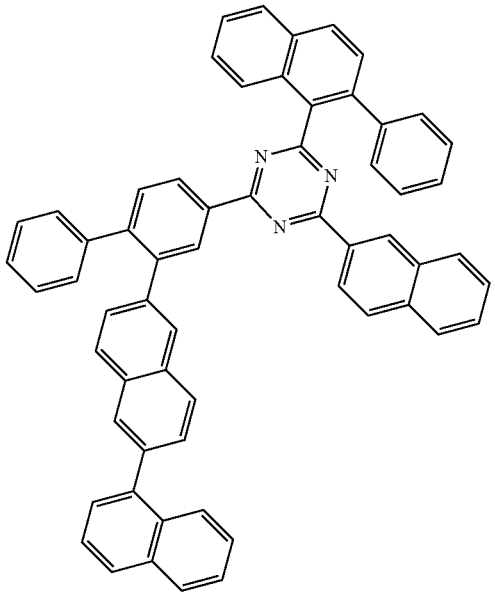
P-63
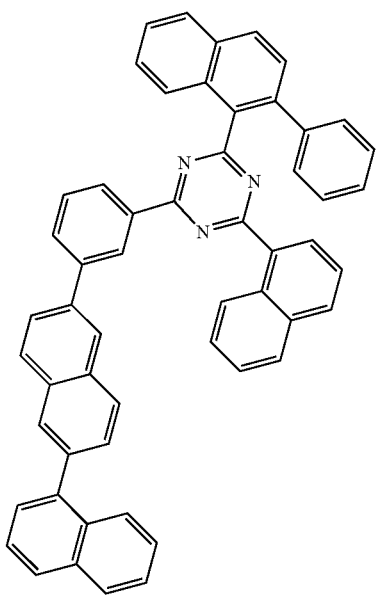

-continued
P-64
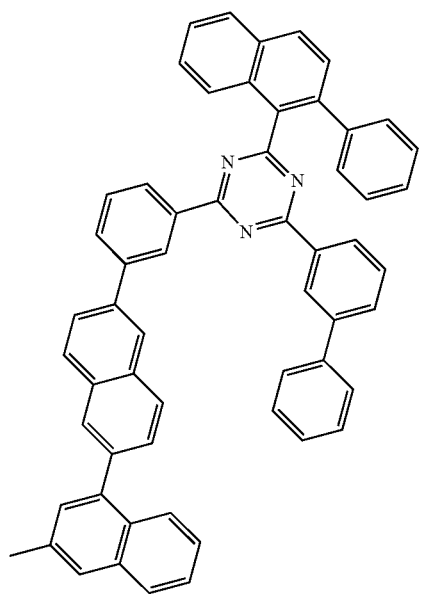
P-66
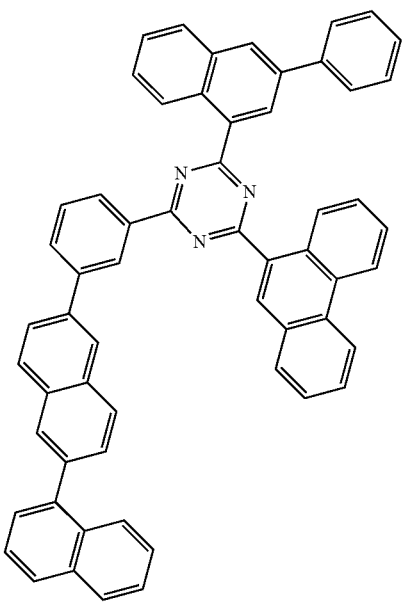
P-65
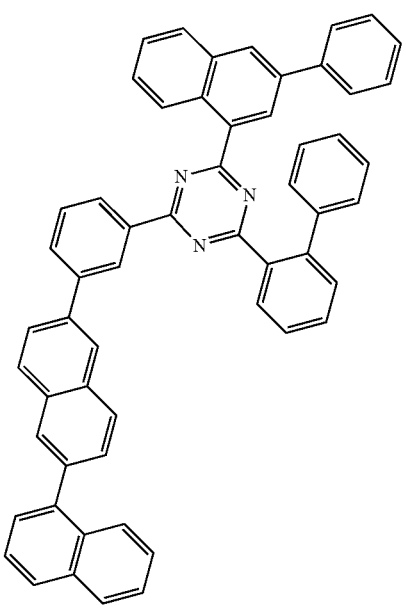
P-67

P-68
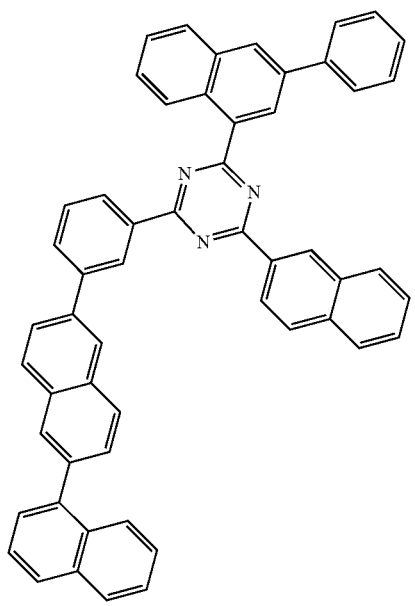
P-69
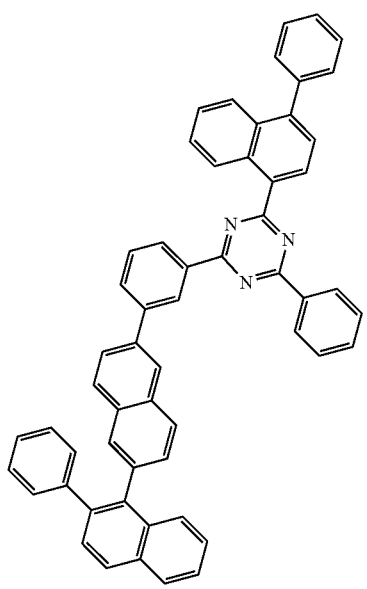
P-70
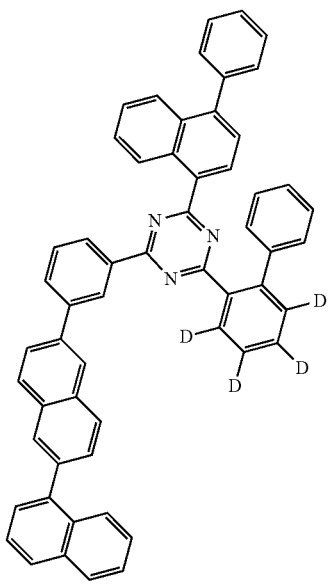
P-71
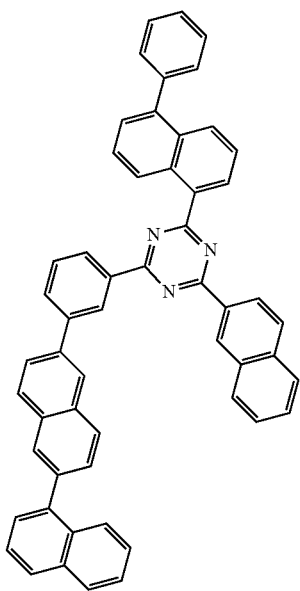

P-72 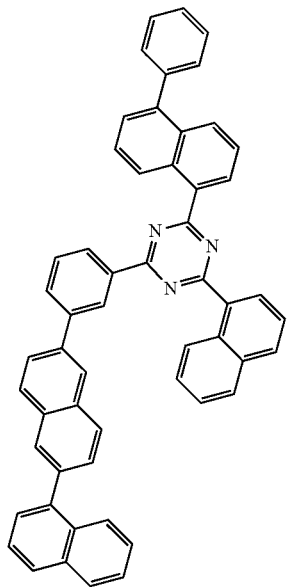
P-74 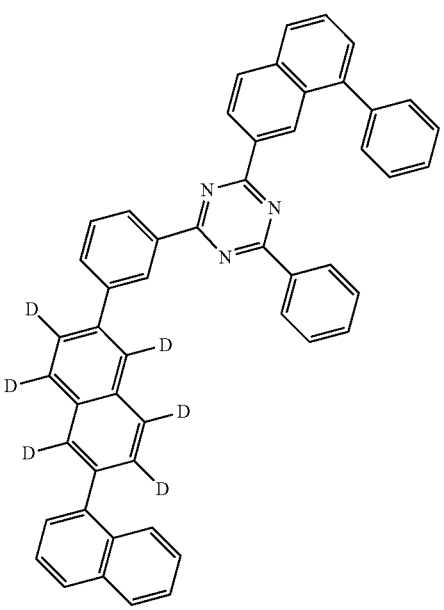
P-73 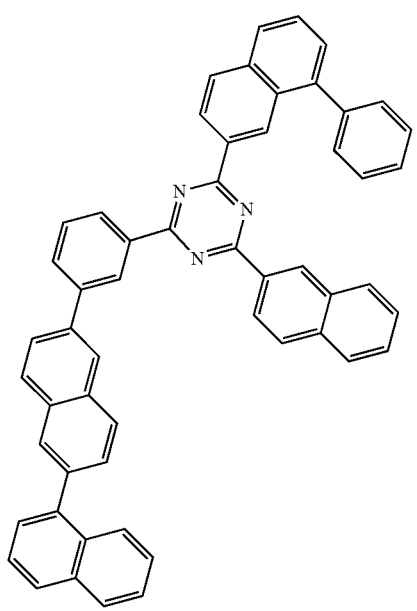
P-75 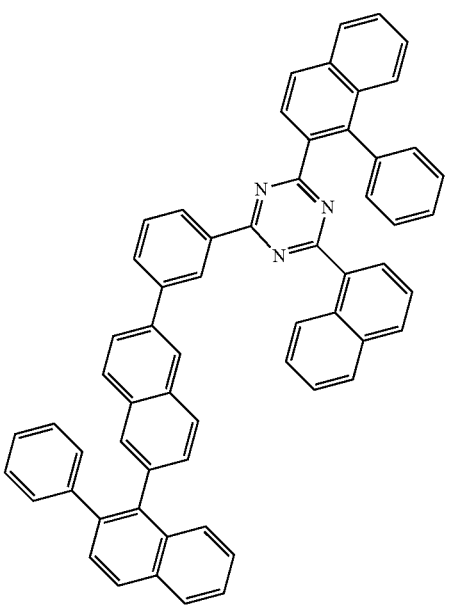

P-76
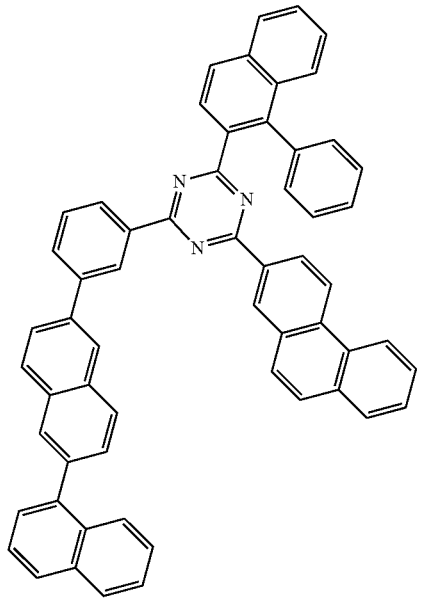
P-77
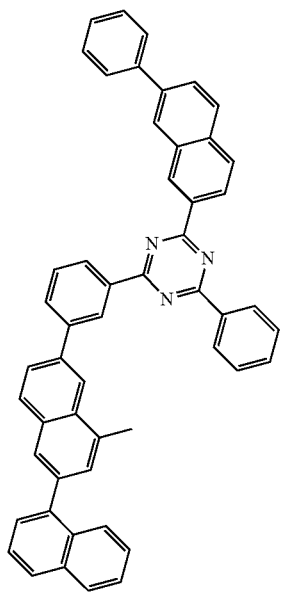
P-78
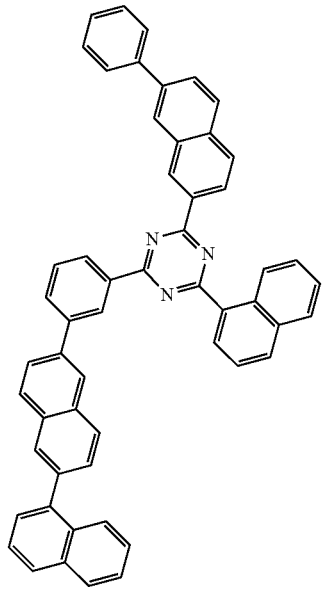
P-79
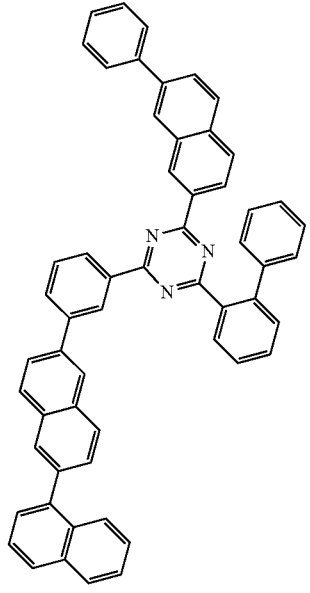

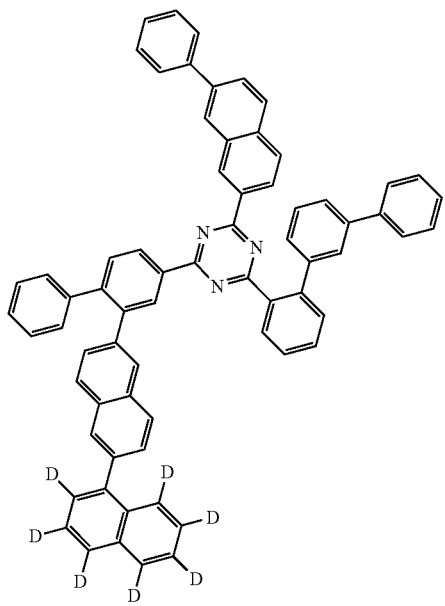
P-80
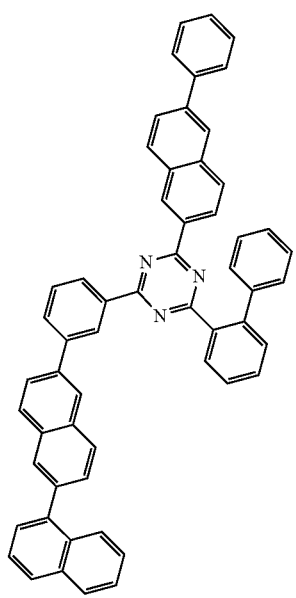
P-82
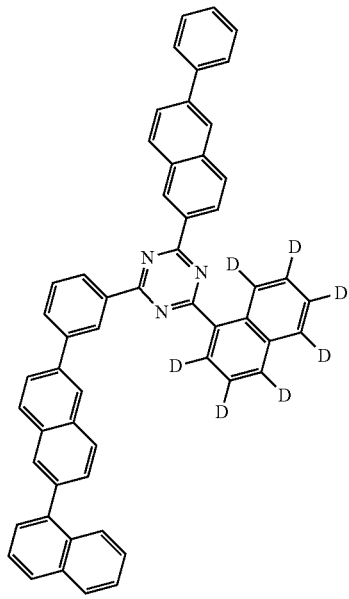
P-81
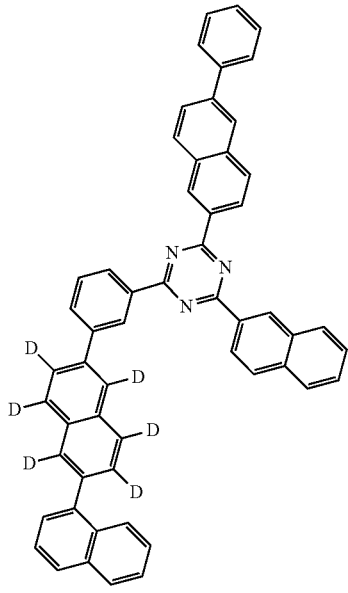
P-83

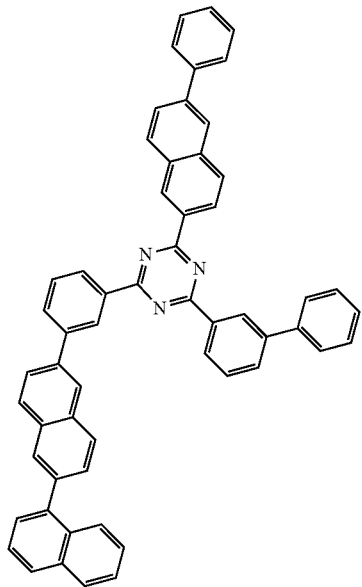
P-84
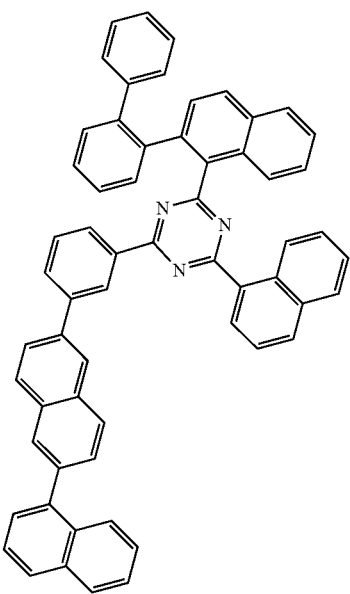
P-86
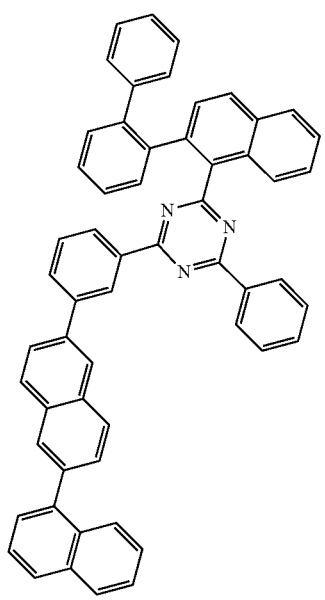
P-85
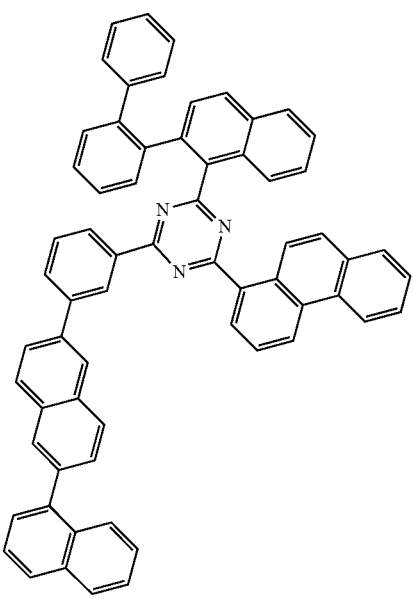
P-87

P-88
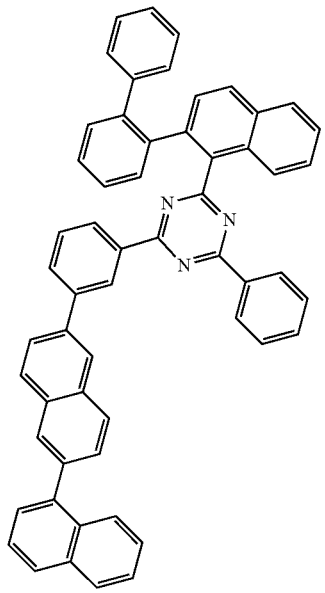
P-89
P-90
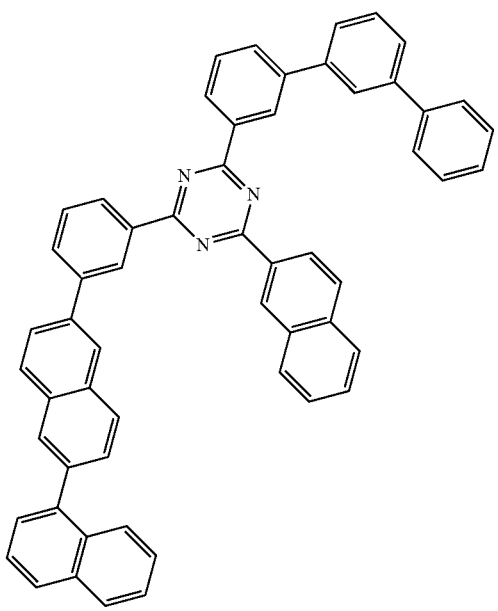
P-91
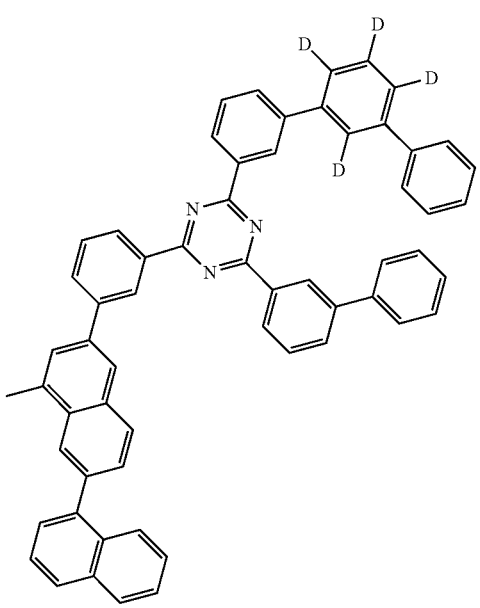

P-92
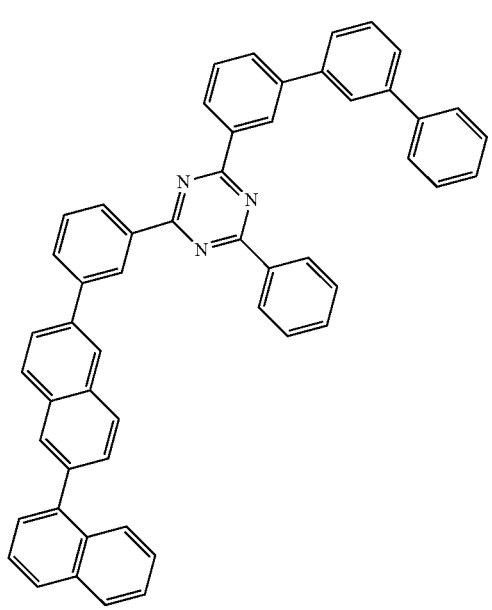
P-93
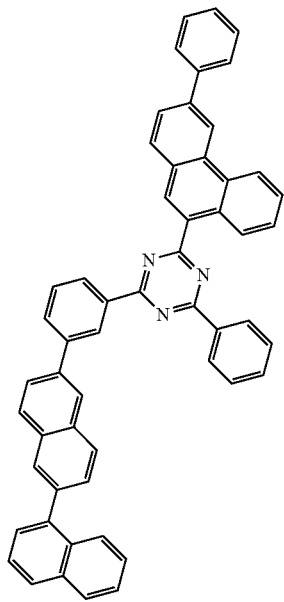
P-94
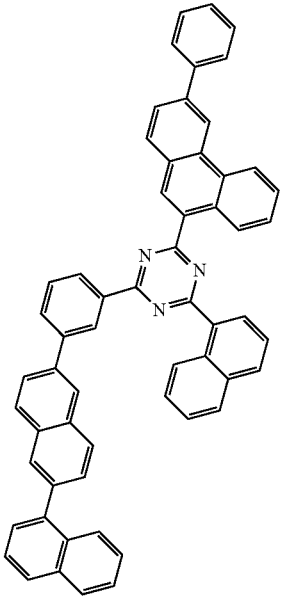
P-95
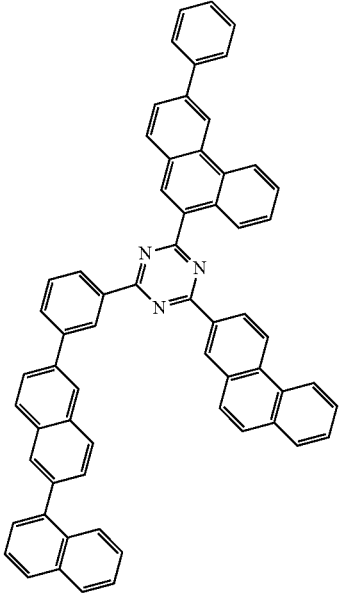

-continued
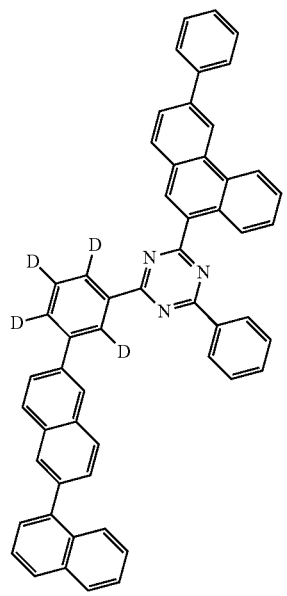
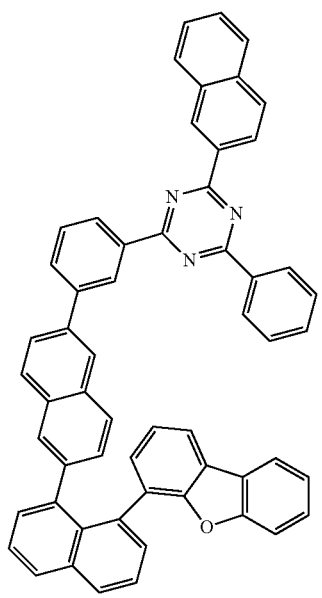
P-96
-continued
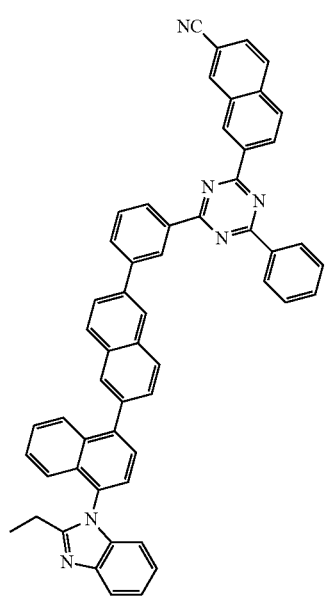
P-97
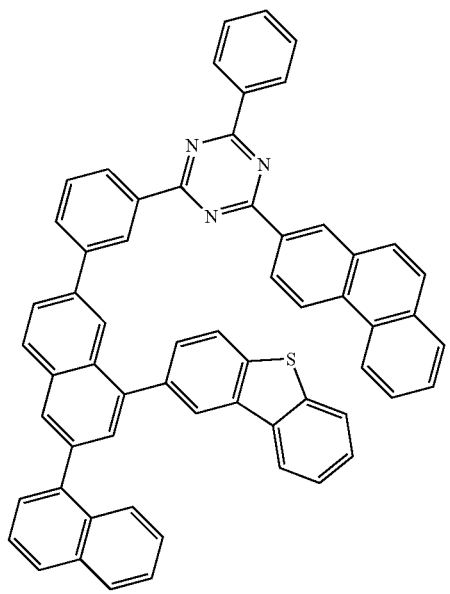
P-98
P-99

P-100
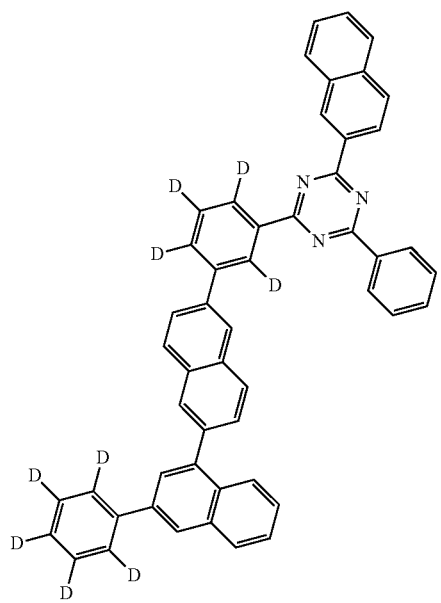
P-101
P-102
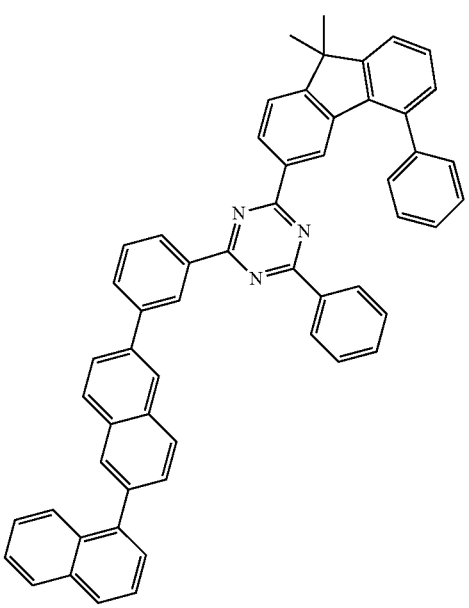
P-103
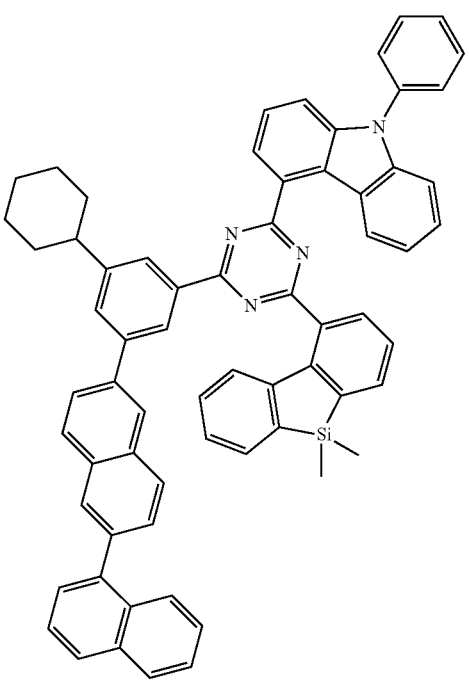

-continued

P-104

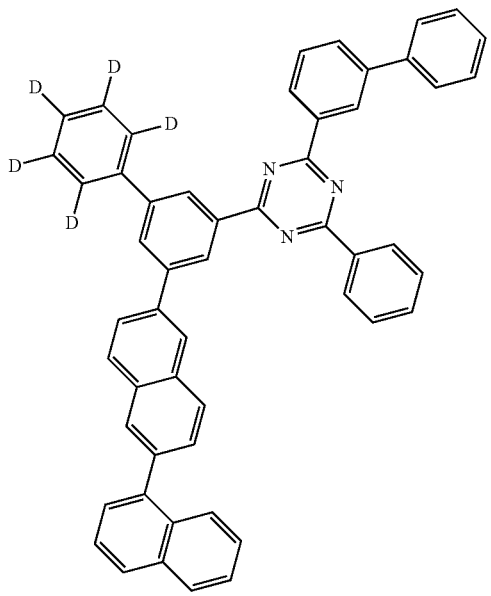

9. A method of reusing a compound represented by Formula 1 according to claim 6, comprising:
a step of depositing an organic light emitting material including the compound represented by Formula 1 in a manufacturing process of an organic light emitting device;
a step of removing impurities from the crude organic light emitting material recovered from the deposition apparatus;
a step of recovering the removed impurities; and
a step of purifying the recovered impurities to a purity of 99.9% or higher.

10. The organic electronic element of claim 1, wherein the organic electronic element further comprises a light efficiency enhancing layer formed on at least one surface of the first electrode and the second electrode, the surface being opposite to the organic material layer.

11. The organic electronic element of claim 1, wherein the organic material layer comprises 2 or more stacks comprising a hole transport layer, an emitting layer, and an electron transport layer sequentially formed on the first electrode.

12. The organic electronic element of claim 11, wherein the organic material layer further comprises a charge generation layer formed between the 2 or more stacks.

13. An electronic device comprising a display device comprising the organic electronic element of claim 1; and a control unit for driving the display device.

14. An electronic device according to claim 13, wherein the organic electronic element is at least one of an OLED, an organic solar cell, an organic photo conductor (OPC), organic transistor (organic TFT) and an element for monochromic or white illumination.

* * * * *

UNITED STATES PATENT AND TRADEMARK OFFICE
CERTIFICATE OF CORRECTION

PATENT NO. : 11,785,847 B2
APPLICATION NO. : 18/310623
DATED : October 10, 2023
INVENTOR(S) : Song et al.

It is certified that error appears in the above-identified patent and that said Letters Patent is hereby corrected as shown below:

In the Claims

Column 270, Claim 1, Line 47:
Please delete: "$C_1$-$C_{60}$" and replace with -- $C_1$-$C_{50}$ --

Column 270, Claim 1, Line 63:
Please delete: "$C_1$-$C_{60}$" and replace with -- $C_1$-$C_{50}$ --

Column 271, Claim 1, Line 5:
Please delete: "$C_1$-$C_{60}$" and replace with -- $C_1$-$C_{50}$ --

Column 271, Claim 1, Line 41:
Please delete: "$C_1$-$C_6$" and replace with -- $C_1$-$C_{60}$ --

Column 271, Claim 1, Line 57:
Please delete: "$C_1$-$C_6$" and replace with -- $C_1$-$C_{60}$ --

Column 272, Claim 2, Line 17:
Please delete: "compound" and replace with -- organic electronic element --

Column 390, Claim 6, Line 37:
Please delete: "compound" and replace with -- organic electronic element --

Column 391, Claim 6, Line 7:
Please delete: "$C_1$-$C_{60}$" and replace with -- $C_1$-$C_{50}$ --

Column 391, Claim 6, Line 18:
Please delete: "$C_1$-$C_{60}$" and replace with -- $C_1$-$C_{50}$ --

Signed and Sealed this
Fifth Day of December, 2023

Katherine Kelly Vidal
*Director of the United States Patent and Trademark Office*